United States Patent

De La Rosa et al.

(10) Patent No.: US 10,899,754 B2
(45) Date of Patent: Jan. 26, 2021

(54) MODULATORS OF INDOLEAMINE 2,3-DIOXYGENASE

(71) Applicant: GLAXOSMITHKLINE INTELLECTUAL PROPERTY DEVELOPMENT LIMITED, Brentford (GB)

(72) Inventors: Martha Alicia De La Rosa, Research Triangle Park, NC (US); Wieslaw Mieczyslaw Kazmierski, Research Triangle Park, NC (US); Vicente Samano, Research Triangle Park, NC (US)

(73) Assignee: GLAXOSMITHKLINE INTELLECTUAL PROPERTY DEVELOPMENT LIMITED, Middlesex (GB)

( * ) Notice: Subject to any disclaimer, the term of this patent is extended or adjusted under 35 U.S.C. 154(b) by 0 days.

(21) Appl. No.: 16/464,858

(22) PCT Filed: Dec. 15, 2017

(86) PCT No.: PCT/IB2017/058014
§ 371 (c)(1),
(2) Date: May 29, 2019

(87) PCT Pub. No.: WO2018/116107
PCT Pub. Date: Jun. 28, 2018

(65) Prior Publication Data
US 2020/0115374 A1  Apr. 16, 2020

Related U.S. Application Data

(60) Provisional application No. 62/436,672, filed on Dec. 20, 2016, provisional application No. 62/481,743, filed on Apr. 5, 2017.

(51) Int. Cl.

| | | |
|---|---|---|
| C07D 417/12 | (2006.01) |
| C07D 417/14 | (2006.01) |
| C07D 405/12 | (2006.01) |
| C07D 285/08 | (2006.01) |
| C07D 241/06 | (2006.01) |
| C07D 233/88 | (2006.01) |
| C07D 233/90 | (2006.01) |
| C07D 213/04 | (2006.01) |
| C07D 249/14 | (2006.01) |
| C07D 237/20 | (2006.01) |
| C07C 229/42 | (2006.01) |
| C07D 207/50 | (2006.01) |
| C07D 213/74 | (2006.01) |
| C07D 235/00 | (2006.01) |
| C07D 235/30 | (2006.01) |
| C07D 241/20 | (2006.01) |
| C07D 257/06 | (2006.01) |
| C07D 263/48 | (2006.01) |
| C07D 271/113 | (2006.01) |
| C07D 277/42 | (2006.01) |

(Continued)

(52) U.S. Cl.
CPC .......... *C07D 417/12* (2013.01); *C07C 229/42* (2013.01); *C07D 207/50* (2013.01); *C07D 213/04* (2013.01); *C07D 213/74* (2013.01); *C07D 233/88* (2013.01); *C07D 233/90* (2013.01); *C07D 235/00* (2013.01); *C07D 235/30* (2013.01); *C07D 237/20* (2013.01); *C07D 241/06* (2013.01); *C07D 241/20* (2013.01); *C07D 249/14* (2013.01); *C07D 257/06* (2013.01); *C07D 263/48* (2013.01); *C07D 271/113* (2013.01); *C07D 277/42* (2013.01); *C07D 277/82* (2013.01); *C07D 285/08* (2013.01); *C07D 305/08* (2013.01); *C07D 333/36* (2013.01); *C07D 335/02* (2013.01); *C07D 405/12* (2013.01); *C07D 413/12* (2013.01); *C07D 417/04* (2013.01); *C07D 417/14* (2013.01); *C07D 471/04* (2013.01)

(58) Field of Classification Search
CPC .. C07D 417/12; C07D 417/14; C07D 405/12; C07D 285/08; C07D 241/06; C07D 233/88; C07D 233/90; C07D 213/04; C07D 249/14; C07D 237/20
See application file for complete search history.

(56) References Cited

FOREIGN PATENT DOCUMENTS

WO  WO 2014/150646 A1   9/2014
WO  WO-2016/161269 A1 * 10/2016   ........... C07D 309/14

(Continued)

*Primary Examiner* — Laura L Stockton
(74) *Attorney, Agent, or Firm* — Robert H. Brink; Duke M. Fitch; Edward R. Gimmi

(57) ABSTRACT

Provided are IDO inhibitor compounds of Formula I and pharmaceutically acceptable salts thereof, their pharmaceutical compositions, their methods of preparation, and methods for their use in the prevention and/or treatment of diseases such as chronic viral infection, chronic bacterial infections, cancer, sepsis or a neurological disorder.

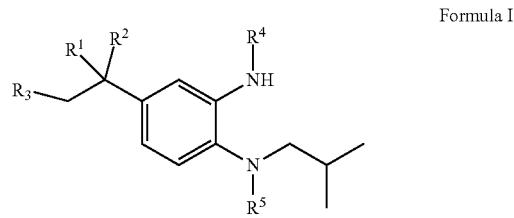

Formula I

5 Claims, 2 Drawing Sheets

(51) Int. Cl.
*C07D 277/82* (2006.01)
*C07D 305/08* (2006.01)
*C07D 333/36* (2006.01)
*C07D 335/02* (2006.01)
*C07D 413/12* (2006.01)
*C07D 417/04* (2006.01)
*C07D 471/04* (2006.01)

(56) References Cited

FOREIGN PATENT DOCUMENTS

| WO | WO-2016/161279 A1 * | 10/2016 | ........... C07D 309/14 |
|----|---------------------|---------|-------------------------|
| WO | WO 2016/161279 A1   | 10/2016 |                         |
| WO | WO 2017/051353 A1   | 3/2017  |                         |
| WO | WO 2017/051354 A1   | 3/2017  |                         |

* cited by examiner

Figure 1    Daily body weights of Beagle dogs during the study
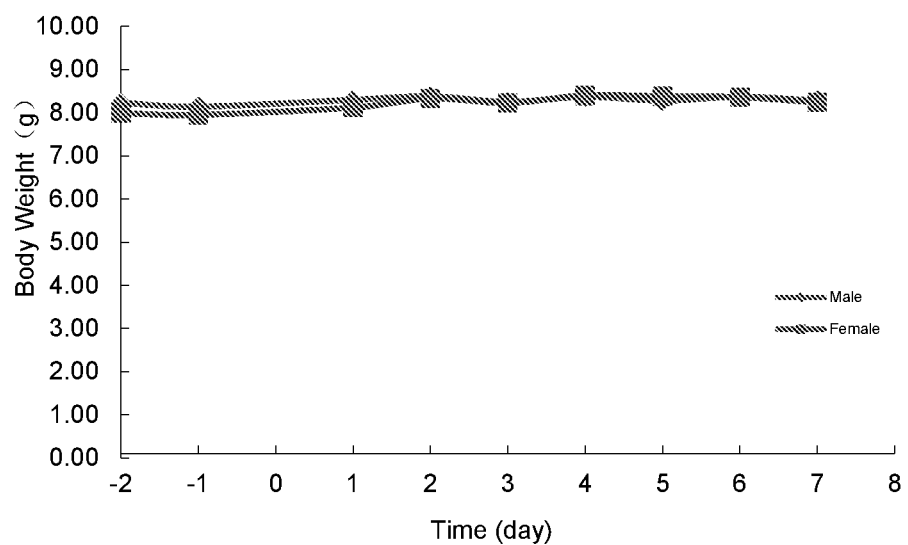

Figure 2    Daily hepatic enzyme levels of Beagle dogs during the study: ALT (alanine aminotransferase), AST (aspartate aminotransferase), ALP (alkaline phosphatase) and T-Bil (total bilirubin)
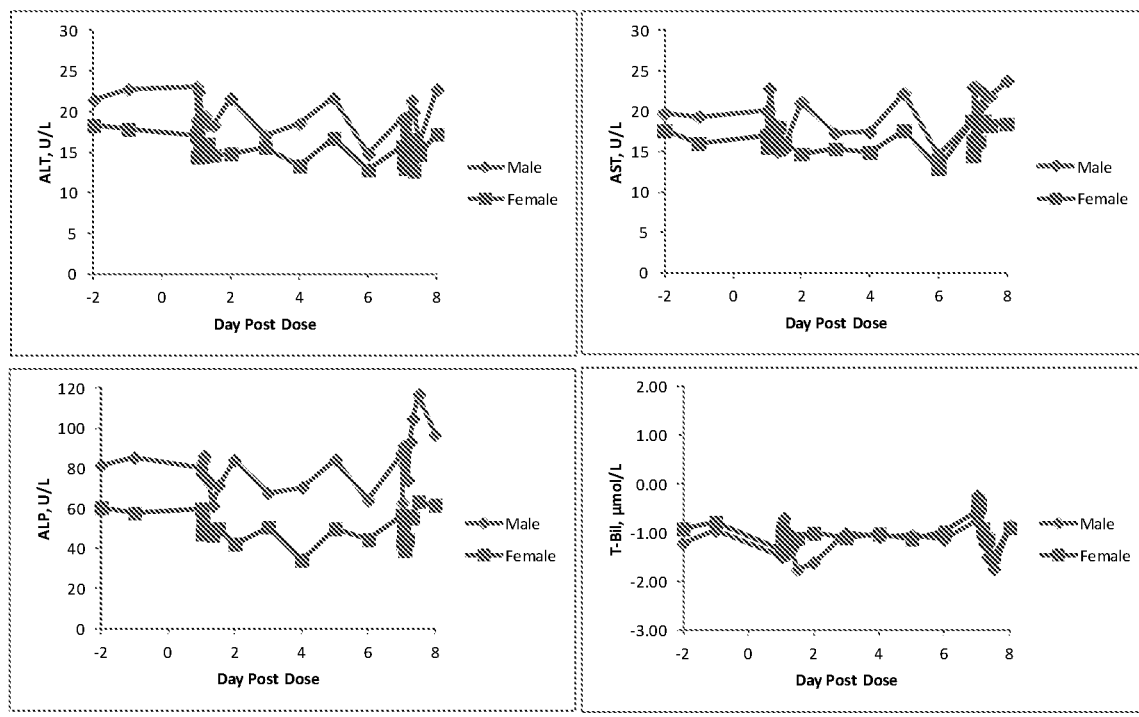

MODULATORS OF INDOLEAMINE 2,3-DIOXYGENASE

This application is a § 371 of International Application No. PCT/IB2017/058014, filed 15 Dec. 2017, which claims the benefit of U.S. Provisional Application Nos. 62/481,743, filed 5 Apr. 2017 and 62/436,672, filed 20 Dec. 2016.

FIELD OF THE INVENTION

Compounds, methods and pharmaceutical compositions for the prevention and/or treatment of HIV; including the prevention of the progression of AIDS and general immunosuppression, by administering certain indoleamine 2,3-dioxygenase compounds in therapeutically effective amounts are disclosed. Methods for preparing such compounds and methods of using the compounds and pharmaceutical compositions thereof are also disclosed.

BACKGROUND OF THE INVENTION

Indoleamine-2,3-dioxygenase 1 (IDO1) is a heme-containing enzyme that catalyzes the oxidation of the indole ring of tryptophan to produce N-formyl kynurenine, which is rapidly and constitutively converted to kynurenine (Kyn) and a series of downstream metabolites. IDO1 is the rate limiting step of this kynurenine pathway of tryptophan metabolism and expression of IDO1 is inducible in the context of inflammation. Stimuli that induce IDO1 include viral or bacterial products, or inflammatory cytokines associated with infection, tumors, or sterile tissue damage. Kyn and several downstream metabolites are immunosuppressive: Kyn is antiproliferative and proapoptotic to T cells and NK cells (Munn, Shafizadeh et al. 1999, Frumento, Rotondo et al. 2002) while metabolites such as 3-hydroxy anthranilic acid (3-HAA) or the 3-HAA oxidative dimerization product cinnabarinic acid (CA) inhibit phagocyte function (Sekkai, Guittet et al. 1997), and induce the differentiation of immunosuppressive regulatory T cells (Treg) while inhibiting the differentiation of gut-protective IL-17 or IL-22-producing CD4+ T cells (Th17 and Th22) (Favre, Mold et al. 2010). IDO1 induction, among other mechanisms, is likely important in limiting immunopathology during active immune responses, in promoting the resolution of immune responses, and in promoting fetal tolerance. However in chronic settings, such as cancer, or chronic viral or bacterial infection, IDO1 activity prevents clearance of tumor or pathogen and if activity is systemic, IDO1 activity may result in systemic immune dysfunction (Boasso and Shearer 2008, Li, Huang et al. 2012).

In addition to these immunomodulatory effects, metabolites of IDO1 such as Kyn and quinolinic acid are also known to be neurotoxic and are observed to be elevated in several conditions of neurological dysfunction and depression. As such, IDO1 is a therapeutic target for inhibition in a broad array of indications, such as to promote tumor clearance, enable clearance of intractable viral or bacterial infections, decrease systemic immune dysfunction manifest as persistent inflammation during HIV infection or immunosuppression during sepsis, and prevent or reverse neurological conditions.

IDO1 and Persistent Inflammation in HIV Infection:

Despite the success of antiretroviral therapy (ART) in suppressing HIV replication and decreasing the incidence of AIDS-related conditions, HIV-infected patients on ART have a higher incidence of non-AIDS morbidities and mortality than their uninfected peers. These non-AIDS conditions include cancer, cardiovascular disease, osteoporosis, liver disease, kidney disease, frailty, and neurocognitive dysfunction (Deeks 2011). Several studies indicate that non-AIDS morbidity/mortality is associated with persistent inflammation, which remains elevated in HIV-infected patients on ART as compared to peers (Deeks 2011). As such, it is hypothesized that persistent inflammation and immune dysfunction despite virologic suppression with ART is a cause of these non-AIDS-defining events (NA-DEs).

HIV infects and kills CD4+ T cells, with particular preference for cells like those CD4+ T cells that reside in the lymphoid tissues of the mucosal surfaces (Mattapallil, Douek et al. 2005). The loss of these cells combined with the inflammatory response to infection result in a perturbed relationship between the host and all pathogens, including HIV itself, but extending to pre-existing or acquired viral infections, fungal infections, and resident bacteria in the skin and mucosal surfaces. This dysfunctional host:pathogen relationship results in the over-reaction of the host to what would typically be minor problems as well as permitting the outgrowth of pathogens among the microbiota. The dysfunctional host:pathogen interaction therefore results in increased inflammation, which in turn leads to deeper dysfunction, driving a vicious cycle. As inflammation is thought to drive non-AIDS morbidity/mortality, the mechanisms governing the altered host:pathogen interaction are therapeutic targets.

IDO1 expression and activity are increased during untreated and treated HIV infection as well as in primate models of SIV infection (Boasso, Vaccari et al. 2007, Favre, Lederer et al. 2009, Byakwaga, Boum et al. 2014, Hunt, Sinclair et al. 2014, Tenorio, Zheng et al. 2014). IDO1 activity, as indicated by the ratio of plasma levels of enzyme substrate and product (Kyn/Tryp or K:T ratio), is associated with other markers of inflammation and is one of the strongest predictors of non-AIDS morbidity/mortality (Byakwaga, Boum et al. 2014, Hunt, Sinclair et al. 2014, Tenorio, Zheng et al. 2014). In addition, features consistent with the expected impact of increased IDO1 activity on the immune system are major features of HIV and SIV induced immune dysfunction, such as decreased T cell proliferative response to antigen and imbalance of Treg:Th17 in systemic and intestinal compartments (Favre, Lederer et al. 2009, Favre, Mold et al. 2010). As such, we and others hypothesize that IDO1 plays a role in driving the vicious cycle of immune dysfunction and inflammation associated with non-AIDS morbidity/mortality. Thus, we propose that inhibiting IDO1 will reduce inflammation and decrease the risk of NADEs in ART-suppressed HIV-infected persons.

IDO1 and Persistent Inflammation Beyond HIV

As described above, inflammation associated with treated chronic HIV infection is a likely driver of multiple end organ diseases [Deeks 2011]. However, these end organ diseases are not unique to HIV infection and are in fact the common diseases of aging that occur at earlier ages in the HIV-infected population. In the uninfected general population inflammation of unknown etiology is a major correlate of morbidity and mortality [Pinti, 2016 #88]. Indeed many of the markers of inflammation are shared, such as IL-6 and CRP. If, as hypothesized above, IDO1 contributes to persistent inflammation in the HIV-infected population by inducing immune dysfunction in the GI tract or systemic tissues, then IDO1 may also contribute to inflammation and therefore end organ diseases in the broader population. These inflammation associated end organ diseases are exemplified by cardiovascular diseases, metabolic syndrome, liver disease (NAFLD, NASH), kidney disease, osteoporosis, and neurocognitive impairment. Indeed, the IDO1 pathway has links in the literature to liver disease (Vivoli abstracts at Italian Assoc. for the Study of the Liver Conference 2015], diabetes [Baban, 2010 #89], chronic kidney disease [Schefold, 2009 #90], cardiovascular disease [Mangge, 2014 #92; Mangge, 2014 #91], as well as general aging and all cause mortality [Pertovaara, 2006 #93]. As such, inhibition of IDO1 may have application in decreasing inflammation in the general population to decrease the incidence of specific end organ diseases associated with inflammation and aging.

IDO1 and Oncology

IDO expression can be detected in a number of human cancers (for example; melanoma, pancreatic, ovarian, AML, CRC, prostate and endometrial) and correlates with poor prognosis (Munn 2011). Multiple immunosuppressive roles have been ascribed to the action of IDO, including the induction of Treg differentiation and hyper-activation, suppression of Teff immune response, and decreased DC function, all of which impair immune recognition and promote tumor growth (Munn 2011). IDO expression in human brain tumors is correlated with reduced survival. Orthotropic and transgenic glioma mouse models demonstrate a correlation between reduced IDO expression and reduced Treg infiltration and a increased long term survival (Wainwright, Balyasnikova et al. 2012). In human melanoma a high proportion of tumors (33 of 36 cases) displayed elevated IDO suggesting an important role in establishing an immunosuppressive tumor microenvironment (TME) characterized by the expansion, activation and recruitment of MDSCs in a Treg-dependent manner (Holmgaard, Zamarin et al. 2015). Additionally, host IDO expressing immune cells have been identified in the draining lymph nodes and in the tumors themselves (Mellor and Munn 2004). Hence, both tumor and host-derived IDO are believed to contribute to the immune suppressed state of the TME.

The inhibition of IDO was one of the first small molecule drug strategies proposed for re-establishment of an immunogenic response to cancer (Mellor and Munn 2004). The d-enantiomer of 1-methyl tryptophan (D-1MTor indoximod) was the first IDO inhibitor to enter clinical trials. While this compound clearly does inhibit the activity of IDO, it is a very weak inhibitor of the isolated enzyme and the in vivo mechanism(s) of action for this compound are still being elucidated. Investigators at Incyte optimized a hit compound obtained from a screening process into a potent and selective inhibitor with sufficient oral exposure to demonstrate a delay in tumor growth in a mouse melanoma model (Yue, Douty et al. 2009). Further development of this series led to INCB204360 which is a highly selective for inhibition of IDO-1 over IDO-2 and TDO in cell lines transiently transfected with either human or mouse enzymes (Liu, Shin et al. 2010). Similar potency was seen for cell lines and primary human tumors which endogenously express IDO1 (IC50 s ~3-20 nM). When tested in co-culture of DCs and naïve $CD4^+CD25^-$ T cells, INCB204360 blocked the conversion of these T cells into $CD4^+FoxP3^+$ Tregs. Finally, when tested in a syngeneic model (PAN02 pancreatic cells) in immunocompetent mice, orally dosed INCB204360 provided a significant dose-dependent inhibition of tumor growth, but was without effect against the same tumor implanted in immune-deficient mice. Additional studies by the same investigators have shown a correlation of the inhibition of IDO1 with the suppression of systemic kynurenine levels and inhibition of tumor growth in an additional syngeneic tumor model in immunocompetent mice. Based upon these preclinical studies, INCB24360 entered clinical trials for the treatment of metastatic melanoma (Beatty, O'Dwyer et al. 2013).

In light of the importance of the catabolism of tryptophan in the maintenance of immune suppression, it is not surprising that overexpression of a second tryptophan metabolizing enzyme, TDO2, by multiple solid tumors (for example, bladder and liver carcinomas, melanomas) has also been detected. A survey of 104 human cell lines revealed 20/104 with TDO expression, 17/104 with IDO1 and 16/104 expressing both (Pilotte, Larrieu et al. 2012). Similar to the inhibition of IDO1, the selective inhibition of TDO2 is effective in reversing immune resistance in tumors overexpressing TDO2 (Pilotte, Larrieu et al. 2012). These results support TDO2 inhibition and/or dual TDO2/IDO1 inhibition as a viable therapeutic strategy to improve immune function.

Multiple pre-clinical studies have demonstrated significant, even synergistic, value in combining IDO-1 inhibitors in combination with T cell checkpoint modulating mAbs to CTLA-4, PD-1, and GITR. In each case, both efficacy and related PD aspects of improved immune activity/function were observed in these studies across a variety of murine models (Balachandran, Cavnar et al. 2011, Holmgaard, Zamarin et al. 2013, M. Mautino 2014, Wainwright, Chang et al. 2014). The Incyte IDO1 inhibitor (INCB204360, epacadostat) has been clinically tested in combination with a CTLA4 blocker (ipilimumab), but it is unclear that an effective dose was achieved due to dose-limited adverse events seen with the combination. In contrast recently released data for an on-going trial combining epacadostat with Merck's PD-1 mAb (pembrolizumab) demonstrated improved tolerability of the combination allowing for higher doses of the IDO1 inhibitor. There have been several clinical responses across various tumor types which is encouraging. However, it is not yet known if this combination is an improvement over the single agent activity of pembrolizumab (Gangadhar, Hamid et al. 2015). Similarly, Roche/Genentech are advancing NGL919/GDC-0919 in combination with both mAbs for PD-L1 (MPDL3280A, Atezo) and OX-40 following the recent completion of a phase 1a safety and PK/PD study in patients with advanced tumors.

IDO1 and Chronic Infections

IDO1 activity generates kynurenine pathway metabolites such as Kyn and 3-HAA that impair at least T cell, NK cell, and macrophage activity (Munn, Shafizadeh et al. 1999, Frumento, Rotondo et al. 2002) (Sekkai, Guittet et al. 1997, Favre, Mold et al. 2010). Kyn levels or the Kyn/Tryp ratio are elevated in the setting of chronic HIV infection (Byakwaga, Boum et al. 2014, Hunt, Sinclair et al. 2014, Tenorio, Zheng et al. 2014), HBV infection (Chen, Li et al. 2009), HCV infection (Larrea, Riezu-Boj et al. 2007, Asghar, Ashiq et al. 2015), and TB infection (Suzuki, Suda et al. 2012) and are associated with antigen-specific T cell dysfunction (Boasso, Herbeuval et al. 2007, Boasso, Hardy et al. 2008, Loughman and Hunstad 2012, Ito, Ando et al. 2014, Lepiller, Soulier et al. 2015). As such, it is thought that in these cases of chronic infection, IDO1-mediated inhibition of the pathogen-specific T cell response plays a role in the persistence of infection, and that inhibition of IDO1 may have a benefit in promoting clearance and resolution of infection.

IDO1 and Sepsis

IDO1 expression and activity are observed to be elevated during sepsis and the degree of Kyn or Kyn/Tryp elevation corresponded to increased disease severity, including mortality (Tattevin, Monnier et al. 2010, Darcy, Davis et al. 2011). In animal models, blockade of IDO1 or IDO1 genetic knockouts protected mice from lethal doses of LPS or from mortality in the cecal ligation/puncture model (Jung, Lee et al. 2009, Hoshi, Osawa et al. 2014). Sepsis is characterized by an immunosuppressive phase in severe cases (Hotchkiss, Monneret et al. 2013), potentially indicating a role for IDO1 as a mediator of immune dysfunction, and indicating that pharmacologic inhibition of IDO1 may provide a clinical benefit in sepsis.

IDO1 and Neurological Disorders

In addition to immunologic settings, IDO1 activity is also linked to disease in neurological settings (reviewed in Lovelace Neuropharmacology 2016 (Lovelace, Varney et al. 2016)). Kynurenine pathway metabolites such as 3-hydroxykynurenine and quinolinic acid are neurotoxic, but are balanced by alternative metabolites kynurenic acid or picolinic acid, which are neuroprotective. Neurodegenerative and psychiatric disorders in which kynurenine pathway metabolites have been demonstrated to be associated with disease include multiple sclerosis, motor neuron disorders such as amyotrophic lateral sclerosis, Huntington's disease, Parkinson's disease, Alzheimer's disease, major depressive disorder, schizophrenia, anorexia (Lovelace, Varney et al. 2016). Animal models of neurological disease have shown some impact of weak IDO1 inhibitors such as 1-methyltryptophan on disease, indicating that IDO1 inhibition may provide clinical benefit in prevention or treatment of neurological and psychiatric disorders.

It would therefore be an advance in the art to discover IDO inhibitors that effective the balance of the aforementioned properties as a disease modifying therapy in chronic HIV infections to decrease the incidence of non-AIDS morbidity/mortality; and/or a disease modifying therapy to prevent mortality in sepsis; and/or an immunotherapy to enhance the immune response to HIV, HBV, HCV and other chronic viral infections, chronic bacterial infections, chronic fungal infections, and to tumors; and/or for the treatment of depression or other neurological/neuropsychiatric disorders.

Asghar, K., M. T. Ashiq, B. Zulfiqar, A. Mahroo, K. Nasir and S. Murad (2015). "Indoleamine 2,3-dioxygenase expression and activity in patients with hepatitis C virus-induced liver cirrhosis." *Exp Ther Med* 9(3): 901-904.

Balachandran, V. P., M. J. Cavnar, S. Zeng, Z. M. Bamboat, L. M. Ocuin, H. Obaid, E. C. Sorenson, R. Popow, C. Ariyan, F. Rossi, P. Besmer, T. Guo, C. R. Antonescu, T. Taguchi, J. Yuan, J. D. Wolchok, J. P. Allison and R. P. Dematteo (2011). "Imatinib potentiates antitumor T cell responses in gastrointestinal stromal tumor through the inhibition of Ido." *Nature Medicine* 17(9): 1094-1100.

Beatty, G. L., P. J. O'Dwyer, J. Clark, J. G. Shi, R. C. Newton, R. Schaub, J. Maleski, L. Leopold and T. Gajewski (2013). "Phase I study of the safety, pharmacokinetics (PK), and pharmacodynamics (PD) of the oral inhibitor of indoleamine 2,3-dioxygenase (IDO1) INCB024360 in patients (pts) with advanced malignancies." *ASCO Meeting Abstracts* 31(15_suppl): 3025.

Boasso, A., A. W. Hardy, S. A. Anderson, M. J. Dolan and G. M. Shearer (2008). "HIV-induced type I interferon and tryptophan catabolism drive T cell dysfunction despite phenotypic activation." *PLoS One* 3(8): e2961.

Boasso, A., J. P. Herbeuval, A. W. Hardy, S. A. Anderson, M. J. Dolan, D. Fuchs and G. M. Shearer (2007). "HIV inhibits CD4+ T-cell proliferation by inducing indoleamine 2,3-dioxygenase in plasmacytoid dendritic cells." *Blood* 109(8): 3351-3359.

Boasso, A. and G. M. Shearer (2008). "Chronic innate immune activation as a cause of HIV-1 immunopathogenesis." *Clin Immunol* 126(3): 235-242.

Boasso, A., M. Vaccari, A. Hryniewicz, D. Fuchs, J. Nacsa, V. Cecchinato, J. Andersson, G. Franchini, G. M. Shearer and C. Chougnet (2007). "Regulatory T-cell markers, indoleamine 2,3-dioxygenase, and virus levels in spleen and gut during progressive simian immunodeficiency virus infection." *J Virol* 81(21): 11593-11603.

Byakwaga, H., Y. Boum, 2nd, Y. Huang, C. Muzoora, A. Kembabazi, S. D. Weiser, J. Bennett, H. Cao, J. E. Haberer, S. G. Deeks, D. R. Bangsberg, J. M. McCune, J. N. Martin and P. W. Hunt (2014). "The kynurenine pathway of tryptophan catabolism, CD4+ T-cell recovery, and mortality among HIV-infected Ugandans initiating antiretroviral therapy." *J Infect Dis* 210(3): 383-391.

Chen, Y. B., S. D. Li, Y. P. He, X. J. Shi, Y. Chen and J. P. Gong (2009). "Immunosuppressive effect of IDO on T cells in patients with chronic hepatitis B*." *Hepatol Res* 39(5): 463-468.

Darcy, C. J., J. S. Davis, T. Woodberry, Y. R. McNeil, D. P. Stephens, T. W. Yeo and N. M. Anstey (2011). "An observational cohort study of the kynurenine to tryptophan ratio in sepsis: association with impaired immune and microvascular function." *PLoS One* 6(6): e21185.

Deeks, S. G. (2011). "HIV infection, inflammation, immunosenescence, and aging." *Annu Rev Med* 62: 141-155.

Favre, D., S. Lederer, B. Kanwar, Z. M. Ma, S. Proll, Z. Kasakow, J. Mold, L. Swainson, J. D. Barbour, C. R. Baskin, R. Palermo, I. Pandrea, C. J. Miller, M. G. Katze and J. M. McCune (2009). "Critical loss of the balance between Th17 and T regulatory cell populations in pathogenic SIV infection." *PLoS Pathog* 5(2): e1000295.

Favre, D., J. Mold, P. W. Hunt, B. Kanwar, P. Loke, L. Seu, J. D. Barbour, M. M. Lowe, A. Jayawardene, F. Aweeka, Y. Huang, D. C. Douek, J. M. Brenchley, J. N. Martin, F. M. Hecht, S. G. Deeks and J. M. McCune (2010). "Tryptophan catabolism by indoleamine 2,3-dioxygenase 1 alters the balance of TH17 to regulatory T cells in HIV disease." *Sci Transl Med* 2(32): 32ra36.

Frumento, G., R. Rotondo, M. Tonetti, G. Damonte, U. Benatti and G. B. Ferrara (2002). "Tryptophan-derived catabolites are responsible for inhibition of T and natural killer cell proliferation induced by indoleamine 2,3-dioxygenase." *J Exp Med* 196(4): 459-468.

Gangadhar, T., O. Hamid, D. Smith, T. Bauer, J. Wasser, J. Luke, A. Balmanoukian, D. Kaufman, Y. Zhao, J. Maleski, L. Leopold and T. Gajewski (2015). "Preliminary results from a Phase I/II study of epacadostat (incb024360) in combination with pembrolizumab in patients with selected advanced cancers." *Journal for ImmunoTherapy of Cancer* 3(Suppl 2): O7.

Holmgaard, R. B., D. Zamarin, Y. Li, B. Gasmi, D. H. Munn, J. P. Allison, T. Merghoub and J. D. Wolchok (2015). "Tumor-Expressed IDO Recruits and Activates MDSCs in a Treg-Dependent Manner." *Cell Reports* 13(2): 412-424.

Holmgaard, R. B., D. Zamarin, D. H. Munn, J. D. Wolchok and J. P. Allison (2013). "Indoleamine 2,3-dioxygenase is a critical resistance mechanism in antitumor T cell immunotherapy targeting CTLA-4." *Journal of Experimental Medicine* 210(7): 1389-1402.

Hoshi, M., Y. Osawa, H. Ito, H. Ohtaki, T. Ando, M. Takamatsu, A. Hara, K. Saito and M. Seishima (2014). "Blockade of indoleamine 2,3-dioxygenase reduces mortality from peritonitis and sepsis in mice by regulating functions of CD11b+ peritoneal cells." *Infect Immun* 82(11): 4487-4495.

Hotchkiss, R. S., G. Monneret and D. Payen (2013). "Sepsis-induced immunosuppression: from cellular dysfunctions to immunotherapy." *Nat Rev Immunol* 13(12): 862-874.

Hunt, P. W., E. Sinclair, B. Rodriguez, C. Shive, B. Clagett, N. Funderburg, J. Robinson, Y. Huang, L. Epling, J. N. Martin, S. G. Deeks, C. L. Meinert, M. L. Van Natta, D. A. Jabs and M. M. Lederman (2014). "Gut epithelial barrier dysfunction and innate immune activation predict mortality in treated HIV infection." *J Infect Dis* 210(8): 1228-1238.

Ito, H., T. Ando, K. Ando, T. Ishikawa, K. Saito, H. Moriwaki and M. Seishima (2014). "Induction of hepatitis B virus surface antigen-specific cytotoxic T lymphocytes can be up-regulated by the inhibition of indoleamine 2, 3-dioxygenase activity." *Immunology* 142(4): 614-623.

Jung, I. D., M. G. Lee, J. H. Chang, J. S. Lee, Y. I. Jeong, C. M. Lee, W. S. Park, J. Han, S. K. Seo, S. Y. Lee and Y. M. Park (2009). "Blockade of indoleamine 2,3-dioxygenase protects mice against lipopolysaccharide-induced endotoxin shock." *J Immunol* 182(5): 3146-3154.

Larrea, E., J. I. Riezu-Boj, L. Gil-Guerrero, N. Casares, R. Aldabe, P. Sarobe, M. P. Civeira, J. L. Heeney, C. Rollier, B. Verstrepen, T. Wakita, F. Borras-Cuesta, J. J. Lasarte and J. Prieto (2007). "Upregulation of indoleamine 2,3-dioxygenase in hepatitis C virus infection." *J Virol* 81 (7): 3662-3666.

Lepiller, Q., E. Soulier, Q. Li, M. Lambotin, J. Berths, D. Fuchs, F. Stoll-Keller, T. J. Liang and H. Barth (2015). "Antiviral and Immunoregulatory Effects of Indoleamine-2,3-Dioxygenase in Hepatitis C Virus Infection." J Innate Immun 7(5): 530-544.

Li, L., L. Huang, H. P. Lemos, M. Mautino and A. L. Mellor (2012). "Altered tryptophan metabolism as a paradigm for good and bad aspects of immune privilege in chronic inflammatory diseases." Front Immunol 3: 109.

Liu, X., N. Shin, H. K. Koblish, G. Yang, Q. Wang, K. Wang, L. Leffet, M. J. Hansbury, B. Thomas, M. Rupar, P. Waeltz, K. J. Bowman, P. Polam, R. B. Sparks, E. W. Yue, Y. Li, R. Wynn, J. S. Fridman, T. C. Burn, A. P. Combs, R. C. Newton and P. A. Scherle (2010). "Selective inhibition of IDO1 effectively regulates mediators of antitumor immunity." *Blood* 115(17): 3520-3530.

Loughman, J. A. and D. A. Hunstad (2012). "Induction of indoleamine 2,3-dioxygenase by uropathogenic bacteria attenuates innate responses to epithelial infection." *J Infect Dis* 205(12): 1830-1839.

Lovelace, M. D., B. Varney, G. Sundaram, M. J. Lennon, C. K. Lim, K. Jacobs, G. J. Guillemin and B. J. Brew (2016). "Recent evidence for an expanded role of the kynurenine pathway of tryptophan metabolism in neurological diseases." *Neuropharmacology*.

M. Mautino, C. J. L., N. Vahanian, J. Adams, C. Van Allen, M. D. Sharma, T. S. Johnson and D. H. Munn (2014). "Synergistic antitumor effects of combinatorial immune checkpoint inhibition with anti-PD-1/PD-L antibodies and the IDO pathway inhibitors NLG919 and indoximod in the context of active immunotherapy." April 2014 *AACR Meeting Poster* #5023.

Mattapallil, J. J., D. C. Douek, B. Hill, Y. Nishimura, M. Martin and M. Roederer (2005). "Massive infection and loss of memory CD4+ T cells in multiple tissues during acute SIV infection." *Nature* 434(7037): 1093-1097.

Mellor, A. L. and D. H. Munn (2004). "IDO expression by dendritic cells: Tolerance and tryptophan catabolism." *Nature Reviews Immunology* 4(10): 762-774.

Munn, D. H. (2011). "Indoleamine 2,3-dioxygenase, Tregs and cancer." *Current Medicinal Chemistry* 18(15): 2240-2246.

Munn, D. H., E. Shafizadeh, J. T. Attwood, I. Bondarev, A. Pashine and A. L. Mellor (1999). "Inhibition of T cell proliferation by macrophage tryptophan catabolism." *J Exp Med* 189(9): 1363-1372.

Pilotte, L., P. Larrieu, V. Stroobant, D. Colau, E. Dolušić, R. Frédérick, E. De Plaen, C. Uyttenhove, J. Wouters, B. Masereel and B. J. Van Den Eynde (2012). "Reversal of tumoral immune resistance by inhibition of tryptophan 2,3-dioxygenase." *Proceedings of the National Academy of Sciences of the United States of America* 109(7): 2497-2502.

Sekkai, D., O. Guittet, G. Lemaire, J. P. Tenu and M. Lepoivre (1997). "Inhibition of nitric oxide synthase expression and activity in macrophages by 3-hydroxyanthranilic acid, a tryptophan metabolite." *Arch Biochem Biophys* 340(1): 117-123.

Suzuki, Y., T. Suda, K. Asada, S. Miwa, M. Suzuki, M. Fujie, K. Furuhashi, Y. Nakamura, N. Inui, T. Shirai, H. Hayakawa, H. Nakamura and K. Chida (2012). "Serum indoleamine 2,3-dioxygenase activity predicts prognosis of pulmonary tuberculosis." *Clin Vaccine Immunol* 19(3): 436-442.

Tattevin, P., D. Monnier, O. Tribut, J. Dulong, N. Bescher, F. Mourcin, F. Uhel, Y. Le Tulzo and K. Tarte (2010). "Enhanced indoleamine 2,3-dioxygenase activity in patients with severe sepsis and septic shock." *J Infect Dis* 201(6): 956-966.

Tenorio, A. R., Y. Zheng, R. J. Bosch, S. Krishnan, B. Rodriguez, P. W. Hunt, J. Plants, A. Seth, C. C. Wilson, S. G. Deeks, M. M. Lederman and A. L. Landay (2014). "Soluble markers of inflammation and coagulation but not T-cell activation predict non-AIDS-defining morbid events during suppressive antiretroviral treatment." *J Infect Dis* 210(8): 1248-1259.

Wainwright, D. A., I. V. Balyasnikova, A. L. Chang, A. U. Ahmed, K.-S. Moon, B. Auffinger, A. L. Tobias, Y. Han and M. S. Lesniak (2012). "IDO Expression in Brain Tumors Increases the Recruitment of Regulatory T Cells and Negatively Impacts Survival." *Clinical Cancer Research* 18(22): 6110-6121.

Wainwright, D. A., A. L. Chang, M. Dey, I. V. Balyasnikova, C. K. Kim, A. Tobias, Y. Cheng, J. W. Kim, J. Qiao, L. Zhang, Y. Han and M. S. Lesniak (2014). "Durable therapeutic efficacy utilizing combinatorial blockade against IDO, CTLA-4, and PD-L1 in mice with brain tumors." *Clinical Cancer Research* 20(20): 5290-5301.

Yue, E. W., B. Douty, B. Wayland, M. Bower, X. Liu, L. Leffet, Q. Wang, K. J. Bowman, M. J. Hansbury, C. Liu, M. Wei, Y. Li, R. Wynn, T. C. Burn, H. K. Koblish, J. S. Fridman, B. Metcalf, P. A. Scherle and A. P. Combs (2009). "Discovery of potent competitive inhibitors of indoleamine 2,3-dioxygenase with in vivo pharmacodynamic activity and efficacy in a mouse melanoma model." *Journal of Medicinal Chemistry* 52(23): 7364-7367.

SUMMARY OF THE INVENTION

Briefly, in one aspect, the present invention discloses compounds of Formula I

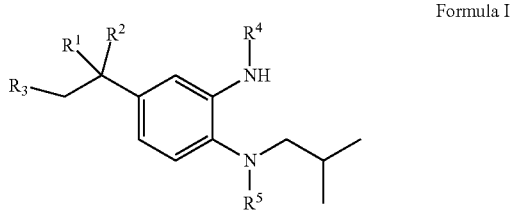

Formula I or a pharmaceutically acceptable salt thereof wherein:

$R^1$ and $R^2$ are independently H or $CH_3$, or $R^1$ and $R^2$ may join together with the carbon atom to which they are bonded to form a 3-6 membered cycloalkyl;

$R^3$ is $CO_2H$ or an acid isostere;

$R^4$ is a 4 to 6-membered heterocycle or heteroaryl containing 1 to 4 heteroatoms selected from N, S, and O, wherein said heterocycle or heteroaryl may optionally be substituted by 1 or 2 substituent selected from the group consisting of halogen, $C_3$-$C_6$cycloalkyl, $CH_2OH$, $C(O)NH_2$, CN, $CH_2OC_{1-3}$alkyl, $C_{1-3}$alkyl optionally substituted by 1-3 halogens, and wherein said $CH_2OH$ is optionally converted into a prodrug by converting the $CH_2OH$ group to a $CH_2OC(O)CH_3$, $CH_2OC(O)C(C_{1-4}alkyl)_3$, or $OP(O)$ $(OH)_2$ group, or $OP(O)(OC_{1-4}alkyl)_2$ group;

$R^5$ is a 4, 5, or 6-membered cycloalkyl substituted with an OH or a $OCH_3$ group or 1 or 2 halogens, or a 5 or 6-membered heterocycle containing an O or a N and may optionally be substituted by a substituent selected from the group consisting of halogen, OH, $C_{1-4}$alkyl; $OC_{1-3}$alkyl, $C(O)C_{3-6}$cycloalkyl, BOC, $C(O)C_{1-3}$alkyl-O—$C_{1-3}$alkyl; $C(O)C_{1-3}$alkyl; $C(O)$—O—$C_{1-3}$alkyl, and a 4 to 6-membered heterocycle or heteroaryl containing 1 to 4 heteroatoms selected from N, S, and O, wherein said heterocycle or heteroaryl may optionally be substituted by 1 substituent selected from the group consisting of halogen, $C_{3-6}$cycloalkyl, $CH_2OH$, $C(O)NH_2$, CN, $CH_2OC_{1-3}$alkyl, $C_{1-3}$alkyl optionally substituted by 1-3 halogens.

In another aspect, the present invention discloses a method for treating diseases or conditions that would benefit from inhibition of IDO.

In another aspect, the present invention discloses pharmaceutical compositions comprising a compound of Formula I or a pharmaceutically acceptable salt thereof.

In another aspect, the present invention provides a compound of Formula I or a pharaceutically acceptable salt thereof for use in therapy.

In another aspect, the present invention provides a compound of Formula I or a pharmaceutically acceptable salt thereof for use in treating diseases or condidtion that would benefit from inhibition of IDO.

In another aspect, the present invention provides a compound of Formula I or a pharmaceutically acceptable salt thereof for use in the manufacture of a medicament for use in treating diseases or conditions that would benefit from inhibition of IDO.

In another aspect, the present invention discloses a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

DISCRIPTION OF FIGURES

FIG. 1 is daily body weights of Beagle dogs during the study of example 23, 20 mg/kg PO BID dose.

FIG. 2 is daily hepatic enzyme levels of Beagle dogs during the study: ALT (alanine aminotransferase), AST (aspartate aminotransferase), ALP (alkaline phosphatase) and T-Bil (total bilirubin) for example 23, 20 mg/kg PO BID dose.

DETAILED DESCRIPTION OF REPRESENTATIVE EMBODIMENTS

Preferably one of $R^1$ and $R^2$ is H and the other is $CH_3$.

Preferably $R^3$ is CO2H.

Preferably $R^4$ is a 5 or 6-membered heterocycle or heteroaryl containing 1 to 3 heteroatoms selected from N, and S. Most preferably $R^4$ is a pyridine, thiadiazole, pyrimidine, pyrazine, pyridazine, triazol, or thiazol.

Preferably $R^4$ is unsubstituted or substituted with 1 or 2 substituent selected from the group consisting of F, Cl, CN, $OCH_3$, $CF_3$, cyclopropyl, $CONH_2$, $CH_2CH_2OCH_3$, and $CH_2OCH_3$.

Preferably $R^5$ is a 6-membered heterocycle containing an O or a N.

Preferably $R^5$ is unsubstituted or substituted on the heteroatom by a substituent selected from the group consisting of halogen, OH, $C_{1-4}$alkyl; $OC_{1-3}$alkyl, $C(O)C_{3-6}$cycloalkyl, $C(O)C_{1-3}$alkyl-O—$C_{1-3}$alkyl; $C(O)C_{1-3}$alkyl; $C(O)$—O—$C_{1-3}$alkyl, and a 4 to 6-membered heterocycle or heteroaryl containing 1 to 4 heteroatoms selected from N, S, and O, wherein said heterocycle or heteroaryl may optionally be substituted by 1 substituent selected from the group consisting of halogen, $C_{3-6}$cycloalkyl, $CH_2OH$, $C(O)NH_2$, CN, $CH_2OC_{1-3}$alkyl, $C_{1-3}$alkyl optionally substituted by 1-3 halogens. Most preferably, $R^5$ is unsubsituted or substitued on the heteroatom with OH or $OCH_3$.

Examples of suitable acid isosteres, includes for example

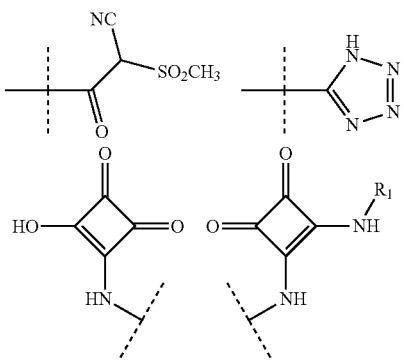

-continued

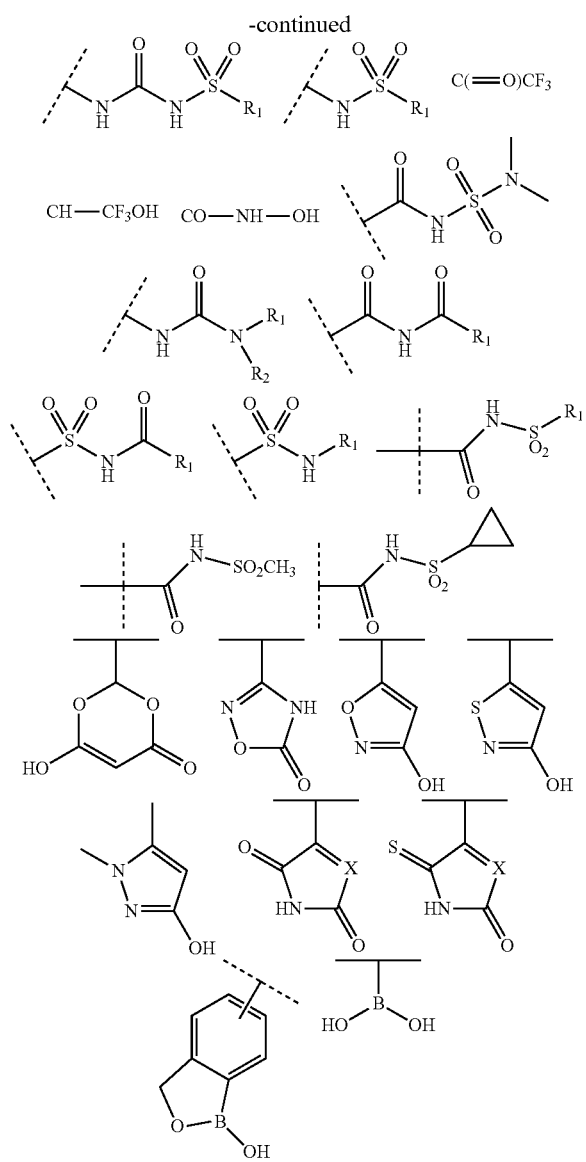

wherein $R^1$ and $R^2$ in the above list of isosters are independently $C_{1-6}$alkyl.

In particular, it is expected that the compounds and composition of this invention will be useful for prevention and/or treatment of HIV; including the prevention of the progression of AIDS and general immunosuppression. It is expected that in many cases such prevention and/or treatment will involve treating with the compounds of this invention in combination with at least one other drug thought to be useful for such prevention and/or treatment. For example, the IDO inhibitors of this invention may be used in combination with other immune therapies such as immune checkpoints (PD1, CTLA4, ICOS, etc.) and possibly in combination with growth factors or cytokine therapies (IL21, IL-7, etc.).

In is common practice in threatment of HIV to employ more than one effective agent. Therefore, in accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors. Examples of such additiona agents are Dolutegravir and Cabotegravir.

It is also common practice in the oncology field to treat with more than one effective agent. Therefore, in accordance with another embodiment of the present invention, there is provided a method for preventing or treating cancer comprising administering to a human in need thereof a therapeutically effective amount of a compound of Formula I or a pharmaceutically acceptable salt thereof further comprising administration of at least one other agent effective tor preventing or treating cancer. Such agents include, for example, anti-neoplastic agents, chemotherapeutic agents, hormonal agents, and antibody agents.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or ACN are preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In another embodiment of the invention, there is provided a pharmaceutical composition comprising a pharmaceutically acceptable diluent and a therapeutically effective amount of a compound as defined in Formula I or a pharmaceutically acceptable salt thereof.

In one embodiment, the pharmaceutical formulation containing a compound of Formula I or a salt thereof is a formulation adapted for parenteral administration. In another embodiment, the formulation is a long-acting parenteral formulation. In a further embodiment, the formulation is a nano-particle formulation.

The present invention is directed to compounds, compositions and pharmaceutical compositions that have utility as novel treatments for immunosuppresion. While not wanting to be bound by any particular theory, it is thought that the present compounds are able to inhibit the enzyme that catalyzes the oxidative pyrrole ring cleavage reaction of I-Trp to N-formylkynurenine utilizing molecular oxygen or reactive oxygen species.

Therefore, in another embodiment of the present invention, there is provided a method for the prevention and/or treatment of HIV; including the prevention of the progression of AIDS and general immunosuppression.

EXAMPLES

The following examples serve to more fully describe the manner of making and using the above-described invention. It is understood that these examples in no way serve to limit the true scope of the invention, but rather are presented for illustrative purposes. In the examples and the synthetic schemes below, the following abbreviations have the following meanings. If an abbreviation is not defined, it has its generally accepted meaning.

ACN=acetonitrile
AIBN=azobisisobutyronitrile
aq.=aqueous
μL or uL=microliters
μM or uM=micromolar
NMR=nuclear magnetic resonance
boc=tert-butoxycarbonyl
br=broad
Cbz=Benzyloxycarbonyl
CDI=1,1'-carbonyldiimidazole
d=doublet
δ=chemical shift
° C.=degrees celcius
DCM=dichloromethane
dd=doublet of doublets
DHP=dihydropyran
DIAD=diisopropyl azodicarboxylate
DIEA or DIPEA=N,N-diisopropylethylamine
DMAP=4-(dimethylamino)pyridine
DMEM=Dulbeco's Modified Eagle's Medium
EtOAc=ethyl acetate
h or hr=hours
HATU=1-[Bis(dimethylamino)methylene]-1H-1,2,3-triazolo[4,5-b]pyridinium 3-oxid hexafluorophosphate
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
LCMS=liquid chromatography-mass spectrometry
m=multiplet
M=molar
$M+H^+$=parent mass spectrum peak plus $H^+$
MeOH=methanol
mg=milligram
min=minutes
mL=milliliter
mM=millimolar
mmol=millimole
MS=mass spectrum
MTBE=methyl tert-butyl ether
N=normal
NFK=N-formylkynurenine
NBS=N-bromosuccinimide
nm=nanomolar
PE=petroleum ether
ppm=parts per million
q.s.=sufficient amount
s=singlet
RT=room temperature
Rf=retardation factor
sat.=saturated
t=triplet
TEA=triethylamine
TFA=trifluoroacetic acid
TFAA=trifluoroacetic anhydride
THF=tetrahydrofuran Equipment Description $^1$H NMR spectra were recorded on a Bruker Ascend 400 spectrometer or a Varian 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters ACQUITY UPLC with SQ Detectors using a Waters BEH C18, 2.1×50 mm, 1.7 μm using a gradient elution method.

Solvent A: 0.1% formic acid (FA) in water;
Solvent B: 0.1% FA in acetonitrile;
30% B for 0.5 min followed by 30-100% B over 2.5 min.

Example 1

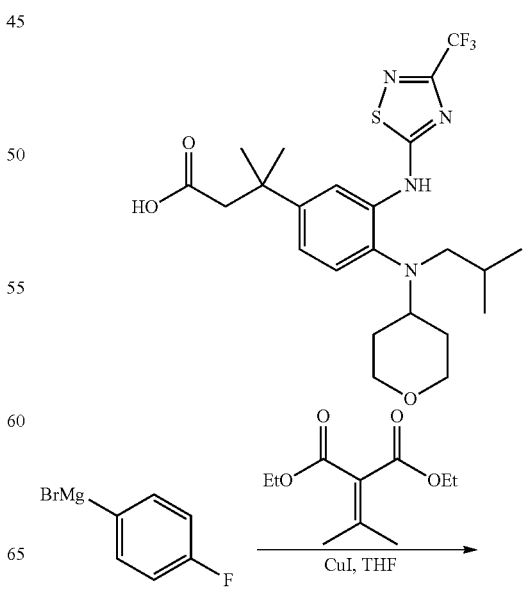

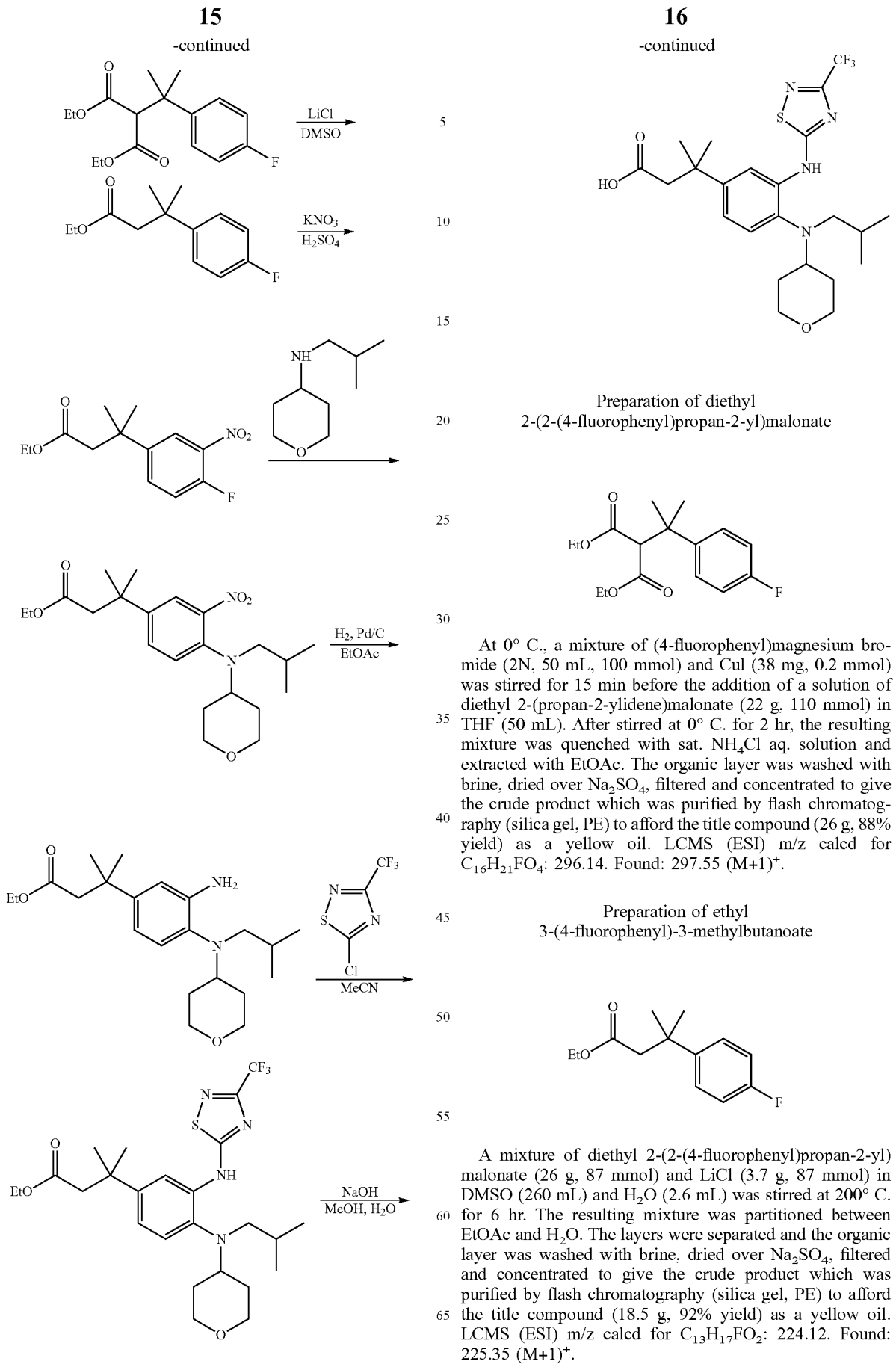

Preparation of diethyl 2-(2-(4-fluorophenyl)propan-2-yl)malonate

At 0° C., a mixture of (4-fluorophenyl)magnesium bromide (2N, 50 mL, 100 mmol) and CuI (38 mg, 0.2 mmol) was stirred for 15 min before the addition of a solution of diethyl 2-(propan-2-ylidene)malonate (22 g, 110 mmol) in THF (50 mL). After stirred at 0° C. for 2 hr, the resulting mixture was quenched with sat. NH$_4$Cl aq. solution and extracted with EtOAc. The organic layer was washed with brine, dried over Na$_2$SO$_4$, filtered and concentrated to give the crude product which was purified by flash chromatography (silica gel, PE) to afford the title compound (26 g, 88% yield) as a yellow oil. LCMS (ESI) m/z calcd for C$_{16}$H$_{21}$FO$_4$: 296.14. Found: 297.55 (M+1)$^+$.

Preparation of ethyl 3-(4-fluorophenyl)-3-methylbutanoate

A mixture of diethyl 2-(2-(4-fluorophenyl)propan-2-yl)malonate (26 g, 87 mmol) and LiCl (3.7 g, 87 mmol) in DMSO (260 mL) and H$_2$O (2.6 mL) was stirred at 200° C. for 6 hr. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, PE) to afford the title compound (18.5 g, 92% yield) as a yellow oil. LCMS (ESI) m/z calcd for C$_{13}$H$_{17}$FO$_2$: 224.12. Found: 225.35 (M+1)$^+$.

Preparation of ethyl 3-(4-fluoro-3-nitrophenyl)-3-methylbutanoate

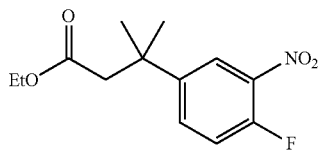 [SMILES: CCOC(=O)CC(C)(C)c1ccc(F)c([N+](=O)[O-])c1]

At 0° C., to a solution of ethyl 3-(4-fluorophenyl)-3-methylbutanoate (18.6 g, 82.3 mmol) in conc. H$_2$SO$_4$ (200 mL) was added KNO$_B$ (8.4 g, 82.3 mmol) portionwise. After stirred 0° C. for 2 hr, the resulting mixture was carefully poured into ice water and extracted with EtOAc. The organic layer was washed with brine, dried over Na$_2$SO$_4$, filtered and concentrated to give to afford the title compound (20 g, 93% yield). LCMS (ESI) m/z calcd for C$_{13}$H$_{16}$FNO$_4$: 269.11. Found: 270.44 (M+1)$^+$.

Preparation of ethyl 3-(4-(isobutyl(tetrahydro-2H-pyran-4-yl)amino)-3-nitro phenyl)-3-methylbutanoate

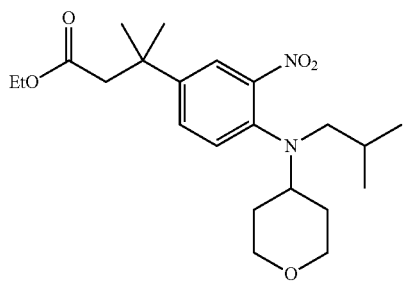 [SMILES: CCOC(=O)CC(C)(C)c1ccc(N(CC(C)C)C2CCOCC2)c([N+](=O)[O-])c1]

A mixture of ethyl 3-(4-fluoro-3-nitrophenyl)-3-methylbutanoate (5.8 g, 21.6 mmol), N-isobutyltetrahydro-2H-pyran-4-amine (10.2 g, 64.8 mmol) was stirred at 150° C. under N$_2$ atmosphere for 8 hr. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-10% EtOAc in PE) to afford the title compound (3.7 g, 42% yield). LCMS (ESI) m/z calcd for C$_{22}$H$_{34}$N$_2$O$_5$: 406.25. Found: 407.65 (M+1)$^+$.

Preparation of ethyl 3-(3-amino-4-(isobutyl(tetrahydro-2H-pyran-4-yl)amino) phenyl)-3-methylbutanoate

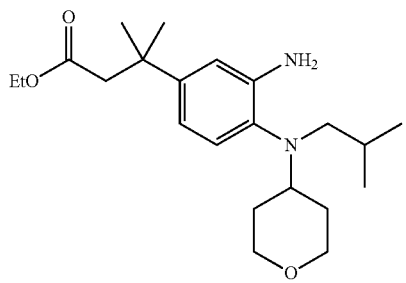

A mixture of ethyl 3-(4-(isobutyl(tetrahydro-2H-pyran-4-yl)amino)-3-nitrophenyl)-3-methylbutanoate (3.7 g, 9.1 mmol) and 10% Pd/C (1.3 g) in EtOAc (50 mL) was purged with H$_2$ and stirred at r.t. overnight. The resulting mixture was filtered through a pad of Celite and the filtrate was concentrated under reduced pressure to give the crude product which was purified by flash chromatography (silica gel, 0-20% EtOAc in PE) to afford the title compound (3.1 g, 90% yield). LCMS (ESI) m/z calcd for C$_{22}$H$_{36}$N$_2$O$_3$: 376.27. Found: 377.67 (M+1)$^+$.

Preparation of ethyl 3-(4-(isobutyl(tetrahydro-2H-pyran-4-yl)amino)-3-((3-(trifluoromethyl)-1,2,4-thiadiazol-5-yl)amino)phenyl)-3-methylbutanoate

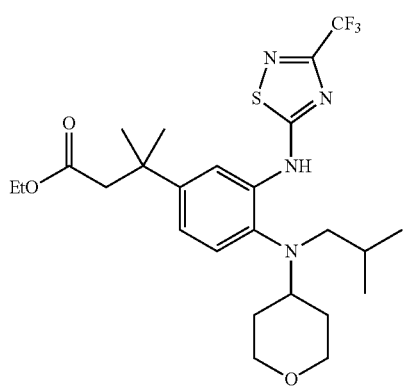 [SMILES: CC(C)CN(c1ccc(C(C)(C)CC(=O)O)cc1Nc1nc(C(F)(F)F)ns1)C1CCOCC1]

A mixture of ethyl 3-(3-amino-4-(isobutyl(tetrahydro-2H-pyran-4-yl)amino)phenyl)-3-methylbutanoate (100 mg, 0.27 mmol) and 5-chloro-3-(trifluoromethyl)-1,2,4-thia diazole (77 mg, 0.41 mmol) in MeCN (2 mL) was stirred at 100° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (70 mg, 48% yield). LCMS (ESI) m/z calcd for C$_{25}$H$_{35}$F$_3$N$_4$O$_3$S: 528.24. Found: 529.23 (M+1)$^+$.

Preparation of 3-(4-(isobutyl(tetrahydro-2H-pyran-4-yl)amino)-3-((3-(trifluoro methyl)-1,2,4-thiadiazol-5-yl)amino)phenyl)-3-methylbutanoic Acid

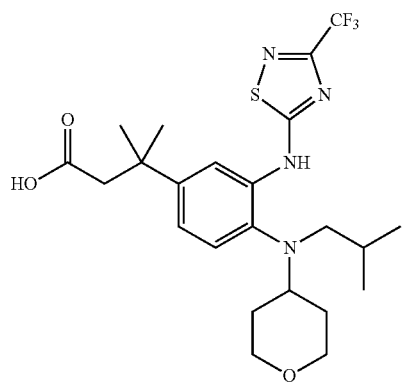

To a solution of ethyl 3-(4-(isobutyl(tetrahydro-2H-pyran-4-yl)amino)-3-((3-(trifluoro methyl)-1,2,4-thiadiazol- 5-yl)amino)phenyl)-3-methylbutanoate (70 mg, 0.13 mmol) in MeOH (3 mL) was added 4N NaOH aq. (0.5 mL). After stirred at r.t. overnight, the resulting mixture was acidified with 4N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (37 mg, 56% yield) as a white powder. $^1$H NMR (400 MHz, DMSO) δ 11.71 (br, 1H), 10.38 (s, 1H), 8.25 (s, 1H), 7.29-7.09 (m, 2H), 3.89-3.78 (m, 2H), 3.18-3.11 (m, 2H), 2.93-2.86 (m, 1H), 2.83-2.75 (m, 2H), 2.54 (s, 2H), 1.71-1.62 (m, 2H), 1.57-1.25 (m, 9H), 0.79 (d, J=6.6 Hz, 6H). LCMS (ESI) m/z calcd for C$_{23}$H$_{31}$F$_3$N$_4$O$_3$S: 500.21. Found: 501.63 (M+1)$^+$.

Example 2

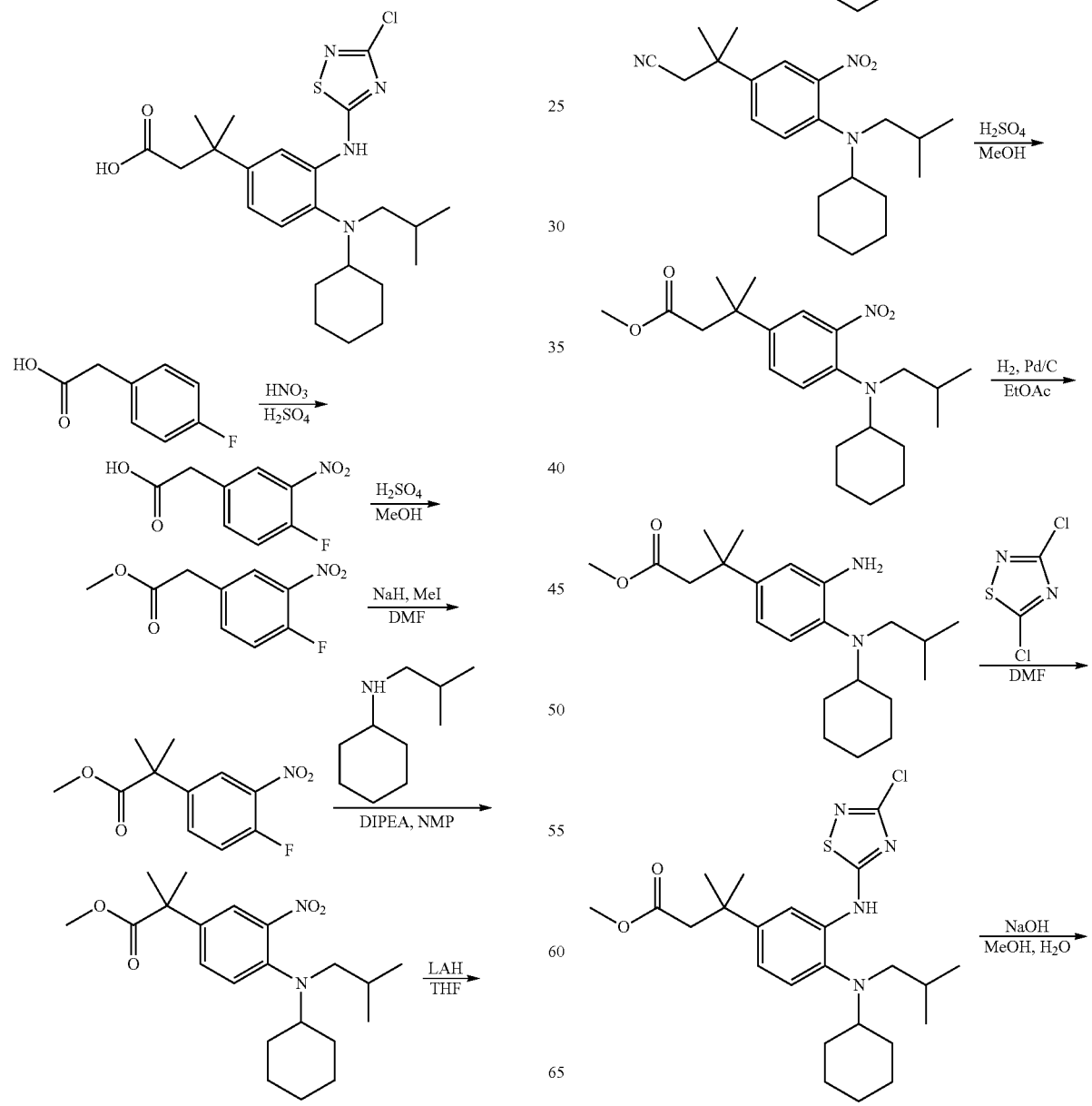

-continued

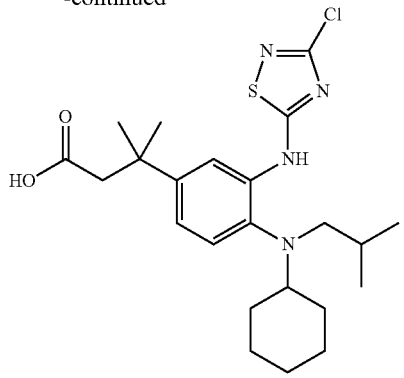

Preparation of 2-(4-fluoro-3-nitrophenyl)acetic Acid

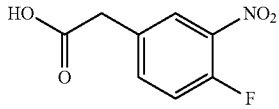 [SMILES: O=C(O)Cc1ccc(F)c([N+](=O)[O-])c1]

At 0° C., to a solution of 2-(4-fluorophenyl)acetic acid (30 g, 0.19 mol) in conc. $H_2SO_4$ (250 mL) was added $KNO_3$ (19.6 g, 0.19 mmol) portionwise. After stirred at 0° C. for 1 hr, the resulting mixture was slowly poured into ice water. The precipitated solid was filtered and dried to give the title compound (28.8 g, 74% yield) as a yellow solid. LCMS (ESI) m/z calcd for $C_8H_6FNO_4$: 199.03. Found: 200.22 $(M+1)^+$.

Preparation of methyl 2-(4-fluoro-3-nitrophenyl)acetate

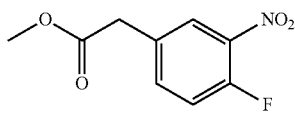

A mixture of 2-(4-fluoro-3-nitrophenyl)acetic acid (28.8 g, 0.14 mmol) and conc. $H_2SO_4$ (10 mL) in MeOH (30 mL) was stirred at 80° C. overnight. The resulting mixture was quenched with ice water and extracted with EtOAc. The organic layer was washed with sat. $NaHCO_3$ aq. solution and brine, dried over $Na_2SO_4$, filtered and concentrated to give the title compound (30 g, 97% yield) as a yellow oil. LCMS (ESI) m/z calcd for $C_9H_8FNO_4$: 213.04. Found: 214.26 $(M+1)^+$.

Preparation of methyl 2-(4-fluoro-3-nitrophenyl)-2-methylpropanoate

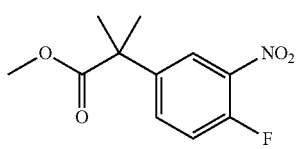 [SMILES: COC(=O)C(C)(C)c1ccc(F)c([N+](=O)[O-])c1]

At 0° C., to a solution of methyl 2-(4-fluoro-3-nitrophenyl)acetate (1.0 g, 4.69 mmol) in DMF (25 mL) was added NaH (60%, 282 mg, 11.73 mmol). The mixture was stirred at 0° C. for 30 min before the addition of MeI (0.73 mL, 11.73 mmol). After stirred at r.t. overnight, the resulting mixture was quenched with sat. $NH_4Cl$ aq. solution and extracted with EtOAc. The organic layer was washed with sat. $NaHCO_3$ aq. solution and brine, dried over $Na_2SO_4$, filtered and concentrated to give the crude product which was purified by flash chromatography (silica gel, 0-10% EtOAc in PE) to afford the title compound (800 mg, 71% yield) as a yellow oil. LCMS (ESI) m/z calcd for $C_{11}H_{12}FNO_4$: 241.08. Found: 242.23 $(M+1)^+$.

Preparation of methyl 2-(4-(cyclohexyl(isobutyl)amino)-3-nitrophenyl)-2-methyl propanoate

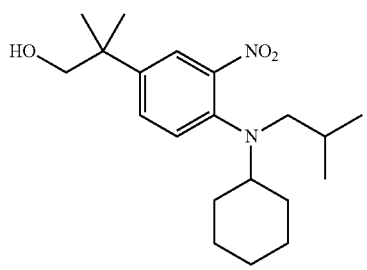

A mixture of methyl 2-(4-fluoro-3-nitrophenyl)-2-methylpropanoate (1.0 g, 4.15 mmol), N-isobutylcyclohexanamine (1.3 g, 8.30 mmol) was stirred at 160° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-5% EtOAc in PE) to afford the title compound (1.5 g, 96% yield). LCMS (ESI) m/z calcd for $C_{21}H_{32}N_2O_4$: 376.24. Found: 377.51 $(M+1)^+$.

Preparation of 2-(4-(cyclohexyl(isobutyl)amino)-3-nitrophenyl)-2-methylpropan-1-ol At 0° C., to a solution of methyl 2-(4-(cyclohexyl(isobutyl)amino)-3-nitrophenyl)-2-methyl propanoate (15 g, 40 mmol) in THF (150 mL) was slowly added $LiAlH_4$ (1.5 g, 40 mmol). After stirred at 0° C. for 30 min, the resulting mixture was quenched with $H_2O$ (1.5 mL), 15% NaOH aq. solution (3 mL) and kept stirring for 30 min before filtration. The filtrate was concentrated under reduced pressure to give the crude product which was purified by flash chromatography (silica gel, 0-20% EtOAc in PE) to afford the title compound (8.1 g, 58% yield) as a brown oil. LCMS (ESI) m/z calcd for $C_{20}H_{32}N_2O_3$: 348.24. Found: 393.21 (M+HCOOH-1).

Preparation of 2-(4-(cyclohexyl(isobutyl)amino)-3-nitrophenyl)-2-methylpropyl methanesulfonate

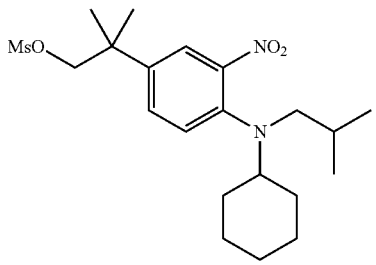 [SMILES: CC(C)CN(c1ccc(C(C)(C)COS(C)(=O)=O)cc1[N+](=O)[O-])C1CCCCC1]

At 0° C., to a solution of 2-(4-(cyclohexyl(isobutyl) amino)-3-nitrophenyl)-2-methylpropan-1-ol (3 g, 8.6 mmol) and TEA (1.4 mL, 10.3 mmol) in DCM (30 mL) was added MsCl (0.8 mL, 10.3 mmol). After stirred at 0° C. for 30 min, the resulting mixture was quenched with $H_2O$. The layers were separated and the organic layer was washed with brine, dried over $Na_2SO_4$, filtered and concentrated to give the title compound (3.7 g, crude product, quant. yield) as a yellow oil which was used in the next step without further purification. LCMS (ESI) m/z calcd for $C_{21}H_{34}N_2O_5S$: 426.22. Found: 427.49 (M+1)$^+$.

Preparation of 3-(4-(cyclohexyl(isobutyl)amino)-3-nitrophenyl)-3-methylbutane nitrile

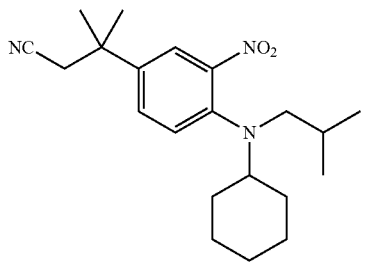 [SMILES: CC(C)CN(c1ccc(C(C)(C)CC#N)cc1[N+](=O)[O-])C1CCCCC1]

A mixture of 2-(4-(cyclohexyl(isobutyl)amino)-3-nitrophenyl)-2-methylpropylmethane sulfonate (3.2 g, 7.5 mmol) and NaCN (1.1 g, 22.5 mmol) in DMSO (20 mL) was stirred at 100° C. overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-10% EtOAc in PE) to afford the title compound (270 mg, 10% yield) as a white solid. LCMS (ESI) m/z calcd for $C_{21}H_{31}N_3O_2$: 357.24. Found: 358.52 (M+1)$^+$.

Preparation of methyl 3-(4-(cyclohexyl(isobutyl)amino)-3-nitrophenyl)-3-methyl butanoate

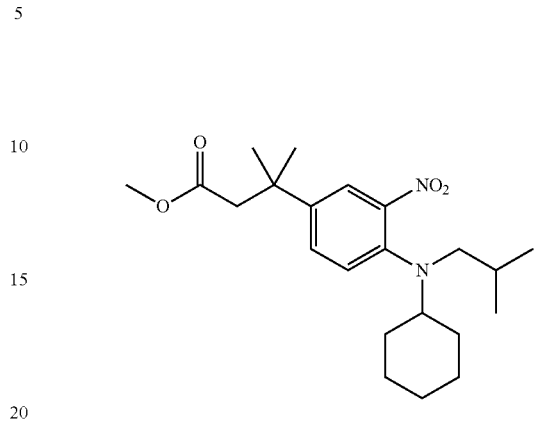

A mixture of 3-(4-(cyclohexyl(isobutyl)amino)-3-nitrophenyl)-3-methylbutanenitrile (270 mg, 0.76 mmol) and conc. $H_2SO_4$ (1.5 g, 15.1 mmol) in MeOH (10 mL) and $H_2O$ (2 mL) was stirred at 80° C. under $N_2$ atmosphere overnight. The resulting mixture was diluted with $H_2O$ and extracted with EtOAc. The organic layer was washed with brine, dried over $Na_2SO_4$, filtered and concentrated to give the crude product which was purified by flash chromatography (silica gel, 0-10% EtOAc in PE) to afford the title compound (100 mg, 34% yield) as a white solid. LCMS (ESI) m/z calcd for $C_{22}H_{34}N_2O_4$: 390.25. Found: 391.46 (M+1)$^+$.

Preparation of methyl 3-(3-amino-4-(cyclohexyl (isobutyl)amino)phenyl)-3-methylbutanoate

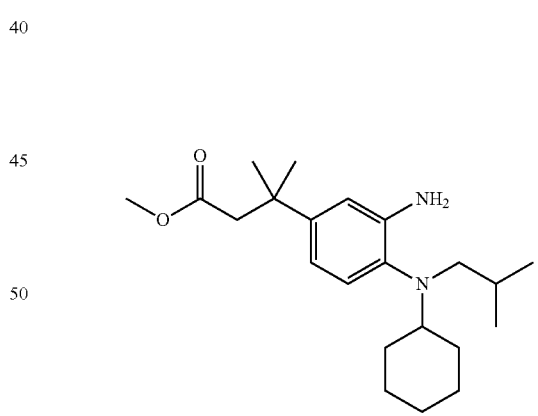

A mixture of methyl 3-(4-(cyclohexyl(isobutyl)amino)-3-nitrophenyl)-3-methyl butanoate (100 mg, 0.26 mmol) and 10% Pd/C (30 mg) in EtOAc (10 mL) was purged with $H_2$ and stirred at 50° C. for 5 hr. The resulting mixture was filtered through a pad of Celite and the filtrate was concentrated under reduced pressure to give the title compound (crude, quant. yield) which was used in the next step without further purification. LCMS (ESI) m/z calcd for $C_{22}H_{36}N_2O_2$: 360.28. Found: 361.71 (M+1)$^+$.

Preparation of methyl 3-(3-((3-chloro-1,2,4-thiadiazol-5-yl)amino)-4-(cyclohexyl (isobutyl)amino)phenyl)-3-methylbutanoate

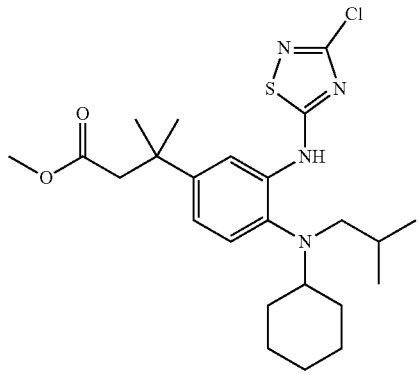 [SMILES: COC(=O)CC(C)(C)c1ccc(N(CC(C)C)C2CCCCC2)c(Nc2nc(Cl)ns2)c1]

A mixture of methyl 3-(3-amino-4-(cyclohexyl(isobutyl)amino)phenyl)-3-methylbutan oate (100 mg, 0.28 mmol) and 3,5-dichloro-1,2,4-thiadiazole (52 mg, 0.33 mmol) in DMF (5 mL) was stirred at 90° C. for 6 hr. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (48 mg, 36% yield). LCMS (ESI) m/z calcd for C$_{24}$H$_{35}$ClN$_4$O$_2$S: 478.22. Found: 479.64/481.34 (M/M+2)$^+$.

Preparation of 3-(3-((3-chloro-1,2,4-thiadiazol-5-yl)amino)-4-(cyclohexyl(isobutyl) amino)phenyl)-3-methylbutanoic Acid

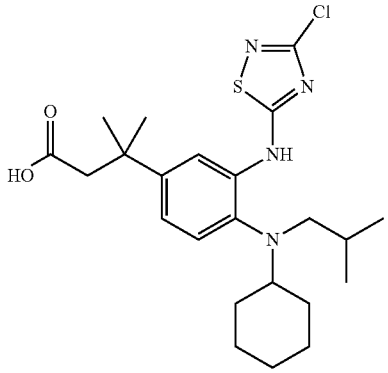 [SMILES: CC(C)CN(c1ccc(C(C)(C)CC(=O)O)cc1Nc1nc(Cl)ns1)C1CCCCC1]

To a solution of methyl 3-(3-((3-chloro-1,2,4-thiadiazol-5-yl)amino)-4-(cyclohexyl (isobutyl)amino)phenyl)-3-methylbutanoate (48 mg, 0.10 mmol) in MeOH (3 mL) was added 4N NaOH aq. (0.5 mL, 2 mmol). After stirred at 50° C. for 4 hr, the resulting mixture was acidified with 4N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (5.1 mg, 11% yield) as a white powder. $^1$H NMR (400 MHz, CDCl$_3$) δ 9.33 (s, 1H), 7.29-7.26 (m, 1H), 7.19 (d, J=8.4 Hz, 1H), 7.08 (dd, J=8.4, 2.1 Hz, 1H), 2.80 (d, J=6.9 Hz, 2H), 2.66 (s, 2H), 2.56-2.49 (m, 1H), 1.92-1.82 (m, 2H), 1.77-1.68 (m, 2H), 1.61-1.55 (m, 1H), 1.50 (s, 6H), 1.39-1.05 (m, 7H), 0.83 (d, J=6.6 Hz, 6H). LCMS (ESI) m/z calcd for C$_{23}$H$_{33}$ClN$_4$O$_2$S: 464.20. Found: 465.61/467.43 (M/M+2)$^+$.

Example 3

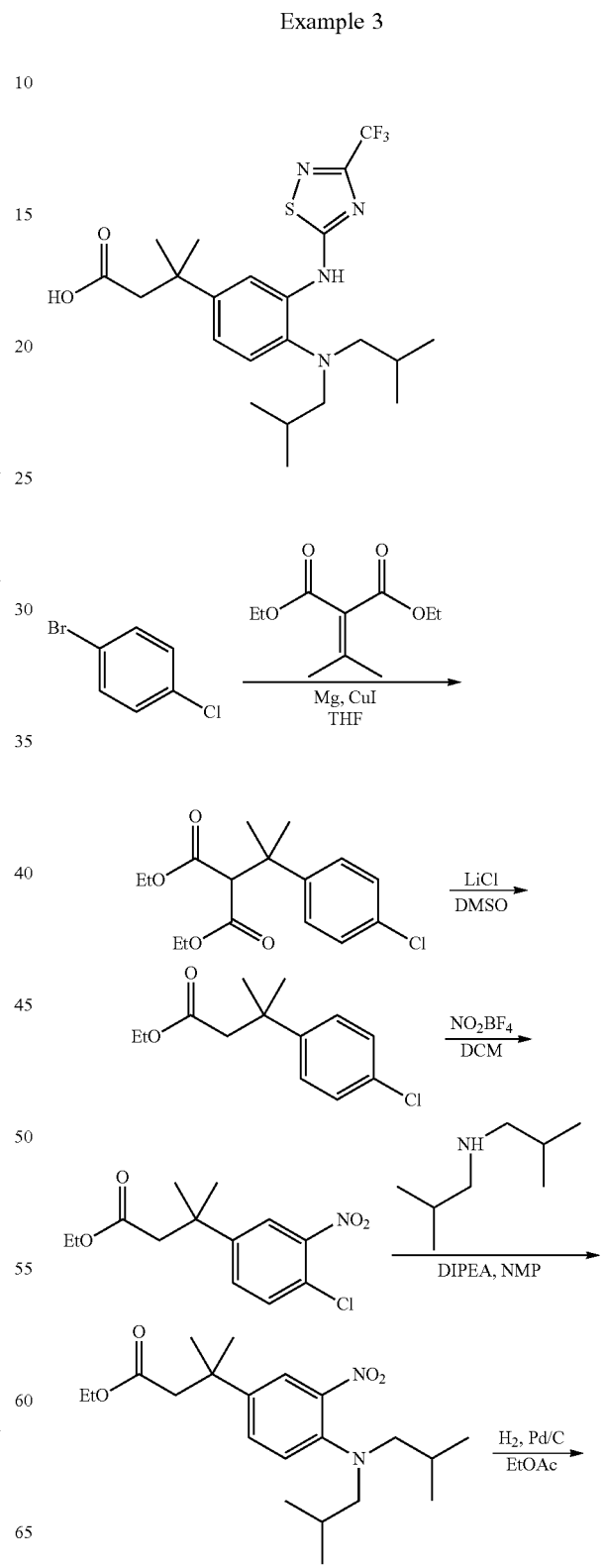

-continued

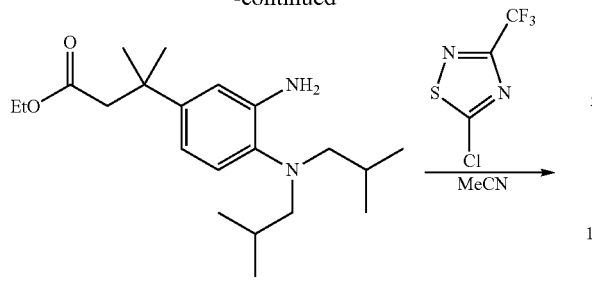
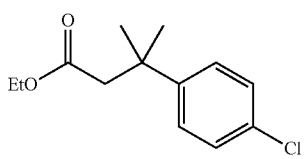 [SMILES: CCOC(=O)CC(C)(C)c1ccc(Cl)cc1]

MeCN

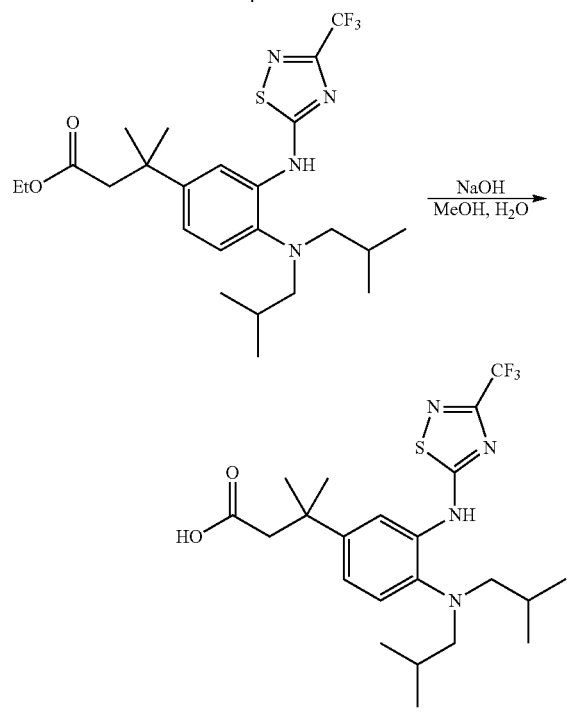

Preparation of diethyl
2-(2-(4-chlorophenyl)propan-2-yl)malonate

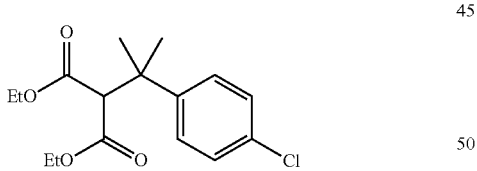

To a suspension of Mg powder (254 mg, 10.5 mmol) in Et$_2$O (5 mL) was slowly added a solution of 1-bromo-4-chlorobenzene (2 g, 10.5 mmol) in ether (5 mL). After stirred at r.t. for 30 min, CuI (103 mg, 1.1 mmol) was introduced and the resulting mixture was cooled down to −10° C. before the addition of diethyl 2-(propan-2-ylidene)malonate (2.1 g, 10.5 mmol). After stirred under refluxing temperature for 3 hr, the reaction was quenched with 1N HCl aq. solution (20 mL) and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (1.7 g, 52% yield). LCMS (ESI) m/z calcd for C$_{16}$H$_{21}$ClO$_4$: 312.11. Found: 313.25/315.25 (M/M+2)$^+$.

Preparation of ethyl
3-(4-chlorophenyl)-3-methylbutanoate

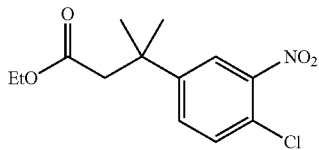

A mixture of diethyl 2-(2-(4-chlorophenyl)propan-2-yl)malonate (8.0 g, 25.6 mmol) and LiCl (2.16 g, 51.1 mmol) in DMSO (48 mL) and H$_2$O (0.5 mL) was stirred at 200° C. under N$_2$ atmosphere for 4 hr. After cooled down to r.t., the resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (5.5 g, 89% yield). LCMS (ESI) m/z calcd for C$_{13}$H$_{17}$ClO$_2$: 240.09. Found: 241.22/243.21 (M/M+2)$^+$.

Preparation of ethyl
3-(4-chloro-3-nitrophenyl)-3-methylbutanoate

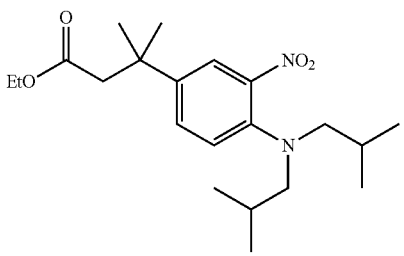 [SMILES: CCOC(=O)CC(C)(C)c1ccc(N(CC(C)C)CC(C)C)c([N+](=O)[O-])c1]

At 0° C., to a solution of ethyl 3-(4-chlorophenyl)-3-methylbutanoate (255 mg, 1.06 mmol) in DCM (10 mL) was added NO$_2$BF$_4$ (174 mg, 1.31 mmol). After stirred at 0° C. for 4 hr, the resulting mixture was partitioned between DCM and H$_2$O. The layers were separated and the organic layer was washed with brine, dried over Na$_2$SO$_4$, filtered and concentrated to give the title compound (272 mg, 90% yield). LCMS (ESI) m/z calcd for C$_{13}$H$_{16}$ClNO$_4$: 285.08. Found: 286.22/288.22 (M/M+2)$^+$.

Preparation of ethyl 3-(4-(diisobutylamino)-3-nitrophenyl)-3-methylbutanoate

A mixture of ethyl 3-(4-chloro-3-nitrophenyl)-3-methylbutanoate (100 mg, 0.35 mmol), diisobutylamine (0.18 mL, 1.05 mmol) and DIPEA (0.31 mL, 1.75 mmol) in NMP (2 mL) was stirred at 160° C. under N$_2$ atmosphere for 16 hr. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-10% EtOAc in PE) to afford the title compound (59 mg, 44% yield). LCMS (ESI) m/z calcd for $C_{21}H_{34}N_2O_4$: 378.25. Found: 379.45 (M+1)⁺.

Preparation of ethyl 3-(3-amino-4-(diisobutylamino) phenyl)-3-methylbutanoate

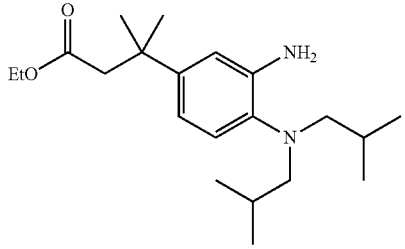 [SMILES: CCOC(=O)CC(C)(C)c1ccc(N(CC(C)C)CC(C)C)c(N)c1]

A mixture of ethyl 3-(4-(diisobutylamino)-3-nitrophenyl)-3-methylbutanoate (200 mg, 0.53 mmol) and 10% Pd/C (100 mg) in EtOAc (10 mL) was purged with H₂ and stirred at 50° C. for 3 hr. The resulting mixture was filtered through a pad of Celite and the filtrate was concentrated under reduced pressure to give the title compound (170 mg, 92% yield). LCMS (ESI) m/z calcd for $C_{21}H_{36}N_2O_2$: 348.28. Found: 349.36 (M+1)⁺.

Preparation of ethyl 3-(4-(diisobutylamino)-3-((3-(trifluoromethyl)-1,2,4-thiadiazol-5-yl)amino)phenyl)-3-methylbutanoate

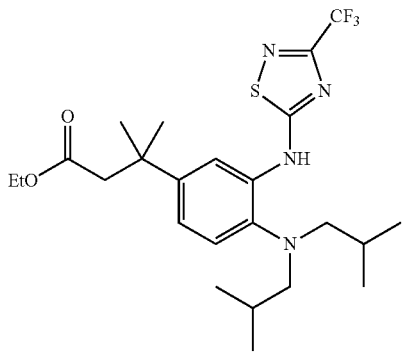

A mixture of ethyl 3-(3-amino-4-(diisobutylamino)phenyl)-3-methylbutanoate (170 mg, 0.49 mmol) and 5-chloro-3-(trifluoromethyl)-1,2,4-thiadiazole (140 mg, 0.74 mmol) in MeCN (2 mL) was stirred at 90° C. under N₂ atmosphere overnight. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-10% EtOAc in PE) to afford the title compound (123 mg, 50% yield). LCMS (ESI) m/z calcd for $C_{24}H_{35}F_3N_4O_2S$: 500.24. Found: 501.47 (M+1)⁺.

Preparation of 3-(4-(diisobutylamino)-3-((3-(trifluoromethyl)-1,2,4-thiadiazol-5-yl) amino)phenyl)-3-methylbutanoic Acid

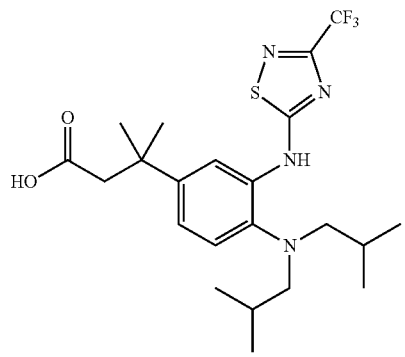 [SMILES: CC(C)CN(CC(C)C)c1ccc(C(C)(C)CC(=O)O)cc1Nc1nc(C(F)(F)F)ns1]

A solution of ethyl 3-(4-(diisobutylamino)-3-((3-(trifluoromethyl)-1,2,4-thiadiazol-5-yl) amino)phenyl)-3-methylbutanoate (123 mg, 0.25 mmol) in EtOH (5 mL) and 1N NaOH aq. solution (3 mL) was stirred at 50° C. for 1 hr. The resulting mixture was neutralized with 1N HCl aq. solution and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (67 mg, 57% yield) as a white powder. ¹H NMR (400 MHz, CDCl₃) δ 9.38 (br, 1H), 7.56 (d, J=1.0 Hz, 1H), 7.14 (d, J=8.4 Hz, 1H), 7.05 (dd, J=8.4, 2.1 Hz, 1H), 2.61 (s, 2H), 2.54 (d, J=7.2 Hz, 4H), 1.68-1.56 (m, 3H), 1.43 (s, 6H), 0.84 (d, J=6.6 Hz, 12H). LCMS (ESI) m/z calcd for $C_{22}H_{31}F_3N_4O_2S$: 472.21. Found: 473.44 (M+1)⁺.

Example 4

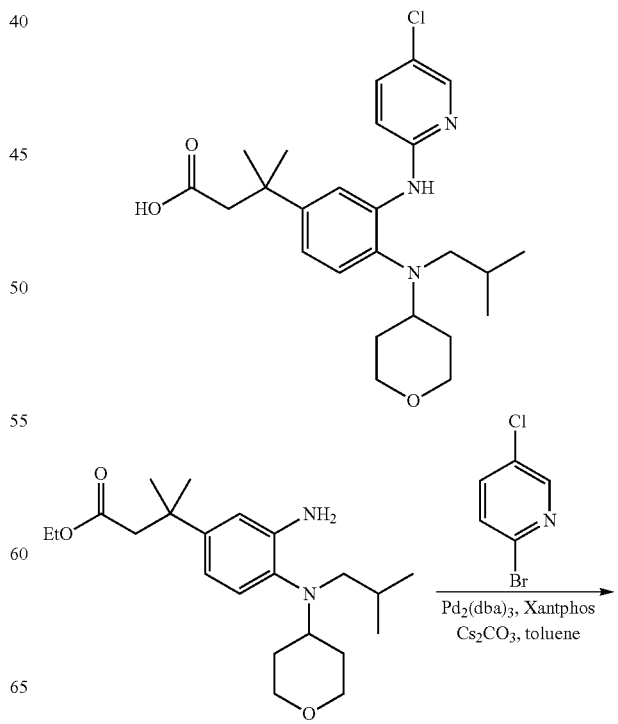

-continued

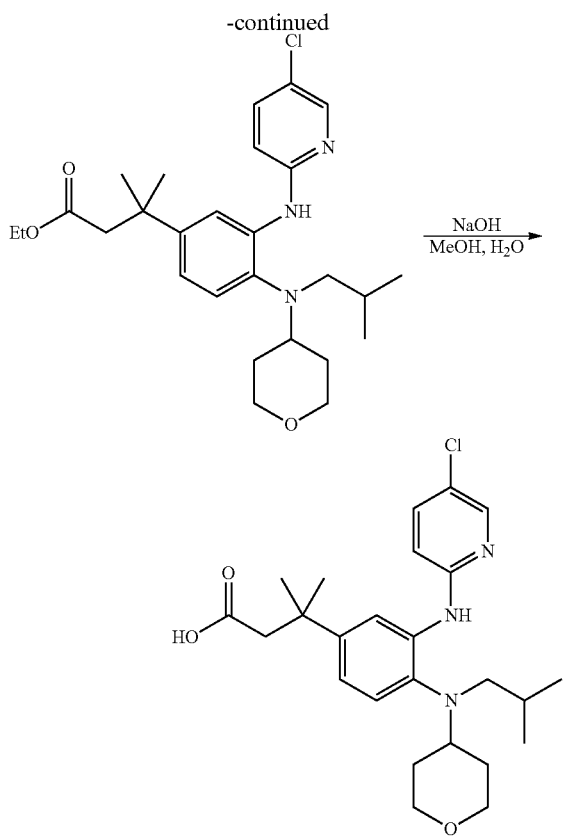

Preparation of ethyl 3-(3-((5-chloropyridin-2-yl)amino)-4-(isobutyl(tetrahydro-2H-pyran-4-yl)amino)phenyl)-3-methylbutanoate A mixture of ethyl 3-(3-amino-4-(isobutyl(tetrahydro-2H-pyran-4-yl)amino)phenyl)-3-methylbutanoate (100 mg, 0.27 mmol), 2-bromo-5-chloropyridine (104 mg, 0.54 mmol), Pd$_2$(dba)$_3$ (25 mg, 0.027 mmol), Xantphos (32 mg, 0.054 mmol) and Cs$_2$CO$_3$ (176 mg, 0.54 mmol) in toluene (3 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (56 mg, 43% yield). LCMS (ESI) m/z calcd for C$_{27}$H$_{38}$ClN$_3$O$_3$: 487.26. Found: 488.75/490.74 (M/M+2)$^+$.

Preparation of 3-(3-((5-chloropyridin-2-yl)amino)-4-(isobutyl(tetrahydro-2H-pyran-4-yl)amino)phenyl)-3-methylbutanoic Acid

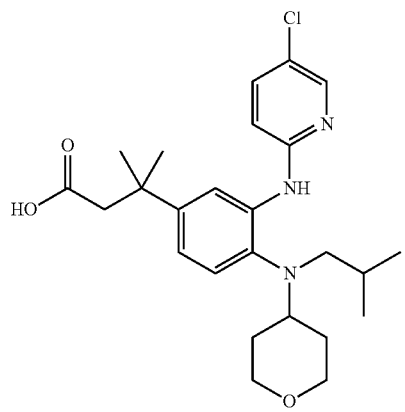 [SMILES: CC(C)CN(c1ccc(C(C)(C)CC(=O)O)cc1Nc1ccc(Cl)cn1)C1CCOCC1]

To a solution of ethyl 3-(3-((5-chloropyridin-2-yl)amino)-4-(isobutyl(tetrahydro-2H-pyran-4-yl)amino)phenyl)-3-methylbutanoate (136 mg, 0.28 mmol) in MeOH (3 mL) was added 4N NaOH aq. (0.5 mL). After stirred at r.t. for 48 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (85 mg, 66% yield) as a white powder. $^1$H NMR (400 MHz, DMSO) δ 11.79 (br, 1H), 8.24-8.16 (m, 2H), 8.13 (s, 1H), 7.65 (dd, J=8.9, 2.7 Hz, 1H), 7.17 (d, J=8.4 Hz, 1H), 7.05-6.93 (m, 2H), 3.80 (dd, J=11.1, 3.5 Hz, 2H), 3.20-3.08 (m, 2H), 2.80 (t, J=8.7 Hz, 3H), 2.56-2.53 (m, 2H), 1.65 (d, J=11.0 Hz, 2H), 1.59-1.23 (m, 9H), 0.82 (d, J=6.6 Hz, 6H). LCMS (ESI) m/z calcd for C$_{25}$H$_{34}$ClN$_3$O$_3$: 459.23. Found: 460.60/462.60 (M/M+2)$^+$.

Example 5

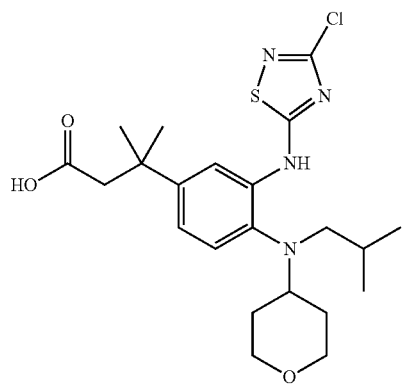 [SMILES: CC(C)CN(c1ccc(C(C)(C)CC(=O)O)cc1Nc1nc(Cl)ns1)C1CCOCC1]

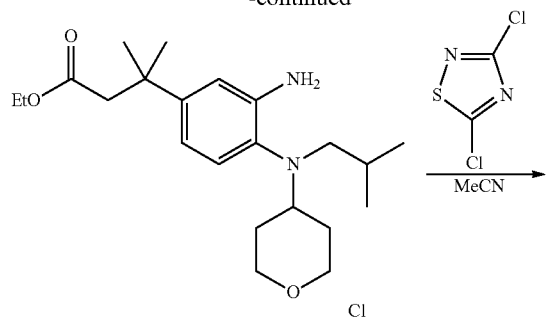

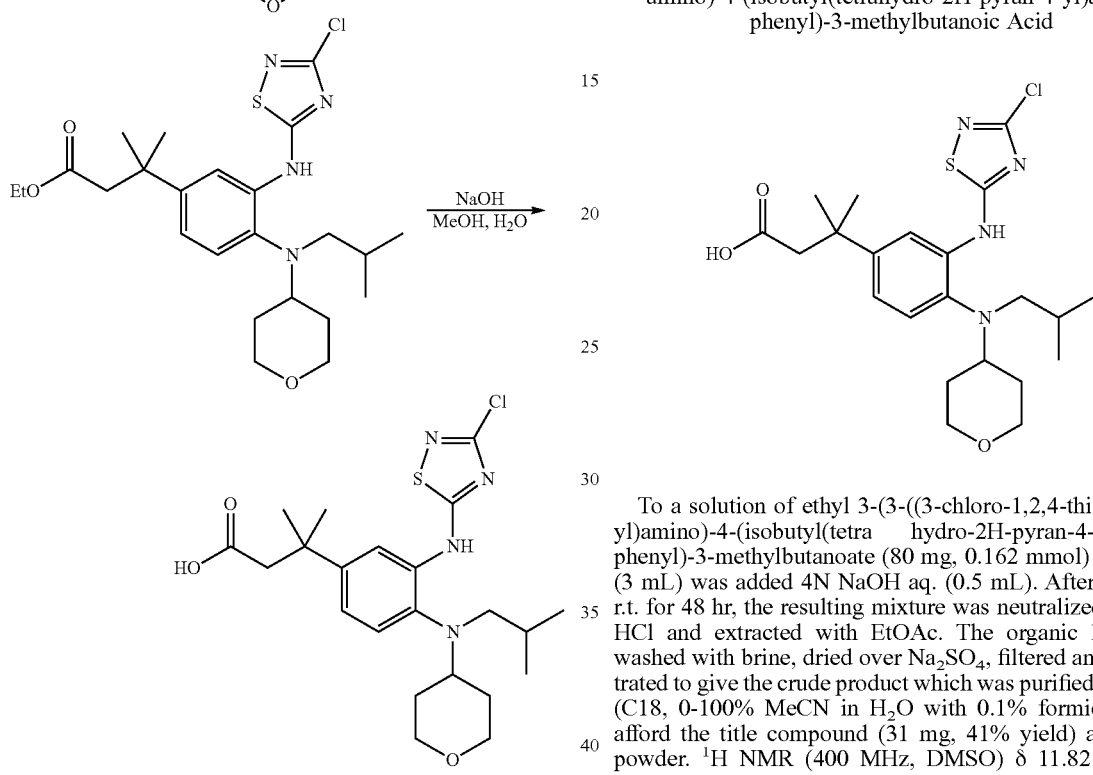

Preparation of ethyl 3-(3-((3-chloro-1,2,4-thiadi-azol-5-yl)amino)-4-(isobutyl(tetra hydro-2H-pyran-4-yl)amino)phenyl)-3-methylbutanoate A mixture of ethyl 3-(3-amino-4-(isobutyl(tetrahydro-2H-pyran-4-yl)amino)phenyl)-3-methylbutanoate (100 mg, 0.27 mmol) and 3,5-dichloro-1,2,4-thiadiazole (64 mg, 0.41 mmol) in DMF (2 mL) was stirred at 100° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (81 mg, 61% yield). LCMS (ESI) m/z calcd for $C_{24}H_{35}ClN_4O_3S$: 494.21. Found: 495.68/497.68 (M/M+2)+.

Preparation of 3-(3-((3-chloro-1,2,4-thiadiazol-5-yl)amino)-4-(isobutyl(tetrahydro-2H-pyran-4-yl)amino)phenyl)-3-methylbutanoic Acid To a solution of ethyl 3-(3-((3-chloro-1,2,4-thiadiazol-5-yl)amino)-4-(isobutyl(tetra hydro-2H-pyran-4-yl)amino)phenyl)-3-methylbutanoate (80 mg, 0.162 mmol) in MeOH (3 mL) was added 4N NaOH aq. (0.5 mL). After stirred at r.t. for 48 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (31 mg, 41% yield) as a white powder. $^1$H NMR (400 MHz, DMSO) δ 11.82 (br, 1H), 10.20 (s, 1H), 8.03 (d, J=1.4 Hz, 1H), 7.31-7.06 (m, 2H), 3.82 (dd, J=11.1, 3.6 Hz, 2H), 3.14 (t, J=11.2 Hz, 2H), 2.95-2.85 (m, 1H), 2.77 (d, J=6.7 Hz, 2H), 2.54 (s, 2H), 1.70-1.57 (m, 2H), 1.57-1.20 (m, 9H), 0.78 (d, J=6.6 Hz, 6H). LCMS (ESI) m/z calcd for $C_{22}H_{31}ClN_4O_3S$: 466.18. Found: 467.57/469.56 (M/M+2)+.

Example 6

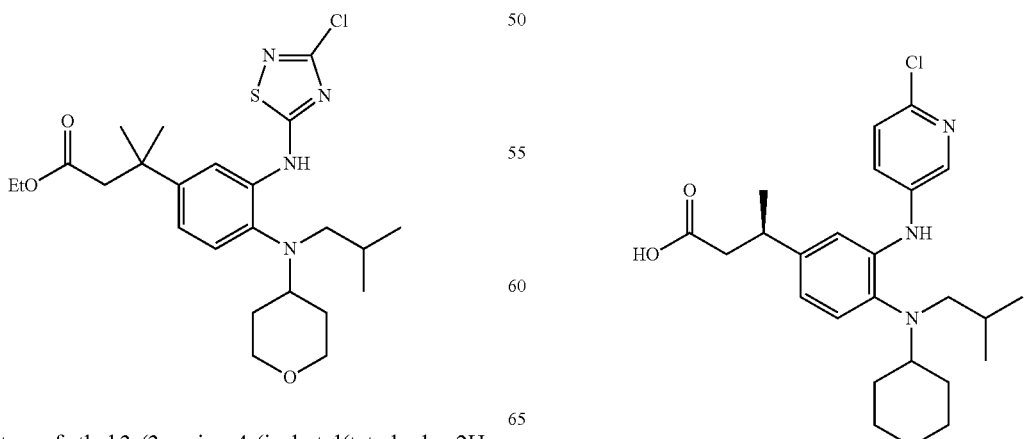

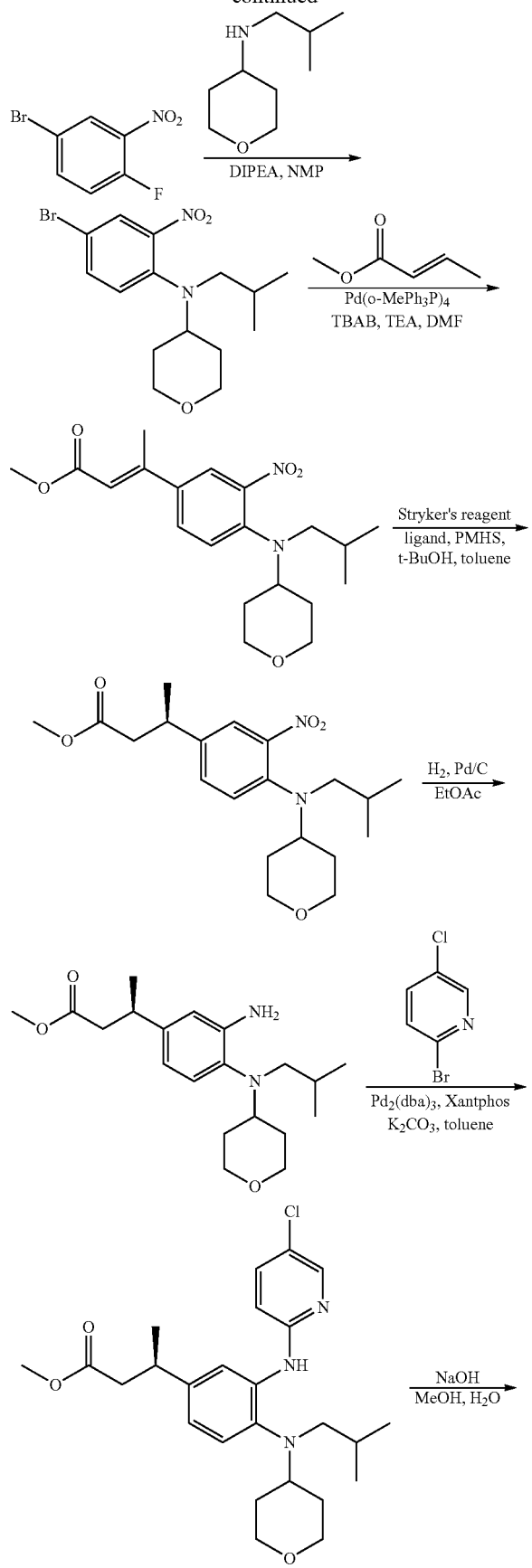

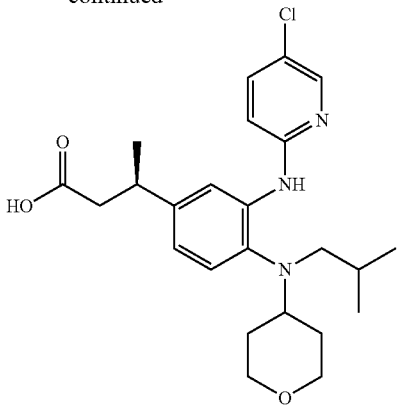

Preparation of N-(4-bromo-2-nitrophenyl)-N-isobutyltetrahydro-2H-pyran-4-amine

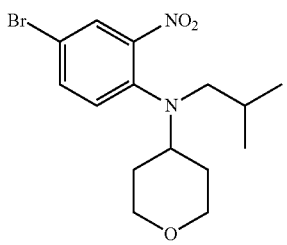 [SMILES: CC(C)CN(c1ccc(Br)cc1[N+](=O)[O-])C1CCOCC1]

A mixture of 4-bromo-1-fluoro-2-nitrobenzene (18.7 g, 84.8 mmol), N-isobutyltetra hydro-2H-pyran-4-amine (20 g, 127.2 mmol) and DIPEA (29.6 mL, 169.6 mmol) in NMP (150 mL) was stirred at 140° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-10% EtOAc in PE) to afford the title compound (14 g, 46% yield) as a yellow oil. LCMS (ESI) m/z calcd for $C_{15}H_{21}BrN_2O_3$: 356.07. Found: 357.32/359.31 (M/M+2)$^+$.

Preparation of methyl (E)-3-(4-(isobutyl(tetrahydro-2H-pyran-4-yl)amino)-3-nitro phenyl)but-2-enoate

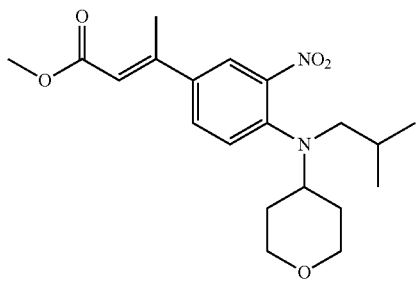 [SMILES: COC(=O)/C=C(\C)c1ccc(N(CC(C)C)C2CCOCC2)c([N+](=O)[O-])c1]

A mixture of N-(4-bromo-2-nitrophenyl)-N-isobutyltetrahydro-2H-pyran-4-amine (14 g, 39.2 mmol), methyl (E)-but-2-enoate (11.8 g, 117.6 mmol), TBAB (2.5 g, 7.8 mmol), Pd(o-MePh$_3$P)$_4$ (1.54 g, 1.96 mmol) and TEA (10.9 mL, 78.4 mmol) in DMF (140 mL) was stirred at 100° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-10% EtOAc in PE) to afford the title compound (7.6 g, 51% yield) as a yellow solid. LCMS (ESI) m/z calcd for C$_{20}$H$_{28}$N$_2$O$_5$: 376.20. Found: 377.40 (M+1)$^+$.

Preparation of methyl (R)-3-(4-(isobutyl(tetrahydro-2H-pyran-4-yl)amino)-3-nitro phenyl)butanoate

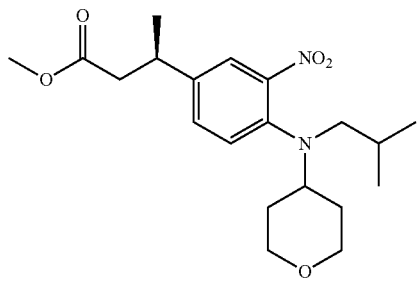

At −5° C., to a mixture of (CuHPh$_3$P)$_6$ (307 mg, 0.156 mmol) and (R,S)—PPF—P(tBu)$_2$ (308 mg, 0.568 mmol) in toluene (80 mL) was added PMHS (3.0 mL) and t-BuOH (2.3 mL) before the introduction of methyl (E)-3-(4-(isobutyl(tetrahydro-2H-pyran-4-yl) amino)-3-nitrophenyl) but-2-enoate (7.6 g, 20.3 mmol). After stirred at −5° C. for 2 hr, the resulting mixture was quenched with sat. NaHCO$_3$ aq. solution and extracted with EtOAc. The organic layer was washed with brine, dried over Na$_2$SO$_4$, filtered and concentrated to give the crude product which was purified by flash chromatography (silica gel, 0-10% EtOAc in PE) to afford the title compound (7.5 g, 99% yield) as a yellow oil. LCMS (ESI) m/z calcd for C$_{20}$H$_{30}$N$_2$O$_5$: 378.22. Found: 379.27 (M+1)$^+$.

Preparation of methyl (R)-3-(3-amino-4-(isobutyl (tetrahydro-2H-pyran-4-yl) amino)phenyl)butanoate

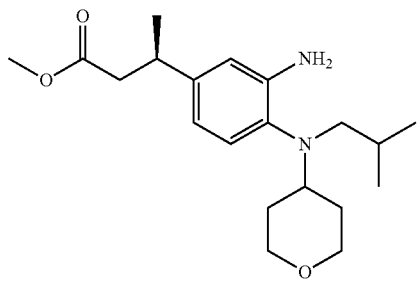 [SMILES: COC(=O)C[C@@H](C)c1ccc(N(CC(C)C)C2CCOCC2)c(N)c1]

A mixture of methyl (R)-3-(4-(isobutyl(tetrahydro-2H-pyran-4-yl)amino)-3-nitrophenyl) butanoate (7.9 g, 20.8 mmol) and 10% Pd/C (2.4 g) in EtOAc (60 mL) was stirred at 50° C. under H$_2$ atmosphere overnight. The resulting mixture was filtered through a pad of Celite and the filtrate was concentrated under reduced pressure to give the crude product which was purified by flash chromatography (silica gel, 0-30% EtOAc in PE) to afford the title compound (6.1 g, 83% yield) as a yellow oil. LCMS (ESI) m/z calcd for C$_{20}$H$_{32}$N$_2$O$_3$: 348.24. Found: 349.15 (M+1)$^+$.

Preparation of methyl (R)-3-(3-((6-chloropyridin-3-yl)amino)-4-(isobutyl(tetra hydro-2H-pyran-4-yl)amino)phenyl)butanoate

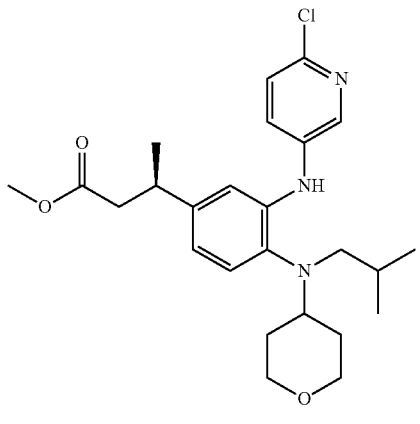 [SMILES: COC(=O)C[C@@H](C)c1ccc(N(CC(C)C)C2CCOCC2)c(Nc2ccc(Cl)nc2)c1]

A mixture of methyl (R)-3-(3-amino-4-(isobutyl(tetrahydro-2H-pyran-4-yl)amino)phenyl) butanoate (100 mg, 0.287 mmol), 5-bromo-2-chloropyridine (110 mg, 0.574 mmol), Pd$_2$(dba)$_3$ (52 mg, 0.057 mmol), Xantphos (66 mg, 0.114 mmol) and K$_2$CO$_3$ (118 mg, 0.861 mmol) in toluene (5 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-40% EtOAc in PE) to afford the title compound (105 mg, 79% yield). LCMS (ESI) m/z calcd for C$_{25}$H$_{34}$ClN$_3$O$_3$: 459.23. Found: 460.37/462.33 (M/M+2)$^+$.

Preparation of (R)-3-(3-((6-chloropyridin-3-yl) amino)-4-(isobutyl(tetrahydro-2H-pyran-4-yl)amino) phenyl)butanoic Acid

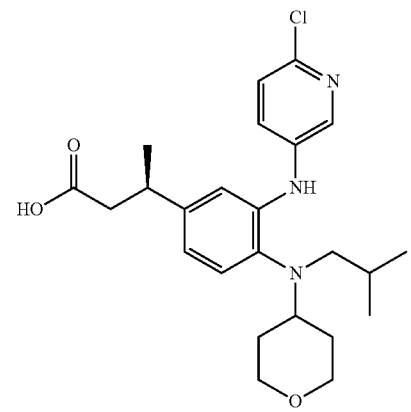 [SMILES: CC(C)CN(c1ccc([C@H](C)CC(=O)O)cc1Nc1ccc(Cl)nc1)C1CCOCC1]

To a solution of methyl (R)-3-(3-((6-chloropyridin-3-yl) amino)-4-(isobutyl(tetra hydro-2H-pyran-4-yl)amino)phenyl)butanoate (105 mg, 0.23 mmol) in MeOH (4 mL) was added 4N NaOH aq. (2 mL). After stirred at r.t. for 5 hr, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (72 mg, 70% yield) as a white powder. ¹H NMR (400 MHz, CDCl₃) δ 8.24 (d, J=2.8 Hz, 1H), 7.41 (dd, J=8.5, 2.6 Hz, 1H), 7.22 (d, J=8.6 Hz, 1H), 7.15-7.00 (m, 3H), 6.77 (d, J=7.5 Hz, 1H), 4.00-3.91 (m, 2H), 3.29-3.17 (m, 3H), 2.84-2.74 (m, 3H), 2.66-2.55 (m, 2H), 1.79-1.55 (m, 4H), 1.50-1.38 (m, 1H), 1.31 (d, J=7.0 Hz, 3H), 0.85 (d, J=6.5 Hz, 6H). LCMS (ESI) m/z calcd for $C_{24}H_{32}ClN_3O_3$: 445.21. Found: 446.31/448.28 (M/M+2)⁺.

Example 7

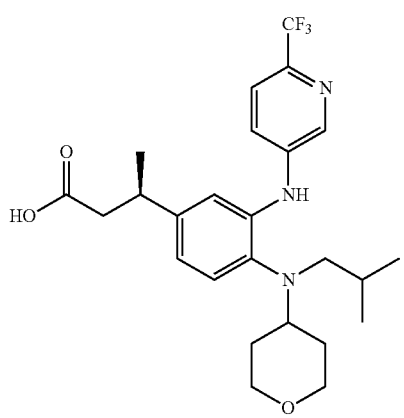

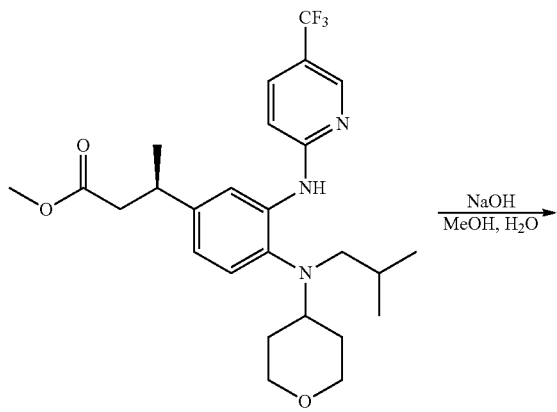

Preparation of methyl (R)-3-(4-(isobutyl(tetrahydro-2H-pyran-4-yl)amino)-3-((6-(trifluoromethyl)pyridin-3-yl)amino)phenyl)butanoate

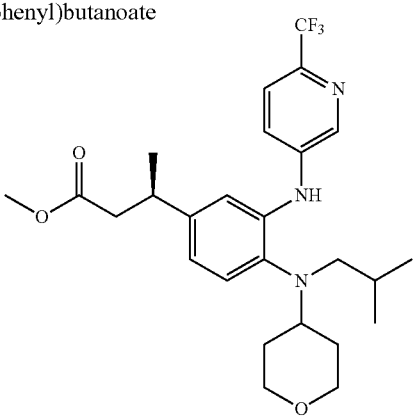

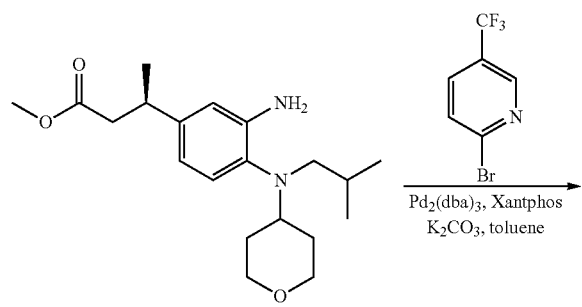

A mixture of methyl (R)-3-(3-amino-4-(isobutyl(tetrahydro-2H-pyran-4-yl)amino)phenyl) butanoate (100 mg, 0.287 mmol), 5-bromo-2-(trifluoromethyl)pyridine (129 mg, 0.57 mmol), Pd₂(dba)₃ (52 mg, 0.057 mmol), Xantphos (66 mg, 0.114 mmol) and K₂CO₃ (118 mg, 0.861 mmol) in toluene (5 mL) was stirred at 100° C. under N₂ atmosphere overnight. The resulting mixture was partitioned between EtOAc and H₂O. The organic layer was washed with brine, dried over Na₂SO₄, filtered and concentrated to give the crude product which was purified by flash chromatography (silica gel, 0-30% EtOAc in PE) to afford the title compound (130 mg, 91% yield). LCMS (ESI) m/z calcd for $C_{26}H_{34}F_3N_3O_3$: 493.26. Found: 494.41 (M+1)⁺.

Preparation of (R)-3-(4-(isobutyl(tetrahydro-2H-pyran-4-yl)amino)-3-((6-(trifluoro methyl)pyridin-3-yl)amino)phenyl)butanoic Acid

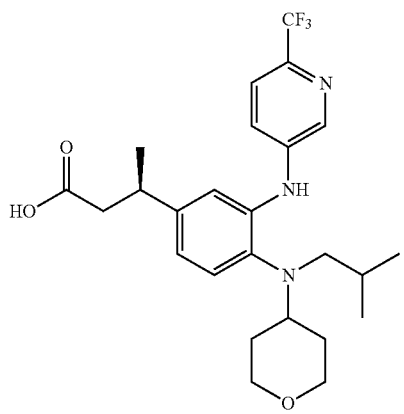

To a solution of methyl (R)-3-(4-(isobutyl(tetrahydro-2H-pyran-4-yl)amino)-3-((6-(trifluoromethyl)pyridin-3-yl)amino)phenyl)butanoate (130 mg, 0.264 mmol) in MeOH (5 mL) was added 4N NaOH aq. (2 mL). After stirred at r.t. for 5 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (96 mg, 76% yield) as a white powder. $^1$H NMR (400 MHz, $CDCl_3$) δ 8.51 (d, J=2.6 Hz, 1H), 7.57 (d, J=8.5 Hz, 1H), 7.49 (dd, J=8.7, 2.2 Hz, 1H), 7.35 (s, 1H), 7.23 (d, J=1.5 Hz, 1H), 7.15 (d, J=8.2 Hz, 1H), 6.84 (dd, J=8.1, 1.4 Hz, 1H), 4.00-3.88 (m, 2H), 3.28-3.18 (m, 3H), 2.83-2.77 (m, 3H), 2.64-2.59 (m, 2H), 1.71-1.53 (m, 4H), 1.49-1.40 (m, 1H), 1.33 (d, J=7.0 Hz, 3H), 0.86 (d, J=6.6 Hz, 6H). LCMS (ESI) m/z calcd for $C_{25}H_{32}F_3N_3O_3$: 479.24. Found: 480.37 $(M+1)^+$.

Example 8

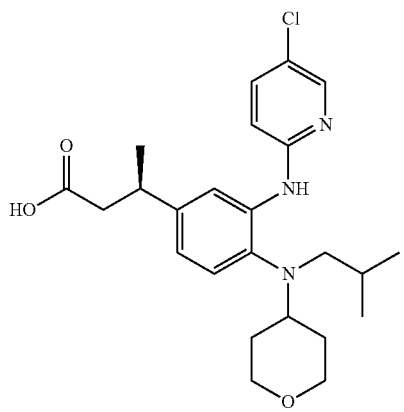

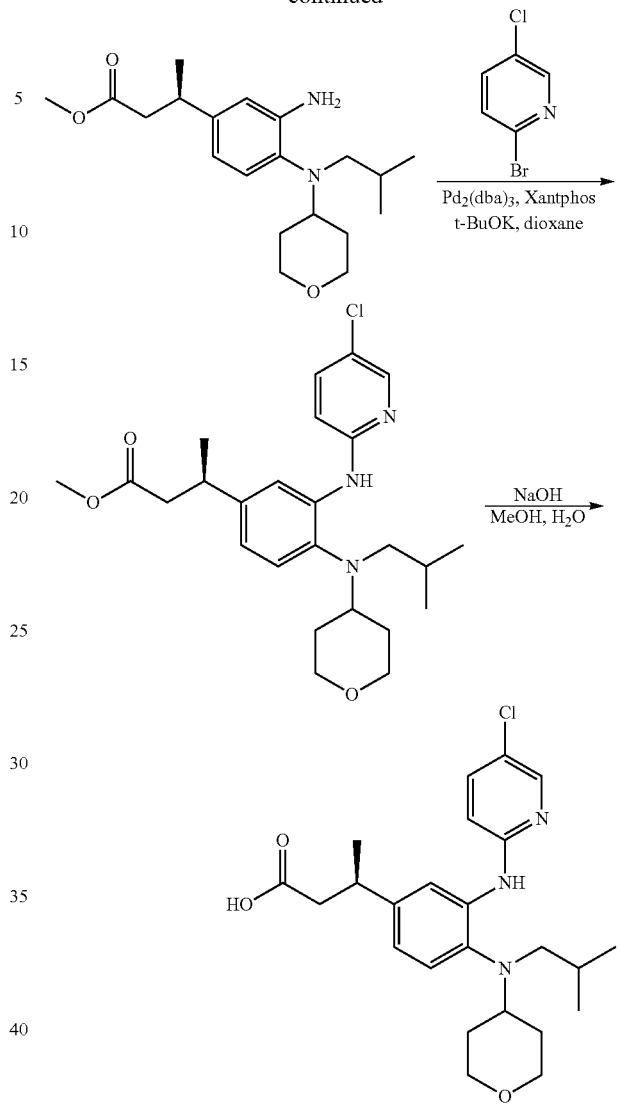

Preparation of methyl (R)-3-(3-((5-chloropyridin-2-yl)amino)-4-(isobutyl(tetra hydro-2H-pyran-4-yl)amino)phenyl)butanoate

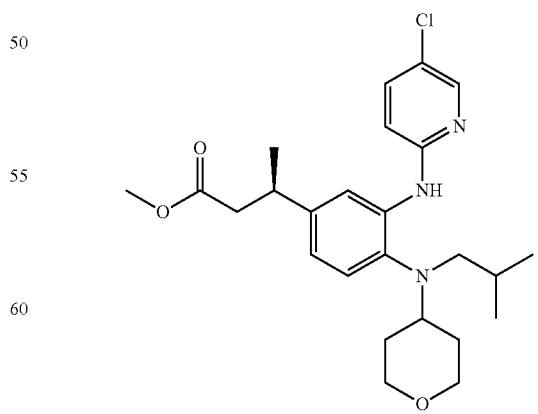

A mixture of methyl (R)-3-(3-amino-4-(isobutyl(tetrahydro-2H-pyran-4-yl)amino)phenyl) butanoate (150 mg, 0.431 mmol), 2-bromo-5-chloropyridine (165 mg, 0.86 mmol), Pd₂(dba)₃ (78 mg, 0.086 mmol), Xantphos (99 mg, 0.172 mmol) and t-BuOK (96 mg, 0.86 mmol) in dioxane (6 mL) was stirred at 100° C. under N₂ atmosphere overnight. The resulting mixture was partitioned between EtOAc and H₂O. The organic layer was washed with brine, dried over Na₂SO₄, filtered and concentrated to give the crude product which was purified by flash chromatography (silica gel, 0-30% EtOAc in PE) to afford the title compound (135 mg, 68% yield). LCMS (ESI) m/z calcd for $C_{25}H_{34}ClN_3O_3$: 459.23. Found: 460.44/462.40 (M/M+2)⁺.

Preparation of (R)-3-(3-((5-chloropyridin-2-yl) amino)-4-(isobutyl(tetrahydro-2H-pyran-4-yl)amino) phenyl)butanoic Acid

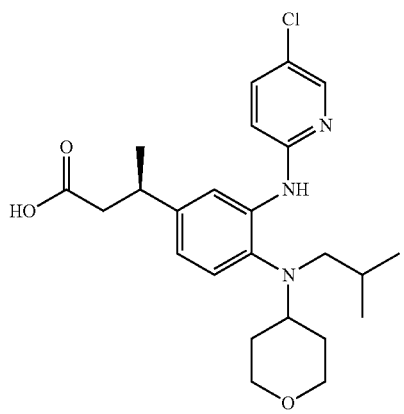 [SMILES: CC(C)CN(c1ccc([C@H](C)CC(=O)O)cc1Nc1ccc(Cl)cn1)C1CCOCC1]

To a solution of methyl (R)-3-(3-((5-chloropyridin-2-yl) amino)-4-(isobutyl(tetra hydro-2H-pyran-4-yl)amino)phenyl)butanoate (135 mg, 0.29 mmol) in MeOH (5 mL) was added 4N NaOH aq. (2 mL). After stirred at r.t. for 5 hr, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (82 mg, 62% yield) as a white powder. ¹H NMR (400 MHz, CDCl₃) δ 8.19 (d, J=2.3 Hz, 1H), 8.10-7.97 (m, 2H), 7.46 (dd, J=8.8, 2.6 Hz, 1H), 7.10 (d, J=8.1 Hz, 1H), 6.80 (d, J=7.2 Hz, 1H), 6.74 (d, J=7.3 Hz, 1H), 3.99-3.89 (m, 2H), 3.34-3.18 (m, 3H), 2.90-2.76 (m, 3H), 2.73-2.57 (m, 2H), 1.62-1.45 (m, 5H), 1.35 (d, J=6.9 Hz, 3H), 0.86 (d, J=6.6 Hz, 6H). LCMS (ESI) m/z calcd for $C_{24}H_{32}ClN_3O_3$: 445.21. Found: 446.22/448.16 (M/M+2)⁺.

Example 9

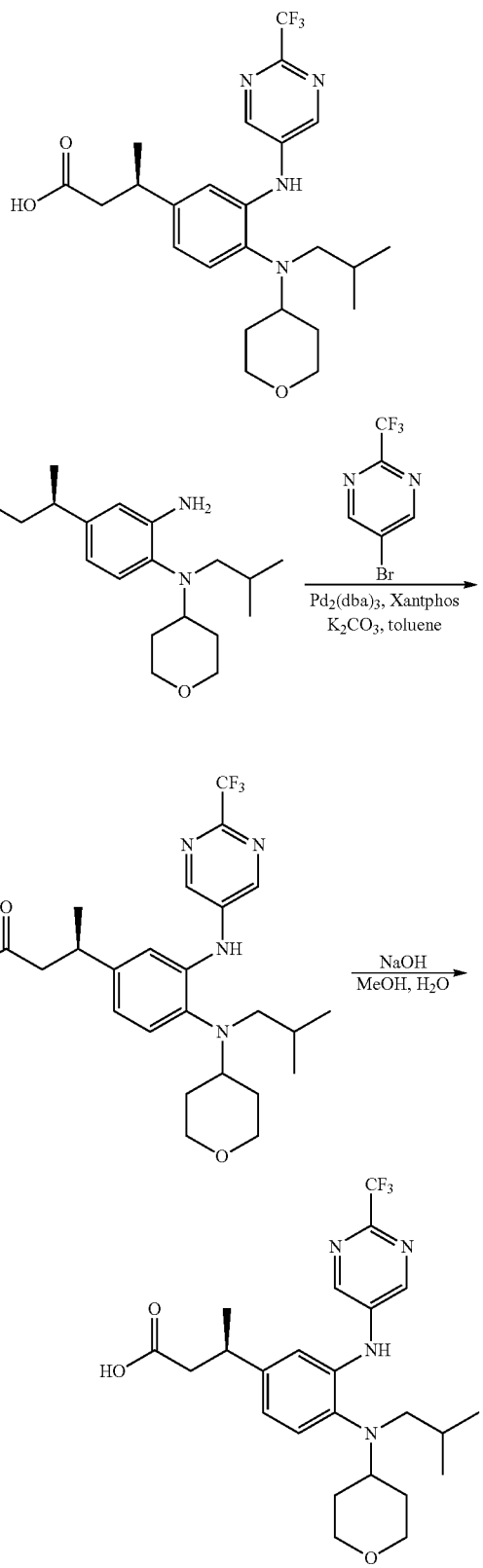

Preparation of methyl (R)-3-(4-(isobutyl(tetrahydro-2H-pyran-4-yl)amino)-3-((2-(trifluoromethyl)pyrimidin-5-yl)amino)phenyl)butanoate

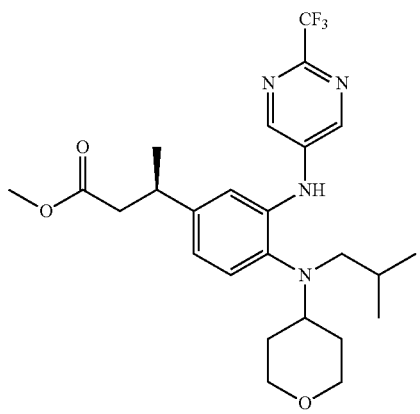 [SMILES: COC(=O)C[C@@H](C)c1ccc(N(CC(C)C)C2CCOCC2)c(Nc2cnc(Cl)nc2)c1]

A mixture of methyl (R)-3-(3-amino-4-(isobutyl(tetrahydro-2H-pyran-4-yl)amino)phenyl) butanoate (120 mg, 0.34 mmol), 5-bromo-2-(trifluoromethyl)pyrimidine (154 mg, 0.68 mmol), Pd$_2$(dba)$_3$ (28 mg, 0.03 mmol), Xantphos (40 mg, 0.07 mmol) and K$_2$CO$_3$ (141 mg, 1.02 mmol) in toluene (4 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (120 mg, 71% yield). LCMS (ESI) m/z calcd for C$_{25}$H$_{33}$F$_3$N$_4$O$_3$: 494.25. Found: 495.45 (M+1)$^+$.

Preparation of (R)-3-(4-(isobutyl(tetrahydro-2H-pyran-4-yl)amino)-3-((2-(trifluoro methyl)pyrimidin-5-yl)amino)phenyl)butanoic Acid

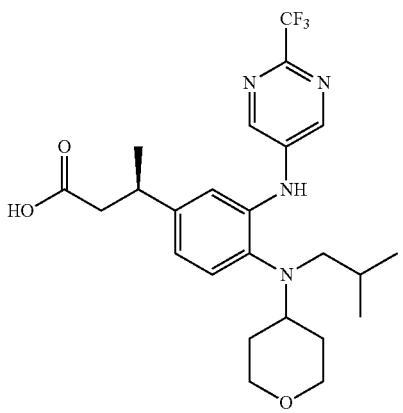

To a solution of methyl (R)-3-(4-(isobutyl(tetrahydro-2H-pyran-4-yl)amino)-3-((2-(trifluoromethyl)pyrimidin-5-yl)amino)phenyl)butanoate (120 mg, 0.24 mmol) in MeOH (6 mL) was added 1N NaOH aq. (3 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (97 mg, 84% yield) as a white powder. $^1$H NMR (400 MHz, CDCl$_3$) δ 8.68 (s, 2H), 7.45 (s, 1H), 7.24 (d, J=1.9 Hz, 1H), 7.18 (d, J=8.2 Hz, 1H), 6.90 (dd, J=8.2, 1.9 Hz, 1H), 3.98-3.90 (m, 2H), 3.33-3.19 (m, 3H), 2.86-2.75 (m, 3H), 2.66-2.57 (m, 2H), 1.74-1.55 (m, 4H), 1.47-1.30 (m, 4H), 0.91-0.77 (m, 6H). LCMS (ESI) m/z calcd for C$_{24}$H$_{31}$F$_3$N$_4$O$_3$: 480.23. Found: 481.67 (M+1)$^+$.

Example 10

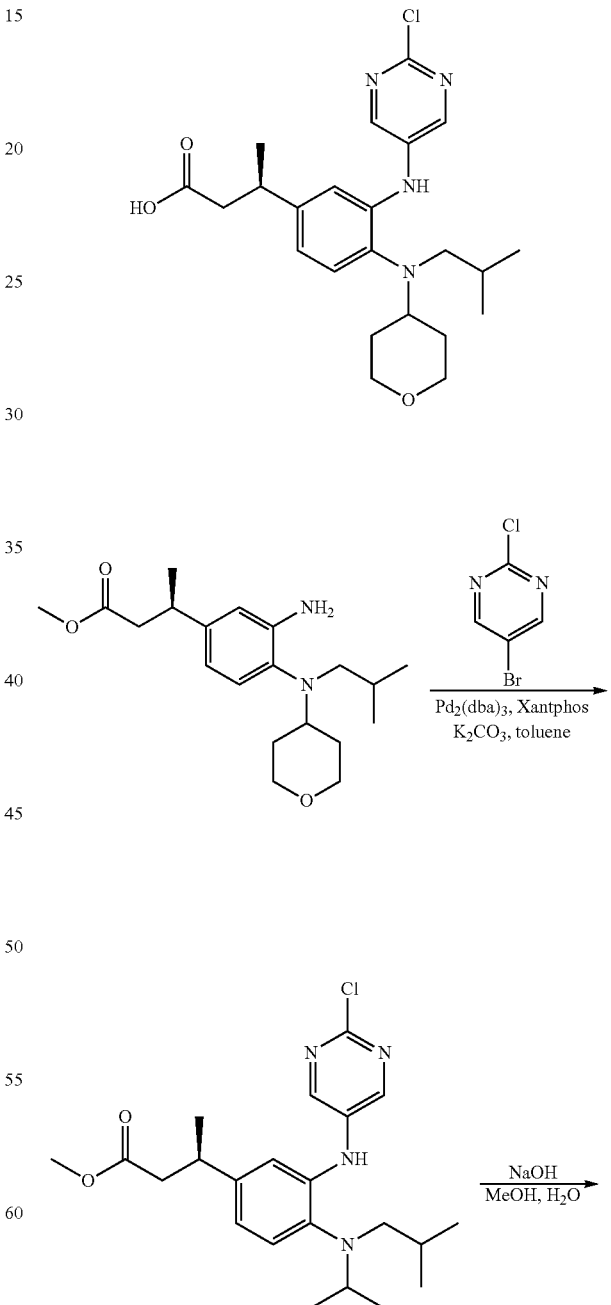

Preparation of methyl (R)-3-(3-((2-chloropyrimidin-5-yl)amino)-4-(isobutyl(tetrahydro-2H-pyran-4-yl)amino)phenyl)butanoate

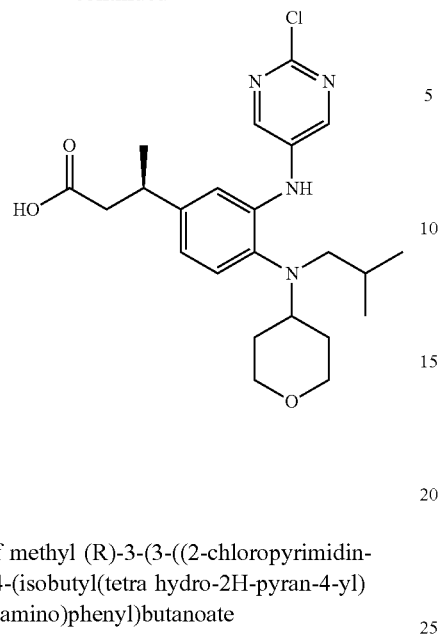

A mixture of methyl (R)-3-(3-amino-4-(isobutyl(tetrahydro-2H-pyran-4-yl)amino)phenyl) butanoate (220 mg, 0.63 mmol), 5-bromo-2-chloropyrimidine (244 mg, 0.68 mmol), Pd$_2$(dba)$_3$ (57.8 mg, 0.063 mmol), Xantphos (73 mg, 0.12 mmol) and K$_2$CO$_3$ (262 mg, 1.9 mmol) in toluene (5 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (171 mg, 59% yield). LCMS (ESI) m/z calcd for C$_{24}$H$_{33}$ClN$_4$O$_3$: 460.22. Found: 461.57/463.54 (M+1)$^+$.

Preparation of (R)-3-(3-((2-chloropyrimidin-5-yl)amino)-4-(isobutyl(tetrahydro-2H-pyran-4-yl)amino)phenyl)butanoic Acid

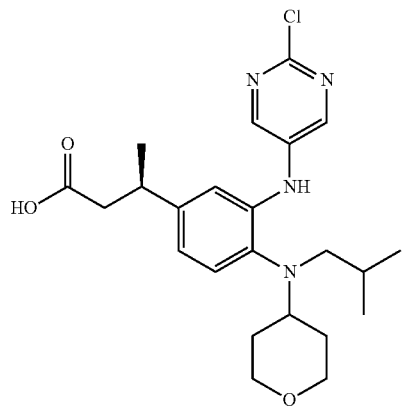

To a solution of methyl (R)-3-(3-((2-chloropyrimidin-5-yl)amino)-4-(isobutyl(tetra hydro-2H-pyran-4-yl)amino)phenyl)butanoate (110 mg, 0.24 mmol) in THF (6 mL) was added 4N NaOH aq. (2 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (58 mg, 54% yield) as a white powder. $^1$H NMR (400 MHz, CDCl$_3$) δ 8.49 (s, 2H), 7.19-7.13 (m, 2H), 7.10 (d, J=1.9 Hz, 1H), 6.84 (dd, J=8.2, 1.9 Hz, 1H), 3.95 (dd, J=10.9, 2.8 Hz, 2H), 3.32-3.22 (m, 3H), 2.85-2.76 (m, 3H), 2.63-2.58 (m, 2H), 1.75-1.56 (m, 4H), 1.49-1.39 (m, 1H), 1.32 (d, J=7.0 Hz, 3H), 0.85 (dd, J=6.6, 1.5 Hz, 6H). LCMS (ESI) m/z calcd for C$_{23}$H$_{31}$ClN$_4$O$_3$: 446.21. Found: 447.53/449.55 (M/M+2)$^+$.

Example 11

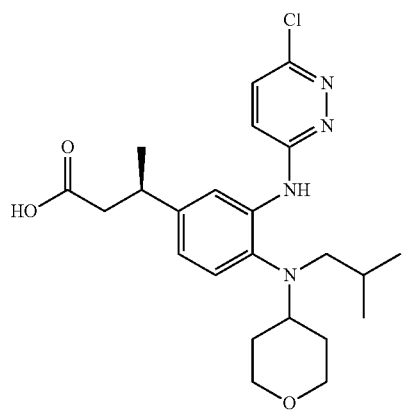

-continued

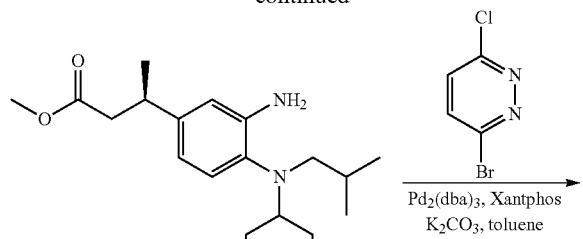

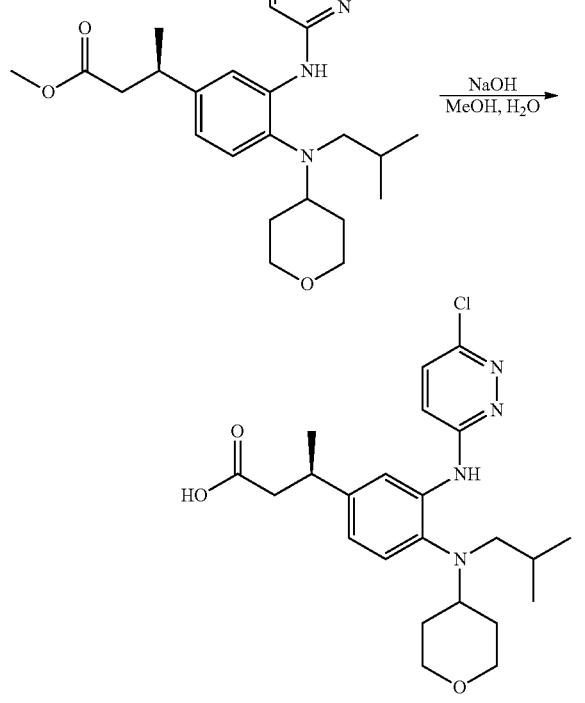

Preparation of methyl (R)-3-(3-((6-chloropyridazin-3-yl)amino)-4-(isobutyl(tetra hydro-2H-pyran-4-yl)amino)phenyl)butanoate

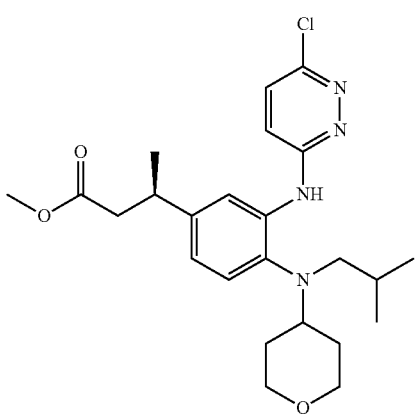

A mixture of methyl (R)-3-(3-amino-4-(isobutyl(tetrahydro-2H-pyran-4-yl)amino)phenyl) butanoate (120 mg, 0.34 mmol), 3,6-dichloropyridazine (104 mg, 0.69 mmol), $Pd_2(dba)_3$ (32.5 mg, 0.036 mmol), Xantphos (40 mg, 0.07 mmol) and $K_2CO_3$ (143 mg, 1.03 mmol) in toluene (5 mL) was stirred at 100° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-50% EtOAc in PE) to afford the title compound (95 mg, 61% yield). LCMS (ESI) m/z calcd for $C_{24}H_{33}ClN_4O_3$: 460.22. Found: 461.25/463.21 (M/M+2)$^+$.

Preparation of (R)-3-(3-((6-chloropyridazin-3-yl)amino)-4-(isobutyl(tetrahydro-2H-pyran-4-yl)amino)phenyl)butanoic Acid

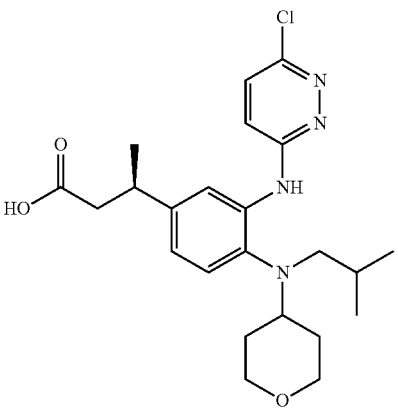

To a solution of methyl (R)-3-(3-((6-chloropyridazin-3-yl)amino)-4-(isobutyl(tetra hydro-2H-pyran-4-yl)amino) phenyl)butanoate (95 mg, 0.21 mmol) in MeOH (10 mL) was added 4N NaOH aq. (4 mL). After stirred at 40° C. for 4 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (34 mg, 36% yield) as a white powder. $^1$H NMR (400 MHz, $CDCl_3$) δ 8.30 (s, 1H), 8.19 (d, J=1.9 Hz, 1H), 7.21 (d, J=9.3 Hz, 1H), 7.07 (d, J=8.2 Hz, 1H), 6.87 (d, J=9.2 Hz, 1H), 6.81 (dd, J=8.1, 1.9 Hz, 1H), 3.87 (dd, J=11.1, 3.5 Hz, 2H), 3.26-3.16 (m, 3H), 2.81-2.72 (m, 3H), 2.66-2.52 (m, 8.0 Hz, 2H), 1.68-1.36 (m, 5H), 1.28 (d, J=7.0 Hz, 3H), 0.79 (d, J=6.6 Hz, 6H) LCMS (ESI) m/z calcd for $C_{23}H_{31}ClN_4O_3$: 446.21. Found: 447.21/449.19 (M+1)$^+$.

Example 12

Preparation of methyl (R)-3-(3-((5-chloropyrazin-2-yl)amino)-4-(isobutyl(tetra hydro-2H-pyran-4-yl)amino)phenyl)butanoate

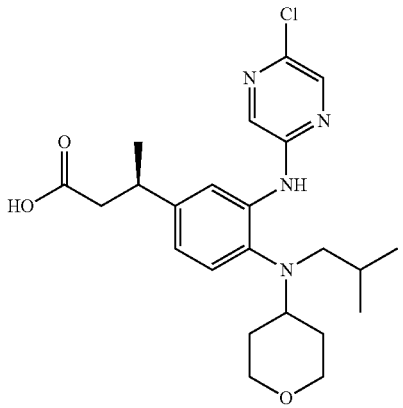 [SMILES: CC(C)CN(c1ccc([C@H](C)CC(=O)O)cc1Nc1cnc(Cl)cn1)C1CCOCC1]

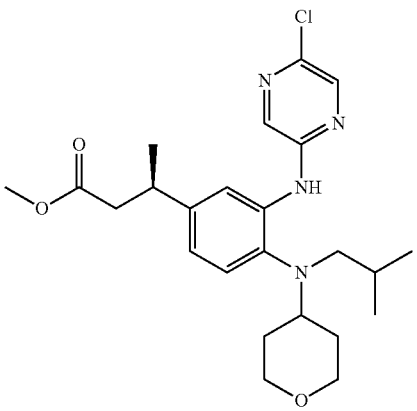 [SMILES: COC(=O)C[C@@H](C)c1ccc(N(CC(C)C)C2CCOCC2)c(Nc2cnc(Cl)cn2)c1]

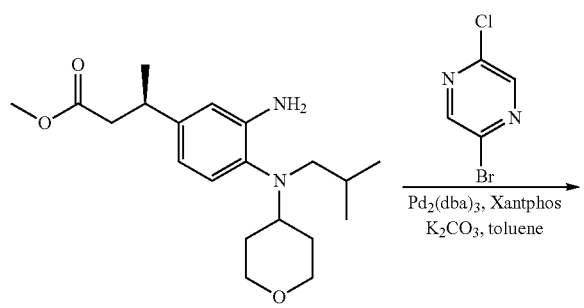

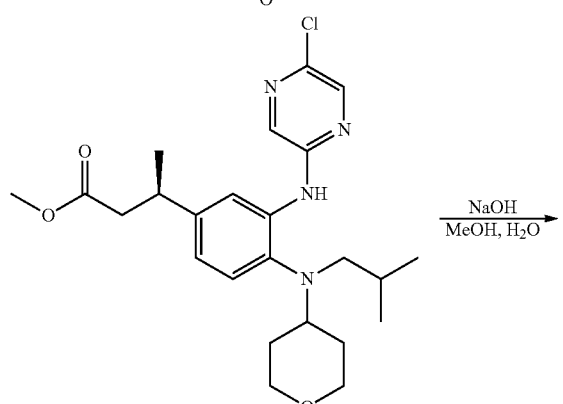

A mixture of methyl (R)-3-(3-amino-4-(isobutyl(tetra-hydro-2H-pyran-4-yl)amino)phenyl) butanoate (120 mg, 0.34 mmol), 2,5-dichloropyrazine (104 mg, 0.69 mmol), Pd$_2$(dba)$_3$ (32.5 mg, 0.036 mmol), Xantphos (40 mg, 0.07 mmol) and K$_2$CO$_3$ (143 mg, 1.03 mmol) in toluene (5 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-50% EtOAc in PE) to afford the title compound (120 mg, 76% yield). LCMS (ESI) m/z calcd for C$_{24}$H$_{33}$ClN$_4$O$_3$: 460.22. Found: 461.41/463.36 (M/M+2)$^+$.

Preparation of (R)-3-(3-((5-chloropyrazin-2-yl)amino)-4-(isobutyl(tetrahydro-2H-pyran-4-yl)amino)phenyl)butanoic Acid

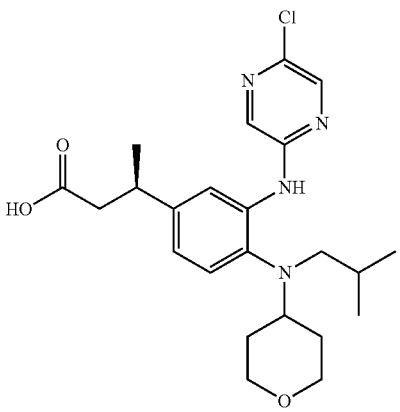 [SMILES: CC(C)CN(c1ccc([C@H](C)CC(=O)O)cc1Nc1cnc(Cl)cn1)C1CCOCC1]

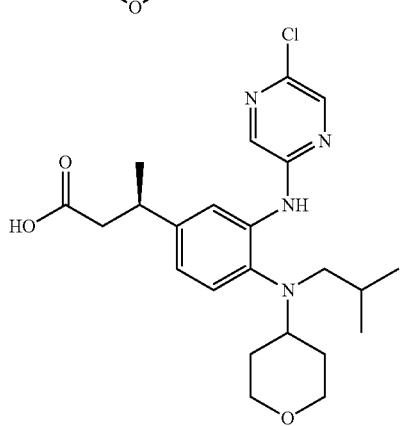

To a solution of methyl (R)-3-(3-((5-chloropyrazin-2-yl)amino)-4-(isobutyl(tetra hydro-2H-pyran-4-yl)amino)phenyl)butanoate (120 mg, 0.26 mmol) in MeOH (10 mL) was added 1N NaOH aq. (4 mL). After stirred at 40° C. for 8 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (86 mg, 74% yield) as a white powder. $^1$H NMR (400 MHz, CDCl$_3$) δ 8.37 (s, 1H), 8.19 (d, J=1.3 Hz, 1H), 8.16 (d, J=2.0 Hz, 1H), 7.95 (d, J=1.4 Hz, 1H), 7.14 (d, J=8.1 Hz, 1H), 6.85 (dd, J=8.1, 2.0 Hz, 1H), 4.01-3.89 (m, 2H), 3.35-3.19 (m, 3H), 2.91-2.52 (m, 5H), 1.76-1.42 (m, 5H), 1.35 (d, J=6.9 Hz, 3H), 0.87 (d, J=6.6 Hz, 6H). LCMS (ESI) m/z calcd for C$_{23}$H$_{31}$ClN$_4$O$_3$: 446.21. Found: 447.26/449.24 (M/M+2)$^+$.

Example 13

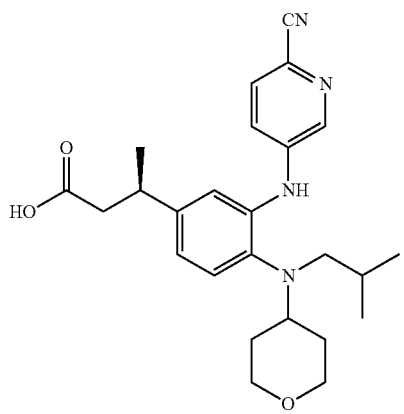

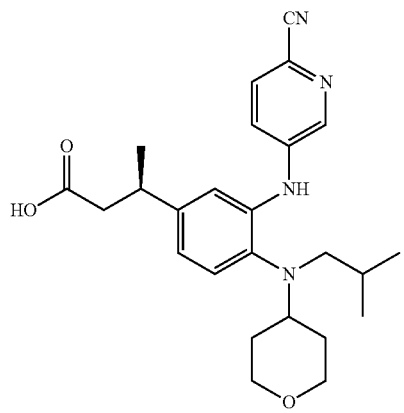

Preparation of methyl (R)-3-(3-(((6-cyanopyridin-3-yl)amino)-4-(isobutyl(tetra hydro-2H-pyran-4-yl)amino)phenyl)butanoate

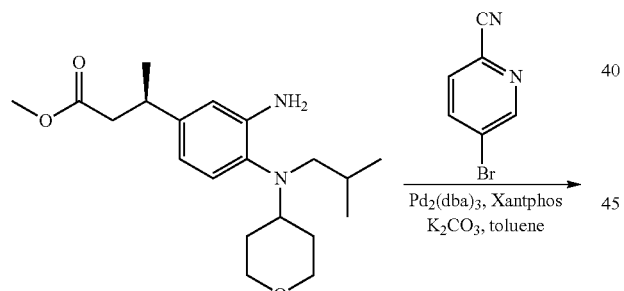

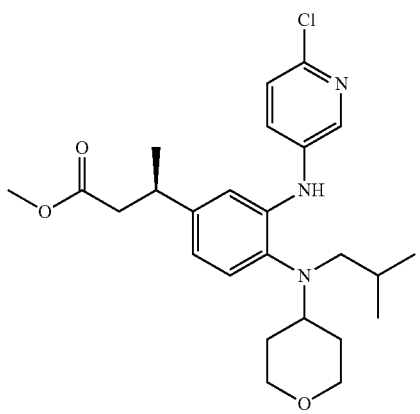 [SMILES: COC(=O)C[C@@H](C)c1ccc(N(CC(C)C)C2CCOCC2)c(Nc2ccc(Cl)nc2)c1]

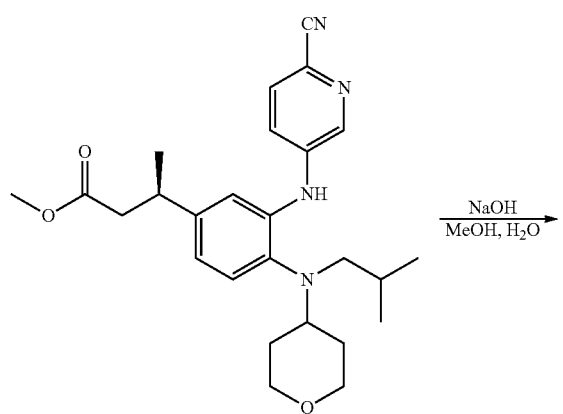

A mixture of methyl (R)-3-(3-amino-4-(isobutyl(tetrahydro-2H-pyran-4-yl)amino)phenyl) butanoate (250 mg, 0.72 mmol), 5-bromopicolinonitrile (263 mg, 1.44 mmol), Pd$_2$(dba)$_3$ (67 mg, 0.072 mmol), Xantphos (83 mg, 0.144 mmol) and K$_2$CO$_3$ (298 mg, 2.16 mmol) in toluene (8 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-50% EtOAc in PE) to afford the title compound (260 mg, 80% yield). LCMS (ESI) m/z calcd for C$_{26}$H$_{34}$N$_4$O$_3$: 450.26. Found: 451.38 (M+1)$^+$.

Preparation of (R)-3-(3-((6-cyanopyridin-3-yl)amino)-4-(isobutyl(tetrahydro-2H-pyran-4-yl)amino)phenyl)butanoic Acid

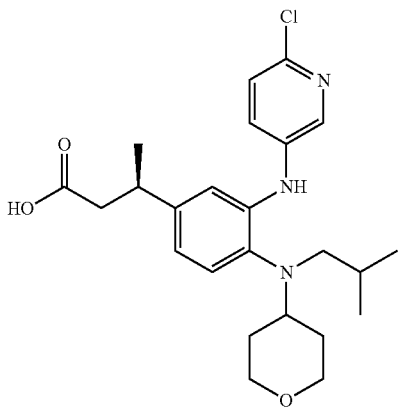

To a solution of methyl (R)-3-(3-((6-cyanopyridin-3-yl)amino)-4-(isobutyl(tetra hydro-2H-pyran-4-yl)amino)phenyl)butanoate (52 mg, 0.11 mmol) in THF (5 mL) was added 1N NaOH aq. (2 mL). After stirred at 30° C. for 24 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (41 mg, 82% yield) as a white powder. $^1$H NMR (400 MHz, $CDCl_3$) δ 8.43 (d, J=2.6 Hz, 1H), 7.56 (d, J=8.6 Hz, 1H), 7.49-7.41 (m, 2H), 7.23 (d, J=1.9 Hz, 1H), 7.16 (d, J=8.2 Hz, 1H), 6.89 (dd, J=8.2, 1.9 Hz, 1H), 3.97-3.87 (m, 2H), 3.30-3.18 (m, 3H), 2.84-2.72 (m, 3H), 2.68-2.60 (m, 2H), 1.68-1.41 (m, 5H), 1.34 (d, J=7.0 Hz, 3H), 0.85 (dd, J=6.6, 0.9 Hz, 6H). LCMS (ESI) m/z calcd for $C_{25}H_{32}N_4O_3$: 436.25. Found: 437.60 (M+1)$^+$.

Example 14

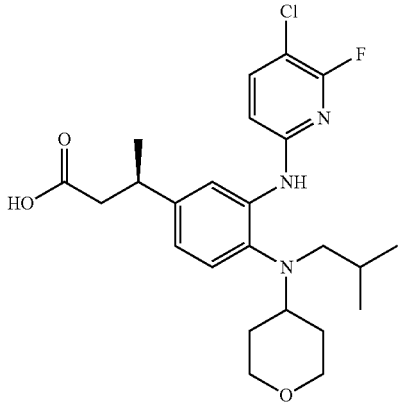 [SMILES: CC(C)CN(c1ccc([C@H](C)CC(=O)O)cc1Nc1ccc(Cl)c(F)n1)C1CCOCC1]

Preparation of (R)-3-(3-((5-chloro-6-fluoropyridin-2-yl)amino)-4-(isobutyl(tetrahydro-2H-pyran-4-yl)amino)phenyl)butanoic acid. A flask was charged with (R)-methyl 3-(3-amino-4-(isobutyl(tetrahydro-2H-pyran-4-yl)amino)phenyl)butanoate (60 mg, 0.172 mmol), 6-bromo-3-chloro-2-fluoropyridine (43.5 mg, 0.207 mmol), cesium carbonate (280 mg, 0.861 mmol), xantphos (39.8 mg, 0.069 mmol) and $Pd_2(dba)_3$ (31.5 mg, 0.034 mmol) while purging with nitrogen. Toluene (2.5 mL) was added and the mixture was degassed with nitrogen for several minutes. The mixture was heated to 100° C. and stirred for 90 minutes. The mixture was cooled, diluted with EtOAc and then filtered over Celite. The filtrate was washed with water, then brine, dried over sodium sulfate, filtered and concentrated. The residue was purified on silica gel (4 g column, 0-20% hexanes/EtOAc gradient elution) to afford (R)-methyl 3-(3-((5-chloro-6-fluoropyridin-2-yl)amino)-4-(isobutyl(tetrahydro-2H-pyran-4-yl)amino)phenyl)butanoate as a pale yellow residue (66 mg). A solution of (R)-methyl 3-(3-((5-chloro-6-fluoropyridin-2-yl)amino)-4-(isobutyl(tetrahydro-2H-pyran-4-yl)amino)phenyl)butanoate (29 mg, 0.061 mmol) in THF (0.6 mL) and MeOH (0.3 mL) was treated with 2M LiOH (0.303 mL, 0.607 mmol) and then allowed to stir at ambient temperature overnight. The mixture was adjusted to ~pH 7 with 1N HCl, then extracted with EtOAc. The extracts were washed with brine, dried over sodium sulfate, filtered and concentrated. The residue was purified by reverse phase chromatography to afford a white solid. An additional sample of (R)-methyl 3-(3-((5-chloro-6-fluoropyridin-2-yl)amino)-4-(isobutyl(tetrahydro-2H-pyran-4-yl)amino)phenyl)butanoate (36 mg) was subjected to the hydrolysis conditions. Following work-up the material was purified by reverse phase chromatography, then combined with the previous batch to afford a white solid (17.5 mg). $^1$H NMR (400 MHz, CHLOROFORM-d) δ=8.12 (s, 1H), 8.04 (m, 1H), 7.56 (t, J=8.9 Hz, 1H), 7.11 (d, J=8.1 Hz, 1H), 6.84 (d, J=8.1 Hz, 1H), 6.59 (d, J=8.4 Hz, 1H), 3.95 (m, 2H), 3.35-3.19 (m, 3H), 2.87-2.67 (m, 4H), 2.66-2.56 (m, 1H), 1.80-1.56 (m, 4H), 1.52-1.40 (m, 1H), 1.36 (m, 3H), 0.86 (d, J=6.4 Hz, 6H); LC/MS (m/z) ES$^+$ calcd for $C_{24}H_{31}ClFN_3O_3$: 463.20. Found: 464 (M+1).

Example 15

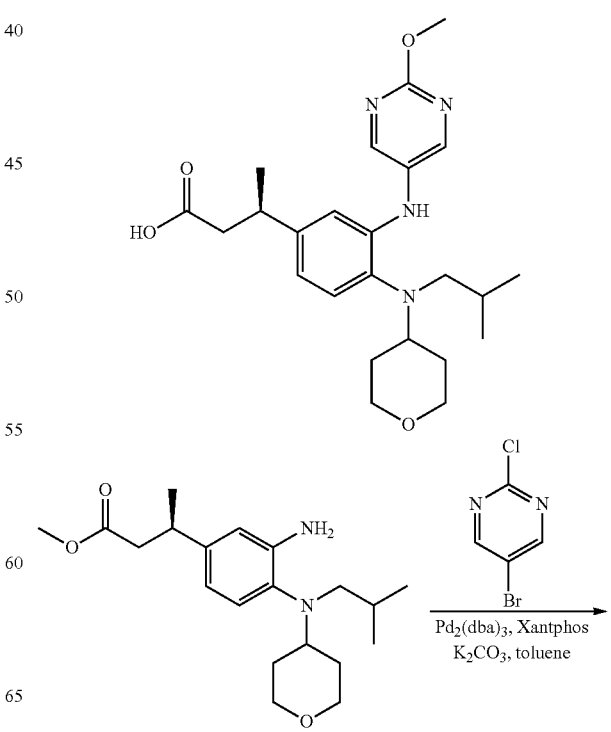

-continued

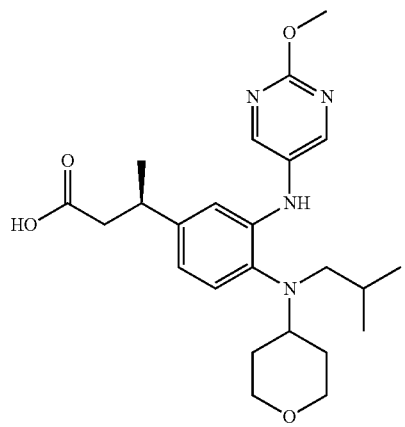 [SMILES: COc1ncc(Nc2cc([C@H](C)CC(=O)O)ccc2N(CC(C)C)C2CCOCC2)cn1]

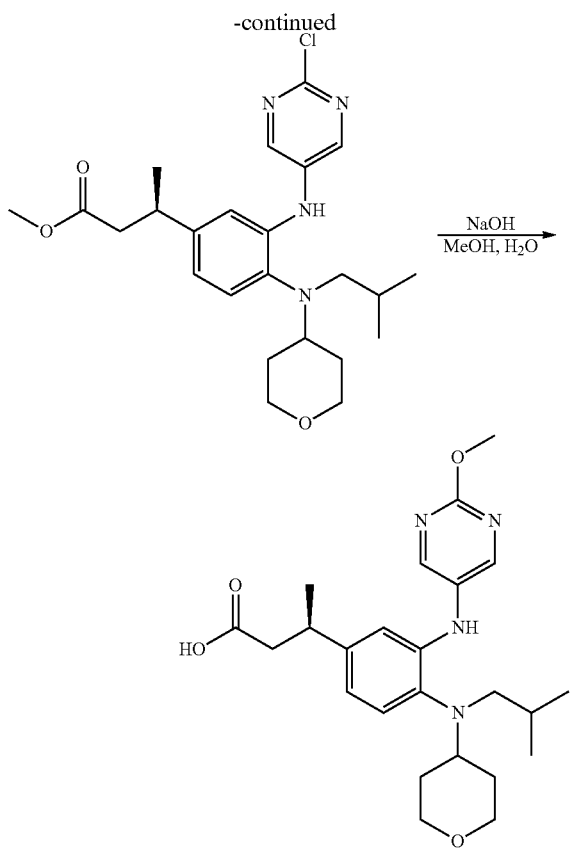

Preparation of methyl (R)-3-(3-((2-chloropyrimidin-5-yl)amino)-4-(isobutyl(tetra hydro-2H-pyran-4-yl)amino)phenyl)butanoate

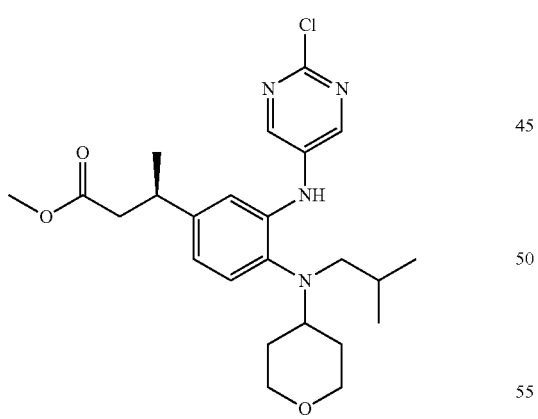

A mixture of methyl (R)-3-(3-amino-4-(isobutyl(tetrahydro-2H-pyran-4-yl)amino)phenyl) butanoate (240 mg, 0.68 mmol), 5-bromo-2-chloropyrimidine (262 mg, 1.36 mmol), Pd$_2$(dba)$_3$ (65 mg, 0.072 mmol), Xantphos (80 mg, 0.14 mmol) and K$_2$CO$_3$ (286 mg, 2.1 mmol) in toluene (10 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (170 mg, 54% yield). LCMS (ESI) m/z calcd for C$_{24}$H$_{33}$ClN$_4$O$_3$: 460.22. Found: 461.57/463.54 (M/M+2)$^+$.

Preparation of (R)-3-(4-(isobutyl(tetrahydro-2H-pyran-4-yl)amino)-3-((2-methoxy pyrimidin-5-yl)amino)phenyl)butanoic Acid

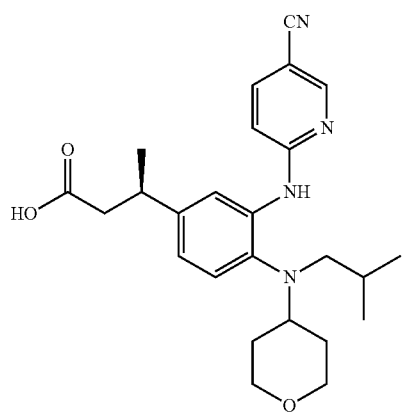

To a solution of methyl (R)-3-(3-((2-chloropyrimidin-5-yl)amino)-4-(isobutyl(tetra hydro-2H-pyran-4-yl)amino) phenyl)butanoate (150 mg, 0.33 mmol) in MeOH (8 mL) was added 1N NaOH aq. (4 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (80 mg, 55% yield) as a white powder. $^1$H NMR (400 MHz, CDCl$_3$) δ 8.42 (s, 2H), 7.09 (d, J=8.1 Hz, 1H), 6.87-6.78 (m, 2H), 6.70 (dd, J=8.1, 1.9 Hz, 1H), 4.02 (s, 3H), 4.00-3.93 (m, 2H), 3.36-3.25 (m, 2H), 3.21-3.12 (m, 1H), 2.87-2.70 (m, 3H), 2.63-2.48 (m, 2H), 1.79-1.39 (m, 5H), 1.27 (d, J=6.9 Hz, 3H), 0.86 (d, J=6.4 Hz, 6H). LCMS (ESI) m/z calcd for C$_{24}$H$_{34}$N$_4$O$_4$: 442.26. Found: 443.66 (M+1)$^+$.

Example 16

-continued

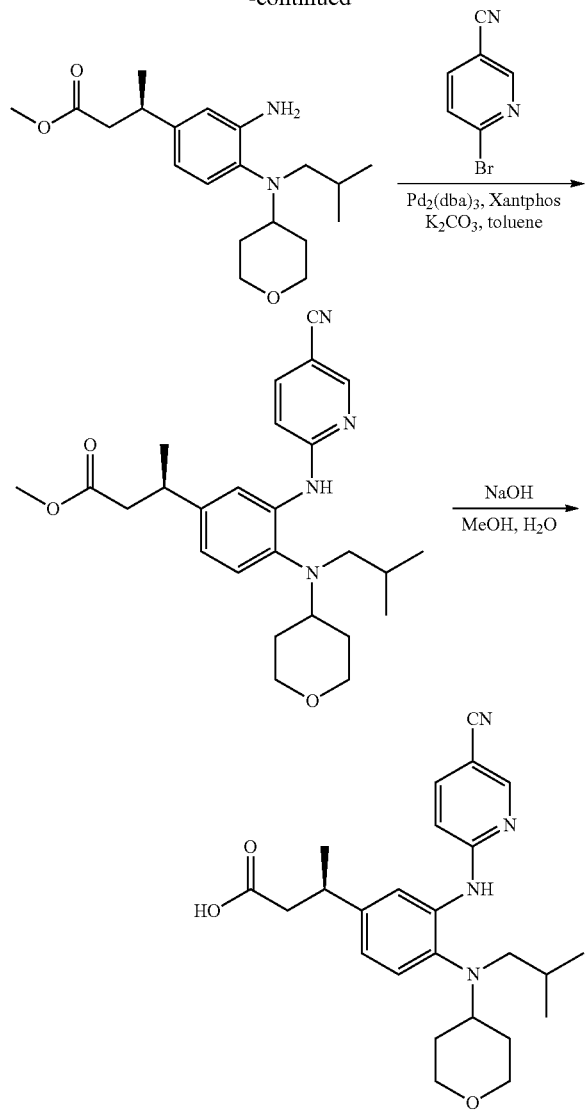

Preparation of methyl (R)-3-(3-((5-cyanopyridin-2-yl)amino)-4-(isobutyl(tetra hydro-2H-pyran-4-yl)amino)phenyl)butanoate

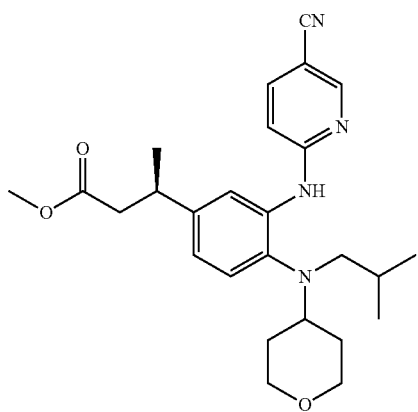 [SMILES: COC(=O)C[C@@H](C)c1ccc(N(CC(C)C)C2CCOCC2)c(Nc2ccc(C#N)cn2)c1]

A mixture of methyl (R)-3-(3-amino-4-(isobutyl(tetrahydro-2H-pyran-4-yl)amino)phenyl) butanoate (200 mg, 0.575 mmol), 6-bromonicotinonitrile (210 mg, 1.15 mmol), $Pd_2(dba)_3$ (60 mg, 0.0575 mmol), Xantphos (66 mg, 0.115 mmol) and $K_2CO_3$ (238 mg, 1.73 mmol) in toluene (8 mL) was stirred at 100° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (100 mg, 38% yield). LCMS (ESI) m/z calcd for $C_{26}H_{34}N_4O_3$: 450.26. Found: 451.38 (M+1)$^+$.

Preparation of (R)-3-(3-((5-cyanopyridin-2-yl)amino)-4-(isobutyl(tetrahydro-2H-pyran-4-yl)amino)phenyl)butanoic Acid

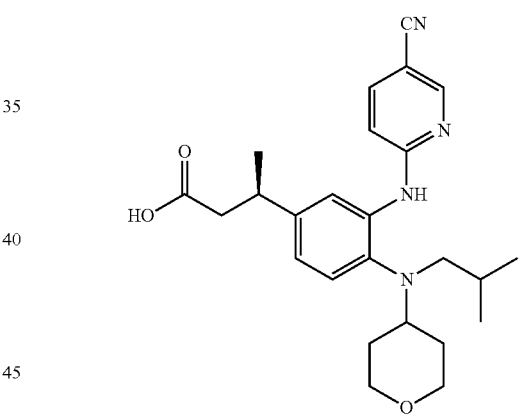

To a solution of methyl (R)-3-(3-((5-cyanopyridin-2-yl)amino)-4-(isobutyl(tetra hydro-2H-pyran-4-yl)amino)phenyl)butanoate (100 mg, 0.22 mmol) in MeOH (4 mL) was added 1N NaOH aq. (2 mL). After stirred at rt for 5 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (27 mg, 28% yield) as a white powder. $^1$H NMR (400 MHz, $CDCl_3$) δ 8.54 (d, J=1.9 Hz, 1H), 8.47 (s, 1H), 8.19 (d, J=1.9 Hz, 1H), 7.67 (dd, J=8.8, 2.3 Hz, 1H), 7.14 (d, J=8.2 Hz, 1H), 6.89 (dd, J=8.2, 2.0 Hz, 1H), 6.73 (d, J=8.7 Hz, 1H), 4.01-3.88 (m, 2H), 3.33-3.18 (m, 3H), 2.89-2.57 (m, 5H), 1.64-1.46 (m, 5H), 1.36 (d, J=7.0 Hz, 3H), 0.86 (d, J=6.6 Hz, 6H). LCMS (ESI) m/z calcd for $C_{25}H_{32}N_4O_3$: 436.25. Found: 437.17 (M+1)$^+$.

Example 17

Preparation of methyl (R)-3-(3-((2-cyanopyrimidin-5-yl)amino)-4-(isobutyl(tetra hydro-2H-pyran-4-yl)amino)phenyl)butanoate

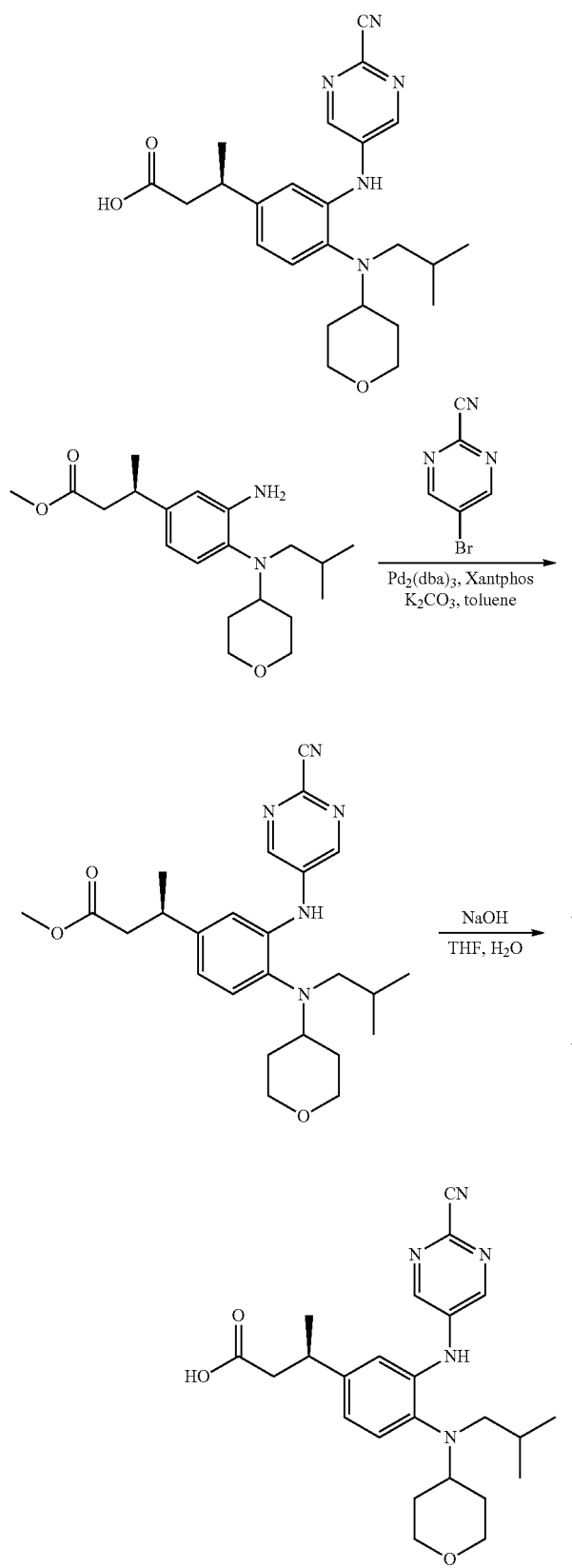

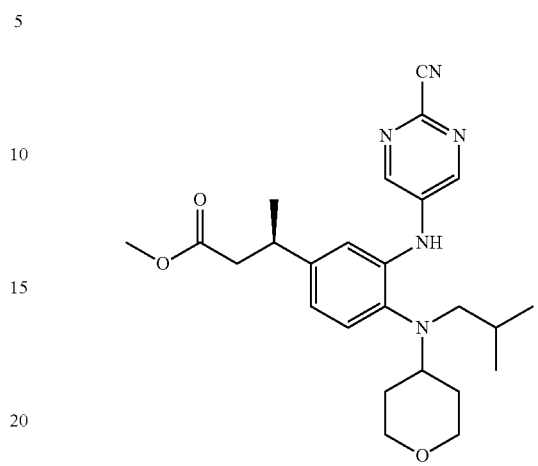

A mixture of methyl (R)-3-(3-amino-4-(isobutyl(tetrahydro-2H-pyran-4-yl)amino)phenyl) butanoate (200 mg, 0.58 mmol), 5-bromopyrimidine-2-carbonitrile (213 mg, 1.16 mmol), Pd$_2$(dba)$_3$ (53 mg, 0.06 mmol), Xantphos (67 mg, 0.12 mmol) and K$_2$CO$_3$ (238 mg, 1.7 mmol) in toluene (10 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-40% EtOAc in PE) to afford the title compound (200 mg, 77% yield). LCMS (ESI) m/z calcd for C$_{25}$H$_{33}$N$_5$O$_3$: 451.26. Found: 452.46 (M+1)$^+$.

Preparation of (R)-3-(3-((2-cyanopyrimidin-5-yl)amino)-4-(isobutyl(tetrahydro-2H-pyran-4-yl)amino)phenyl)butanoic Acid To a solution of methyl (R)-3-(3-((2-cyanopyrimidin-5-yl)amino)-4-(isobutyl(tetra hydro-2H-pyran-4-yl)amino)phenyl)butanoate (200 mg, 0.44 mmol) in THF (5 mL) was added 1N NaOH aq. (3 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H₂O with 0.1% formic acid) to afford the title compound (95 mg, 49% yield) as a white powder. ¹H NMR (400 MHz, CDCl₃) δ 8.59 (s, 2H), 7.54 (s, 1H), 7.24 (d, J=1.9 Hz, 1H), 7.19 (d, J=8.2 Hz, 1H), 6.94 (dd, J=8.2, 1.9 Hz, 1H), 3.99-3.88 (m, 2H), 3.35-3.16 (m, 3H), 2.87-2.72 (m, 3H), 2.63 (d, J=7.4 Hz, 2H), 1.71-1.41 (m, 5H), 1.34 (d, J=7.0 Hz, 3H), 0.85 (dd, J=6.6, 1.1 Hz, 6H). LCMS (ESI) m/z calcd for $C_{24}H_{31}N_5O_3$: 437.24. Found: 438.70 (M+1)⁺.

Example 18

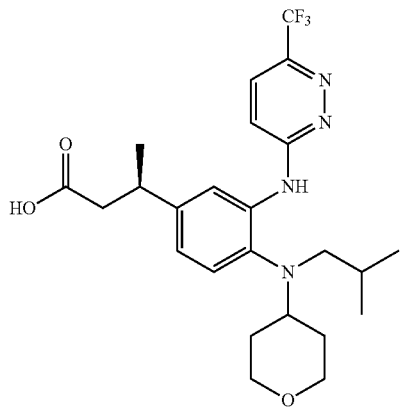

Preparation of methyl (R)-3-(4-(isobutyl(tetrahydro-2H-pyran-4-yl)amino)-3-((6-(trifluoromethyl)pyridazin-3-yl)amino)phenyl)butanoate

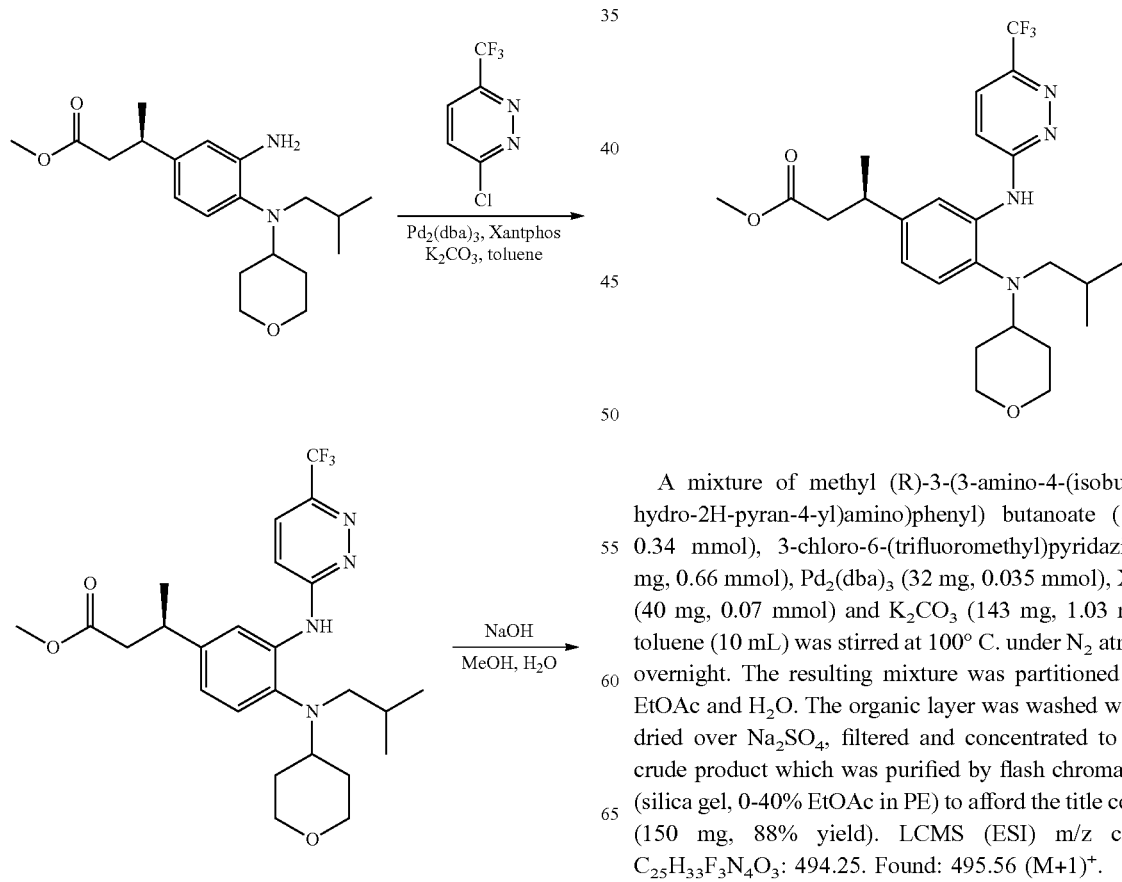

A mixture of methyl (R)-3-(3-amino-4-(isobutyl(tetrahydro-2H-pyran-4-yl)amino)phenyl) butanoate (120 mg, 0.34 mmol), 3-chloro-6-(trifluoromethyl)pyridazine (121 mg, 0.66 mmol), Pd₂(dba)₃ (32 mg, 0.035 mmol), Xantphos (40 mg, 0.07 mmol) and K₂CO₃ (143 mg, 1.03 mmol) in toluene (10 mL) was stirred at 100° C. under N₂ atmosphere overnight. The resulting mixture was partitioned between EtOAc and H₂O. The organic layer was washed with brine, dried over Na₂SO₄, filtered and concentrated to give the crude product which was purified by flash chromatography (silica gel, 0-40% EtOAc in PE) to afford the title compound (150 mg, 88% yield). LCMS (ESI) m/z calcd for $C_{25}H_{33}F_3N_4O_3$: 494.25. Found: 495.56 (M+1)⁺.

Preparation of (R)-3-(4-(isobutyl(tetrahydro-2H-pyran-4-yl)amino)-3-((6-(trifluoro methyl)pyridazin-3-yl)amino)phenyl)butanoic Acid

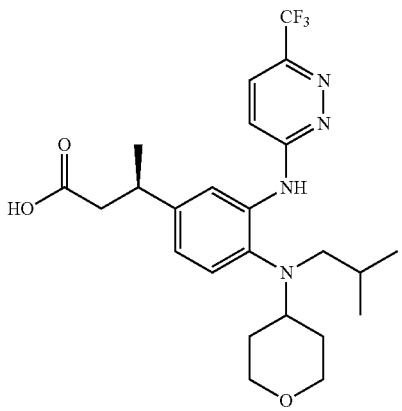

To a solution of methyl (R)-3-(4-(isobutyl(tetrahydro-2H-pyran-4-yl)amino)-3-((6-(trifluoromethyl)pyridazin-3-yl)amino)phenyl)butanoate (150 mg, 0.30 mmol) in MeOH (10 mL) was added 1N NaOH aq. (4 mL). After stirred at r.t. overnight, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (69 mg, 48% yield) as a white powder. $^1$H NMR (400 MHz, $CDCl_3$) δ 8.74 (br, 1H), 8.20 (d, J=1.9 Hz, 1H), 7.50 (d, J=9.3 Hz, 1H), 7.10 (d, J=8.2 Hz, 1H), 7.00 (d, J=7.7 Hz, 1H), 6.88 (dd, J=8.2, 1.9 Hz, 1H), 3.95-3.82 (m, 2H), 3.32-3.14 (m, 3H), 2.86-2.78 (m, 3H), 2.65-2.57 (m, 2H), 1.77-1.36 (m, 5H), 1.29 (d, J=7.0 Hz, 3H), 0.80 (d, J=6.6 Hz, 6H). LCMS (ESI) m/z calcd for $C_{24}H_{31}F_3N_4O_3$: 480.23. Found: 481.49 (M+1)$^+$.

Example 19

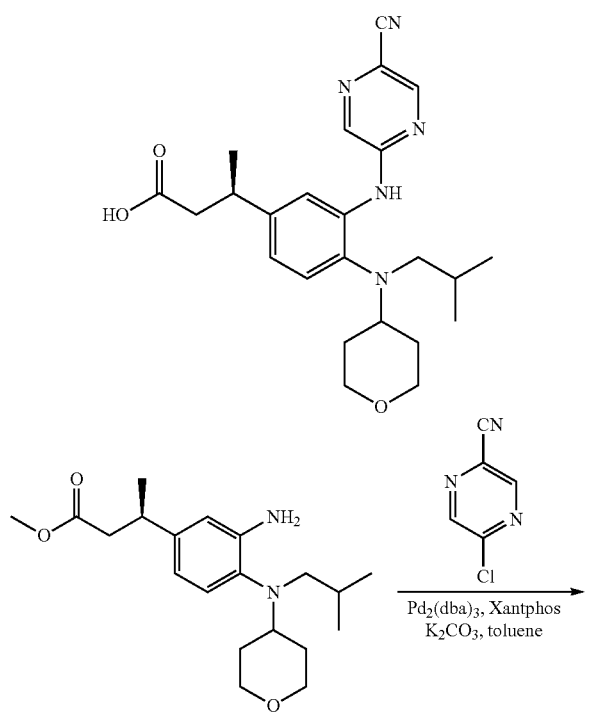

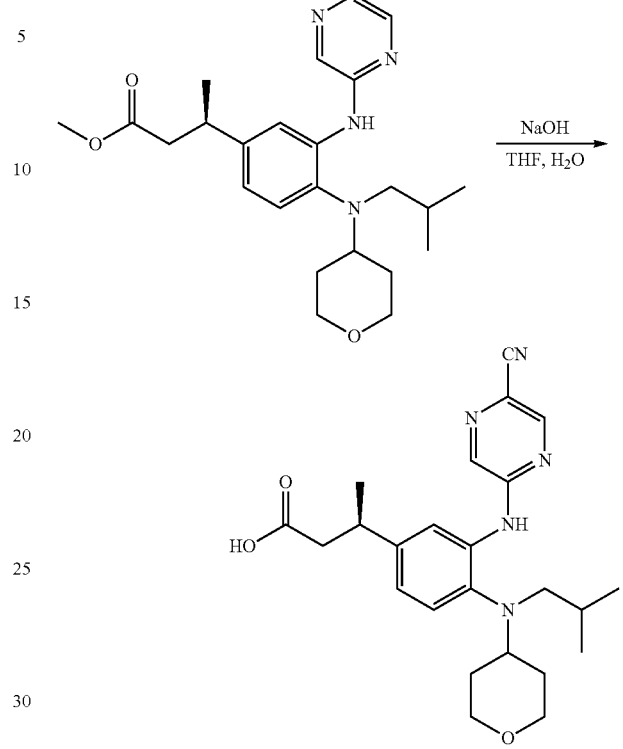

Preparation of methyl (R)-3-(3-((5-cyanopyrazin-2-yl)amino)-4-(isobutyl(tetra hydro-2H-pyran-4-yl)amino)phenyl)butanoate A mixture of methyl (R)-3-(3-amino-4-(isobutyl(tetrahydro-2H-pyran-4-yl)amino)phenyl) butanoate (220 mg, 0.63 mmol), 5-chloropyrazine-2-carbonitrile (177 mg, 1.27 mmol), $Pd_2(dba)_3$ (58 mg, 0.064 mmol), Xantphos (74 mg, 0.13 mmol) and $K_2CO_3$ (262 mg, 1.9 mmol) in toluene (10 mL) was stirred at 100° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-40% EtOAc in PE) to afford the title compound (70 mg, 25% yield). LCMS (ESI) m/z calcd for $C_{25}H_{33}N_5O_3$: 451.26. Found: 452.46 (M+1)+.

Preparation of (R)-3-(3-((5-cyanopyrazin-2-yl) amino)-4-(isobutyl(tetrahydro-2H-pyran-4-yl)amino) phenyl)butanoic Acid

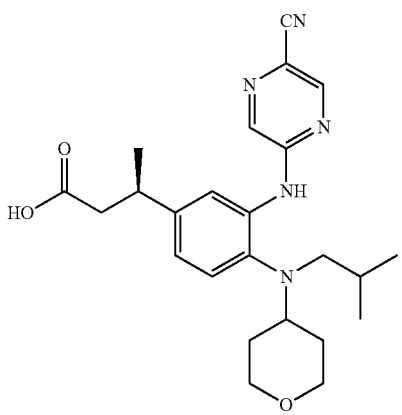

To a solution of methyl (R)-3-(3-((5-cyanopyrazin-2-yl) amino)-4-(isobutyl(tetra hydro-2H-pyran-4-yl)amino)phenyl)butanoate (70 mg, 0.16 mmol) in THF (6 mL) was added 1N NaOH aq. (3 mL). After stirred at r.t. overnight, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (27 mg, 39% yield) as a white powder. $^1$H NMR (400 MHz, $CDCl_3$) δ 8.96 (s, 1H), 8.50 (d, J=1.3 Hz, 1H), 8.36 (d, J=1.9 Hz, 1H), 8.10 (d, J=1.3 Hz, 1H), 7.19 (d, J=8.2 Hz, 1H), 6.95 (dd, J=8.2, 2.0 Hz, 1H), 4.01-3.88 (m, J=10.7 Hz, 2H), 3.37-3.24 (m, 3H), 2.94-2.76 (m, 3H), 2.77-2.60 (m, 2H), 1.73-1.44 (m, 5H), 1.36 (d, J=6.9 Hz, 3H), 0.88 (d, J=6.6 Hz, 6H). LCMS (ESI) m/z calcd for $C_{24}H_{31}N_5O_3$: 437.24. Found: 438.65 (M+1)+.

Example 20

Step A (R)-Methyl 3-(4-(isobutyl(tetrahydro-2H-pyran-4-yl) amino)-3-((3-(trifluoromethyl)-1,2,4-thiadiazol-5-yl) amino)phenyl)butanoate

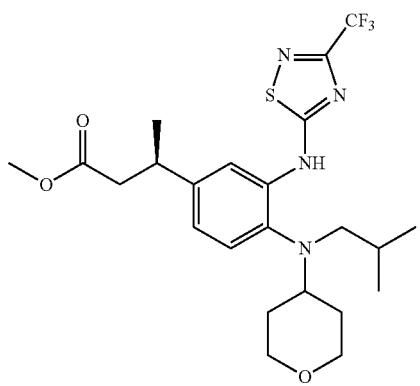 [SMILES: COC(=O)C[C@@H](C)c1ccc(N(CC(C)C)C2CCOCC2)c(Nc2nc(C(F)(F)F)ns2)c1]

5-chloro-3-(trifluoromethyl)-1,2,4-thiadiazole (72.7 mg, 0.386 mmol) was added to a solution of (R)-methyl 3-(3-amino-4-(isobutyl(tetrahydro-2H-pyran-4-yl)amino)phenyl)butanoate (103.4 mg, 0.297 mmol) in N,N-Dimethylformamide (989 μl). The reaction mixture was heated at 90° C. overnight. Aqueous sodium bicarbonate solution was added and the reaction mixture was extracted with EtOAc. The organic layer was dried ($Na_2SO_4$), filtered, evaporated and purified by silica gel chromatography (0-40% EtOAc/hexanes) to obtain (R)-methyl 3-(4-(isobutyl(tetrahydro-2H-pyran-4-yl)amino)-3-((3-(trifluoromethyl)-1,2,4-thiadiazol-5-yl)amino)phenyl)butanoate (89.9 mg, 0.180 mmol, 61 yield). LCMS (M+H)+: m/z=501.3.

Step B (R)-3-(4-(Isobutyl(tetrahydro-2H-pyran-4-yl)amino)- 3-((3-(trifluoromethyl)-1,2,4-thiadiazol-5-yl)amino) phenyl)butanoic Acid

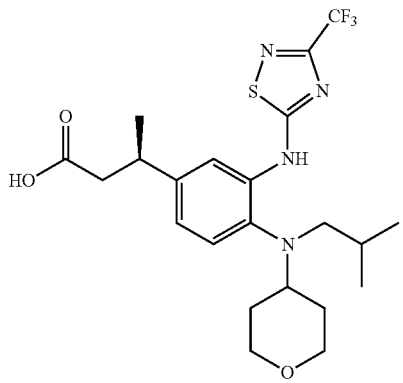

(R)-methyl 3-(4-(isobutyl(tetrahydro-2H-pyran-4-yl) amino)-3-((3-(trifluoromethyl)-1,2,4-thiadiazol-5-yl)amino) phenyl)butanoate (0.0899 g, 0.18 mmol) was subjected to base hydrolysis as previously described and purified by reverse phase chromatography (10-100% $CH_3CN/H_2O$ (0.1% formic acid)) to afford the title compound (0.0586 g, 67%) as a white solid. LCMS (M+H)+: m/z=487.3. $^1$H NMR (400 MHz, $CD_3OD$) δ ppm 7.82 (s, 1H), 7.28 (d, J=8.2 Hz, 1H), 7.06 (dd, J=8.2, 2.0 Hz, 1H), 3.88 (dd, J=11.4, 4.0 Hz, 2H), 3.20-3.26 (m, 3H), 2.87-2.96 (m, 1H), 2.84 (d, J=6.8 Hz, 2H), 2.48-2.64 (m, 2H), 1.72 (m, 2H), 1.56 (qd, J=12.2, 4.5 Hz, 2H), 1.37 (m, 1H), 1.31 (d, J=7.0 Hz, 3H), 0.82 (d, J=6.6 Hz, 6H). LCMS (M+H)+: m/z=487.3.

Example 21

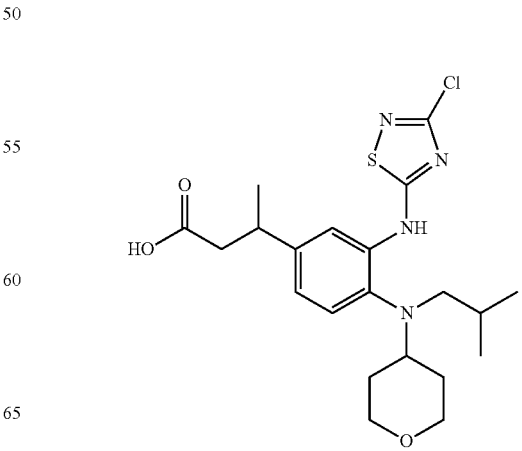

-continued

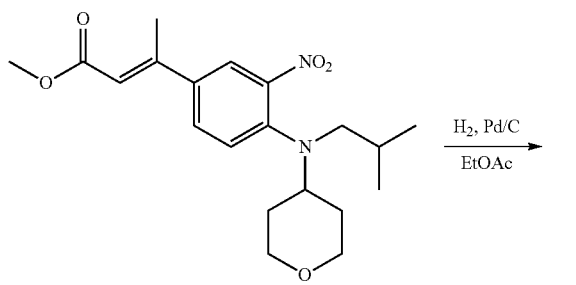

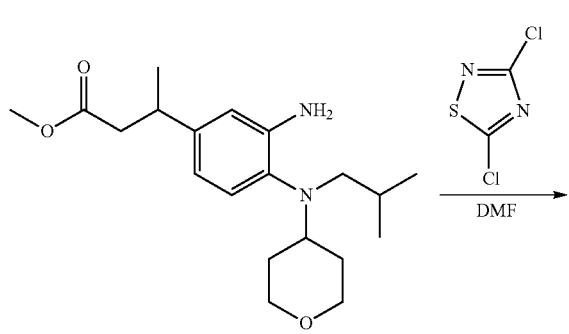

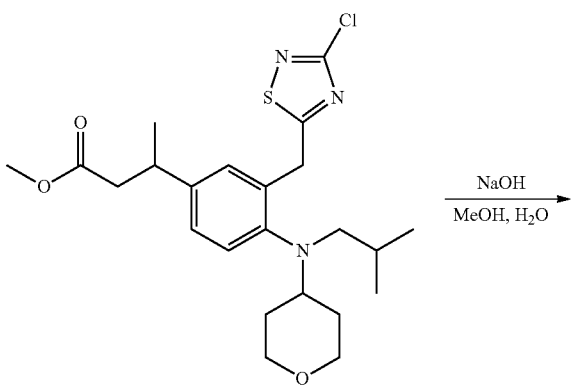

Preparation of methyl 3-(3-amino-4-(isobutyl(tetrahydro-2H-pyran-4-yl)amino) phenyl)butanoate

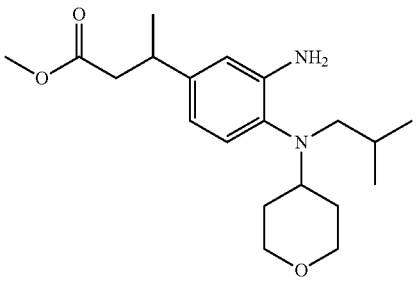 [SMILES: COC(=O)CC(C)c1ccc(N(CC(C)C)C2CCOCC2)c(N)c1]

A mixture of methyl (E)-3-(4-(isobutyl(tetrahydro-2H-pyran-4-yl)amino)-3-nitrophenyl) but-2-enoate (1.3 g, 3.44 mmol) and 10% Pd/C (750 mg) in EtOAc (20 mL) was stirred at 50° C. under H₂ atmosphere for 4 hr. The resulting mixture was filtered through a pad of Celite and the filtrate was concentrated under reduced pressure to give the crude product which was purified by flash chromatography (silica gel, 0-30% EtOAc in PE) to afford the title compound (1.1 g, 92% yield). LCMS (ESI) m/z calcd for $C_{20}H_{32}N_2O_3$: 348.24. Found: 349.64 (M+1)⁺.

Preparation of methyl 3-(3-((3-chloro-1,2,4-thiadiazol-5-yl)amino)-4-(isobutyl (tetrahydro-2H-pyran-4-yl)amino)phenyl)butanoate

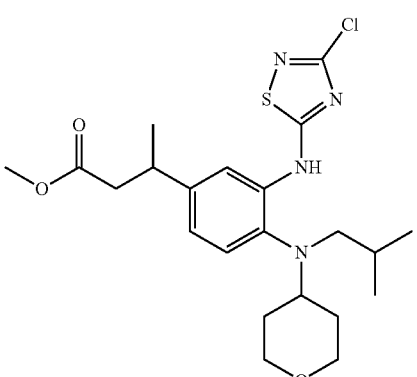

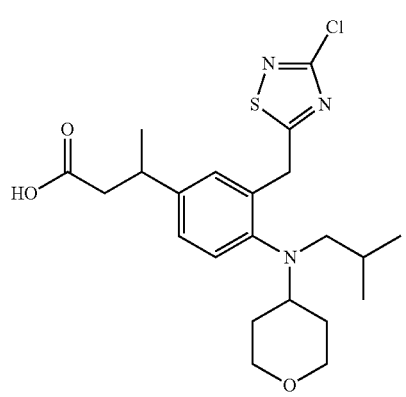

A mixture of methyl 3-(3-amino-4-(isobutyl(tetrahydro-2H-pyran-4-yl)amino)phenyl) butanoate (200 mg, 0.57 mmol) and 3,5-dichloro-1,2,4-thiadiazole (177 mg, 1.14 mmol) in DMF (4 mL) was stirred at 90° C. overnight. The resulting mixture was partitioned between EtOAc and H₂O. The organic layer was washed with brine, dried over Na₂SO₄, filtered and concentrated to give the crude product which was purified by flash chromatography (silica gel, 0-20% EtOAc in PE) to afford the title compound (170 mg, 64% yield). LCMS (ESI) m/z calcd for $C_{22}H_{31}ClN_4O_3S$: 466.18. Found: 467.21/469.15 (M/M+2)⁺.

Preparation of 3-(3-((3-chloro-1,2,4-thiadiazol-5-yl)amino)-4-(isobutyl(tetrahydro-2H-pyran-4-yl)amino)phenyl)butanoic Acid

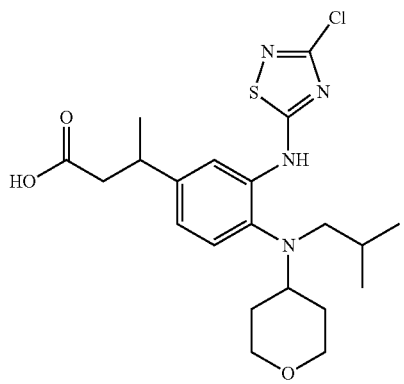 [SMILES: CC(C)CN(c1ccc(C(C)CC(=O)O)cc1Nc1nc(Cl)ns1)C1CCOCC1]

To a solution of methyl 3-(3-((3-chloro-1,2,4-thiadiazol-5-yl)amino)-4-(isobutyl (tetrahydro-2H-pyran-4-yl)amino)phenyl)butanoate (170 mg, 0.36 mmol) in MeOH (2 mL) was added 4N NaOH aq. (0.5 mL). After stirred at r.t. for 6 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (24 mg, 14% yield) as a white powder. $^1$H NMR (400 MHz, $CDCl_3$) δ 9.39 (s, 1H), 7.21 (d, J=8.2 Hz, 1H), 7.17 (d, J=1.7 Hz, 1H), 6.98 (dd, J=8.2, 1.8 Hz, 1H), 4.02-3.91 (m, 2H), 3.36-3.22 (m, 3H), 2.88-2.76 (m, 3H), 2.74-2.59 (m, 2H), 1.79-1.43 (m, 5H), 1.37 (d, J=7.0 Hz, 3H), 0.85 (d, J=6.6 Hz, 6H). LCMS (ESI) m/z calcd for $C_{21}H_{29}ClN_4O_3S$: 452.16. Found: 453.18/455.17 $(M/M+2)^+$.

Example 22

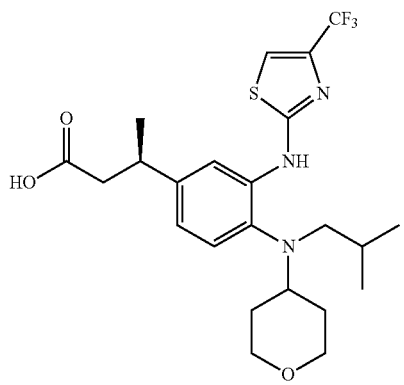 [SMILES: CC(C)CN(c1ccc([C@H](C)CC(=O)O)cc1Nc1nc(C(F)(F)F)cs1)C1CCOCC1]

Preparation of (R)-3-(4-(Isobutyl(tetrahydro-2H-pyran-4-yl)amino)-3-((4-(trifluoromethyl)thiazol-2-yl)amino)phenyl)butanoic Acid 3-Bromo-1,1,1-trifluoropropan-2-one (78 mg, 0.410 mmol) was added to a solution of (R)-methyl 3-(4-(isobutyl(tetrahydro-2H-pyran-4-yl)amino)-3-thioureidophenyl)butanoate (84 mg, 0.205 mmol) in ethanol (2 mL). The reaction mixture was heated for 3 h at 80° C. Aqueous sodium bicarbonate solution was added and the reaction mixture was extracted with EtOAc. The organic layer was washed with brine, dried ($Na_2SO_4$), filtered, evaporated. The residue was subjected to base hydrolysis as previously described and purified by reverse phase chromatography (10-100% $CH_3CN/H_2O$ (0.1% formic acid)) to afford the title compound (0.0877 g, 88%) as a white solid. LCMS $(M+H)^+$: m/z=486.3. $^1$H NMR (400 MHz, $CD_3OD$) δ ppm 7.84 (br. s, 1H), 7.39 (s, 1H), 7.27 (d, J=8.2 Hz, 1H), 6.96-7.02 (m, 1H), 3.91 (dd, J=11.5, 3.8 Hz, 2H), 3.20-3.28 (m, 3H), 2.81-2.97 (m, 3H), 2.51-2.67 (m, 2H), 1.77 (m, 2H), 1.58 (qd, J=12.2, 4.5 Hz, 2H), 1.41 (m, 1H), 1.33 (d, J=6.8 Hz, 3H), 0.87 (d, J=6.6 Hz, 6H).

Example 23

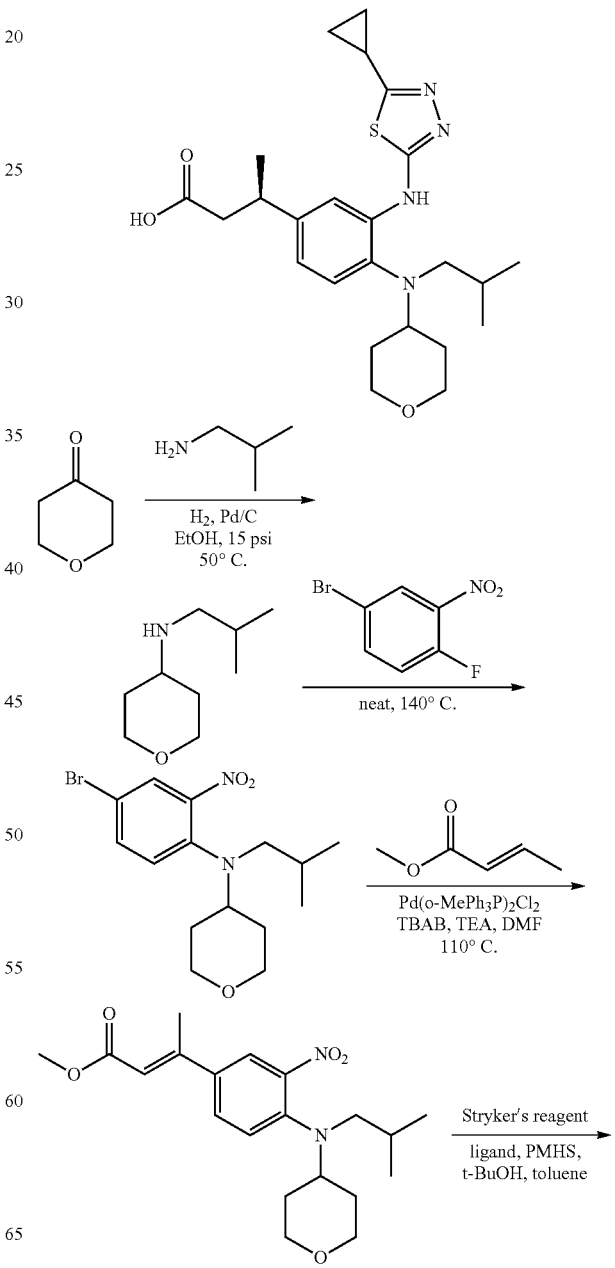

73

-continued

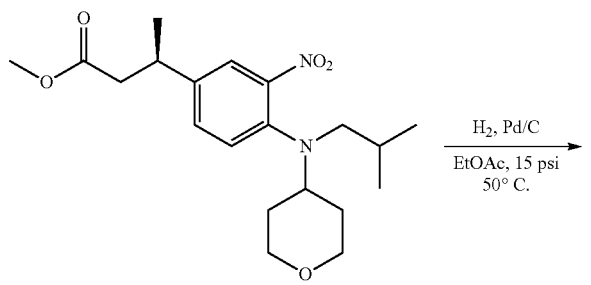

H₂, Pd/C
────────
EtOAc, 15 psi
50° C.

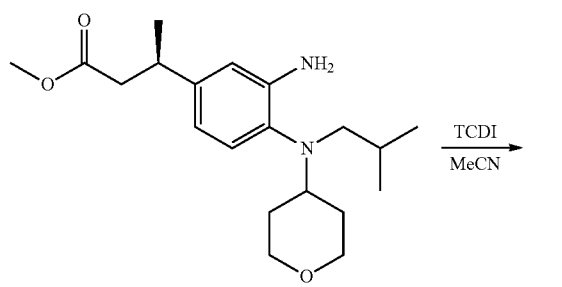

TCDI
────
MeCN

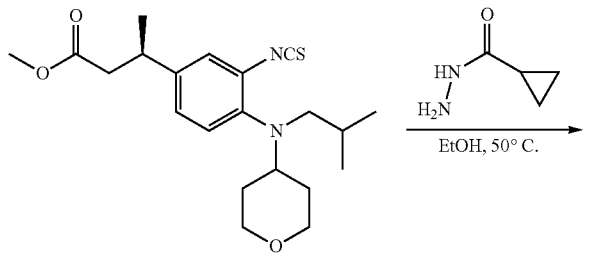

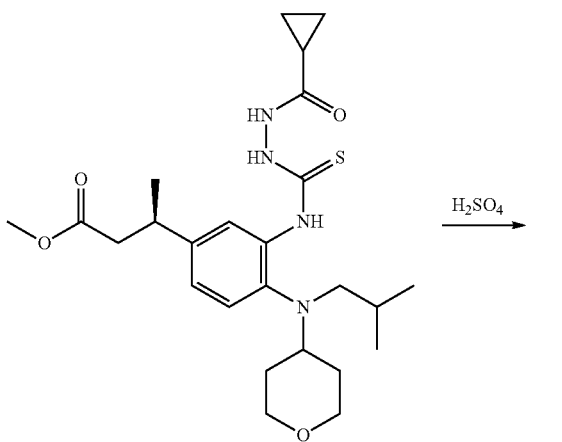

H₂SO₄
─────

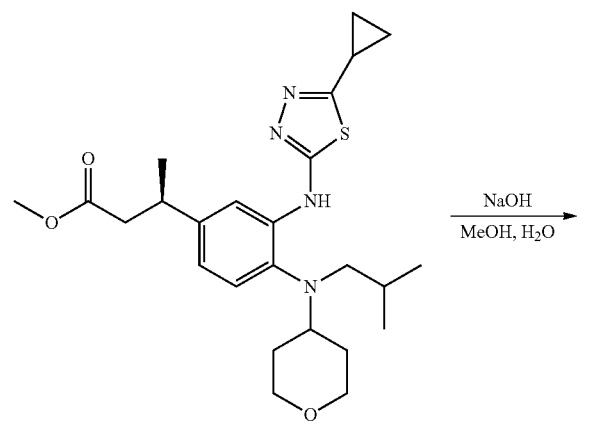

NaOH
────────
MeOH, H₂O

74

-continued

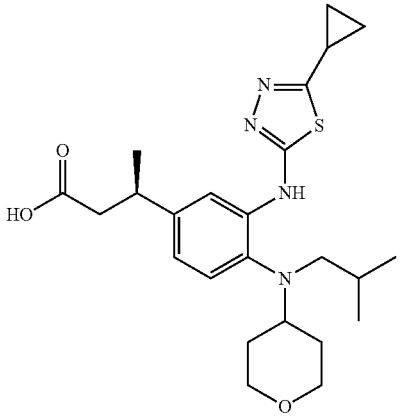 [SMILES: CC(C)CN(c1ccc([C@H](C)CC(=O)O)cc1Nc1nnc(C2CC2)s1)C1CCOCC1]

Preparation of
N-isobutyltetrahydro-2H-pyran-4-amine

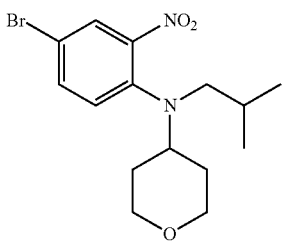 [SMILES: CC(C)CN(c1ccc(Br)cc1[N+](=O)[O-])C1CCOCC1]

To a solution of tetrahydro-4H-pyran-4-one (181.4 g, 1811 mmol) in ethanol (1.8 L) was added isobutylamine (183 mL, 1811 mmol). After stirring at 50° C. under H₂ atmosphere (15 psi) overnight, the resulting mixture was concentrated under reduced pressure to afford the title compound (285 g, 100% yield) as a yellow oil, which was used in the following step without purification. ¹H NMR (400 MHz, CDCl₃) δ 4.01-3.93 (m, 2H), 3.39 (td, J=11.7, 2.2 Hz, 2H), 2.67-2.60 (m, 1H), 2.44 (d, J=6.8 Hz, 2H), 1.87-1.78 (m, 2H), 1.76-1.66 (m, 1H), 1.44-1.34 (m, 2H), 0.91 (d, J=6.6 Hz, 6H).

Preparation of N-(4-bromo-2-nitrophenyl)-N-isobutyltetrahydro-2H-pyran-4-amine

A mixture of 4-bromo-1-fluoro-2-nitrobenzene (199 g, 906 mmol) and N-isobutyltetra hydro-2H-pyran-4-amine (285 g, 1811 mmol) was stirred at 140° C. under N₂ atmosphere for 9 hr. The resulting mixture was purified on silica gel (0-10% EtOAc in PE) to afford the title compound (237 g, 73% yield) as a red oil. LCMS (ESI) m/z calcd for C₁₅H₂₁BrN₂O₃: 356.07. Found: 357.24/359.25 (M/M+2)⁺. ¹H NMR (400 MHz, CDCl₃) δ 7.80 (d, J=2.4 Hz, 1H), 7.51

(dd, J=8.8, 2.4 Hz, 1H), 7.12 (d, J=8.8 Hz, 1H), 3.97 (dd, J=11.4, 4.4 Hz, 2H), 3.30 (td, J=11.7, 2.3 Hz, 2H), 3.13-3.06 (m, 1H), 2.86 (d, J=7.2 Hz, 2H), 1.85-1.66 (m, 4H), 1.63-1.52 (m, 1H), 0.86 (d, J=6.6 Hz, 6H).

Preparation of methyl (E)-3-(4-(isobutyl(tetrahydro-2H-pyran-4-yl)amino)-3-nitro phenyl)but-2-enoate

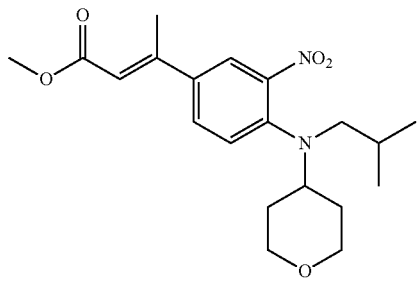 [SMILES: COC(=O)/C=C(\C)c1ccc(N(CC(C)C)C2CCOCC2)c([N+](=O)[O-])c1]

A mixture of N-(4-bromo-2-nitrophenyl)-N-isobutyltetrahydro-2H-pyran-4-amine (237 g, 663.4 mmol), methyl (E)-but-2-enoate (133 g, 1327 mmol), TBAB (42.8 g, 132.7 mmol), Pd(o-MePh$_3$P)$_2$Cl$_2$ (25.4 g, 33.17 mmol) and TEA (185 mL, 1327 mmol) in DMF (1200 mL) was stirred at 110° C. under N$_2$ atmosphere overnight. The resulting mixture was diluted with water (2.5 L) and extracted with EtOAc (1 L×2). The layers were separated and the organic layer was washed with brine, dried over Na$_2$SO$_4$, filtered and concentrated to give the crude product which was purified on silica gel (0-10% EtOAc in PE) to afford the title compound (141 g, 56% yield) as a yellow solid. LCMS (ESI) m/z calcd for C$_{20}$H$_{28}$N$_2$O$_5$: 376.20. Found: 377.62 (M+1)$^+$. $^1$H NMR (400 MHz, CDCl$_3$) δ 7.83 (d, J=2.4 Hz, 1H), 7.54 (dd, J=8.7, 2.4 Hz, 1H), 7.17 (d, J=8.8 Hz, 1H), 6.15 (d, J=1.2 Hz, 1H), 4.05-3.93 (m, 2H), 3.76 (s, 3H), 3.32 (td, J=11.7, 2.1 Hz, 2H), 3.22-3.10 (m, 1H), 2.92 (d, J=7.2 Hz, 2H), 2.56 (d, J=1.2 Hz, 3H), 1.85-1.64 (m, 5H), 0.89 (d, J=6.6 Hz, 6H).

Preparation of methyl (R)-3-(4-(isobutyl(tetrahydro-2H-pyran-4-yl)amino)-3-nitro phenyl)butanoate

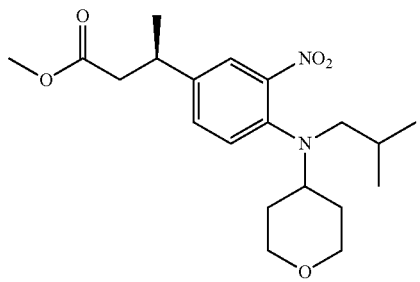 [SMILES: COC(=O)C[C@@H](C)c1ccc(N(CC(C)C)C2CCOCC2)c([N+](=O)[O-])c1]

At –5° C., to a mixture of (CuHPh$_3$P)$_6$ (5.9 g, 3.0 mmol) and (R,S)—PPF—P(tBu)$_2$ (5.9 g, 10.70 mmol) in toluene (1.2 L) was added PMHS (57.6 mL) and t-BuOH (42 mL) before the introduction of methyl (E)-3-(4-(isobutyl(tetrahydro-2H-pyran-4-yl)amino)-3-nitro phenyl)but-2-enoate (141 g, 375 mmol). After stirred at –5° C. for 2 hr, the resulting mixture was quenched with sat. aq. NaHCO$_3$ solution (500 mL) and extracted with EtOAc (1 L×2). The organic layer was washed with brine, dried over Na$_2$SO$_4$, filtered and concentrated to give the crude product which was purified on silica gel (0-10% EtOAc in PE) to afford the title compound (133 g, 94% yield) as a red oil. LCMS (ESI) m/z calcd for C$_{20}$H$_{30}$N$_2$O$_6$: 378.22. Found: 379.52 (M+1)$^+$. $^1$H NMR (400 MHz, CDCl$_3$) δ 7.51 (d, J=2.2 Hz, 1H), 7.29 (dd, J=8.5, 2.2 Hz, 1H), 7.21-7.15 (m, 1H), 3.97 (dd, J=10.9, 3.8 Hz, 2H), 3.65 (s, 3H), 3.36-3.25 (m, 3H), 3.15-3.03 (m, 1H), 2.83 (d, J=7.1 Hz, 2H), 2.64-2.51 (m, 2H), 1.80-1.67 (m, 4H), 1.58-1.49 (m, 1H), 1.30 (d, J=7.0 Hz, 3H), 0.84 (d, J=6.6 Hz, 6H).

Preparation of methyl (R)-3-(3-amino-4-(isobutyl (tetrahydro-2H-pyran-4-yl) amino)phenyl)butanoate

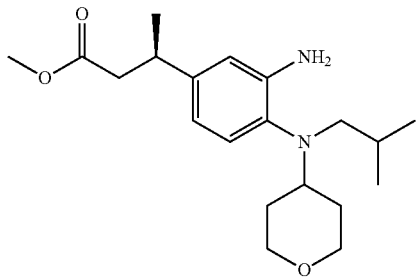

A mixture of methyl (R)-3-(4-(isobutyl(tetrahydro-2H-pyran-4-yl)amino)-3-nitrophenyl) butanoate (130 g, 343 mmol) and 10% Pd/C (45.5 g) in EtOAc (1.3 L) was stirred at 50° C. under H$_2$ atmosphere (15 psi) overnight. The resulting mixture was filtered through a pad of Celite and the filtrate was concentrated under reduced pressure to give the crude product which was purified on silica gel (0-20% EtOAc in PE) to afford the title compound (109 g, 91% yield) as a yellow oil. LCMS (ESI) m/z calcd for C$_{20}$H$_{32}$N$_2$O$_3$: 348.24. Found: 349.52 (M+1)$^+$. $^1$H NMR (400 MHz, CDCl$_3$) δ 6.84 (d, J=8.1 Hz, 1H), 6.46 (d, J=2.0 Hz, 1H), 6.41 (dd, J=8.1, 2.0 Hz, 1H), 3.95 (s, 2H), 3.87-3.78 (m, 2H), 3.50 (s, 3H), 3.27-3.10 (m, 2H), 3.06-2.97 (m, 1H), 2.93-2.51 (m, 3H), 2.47 (dd, J=15.0, 6.2 Hz, 1H), 2.35 (dd, J=15.0, 8.9 Hz, 1H), 1.75-1.43 (m, 4H), 1.40-1.28 (m, 1H), 1.13 (d, J=6.9 Hz, 3H), 0.71 (d, J=6.4 Hz, 6H).

Preparation of methyl (R)-3-(3-(2-(cyclopropanecarbonyl)hydrazine-1-carbothio amido)-4-(isobutyl (tetrahydro-2H-pyran-4-yl)amino)phenyl)butanoate

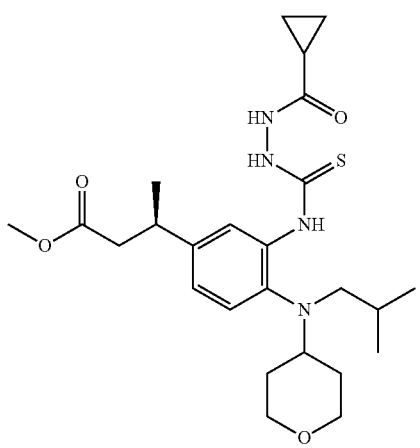 [SMILES: COC(=O)C[C@@H](C)c1ccc(N(CC(C)C)C2CCOCC2)c(NC(=S)NNC(=O)C2CC2)c1]

To a solution of methyl (R)-3-(3-amino-4-(isobutyl(tetrahydro-2H-pyran-4-yl)amino) phenyl)butanoate (95 g, 272.6 mmol) in MeCN (1 L) was added TCDI (72.9 g, 408.9 mmol) and the resulting reaction mixture was stirred at 25° C. under N₂ atmosphere for 3 hr. The resulting mixture was concentrated to give the crude isothiocyanate intermediate which was dissolved in EtOH (1 L) and treated with cyclopropanecarbo hydrazide (41 g, 408.9 mmol). After stirred at 50° C. overnight, the reaction mixture was concentrated to about one-third volume and the precipitated solid was collected by filtration and the solid was washed with cold EtOH to afford the title compound (96.4 g, 72% yield) as a white solid. LCMS (ESI) m/z calcd for C₂₅H₃₈N₄O₄S: 490.26. Found: 491.49 (M+1)⁺. ¹H NMR (400 MHz, CDCl₃) δ 9.36 (s, 1H), 8.48 (br, 2H), 7.10 (dd, J=9.2, 4.5 Hz, 1H), 6.98 (d, J=8.1 Hz, 1H), 4.04-3.87 (m, 2H), 3.63 (s, 3H), 3.40-3.16 (m, 3H), 2.91-2.71 (m, 3H), 2.65 (dd, J=15.2, 6.5 Hz, 1H), 2.55 (dd, J=15.2, 8.4 Hz, 1H), 1.71-1.49 (m, 5H), 1.44-1.35 (m, 1H), 1.31 (d, J=6.9 Hz, 3H), 1.13-1.03 (m, 2H), 0.95-0.87 (m, 2H), 0.82 (d, J=6.5 Hz, 6H).

Preparation of methyl (R)-3-(3-((5-cyclopropyl-1,3,4-thiadiazol-2-yl)amino)-4-(isobutyl(tetrahydro-2H-pyran-4-yl)amino)phenyl)butanoate

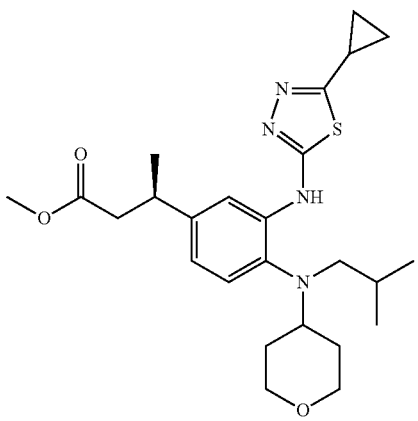 [SMILES: COC(=O)C[C@@H](C)c1ccc(N(CC(C)C)C2CCOCC2)c(Nc2nnc(C3CC3)s2)c1]

Methyl (R)-3-(3-(2-(cyclopropanecarbonyl)hydrazine-1-carbothioamido)-4-(isobutyl(tetra hydro-2H-pyran-4-yl)amino)phenyl)butanoate (101 g, 205.8 mmol) was added portion wise to conc. H₂SO₄ (200 mL) at 0° C. After stirred at room temperature for 3 hr, the mixture was carefully neutralized with aq. NaOH solution (4 N) to pH 5-6 and extracted with DCM (500 mL×2). The combined organic layers were dried over Na₂SO₄ and concentrated to give the crude product which was used in the next step without purification.

Preparation of (R)-3-(3-((5-cyclopropyl-1,3,4-thiadiazol-2-yl)amino)-4-(isobutyl (tetrahydro-2H-pyran-4-yl)amino)phenyl)butanoic Acid

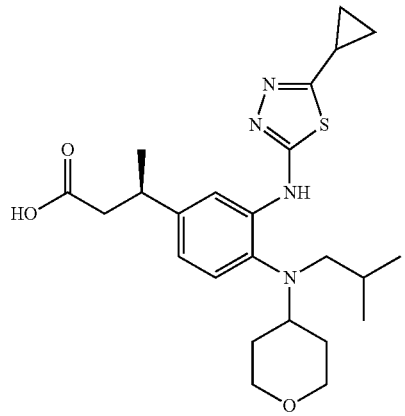 [SMILES: CC(C)CN(c1ccc([C@H](C)CC(=O)O)cc1Nc1nnc(C2CC2)s1)C1CCOCC1]

To a solution of methyl (R)-3-(3-((5-cyclopropyl-1,3,4-thiadiazol-2-yl)amino)-4-(isobutyl (tetrahydro-2H-pyran-4-yl)amino)phenyl)butanoate (the crude product obtained from the previous step, 205.8 mmol) in MeOH (600 mL) was added 1N aq. NaOH (1N, 617 mL). After stirred at r.t. for 5 hr, the resulting mixture was neutralized with 1N HCl and extracted with EtOAc (600 mL×2). The layers were separated and the organic layer was washed with brine, dried over Na₂SO₄ and concentrated to give the crude product which was recrystallized in Et₂O (500 mL) to afford the title product (63.7 g, 68%) as a pale powder. LCMS (ESI) m/z calcd for C₂₄H₃₄N₄O₃S: 458.24. Found: 457.35 (M−1)⁻. ¹H NMR (400 MHz, DMSO) δ 12.09 (s, 1H), 8.96 (s, 1H), 7.97 (d, J=2.0 Hz, 1H), 7.20 (d, J=8.2 Hz, 1H), 6.90 (dd, J=8.2, 2.0 Hz, 1H), 3.81 (dd, J=11.1, 3.5 Hz, 2H), 3.23-3.07 (m, 3H), 2.93-2.82 (m, 1H), 2.77 (d, J=6.7 Hz, 2H), 2.51-2.41 (m, 2H), 2.37-2.23 (m, 1H), 1.67 (d, J=11.1 Hz, 2H), 1.54-1.39 (m, 2H), 1.36-1.26 (m, 1H), 1.23 (d, J=9.1 Hz, 3H), 1.12-1.06 (m, 2H), 0.97-0.88 (m, 2H), 0.80 (d, J=6.6 Hz, 6H).

Example 24

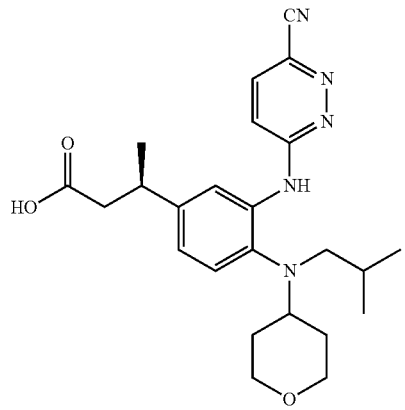

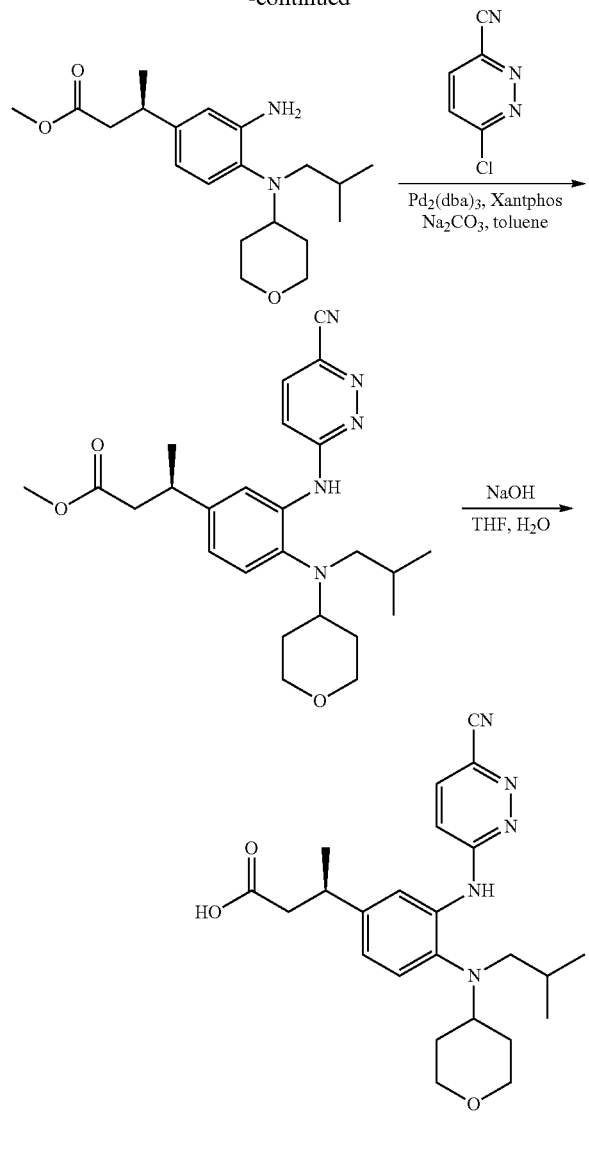

Preparation of methyl (R)-3-(3-((6-cyanopyridazin-3-yl)amino)-4-(isobutyl(tetra hydro-2H-pyran-4-yl)amino)phenyl)butanoate

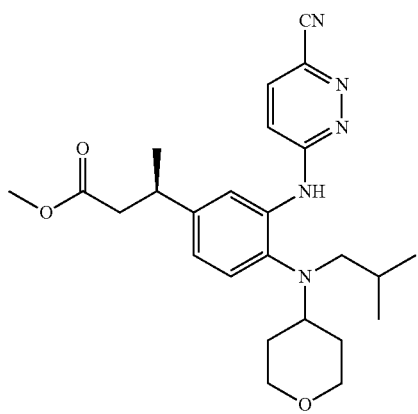 [SMILES: COC(=O)C[C@@H](C)c1ccc(N(CC(C)C)C2CCOCC2)c(Nc2ccc(C#N)nn2)c1]

A mixture of methyl (R)-3-(3-amino-4-(isobutyl(tetrahydro-2H-pyran-4-yl)amino)phenyl) butanoate (120 mg, 0.34 mmol), 6-chloropyridazine-3-carbonitrile (96 mg, 0.69 mmol), Pd$_2$(dba)$_3$ (32 mg, 0.035 mmol), Xantphos (40 mg, 0.07 mmol) and Na$_2$CO$_3$ (110 mg, 1.04 mmol) in toluene (10 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-40% EtOAc in PE) to afford the title compound (50 mg, 32% yield). LCMS (ESI) m/z calcd for C$_{25}$H$_{33}$N$_5$O$_3$: 451.26. Found: 452.46 (M+1)$^+$.

Preparation of (R)-3-(3-((6-cyanopyridazin-3-yl)amino)-4-(isobutyl(tetrahydro-2H-pyran-4-yl)amino)phenyl)butanoic Acid

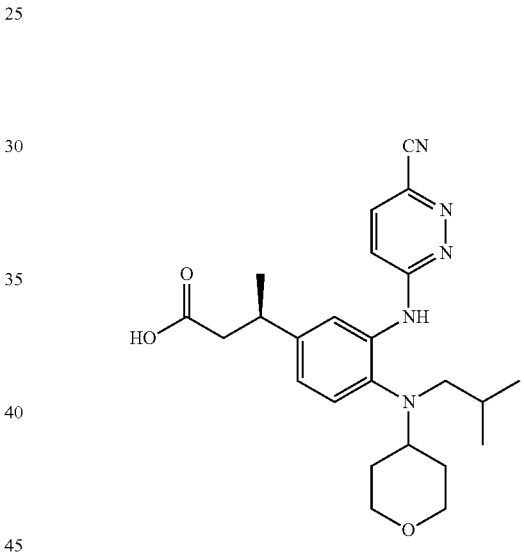

To a solution of methyl (R)-3-(3-((6-cyanopyridazin-3-yl)amino)-4-(isobutyl(tetra hydro-2H-pyran-4-yl)amino)phenyl)butanoate (50 mg, 0.11 mmol) in THF (6 mL) was added 1N NaOH aq. (3 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (20 mg, 42% yield) as a white powder. $^1$H NMR (400 MHz, CDCl$_3$) δ 8.74 (s, 1H), 8.11 (d, J=1.6 Hz, 1H), 7.53 (d, J=9.3 Hz, 1H), 7.19 (d, J=8.2 Hz, 1H), 7.02 (d, J=9.3 Hz, 1H), 6.97 (dd, J=8.2, 2.0 Hz, 1H), 4.01-3.87 (m, 2H), 3.35-3.19 (m, 3H), 2.88-2.78 (m, 3H), 2.71-2.59 (m, 2H), 1.77-1.44 (m, 5H), 1.35 (d, J=7.0 Hz, 3H), 0.86 (d, J=6.6 Hz, 6H). LCMS (ESI) m/z calcd for C$_{24}$H$_{31}$N$_5$O$_3$: 437.24. Found: 438.47 (M+1)$^+$.

Example 25

Preparation of (R)-methyl 3-(3-((3-chloro-1,2,4-thiadiazol-5-yl)amino)-4-(isobutyl(tetrahydro-2H-pyran-4-yl)amino)phenyl)butanoate

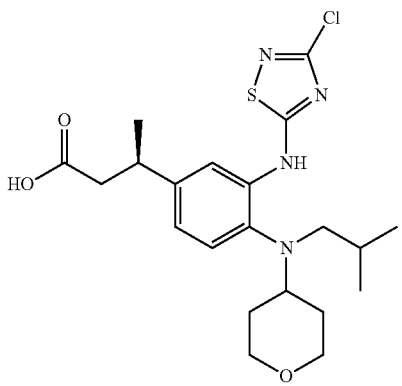

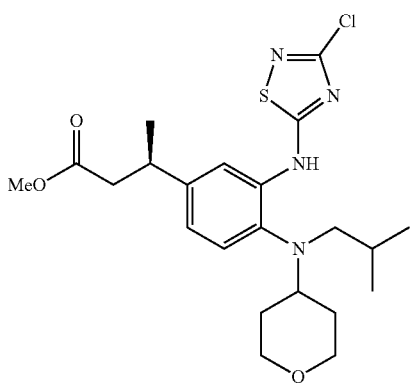 [SMILES: COC(=O)C[C@@H](C)c1ccc(N(CC(C)C)C2CCOCC2)c(Nc2nc(Cl)ns2)c1]

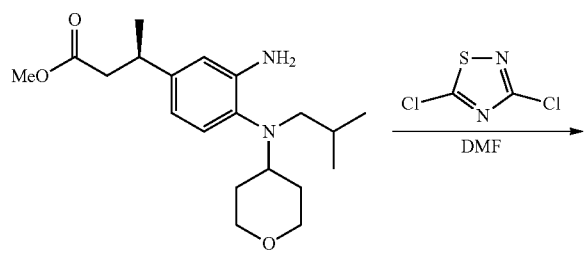

A mixture of (R)-methyl 3-(3-amino-4-(isobutyl(tetrahydro-2H-pyran-4-yl)amino)phenyl)butanoate (quantity) and 3,5-dichloro-1,2,4-thiadiazole (0.040 mL, 0.430 mmol) in N,N-Dimethylformamide (DMF) (2.0 mL) was heated at 90° C. for 16 h. The reaction mixture was cooled to rt, diluted with water, extracted with ethyl acetate, dried over sodium sulfate and concentrated. Purification by prep. TLC (DCM/MeOH 5%) afforded the pure ester.

Preparation of (R)-3-(3-((3-chloro-1,2,4-thiadiazol-5-yl)amino)-4-(isobutyl(tetrahydro-2H-pyran-4-yl)amino)phenyl)butanoic Acid

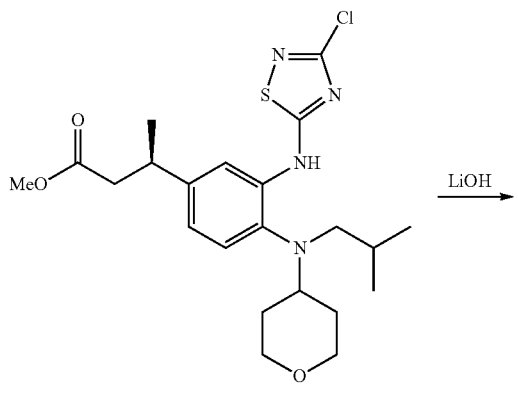

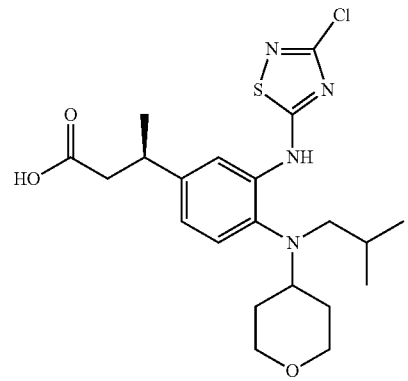 [SMILES: CC(C)CN(c1ccc([C@H](C)CC(=O)O)cc1Nc1nc(Cl)ns1)C1CCOCC1]

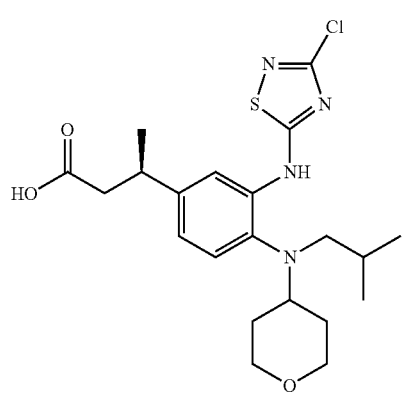

(R)-methyl 3-(3-((3-chloro-1,2,4-thiadiazol-5-yl)amino)-4-(isobutyl(tetrahydro-2H-pyran-4-yl)amino)phenyl)butanoate was dissolved in THF (5 mL) and MeOH (1 mL) and treated with LiOH (1.435 mL, 1.435 mmol) and the mixture was stirred at r.t. overnight. The reaction mixture was concentrated to a smaller volume, acidified with 1 N HCl, extracted with ethyl acetate, dried over sodium sulfate and concentrated. The acid was obtained with 93% (68 mg, 48.6% yield). LCMS calculated for $C_{21}H_{29}ClN_4O_3S$: 452.16, found (M+H)$^+$: m/z=453.54.

$^1$H NMR (400 MHz, METHANOL-d$_4$) δ ppm 7.66 (s, 1H) 7.31 (d, J=8.1 Hz, 1H) 7.09 (d, J=8.1 Hz, 1H) 3.84-4.00 (m, 2H) 3.25 (m, 1H) 2.93 (m, 1H) 2.87 (d, J=6.6 Hz, 2H) 2.60 (m, 3H) 1.75 (m, 2H) 1.50-1.67 (m, 2H) 1.36-1.45 (m, 2H) 1.34 (d, J=7.0 Hz, 3H) 0.86 (d, J=6.4 Hz, 6H).

Example 26

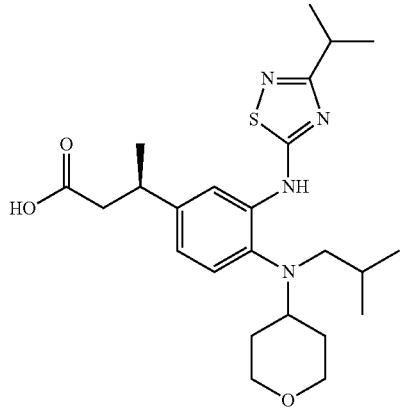 [SMILES: CC(C)CN(c1ccc([C@H](C)CC(=O)O)cc1Nc1nc(C(C)C)ns1)C1CCOCC1]

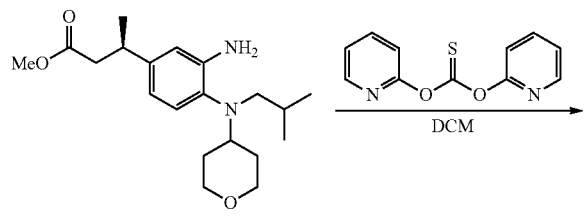

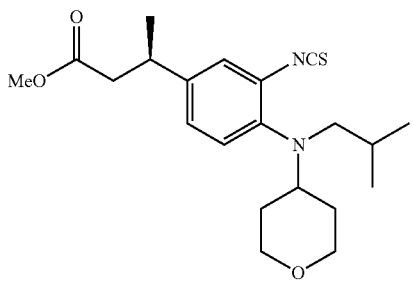

Preparation of (R)-methyl 3-(4-(isobutyl(tetrahydro-2H-pyran-4-yl)amino)-3-isothiocyanatophenyl)butanoate

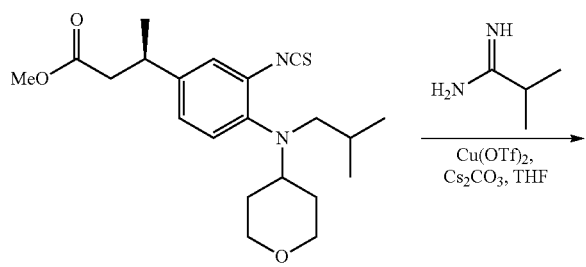

A mixture of (R)-methyl 3-(3-amino-4-(isobutyl(tetrahydro-2H-pyran-4-yl)amino)phenyl)butanoate (100 mg, 0.287 mmol) and O,O-di(pyridin-2-yl) carbonothioate (100 mg, 0.430 mmol) in Dichloromethane (DCM) (3.0 mL) was stirred at r.t. for 16 h. The reaction mixture was concentrated and used in the next step without further purification.

Preparation of (R)-methyl 3-(4-(isobutyl(tetrahydro-2H-pyran-4-yl)amino)-3-isothiocyanatophenyl)butanoate

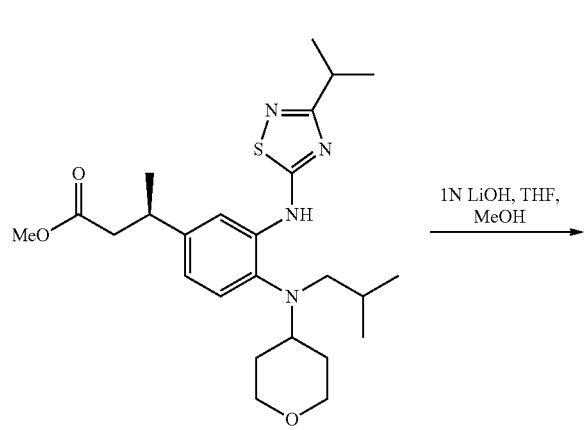

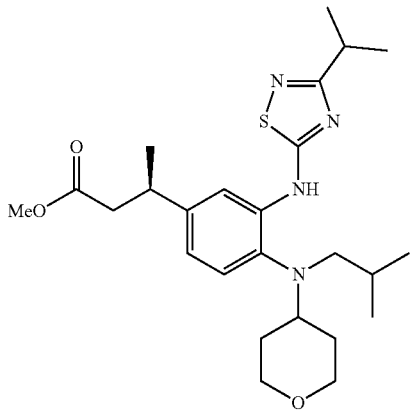 [SMILES: COC(=O)C[C@@H](C)c1ccc(N(CC(C)C)C2CCOCC2)c(Nc2nc(C(C)C)ns2)c1]

(R)-methyl 3-(4-(isobutyl(tetrahydro-2H-pyran-4-yl) amino)-3-isothiocyanatophenyl)butanoate and cesium carbonate (280 mg, 0.861 mmol) were dissolved in Acetonitrile (3.00 mL), copper(II) trifluoromethanesulfonate (5.19 mg, 0.014 mmol) and isobutyrimidamide, Hydrochloride (52.8 mg, 0.430 mmol) were added to the solution and the mixture was stirred at r.t. for 2 h under air. The reaction mixture was diluted with water, extracted with ethyl acetate, the organic phase was dried over sodium sulfate and concentrated. crude product was used in the next step without further purification.

Preparation of (R)-3-(4-(isobutyl(tetrahydro-2H-pyran-4-yl)amino)-3-((3-isopropyl-1,2,4-thiadiazol-5-yl)amino)phenyl)butanoic Acid

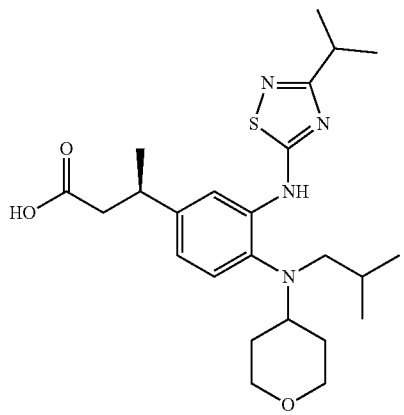 [SMILES: CC(C)CN(c1ccc([C@H](C)CC(=O)O)cc1Nc1nc(C(C)C)ns1)C1CCOCC1]

(R)-methyl 3-(4-(isobutyl(tetrahydro-2H-pyran-4-yl) amino)-3-isothiocyanatophenyl)butanoate was dissolved in THF (5 mL) and MeOH (3 mL) and treated with LiOH (1.435 mL, 1.435 mmol) and the mixture was stirred at r.t. for 3 h. The reaction mixture was concentrated to a smaller volume, neutralized with 1N HCl, extracted with ethyl acetate, dried over sodium sulfate and concentrated. Purification by Gilson (reverse phase chromatography) afforded the desired product.

LCMS calculated for $C_{24}H_{36}N_4O_3S$: 460.25, found (M+H)$^+$: m/z=461.61 $^1$H NMR (400 MHz, METHANOL-$d_4$) δ ppm 7.59 (s, 1H) 7.27 (d, J=8.2 Hz, 1H) 7.01 (d, J=8.0 Hz, 1H) 3.87 (d, J=10.9 Hz, 2H) 3.24 (m, 1H) 2.99-3.15 (m, 1H) 2.79-2.93 (m, 3H) 2.49-2.68 (m, 3H) 1.74 (d, J=11.5 Hz, 2H) 1.49-1.63 (m, 2H) 1.26-1.38 (m, 2) 1.381-1.33 (d, J=6.1 Hz, 9H) 0.83 (d, J=6.6 Hz, 6H).

Example 27

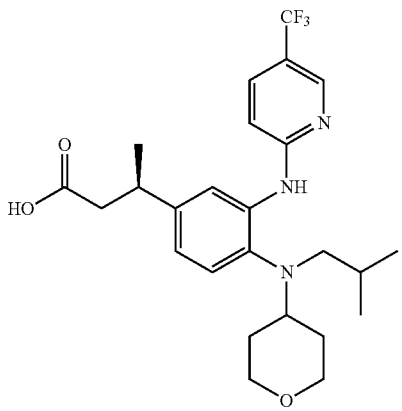

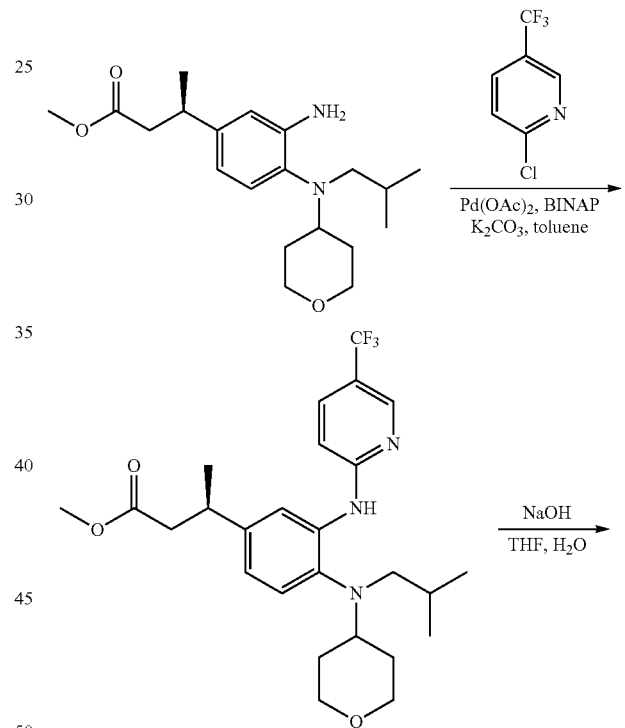

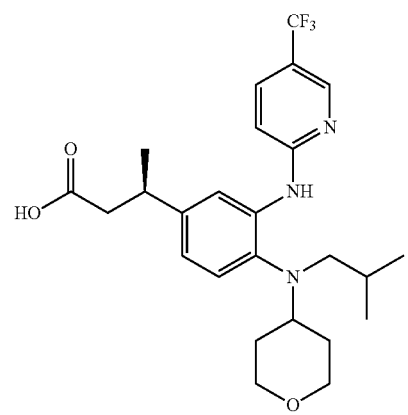

Preparation of methyl (R)-3-(4-(isobutyl(tetrahydro-2H-pyran-4-yl)amino)-3-((5-(trifluoromethyl)pyridin-2-yl)amino)phenyl)butanoate

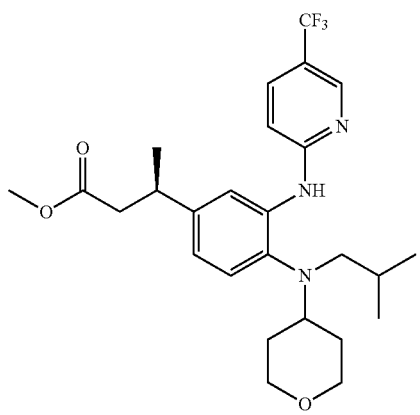

A mixture of methyl (R)-3-(3-amino-4-(isobutyl(tetrahydro-2H-pyran-4-yl)amino)phenyl) butanoate (150 mg, 0.43 mmol), 2-chloro-5-(trifluoromethyl)pyridine (156 mg, 0.86 mmol), Pd(OAc)$_2$ (4.0 mg, 0.007 mmol), BINAP (4.8 mg, 0.0077 mmol) and K$_2$CO$_3$ (178 mg mg, 1.29 mmol) in toluene (5 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-40% EtOAc in PE) to afford the title compound (106 mg, 50% yield). LCMS (ESI) m/z calcd for C$_{26}$H$_{34}$F$_3$N$_3$O$_3$: 493.26. Found: 494.48 (M+1)$^+$.

Preparation of (R)-3-(4-(isobutyl(tetrahydro-2H-pyran-4-yl)amino)-3-((5-(trifluoro methyl)pyridin-2-yl)amino)phenyl)butanoic Acid

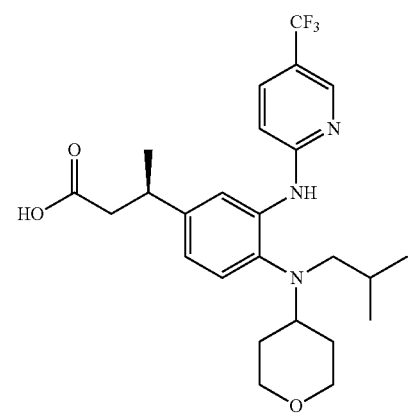

To a solution of methyl (R)-3-(4-(isobutyl(tetrahydro-2H-pyran-4-yl)amino)-3-((5-(trifluoromethyl)pyridin-2-yl)amino)phenyl)butanoate (106 mg, 0.214 mmol) in MeOH (6 mL) was added 4N NaOH aq. (2 mL). After stirred at r.t. for 5 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (69 mg, 67% yield) as a white powder. $^1$H NMR (400 MHz, CDCl$_3$) δ 8.51 (s, 1H), 8.32 (s, 1H), 8.19 (s, 1H), 7.68 (dd, J=8.8, 2.3 Hz, 1H), 7.13 (d, J=8.2 Hz, 1H), 6.86 (d, J=6.8 Hz, 1H), 6.78 (d, J=7.7 Hz, 1H), 3.99-3.88 (m, 2H), 3.33-3.17 (m, 3H), 2.90-2.52 (m, 5H), 1.76-1.47 (m, 5H), 1.36 (d, J=6.9 Hz, 3H), 0.87 (d, J=6.6 Hz, 6H). LCMS (ESI) m/z calcd for C$_{25}$H$_{32}$F$_3$N$_3$O$_3$: 479.24. Found: 480.24 (M+1)$^+$.

Example 28

(R)-3-(3-((3-cyclopropyl-1,2,4-thiadiazol-5-yl)amino)-4-(isobutyl(tetrahydro-2H-pyran-4-yl)amino)phenyl)butanoic Acid

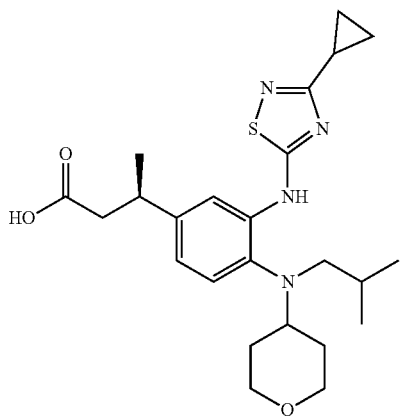 [SMILES: CC(C)CN(c1ccc([C@H](C)CC(=O)O)cc1Nc1nc(C2CC2)ns1)C1CCOCC1]

LCMS calculated for C$_{24}$H$_{34}$N$_4$O$_3$S: 458.24, found (M+H)$^+$: m/z=459.36 $^1$H NMR (400 MHz, METHANOL-d$_4$) δ ppm 7.60 (s, 1H) 7.25 (d, J=8.2 Hz, 1H) 6.99 (d, J=6.6 Hz, 1H) 3.87 (dd, J=11.4, 3.6 Hz, 2H) 3.23 (m, 1H) 2.76-2.94 (m, 3H) 2.57 (dd, J=7.3, 5.6 Hz, 2H) 2.08 (m, 1H) 1.73 (d, J=11.5 Hz, 2H) 1.53 (dd, J=12.1, 4.1 Hz, 2H) 1.34 (d, J=6.8 Hz, 1H) 1.31 (d, J=6.8 Hz, 3H) 1.03-1.09 (m, 3H) 0.98-1.03 (m, 3H) 0.82 (d, J=6.4 Hz, 6H).

Example 29

(R)-3-(4-(isobutyl(tetrahydro-2H-pyran-4-yl)amino)-3-((4-(methoxycarbonyl)-1H-imidazol-2-yl)amino)phenyl)butanoic acid

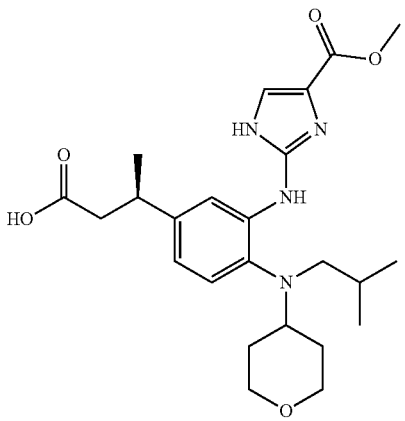 [SMILES: COC(=O)c1c[nH]c(Nc2cc([C@H](C)CC(=O)O)ccc2N(CC(C)C)C2CCOCC2)n1]

(R)-3-(4-(isobutyl(tetrahydro-2H-pyran-4-yl)amino)-3-((4-(trifluoromethyl)-1H-imidazol-2-yl)amino)phenyl)butanoic acid (28.2 mg, 0.060 mmol) was stirred in a solution of methanol (0.45 mL), tetrahydrofuran (0.45 mL), and 1M lithium hydroxide (0.6 mL, 0.602 mmol) at 40° C. for 1 h. The reaction mixture was acidified with 1M citric acid and extracted with EtOAc. The organic phase was washed with brine, dried (Na$_2$SO$_4$), filtered, and evaporated. The residue was purified by reverse phase chrom. 10-100% CH$_3$CN/H$_2$O (0.1% FA) to afford the title compound (15.5 mg, 56%) as a white solid. LCMS (M+H)$^+$: m/z=459.3. $^1$H NMR (400 MHz, CD$_3$OD) δ ppm 7.85 (d, J=1.8 Hz, 1H), 7.46 (s, 1H), 7.15 (d, J=8.2 Hz, 1H), 6.82 (dd, J=8.1, 1.9 Hz, 1H), 3.85-3.93 (m, 2H), 3.81 (s, 3H), 3.16-3.33 (m, 3H), 2.78-2.90 (m, 3H), 2.47-2.66 (m, 2H), 1.69-1.82 (m, 2H), 1.52-1.66 (m, 2H), 1.33-1.45 (m, 1H), 1.29 (d, J=6.8 Hz, 3H), 0.83 (d, J=6.6 Hz, 6H).

Example 30

(R)-3-(3-((5-chloro-6-cyanopyridin-2-yl)amino)-4-(isobutyl(tetrahydro-2H-pyran-4-yl)amino)phenyl)butanoic Acid

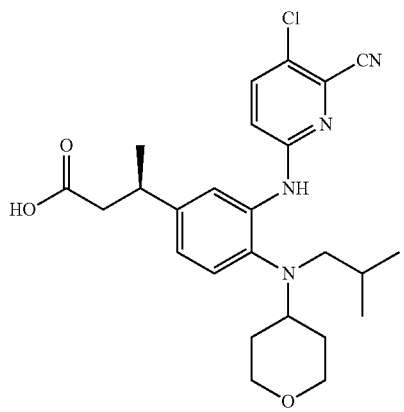 [SMILES: CC(C)CN(c1ccc([C@H](C)CC(=O)O)cc1Nc1ccc(Cl)c(C#N)n1)C1CCOCC1]

Preparation of (R)-3-(3-((5-chloro-6-cyanopyridin-2-yl)amino)-4-(isobutyl(tetrahydro-2H-pyran-4-yl)amino)phenyl)butanoic acid. A flask was charged with (R)-methyl 3-(3-amino-4-(isobutyl(tetrahydro-2H-pyran-4-yl)amino)phenyl)butanoate (61.2 mg, 0.176 mmol), 6-bromo-3-chloropicolinonitrile (45.8 mg, 0.211 mmol), cesium carbonate (286 mg, 0.878 mmol), xantphos (40.6 mg, 0.070 mmol) and Pd$_2$(dba)$_3$ (32.2 mg, 0.035 mmol) while purging with nitrogen. Toluene (2.5 mL) was added and the mixture was degassed with nitrogen for several minutes. The mixture was heated to 100° C. and stirred for 90 minutes. The mixture was cooled, diluted with EtOAc and then filtered over Celite. The filtrate was washed with water, then brine, dried over sodium sulfate, filtered and concentrated. The residue was purified on silica gel (4 g column, 0-20% hexanes/EtOAc gradient elution) to afford (R)-methyl 3-(3-((5-chloro-6-cyanopyridin-2-yl)amino)-4-(isobutyl(tetrahydro-2H-pyran-4-yl)amino)phenyl)butanoate as a pale yellow residue. A solution of (R)-methyl 3-(3-((5-chloro-6-cyanopyridin-2-yl)amino)-4-(isobutyl(tetrahydro-2H-pyran-4-yl)amino)phenyl)butanoate (64 mg, 0.132 mmol) THF (1.0 mL) and MeOH (0.5 mL) was treated with 2M LiOH (0.396 mL, 0.792 mmol) and allowed to stir at ambient temperature overnight. The mixture was adjusted to ~pH 7 with 1N HCl, then extracted with EtOAc. The extracts were washed with brine, dried over sodium sulfate, filtered and concentrated. The residue was purified by by reverse phase chromatography to afford a pale yellow solid (9.3 mg). $^1$H NMR (400 MHz, CHLOROFORM-d) δ=8.42 (s, 1H), 8.22 (m, 1H), 7.57 (d, J=9.0 Hz, 1H), 7.14 (d, J=8.1 Hz, 1H), 6.87 (m, 2H), 3.96 (m, 2H), 3.35-3.22 (m, 3H), 2.88-2.56 (m, 5H), 1.79-1.54 (m, 4H), 1.51-1.34 (m, 4H), 0.86 (d, J=6.4 Hz, 6H); LC/MS (m/z) ES$^+$ calcd for C$_{25}$H$_{31}$ClN$_4$O$_3$: 470.21. Found: 471 (M+1).

Example 31

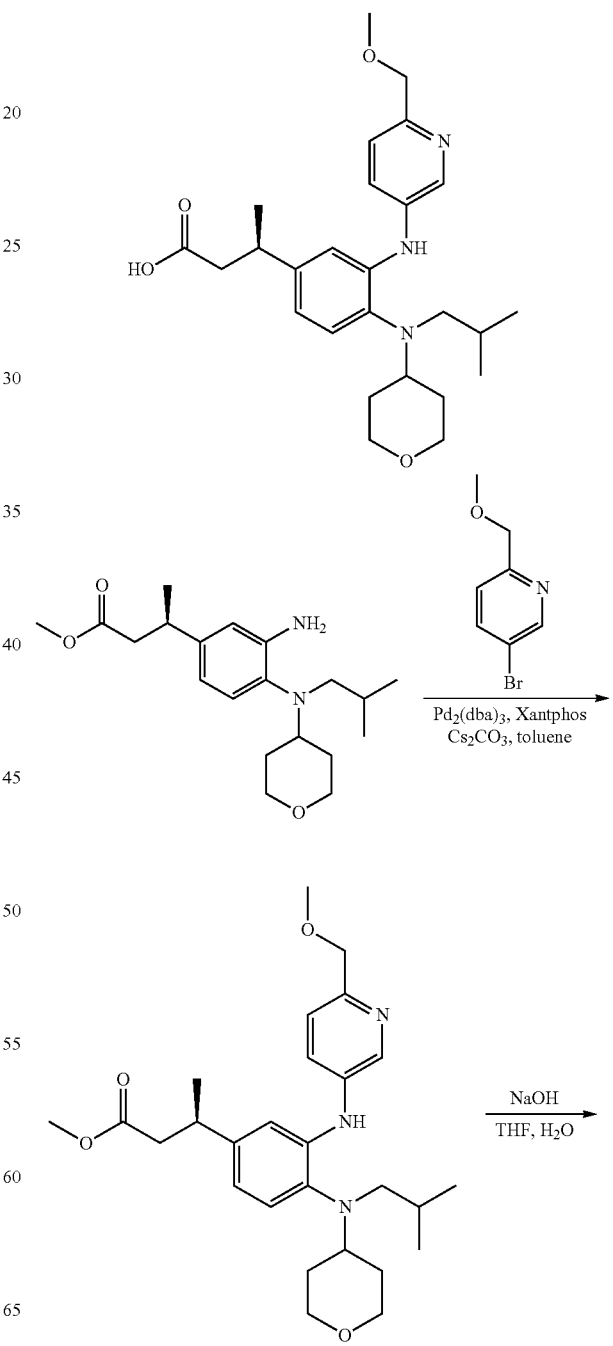

91

-continued

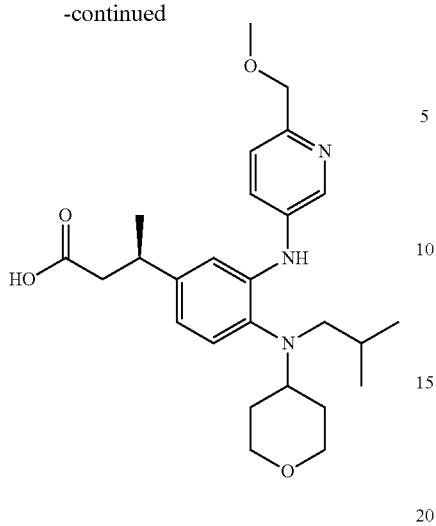

Preparation of methyl (R)-3-(4-(isobutyl(tetrahydro-2H-pyran-4-yl)amino)-3-((6-(methoxymethyl)pyridin-3-yl)amino)phenyl)butanoate

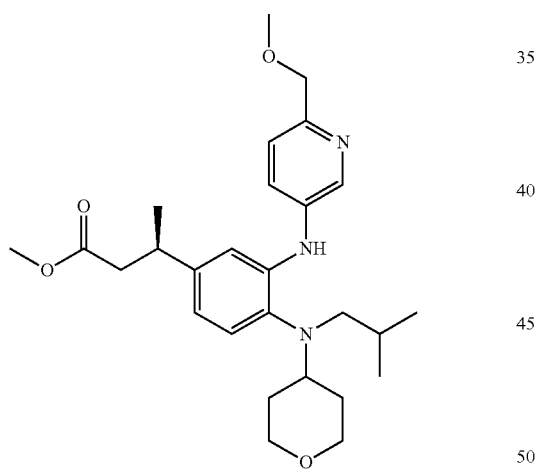

A mixture of methyl (R)-3-(3-amino-4-(isobutyl(tetrahydro-2H-pyran-4-yl)amino)phenyl) butanoate (120 mg, 0.34 mmol), 5-bromo-2-(methoxymethyl)pyridine (138 mg, 0.68 mmol), Pd$_2$(dba)$_3$ (28 mg, 0.03 mmol), Xantphos (40 mg, 0.07 mmol) and Cs$_2$CO$_3$ (332 mg, 1.02 mmol) in toluene (4 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (120 mg, 75% yield). LCMS (ESI) m/z calcd for C$_{27}$H$_{39}$N$_3$O$_4$: 469.29. Found: 470.35 (M+1)$^+$.

92

Preparation of (R)-3-(4-(isobutyl(tetrahydro-2H-pyran-4-yl)amino)-3-((6-(methoxymethyl)pyridin-3-yl)amino)phenyl)butanoic Acid

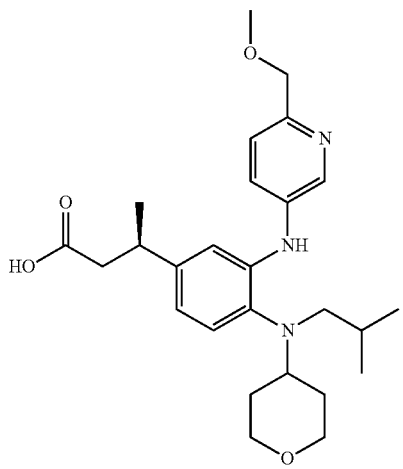 [SMILES: COCc1ccc(Nc2cc([C@H](C)CC(=O)O)ccc2N(CC(C)C)C2CCOCC2)cn1]

To a solution of methyl (R)-3-(4-(isobutyl(tetrahydro-2H-pyran-4-yl)amino)-3-((6-(methoxymethyl)pyridin-3-yl)amino)phenyl)butanoate (120 mg, 0.26 mmol) in MeOH (8 mL) was added 1N NaOH aq. (4 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (70 mg, 59% yield) as a white powder. $^1$H NMR (400 MHz, CDCl$_3$) δ 8.55 (d, J=2.5 Hz, 1H), 7.41 (dd, J=8.4, 2.6 Hz, 1H), 7.34 (d, J=8.4 Hz, 1H), 7.19 (d, J=1.9 Hz, 1H), 7.12-7.07 (m, 2H), 6.76 (dd, J=8.1, 1.8 Hz, 1H), 4.54 (s, 2H), 3.97-3.86 (m, 2H), 3.47 (s, 3H), 3.28-3.21 (m, 3H), 2.82-2.57 (m, 5H), 1.75-1.44 (m, 5H), 1.31 (d, J=6.9 Hz, 3H), 0.85 (d, J=6.5 Hz, 6H). LCMS (ESI) m/z calcd for C$_{26}$H$_{37}$N$_3$O$_4$: 455.28. Found: 456.56 (M+1)$^+$.

Example 32

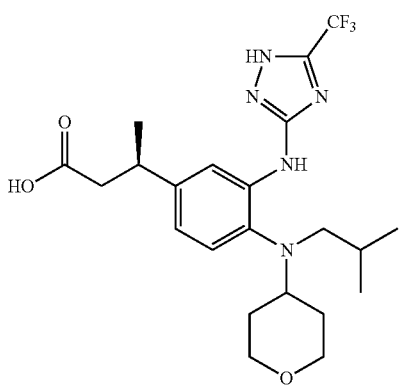

Step A

3-Bromo-5-(trifluoromethyl)-1-((2-(trimethylsilyl)ethoxy)methyl)-1H-1,2,4-triazole

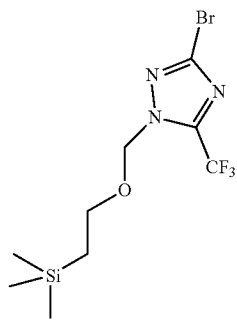 [SMILES: C[Si](C)(C)CCOCn1nc(Br)nc1C(F)(F)F]

A suspension of sodium hydride (60% disp in mineral oil) (0.407 g, 10.2 mmol) in 46 mL THF was stirred at 0° C. A solution of 3-bromo-5-(trifluoromethyl)-1H-1,2,4-triazole (2.00 g, 9.26 mmol) in THF (10 mL) was added dropwise. The solution was stirred at RT for 2 h and SEM-Cl (2.14 ml, 12.04 mmol) was added. After stirring at RT overnight, saturated aqueous NaHCO$_3$ solution and EtOAc were added. The organic layer was dried (Na$_2$SO$_4$), filtered, evaporated and purified by silica gel chromatography (0-40% EtOAc/hexanes) to afford 4-(trifluoromethyl)-1-((2-(trimethylsilyl)ethoxy)methyl)-1H-imidazole (1.23 g, 38%). $^1$H NMR (400 MHz, CDCl$_3$) δ ppm 5.56 (s, 2H), 3.70 (t, J=8.2 Hz, 2H), 0.95 (t, J=8.2 Hz, 2H), 0.01 (s, 9H).

Step B

(R)-Methyl 3-(4-(isobutyl(tetrahydro-2H-pyran-4-yl)amino)-3-((5-(trifluoromethyl)-1-((2-(trimethylsilyl)ethoxy)methyl)-1H-1,2,4-triazol-3-yl)amino)phenyl)butanoate

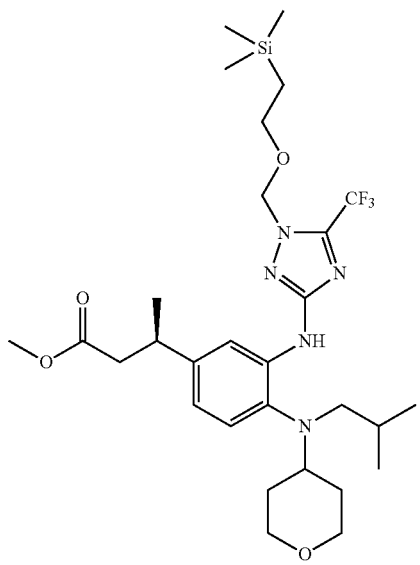 [SMILES: COC(=O)C[C@@H](C)c1ccc(N(CC(C)C)C2CCOCC2)c(Nc2nc(C(F)(F)F)n(COCC[Si](C)(C)C)n2)c1]

A mixture of (R)-methyl 3-(3-amino-4-(isobutyl(tetrahydro-2H-pyran-4-yl)amino)phenyl)butanoate (0.100 g, 0.287 mmol), 3-bromo-5-(trifluoromethyl)-1-((2-(trimethylsilyl)ethoxy)methyl)-1H-1,2,4-triazole (0.119 g, 0.344 mmol), Pd$_2$dba$_3$ (0.053 g, 0.057 mmol), Xantphos (0.066 g, 0.115 mmol), and cesium carbonate (0.467 g, 1.435 mmol) was flushed with nitrogen and then stirred in toluene (4.10 ml) and heated at 100° C. for 8 h, then filtered through celite, evaporated, and purified by silica gel chromatography (0-40% EtOAc/hexanes) to afford (R)-methyl 3-(4-(isobutyl(tetrahydro-2H-pyran-4-yl)amino)-3-((5-(trifluoromethyl)-1-((2-(trimethylsilyl)ethoxy)methyl)-1H-1,2,4-triazol-3-yl)amino)phenyl)butanoate (165.6 mg, 94%). LCMS (M+H)$^+$: m/z=614.5.

Step C

(R)-3-(4-(Isobutyl(tetrahydro-2H-pyran-4-yl)amino)-3-((5-(trifluoromethyl)-1H-1,2,4-triazol-3-yl)amino)phenyl)butanoic Acid

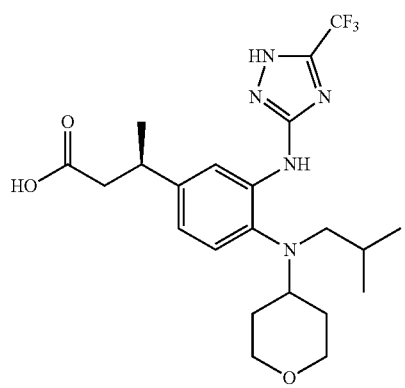

TFA (0.85 mL) was added to a solution of (R)-methyl 3-(4-(isobutyl(tetrahydro-2H-pyran-4-yl)amino)-3-((5-(trifluoromethyl)-1-((2-(trimethylsilyl)ethoxy)methyl)-1H-1,2,4-triazol-3-yl)amino)phenyl)butanoate (0.1656 g, 0.270 mmol) in CH$_2$Cl$_2$ (2.8 mL). The reaction mixture was stirred at RT overnight, then evaporated to dryness and taken up in CH$_2$Cl$_2$ and sat'd aqueous NaHCO3 solution. The organic phase was isolated, evaporated, and the residue was subjected to base hydrolysis as previously described and purified by reverse phase chromatography (10-100% CH$_3$CN/H$_2$O (0.1% formic acid)) to afford the title compound (0.0706 g, 56%) as a white solid. LCMS (M+H)$^+$: m/z=470.4. $^1$H NMR (400 MHz, CD$_3$OD) δ ppm 8.00 (d, J=1.8 Hz, 1H), 7.20 (d, J=8.2 Hz, 1H), 6.89 (dd, J=8.2, 1.8 Hz, 1H), 3.88 (dd, J=11.3, 3.7 Hz, 2H), 3.17-3.35 (m, 3H), 2.76-2.92 (m, 3H), 2.46-2.67 (m, 2H), 1.75 (m, 2H), 1.61 (m, 2H), 1.37 (m, 1H), 1.29 (d, J=6.8 Hz, 3H), 0.78-0.89 (m, 6H).

Example 33

(R)-3-(3-((5,6-Dichloropyridin-2-yl)amino)-4-(isobutyl(tetrahydro-2H-pyran-4-yl)amino)phenyl)butanoic Acid

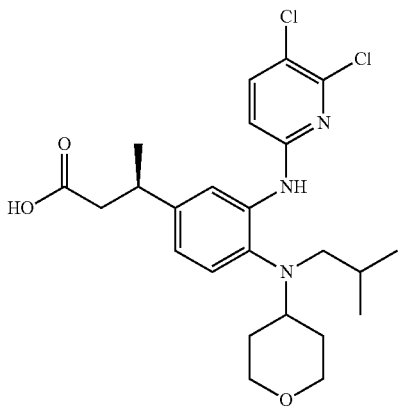 [SMILES: CC(C)CN(c1ccc([C@H](C)CC(=O)O)cc1Nc1ccc(Cl)c(Cl)n1)C1CCOCC1]

Preparation of (R)-3-(3-((5,6-dichloropyridin-2-yl)amino)-4-(isobutyl(tetrahydro-2H-pyran-4-yl)amino)phenyl)butanoic acid. A flask was charged with (R)-methyl 3-(3-amino-4-(isobutyl(tetrahydro-2H-pyran-4-yl)amino)phenyl)butanoate (62.2 mg, 0.178 mmol), 6-bromo-2,3-dichloropyridine (48.6 mg, 0.214 mmol), cesium carbonate (291 mg, 0.892 mmol), xantphos (41.3 mg, 0.071 mmol) and Pd$_2$(dba)$_3$ (32.7 mg, 0.036 mmol) while purging with nitrogen. Toluene (2.5 mL) was added and the mixture was degassed with nitrogen for several minutes. The mixture was heated to 100° C. and stirred for 2 hours. The mixture was cooled, diluted with EtOAc and then filtered over Celite. The filtrate was washed with water, then brine, dried over sodium sulfate, filtered and concentrated. The residue was purified on silica gel (4 g column, 0-20% hexanes/EtOAc gradient elution) to afford (R)-methyl 3-(3-((5,6-dichloropyridin-2-yl)amino)-4-(isobutyl(tetrahydro-2H-pyran-4-yl)amino)phenyl)butanoate as a pale yellow residue. A solution of (R)-methyl 3-(3-((5,6-dichloropyridin-2-yl)amino)-4-(isobutyl(tetrahydro-2H-pyran-4-yl)amino)phenyl)butanoate (39 mg, 0.079 mmol) in THF (0.8 mL) and MeOH (0.4 mL) was treated with 2M LiOH (0.394 mL, 0.789 mmol) and allowed to stir at ambient temperature overnight. The mixture was adjusted to ~pH 7 with 1N HCl, then extracted with EtOAc. The extracts were washed with brine, dried over sodium sulfate, filtered and concentrated. The residue was purified by reverse phase chromatography to afford a white solid. An additional sample of (R)-methyl 3-(3-((5,6-dichloropyridin-2-yl)amino)-4-(isobutyl(tetrahydro-2H-pyran-4-yl)amino)phenyl)butanoate (29 mg) was subjected to the hydrolysis conditions. Following work-up the material was purified by reverse phase chromatography, then combined with the previous batch to afford a white solid (21.5 mg). $^1$H NMR (400 MHz, CHLOROFORM-d) δ=8.15 (m, 2H), 7.52 (d, J=8.6 Hz, 1H), 7.11 (d, J=8.1 Hz, 1H), 6.84 (m, 1H), 6.62 (d, J=8.6 Hz, 1H), 3.95 (m, 2H), 3.35-3.17 (m, 3H), 2.88-2.67 (m, 4H), 2.65-2.55 (m, 1H), 1.79-1.55 (m, 4H), 1.45 (m, 1H), 1.37 (m, 3H), 0.86 (d, J=6.4 Hz, 6H); LC/MS (m/z) ES$^+$ calcd for C$_{24}$H$_{31}$Cl$_2$N$_3$O$_3$: 479.17. Found: 480 (M+1).

Example 34

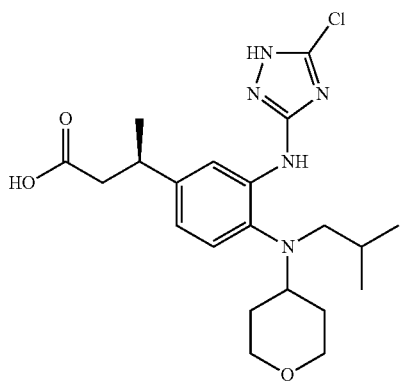 [SMILES: CC(C)CN(c1ccc([C@H](C)CC(=O)O)cc1Nc1n[nH]c(Cl)n1)C1CCOCC1]

Step A 3,5-Dibromo-1-((2-(trimethylsilyl)ethoxy)methyl)-1H-1,2,4-triazole

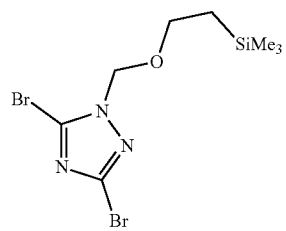 [SMILES: C[Si](C)(C)CCOCn1nc(Br)nc1Cl]

3,5-dibromo-1H-1,2,4-triazole (2 g, 8.82 mmol) was converted to 3,5-dibromo-1-((2-(trimethylsilyl)ethoxy)methyl)-1H-1,2,4-triazole (2.82 g, 90%) following a previously described procedure. $^1$H NMR (400 MHz, CDCl$_3$) δ ppm 5.46 (s, 2H), 3.63-3.72 (m, 2H), 0.90-0.98 (m, 2H), 0.01 (s, 9H).

Step B

3-Bromo-5-chloro-1-((2-(trimethylsilyl)ethoxy)methyl)-1H-1,2,4-triazole

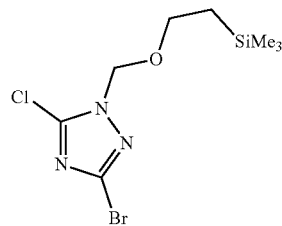

Ethylmagnesium bromide (3M in Et2O) (0.235 ml, 0.705 mmol) was added dropwise to a solution of 3,5-dibromo-1-((2-(trimethylsilyl)ethoxy)methyl)-1H-1,2,4-triazole (0.2289 g, 0.641 mmol) in THF (6.41 ml) at RT. The reaction mixture was stirred for 1 h, and hexachloroethane (0.303 g, 1.282 mmol) was added and stirring was continued overnight.

Aqueous NH₄Cl was added and the solution was extracted with EtOAc. The organic phase was washed with brine, dried (Na₂SO₄), filtered, evaporated and purified by silica gel chromatography (0-50% EtOAc/hexanes) to afford 3-bromo-5-chloro-1-((2-(trimethylsilyl)ethoxy)methyl)-1H-1,2,4-triazole (178 mg, 89%) as a clear oil. ¹H NMR (400 MHz, CDCl₃) δ ppm 5.42 (s, 2H), 3.61-3.70 (m, 2H), 0.87-0.96 (m, 2H), −0.02 (s, 9H).

Step C (R)-3-(3-((5-Chloro-1H-1,2,4-triazol-3-yl)amino)-4-(isobutyl(tetrahydro-2H-pyran-4-yl)amino)phenyl)butanoic Acid

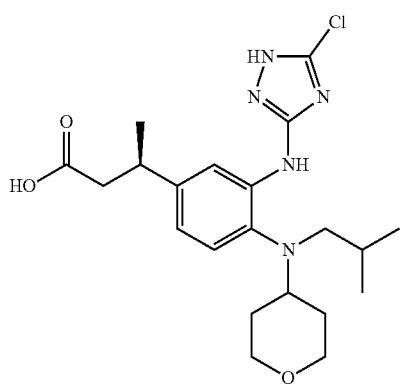 [SMILES: CC(C)CN(c1ccc([C@H](C)CC(=O)O)cc1Nc1n[nH]c(Cl)n1)C1CCOCC1]

A mixture of (R)-methyl 3-(3-amino-4-(isobutyl(tetrahydro-2H-pyran-4-yl)amino)phenyl)butanoate (0.102 g, 0.292 mmol), 3-bromo-5-chloro-1-((2-(trimethylsilyl)ethoxy)methyl)-1H-1,2,4-triazole (0.0913 g, 0.292 mmol), Xantphos (0.068 g, 0.117 mmol), and cesium carbonate (0.476 g, 1.460 mmol) was flushed with nitrogen and then stirred in toluene (4.2 ml) and heated at 100° C. for 7 h. The reaction mixture was filtered through celite, evaporated, and purified by silica gel chromatography (0-40% EtOAc/hexanes). The product was stirred in TFA (1 mL) and CH₂Cl₂ (1 mL) for 1 h and then evaporated. The residue was subjected to base hydrolysis as previously described and purified by reverse phase chromatography (10-100% CH₃CN/H₂O (0.1% formic acid)) to afford the title compound (0.0293 g, 23%) as a white solid. LCMS (M+H)⁺: m/z=436.4, 438.2. ¹H NMR (400 MHz, CD₃OD) δ ppm 7.85 (d, J=1.4 Hz, 1H), 7.19 (d, J=8.2 Hz, 1H), 6.88 (dd, J=8.1, 1.5 Hz, 1H), 3.88 (dd, J=11.2, 3.6 Hz, 2H), 3.17-3.33 (m, 3H), 2.78-2.90 (m, 3H), 2.47-2.65 (m, 2H), 1.74 (d, J=11.5 Hz, 2H), 1.55 (qd, J=12.2, 4.3 Hz, 2H), 1.36 (m, 1H), 1.29 (d, J=6.8 Hz, 3H), 0.83 (d, J=6.6 Hz, 6H).

Example 35

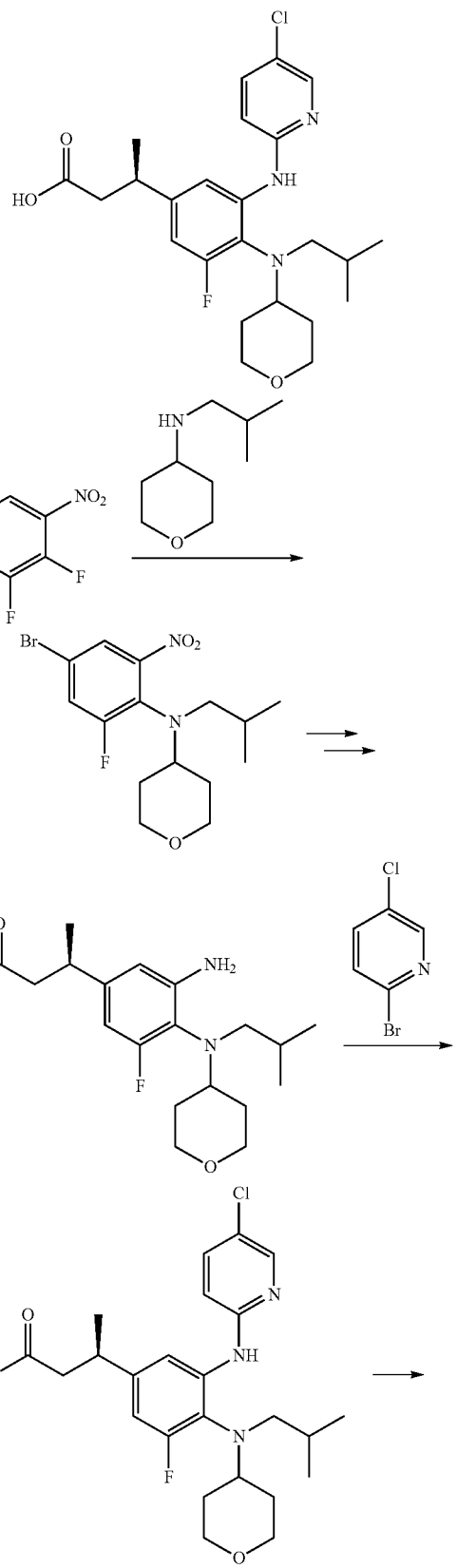

-continued

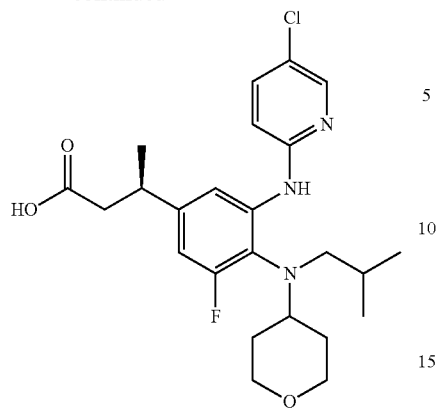

Preparation of N-(4-bromo-2-fluoro-6-nitrophenyl)-N-isobutyltetrahydro-2H-pyran-4-amine

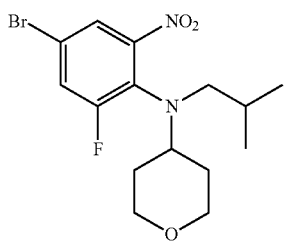 [SMILES: CC(C)CN(c1c(F)cc(Br)cc1[N+](=O)[O-])C1CCOCC1]

A solution of 5-bromo-1,2-difluoro-3-nitrobenzene (2 g, 8.40 mmol) in N-Methyl-2-pyrrolidone (NMP) (10 mL) was treated with DIEA (4.40 mL, 25.2 mmol), N-isobutyltetrahydro-2H-pyran-4-amine (1.454 g, 9.24 mmol), stirred at 110° C. over the weekend, and then cooled to rt. The reaction was combined with another batch reaction (0.42 mmol scale), diluted with Et$_2$O, washed with 1N HCl, sat. NaHCO$_3$, Brine, dried over Na$_2$SO$_4$, filtered, and concentrated. Purification with column chromatography (0-30% EtOAc/Hexane) afforded slightly mix N-(4-bromo-2-fluoro-6-nitrophenyl)-N-isobutyltetrahydro-2H-pyran-4-amine (1.615 g, 4.30 mmol, 48.8% yield) as dark red oil. $^1$H NMR (400 MHz, CHLOROFORM-d) δ ppm 7.54 (d, J=1.5 Hz, 1H), 7.41 (dd, J=2.2, 10.6 Hz, 1H), 4.01 (d, J=10.1 Hz, 2H), 3.44-3.30 (m, 2H), 3.25-3.11 (m, 1H), 2.78 (br. s., 2H), 1.87-1.67 (m, 4H), 1.45-1.34 (m, 1H), 0.85-0.73 (m, 6H). LCMS (ESI) m/z calcd for C$_{15}$H$_{20}$BrFN$_2$O$_3$: 374.06. Found: 375.3/377.3 (M+1)$^+$.

Preparation of (R)-ethyl 3-(3-amino-5-fluoro-4-(isobutyl(tetrahydro-2H-pyran-4-yl)amino)phenyl)butanoate

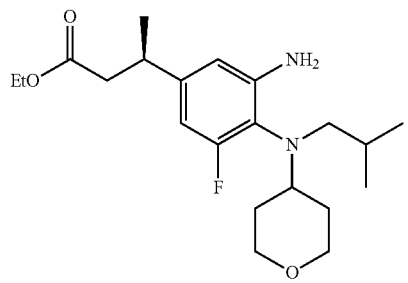

A degassed solution of N-(4-bromo-2-fluoro-6-nitrophenyl)-N-isobutyltetrahydro-2H-pyran-4-amine (1.449 g, 3.86 mmol) in N,N-Dimethylformamide (DMF) (38.6 mL) was treated with ethyl but-2-enoate (3.84 mL, 30.9 mmol), K$_2$CO$_3$ (1.601 g, 11.58 mmol), PdCl$_2$(dppf)-CH$_2$Cl$_2$ adduct (0.315 g, 0.386 mmol), bubbled with N$_2$ for 5 min, and stirred at 110° C. for 1 hour. The reaction was cooled to rt, treated with celite, and stirred for 15 min. The suspension was filtered, the filtrate was concentrated. The residue was diluted with water, extracted with EtOAc, washed with water, Brine, dried over Na$_2$SO$_4$, filtered, and concentrated. Purification with column chromatography (0-40% EtOAc/Hexane) afforded (E)-ethyl 3-(3-fluoro-4-(isobutyl(tetrahydro-2H-pyran-4-yl)amino)-5-nitrophenyl)but-2-enoate (660.9 mg, 1.618 mmol, 41.9% yield) as bright orange/yellow oil. This material was then converted to title compound in two steps according to example 6 step 3 and example 97 step D. Chiral analytical chromatography showed product had >97% ee. $^1$H NMR (400 MHz, CHLOROFORM-d) δ ppm 6.36 (s, 1H), 6.25 (d, J=13.0 Hz, 1H), 4.43-4.05 (m, 4H), 4.03-3.86 (m, 2H), 3.41-3.28 (m, 2H), 3.18-3.06 (m, 1H), 3.05-2.89 (m, 2H), 2.76-2.64 (m, 1H), 2.60-2.36 (m, 2H), 1.91 (d, J=12.6 Hz, 1H), 1.70-1.39 (m, 4H), 1.24 (d, J=6.8 Hz, 3H), 1.19 (t, J=7.1 Hz, 3H), 0.96-0.73 (m, 6H). LCMS (ESI) m/z calcd for C$_{21}$H$_{33}$FN$_2$O$_3$: 380.25. Found: 381.2 (M+1)$^+$.

Preparation of (R)-ethyl 3-(3-((5-chloropyridin-2-yl)amino)-5-fluoro-4-(isobutyl(tetrahydro-2H-pyran-4-yl)amino)phenyl)butanoate

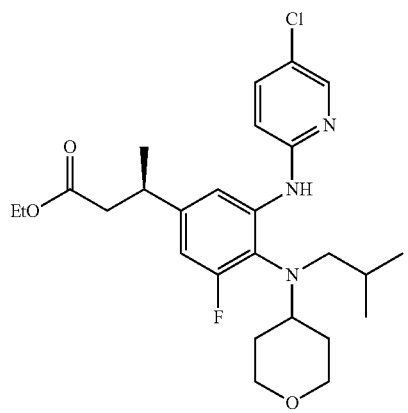 [SMILES: CC(C)CN(c1c(F)cc([C@H](C)CC(=O)O)cc1Nc1ccc(Cl)cn1)C1CCOCC1]

A degassed solution of ethyl (R)-3-(3-amino-5-fluoro-4-(isobutyl(tetrahydro-2H-pyran-4-yl)amino)phenyl)butanoate (80 mg, 0.210 mmol) in Toluene (4205 μl) was treated with 2-bromo-5-chloropyridine (48.6 mg, 0.252 mmol), PdOAc$_2$ (9.44 mg, 0.042 mmol), rac-BINAP (36.7 mg, 0.059 mmol), and Cs$_2$CO$_3$ (123 mg, 0.378 mmol). The mixture was bubbled with N$_2$ for 5 min, and then stirred at 100° C. for 1 hour. The reaction was cooled to rt, combined with another batch reaction (0.105 mmol scale), diluted with EtOAc, and filtered through a pad of celite. The filtrate was washed with water, Brine, dried over Na$_2$SO$_4$, filtered, and concentrated. Purification with column chromatography (0-40% EtOAc/Hexane) afforded (R)-ethyl 3-(3-((5-chloropyridin-2-yl)amino)-5-fluoro-4-(isobutyl(tetrahydro-2H-pyran-4-yl)amino)phenyl)butanoate (140.7 mg, 0.286 mmol, 91 yield) as white solid. $^1$H NMR (400 MHz, CHLOROFORM-d) δ ppm 8.48-8.15 (m, 2H), 8.02 (br. s., 1H), 7.49 (d, J=8.8 Hz, 1H), 6.70 (d, J=8.8 Hz, 1H), 6.50 (d, J=12.6 Hz, 1H), 4.11 (q, J=7.0 Hz, 2H), 4.03-3.84 (m, 2H), 3.44-3.21 (m, 3H), 3.08 (t, J=11.0 Hz, 1H), 2.99 (dd, J=3.9, 12.5 Hz, 1H), 2.85-2.73 (m, 1H), 2.68-2.45 (m, 2H), 1.99 (d, J=12.6 Hz, 1H), 1.72-1.38 (m, 4H), 1.32 (d, J=7.0 Hz, 3H), 1.20 (t, J=7.1 Hz, 3H), 1.00-0.78 (m, 6H). LCMS (ESI) m/z calcd for C$_{26}$H$_{35}$ClFN$_3$O$_3$: 491.24. Found: 492.2/494.4 (M+1)$^+$.

Preparation of (R)-3-(3-((5-chloropyridin-2-yl)amino)-5-fluoro-4-(isobutyl(tetrahydro-2H-pyran-4-yl)amino)phenyl)butanoic Acid

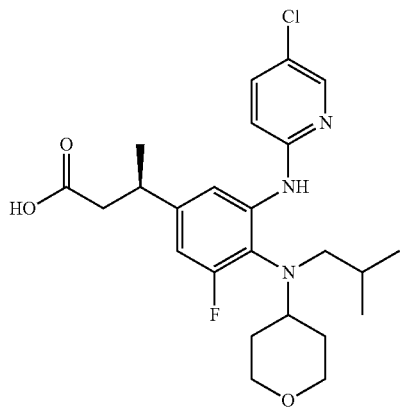

A solution of (R)-ethyl 3-(3-((5-chloropyridin-2-yl)amino)-5-fluoro-4-(isobutyl(tetrahydro-2H-pyran-4-yl)amino)phenyl)butanoate (140 mg, 0.285 mmol) in Tetrahydrofuran (THF) (4.2 mL) and Ethanol (1.400 mL) was treated with 2M LiOH (1.423 mL, 2.85 mmol) and stirred at rt for 18 hours. The reaction was diluted with 1N HCl, extracted with EtOAc, washed with Brine, dried over Na$_2$SO$_4$, filtered, and concentrated. Purification with reverse phase HPLC (50-100% MeCN-0.1% formic acid/H$_2$O-0.1% formic acid) afforded (R)-3-(3-((5-chloropyridin-2-yl)amino)-5-fluoro-4-(isobutyl(tetrahydro-2H-pyran-4-yl)amino)phenyl)butanoic acid (107.5 mg, 0.220 mmol, 77% yield, 95% purity) as off-white solid. $^1$H NMR (400 MHz, CHLOROFORM-d) δ ppm 8.28 (s, 1H), 8.24 (s, 1H), 8.05 (s, 1H), 7.49 (d, J=8.8 Hz, 1H), 6.69 (d, J=8.8 Hz, 1H), 6.51 (d, J=12.6 Hz, 1H), 4.07-3.84 (m, 2H), 3.45-3.20 (m, 3H), 3.09 (t, J=10.9 Hz, 1H), 2.99 (dd, J=3.8, 12.6 Hz, 1H), 2.87-2.75 (m, 1H), 2.75-2.51 (m, 2H), 1.99 (d, J=12.6 Hz, 1H), 1.69-1.39 (m, 4H), 1.34 (d, J=6.8 Hz, 3H), 1.01-0.76 (m, 6H). LCMS (ESI) m/z calcd for C$_{24}$H$_{31}$ClFN$_3$O$_3$: 463.20. Found: 464.4 (M+1)$^+$, 462.3 (M−1)$^−$.

Example 36

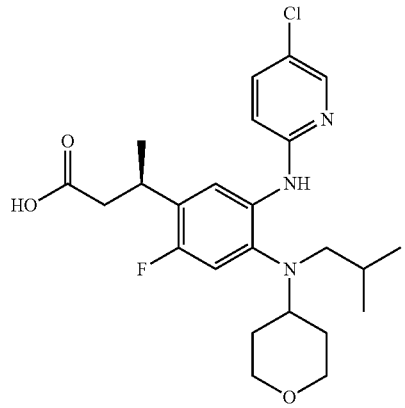

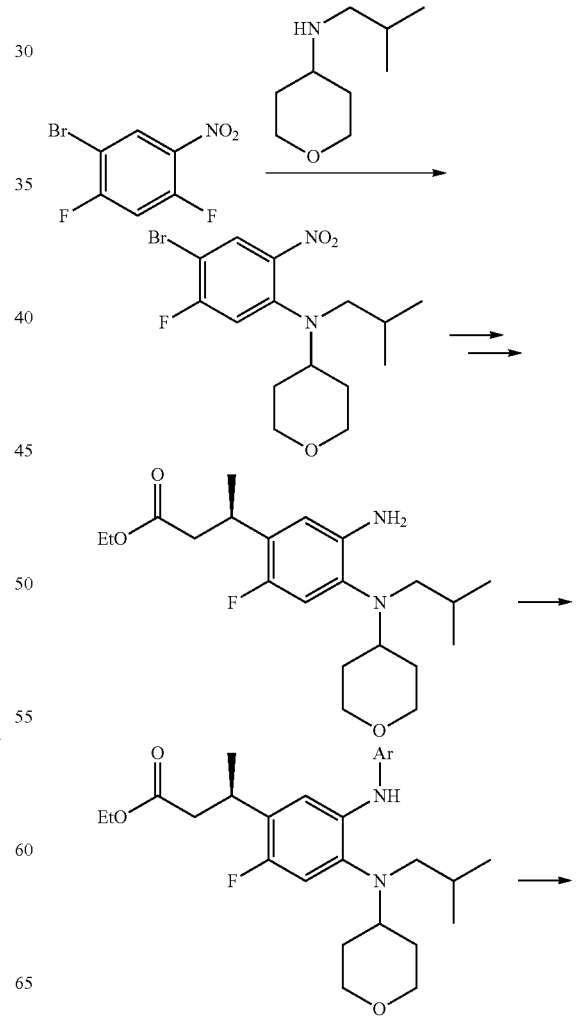

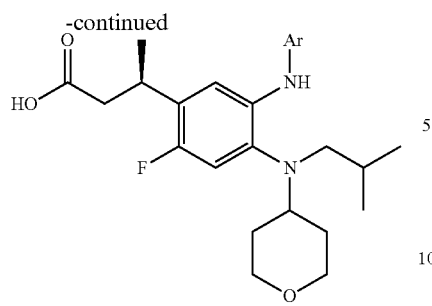

Preparation of N-(4-bromo-5-fluoro-2-nitrophenyl)-N-isobutyltetrahydro-2H-pyran-4-amine

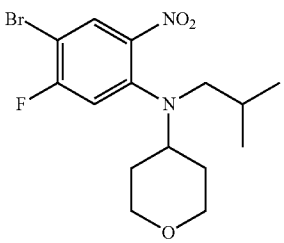 [SMILES: CC(C)CN(c1cc(F)c(Br)cc1[N+](=O)[O-])C1CCOCC1]

A solution of 1-bromo-2,4-difluoro-5-nitrobenzene (1.806 g, 7.59 mmol) in N-Methyl-2-pyrrolidone (NMP) (3 mL) was treated with DIEA (3.98 mL, 22.77 mmol), followed by a solution of N-isobutyltetrahydro-2H-pyran-4-amine (1.313 g, 8.35 mmol) in N-Methyl-2-pyrrolidone (NMP) (12 mL). The reaction was stirred at 110° C. under Ar for 23 hours and then cooled to rt. The mixture was diluted with Et$_2$O, washed with 1N HCl, sat. NaHCO$_3$, Brine, dried over Na$_2$SO$_4$, filtered, and concentrated. Purification with column chromatography (0-40% EtOAc/Hexane) afforded N-(4-bromo-5-fluoro-2-nitrophenyl)-N-isobutyltetrahydro-2H-pyran-4-amine (1.5138 g, 4.03 mmol, 53.2% yield) as bright yellow oil that slowly became orange solid. $^1$H NMR (400 MHz, CHLOROFORM-d) δ ppm 8.00 (d, J=7.3 Hz, 1H), 6.92 (d, J=10.6 Hz, 1H), 3.99 (dd, J=2.9, 11.5 Hz, 2H), 3.32 (t, J=11.7 Hz, 2H), 3.16-3.03 (m, 1H), 2.88 (d, J=7.1 Hz, 2H), 1.89-1.62 (m, 5H), 0.90 (d, J=6.4 Hz, 6H). LCMS (ESI) m/z calcd for C$_{15}$H$_{20}$BrFN$_2$O$_3$: 374.06. Found: 375.3/377.2 (M+1)$^+$.

Preparation of (R)-ethyl 3-(5-amino-2-fluoro-4-(isobutyl(tetrahydro-2H-pyran-4-yl)amino)phenyl)butanoate

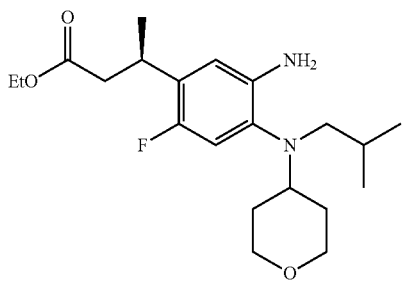

Preparation of (R)-ethyl 3-(5-amino-2-fluoro-4-(isobutyl(tetrahydro-2H-pyran-4-yl)amino)phenyl)butanoate Title compound (purple oil) was prepared from N-(4-bromo-5-fluoro-2-nitrophenyl)-N-isobutyltetrahydro-2H-pyran-4-amine in three steps according to example 6 step 2-3, and example 97 step D. Chiral analytical chromatography showed product had −94.7% ee $^1$H NMR (400 MHz, CHLOROFORM-d) δ ppm 6.74 (d, J=11.9 Hz, 1H), 6.56 (d, J=7.5 Hz, 1H), 4.18-4.04 (m, 2H), 4.04-3.59 (m, 4H), 3.51-3.38 (m, 1H), 3.32 (t, J=10.6 Hz, 2H), 2.97-2.42 (m, 5H), 1.80-1.61 (m, 4H), 1.53-1.40 (m, 1H), 1.33-1.26 (m, 3H), 1.18 (t, J=7.1 Hz, 3H), 0.84 (d, J=6.4 Hz, 6H). LCMS (ESI) m/z calcd for C$_{21}$H$_{33}$FN$_2$O$_3$: 380.25. Found: 381.2/382.6 (M+1)$^+$.

Preparation of (R)-ethyl 3-(5-((5-chloropyridin-2-yl)amino)-2-fluoro-4-(isobutyl(tetrahydro-2H-pyran-4-yl)amino)phenyl)butanoate

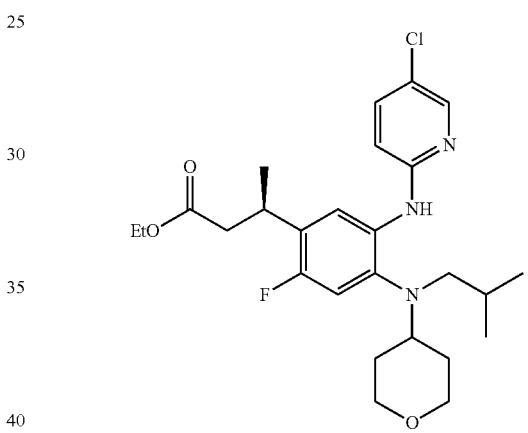

A degassed solution of (R)-ethyl 3-(5-amino-2-fluoro-4-(isobutyl(tetrahydro-2H-pyran-4-yl)amino)phenyl)butanoate (100 mg, 0.263 mmol) in Toluene (5.3 mL) was treated with 2-bromo-5-chloropyridine (60.7 mg, 0.315 mmol), PdOAc$_2$ (11.80 mg, 0.053 mmol), rac-BINAP (45.8 mg, 0.074 mmol), and Cs$_2$CO$_3$ (154 mg, 0.473 mmol). The mixture was bubbled with N$_2$ for 5 min, and then stirred at 100° C. for 1 hour. The reaction was cooled to rt, diluted with EtOAc, and filtered through a pad of celite. The filtrate was washed with water, Brine, dried over Na$_2$SO$_4$, filtered, and concentrated. Purification with column chromatography (0-50% EtOAc/Hexane) afforded (R)-ethyl 3-(5-((5-chloropyridin-2-yl)amino)-2-fluoro-4-(isobutyl(tetrahydro-2H-pyran-4-yl)amino)phenyl)butanoate (94.5 mg, 0.192 mmol, 73.1% yield) as pale yellow oil. $^1$H NMR (400 MHz, CHLOROFORM-d) δ ppm 8.19 (s, 1H), 8.06 (d, J=7.5 Hz, 1H), 7.67 (br. s., 1H), 7.46 (dd, J=2.4, 8.8 Hz, 1H), 6.86 (d, J=11.4 Hz, 1H), 6.66 (d, J=8.8 Hz, 1H), 4.12 (q, J=7.1 Hz, 2H), 3.94 (d, J=11.4 Hz, 2H), 3.62-3.48 (m, 1H), 3.23 (t, J=11.0 Hz, 2H), 2.90-2.75 (m, 3H), 2.74-2.55 (m, 2H), 1.75-1.63 (m, 4H), 1.54-1.41 (m, 1H), 1.35 (d, J=7.0 Hz, 3H), 1.20 (t, J=7.1 Hz, 3H), 0.86 (d, J=6.6 Hz, 6H). LCMS (ESI) m/z calcd for C$_{26}$H$_{35}$ClFN$_3$O$_3$: 491.24. Found: 492.1/494.5 (M+1)$^+$, 490.5 (M−1)$^−$.

Preparation of (R)-3-(5-((5-chloropyridin-2-yl)amino)-2-fluoro-4-(isobutyl(tetrahydro-2H-pyran-4-yl)amino)phenyl)butanoic Acid

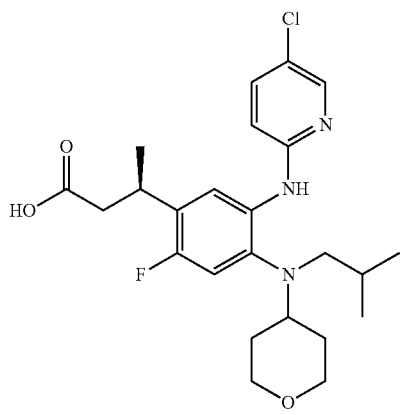

Preparation of (R)-3-(5-((5-chloropyridin-2-yl)amino)-2-fluoro-4-(isobutyl(tetrahydro-2H-pyran-4-yl)amino)phenyl)butanoic Acid A solution of (R)-ethyl 3-(5-((5-chloropyridin-2-yl)amino)-2-fluoro-4-(isobutyl(tetrahydro-2H-pyran-4-yl)amino)phenyl)butanoate (88 mg, 0.179 mmol) in Tetrahydrofuran (THF) (2.7 mL) and Ethanol (0.9 mL) was treated with 2M LiOH (0.894 mL, 1.789 mmol) and stirred at rt for 18 hours. The reaction was diluted with 1N HCl, extracted with EtOAc, washed with Brine, dried over Na$_2$SO$_4$, filtered, and concentrated. Purification with reverse phase HPLC (30-100% MeCN-0.1% formic acid/H$_2$O-0.1% formic acid) afforded (R)-3-(5-((5-chloropyridin-2-yl)amino)-2-fluoro-4-(isobutyl(tetrahydro-2H-pyran-4-yl)amino)phenyl)butanoic acid (75.4 mg, 0.158 mmol, 88% yield, 97% purity) as off-white solid. $^1$H NMR (400 MHz, CHLOROFORM-d) δ ppm 8.18 (s, 1H), 8.03 (d, J=7.7 Hz, 1H), 7.69 (br. s., 1H), 7.46 (d, J=8.8 Hz, 1H), 6.86 (d, J=11.5 Hz, 1H), 6.65 (d, J=8.8 Hz, 1H), 3.95 (d, J=11.2 Hz, 2H), 3.60-3.44 (m, 1H), 3.32-3.13 (m, 2H), 2.88-2.72 (m, 4H), 2.71-2.61 (m, 1H), 1.73-1.61 (m, 4H), 1.53-1.44 (m, 1H), 1.38 (d, J=7.0 Hz, 3H), 0.87 (d, J=6.4 Hz, 6H). LCMS (ESI) m/z calcd for C$_{24}$H$_{31}$ClFN$_3$O$_3$: 463.20. Found: 464.4 (M+1)$^+$, 462.3 (M−1)$^−$.

Example 37

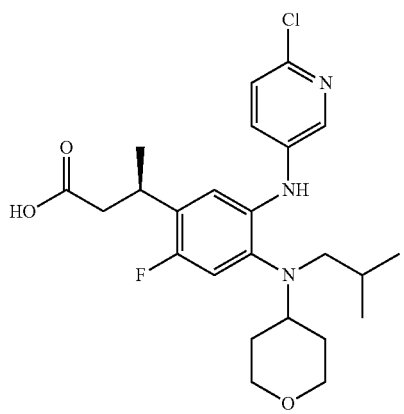

Step 1: (R)-ethyl 3-(5-((6-chloropyridin-3-yl)amino)-2-fluoro-4-(isobutyl(tetrahydro-2H-pyran-4-yl)amino)phenyl)butanoate

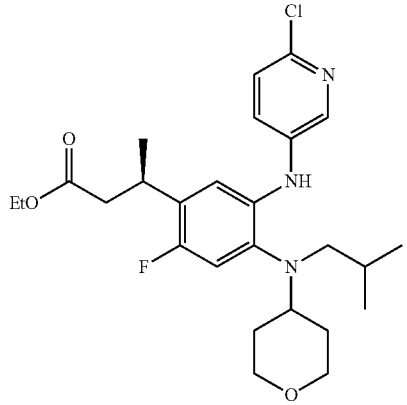 [SMILES: CC(C)CN(c1cc(F)c([C@H](C)CC(=O)O)cc1Nc1ccc(Cl)nc1)C1CCOCC1]

A degassed solution of (R)-ethyl 3-(5-amino-2-fluoro-4-(isobutyl(tetrahydro-2H-pyran-4-yl)amino)phenyl)butanoate (80 mg, 0.210 mmol) in Toluene (3 mL) was treated with 5-bromo-2-chloropyridine (60.7 mg, 0.315 mmol), K$_2$CO$_3$ (145 mg, 1.051 mmol), xantphos (48.7 mg, 0.084 mmol), and Pd$_2$(dba)$_3$ (38.5 mg, 0.042 mmol). The mixture was bubbled with N$_2$ for 3 min, and then stirred at 100° C. for 6 hours. The reaction was cooled to rt, diluted with EtOAc, and filtered through a pad of celite. The filtrate was washed with water, Brine, dried over Na$_2$SO$_4$, filtered, and concentrated. Purification with column chromatography (0-60% EtOAc/Hexane) afforded (R)-ethyl 3-(5-((6-chloropyridin-3-yl)amino)-2-fluoro-4-(isobutyl(tetrahydro-2H-pyran-4-yl)amino)phenyl)butanoate (75.6 mg, 0.154 mmol, 73.1% yield) as yellow oil. $^1$H NMR (400 MHz, CHLOROFORM-d) δ ppm 8.17 (br. s., 1H), 7.38 (dd, J=2.2, 8.2 Hz, 1H), 7.22 (d, J=8.6 Hz, 1H), 7.05 (d, J=7.3 Hz, 1H), 6.87 (d, J=11.5 Hz, 1H), 6.69 (br. s., 1H), 4.13-4.06 (m, 2H), 3.95 (d, J=11.2 Hz, 2H), 3.49 (sxt, J=7.0 Hz, 1H), 3.30-3.12 (m, 2H), 2.86-2.70 (m, 3H), 2.68-2.48 (m, 2H), 1.72-1.62 (m, 4H), 1.52-1.39 (m, 1H), 1.30 (d, J=7.0 Hz, 3H), 1.18 (t, J=7.1 Hz, 3H), 0.86 (d, J=6.6 Hz, 6H). LCMS (ESI) m/z calcd for C$_{26}$H$_{35}$ClFN$_3$O$_3$: 491.24. Found: 492.3 (M+1)$^+$, 490.6 (M−1)$^−$.

Step 2: (R)-3-(5-((6-chloropyridin-3-yl)amino)-2-fluoro-4-(isobutyl(tetrahydro-2H-pyran-4-yl)amino)phenyl)butanoic Acid

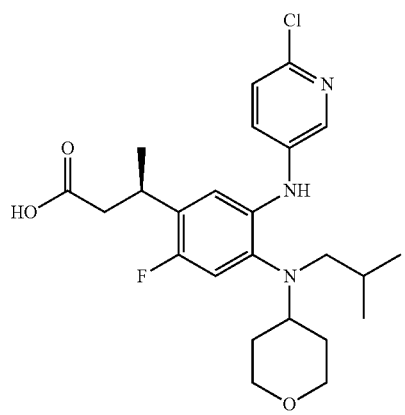 [SMILES: CC(C)CN(c1cc(F)c([C@H](C)CC(=O)O)cc1Nc1ccc(Cl)nc1)C1CCOCC1]

A solution of (R)-ethyl 3-(5-((6-chloropyridin-3-yl)amino)-2-fluoro-4-(isobutyl(tetrahydro-2H-pyran-4-yl)amino)phenyl)butanoate (72 mg, 0.146 mmol) in Tetrahydrofuran (THF) (2195 µl) and Ethanol (732 µl) was treated with 2M LiOH (732 µl, 1.463 mmol) and stirred at rt for 18 hours. The reaction was diluted with 1N HCl, extracted with EtOAc, washed with Brine, dried over $Na_2SO_4$, filtered, and concentrated. Purification with reverse phase HPLC (30-100% MeCN-0.1% formic acid/$H_2O$-0.1% formic acid) afforded (R)-3-(5-((6-chloropyridin-3-yl)amino)-2-fluoro-4-(isobutyl(tetrahydro-2H-pyran-4-yl)amino)phenyl)butanoic acid (51 mg, 0.104 mmol, 71.4% yield, 95% purity) as light beige solid. $^1$H NMR (400 MHz, CHLOROFORM-d) δ ppm 8.20 (br. s., 1H), 7.42-7.32 (m, 1H), 7.22 (d, J=8.4 Hz, 1H), 7.07 (d, J=7.3 Hz, 1H), 6.88 (d, J=11.5 Hz, 1H), 6.67 (br. s., 1H), 3.95 (d, J=10.8 Hz, 2H), 3.56-3.41 (m, 1H), 3.32-3.14 (m, 2H), 2.86-2.53 (m, 5H), 1.75-1.57 (m, 4H), 1.52-1.40 (m, 1H), 1.34 (d, J=6.6 Hz, 3H), 0.86 (d, J=6.0 Hz, 6H). LCMS (ESI) m/z calcd for $C_{24}H_{31}ClFN_3O_3$: 463.20. Found: 464.5 (M+1)$^+$, 462.5 (M−1)$^−$.

Example 38

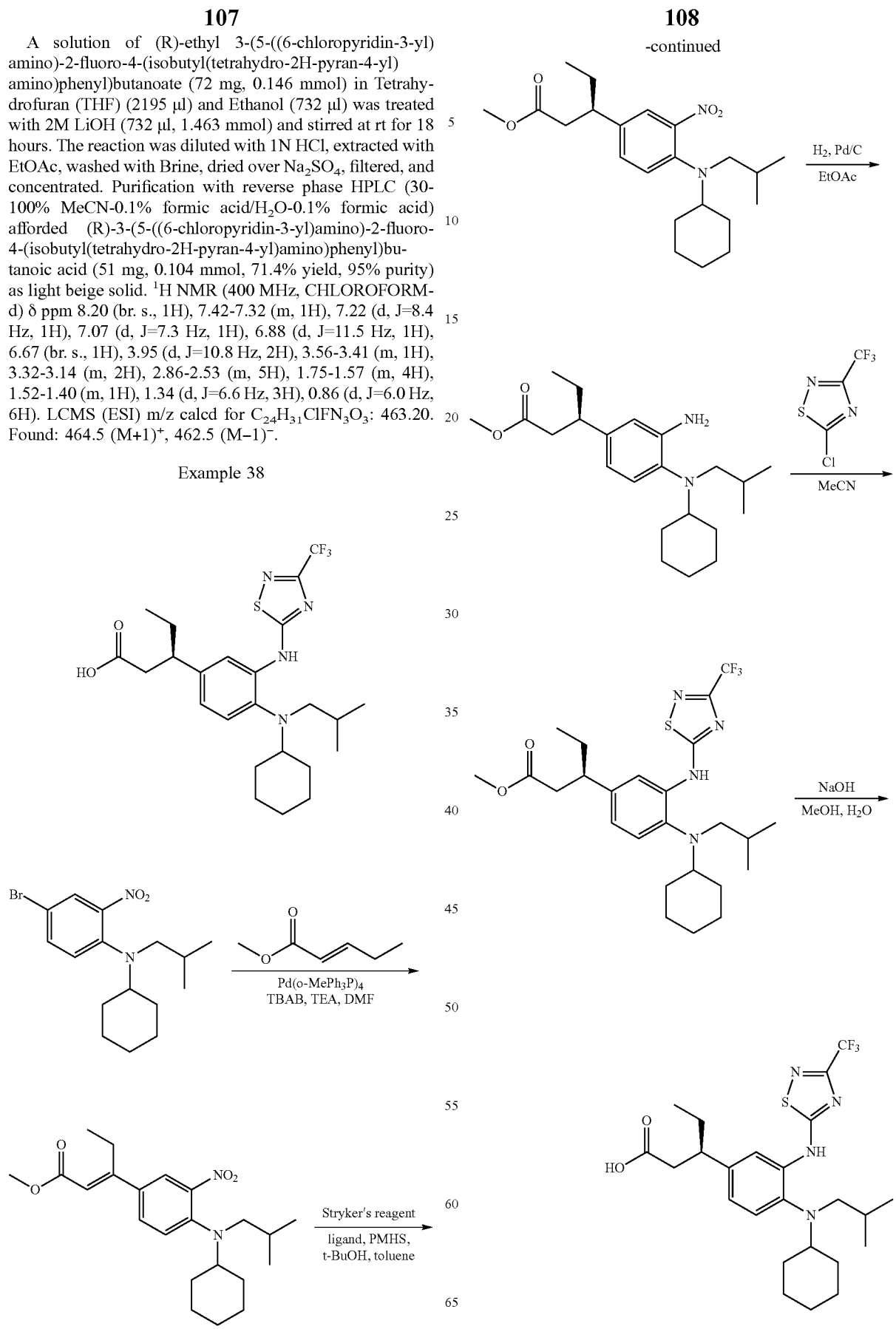

Preparation of methyl (E)-3-(4-(cyclohexyl (isobutyl)amino)-3-nitrophenyl)pent-2-enoate

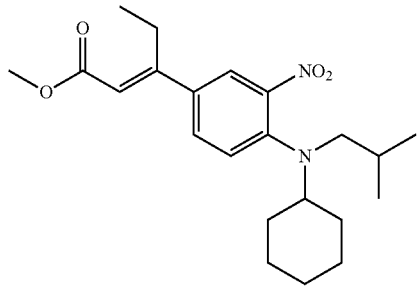 [SMILES: CC/C(=C\C(=O)OC)c1ccc(N(CC(C)C)C2CCCCC2)c([N+](=O)[O-])c1]

A mixture of 4-bromo-N-cyclohexyl-N-isobutyl-2-nitroaniline (500 mg, 1.54 mmol), methyl (E)-pent-2-enoate (393 mg, 3.07 mmol), TBAB (100 mg, 0.31 mmol), Pd(o-MePh₃P)₄ (61 mg, 0.08 mmol) and TEA (0.43 mL, 3.07 mmol) in DMF (5 mL) was stirred at 110° C. under N₂ atmosphere overnight. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-10% EtOAc in PE) to afford the title compound (90 mg, 15% yield). LCMS (ESI) m/z calcd for $C_{22}H_{32}N_2O_4$: 388.24. Found: 389.11 (M+1)$^+$.

Preparation of methyl (R)-3-(4-(cyclohexyl (isobutyl)amino)-3-nitrophenyl) pentanoate

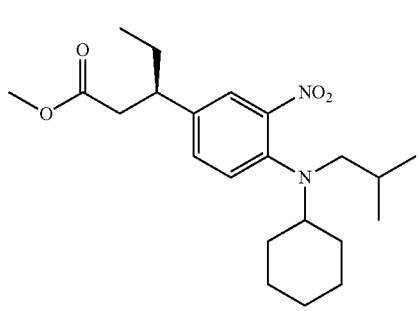 [SMILES: CC[C@H](CC(=O)OC)c1ccc(N(CC(C)C)C2CCCCC2)c([N+](=O)[O-])c1]

At −5° C., to a mixture of (CuHPh₃P)₆ (6 mg, 0.003 mmol) and (R,S)-PPF-P(tBu)₂ (6 mg, 0.011 mmol) in toluene (2 mL) was added PMHS (30 mg) and t-BuOH (21 mg) before the introduction of methyl (E)-3-(4-(cyclohexyl (isobutyl)amino)-3-nitrophenyl)pent-2-enoate (100 mg, 0.258 mmol). After stirred at −5° C. for 2 hr, the resulting mixture was quenched with sat. NaHCO₃ aq. solution and extracted with EtOAc. The organic layer was washed with brine, dried over Na₂SO₄, filtered and concentrated to give the crude product which was purified by flash chromatography (silica gel, 0-10% EtOAc in PE) to afford the title compound (30 mg, 30% yield). LCMS (ESI) m/z calcd for $C_{22}H_{34}N_2O_4$: 390.25. Found: 391.33 (M+1)$^+$.

Preparation of methyl (R)-3-(3-amino-4-(cyclohexyl (isobutyl)amino)phenyl) pentanoate

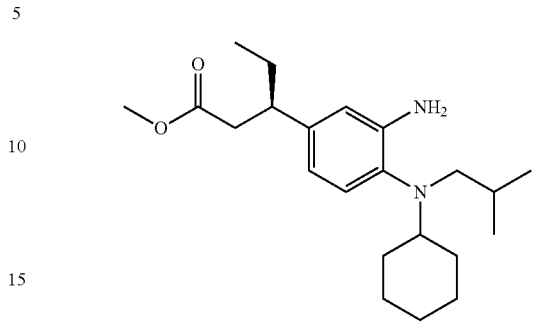

A mixture of methyl (R)-3-(4-(cyclohexyl(isobutyl) amino)-3-nitrophenyl)pentanoate (70 mg, 0.179 mmol) and 10% Pd/C (20 mg) in EtOAc (10 mL) was stirred at r.t. under H₂ atmosphere for 2 hr. The resulting mixture was filtered through a pad of Celite and the filtrate was concentrated under reduced pressure to give the crude product which was purified by flash chromatography (silica gel, 0-10% EtOAc in PE) to afford the title compound (50 mg, 78% yield). LCMS (ESI) m/z calcd for $C_{22}H_{36}N_2O_2$: 360.28. Found: 361.63 (M+1)$^+$.

Preparation of methyl (R)-3-(4-(cyclohexyl (isobutyl)amino)-3-((3-(trifluoro methyl)-1,2,4-thiadiazol-5-yl)amino)phenyl)pentanoate

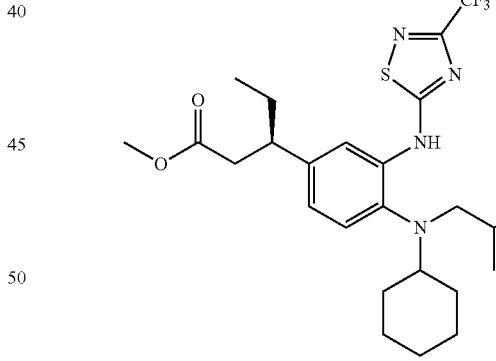

A mixture of methyl (R)-3-(3-amino-4-(cyclohexyl (isobutyl)amino)phenyl)pentanoate (130 mg, 0.36 mmol) and 5-chloro-3-(trifluoromethyl)-1,2,4-thiadiazole (104 mg, 0.55 mmol) in MeCN (5 mL) was stirred at 90° C. under N₂ atmosphere for 24 hr. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-20% EtOAc in PE) to afford the title compound (113 mg, 61% yield). LCMS (ESI) m/z calcd for $C_{25}H_{35}F_3N_4O_2S$: 512.24. Found: 513.12 (M+1)$^+$.

Preparation of (R)-3-(4-(cyclohexyl(isobutyl) amino)-3-((3-(trifluoromethyl)-1,2,4-thiadiazol-5-yl) amino)phenyl)pentanoic Acid

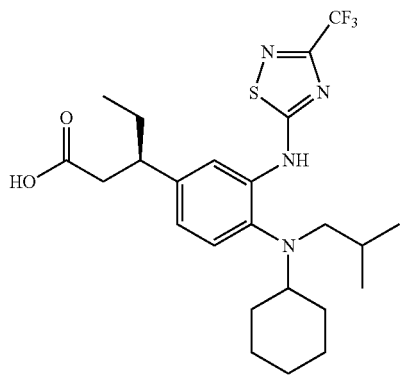 [SMILES: CC[C@H](CC(=O)O)c1ccc(N(CC(C)C)C2CCCCC2)c(Nc2nc(C(F)(F)F)ns2)c1]

To a solution of methyl (R)-3-(4-(cyclohexyl(isobutyl)amino)-3-((3-(trifluoromethyl)-1,2,4-thiadiazol-5-yl)amino)phenyl)pentanoate (110 mg, 0.22 mmol) in MeOH (5 mL) was added 1N NaOH aq. (1.1 mL). After stirred at rt. overnight, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (55 mg, 51% yield) as a white powder. $^1$H NMR (400 MHz, $CDCl_3$) δ 9.43 (s, 1H), 7.24 (d, J=1.5 Hz, 1H), 7.19 (d, J=8.2 Hz, 1H), 6.93 (dd, J=8.2, 1.8 Hz, 1H), 3.10-2.99 (m, 1H), 2.81 (d, J=6.8 Hz, 2H), 2.75-2.51 (m, 3H), 1.89-1.55 (m, 7H), 1.42-1.04 (m, 6H), 0.92-0.76 (m, 9H). LCMS (ESI) m/z calcd for $C_{24}H_{33}F_3N_4O_2S$: 498.23. Found: 496.97 (M−1)⁻.

Example 39

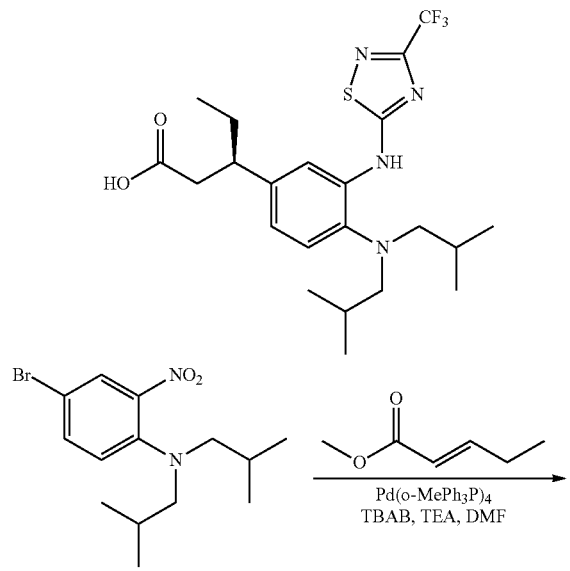

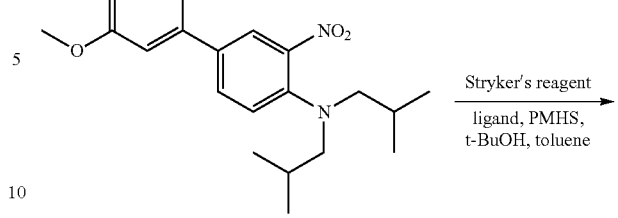

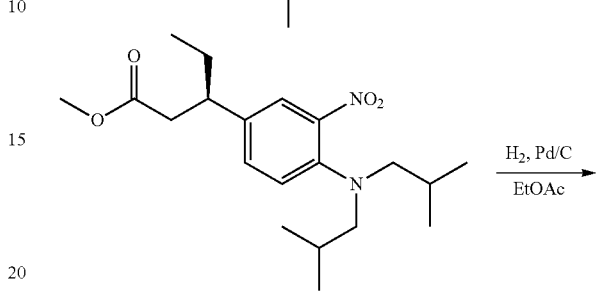

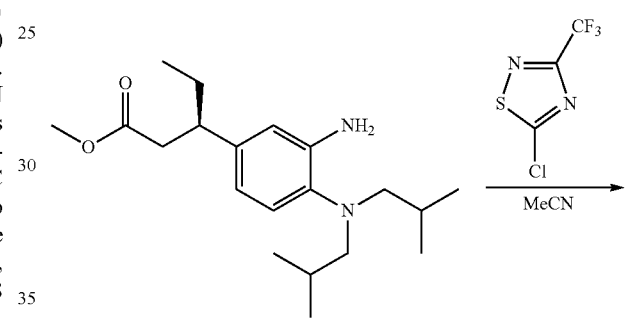

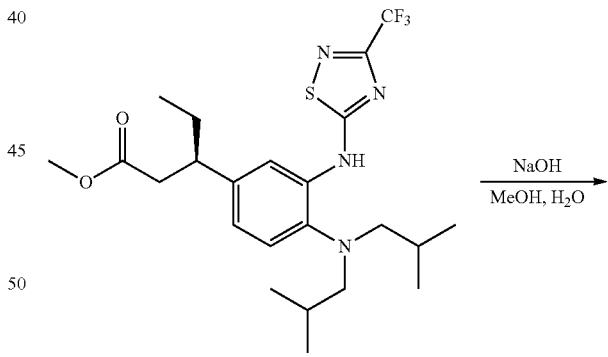

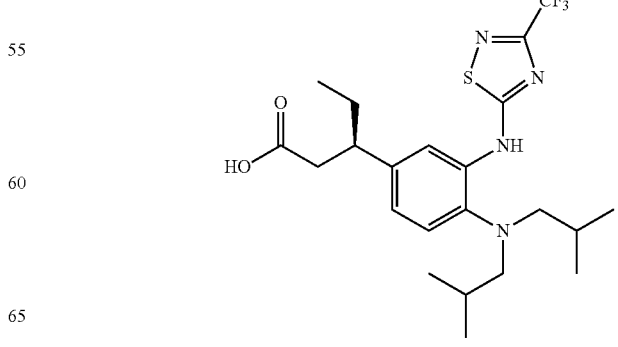

113

Preparation of methyl (E)-3-(4-(diisobutylamino)-3-nitrophenyl)pent-2-enoate

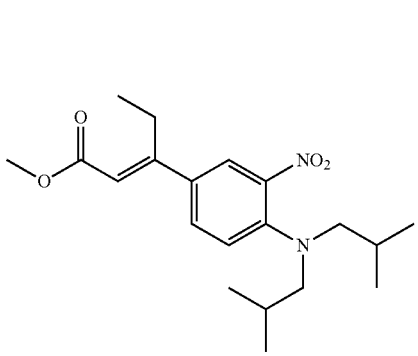 [SMILES: CC/C(=C\C(=O)OC)c1ccc(N(CC(C)C)CC(C)C)c([N+](=O)[O-])c1]

A mixture of 4-bromo-N,N-diisobutyl-2-nitroaniline (5.0 g, 15.2 mmol), methyl (E)-pent-2-enoate (3.9 g, 30.3 mmol), TBAB (980 mg, 3.04 mmol), Pd(o-MePh$_3$P)$_4$ (597 mg, 0.76 mmol) and TEA (4.2 mL, 30.3 mmol) in DMF (10 mL) was stirred at 110° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-10% EtOAc in PE) to afford the title compound (270 mg, 5% yield). LCMS (ESI) m/z calcd for C$_{20}$H$_{30}$N$_2$O$_4$: 362.22. Found: 363.63 (M+1)$^+$.

Preparation of methyl (R)-3-(4-(diisobutylamino)-3-nitrophenyl)pentanoate

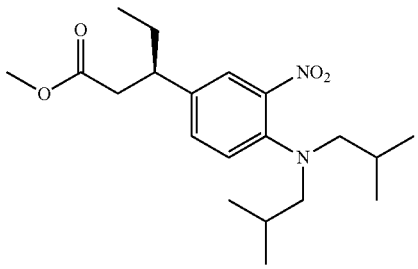 [SMILES: CC[C@H](CC(=O)OC)c1ccc(N(CC(C)C)CC(C)C)c([N+](=O)[O-])c1]

At −5° C., to a mixture of (CuHPh$_3$P)$_6$ (17 mg, 0.052 mmol) and (R,S)—PPF—P(tBu)$_2$ (8 mg, 0.015 mmol) in toluene (5 mL) was added PMHS (90 mg) and t-BuOH (61 mg) before the introduction of methyl (E)-3-(4-(diisobutylamino)-3-nitrophenyl)pent-2-enoate (270 mg, 0.747 mmol). After stirred at r.t. overnight, the resulting mixture was quenched with sat. NaHCO$_3$ aq. solution and extracted with EtOAc. The organic layer was washed with brine, dried over Na$_2$SO$_4$, filtered and concentrated to give the crude product which was purified by flash chromatography (silica gel, 0-10% EtOAc in PE) to afford the title compound (180 mg, 66% yield). LCMS (ESI) m/z calcd for C$_{20}$H$_{32}$N$_2$O$_4$: 364.24. Found: 365.65 (M+1)$^+$.

114

Preparation of methyl (R)-3-(3-amino-4-(diisobutylamino)phenyl)pentanoate

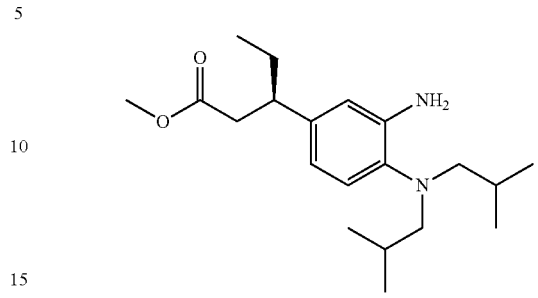

A mixture of methyl (R)-3-(4-(diisobutylamino)-3-nitrophenyl)pentanoate (180 mg, 0.495 mmol) and 10% Pd/C (100 mg) in EtOAc (10 mL) was stirred at 40° C. under H$_2$ atmosphere for 1 hr. The resulting mixture was filtered through a pad of Celite and the filtrate was concentrated under reduced pressure to give the crude product which was purified by flash chromatography (silica gel, 0-20% EtOAc in PE) to afford the title compound (165 mg, 99% yield). LCMS (ESI) m/z calcd for C$_{20}$H$_{34}$N$_2$O$_2$: 334.26. Found: 335.53 (M+1)$^+$.

Preparation of methyl (R)-3-(4-(diisobutylamino)-3-((3-(trifluoromethyl)-1,2,4-hiadiazol-5-yl)amino)phenyl)pentanoate

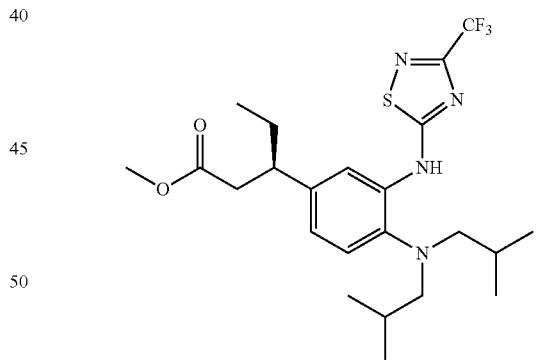

A mixture of methyl (R)-3-(3-amino-4-(diisobutylamino)phenyl)pentanoate (60 mg, 0.179 mmol) and 5-chloro-3-(trifluoromethyl)-1,2,4-thiadiazole (101 mg, 0.538 mmol) in MeCN (2 mL) was stirred at 90° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-10% EtOAc in PE) to afford the title compound (44 mg, 51% yield). LCMS (ESI) m/z calcd for C$_{23}$H$_{33}$F$_3$N$_4$O$_2$S: 486.23. Found: 485.20 (M−1)$^-$.

Preparation of (R)-3-(4-(diisobutylamino)-3-((3-(trifluoromethyl)-1,2,4-thiadiazol-yl)amino)phenyl)pentanoic Acid

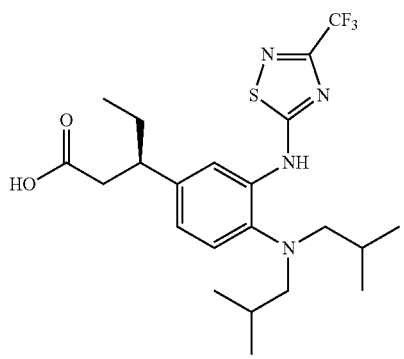

To a solution of methyl (R)-3-(4-(diisobutylamino)-3-((3-(trifluoromethyl)-1,2,4-hiadiazol-5-yl)amino)phenyl)pentanoate (44 mg, 0.09 mmol) in MeOH (5 mL) was added 1N NaOH aq. (2 mL). After stirred at r.t. overnight, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (29 mg, 68% yield) as a white powder. $^1$H NMR (400 MHz, $CDCl_3$) δ 9.51 (s, 1H), 7.38 (s, 1H), 7.20 (d, J=8.2 Hz, 1H), 6.95 (dd, J=8.2, 1.7 Hz, 1H), 3.09-3.00 (m, 1H), 2.70-2.58 (m, 5H), 1.87-1.57 (m, 5H), 0.93-0.82 (m, 15H). (Found: 30H, the proton on the carboxylic acid was not observed, J confirmed). LCMS (ESI) m/z calcd for $C_{22}H_{31}F_3N_4O_2S$: 472.21. Found: 473.00 (M+1)$^+$.

Example 40

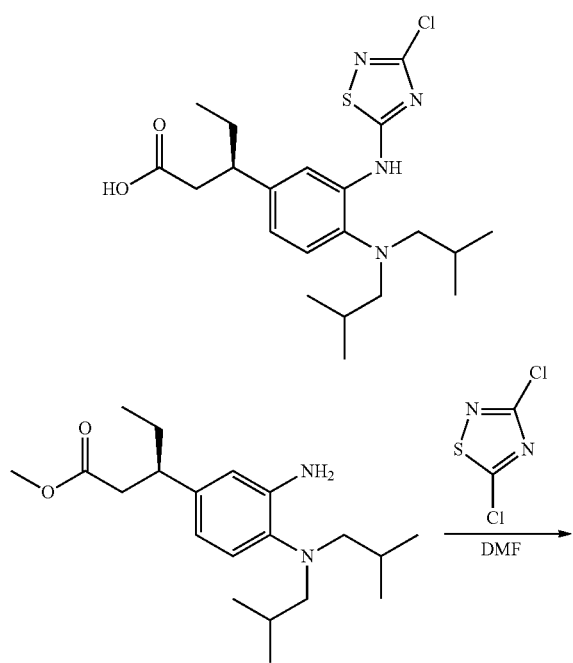

-continued

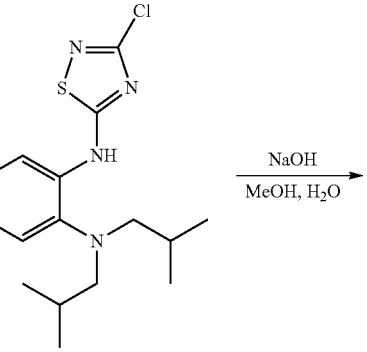

Preparation of methyl (R)-3-(3-((3-chloro-1,2,4-thiadiazol-5-yl)amino)-4-(diiso butylamino)phenyl)pentanoate

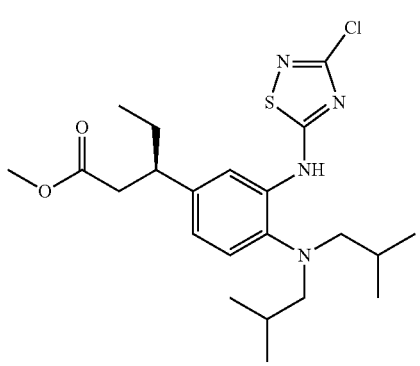 [SMILES: CC[C@H](CC(=O)OC)c1ccc(N(CC(C)C)CC(C)C)c(Nc2nc(Cl)ns2)c1]

A mixture of methyl (R)-3-(3-amino-4-(diisobutylamino)phenyl)pentanoate (120 mg, 0.358 mmol) and 3,5-dichloro-1,2,4-thiadiazole (166 mg, 1.07 mmol) in DMF (2 mL) was stirred at 80° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-10% EtOAc in PE) to afford the title compound (70 mg, 43% yield). LCMS (ESI) m/z calcd for $C_{22}H_{33}ClN_4O_2S$: 452.20. Found: 453.54/455.31 (M/M+2)$^+$.

Preparation of (R)-3-(3-((3-chloro-1,2,4-thiadiazol-5-yl)amino)-4-(diisobutyl mino)phenyl)pentanoic Acid

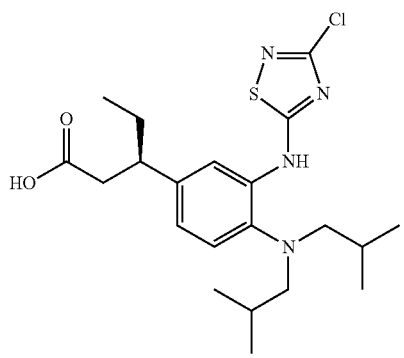 [SMILES: CC[C@H](CC(=O)O)c1ccc(N(CC(C)C)CC(C)C)c(Nc2nc(Cl)ns2)c1]

To a solution of methyl (R)-3-(3-((3-chloro-1,2,4-thiadiazol-5-yl)amino)-4-(diisobutyl amino)phenyl)pentanoate (70 mg, 0.155 mmol) in MeOH (5 mL) was added 1N NaOH aq. (2 mL). After stirred at 40° C. for 6 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (38 mg, 56% yield) as a white powder. $^1$H NMR (400 MHz, CDCl$_3$) δ 9.45 (s, 1H), 7.22 (d, J=1.3 Hz, 1H), 7.19 (d, J=8.2 Hz, 1H), 6.93 (dd, J=8.2, 1.8 Hz, 1H), 3.07-2.98 (m, 1H), 2.72-2.54 (m, 6H), 1.83-1.60 (m, 4H), 0.93-0.80 (m, 15H). LCMS (ESI) m/z calcd for C$_{21}$H$_{31}$ClN$_4$O$_2$S: 438.19. Found: 439.21/441.18. (M/M+2)$^+$.

Example 41

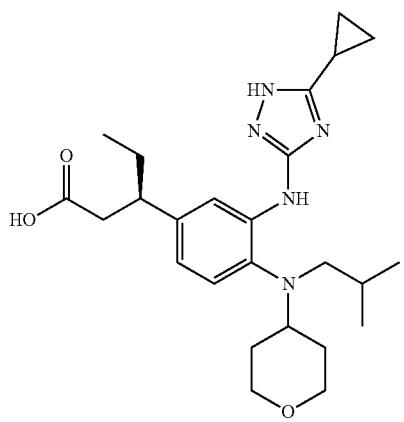 [SMILES: CC[C@H](CC(=O)O)c1ccc(N(CC(C)C)C2CCOCC2)c(Nc2n[nH]c(C3CC3)n2)c1]

Step A (R)-methyl 3-(3-((5-cyclopropyl-1-((2-(trimethylsilyl)ethoxy)methyl)-1H-1,2,4-triazol-3-yl)amino)-4-(isobutyl(tetrahydro-2H-pyran-4-yl)amino)phenyl) pentanoate

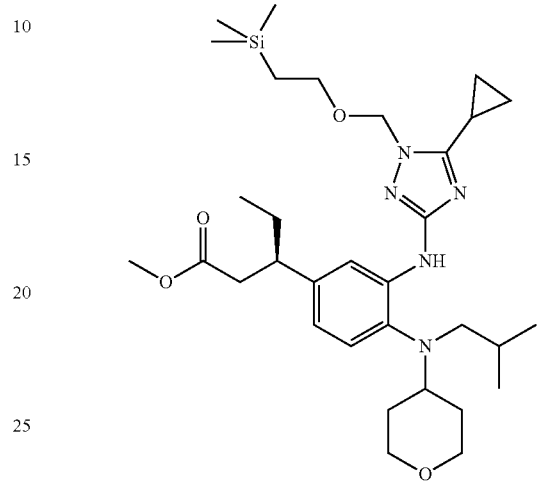

A mixture of (R)-methyl 3-(3-amino-4-(isobutyl(tetrahydro-2H-pyran-4-yl)amino)phenyl)pentanoate (0.0976 g, 0.269 mmol), 5-bromo-3-cyclopropyl-1-((2-(trimethylsilyl)ethoxy)methyl)-1H-1,2,4-triazole (0.103 g, 0.323 mmol), Pd$_2$dba$_3$ (0.049 g, 0.054 mmol), Xantphos (0.062 g, 0.108 mmol), and cesium carbonate (0.439 g, 1.346 mmol) was flushed with nitrogen and then stirred in toluene (3.9 mL) and heated at 100° C. for 8 h. The reaction mixture was filtered through celite, evaporated, and purified by silica gel chromatography (0-50% EtOAc/hexanes) to afford (R)-methyl 3-(3-((5-cyclopropyl-1-((2-(trimethylsilyl)ethoxy)methyl)-1H-1,2,4-triazol-3-yl)amino)-4-(isobutyl(tetrahydro-2H-pyran-4-yl)amino)phenyl)pentanoate (125 mg, 77% yield). LCMS (M+H)$^+$: m/z=600.6.

Step B (R)-3-(3-((5-cyclopropyl-1H-1,2,4-triazol-3-yl)amino)-4-(isobutyl(tetrahydro-2H-pyran-4-yl)amino) phenyl)pentanoic Acid

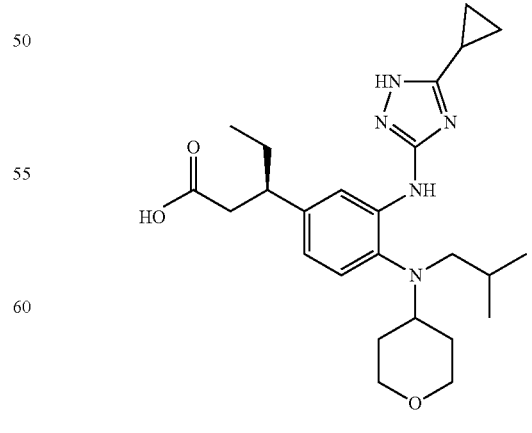

(R)-methyl 3-(3-((5-cyclopropyl-1-((2-(trimethylsilyl)ethoxy)methyl)-1H-1,2,4-triazol-3-yl)amino)-4-(isobutyl (tetrahydro-2H-pyran-4-yl)amino)phenyl)pentanoate (0.125 g, 0.208 mmol) was treated with TFA and then subjected to base hydrolysis as previously described and purified by reverse phase chromatography (10-100% CH₃CN/H₂O (0.1% formic acid)) to afford the title compound (0.0567 g, 60%) as a white solid. LCMS (M+H)⁺: m/z=456.4. ¹H NMR (400 MHz, CD₃OD) δ ppm 7.92 (d, J=1.76 Hz, 1H), 7.12 (d, J=8.01 Hz, 1H), 6.71 (dd, J=8.20, 1.76 Hz, 1H), 3.88 (m, 2H), 3.30-3.33 (m, 2H), 2.73-2.99 (m, 4H), 2.47-2.64 (m, 2H), 1.91-2.04 (m, 1H), 1.49-1.85 (m, 6H), 1.31-1.45 (m, 1H), 0.93-1.10 (m, 4H), 0.83 (d, J=6.05 Hz, 6H), 0.79 (t, J=7.32 Hz, 3H).

Example 42

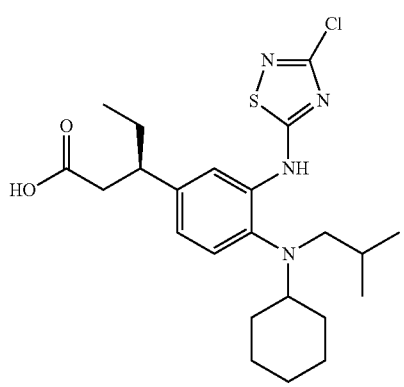

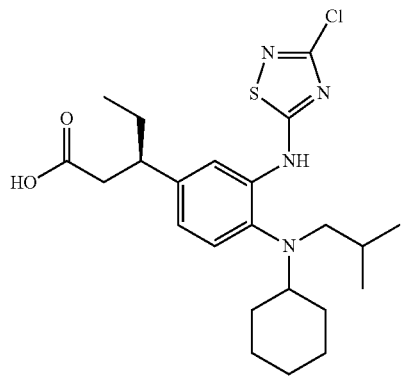

Preparation of methyl (R)-3-(3-((3-chloro-1,2,4-thiadiazol-5-yl)amino)-4-(cyclo exyl(isobutyl)amino)phenyl)pentanoate

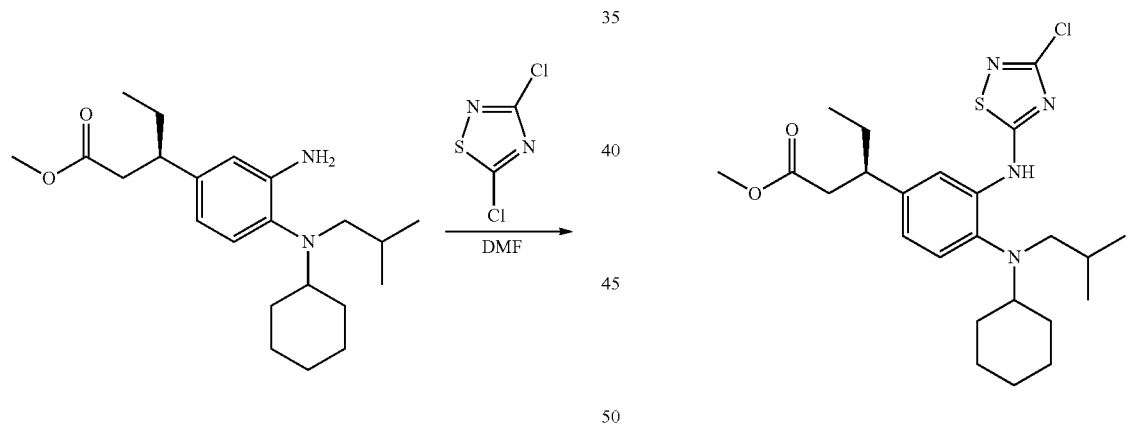

A mixture of methyl (R)-3-(3-amino-4-(cyclohexyl(isobutyl)amino)phenyl)pentanoate (100 mg, 0.28 mmol) and 3,5-dichloro-1,2,4-thiadiazole (128 mg, 0.84 mmol) in DMF (3 mL) was stirred at 80° C. under N₂ atmosphere for 5 hr. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-10% EtOAc in PE) to afford the title compound (73 mg, 54% yield). LCMS (ESI) m/z calcd for C₂₄H₃₅ClN₄O₂S: 478.22. Found: 479.79/481.52 (M/M+2)⁺.

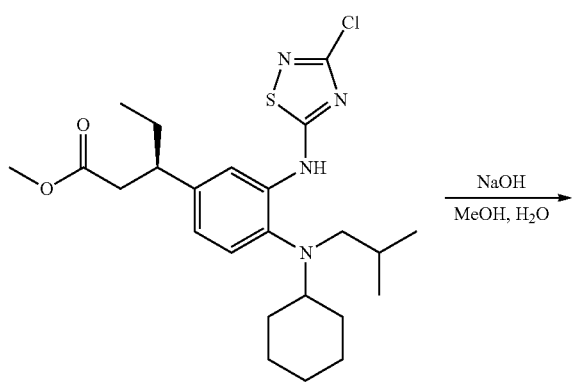

121

Preparation of (R)-3-(3-((3-chloro-1,2,4-thiadiazol-5-yl)amino)-4-(cyclohexyl isobutyl)amino)phenyl)pentanoic Acid

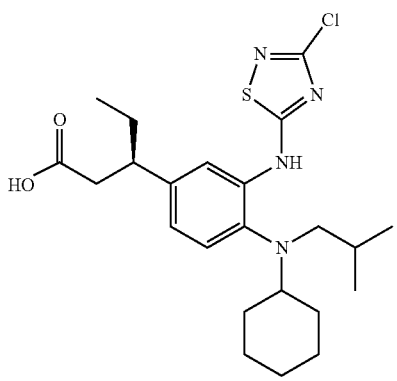 [SMILES: CC[C@H](CC(=O)O)c1ccc(N(CC(C)C)C2CCCCC2)c(Nc2nc(Cl)ns2)c1]

To a solution of methyl (R)-3-(3-((3-chloro-1,2,4-thiadiazol-5-yl)amino)-4-(cyclo exyl(isobutyl)amino)phenyl)pentanoate (40 mg, 0.083 mmol) in MeOH (5 mL) was added 1N NaOH aq. (1 mL). After stirred at r.t. overnight, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (9.3 mg, 24% yield) as a white powder. $^1$H NMR (400 MHz, $CDCl_3$) δ 9.40 (s, 1H), 7.18 (d, J=8.2 Hz, 1H), 7.10 (d, J=1.7 Hz, 1H), 6.92 (dd, J=8.2, 1.9 Hz, 1H), 3.08-2.98 (m, 1H), 2.80 (d, J=6.8 Hz, 2H), 2.73-2.51 (m, 3H), 1.90-1.60 (m, 7H), 1.33-1.01 (m, 6H), 0.90-0.77 (m, 9H). LCMS (ESI) m/z calcd for $C_{23}H_{33}ClN_4O_2S$: 464.20. Found: 465.21/467.18 $(M/M+2)^+$.

Example 43

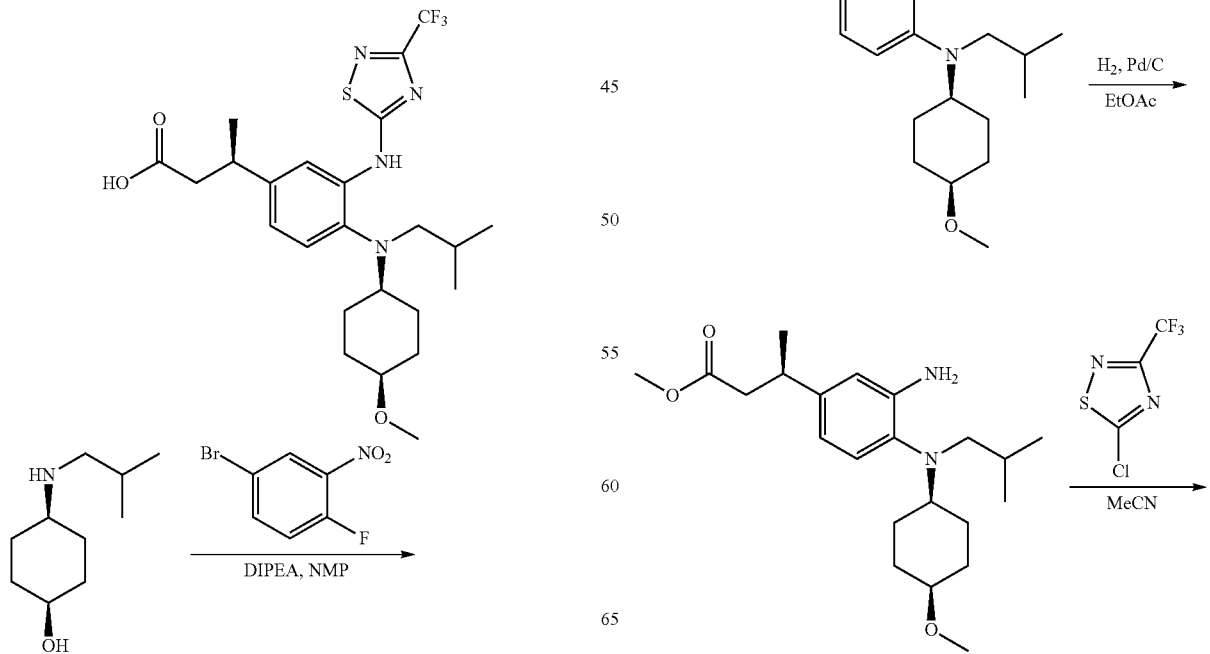

122

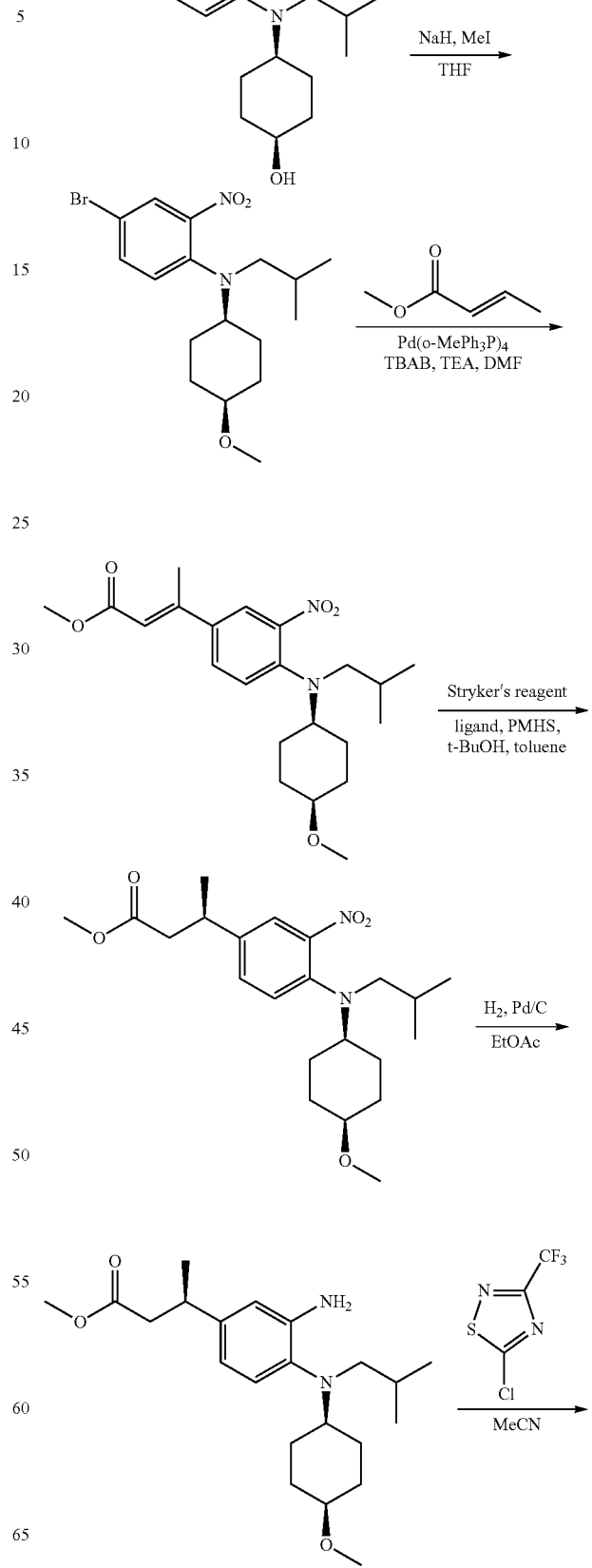

123
-continued

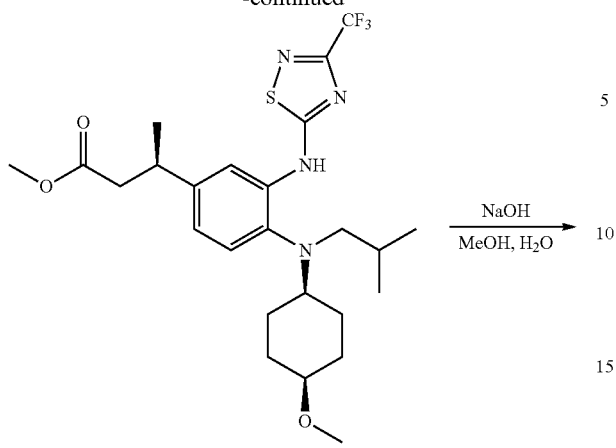

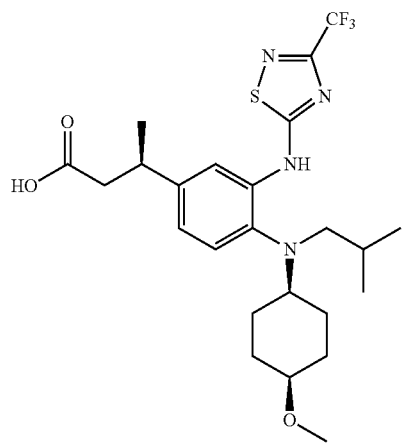 [SMILES: CO[C@H]1CC[C@@H](N(CC(C)C)c2ccc([C@H](C)CC(=O)O)cc2Nc2nc(C(F)(F)F)ns2)CC1]

Preparation of (1s,4s)-4-((4-bromo-2-nitrophenyl)(isobutyl)amino)cyclohexan-1-ol

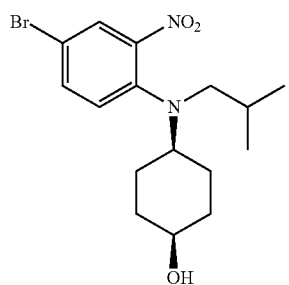 [SMILES: CC(C)CN(c1ccc(Br)cc1[N+](=O)[O-])[C@H]1CC[C@@H](O)CC1]

A mixture of 4-bromo-1-fluoro-2-nitrobenzene (7.4 g, 33.5 mmol), (1s,4s)-4-(isobutyl amino)cyclohexan-1-ol (6.7 g, 40.2 mmol) and DIPEA (11.7 mL, 67.0 mmol) in NMP (80 mL) was stirred at 140° C. under $N_2$ atmosphere for 6 hr. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (8.4 g, 67% yield) as a red oil. LCMS (ESI) m/z calcd for $C_{16}H_{23}BrN_2O_3$: 370.09. Found: 371.26/373.25 (M/M+2)$^+$.

124

Preparation of 4-bromo-N-isobutyl-N-((1s,4s)-4-methoxycyclohexyl)-2-nitro niline

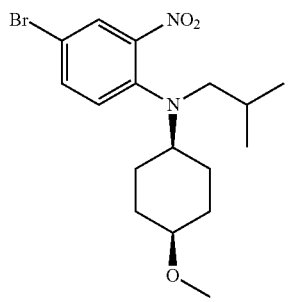 [SMILES: CO[C@H]1CC[C@@H](N(CC(C)C)c2ccc(Br)cc2[N+](=O)[O-])CC1]

At 0° C., to a solution of (1s,4s)-4-((4-bromo-2-nitrophenyl)(isobutyl)amino)cyclohexan-1-ol (8.4 g, 22.5 mmol) in THF (100 mL) was added NaH (60%, 5.4 g, 135 mmol). The reaction mixture was stirred at 0° C. for 2 hr before the addition of MeI (14 mL, 225 mmol). After stirred at r.t. overnight, the resulting mixture was quenched with sat. $NH_4Cl$ aq. solution and extracted with EtOAc. The organic layer was washed with brine, dried over $Na_2SO_4$, filtered and concentrated to give the crude product which was purified by flash chromatography (silica gel, 0-20% EtOAc in PE) to afford the title compound (5.3 g, 61% yield). LCMS (ESI) m/z calcd for $C_{17}H_{25}BrN_2O_3$: 384.10. Found: 385.53/387.51 (M/M+2)$^+$.

Preparation of methyl (E)-3-(4-(isobutyl((1s,4s)-4-methoxycyclohexyl)amino)-3-itrophenyl)but-2-enoate

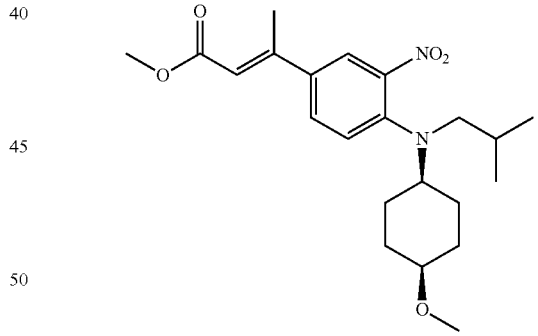

A mixture of 4-bromo-N-isobutyl-$N_4$(1s,4s)-4-methoxycyclohexyl)-2-nitroniline (5.3 g, 13.8 mmol), methyl (E)-but-2-enoate (4.2 g, 41.4 mmol), TBAB (890 mg, 2.76 mmol), Pd(o-MePh$_3$P)$_4$ (543 mg, 0.69 mmol) and TEA (2.9 g, 27.6 mmol) in DMF (70 mL) was stirred at 100° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (3.5 g, 63% yield). LCMS (ESI) m/z calcd for $C_{22}H_{32}N_2O_5$: 404.23. Found: 405.92 (M+1)$^+$.

Preparation of methyl (R)-3-(4-(isobutyl((1s,4S)-4-methoxycyclohexyl)amino)-3-nitrophenyl)butanoate

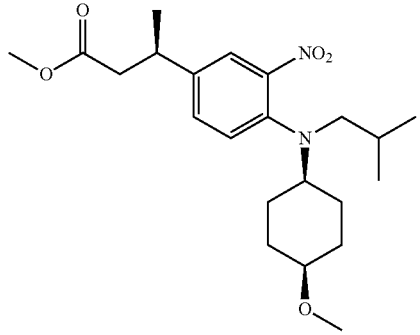

At −5° C., to a mixture of (CuHPh₃P)₆ (137 mg, 0.07 mmol) and (R,S)—PPF—P(tBu)₂ (137 mg, 0.245 mmol) in toluene (40 mL) was added PMHS (1.4 mL) and t-BuOH (1.1 mL) before the introduction of methyl (E)-3-(4-(isobutyl((1s,4s)-4-methoxycyclohexyl) amino)-3-nitrophenyl)but-2-enoate (3.5 g, 8.61 mmol). After stirred at −5° C. for 3 hr, the resulting mixture was quenched with sat. NaHCO₃ aq. solution and extracted with EtOAc. The organic layer was washed with brine, dried over Na₂SO₄, filtered and concentrated to give the crude product which was purified by flash chromatography (silica gel, 0-10% EtOAc in PE) to afford the title compound (3.0 g, 86% yield). LCMS (ESI) m/z calcd for C₂₂H₃₄N₂O₅: 406.25. Found: 407.67 (M+1)⁺.

Preparation of methyl (R)-3-(3-amino-4-(isobutyl((1s,4S)-4-methoxycyclohexyl) amino)phenyl)butanoate

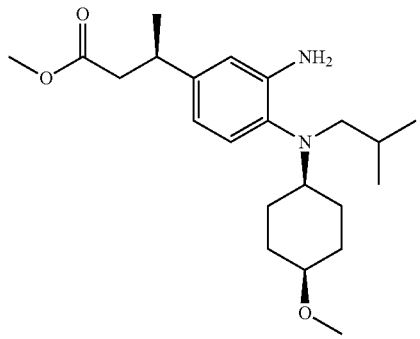 [SMILES: COC(=O)C[C@@H](C)c1ccc(N(CC(C)C)[C@H]2CC[C@@H](OC)CC2)c([N+](=O)[O-])c1]

A mixture of methyl (R)-3-(4-(isobutyl((1s,4S)-4-methoxycyclohexyl)amino)-3-nitrophenyl)butanoate (3.0 g, 7.4 mmol) and 10% Pd/C (900 mg) in EtOAc (30 mL) was stirred at 50° C. under H₂ atmosphere for 4 hr. The resulting mixture was filtered through a pad of Celite and the filtrate was concentrated under reduced pressure to give the crude product which was purified by flash chromatography (silica gel, 0-20% EtOAc in PE) to afford the title compound (2.2 g, 77% yield). LCMS (ESI) m/z calcd for C₂₂H₃₆N₂O₃: 376.27. Found: 377.77 (M+1)⁺.

Preparation of methyl (R)-3-(4-(isobutyl((1s,4S)-4-methoxycyclohexyl)amino)-3-(3-(trifluoromethyl)-1,2,4-thiadiazol-5-yl)amino)phenyl)butanoate

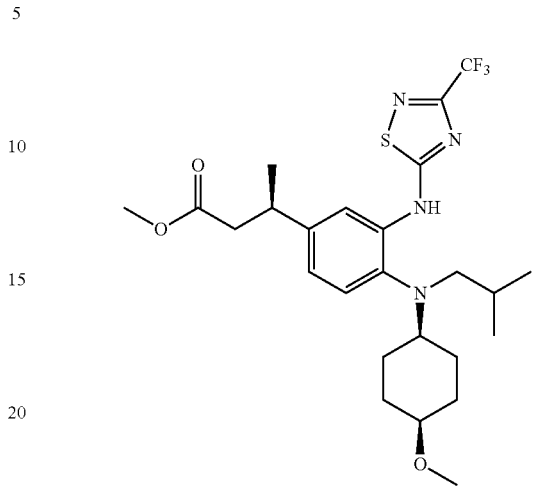

A mixture of methyl (R)-3-(3-amino-4-(isobutyl((1s,4S)-4-methoxycyclohexyl)amino) phenyl)butanoate (100 mg, 0.27 mmol) and 5-chloro-3-(trifluoromethyl)-1,2,4-thiadiazole (100 mg, 0.54 mmol) in MeCN (2 mL) was stirred at 90° C. under N₂ atmosphere overnight. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-20% EtOAc in PE) to afford the title compound (80 mg, 57% yield). LCMS (ESI) m/z calcd for C₂₆H₃₆F₃N₄O₃S: 528.24. Found: 529.39 (M+1)⁺.

Preparation of (R)-3-(4-(isobutyl((1s,4S)-4-methoxycyclohexyl)amino)-3-((3-(tri fluoromethyl)-1,2,4-thiadiazol-5-yl)amino)phenyl)butanoic Acid

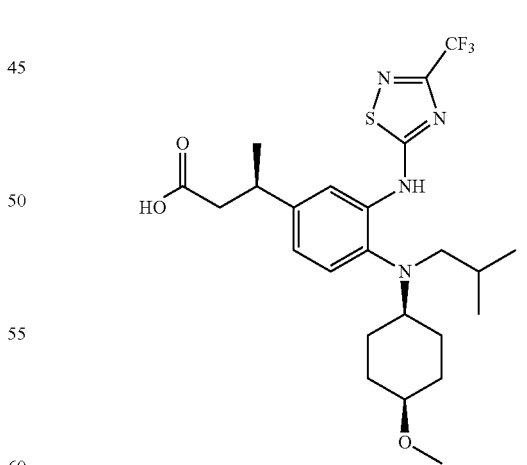

To a solution of methyl (R)-3-(4-(isobutyl((1s,4S)-4-methoxycyclohexyl)amino)-3-(3-(trifluoromethyl)-1,2,4-thiadiazol-5-yl)amino)phenyl)butanoate (80 mg, 0.15 mmol) in MeOH (3 mL) was added 4N NaOH aq. (0.5 mL). After stirred at 50° C. for 6 hr, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (64 mg, 82% yield) as a white powder. ¹H NMR (400 MHz, CDCl₃) δ 9.34 (s, 1H), 7.31 (d, J=1.4 Hz, 1H), 7.20 (d, J=8.2 Hz, 1H), 6.98 (dd, J=8.2, 1.8 Hz, 1H), 3.39-3.24 (m, 5H), 2.83 (d, J=6.2 Hz, 2H), 2.72-2.52 (m, 3H), 2.01-1.95 (m, 2H), 1.70-1.61 (m, 4H), 1.41-1.26 (m, 6H), 0.83 (d, J=6.6 Hz, 6H). LCMS (ESI) m/z calcd for C₂₄H₃₃F₃N₄O₃S: 514.22. Found: 515.33 (M+1)⁺.
Example 44
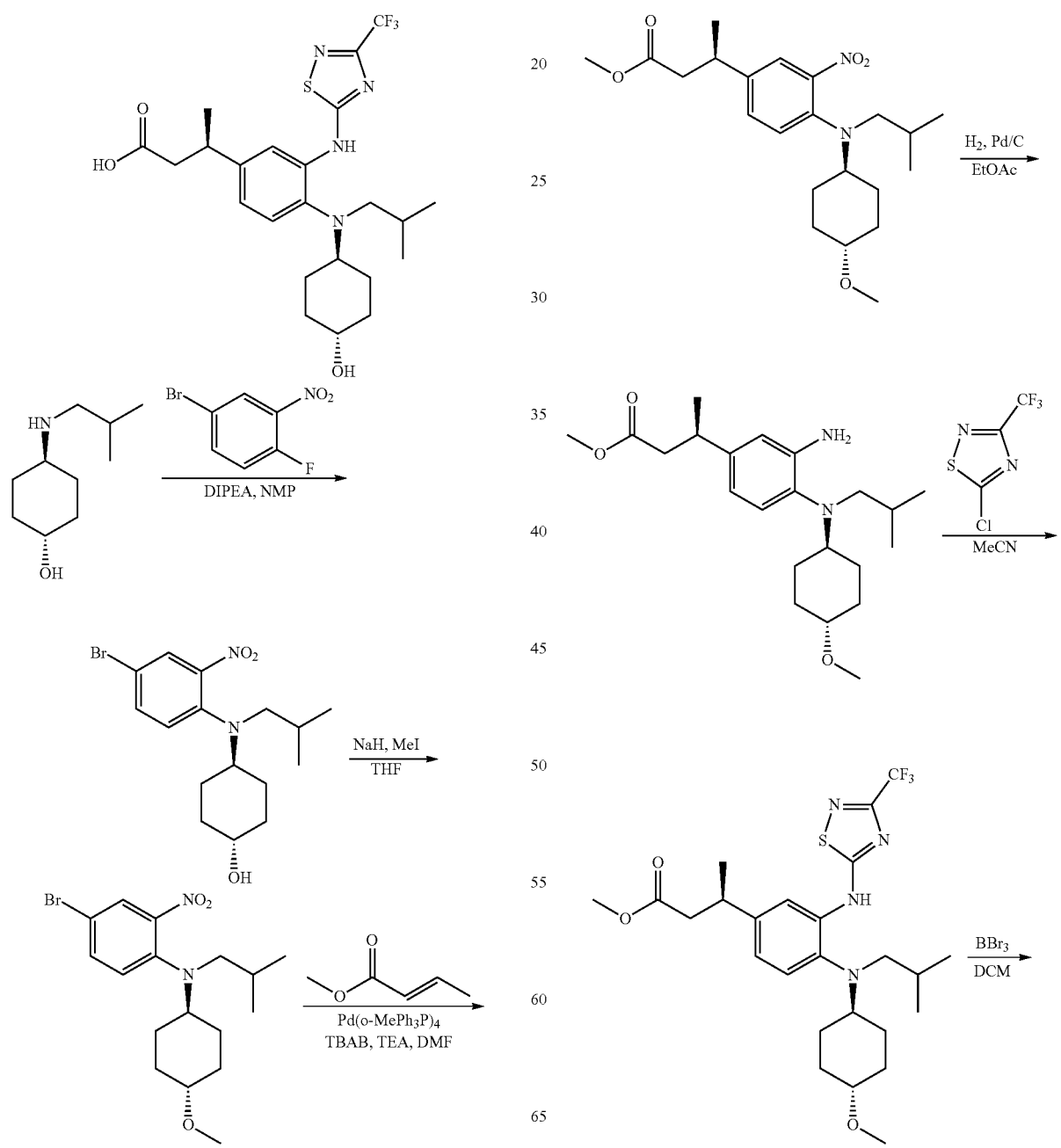

129
-continued

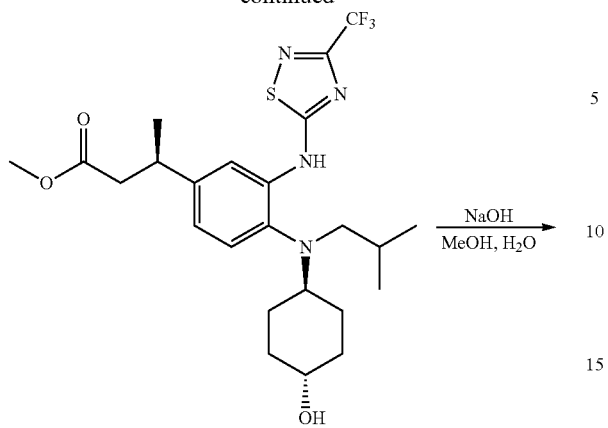

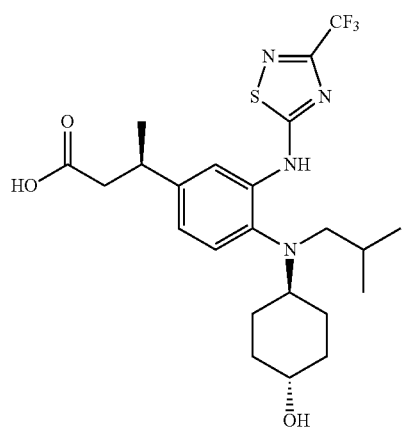 [SMILES: CC(C)CN(c1ccc([C@H](C)CC(=O)O)cc1Nc1nc(C(F)(F)F)ns1)[C@H]1CC[C@H](O)CC1]

Preparation of (1r,4r)-4-((4-bromo-2-nitrophenyl)(isobutyl)amino)cyclohexan-1-ol

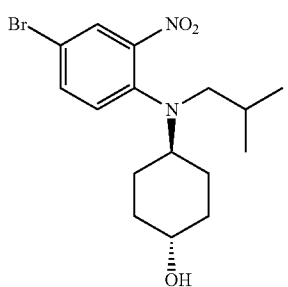 [SMILES: CC(C)CN(c1ccc(Br)cc1[N+](=O)[O-])[C@H]1CC[C@H](O)CC1]

A mixture of 4-bromo-1-fluoro-2-nitrobenzene (7.7 g, 35.0 mmol), (1r,4r)-4-(isobutyl amino)cyclohexan-1-ol (7.0 g, 41.9 mmol) and DIPEA (12.2 mL, 70.0 mmol) in NMP (100 mL) was stirred at 140° C. under N$_2$ atmosphere for 5 hr. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (5.5 g, 42% yield) as a red oil. LCMS (ESI) m/z calcd for C$_{16}$H$_{23}$BrN$_2$O$_3$: 370.09. Found: 371.42/373.42 (M/M+2)$^+$.

130
Preparation of 4-bromo-N-isobutyl-N-((1r,4r)-4-methoxycyclohexyl)-2-nitroaniline

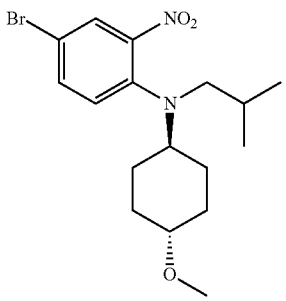 [SMILES: CO[C@H]1CC[C@H](N(CC(C)C)c2ccc(Br)cc2[N+](=O)[O-])CC1]

At 0° C., to a solution of (1r,4r)-4-((4-bromo-2-nitrophenyl)(isobutyl)amino)cyclohexan-1-ol (5.5 g, 14.8 mmol) in THF (70 mL) was added NaH (60%, 3.6 g, 88.8 mmol). The reaction mixture was stirred at 0° C. for 2 hr before the addition of MeI (9.2 mL, 148 mmol). After stirred at r.t. overnight, the resulting mixture was quenched with sat. NH$_4$Cl aq. solution and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (4.8 g, 85% yield) as a red oil. LCMS (ESI) m/z calcd for C$_{17}$H$_{25}$BrN$_2$O$_3$: 384.10. Found: 385.54/387.52 (M/M+2)$^+$.

Preparation of methyl (E)-3-(4-(isobutyl((1r,4r)-4-methoxycyclohexyl)amino)-3-nitrophenyl)but-2-enoate

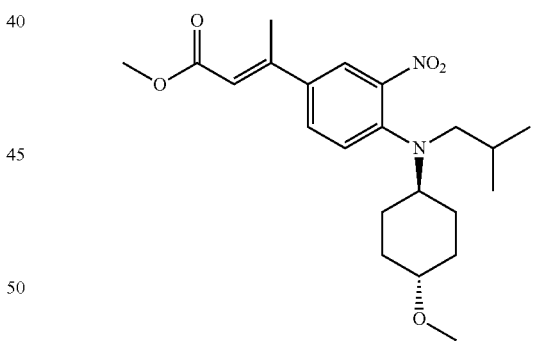

A mixture of 4-bromo-N-isobutyl-N-((1r,4r)-4-methoxycyclohexyl)-2-nitroaniline (4.8 g, 12.5 mmol), methyl (E)-but-2-enoate (3.8 g, 37.5 mmol), TBAB (806 mg, 2.50 mmol), Pd(o-MePh$_3$P)$_4$ (495 mg, 0.63 mmol) and TEA (2.6 g, 25.0 mmol) in DMF (50 mL) was stirred at 100° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (3.5 g, 69% yield). LCMS (ESI) m/z calcd for C$_{22}$H$_{32}$N$_2$O$_5$: 404.23. Found: 405.00 (M+1)$^+$.

Preparation of methyl (R)-3-(4-(isobutyl((1r,4R)-4-methoxycyclohexyl)amino)-3-nitrophenyl)butanoate

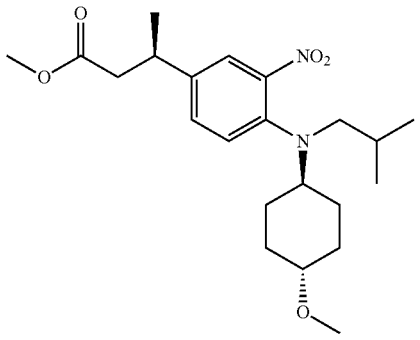 [SMILES: COC(=O)C[C@@H](C)c1ccc(N(CC(C)C)[C@H]2CC[C@H](OC)CC2)c([N+](=O)[O-])c1]

At −5° C., to a mixture of (CuHPh₃P)₆ (19.6 mg, 0.01 mmol) and (R,S)—PPF—P(tBu)₂ (19.0 mg, 0.035 mmol) in toluene (5 mL) was added PMHS (0.2 mL) and t-BuOH (0.15 mL) before the introduction of methyl (E)-3-(4-(isobutyl((1r,4r)-4-methoxycyclo hexyl)amino)-3-nitrophenyl)but-2-enoate (500 mg, 1.23 mmol). After stirred at −5° C. for 1 hr, the resulting mixture was quenched with sat. NaHCO₃ aq. solution and extracted with EtOAc. The organic layer was washed with brine, dried over Na₂SO₄, filtered and concentrated to give the crude product which was purified by flash chromatography (silica gel, 0-10% EtOAc in PE) to afford the title compound (430 mg, 86% yield). LCMS (ESI) m/z calcd for $C_{22}H_{34}N_2O_6$: 406.25. Found: 407.15 (M+1)⁺.

Preparation of methyl (R)-3-(3-amino-4-(isobutyl ((1r,4R)-4-methoxycyclohexyl) amino)phenyl)butanoate

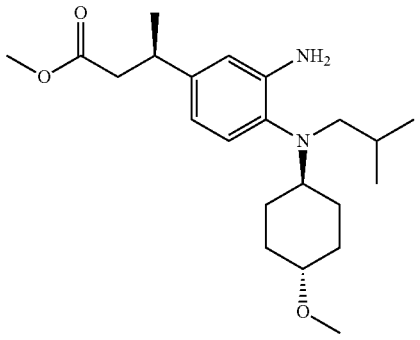 [SMILES: COC(=O)C[C@@H](C)c1ccc(N(CC(C)C)[C@H]2CC[C@H](OC)CC2)c(N)c1]

A mixture of methyl (R)-3-(4-(isobutyl((1r,4R)-4-methoxycyclohexyl)amino)-3-nitro phenyl)butanoate (3.0 g, 7.4 mmol) and 10% Pd/C (1.0 g) in EtOAc (50 mL) was stirred at 50° C. under H₂ atmosphere for 5 hr. The resulting mixture was filtered through a pad of Celite and the filtrate was concentrated under reduced pressure to give the crude product which was purified by flash chromatography (silica gel, 0-20% EtOAc in PE) to afford the title compound (2.0 g, 73% yield). LCMS (ESI) m/z calcd for $C_{22}H_{36}N_2O_3$: 376.27. Found: 377.94 (M+1)⁺.

Preparation of methyl (R)-3-(4-(isobutyl((1 r,4R)-4-methoxycyclohexyl)amino)-3-((3-(trifluoromethyl)-1,2,4-thiadiazol-5-yl)amino)phenyl)butanoate

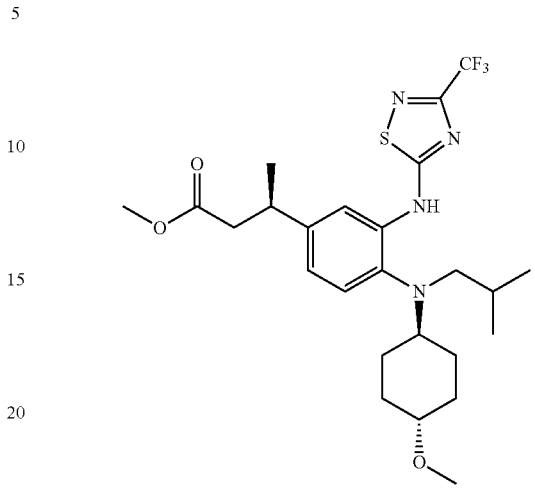

A mixture of methyl (R)-3-(3-amino-4-(isobutyl((1r,4R)-4-methoxycyclohexyl)amino) phenyl)butanoate (100 mg, 0.265 mmol) and 5-chloro-3-(trifluoromethyl)-1,2,4-thiadiazole (100 mg, 0.53 mmol) in MeCN (2 mL) was stirred at 90° C. under N₂ atmosphere overnight. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-20% EtOAc in PE) to afford the title compound (60 mg, 43% yield). LCMS (ESI) m/z calcd for $C_{25}H_{35}F_3N_4O_3S$: 528.24. Found: 529.31 (M+1)⁺.

Preparation of methyl (R)-3-(4-(((1r,4R)-4-hydroxycyclohexyl) (isobutyl)amino)-3-((3-(trifluoromethyl)-1,2,4-thiadiazol-5-yl)amino)phenyl)butanoate

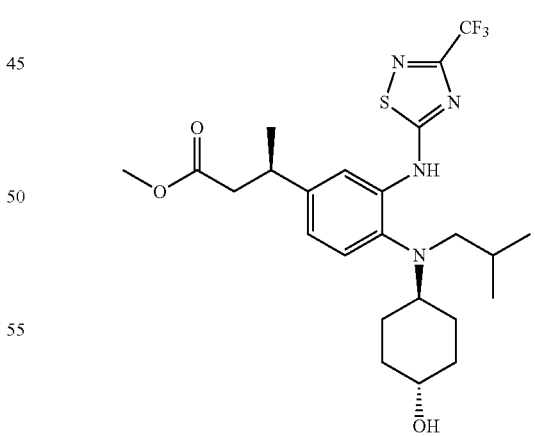

At 0° C., to a solution of methyl (R)-3-(4-(isobutyl((1r,4R)-4-methoxycyclohexyl)amino)-3-((3-(trifluoromethyl)-1,2,4-thiadiazol-5-yl)amino)phenyl)butanoate (36 mg, 0.068 mmol) in DCM (2 mL) was added BBr₃ (0.038 mL, 0.341 mmol). After stirred at 0° C. for 30 min, the resulting mixture was quenched with sat. NH₄Cl aq. solution and extracted with DCM. The organic layer was washed with brine, dried over Na₂SO₄, filtered and concentrated to give the crude product which was purified by flash chromatography (silica gel, 0-50% EtOAc in PE) to afford the title compound (18 mg, 51% yield). LCMS (ESI) m/z calcd for $C_{24}H_{33}F_3N_4O_3S$: 514.22. Found: 515.60 (M+1)⁺.

Preparation of (R)-3-(4-(((1r,4R)-4-hydroxycyclohexyl) (isobutyl)amino)-3-((3-(tri fluoromethyl)-1,2,4-thiadiazol-5-yl)amino)phenyl)butanoic Acid

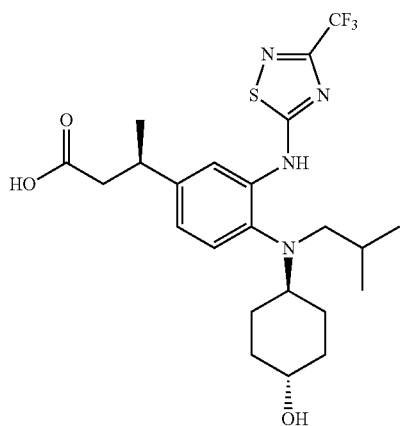 [SMILES: CC(C)CN(c1ccc([C@H](C)CC(=O)O)cc1Nc1nc(C(F)(F)F)ns1)[C@H]1CC[C@H](O)CC1]

To a solution of methyl (R)-3-(4-(((1r,4R)-4-hydroxycyclohexyl) (isobutyl)amino)-3-((3-(trifluoromethyl)-1,2,4-thiadiazol-5-yl)amino)phenyl)butanoate (53 mg, 0.103 mmol) in MeOH (3 mL) was added 4N NaOH aq. (0.5 mL). After stirred at r.t. overnight, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (11 mg, 21% yield) as a white powder. ¹H NMR (400 MHz, CDCl₃) δ 9.41 (s, 1H), 7.29 (d, J=1.6 Hz, 1H), 7.20 (d, J=8.2 Hz, 1H), 6.99 (dd, J=8.2, 1.8 Hz, 1H), 3.57-3.33 (m, 2H), 2.87-2.58 (m, 5H), 2.02-1.87 (m, 4H), 1.47-1.15 (m, 9H), 0.83 (d, J=6.6 Hz, 6H). LCMS (ESI) m/z calcd for $C_{23}H_{31}F_3N_4O_3S$: 500.21. Found: 501.41 (M+1)⁺.

Example 45

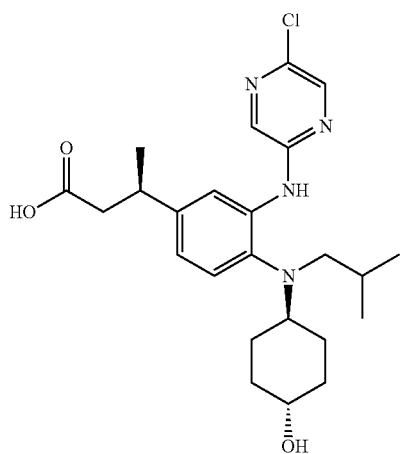 [SMILES: CC(C)CN(c1ccc([C@H](C)CC(=O)O)cc1Nc1cnc(Cl)cn1)[C@H]1CC[C@H](O)CC1]

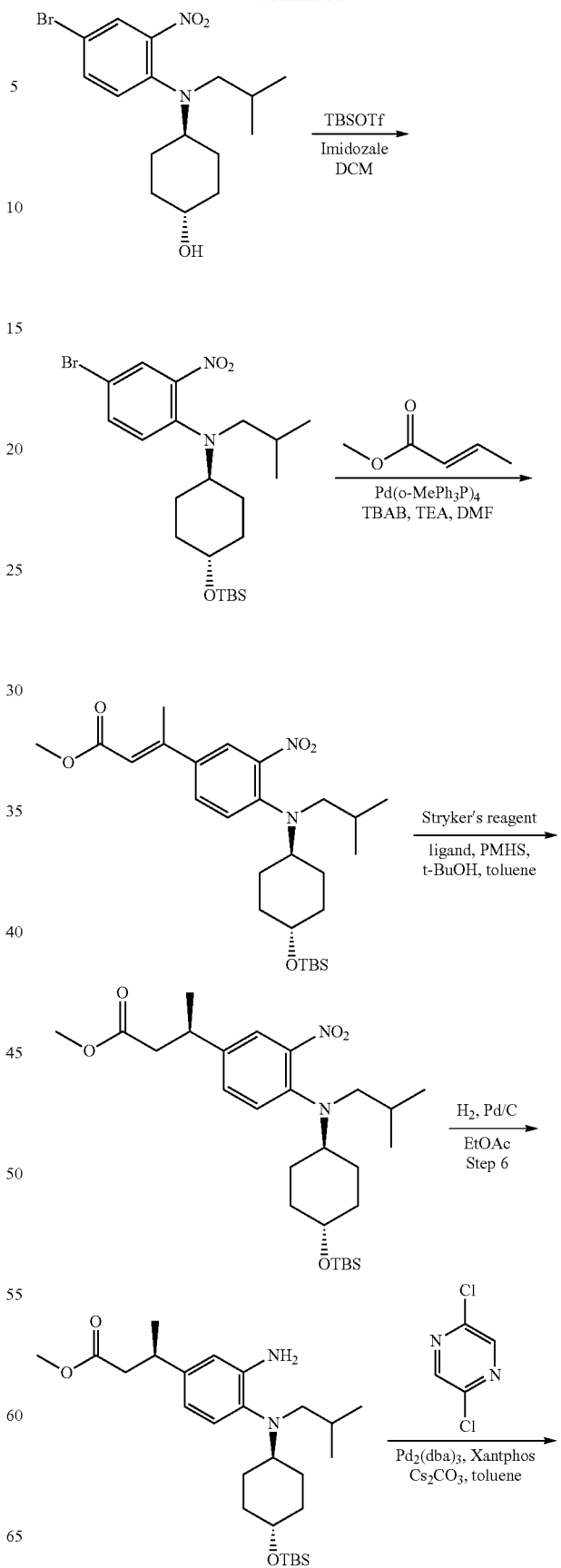

-continued

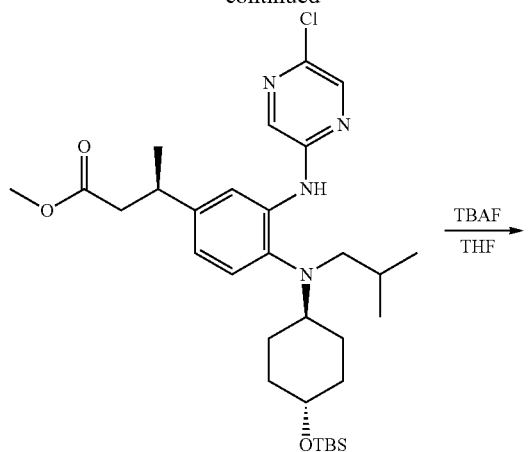

TBAF
THF

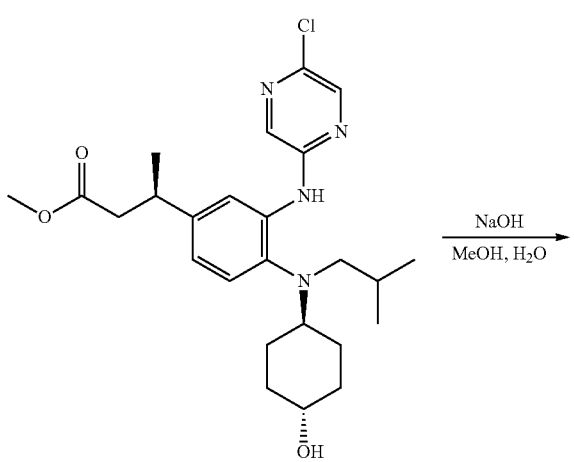

NaOH
MeOH, H₂O

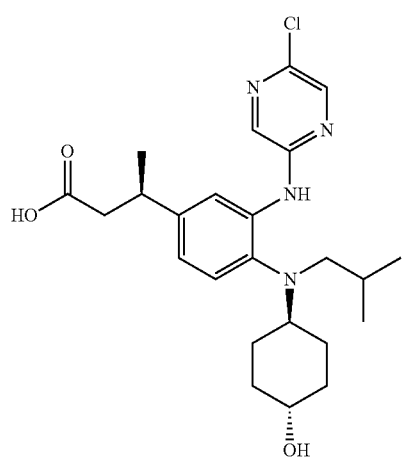

Preparation of 4-bromo-N-((1r,4r)-4-((tert-butyldimethylsilyl)oxy)cyclohexyl)-N-isobutyl-2-nitroaniline

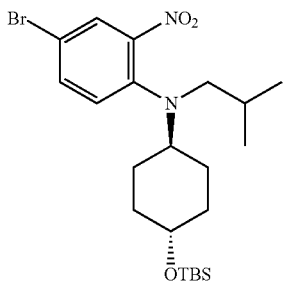 [SMILES: CC(C)CN(c1ccc(Br)cc1[N+](=O)[O-])[C@H]1CC[C@H](O[Si](C)(C)C(C)(C)C)CC1]

To a solution of (1r,4r)-4-((4-bromo-2-nitrophenyl)(isobutyl)amino)cyclohexan-1-ol (16.2 g, 43.7 mmol) in DCM (100 mL) was added imidazole (5.9 g, 87.4 mmol) and TBSOTf (17.3 g, 65.6 mmol). After stirred at r.t. for 5 hr, the resulting mixture was quenched with H₂O and extracted with DCM. The organic layer was washed with brine, dried over Na₂SO₄, filtered and concentrated to give the crude product which was purified by flash chromatography (silica gel, 0-20% EtOAc in PE) to afford the title compound (20.5 g, 96% yield). LCMS (ESI) m/z calcd for $C_{22}H_{37}BrN_2O_3Si$: 484.18. Found: 485.52/487.51 $(M/M+2)^+$.

Preparation of methyl (E)-3-(4-(((1r,4r)-4-((tert-butyldimethylsilyl)oxy)cyclohexyl) (isobutyl) amino)-3-nitrophenyl)but-2-enoate

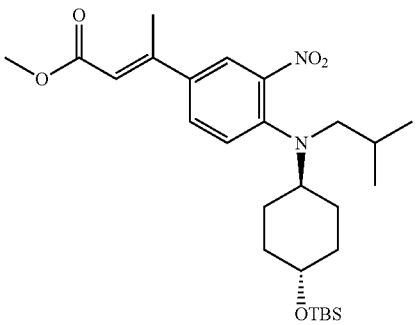 [SMILES: COC(=O)/C=C(\C)c1ccc(N(CC(C)C)[C@H]2CC[C@H](O[Si](C)(C)C(C)(C)C)CC2)c([N+](=O)[O-])c1]

A mixture of 4-bromo-N-((1r,4r)-4-((tert-butyldimethylsilyl)oxy)cyclohexyl)-N-isobutyl-2-nitroaniline (18.5 g, 38.14 mmol), methyl (E)-but-2-enoate (11.4 g, 114.4 mmol), TBAB (2.46 g, 7.6 mmol), Pd(o-MePh₃P)₄ (1.5 g, 1.91 mmol) and TEA (10.6 mL, 76.28 mmol) in DMF (200 mL) was stirred at 100° C. under N₂ atmosphere overnight. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-10% EtOAc in PE) to afford the title compound (9.67 g, 50% yield). LCMS (ESI) m/z calcd for $C_{27}H_{44}N_2O_5Si$: 504.30. Found: 505.69 $(M+1)^+$.

Preparation of methyl (R)-3-(4-(((1r,4R)-4-((tert-butyldimethylsilyl)oxy)cyclo hexyl) (isobutyl) amino)-3-nitrophenyl)butanoate

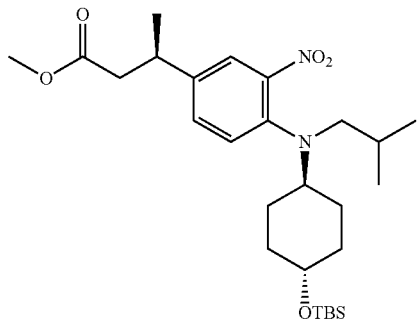 [SMILES: COC(=O)C[C@@H](C)c1ccc(N(CC(C)C)[C@H]2CC[C@H](O[Si](C)(C)C(C)(C)C)CC2)c([N+](=O)[O-])c1]

At −5° C., to a mixture of (CuHPh₃P)₆ (288 mg, 0.147 mmol) and (R,S)—PPF—P(tBu)₂ (289 mg, 0.535 mmol) in toluene (90 mL) was added PMH98S (2.9 mL) and t-BuOH (2.3 mL) before the introduction of methyl (E)-3-(4-(((1r,4r)-4-((tert-butyldimethylsilyl)oxy) cyclohexyl) (isobutyl) amino)-3-nitrophenyl)but-2-enoate (9.67 g, 19.1 mmol). After stirred at r.t. for 2 hr, the resulting mixture was quenched with sat. NaHCO₃ aq. solution and extracted with EtOAc. The organic layer was washed with brine, dried over Na₂SO₄, filtered and concentrated to give the crude product which was purified by flash chromatography (silica gel, 0-10% EtOAc in PE) to afford the title compound (8.16 g, 88% yield). LCMS (ESI) m/z calcd for C₂₇H₄₆N₂O₅Si: 506.32. Found: 507.82 (M+1)⁺.

Preparation of methyl (R)-3-(3-amino-4-(((1 r,4R)-4-((tert-butyldimethylsilyl)oxy) cyclohexyl) (isobutyl)amino)phenyl)butanoate

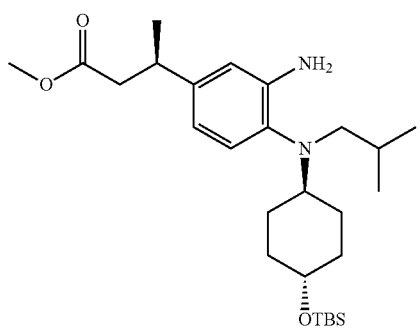 [SMILES: COC(=O)C[C@@H](C)c1ccc(N(CC(C)C)[C@H]2CC[C@H](O[Si](C)(C)C(C)(C)C)CC2)c(N)c1]

A mixture of methyl (R)-3-(4-(((1r,4R)-4-((tert-butyldimethylsilyl)oxy)cyclohexyl) (iso butyl)amino)-3-nitrophenyl)butanoate (3.0 g, 5.92 mmol) and 10% Pd/C (1.5 g) in EtOAc (30 mL) was stirred at 50° C. under H₂ atmosphere for 5 hr. The resulting mixture was filtered through a pad of Celite and the filtrate was concentrated under reduced pressure to give the crude product which was purified by flash chromatography (silica gel, 0-20% EtOAc in PE) to afford the title compound (2.6 g, 92% yield) as a yellow oil. LCMS (ESI) m/z calcd for C₂₇H₄₈N₂O₃Si: 476.34. Found: 477.82 (M+1)⁺.

Preparation of methyl (R)-3-(4-(((1r,4R)-4-((tert-butyldimethylsilyl)oxy)cyclo hexyl) (isobutyl) amino)-3-((5-chloropyrazin-2-yl)amino)phenyl)butanoate

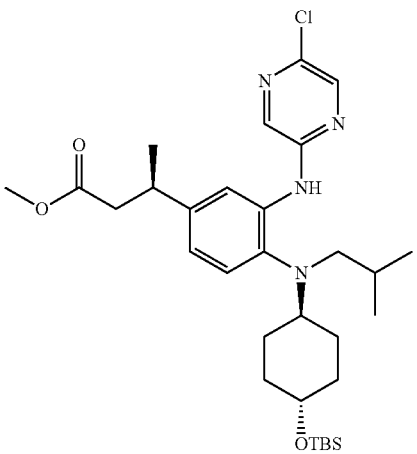 [SMILES: COC(=O)C[C@@H](C)c1ccc(N(CC(C)C)[C@H]2CC[C@H](O[Si](C)(C)C(C)(C)C)CC2)c(Nc2cnc(Cl)cn2)c1]

A mixture of methyl (R)-3-(3-amino-4-(((1r,4R)-4-((tert-butyldimethylsilyl)oxy)cyclo hexyl) (isobutyl)amino)phenyl)butanoate (200 mg, 0.42 mmol), 2,5-dichloropyrazine (125 mg, 0.84 mmol), Pd₂(dba)₃ (76 mg, 0.084 mmol), Xantphos (96 mg, 0.168 mmol) and Cs₂CO₃ (273 mg, 0.84 mmol) in toluene (10 mL) was stirred at 100° C. under N₂ atmosphere overnight. The resulting mixture was partitioned between EtOAc and H₂O. The organic layer was washed with brine, dried over Na₂SO₄, filtered and concentrated to give the crude product which was purified by flash chromatography (silica gel, 0-10% EtOAc in PE) to afford the title compound (170 mg, 68% yield). LCMS (ESI) m/z calcd for C₃₁H₄₉ClN₄O₃Si: 588.33. Found: 589.62/591.59 (M/M+2)⁺.

Preparation of methyl (R)-3-(3-((5-chloropyrazin-2-yl)amino)-4-(((1r,4R)-4-hydroxycyclohexyl) (isobutyl)amino)phenyl)butanoate

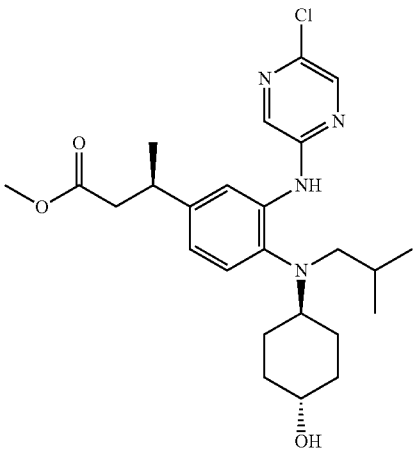 [SMILES: COC(=O)C[C@@H](C)c1ccc(N(CC(C)C)[C@H]2CC[C@H](O)CC2)c(Nc2cnc(Cl)cn2)c1]

To a solution of methyl (R)-3-(4-(((1r,4R)-4-((tert-butyldimethylsilyl)oxy)cyclohexyl) (isobutyl)amino)-3-((5- chloropyrazin-2-yl)amino)phenyl)butanoate (190 mg, 0.32 mmol) in THF (5 mL) was added TBAF (1N in THF, 5 mL). After stirred at r.t. overnight, the resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (130 mg, 95% yield). LCMS (ESI) m/z calcd for C$_{25}$H$_{35}$ClN$_4$O$_3$: 474.24. Found: 475.74/477.75 (M/M+2)$^+$.

Preparation of (R)-3-(3-((5-chloropyrazin-2-yl)amino)-4-(((1r,4R)-4-hydroxycyclo hexyl) (isobutyl) amino)phenyl)butanoic Acid

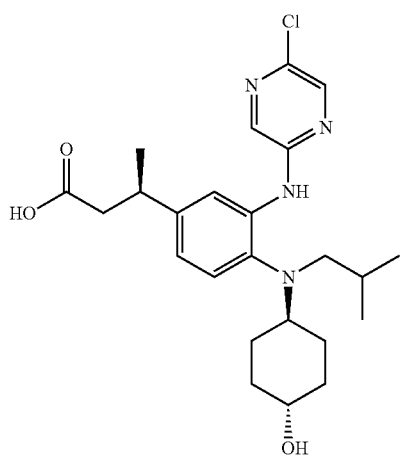 [SMILES: CC(C)CN(c1ccc([C@H](C)CC(=O)O)cc1Nc1cnc(Cl)cn1)[C@H]1CC[C@H](O)CC1]

To a solution of methyl (R)-3-(3-((5-chloropyrazin-2-yl)amino)-4-(((1 r,4R)-4-hydroxyl cyclohexyl) (isobutyl)amino)phenyl)butanoate (130 mg, 0.27 mmol) in MeOH (4 mL) was added 1N NaOH aq. (3 mL). After stirred at r.t. for 8 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (96 mg, 76% yield) as a white powder. $^1$H NMR (400 MHz, DMSO) δ 11.98 (br, 1H), 8.39 (s, 1H), 8.28 (d, J=1.3 Hz, 1H), 8.24 (d, J=1.3 Hz, 1H), 7.94 (d, J=1.6 Hz, 1H), 7.17 (d, J=8.2 Hz, 1H), 6.91 (dd, J=7.9, 1.2 Hz, 1H), 3.29-3.25 (m, 1H), 3.14-3.08 (m, 1H), 2.77 (d, J=6.2 Hz, 2H), 2.49-2.41 (m, 3H), 1.86-1.67 (m, 4H), 1.37-1.18 (m, 7H), 1.05-0.92 (m, 2H), 0.80 (d, J=6.6 Hz, 6H). LCMS (ESI) m/z calcd for C$_{24}$H$_{33}$ClN$_4$O$_3$: 460.22. Found: 461.59/463.57 (M/M+2)$^+$.

Example 46

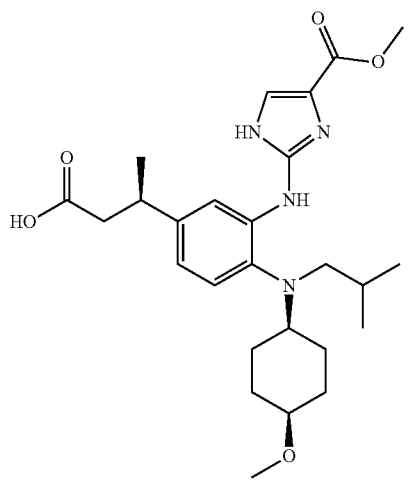 [SMILES: COC(=O)c1c[nH]c(Nc2cc([C@H](C)CC(=O)O)ccc2N(CC(C)C)[C@H]2CC[C@@H](OC)CC2)n1]

Step A (R)-methyl 3-(4-(isobutyl((cis)-4-methoxycyclohexyl)amino)-3-((4-(trifluoromethyl)-1-((2-(trimethylsilyl)ethoxy)methyl)-1H-imidazol-2-yl)amino) phenyl)butanoate

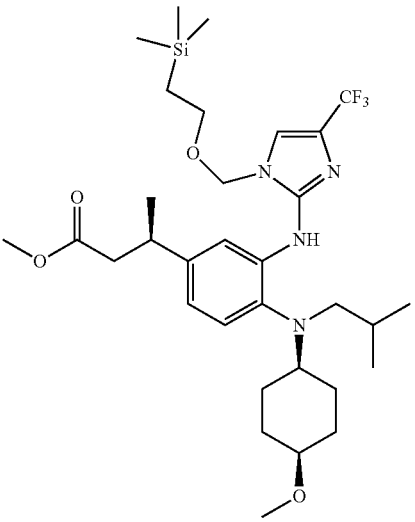 [SMILES: COC(=O)C[C@@H](C)c1ccc(N(CC(C)C)[C@H]2CC[C@@H](OC)CC2)c(Nc2nc(C(F)(F)F)cn2COCC[Si](C)(C)C)c1]

A mixture of (R)-methyl 3-(3-amino-4-(isobutyl((cis)-4-methoxycyclohexyl)amino)phenyl)butanoate (0.134 g, 0.356 mmol), 2-bromo-4-(trifluoromethyl)-1-((2-(trimethylsilyl)ethoxy)methyl)-1H-imidazole (0.147 g, 0.427 mmol), Pd$_2$dba$_3$ (0.065 g, 0.071 mmol), Xantphos (0.082 g, 0.142 mmol), and cesium carbonate (0.580 g, 1.779 mmol) was flushed with nitrogen and then stirred in toluene (5.1 mL). The reaction mixture was heated at 100° C. for 8 h, then filtered through celite, evaporated, and purified by silica gel chromatography (0-40% EtOAc/hexanes) to afford (R)-methyl 3-(4-(isobutyl((cis)-4-methoxycyclohexyl)amino)-3-((4-(trifluoromethyl)-1-((2-(trimethylsilyl)ethoxy) methyl)-1H-imidazol-2-yl)amino)phenyl)butanoate (131 mg, 57%). LCMS (M+H)$^+$: m/z=641.5.

Step B (R)-3-(4-(isobutyl((1s,4s)-4-methoxycyclohexyl)amino)-3-((4-(methoxycarbonyl)-1H-imidazol-2-yl)amino)phenyl)butanoic Acid

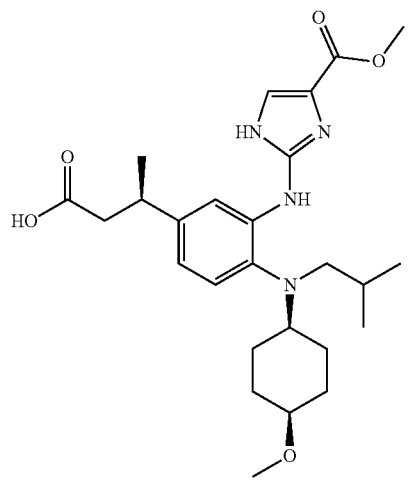

(R)-methyl 3-(4-(isobutyl((cis)-4-methoxycyclohexyl)amino)-3-((4-(trifluoromethyl)-1-((2-(trimethylsilyl)ethoxy)methyl)-1H-imidazol-2-yl)amino)phenyl)butanoate (0.0625 g, 0.098 mmol) was treated with TFA and then subjected to base hydrolysis in MeOH as previously described and purified by reverse phase chromatography (10-100% CH$_3$CN/H$_2$O (0.1% formic acid)) to afford the title compound (0.0296 g, 62%) as a white solid. LCMS (M+H)$^+$: m/z=487.4 $^1$H NMR (400 MHz, CD$_3$OD) δ ppm 7.79 (d, J=2.0 Hz, 1H), 7.45 (s, 1H), 7.12 (d, J=8.2 Hz, 1H), 6.80 (dd, J=8.1, 1.9 Hz, 1H), 3.81 (s, 3H), 3.31-3.36 (m, 1H), 3.22-3.26 (m, 3H), 3.15-3.22 (m, 1H), 2.81 (br. s., 2H), 2.46-2.66 (m, 3H), 1.93 (d, J=14.6 Hz, 2H), 1.63 (br. s., 4H), 1.33-1.45 (m, 1H), 1.22-1.33 (m, 5H), 0.82 (d, J=6.6 Hz, 6H).

Example 47

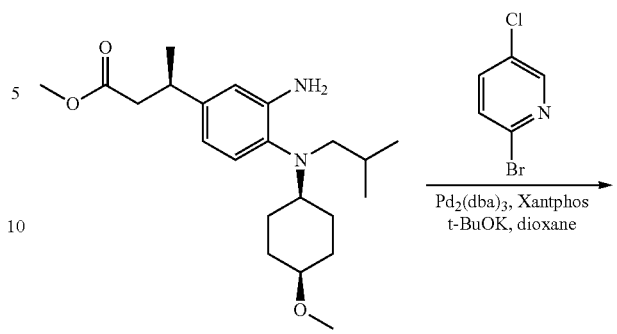

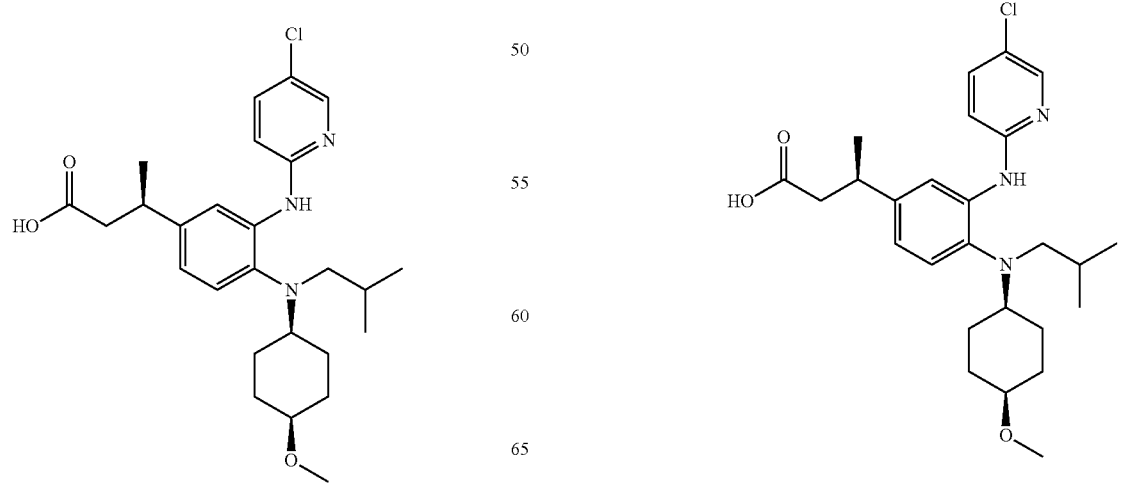

Preparation of methyl (R)-3-(3-((5-chloropyridin-2-yl)amino)-4-(isobutyl((1s,4S)-4-methoxycyclohexyl)amino)phenyl)butanoate

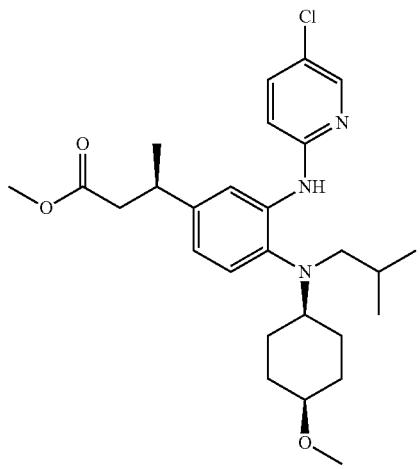 [SMILES: COC(=O)C[C@@H](C)c1ccc(N(CC(C)C)[C@H]2CC[C@@H](OC)CC2)c(Nc2ccc(Cl)cn2)c1]

A mixture of methyl (R)-3-(3-amino-4-(isobutyl((1s,4S)-4-methoxycyclohexyl) amino)phenyl)butanoate (100 mg, 0.32 mmol), 2-bromo-5-chloropyridine (104 mg, 0.54 mmol), Pd$_2$(dba)$_3$ (24 mg, 0.027 mmol), Xantphos (31.2 mg, 0.054 mmol) and t-BuOK (60 mg, 0.54 mmol) in dioxane (2 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (78 mg, 60% yield). LCMS (ESI) m/z calcd for C$_{27}$H$_{38}$ClN$_3$O$_3$: 487.26. Found: 488.47/490.41 (M/M+2)$^+$.

Preparation of (R)-3-(3-((5-chloropyridin-2-yl)amino)-4-(isobutyl((1s,4S)-4-methoxycyclohexyl)amino)phenyl)butanoic Acid

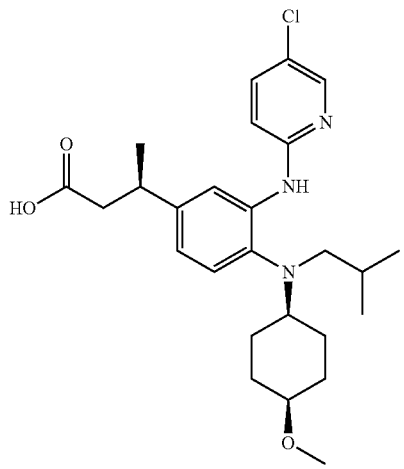 [SMILES: CO[C@H]1CC[C@@H](N(CC(C)C)c2ccc([C@H](C)CC(=O)O)cc2Nc2ccc(Cl)cn2)CC1]

To a solution of methyl (R)-3-(3-((5-chloropyridin-2-yl)amino)-4-(isobutyl((1s,4S)-4-methoxycyclohexyl)amino)phenyl)butanoate (78 mg, 0.16 mmol) in MeOH (3 mL) was added 4N NaOH aq. (0.5 mL). After stirred at r.t. for 6 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (41 mg, 54% yield) as a white powder. $^1$H NMR (400 MHz, CDCl$_3$) δ 8.19 (d, J=2.4 Hz, 1H), 8.03 (d, J=1.8 Hz, 1H), 7.92 (s, 1H), 7.44 (dd, J=8.8, 2.6 Hz, 1H), 7.09 (d, J=8.1 Hz, 1H), 6.75 (dd, J=21.8, 7.7 Hz, 2H), 3.35-3.20 (m, 5H), 2.88-2.78 (m, 2H), 2.72-2.51 (m, 3H), 1.98-1.90 (m, 2H), 1.75-1.56 (m, 4H), 1.39-1.23 (m, 6H), 0.84 (d, J=6.6 Hz, 6H). LCMS (ESI) m/z calcd for C$_{26}$H$_{36}$ClN$_3$O$_3$: 473.24. Found: 474.36/476.31 (M/M+2)$^+$.

Example 48

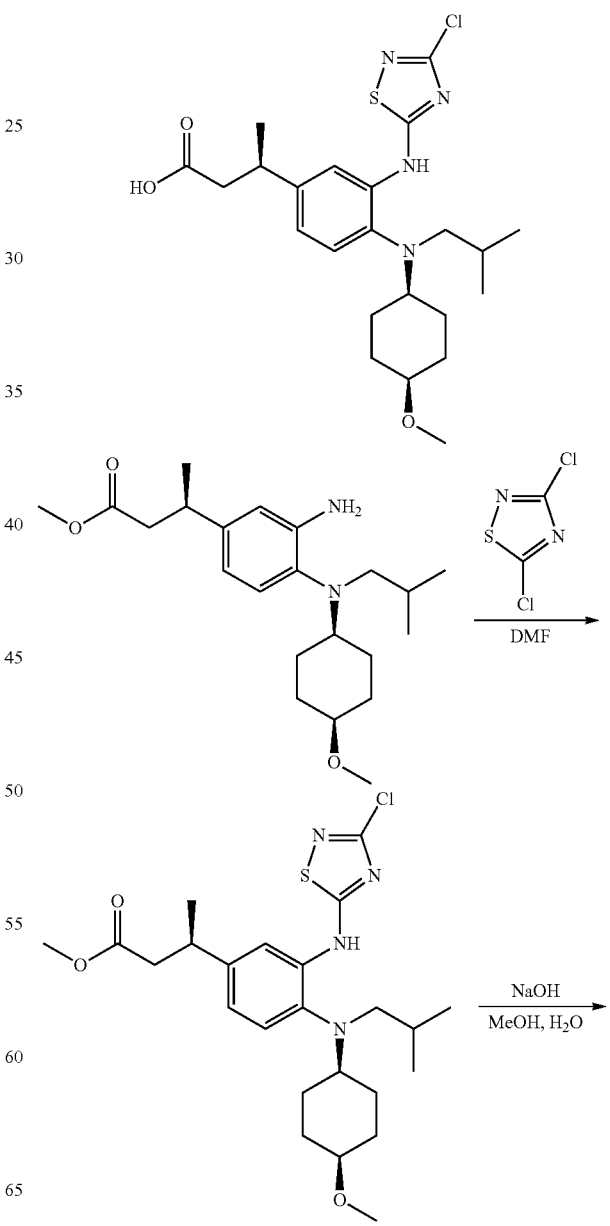

-continued

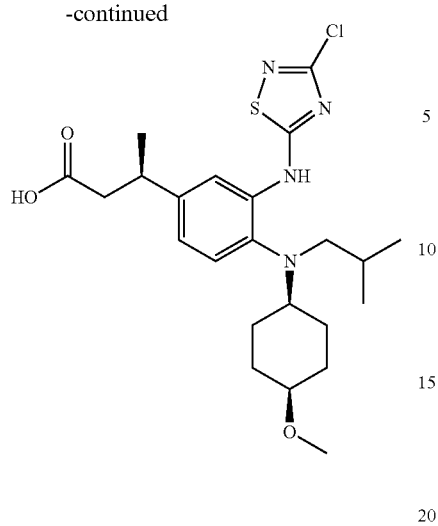

Preparation of methyl (R)-3-(3-((3-chloro-1,2,4-thiadiazol-5-yl)amino)-4-(isobutyl ((1s,4S)-4-methoxycyclohexyl)amino)phenyl)butanoate

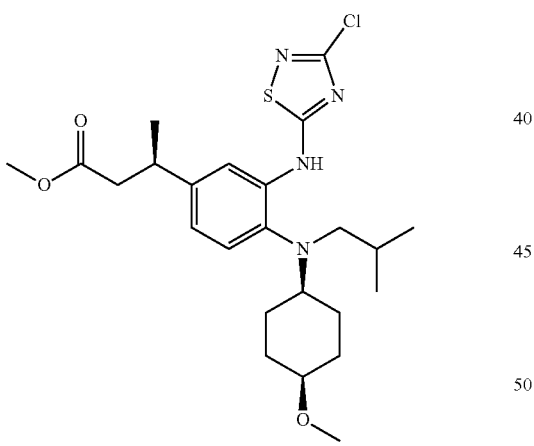

A mixture of methyl (R)-3-(3-amino-4-(isobutyl((1s,4S)-4-methoxycyclohexyl)amino) phenyl)butanoate (100 mg, 0.27 mmol) and 3,5-dichloro-1,2,4-thiadiazole (82 mg, 0.54 mmol) in DMF (2 mL) was stirred at 90° C. for 5 hr. The resulting mixture was partitioned between EtOAc and H₂O. The organic layer was washed with brine, dried over Na₂SO₄, filtered and concentrated to give the crude product which was purified by flash chromatography (silica gel, 0-20% EtOAc in PE) to afford the title compound (30 mg, 23% yield). LCMS (ESI) m/z calcd for $C_{24}H_{35}ClN_4O_3S$: 494.21. Found: 495.33/497.36 (M/M+2)⁺.

Preparation of (R)-3-(3-((3-chloro-1,2,4-thiadiazol-5-yl)amino)-4-(isobutyl((1s,4S)-4-methoxycyclohexyl)amino)phenyl)butanoic Acid

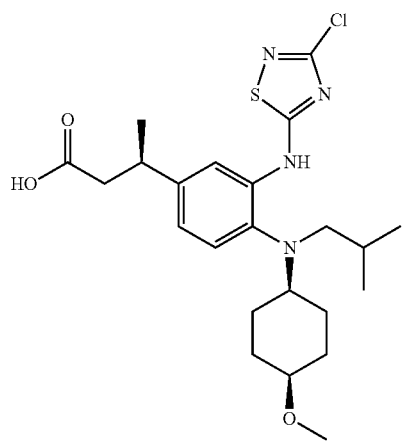 [SMILES: CO[C@H]1CC[C@@H](N(CC(C)C)c2ccc([C@H](C)CC(=O)O)cc2Nc2nc(Cl)ns2)CC1]

To a solution of methyl (R)-3-(3-((3-chloro-1,2,4-thiadiazol-5-yl)amino)-4-(isobutyl ((1s,4S)-4-methoxycyclohexyl)amino)phenyl)butanoate (30 mg, 0.06 mmol) in MeOH (3 mL) was added 4N NaOH aq. (0.5 mL). After stirred at r.t. for 5 hr, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (14 mg, 49% yield) as a white powder. ¹H NMR (400 MHz, CDCl₃) δ 9.30 (s, 1H), 7.22-7.15 (m, 2H), 6.96 (dd, J=8.2, 1.8 Hz, 1H), 3.37-3.25 (m, 5H), 2.88-2.77 (m, 2H), 2.71-2.49 (m, 3H), 2.03-1.94 (m, 2H), 1.70-1.58 (m, 4H), 1.39-1.25 (m, 6H), 0.83 (d, J=6.6 Hz, 6H). LCMS (ESI) m/z calcd for $C_{23}H_{33}ClN_4O_3S$: 480.20. Found: 481.51/483.51 (M/M+2)⁺.

Example 49

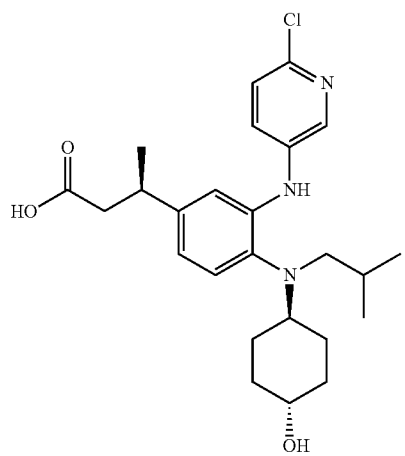 [SMILES: CC(C)CN(c1ccc([C@H](C)CC(=O)O)cc1Nc1ccc(Cl)nc1)[C@H]1CC[C@H](O)CC1]

147

-continued

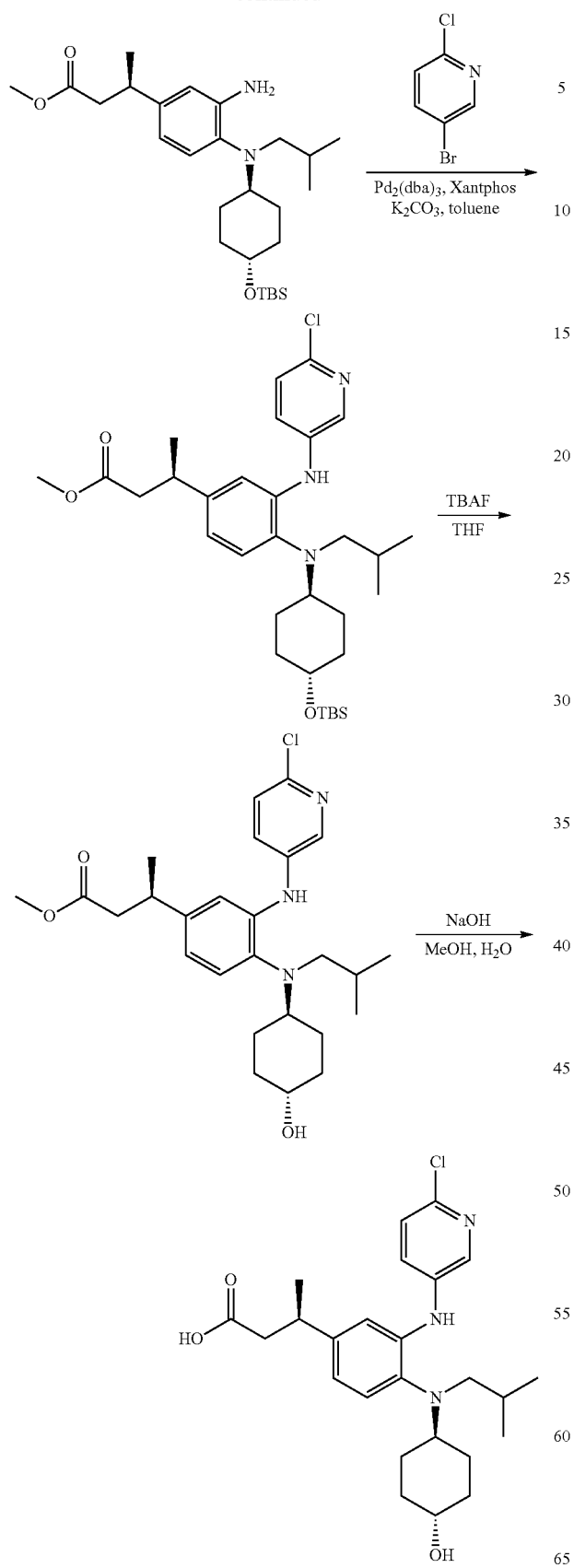

148

Preparation of methyl (R)-3-(4-(((1r,4R)-4-((tert-butyldimethylsilyl)oxy)cyclohexyl)(isobutyl)amino)-3-((6-chloropyridin-3-yl)amino)phenyl)butanoate

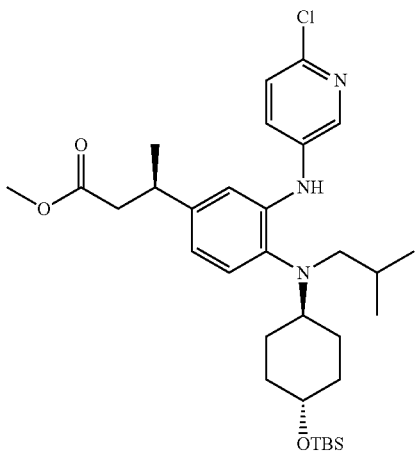 [SMILES: COC(=O)C[C@@H](C)c1ccc(N(CC(C)C)[C@H]2CC[C@H](O[Si](C)(C)C(C)(C)C)CC2)c(Nc2ccc(Cl)nc2)c1]

A mixture of methyl (R)-3-(3-amino-4-(((1r,4R)-4-((tert-butyldimethylsilyl)oxy)cyclohexyl)(isobutyl)amino)phenyl)butanoate (200 mg, 0.42 mmol), 5-bromo-2-chloropyridine (161 mg, 0.84 mmol), $Pd_2(dba)_3$ (76 mg, 0.084 mmol), Xantphos (96 mg, 0.168 mmol) and $K_2CO_3$ (173 mg, 1.26 mmol) in toluene (10 mL) was stirred at 100° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-10% EtOAc in PE) to afford the title compound (190 mg, 76% yield). LCMS (ESI) m/z calcd for $C_{32}H_{50}ClN_3O_3Si$: 587.33. Found: 588.62/590.60 (M/M+ 2)$^+$.

Preparation of methyl (R)-3-(3-((6-chloropyridin-3-yl)amino)-4-(((1r,4R)-4-hydroxycyclohexyl)(isobutyl)amino)phenyl)butanoate

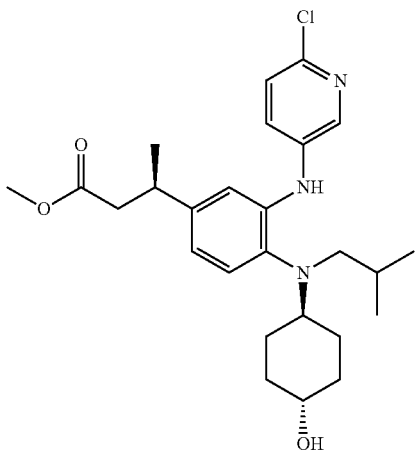 [SMILES: COC(=O)C[C@@H](C)c1ccc(N(CC(C)C)[C@H]2CC[C@H](O)CC2)c(Nc2ccc(Cl)nc2)c1]

A mixture of methyl (R)-3-(4-(((1r,4R)-4-((tert-butyldimethylsilyl)oxy)cyclohexyl) (iso butyl)amino)-3-((6-chloropyridin-3-yl)amino)phenyl)butanoate (190 mg, 0.32 mmol) and TBAF (1M in THF, 5 mL) in THF (5 mL) was stirred at r.t. overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (140 mg, 91% yield). LCMS (ESI) m/z calcd for C$_{26}$H$_{36}$ClN$_3$O$_3$: 473.24. Found: 474.75/476.74 (M/M+2)$^+$.

Preparation of (R)-3-(3-((6-chloropyridin-3-yl)amino)-4-(((1r,4R)-4-hydroxy cyclohexyl) (isobutyl)amino)phenyl)butanoic Acid

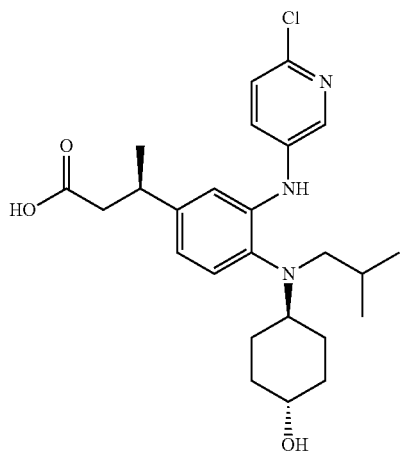 [SMILES: CC(C)CN(c1ccc([C@H](C)CC(=O)O)cc1Nc1ccc(Cl)nc1)[C@H]1CC[C@H](O)CC1]

To a solution of methyl (R)-3-(3-((6-chloropyridin-3-yl)amino)-4-(((1r,4R)-4-hydroxyl cyclohexyl) (isobutyl)amino)phenyl)butanoate (120 mg, 0.25 mmol) in MeOH (4 mL) was added 1N NaOH aq. (3 mL). After stirred at r.t. for 8 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (76 mg, 66% yield) as a white powder. $^1$H NMR (400 MHz, DMSO) δ 11.91 (br, 1H), 8.17 (d, J=2.9 Hz, 1H), 7.50 (dd, J=8.7, 3.0 Hz, 1H), 7.29 (d, J=8.7 Hz, 1H), 7.18 (s, 1H), 7.13-7.05 (m, 2H), 6.84 (dd, J=8.1, 1.7 Hz, 1H), 4.40 (d, J=4.4 Hz, 1H), 3.28-3.22 (m, 1H), 3.13-3.04 (m, 1H), 2.73 (d, J=6.3 Hz, 2H), 2.48-2.45 (m, 2H), 1.80-1.61 (m, 4H), 1.40-1.19 (m, 7H), 0.96-0.87 (m, 2H), 0.79 (d, J=6.6 Hz, 6H). LCMS (ESI) m/z calcd for C$_{25}$H$_{34}$ClN$_3$O$_3$: 459.23. Found: 460.77/462.76 (M/M+2)$^+$.

Example 50

Preparation of (R)-3-(4-(isobutyl((1r,4R)-4-methoxycyclohexyl)amino)-3-((3-(tri fluoromethyl)-1,2,4-thiadiazol-5-yl)amino)phenyl)butanoic Acid

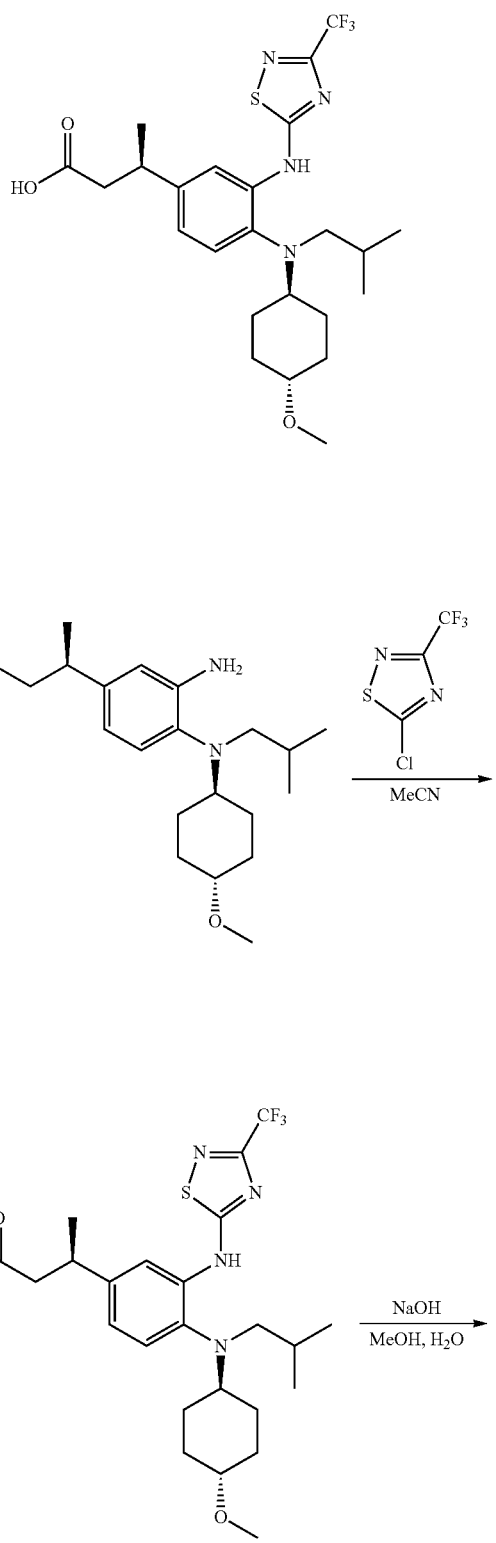

151
-continued

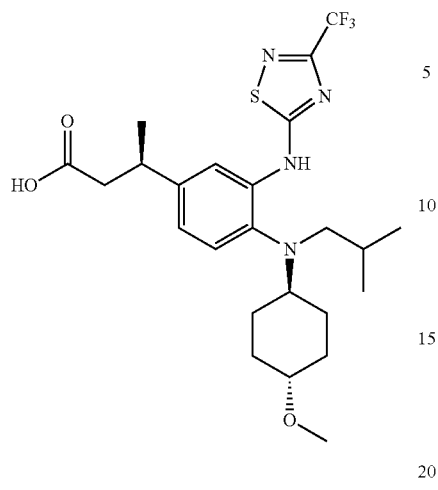

Preparation of methyl (R)-3-(4-(isobutyl((1 r,4R)-4-methoxycyclohexyl)amino)-3-((3-(trifluoromethyl)-1,2,4-thiadiazol-5-yl)amino)phenyl)butanoate

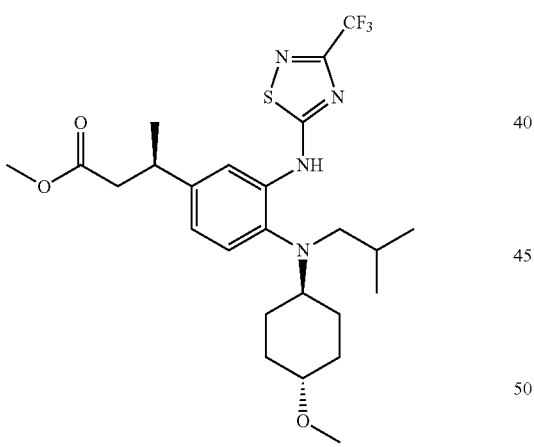

A mixture of methyl (R)-3-(3-amino-4-(isobutyl((1r,4R)-4-methoxycyclohexyl)amino) phenyl)butanoate (100 mg, 0.265 mmol) and 5-chloro-3-(trifluoromethyl)-1,2,4-thiadiazole (100 mg, 0.53 mmol) in MeCN (2 mL) was stirred at 90° C. overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (60 mg, 43% yield). LCMS (ESI) m/z calcd for C$_{25}$H$_{35}$F$_3$N$_4$O$_3$S: 528.24. Found: 529.41 (M+1)$^+$.

152

Preparation of (R)-3-(4-(isobutyl((1r,4R)-4-methoxycyclohexyl)amino)-3-((3-(tri fluoromethyl)-1,2,4-thiadiazol-5-yl)amino)phenyl)butanoic Acid

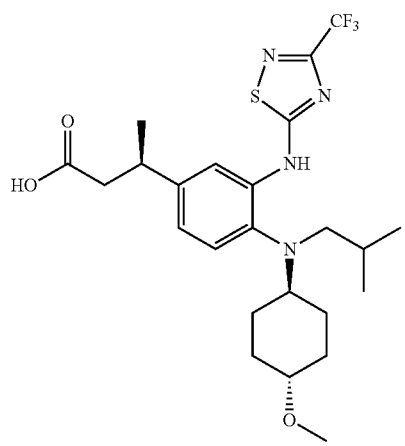 [SMILES: CO[C@H]1CC[C@H](N(CC(C)C)c2ccc([C@H](C)CC(=O)O)cc2Nc2nc(C(F)(F)F)ns2)CC1]

To a solution of methyl (R)-3-(4-(isobutyl((1 r,4R)-4-methoxycyclohexyl)amino)-3-((3-(trifluoromethyl)-1,2,4-thiadiazol-5-yl)amino)phenyl)butanoate (30 mg, 0.057 mmol) in MeOH (3 mL) was added 4N NaOH aq. 0.5 mL). After stirred at 50° C. for 4 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (13.7 mg, 47% yield) as a white powder. $^1$H NMR (400 MHz, CDCl$_3$) δ 9.44 (s, 1H), 7.30 (d, J=1.6 Hz, 1H), 7.20 (d, J=8.2 Hz, 1H), 6.99 (dd, J=8.2, 1.8 Hz, 1H), 3.39-3.26 (m, 4H), 3.06-2.98 (m, 1H), 2.80 (d, J=6.0 Hz, 2H), 2.73-2.60 (m, 3H), 2.11-2.02 (m, 2H), 1.97-1.90 (m, 2H), 1.39-1.16 (m, 8H), 0.84 (d, J=6.6 Hz, 6H). LCMS (ESI) m/z calcd for C$_{24}$H$_{33}$F$_3$N$_4$O$_3$S: 514.22. Found: 515.54 (M+1)$^+$.

Example 51

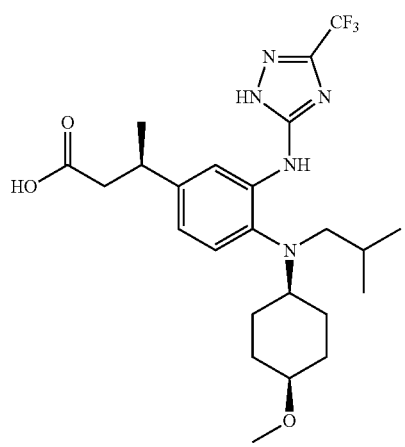 [SMILES: CO[C@H]1CC[C@@H](N(CC(C)C)c2ccc([C@H](C)CC(=O)O)cc2Nc2nc(C(F)(F)F)n[nH]2)CC1]

Step A (R)-methyl 3-(4-(isobutyl((cis)-4-methoxycyclohexyhamino)-3-((3-(trifluoromethyl)-1H-1,2,4-triazol-5-yl)amino)phenyl)butanoate

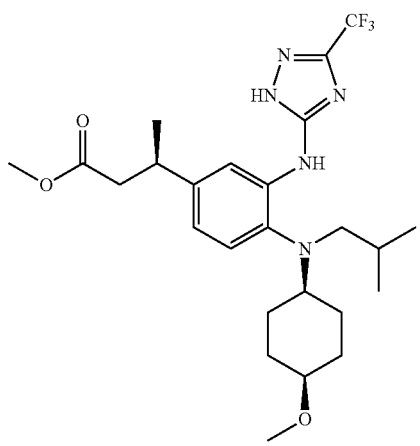 [SMILES: COC(=O)C[C@@H](C)c1ccc(N(CC(C)C)[C@H]2CC[C@@H](OC)CC2)c(Nc2nc(C(F)(F)F)n[nH]2)c1]

A mixture of (R)-methyl 3-(3-amino-4-(isobutyl((cis)-4-methoxycyclohexyl)amino)phenyl)butanoate (0.135 g, 0.359 mmol), 3-bromo-5-(trifluoromethyl)-1-((2-(trimethylsilyl)ethoxy)methyl)-1H-1,2,4-triazole (0.149 g, 0.430 mmol), Pd$_2$dba$_3$ (0.066 g, 0.072 mmol), Xantphos (0.083 g, 0.143 mmol), and cesium carbonate (0.584 g, 1.793 mmol) was flushed with nitrogen and then stirred in toluene (5.1 ml) and heated at 100° C. for 6 h. The reaction mixture was filtered through celite, evaporated, and purified by silica gel chromatography (0-30% EtOAc/hexanes). The product was stirred in TFA (0.5 mL) and CH$_2$Cl$_2$ (0.5 mL) for 3 h, evaporated and purified by silica gel chromatography (0-40% EtOAc/hexanes) to afford (R)-methyl 3-(4-(isobutyl((cis)-4-methoxycyclohexyhamino)-3-((5-(trifluoromethyl)-1H-1,2,4-triazol-3-yl)amino)phenyl)butanoate (138.7 mg, 76%). LCMS (M+H)$^+$: m/z=512.5.

Step B (R)-3-(4-(isobutyl((cis)-4-methoxycyclohexyhamino)-3-((3-(trifluoromethyl)-1H-1,2,4-triazol-5-yl)amino)phenyl)butanoic Acid

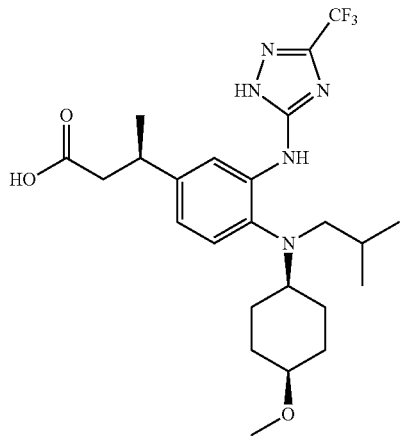 [SMILES: CO[C@H]1CC[C@@H](N(CC(C)C)c2ccc([C@H](C)CC(=O)O)cc2Nc2nc(C(F)(F)F)n[nH]2)CC1]

(R)-methyl 3-(4-(isobutyl((cis)-4-methoxycyclohexyhamino)-3-((3-(trifluoromethyl)-1H-1,2,4-triazol-5-yl) amino)phenyl)butanoate (0.085 g, 0.166 mmol) was subjected to base hydrolysis as previously described and purified by reverse phase chromatography (10-100% CH$_3$CN/H$_2$O (0.1% formic acid)) to afford the title compound (0.0497 g, 60%) as a white solid. LCMS (M+H)$^+$: m/z=498.2. $^1$H NMR (400 MHz, CD$_3$OD) δ ppm 7.95 (d, J=1.8 Hz, 1H), 7.18 (d, J=8.2 Hz, 1H), 6.88 (dd, J=8.2, 2.0 Hz, 1H), 3.15-3.37 (m, 5H), 2.82 (d, J=6.6 Hz, 2H), 2.45-2.66 (m, 3H), 1.93 (d, J=14.8 Hz, 2H), 1.54-1.67 (m, 4H), 1.25-1.41 (m, 6H), 0.83 (d, J=6.4 Hz, 6H).

Example 52

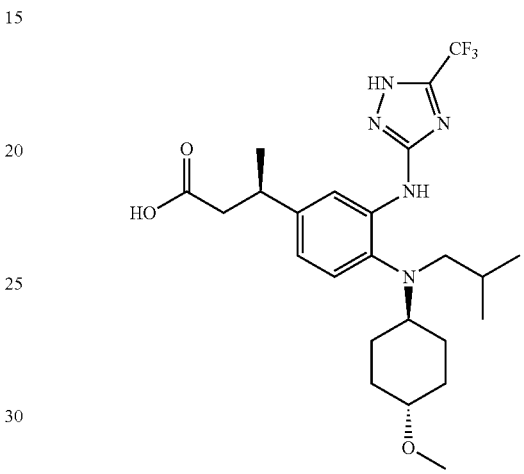

Step A (R)-methyl 3-(4-(isobutyl((trans)-4-methoxycyclohexyl)amino)-3-((5-(trifluoromethyl)-1-((2-(trimethylsilyl)ethoxy)methyl)-1H-1,2,4-triazol-3-yl)amino)phenyl)butanoate

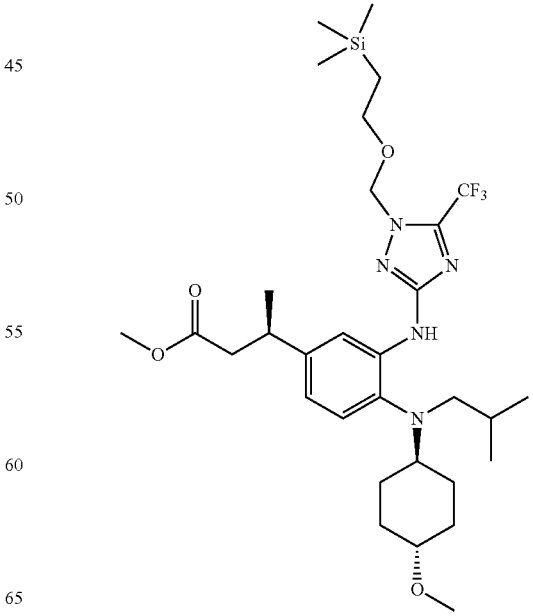

A mixture of ((R)-methyl 3-(3-amino-4-(isobutyl((trans)-4-methoxycyclohexyl)amino)phenyl)butanoate (132 mg, 0.35 mmol), 3-bromo-5-(trifluoromethyl)-1-((2-(trimethylsilyl)ethoxy)methyl)-1H-1,2,4-triazole (145 mg, 0.420 mmol), Pd$_2$dba$_3$ (64.1 mg, 0.070 mmol), Xantphos (81 mg, 0.140 mmol), and cesium carbonate (570 mg, 1.750 mmol) was flushed with nitrogen and then stirred in toluene (5.0 ml) and heated at 100° C. for 6 h. The reaction mixture was filtered through celite, evaporated, and purified by silica gel chromatography (0-30% EtOAc/hexanes) to afford (R)-methyl 3-(4-(isobutyl((trans)-4-methoxycyclohexyl)amino)-3-((5-(trifluoromethyl)-1-((2-(trimethylsilyl)ethoxy)methyl)-1H-1,2,4-triazol-3-yl)amino)phenyl)butanoate (188.8 mg, 84%). LCMS (M+H)$^+$: m/z=642.5.

Step B (R)-3-(4-(isobutyl((trans)-4-methoxycyclohexyhamino)-3-((5-(trifluoromethyl)-1H-1,2,4-triazol-3-yl)amino)phenyl)butanoic Acid (R)-methyl 3-(4-(isobutyl((trans)-4-methoxycyclohexyl)amino)-3-((5-(trifluoromethyl)-1-((2-(trimethylsilyl)ethoxy)methyl)-1H-1,2,4-triazol-3-yl)amino)phenyl)butanoate (0.081 g, 0.126 mmol) was treated with TFA and then subjected to base hydrolysis as previously described and purified by reverse phase chromatography (10-100% CH$_3$CN/H$_2$O (0.1% formic acid)) to afford the title compound (0.053 g, 84%) as a white solid. LCMS (M+H)$^+$: m/z=498.3. $^1$H NMR (400 MHz, CD$_3$OD) δ ppm 7.95 (d, J=2.0 Hz, 1H), 7.18 (d, J=8.2 Hz, 1H), 6.89 (dd, J=8.2, 1.8 Hz, 1H), 3.26 (s, 3H), 3.16-3.25 (m, 1H), 3.02-3.11 (m, 1H), 2.82 (d, J=6.3 Hz, 2H), 2.47-2.67 (m, 3H), 1.87-2.08 (m, 4H), 1.25-1.43 (m, 6H), 1.01-1.14 (m, 2H), 0.83 (d, J=6.6 Hz, 6H).

Example 53

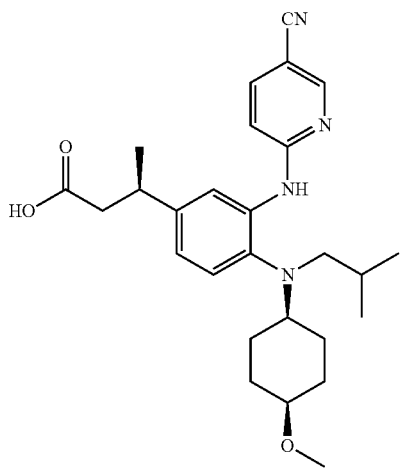

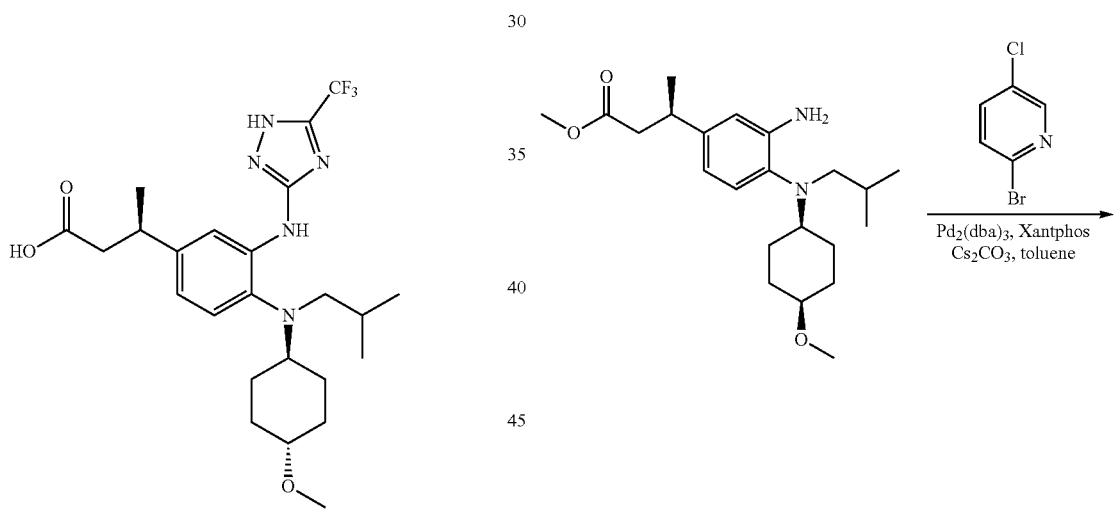

157

-continued

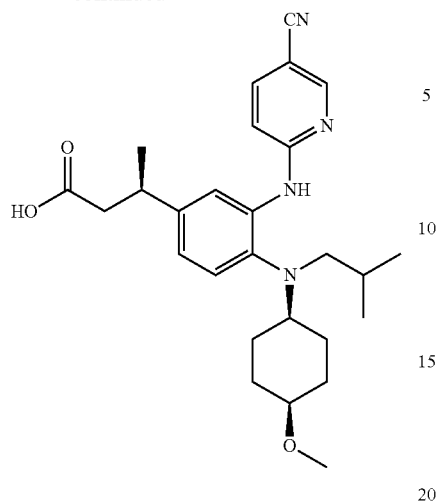

Preparation of methyl (R)-3-(3-((5-cyanopyridin-2-yl)amino)-4-(isobutyl((1s,4S)-4-methoxycyclohexyl)amino)phenyl)butanoate

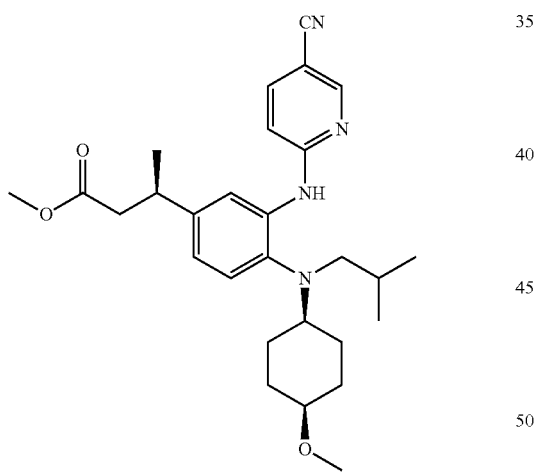

A mixture of methyl (R)-3-(3-amino-4-(isobutyl((1s,4S)-4-methoxycyclohexyl)amino) phenyl)butanoate (100 mg, 0.27 mmol), 6-bromonicotinonitrile (98 mg, 0.54 mmol), Pd$_2$(dba)$_3$ (24 mg, 0.027 mmol), Xantphos (31 mg, 0.054 mmol) and Cs$_2$CO$_3$ (175 mg, 0.54 mmol) in toluene (5 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (80 mg, 63% yield). LCMS (ESI) m/z calcd for C$_{28}$H$_{38}$N$_4$O$_3$: 478.29. Found: 479.62 (M+1)$^+$.

158

Preparation of (R)-3-(3-((5-cyanopyridin-2-yl)amino)-4-(isobutyl((1s,4S)-4-methoxycyclohexyl)amino)phenyl)butanoic Acid

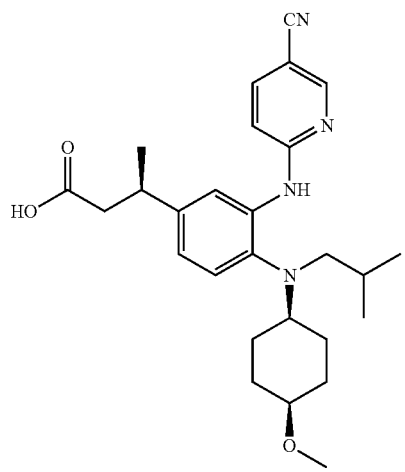 [SMILES: CO[C@H]1CC[C@@H](N(CC(C)C)c2ccc([C@H](C)CC(=O)O)cc2Nc2ccc(C#N)cn2)CC1]

To a solution of methyl (R)-3-(3-((5-cyanopyridin-2-yl)amino)-4-(isobutyl((1s,4S)-4-methoxycyclohexyl)amino) phenyl)butanoate (80 mg, 0.167 mmol) in MeOH (3 mL) was added 1N NaOH aq. (1 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (10 mg, 13% yield) as a white powder. $^1$H NMR (400 MHz, CDCl$_3$) δ 8.53 (d, J=1.9 Hz, 1H), 8.37 (s, 1H), 8.11 (d, J=1.9 Hz, 1H), 7.65 (dd, J=8.8, 2.3 Hz, 1H), 7.13 (d, J=8.2 Hz, 1H), 6.87 (dd, J=8.2, 2.0 Hz, 1H), 6.74 (d, J=8.7 Hz, 1H), 3.37-3.24 (m, 5H), 2.82 (d, J=6.6 Hz, 2H), 2.75-2.52 (m, 3H), 1.99-1.91 (m, 2H), 1.73-1.54 (m, 4H), 1.42-1.23 (m, 6H), 0.84 (d, J=6.6 Hz, 6H). LCMS (ESI) m/z calcd for C$_{27}$H$_{36}$N$_4$O$_3$: 464.28. Found: 465.36 (M+1)$^+$.

Example 54

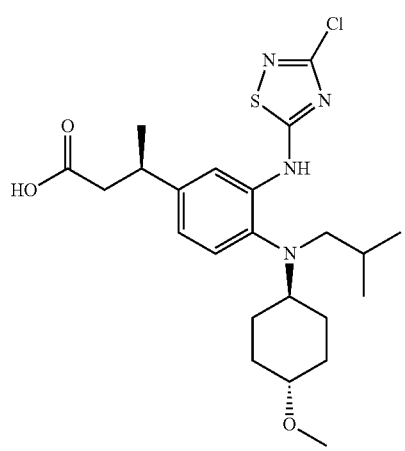 [SMILES: CO[C@H]1CC[C@H](N(CC(C)C)c2ccc([C@H](C)CC(=O)O)cc2Nc2nc(Cl)ns2)CC1]

159

-continued

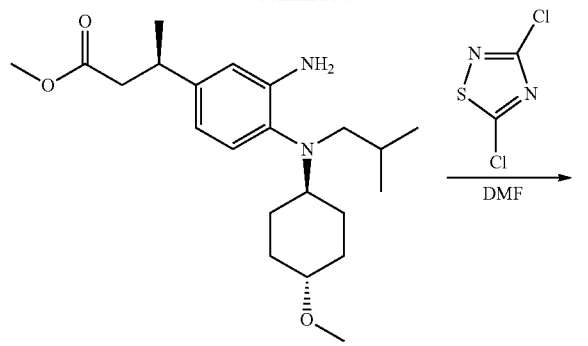

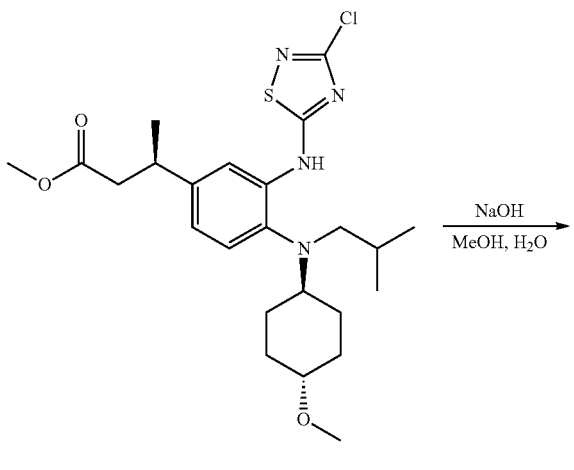

160

Preparation of methyl (R)-3-(3-((3-chloro-1,2,4-thiadiazol-5-yl)amino)-4-(isobutyl ((1r,4R)-4-methoxycyclohexyl)amino)phenyl)butanoate

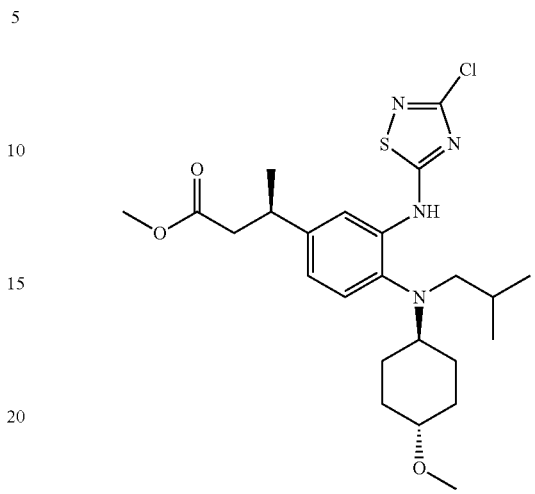

A mixture of methyl (R)-3-(3-amino-4-(isobutyl((1r,4R)-4-methoxycyclohexyl)amino) phenyl)butanoate (100 mg, 0.265 mmol) and 3,5-dichloro-1,2,4-thiadiazole (82 mg, 0.53 mmol) in DMF (2 mL) was stirred at 90° C. overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (60 mg, 46% yield). LCMS (ESI) m/z calcd for C$_{24}$H$_{35}$ClN$_4$O$_3$S: 494.21. Found: 495.82/497.49 (M/M+2)$^+$.

Preparation of (R)-3-(3-((3-chloro-1,2,4-thiadiazol-5-yl)amino)-4-(isobutyl((1r,4R)-4-methoxycyclohexyl)amino)phenyl)butanoic Acid

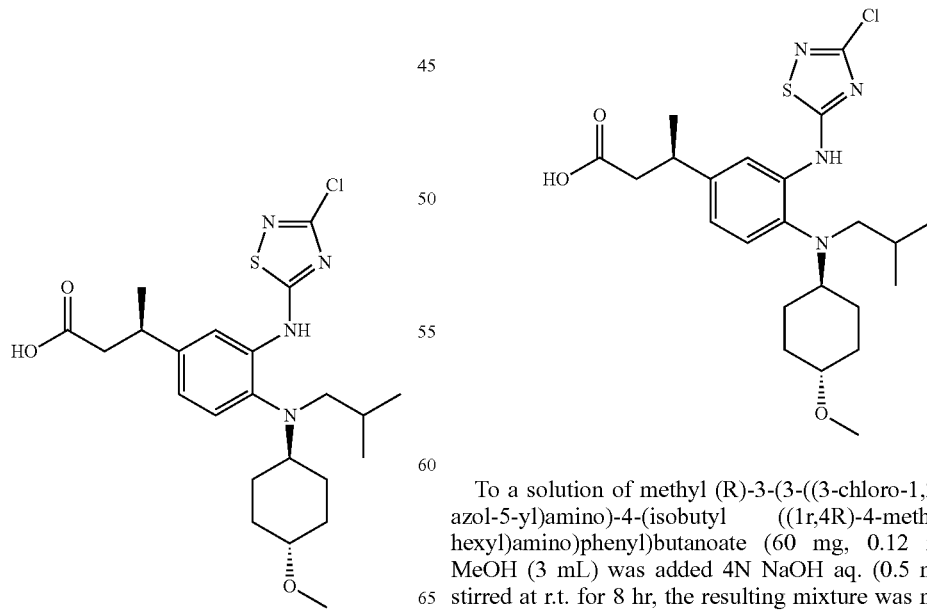

To a solution of methyl (R)-3-(3-((3-chloro-1,2,4-thiadiazol-5-yl)amino)-4-(isobutyl ((1r,4R)-4-methoxycyclohexyl)amino)phenyl)butanoate (60 mg, 0.12 mmol) in MeOH (3 mL) was added 4N NaOH aq. (0.5 mL). After stirred at r.t. for 8 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H₂O with 0.1% formic acid) to afford the title compound (27 mg, 47% yield) as a white powder. ¹H NMR (400 MHz, CDCl₃) δ 9.39 (s, 1H), 7.19 (d, J=8.2 Hz, 1H), 7.15 (d, J=1.7 Hz, 1H), 6.97 (dd, J=8.2, 1.8 Hz, 1H), 3.37-3.27 (m, 4H), 3.06-2.99 (m, 1H), 2.79 (d, J=5.6 Hz, 2H), 2.73-2.59 (m, 3H), 2.10-2.01 (m, 2H), 1.96-1.86 (m, 2H), 1.41-1.14 (m, 8H), 0.83 (d, J=6.6 Hz, 6H). LCMS (ESI) m/z calcd for $C_{23}H_{33}ClN_4O_3S$: 480.20. Found: 481.52/483.51 (M/M+2)⁺.

Example 55

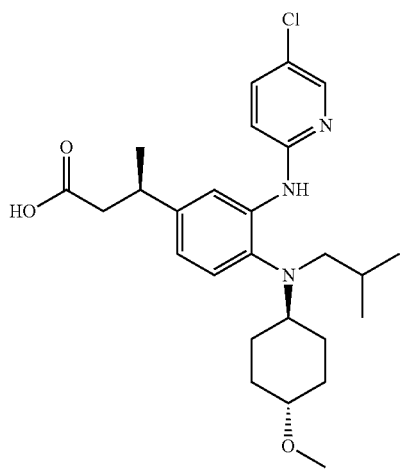

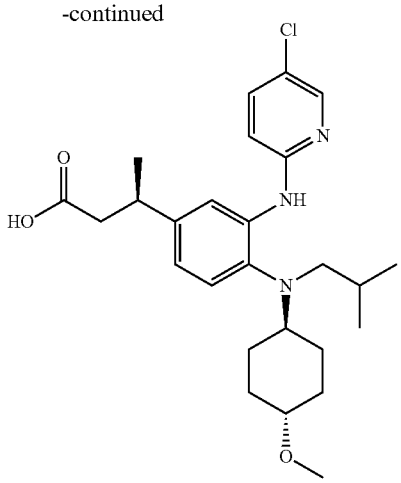

Preparation of methyl (R)-3-(3-((5-chloropyridin-2-yl)amino)-4-(isobutyl((1r,4R)-4-methoxycyclohexyl)amino)phenyl)butanoate

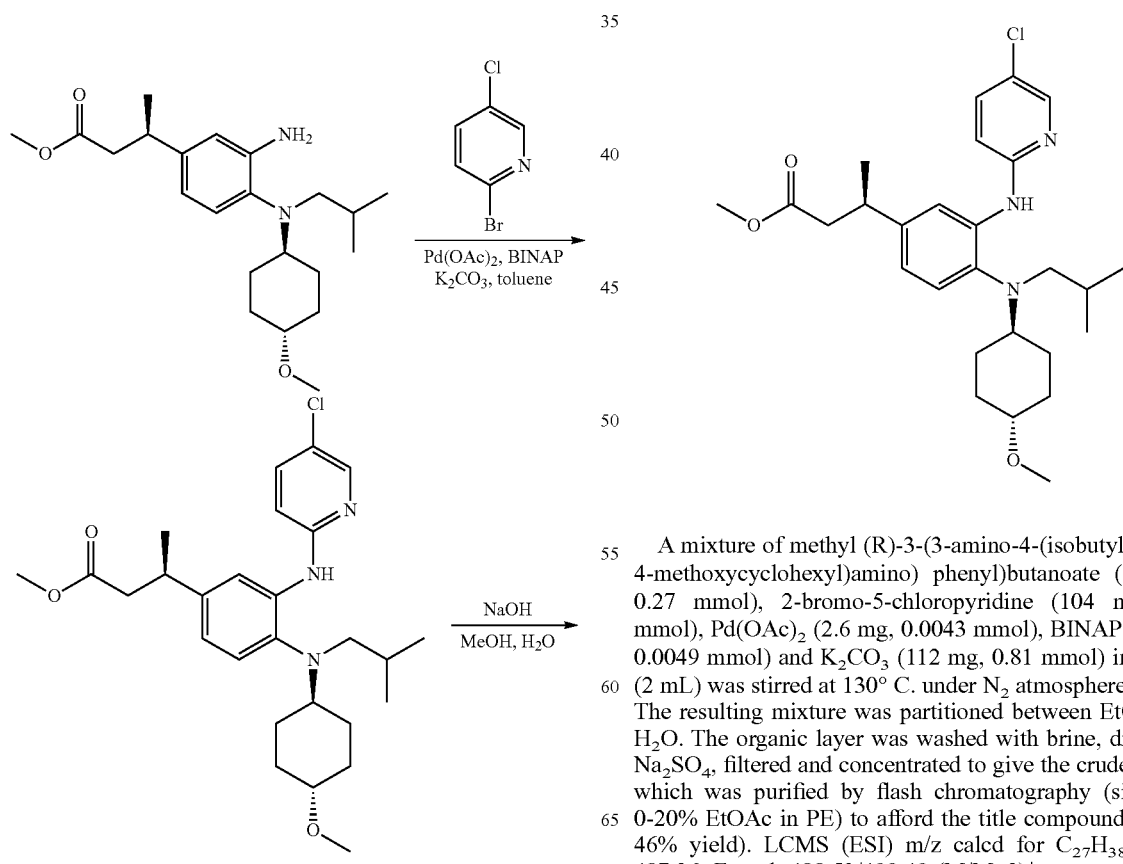

A mixture of methyl (R)-3-(3-amino-4-(isobutyl((1r,4R)-4-methoxycyclohexyl)amino) phenyl)butanoate (100 mg, 0.27 mmol), 2-bromo-5-chloropyridine (104 mg, 0.54 mmol), Pd(OAc)₂ (2.6 mg, 0.0043 mmol), BINAP (3.1 mg, 0.0049 mmol) and K₂CO₃ (112 mg, 0.81 mmol) in toluene (2 mL) was stirred at 130° C. under N₂ atmosphere for 5 hr. The resulting mixture was partitioned between EtOAc and H₂O. The organic layer was washed with brine, dried over Na₂SO₄, filtered and concentrated to give the crude product which was purified by flash chromatography (silica gel, 0-20% EtOAc in PE) to afford the title compound (60 mg, 46% yield). LCMS (ESI) m/z calcd for $C_{27}H_{38}ClN_3O_3$: 487.26. Found: 488.53/490.49 (M/M+2)⁺.

163

Preparation of (R)-3-(3-((5-chloropyridin-2-yl)amino)-4-(isobutyl((1r,4R)-4-methoxycyclohexyl)amino)phenyl)butanoic Acid

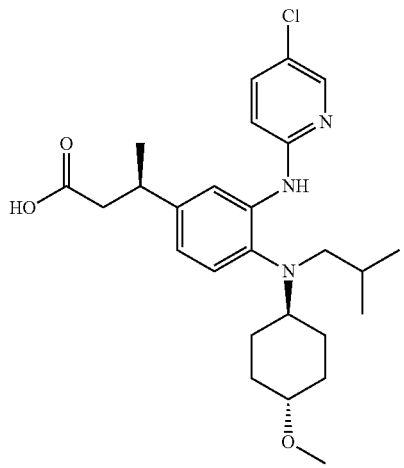 [SMILES: CO[C@H]1CC[C@H](N(CC(C)C)c2ccc([C@H](C)CC(=O)O)cc2Nc2ccc(Cl)cn2)CC1]

To a solution of methyl (R)-3-(3-((5-chloropyridin-2-yl)amino)-4-(isobutyl((1r,4R)-4-methoxycyclohexyl)amino)phenyl)butanoate (60 mg, 0.123 mmol) in MeOH (3 mL) was added 4N NaOH aq. (0.5 mL). After stirred at r.t. for 8 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (12.4 mg, 21% yield) as a white powder. $^1$H NMR (400 MHz, CDCl$_3$) δ 8.20 (d, J=2.1 Hz, 1H), 8.03 (s, 1H), 7.97 (s, 1H), 7.45 (dd, J=8.8, 2.6 Hz, 1H), 7.08 (d, J=8.2 Hz, 1H), 6.83-6.70 (m, 2H), 3.34-3.20 (m, 4H), 3.06-2.96 (m, 1H), 2.85-2.56 (m, 5H), 2.07-1.99 (m, 2H), 1.95-1.85 (m, 2H), 1.36-1.08 (m, 8H), 0.85 (d, J=6.6 Hz, 6H). LCMS (ESI) m/z calcd for C$_{26}$H$_{36}$ClN$_3$O$_3$: 473.24. Found: 474.32/476.31 (M/M+2)$^+$.

Example 56

164

-continued

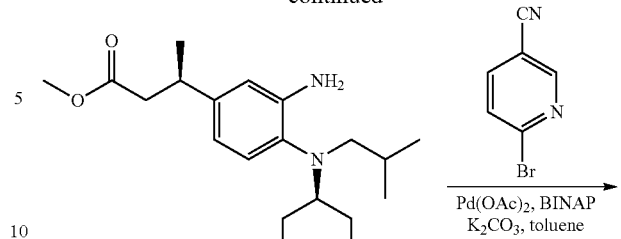

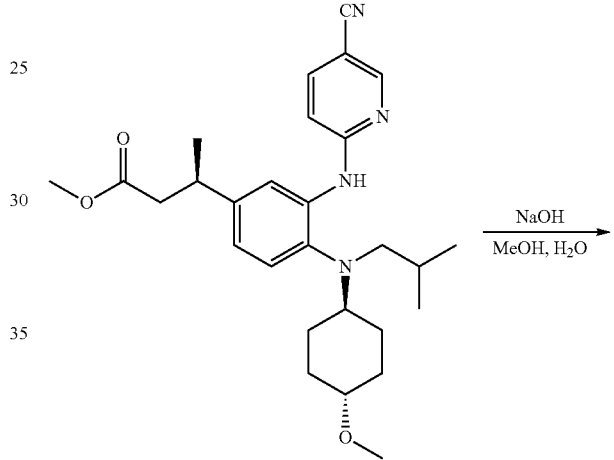

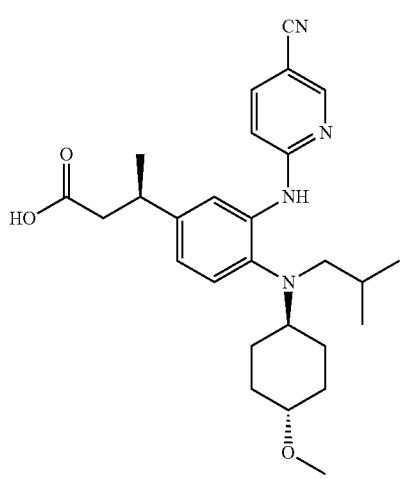

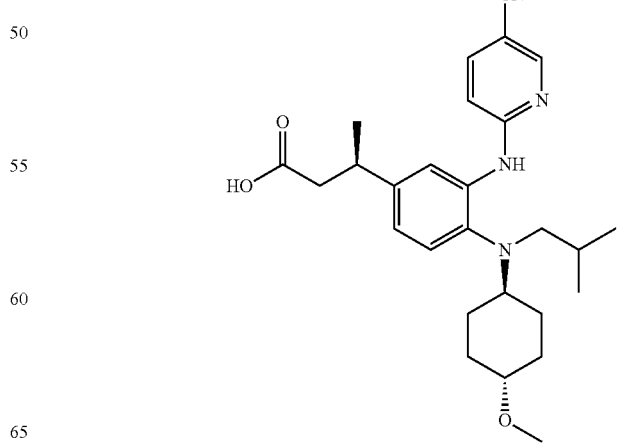

Preparation of methyl (R)-3-(3-((5-cyanopyridin-2-yl)amino)-4-(isobutyl((1r,4R)-4-methoxycyclohexyl)amino)phenyl)butanoate

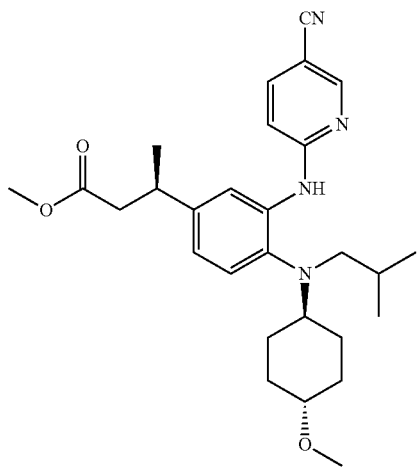 [SMILES: COC(=O)C[C@@H](C)c1ccc(N(CC(C)C)[C@H]2CC[C@H](OC)CC2)c(Nc2ccc(C#N)cn2)c1]

A mixture of methyl (R)-3-(3-amino-4-(isobutyl((1r,4R)-4-methoxycyclohexyl)amino) phenyl)butanoate (100 mg, 0.27 mmol), 6-bromonicotinonitrile (100 mg, 0.54 mmol), Pd(OAc)$_2$ (2.6 mg, 0.0043 mmol), BINAP (3.1 mg, 0.0049 mmol) and K$_2$CO$_3$ (112 mg, 0.81 mmol) in toluene (2 mL) was stirred at 130° C. under N$_2$ atmosphere for 8 hr. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (30 mg, 24% yield). LCMS (ESI) m/z calcd for C$_{28}$H$_{38}$N$_4$O$_3$: 478.29. Found: 479.42 (M+1)$^+$.

Preparation of (R)-3-(3-((5-cyanopyridin-2-yl)amino)-4-(isobutyl((1r,4R)-4-methoxycyclohexyl)amino)phenyl)butanoic Acid

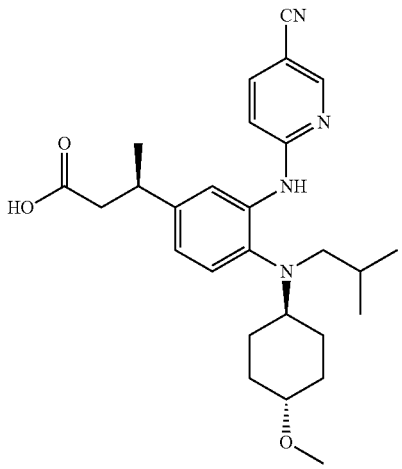 [SMILES: CO[C@H]1CC[C@H](N(CC(C)C)c2ccc([C@H](C)CC(=O)O)cc2Nc2ccc(C#N)cn2)CC1]

To a solution of methyl (R)-3-(3-((5-cyanopyridin-2-yl)amino)-4-(isobutyl((1r,4R)-4-methoxycyclohexyl)amino)phenyl)butanoate (30 mg, 0.06 mmol) in MeOH (3 mL) was added 4N NaOH aq. (0.5 mL). After stirred at r.t. for 8 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (5.7 mg, 20% yield) as a white powder. $^1$H NMR (400 MHz, CDCl$_3$) δ 8.54 (d, J=1.6 Hz, 1H), 8.43 (s, 1H), 8.15 (s, 1H), 7.66 (dd, J=8.7, 2.2 Hz, 1H), 7.13 (d, J=8.2 Hz, 1H), 6.88 (d, J=8.2 Hz, 1H), 6.73 (d, J=8.7 Hz, 1H), 3.36-3.20 (m, 4H), 3.06-2.95 (m, 1H), 2.87-2.52 (m, 5H), 2.10-1.99 (m, 2H), 1.93-1.84 (m, 2H), 1.41-1.22 (m, 8H), 0.85 (d, J=6.6 Hz, 6H). LCMS (ESI) m/z calcd for C$_{27}$H$_{36}$N$_4$O$_3$: 464.28. Found: 465.31 (M+1)$^+$.

Example 57

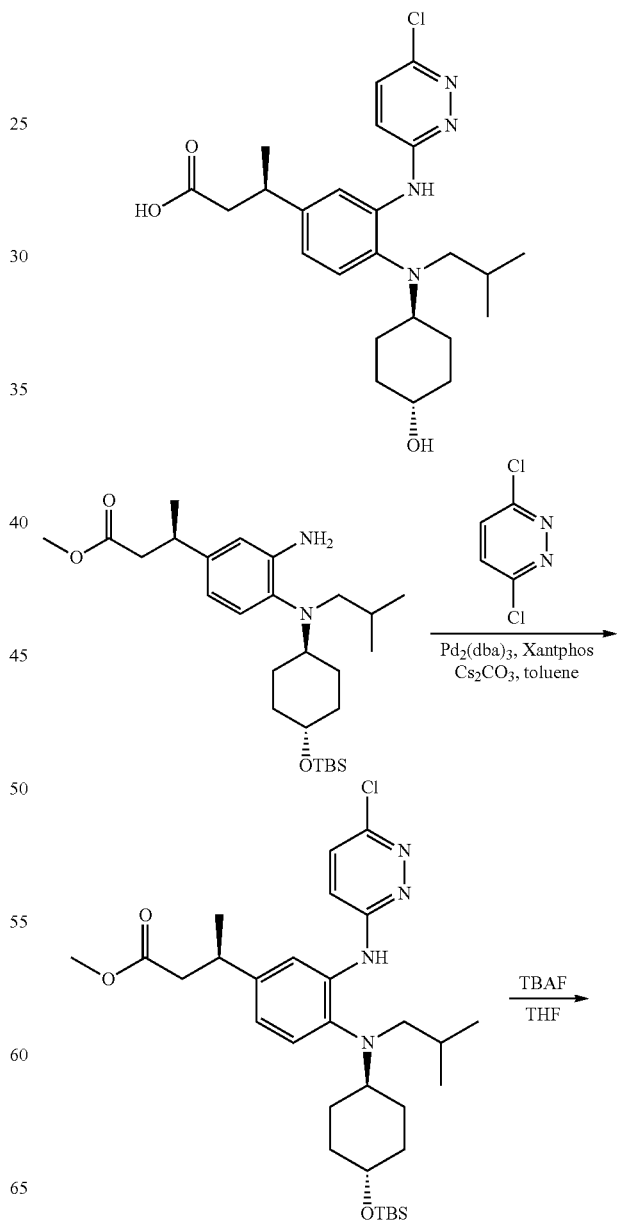

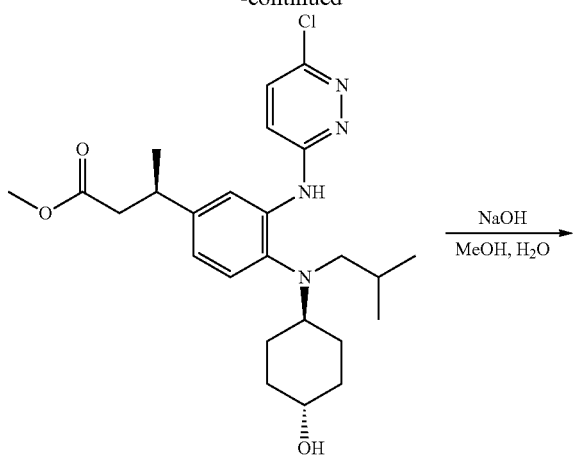

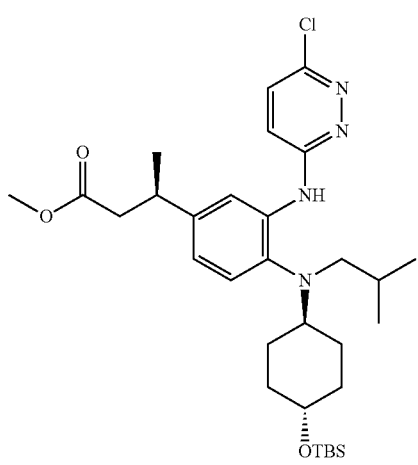 [SMILES: COC(=O)C[C@@H](C)c1ccc(N(CC(C)C)[C@H]2CC[C@H](O[Si](C)(C)C(C)(C)C)CC2)c(Nc2ccc(Cl)nn2)c1]

Preparation of methyl (R)-3-(4-(((1r,4R)-4-((tert-butyldimethylsilyl)oxy)cyclo hexyl) (isobutyl) amino)-3-((6-chloropyridazin-3-yl)amino)phenyl) butanoate A mixture of methyl (R)-3-(3-amino-4-(((1r,4R)-4-((tert-butyldimethylsilyl)oxy)cyclo hexyl) (isobutyl)amino)phenyl)butanoate (250 mg, 0.53 mmol), 3,6-dichloropyridazine (156 mg, 1.06 mmol), $Pd_2(dba)_3$ (97 mg, 0.106 mmol), Xantphos (122 mg, 0.212 mmol) and $Cs_2CO_3$ (344 mg, 1.06 mmol) in toluene (10 mL) was stirred at 100° C. under $N_2$ atmosphere overnight. The resulting mixture was partitioned between EtOAc and $H_2O$.

The organic layer was washed with brine, dried over $Na_2SO_4$, filtered and concentrated to give the crude product which was purified by flash chromatography (silica gel, 0-10% EtOAc in PE) to afford the title compound (103 mg, 33% yield). LCMS (ESI) m/z calcd for $C_{31}H_{49}ClN_4O_3Si$: 588.33. Found: 589.96/591.96 (M/M+2)$^+$.

Preparation of methyl (R)-3-(3-((6-ch loro-pyridazin-3-yl)amino)-4-(((1 r,4R)-4-hydroxycyclo-hexyl) (isobutyl)amino)phenyl)butanoate

A mixture of methyl (R)-3-(4-(((1r,4R)-4-((tert-butyldimethylsilyl)oxy)cyclohexyl) (iso butyl)amino)-3-((6-chloropyridazin-3-yl)amino)phenyl)butanoate (103 mg, 0.175 mmol) and TBAF (1M in THF, 3 mL) in THF (4 mL) was stirred at r.t. overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (80 mg, 96% yield). LCMS (ESI) m/z calcd for $C_{25}H_{35}ClN_4O_3$: 474.24. Found: 475.68/477.65 (M/M+2)$^+$.

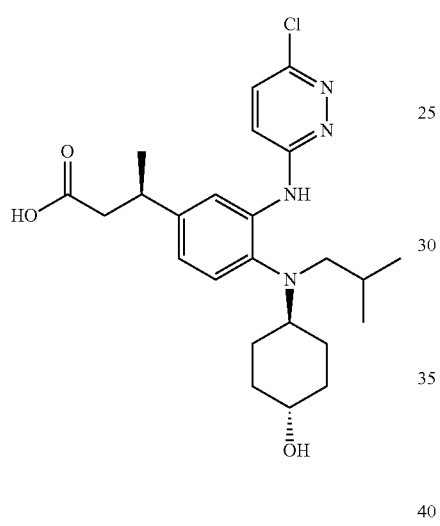

Preparation of (R)-3-(3-((6-chloropyridazin-3-yl)amino)-4-(((1r,4R)-4-hydroxy cyclohexyl) (isobutyl) amino)phenyl)butanoic Acid

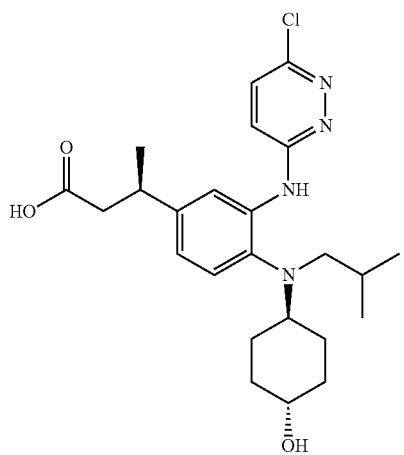

To a solution of methyl (R)-3-(3-((6-chloropyridazin-3-yl)amino)-4-(((1r,4R)-4-hydroxyl cyclohexyl) (isobutyl)amino)phenyl)butanoate (80 mg, 0.168 mmol) in MeOH (3 mL) was added 1N NaOH aq. (3 mL). After stirred at r.t. for 6 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (52 mg, 67% yield) as a white powder. $^1$H NMR (400 MHz, DMSO) δ 11.99 (s, 1H), 8.31 (s, 1H), 8.03 (d, J=2.0 Hz, 1H), 7.60 (d, J=9.3 Hz, 1H), 7.43 (d, J=9.4 Hz, 1H), 7.17 (d, J=8.2 Hz, 1H), 6.92 (dd, J=8.2, 2.0 Hz, 1H), 4.43 (d, J=4.3 Hz, 1H), 3.28-3.21 (m, 1H), 3.17-3.07 (m, 1H), 2.77 (d, J=6.7 Hz, 2H), 2.61-2.51 (m, 2H), 1.82-1.65 (m, 4H), 1.38-1.21 (m, 7H), 1.06-0.93 (m, 2H), 0.80 (d, J=6.6 Hz, 6H). LCMS (ESI) m/z calcd for $C_{24}H_{33}ClN_4O_3$: 460.22. Found: 461.80/463.76 (M/M+2)$^+$.

Example 58

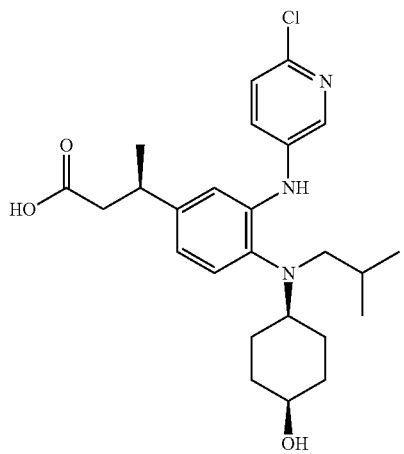

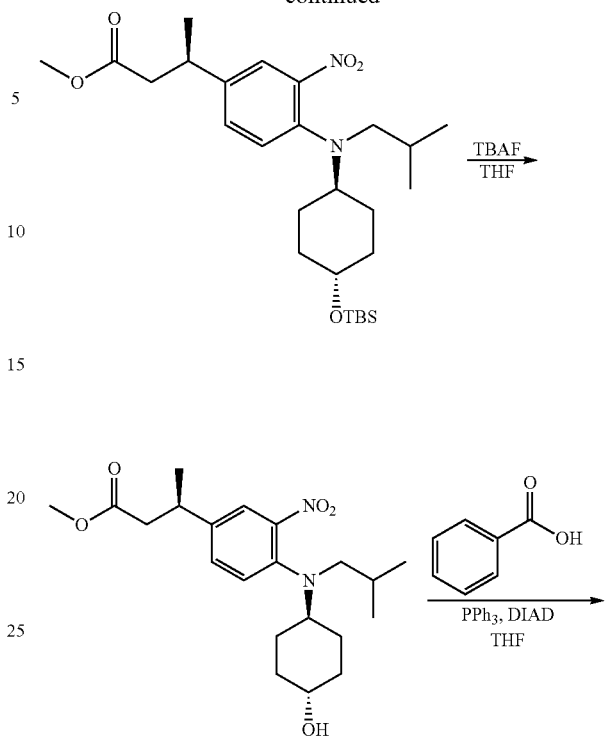

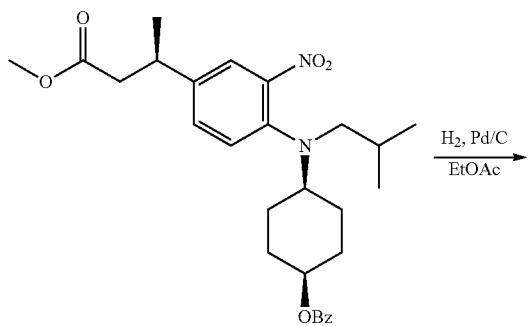

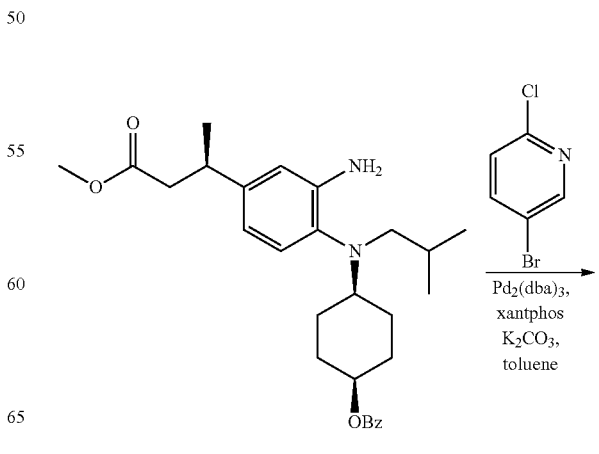

171

-continued

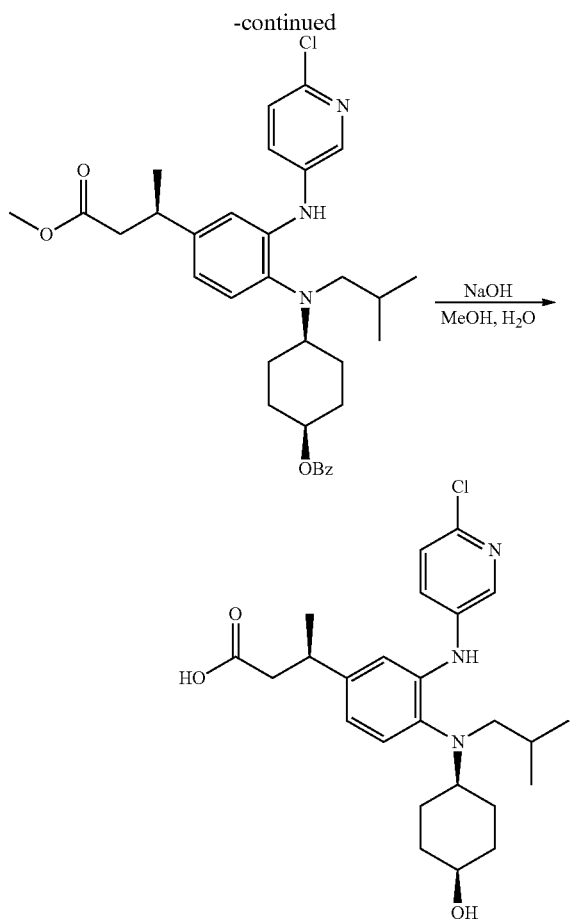

Preparation of methyl (R)-3-(4-(((1r,4R)-4-hydroxy-cyclohexyl) (isobutyl)amino)-3-nitrophenyl)butanoate A mixture of methyl (R)-3-(4-(((1r,4R)-4-((tert-butyldimethylsilyl)oxy)cyclohexyl) (iso butyl)amino)-3-nitrophenyl)butanoate (4.8 g, 9.47 mmol) and TBAF (1M in THF, 30 mL) in THF (40 mL) was stirred at r.t. overnight. The resulting mixture was partitioned between EtOAc and H₂O. The organic layer was washed with brine, dried over Na₂SO₄, filtered and concentrated to give the crude product which was purified by flash chromatography (silica gel, 0-10% EtOAc in PE) to afford the title compound (3.17 g, 85% yield). LCMS (ESI) m/z calcd for $C_{21}H_{32}N_2O_5$: 392.23. Found: 393.60 (M+1)⁺.

172

Preparation of (1S,4s)-4-(isobutyl(4-((R)-4-methoxy-4-oxobutan-2-yl)-2-nitro phenyl)amino) cyclohexyl benzoate

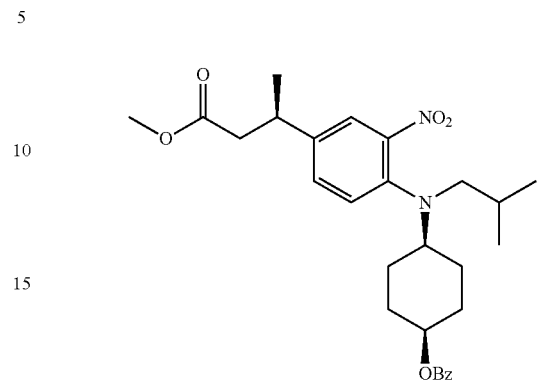

At 0° C., to a solution of methyl (R)-3-(4-(((1r,4R)-4-hydroxycyclohexyl) (isobutyl) amino)-3-nitrophenyl)butanoate (3.17 g, 8.07 mmol), benzoic acid (1.97 g, 16.13 mmol) and PPh₃ (6.34 g, 24.19 mmol) in THF (30 mL) was added DIAD (4.89 g, 24.19 mmol). After stirred at 60° C. overnight, the resulting mixture was partitioned between EtOAc and H₂O. The organic layer was washed with brine, dried over Na₂SO₄, filtered and concentrated to give the crude product which was purified by flash chromatography (silica gel, 0-20% EtOAc in PE) to afford the title compound (2.93 g, 73% yield). LCMS (ESI) m/z calcd for $C_{28}H_{36}N_2O_6$: 496.26. Found: 497.70 (M+1)⁺.

Preparation of (1S,4s)-4-((2-amino-4-((R)-4-methoxy-4-oxobutan-2-yl)phenyl) (isobutyl)amino) cyclohexyl benzoate

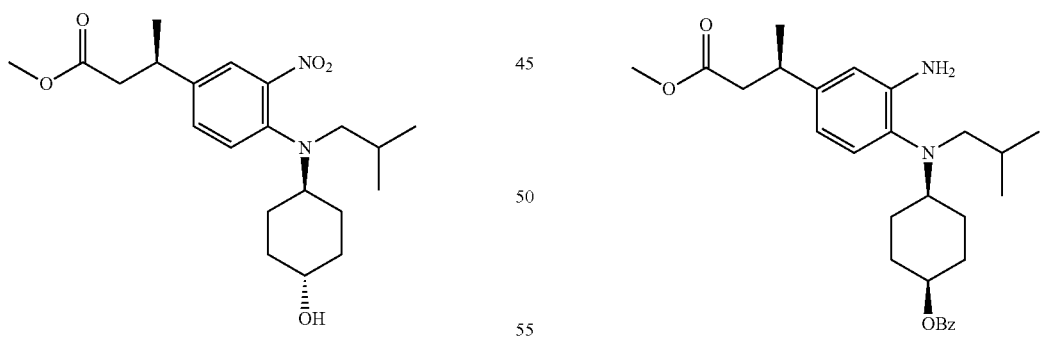

A mixture of (1S,4s)-4-(isobutyl(4-((R)-4-methoxy-4-oxobutan-2-yl)-2-nitrophenyl) amino)cyclohexylbenzoate (2.93 g, 5.91 mmol) and 10% Pd/C (1.5 g) in EtOAc (30 mL) was stirred at 50° C. under H₂ atmosphere for 6 hr. The resulting mixture was filtered through a pad of Celite and the filtrate was concentrated under reduced pressure to give the crude product which was purified by flash chromatography (silica gel, 0-30% EtOAc in PE) to afford the title compound (1.86 g, 67% yield). LCMS (ESI) m/z calcd for $C_{28}H_{38}N_2O_4$: 466.28. Found: 467.84 (M+1)⁺.

Preparation of (1S,4s)-4-((2-(((6-chloropyridin-3-yl)amino)-4-((R)-4-methoxy-4-oxobutan-2-yl)phenyl)(isobutyl)amino)cyclohexyl benzoate

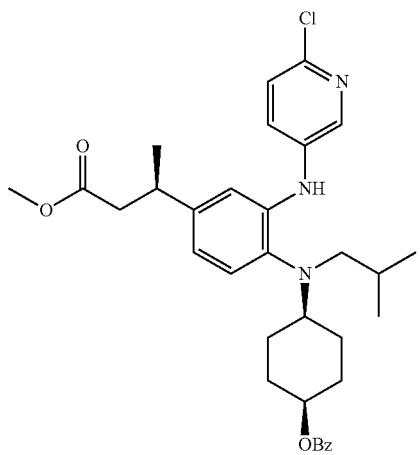

A mixture of (1S,4s)-4-((2-amino-4-((R)-4-methoxy-4-oxobutan-2-yl)phenyl)(isobutyl)amino)cyclohexyl benzoate (150 mg, 0.321 mmol), 5-bromo-2-chloropyridine (123 mg, 0.642 mmol), Pd$_2$(dba)$_3$ (59 mg, 0.064 mmol), Xantphos (74 mg, 0.128 mmol) and K$_2$CO$_3$ (132 mg, 0.963 mmol) in toluene (8 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (140 mg, 75% yield). LCMS (ESI) m/z calcd for C$_{33}$H$_{40}$ClN$_3$O$_4$: 577.27. Found: 578.80/580.79 (M/M+2)$^+$.

Preparation of (R)-3-(3-((6-chloropyridin-3-yl)amino)-4-(((1s,4S)-4-hydroxycyclo hexyl) (isobutyl)amino)phenyl)butanoic Acid

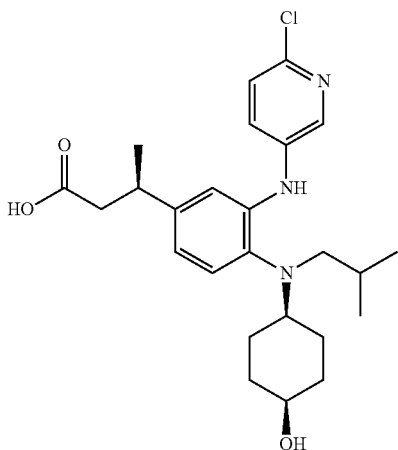 [SMILES: CC(C)CN(c1ccc([C@H](C)CC(=O)O)cc1Nc1ccc(Cl)nc1)[C@H]1CC[C@@H](O)CC1]

To a solution of (1 S,4 s)-4-((2-(((6-chloropyridin-3-yl)amino)-4-((R)-4-methoxy-4-oxo butan-2-yl)phenyl)(isobutyl)amino)cyclohexyl benzoate (140 mg, 0.242 mmol) in MeOH (6 mL) was added 1N NaOH aq. (4 mL). After stirred at r.t. for 48 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (66 mg, 59% yield) as a white powder. $^1$H NMR (400 MHz, DMSO) δ 12.10 (br, 1H), 8.17 (d, J=2.9 Hz, 1H), 7.51 (dd, J=8.7, 3.0 Hz, 1H), 7.29 (d, J=8.7 Hz, 1H), 7.22 (s, 1H), 7.16-7.05 (m, 2H), 6.84 (dd, J=8.2, 1.9 Hz, 1H), 4.22 (br, 1H), 3.70-3.61 (m, 1H), 3.13-3.02 (m, 1H), 2.84-2.69 (m, 2H), 2.49-2.42 (m, 3H), 1.80-1.52 (m, 4H), 1.48-1.30 (m, 3H), 1.27-1.03 (m, 5H), 0.81 (d, J=6.6 Hz, 6H). LCMS (ESI) m/z calcd for C$_{25}$H$_{34}$ClN$_3$O$_3$: 459.23. Found: 460.47/462.45 (M/M+2)$^+$.

Example 59

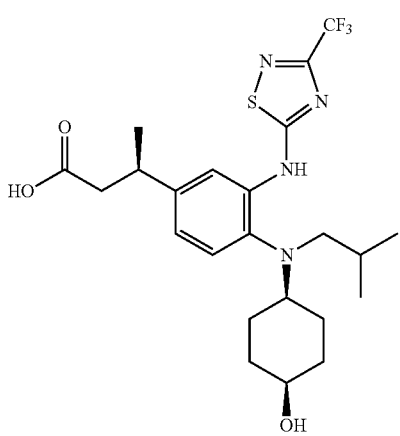

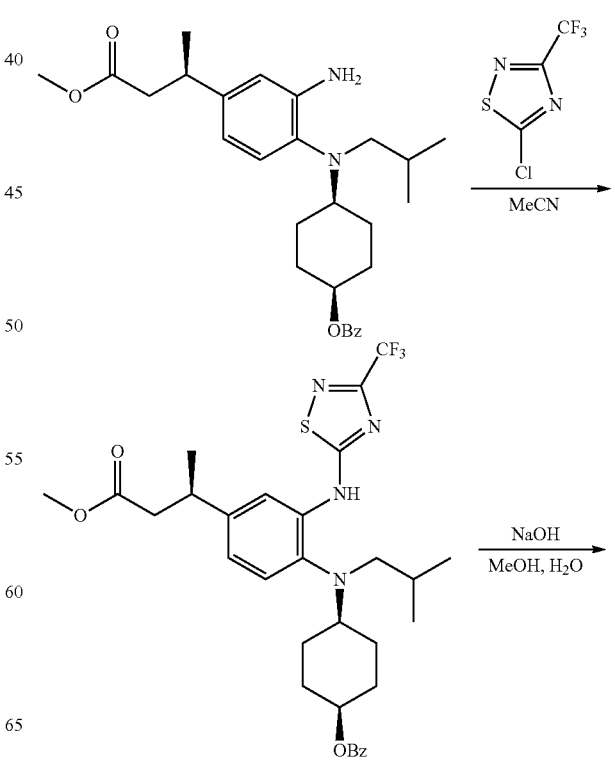

Preparation of (1S,4s)-4-(isobutyl(4-((R)-4-methoxy-4-oxobutan-2-yl)-2-((3-(tri fluoromethyl)-1,2,4-thiadiazol-5-yl)amino)phenyl)amino)cyclohexylbenzoate

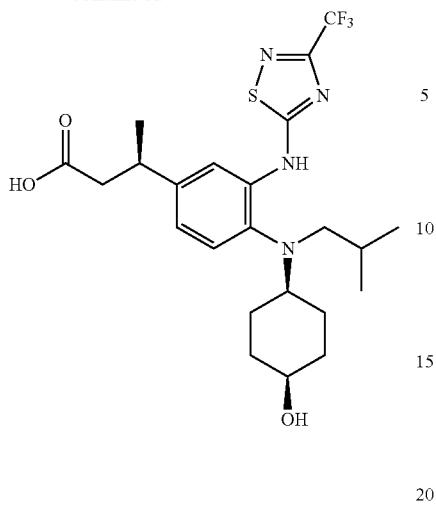

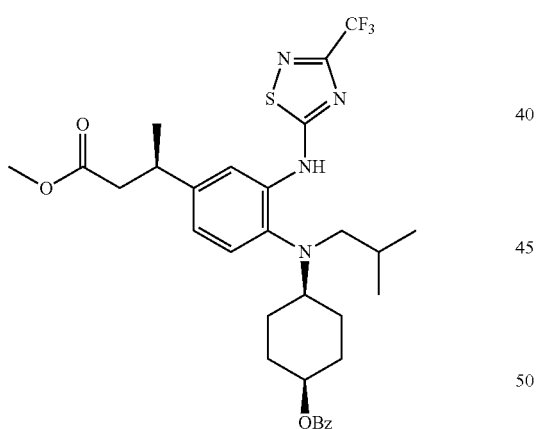

A mixture of (1S,4s)-4-((2-amino-4-((R)-4-methoxy-4-oxobutan-2-yl)phenyl) (isobutyl) amino)cyclohexyl benzoate (200 mg, 0.429 mmol) and 5-chloro-3-(trifluoromethyl)-1,2,4-thiadiazole (161 mg, 0.858 mmol) in MeCN (5 mL) was stirred at 90° C. under N₂ atmosphere overnight. The resulting mixture was partitioned between EtOAc and H₂O. The organic layer was washed with brine, dried over Na₂SO₄, filtered and concentrated to give the crude product which was purified by flash chromatography (silica gel, 0-10% EtOAc in PE) to afford the title compound (140 mg, 52% yield). LCMS (ESI) m/z calcd for $C_{31}H_{37}F_3O_4S$: 618.25. Found: 619.65 (M+1)⁺.

Preparation of (R)-3-(4-(((1s,4S)-4-hydroxycyclohexyl) (isobutyl)amino)-3-((3-(tri fluoromethyl)-1,2,4-thiadiazol-5-yl)amino)phenyl)butanoic Acid

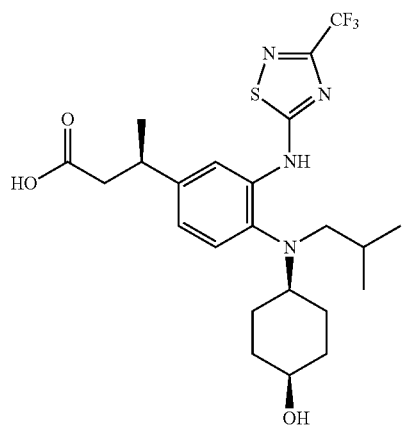 [SMILES: CC(C)CN(c1ccc([C@H](C)CC(=O)O)cc1Nc1nc(C(F)(F)F)ns1)[C@H]1CC[C@@H](O)CC1]

To a solution of (1S,4S)-4-(isobutyl(4-((R)-4-methoxy-4-oxobutan-2-yl)-2-((3-(tri fluoromethyl)-1,2,4-thiadiazol-5-yl)amino)phenyl)amino)cyclohexylbenzoate (140 mg, 0.226 mmol) in MeOH (6 mL) was added 1N NaOH aq. (4 mL). After stirred at r.t. for 48 hr, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (74 mg, 65% yield) as a white powder. ¹H NMR (400 MHz, DMSO) δ 12.10 (br, 1H), 10.24 (s, 1H), 7.83 (s, 1H), 7.18 (d, J=8.3 Hz, 1H), 7.04 (dd, J=8.2, 2.0 Hz, 1H), 4.28-4.16 (m, 1H), 3.68 (br, 1H), 3.16-3.07 (m, 1H), 2.79 (d, J=6.6 Hz, 2H), 2.68-2.58 (m, 1H), 2.49-2.41 (m, 2H), 1.78-1.42 (m, 6H), 1.41-1.32 (m, 1H), 1.28-1.10 (m, 5H), 0.79 (d, J=6.6 Hz, 6H) LCMS (ESI) m/z calcd for $C_{23}H_{31}F_3N_4O_3S$: 500.21. Found: 501.51 (M+1)⁺.

Example 60

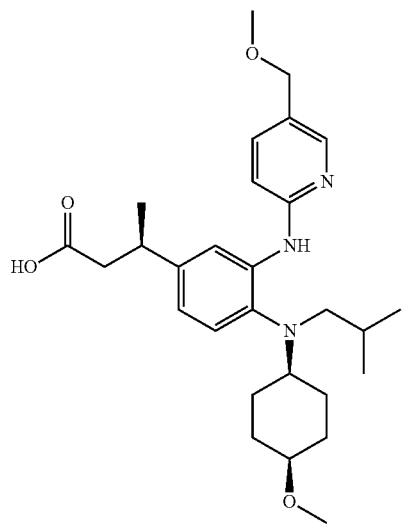 [SMILES: COCc1ccc(Nc2cc([C@H](C)CC(=O)O)ccc2N(CC(C)C)[C@H]2CC[C@@H](OC)CC2)nc1]

177
-continued

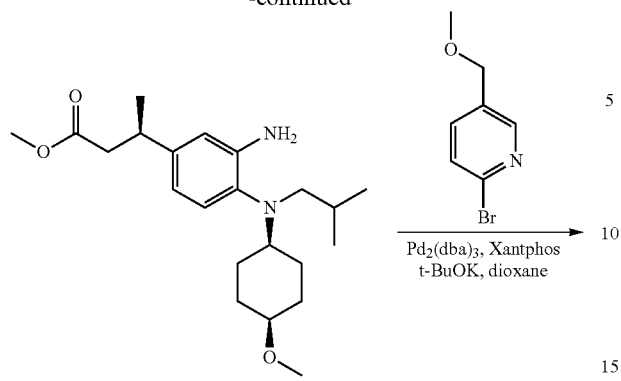

178
Preparation of methyl (R)-3-(4-(isobutyl((1s,4S)-4-methoxycyclohexyl)amino)-3-((5-(methoxymethyl)pyridin-2-yl)amino)phenyl)butanoate

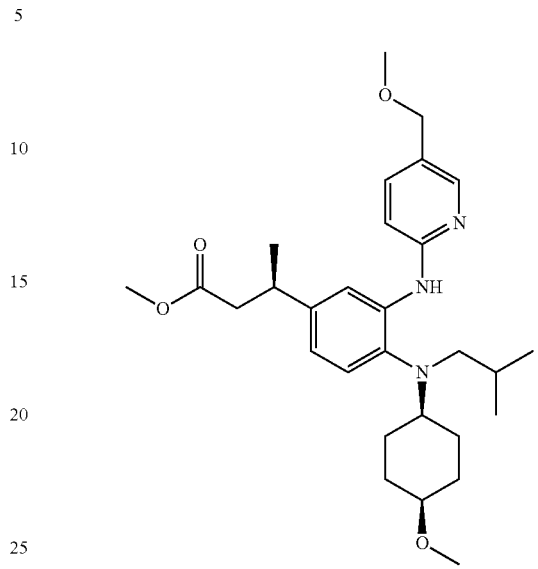

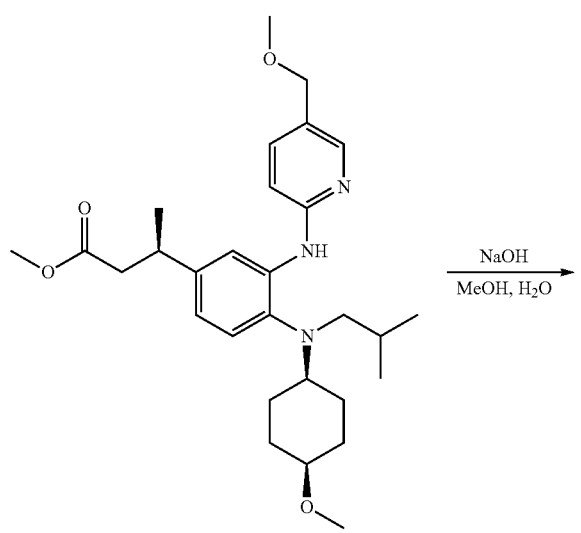

A mixture of methyl (R)-3-(3-amino-4-(isobutyl((1s,4S)-4-methoxycyclohexyl)amino) phenyl)butanoate (100 mg, 0.27 mmol), 2-bromo-5-(methoxymethyl)pyridine (108 mg, 0.54 mmol), Pd$_2$(dba)$_3$ (24 mg, 0.027 mmol), Xantphos (31.2 mg, 0.054 mmol) and t-BuOK (60 mg, 0.54 mmol) in dioxane (2 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (40 mg, 30% yield). LCMS (ESI) m/z calcd for C$_{29}$H$_{43}$N$_3$O$_4$: 497.33. Found: 498.35 (M+1)$^+$.

Preparation of (R)-3-(4-(isobutyl((1s,4S)-4-methoxycyclohexyl)amino)-3-((5-(methoxymethyl)pyridin-2-yl)amino)phenyl)butanoic Acid

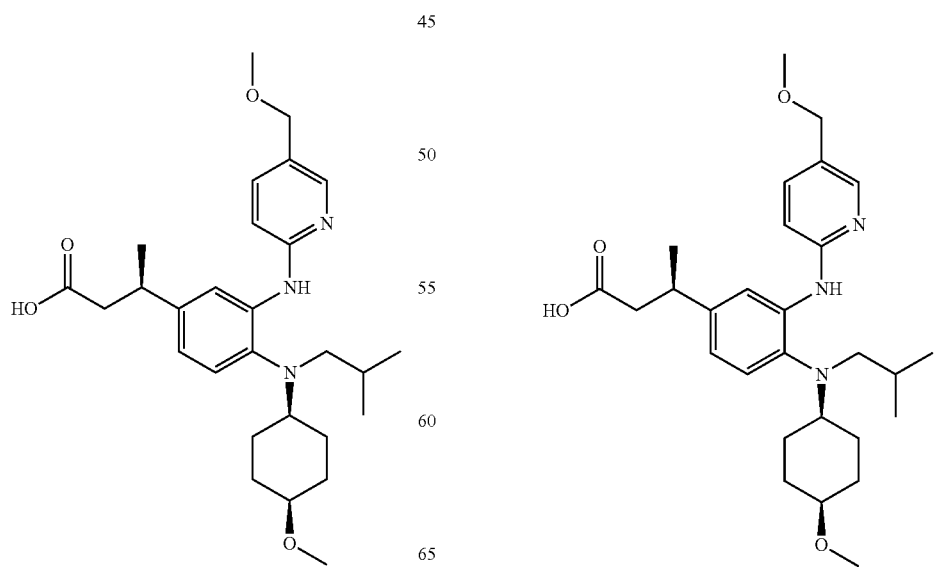

To a solution of methyl (R)-3-(4-(isobutyl((1s,4S)-4-methoxycyclohexyl)amino)-3-((5-(methoxymethyl)pyridin-2-yl)amino)phenyl)butanoate (40 mg, 0.08 mmol) in MeOH (3 mL) was added 4N NaOH aq. (0.5 mL). After stirred at rt for 6 hr, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (17 mg, 44% yield) as a white powder. $^1$H NMR (400 MHz, CDCl₃) δ 8.19 (d, J=1.8 Hz, 1H), 8.04 (s, 1H), 7.90 (s, 1H), 7.52 (dd, J=8.5, 2.3 Hz, 1H), 7.08 (d, J=8.1 Hz, 1H), 6.82-6.72 (m, 2H), 4.36 (s, 2H), 3.36 (s, 3H), 3.33-3.23 (m, 5H), 2.81 (d, J=6.4 Hz, 2H), 2.74-2.57 (m, 3H), 1.98-1.89 (m, 2H), 1.77-1.57 (m, 4H), 1.40-1.22 (m, 6H), 0.84 (d, J=6.6 Hz, 6H). LCMS (ESI) m/z calcd for $C_{28}H_{41}N_3O_4$: 483.31. Found: 484.42 (M+1)⁺.

Example 61

(R)-3-(3-((5-chloro-1H-1,2,4-triazol-3-yl)amino)-4-(isobutyl((cis)-4-methoxycyclohexyl)amino)phenyl)butanoic Acid

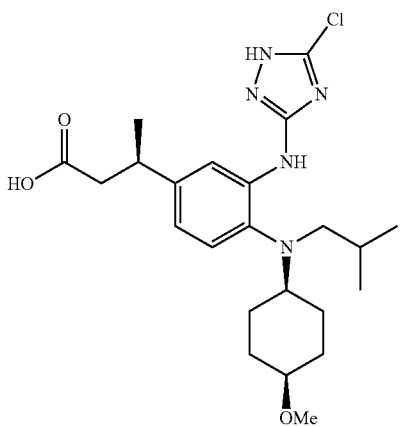

A mixture of (R)-methyl 3-(3-amino-4-(isobutyl((cis)-4-methoxycyclohexyl)amino)phenyl)butanoate (0.105 mg, 0.279 μmol), 3-bromo-5-chloro-1-((2-(trimethylsilyl)ethoxy)methyl)-1H-1,2,4-triazole (0.0873 mg, 0.279 μmol), Pd₂dba₃ (0.051 mg, 0.056 μmol), Xantphos (0.065 mg, 0.112 μmol), and cesium carbonate (0.455 mg, 1.396 μmol) was flushed with nitrogen and then stirred in toluene (4.0 ml) and heated at 100° C. for 7 h. The reaction mixture was filtered through celite, evaporated, and purified by silica gel chromatography (0-40% EtOAc/hexanes). The product was stirred in TFA (1 mL) and CH₂Cl₂ (1 mL) for 2 h and then evaporated. The residue was subjected to base hydrolysis as previously described and purified by reverse phase chromatography (10-100% CH₃CN/H₂O (0.1% formic acid)) to afford the title compound (0.0606 g, 47%) as a white solid. LCMS (M+H)⁺: m/z=464.5, 466.3. $^1$H NMR (400 MHz, CD₃OD) δ ppm 7.81 (d, J=1.4 Hz, 1H), 7.16 (d, J=8.0 Hz, 1H), 6.86 (d, J=6.8 Hz, 1H), 3.15-3.36 (m, 5H), 2.81 (m, 2H), 2.46-2.67 (m, 3H), 1.93 (d, J=14.8 Hz, 2H), 1.61 (br. s., 4H), 1.23-1.40 (m, 6H), 0.82 (d, J=6.6 Hz, 6H).

Example 62

(R)-3-(4-(isobutyl((cis)-4-methoxycyclohexyl)amino)-3-((4-(trifluoromethyl)-1H-imidazol-2-yl)amino)phenyl)butanoic Acid

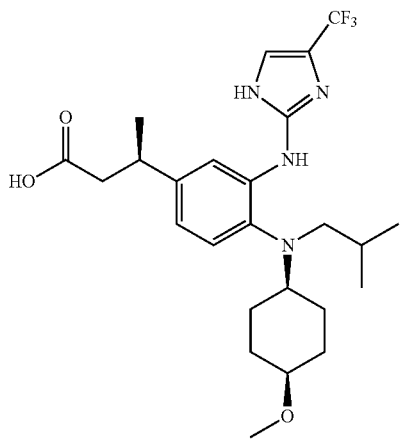

(R)-methyl 3-(4-(isobutyl((cis)-4-methoxycyclohexyl)amino)-3-((4-(trifluoromethyl)-1-((2-(trimethylsilyl)ethoxy)methyl)-1H-imidazol-2-yl)amino)phenyl)butanoate (68.8 mg, 0.107 mmol) was subjected to base hydrolysis as previously described. The acid was then stirred in neat TFA (1 mL) at RT for 2 h, evaporated to dryness, neutralized with Et₃N (1 mL), evaporated and partitioned between 1M citric acid and EtOAc. The organic phase was dried (Na₂SO₄), filtered, evaporated and purified by reverse phase chromatography (10-100% CH₃CN/H₂O (0.1% formic acid)) to afford the title compound (0.0533 g, 84%) as a white solid. LCMS (M+H)⁺: m/z=497.4. $^1$H NMR (400 MHz, CD₃OD) δ ppm 7.65 (d, J=1.8 Hz, 1H), 7.19 (d, J=1.4 Hz, 1H), 7.12 (d, J=8.0 Hz, 1H), 6.79 (dd, J=8.1, 1.9 Hz, 1H), 3.31-3.36 (m, 1H), 3.25 (s, 3H), 3.11-3.22 (m, 1H), 2.81 (br. s., 2H), 2.44-2.67 (m, 3H), 1.93 (d, J=14.6 Hz, 2H), 1.56-1.71 (m, 4H), 1.34-1.46 (m, 1H), 1.22-1.34 (m, 5H), 0.83 (d, J=6.4 Hz, 6H).

Example 63

Step A 3-bromo-5-cyclopropyl-1-((2-(trimethylsilyl)ethoxy)methyl)-1H-1,2,4-triazole and regioisomer

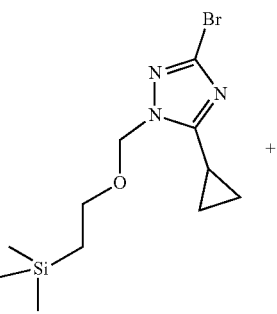

181

-continued

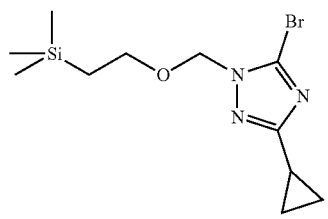

3-bromo-5-cyclopropyl-1H-1,2,4-triazole (0.700 g, 3.72 mmol) was converted to 3-bromo-5-cyclopropyl-1-((2-(trimethylsilyl)ethoxy)methyl)-1H-1,2,4-triazole and its regioisomer (632.9 mg, 53%) following a previously described procedure. $^1$H NMR (400 MHz, CDCl$_3$) δ ppm 5.36-5.52 (m, 2H), 3.66 (m, 2H), 1.96-2.07 (m, 1H), 1.11-1.22 (m, 2H), 0.89-1.01 (m, 2H), 0.76-0.88 (m, 2H), 0.00 (s, 9H).

Step B (R)-methyl 3-(3-((3-cyclopropyl-1-((2-(trimethylsilyl)ethoxy)methyl)-1H-1,2,4-triazol-5-yl)amino)-4-(isobutyl((cis)-4-methoxycyclohexyl)amino)phenyl)butanoate

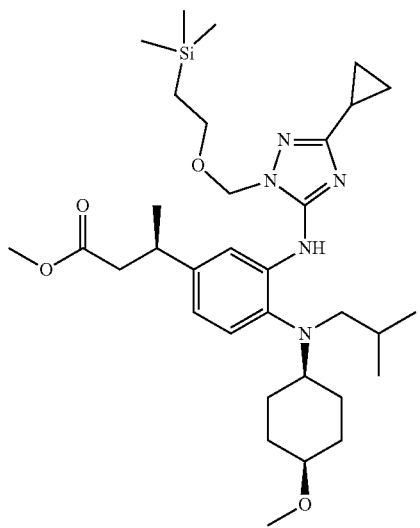 [SMILES: COC(=O)C[C@@H](C)c1ccc(N(CC(C)C)[C@H]2CC[C@@H](OC)CC2)c(Nc2nc(C3CC3)nn2COCC[Si](C)(C)C)c1]

A mixture of (R)-methyl 3-(3-amino-4-(isobutyl((cis)-4-methoxycyclohexyl)amino)phenyl)butanoate (0.128 g, 0.340 mmol), 5-bromo-3-cyclopropyl-1-((2-(trimethylsilyl)ethoxy)methyl)-1H-1,2,4-triazole (0.119 g, 0.374 mmol), Pd$_2$dba$_3$ (0.062 g, 0.068 mmol), Xantphos (0.079 g, 0.136 mmol), and cesium carbonate (0.554 g, 1.700 mmol) was flushed with nitrogen and then stirred in toluene (4.8 mL) and heated at 100° C. for 10 h. The reaction mixture was filtered through celite, evaporated, and purified by silica gel chromatography (0-40% EtOAc/hexanes) to afford (R)-methyl 3-(3-((3-cyclopropyl-1-((2-(trimethylsilyl)ethoxy)methyl)-1H-1,2,4-triazol-5-yl)amino)-4-(isobutyl((cis)-4-methoxycyclohexyl)amino)phenyl)butanoate (155.5 mg, 75% yield). LCMS (M+H)$^+$: m/z=614.7.

182

Step C (R)-3-(3-((5-cyclopropyl-1H-1,2,4-triazol-3-yl)amino)-4-(isobutyl((cis)-4-methoxycyclohexyl)amino)phenyl)butanoic Acid

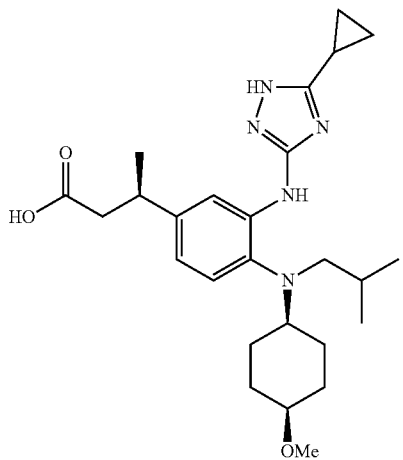 [SMILES: CO[C@H]1CC[C@@H](N(CC(C)C)c2ccc([C@H](C)CC(=O)O)cc2Nc2n[nH]c(C3CC3)n2)CC1]

(R)-methyl 3-(3-((5-cyclopropyl-1-((2-(trimethylsilyl)ethoxy)methyl)-1H-1,2,4-triazol-3-yl)amino)-4-(isobutyl((cis)-4-methoxycyclohexyl)amino)phenyl)butanoate (0.1856 g, 0.302 mmol) was treated with TFA and then subjected to base hydrolysis as previously described and purified by reverse phase chromatography (10-100% CH$_3$CN/H$_2$O (0.1% formic acid)) to afford the title compound (0.0707 g, 50%) as a white solid. LCMS (M+H)$^+$: m/z=470.5. $^1$H NMR (400 MHz, CD$_3$OD) δ ppm 7.91 (d, J=1.8 Hz, 1H), 7.09 (d, J=8.2 Hz, 1H), 6.73 (dd, J=8.0, 1.8 Hz, 1H), 3.30-3.36 (m, 1H), 3.24 (s, 3H), 3.10-3.2 (m, 1H), 2.68-2.94 (m, 2H), 2.44-2.64 (m, 3H), 1.89-2.02 (m, 3H), 1.56-1.72 (m, 4H), 1.20-1.42 (m, 6H), 0.93-1.08 (m, 4H), 0.82 (d, J=6.4 Hz, 6H).

Example 64

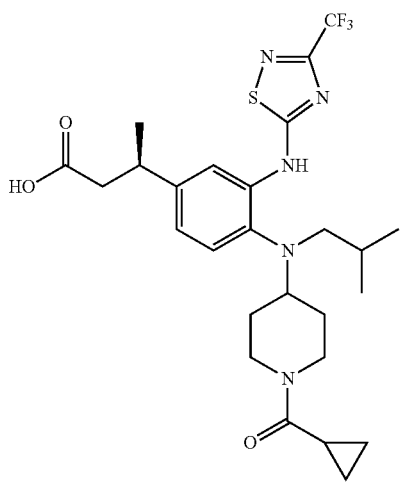 [SMILES: CC(C)CN(c1ccc([C@H](C)CC(=O)O)cc1Nc1nc(C(F)(F)F)ns1)C1CCN(C(=O)C2CC2)CC1]

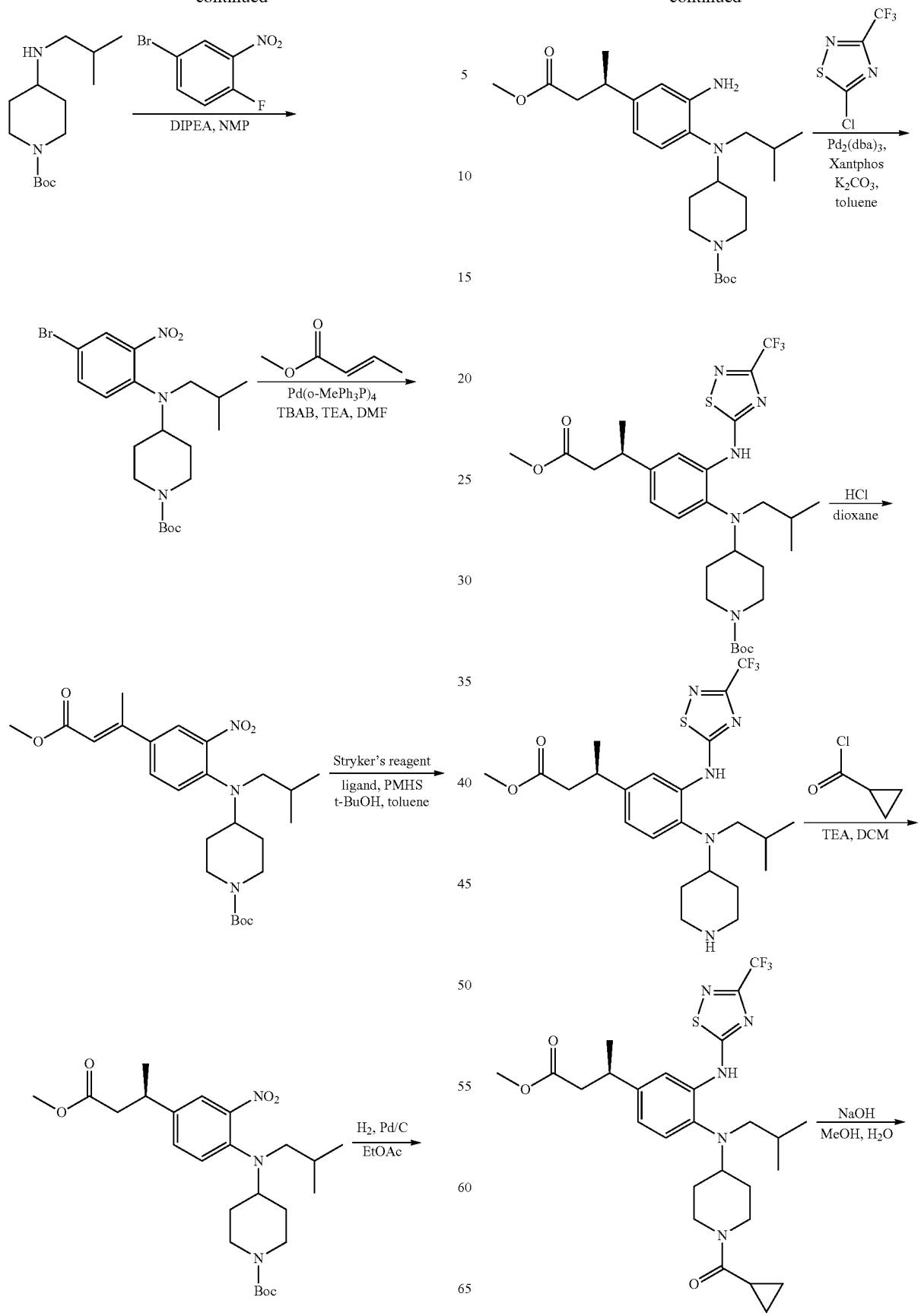

185
-continued

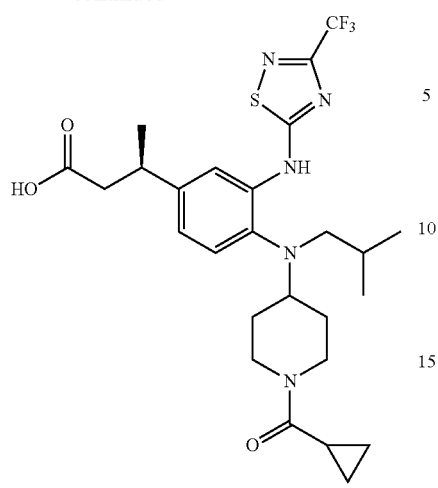

Preparation of tert-butyl 4-((4-bromo-2-nitrophenyl)(isobutyl)amino)piperidine-1-carboxylate

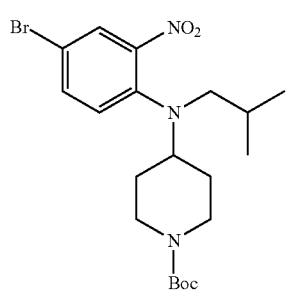

A mixture of 4-bromo-1-fluoro-2-nitrobenzene (5.4 g, 24.5 mmol), tert-butyl 4-(isobutylamino)piperidine-1-carboxylate (12.58 g, 49.0 mmol) and DIPEA (9.69 g, 74.9 mmol) in NMP (60 mL) was stirred at 140° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-10% EtOAc in PE) to afford the title compound (4.14 g, 37% yield). LCMS (ESI) m/z calcd for $C_{20}H_{30}BrN_3O_4$: 455.14. Found: 456.32/458.40 (M/M+2)$^+$.

186
Preparation of tert-butyl (E)-4-(isobutyl(4-(4-methoxy-4-oxobut-2-en-2-yl)-2-nitro phenyl)amino)piperidine-1-carboxylate

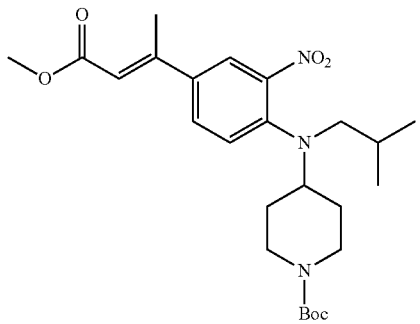 [SMILES: COC(=O)/C=C(\C)c1ccc(N(CC(C)C)C2CCN(C(=O)OC(C)(C)C)CC2)c([N+](=O)[O-])c1]

A mixture of tert-butyl 4-((4-bromo-2-nitrophenyl)(isobutyl)amino)piperidine-1-carboxylate (2 g, 4.39 mmol), methyl (E)-but-2-enoate (1.3 g, 13.2 mmol), TBAB (0.3 g, 0.93 mmol), Pd(o-MePh$_3$P)$_4$ (173 mg, 0.22 mmol) and TEA (0.9 g, 8.9 mmol) in DMF (20 mL) was stirred at 110° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-10% EtOAc in PE) to afford the title compound (680 mg, 33% yield). LCMS (ESI) m/z calcd for $C_{25}H_{37}N_3O_6$: 475.27. Found: 476.40 (M+1)$^+$.

Preparation of tert-butyl (R)-4-(isobutyl(4-(4-methoxy-4-oxobutan-2-yl)-2-nitro phenyl)amino)piperidine-1-carboxylate

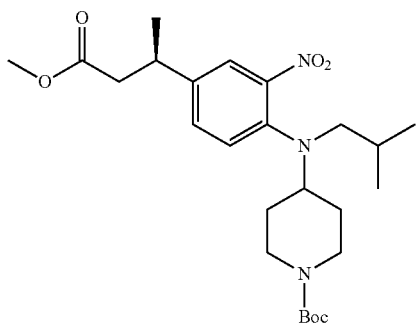 [SMILES: COC(=O)C[C@@H](C)c1ccc(N(CC(C)C)C2CCN(C(=O)OC(C)(C)C)CC2)c([N+](=O)[O-])c1]

At −5° C., to a mixture of (CuHPh$_3$P)$_6$ (85 mg, 0.043 mmol) and (R,S)—PPF—P(tBu)$_2$ (88 mg, 0.16 mmol) in toluene (14 mL) was added PMHS (0.4 mL) and t-BuOH (0.33 mL) before the introduction of methyl (E)-3-(4-(isobutyl(tetrahydro-2H-pyran-4-yl)amino)-3-nitrophenyl)but-2-enoate (1.4 g, 2.94 mmol). After stirred at 0° C. for 4 hr, the resulting mixture was quenched with sat. NaHCO$_3$ aq. solution and extracted with EtOAc. The organic layer was washed with brine, dried over Na$_2$SO$_4$, filtered and concentrated to give the crude product which was purified by flash chromatography (silica gel, 0-10% EtOAc in PE) to afford the title compound (660 mg, 47% yield) as a red oil. LCMS (ESI) m/z calcd for $C_{25}H_{39}N_3O_6$: 477.28. Found: 478.77 (M+1)$^+$.

Preparation of tert-butyl (R)-4-((2-amino-4-(4-methoxy-4-oxobutan-2-yl)phenyl) (isobutyl)amino)piperidine-1-carboxylate

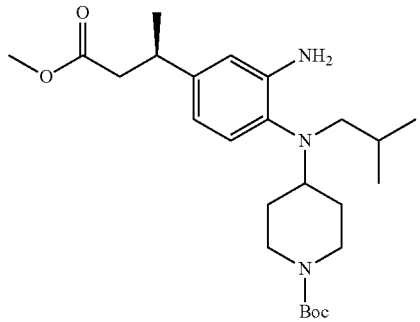 [SMILES: COC(=O)C[C@@H](C)c1ccc(N(CC(C)C)C2CCN(C(=O)OC(C)(C)C)CC2)c(N)c1]

A mixture of tert-butyl (R)-4-(isobutyl(4-(4-methoxy-4-oxobutan-2-yl)-2-nitrophenyl) amino)piperidine-1-carboxylate (200 mg, 0.42 mmol) and 10% Pd/C (100 mg) in EtOAc (5 mL) was stirred at r.t. under $H_2$ atmosphere for 6 hr. The resulting mixture was filtered through a pad of Celite and the filtrate was concentrated under reduced pressure to give the crude product which was purified by flash chromatography (silica gel, 0-20% EtOAc in PE) to afford the title compound (180 mg, 96% yield). LCMS (ESI) m/z calcd for $C_{25}H_{41}N_3O_4$: 447.31. Found: 448.94 (M+1)$^+$.

Preparation of tert-butyl (R)-4-(isobutyl(4-(4-methoxy-4-oxobutan-2-yl)-2-((3-(tri fluoromethyl)-1,2,4-thiadiazol-5-yl)amino)phenyl)amino)piperidine-1-carboxylate

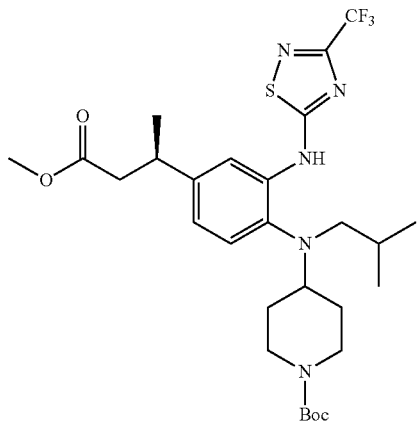 [SMILES: COC(=O)C[C@@H](C)c1ccc(N(CC(C)C)C2CCN(C(=O)OC(C)(C)C)CC2)c(Nc2nc(C(F)(F)F)ns2)c1]

A mixture of tert-butyl (R)-4-((2-amino-4-(4-methoxy-4-oxobutan-2-yl)phenyl) (isobutyl) amino)piperidine-1-carboxylate (100 mg, 0.22 mmol), 5-chloro-3-(trifluoromethyl)-1,2,4-thiadiazole (50 mg, 0.27 mmol), $Pd_2(dba)_3$ (20 mg, 0.022 mmol), Xantphos (25.5 mg, 0.044 mmol) and $K_2CO_3$ (61 mg, 0.44 mmol) in toluene (2 mL) was stirred at 100° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (82 mg, 61% yield). LCMS (ESI) m/z calcd for $C_{28}H_{40}F_3N_5O_4S$: 599.28. Found: 600.40 (M+1)$^+$.

Preparation of methyl (R)-3-(4-(isobutyl(piperidin-4-yl)amino)-3-((3-(trifluoro methyl)-1,2,4-thiadiazol-5-yl)amino)phenyl)butanoate

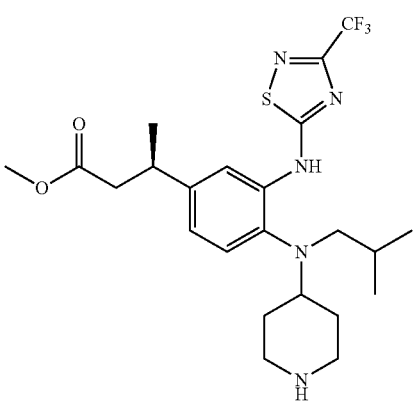 [SMILES: COC(=O)C[C@@H](C)c1ccc(N(CC(C)C)C2CCNCC2)c(Nc2nc(C(F)(F)F)ns2)c1]

A mixture of tert-butyl (R)-4-((2-amino-4-(4-methoxy-4-oxobutan-2-yl)phenyl) (isobutyl) amino)piperidine-1-carboxylate (570 mg, 0.95 mmol) in 4N HCl in dioxane (10 mL) was stirred at r.t. for 30 min. The resulting mixture was concentrated and the residue was quenched with sat. $NaHCO_3$ aq. solution and extracted with EtOAc. The organic layer was washed with brine, dried over $Na_2SO_4$, filtered and concentrated to afford the title compound (542 mg, quant. yield, as 2HCl salt). LCMS (ESI) m/z calcd for $C_{23}H_{32}F_3N_5O_2S$: 499.22. Found: 500.56 (M+1)$^+$.

Preparation of methyl (R)-3-(4-((1-(cyclopropanecarbonyl)piperidin-4-yl) (iso butyl)amino)-3-((3-(trifluoromethyl)-1,2,4-thiadiazol-5-yl)amino)phenyl)butanoate

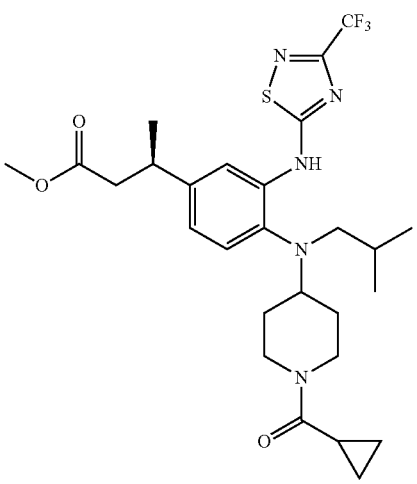 [SMILES: COC(=O)C[C@@H](C)c1ccc(N(CC(C)C)C2CCN(C(=O)C3CC3)CC2)c(Nc2nc(C(F)(F)F)ns2)c1]

To a solution of methyl (R)-3-(4-(isobutyl(piperidin-4-yl)amino)-3-((3-(trifluoromethyl)-1,2,4-thiadiazol-5-yl)amino)phenyl)butanoate (100 mg, 0.20 mmol) in DCM (2 mL) was added TEA (60.6 mg, 0.60 mmol) and cyclopropanecarbonyl chloride (25 mg, 0.24 mmol). After stirred at r.t. for 2 hr, the resulting mixture was partitioned between DCM and H₂O. The organic layer was washed with brine, dried over Na₂SO₄, filtered and concentrated to give the crude product which was purified by flash chromatography (silica gel, 0-30% EtOAc in PE) to afford the title compound (100 mg, 88% yield). LCMS (ESI) m/z calcd for C₂₇H₃₆F₃N₅O₃S: 567.25. Found: 568.30 (M+1)⁺.

Preparation of (R)-3-(4-((1-(cyclopropanecarbonyl)piperidin-4-yl) (isobutyl) amino)-3-((3-(trifluoromethyl)-1,2,4-thiadiazol-5-yl)amino)phenyl)butanoic Acid

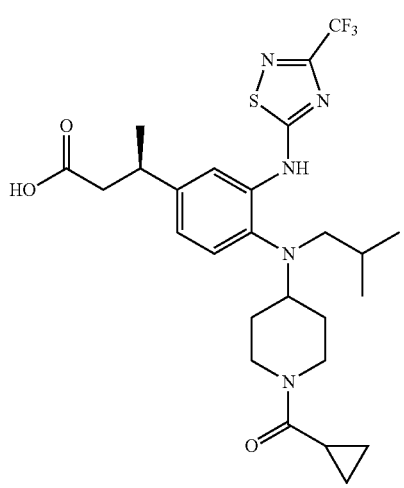 [SMILES: CC(C)CN(c1ccc([C@H](C)CC(=O)O)cc1Nc1nc(C(F)(F)F)ns1)C1CCN(C(=O)C2CC2)CC1]

To a solution of methyl (R)-3-(4-((1-(cyclopropanecarbonyhpiperidin-4-yl) (iso butyl)amino)-3-((3-(trifluoromethyl)-1,2,4-thiadiazol-5-yl)amino)phenyl)butanoate (100 mg, 0.176 mmol) in MeOH (3 mL) was added 1N NaOH aq. (1 mL). After stirred at r.t. overnight, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (54 mg, 55% yield) as a white powder. ¹H NMR (400 MHz, CDCl₃) δ 9.40 (s, 1H), 7.29 (d, J=1.7 Hz, 1H), 7.21 (d, J=8.2 Hz, 1H), 7.00 (dd, J=8.2, 1.8 Hz, 1H), 4.64 (d, J=10.7 Hz, 1H), 4.23 (d, J=11.5 Hz, 1H), 3.40-3.29 (m, 1H), 3.02-2.43 (m, 8H), 1.98-1.82 (m, 2H), 1.51-1.32 (m, 6H), 0.96-0.68 (m, 10H). LCMS (ESI) m/z calcd for C₂₆H₃₄F₃N₅O₃S: 553.23. Found: 554.32 (M+1)⁺.

Example 65

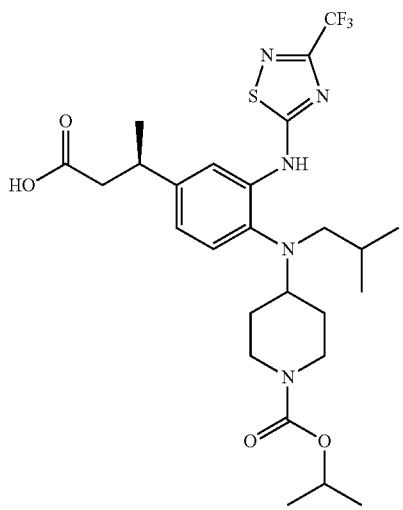

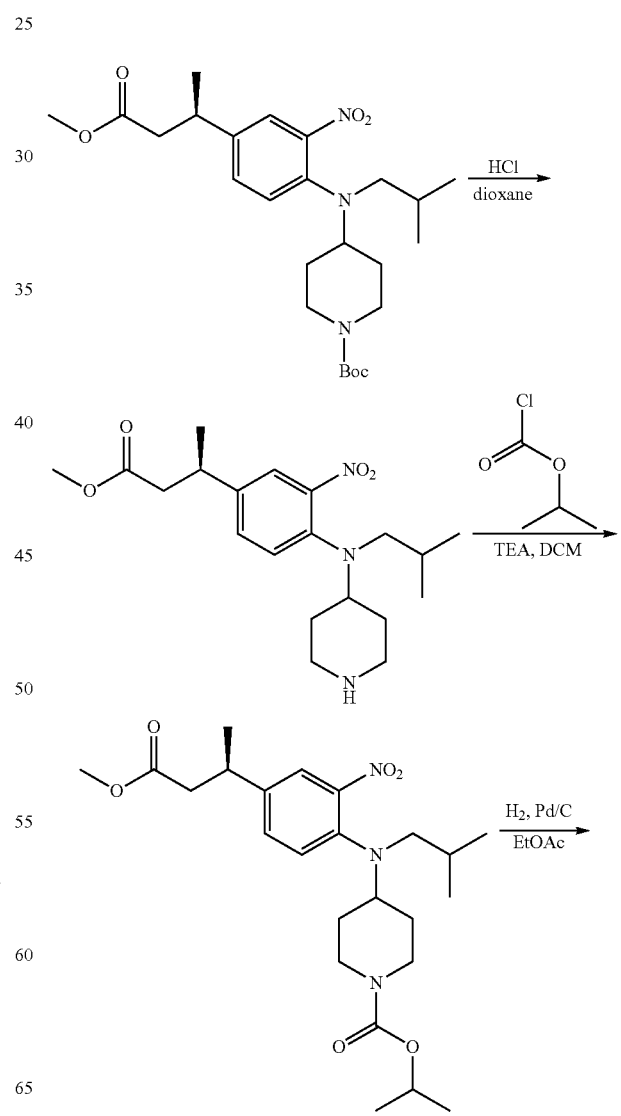

191
-continued

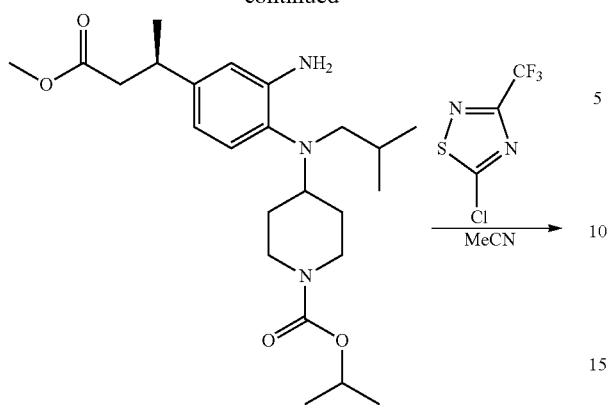

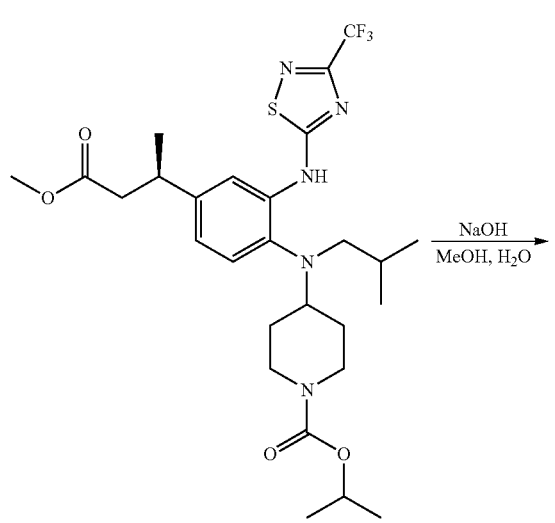

192
Preparation of methyl (R)-3-(4-(isobutyl(piperidin-4-yl)amino)-3-nitrophenyl) butanoate

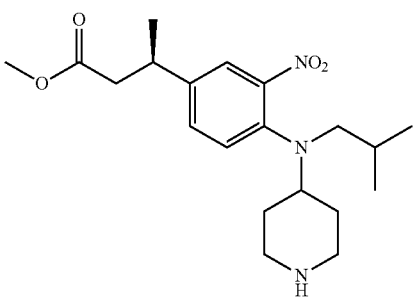 [SMILES: COC(=O)C[C@@H](C)c1ccc(N(CC(C)C)C2CCNCC2)c([N+](=O)[O-])c1]

A mixture of tert-butyl (R)-4-(isobutyl(4-(4-methoxy-4-oxobutan-2-yl)-2-nitrophenyl) amino)piperidine-1-carboxylate (1.2 g, 2.52 mmol) in 4N HCl in dioxane (20 mL) was stirred at r.t. for 2 hr. The reaction mixture was concentrated under reduced pressure to give the title compound (1 g, 96% yield, as HCl salt) which was used in he next step without further purification. LCMS (ESI) m/z calcd for $C_{20}H_{31}N_3O_4$: 377.23. Found: 378.38 $(M+1)^+$.

Preparation of isopropyl (R)-4-(isobutyl(4-(4-methoxy-4-oxobutan-2-yl)-2-nitro phenyl)amino) piperidine-1-carboxylate

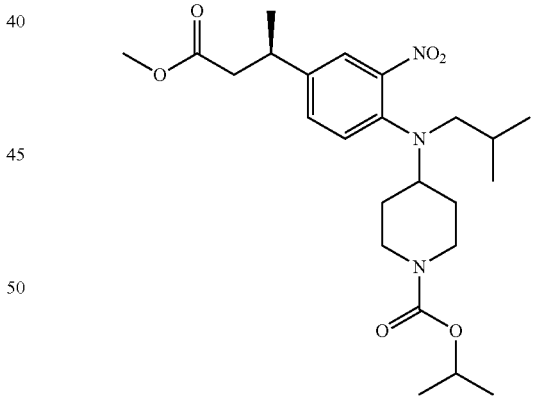

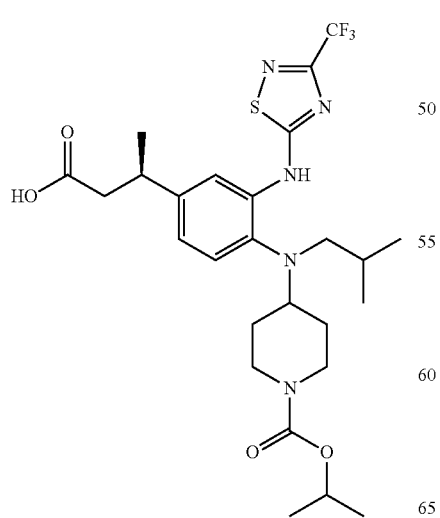

To a solution of methyl (R)-3-(4-(isobutyl(piperidin-4-yl) amino)-3-nitrophenyl) butanoate (300 mg, 0.796 mmol) in DCM (10 mL) was added TEA (0.33 mL, 2.39 mmol) and isopropyl carbonochloridate (0.16 mL, 1.19 mmol). After stirred at rt. for 3 hr, the resulting mixture was partitioned between DCM and $H_2O$. The organic layer was washed with brine, dried over $Na_2SO_4$, filtered and concentrated to give the crude product which was purified by flash chromatography (silica gel, 0-30% EtOAc in PE) to afford the title compound (300 mg, 81% yield). LCMS (ESI) m/z calcd for $C_{24}H_{37}N_3O_6$: 463.27. Found: 464.63 $(M+1)^+$.

Preparation of isopropyl (R)-4-((2-amino-4-(4-methoxy-4-oxobutan-2-yl)phenyl) (isobutyl)amino) piperidine-1-carboxylate

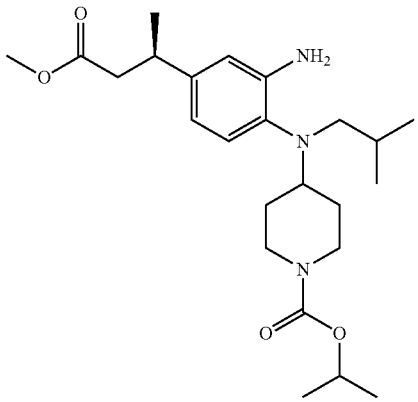 [SMILES: COC(=O)C[C@@H](C)c1ccc(N(CC(C)C)C2CCN(C(=O)OC(C)C)CC2)c(N)c1]

A mixture of isopropyl (R)-4-(isobutyl(4-(4-methoxy-4-oxobutan-2-yl)-2-nitrophenyl) amino)piperidine-1-carboxylate (300 mg, 0.65 mmol) and 10% Pd/C (150 mg) in EtOAc (20 mL) was stirred at 50° C. under $H_2$ atmosphere for 3 hr. The resulting mixture was filtered through a pad of Celite and the filtrate was concentrated under reduced pressure to give the crude product which was purified by flash chromatography (silica gel, 0-30% EtOAc in PE) to afford the title compound (220 mg, 78% yield) as a yellow oil. LCMS (ESI) m/z calcd for $C_{24}H_{39}N_3O_4$: 433.29. Found: 434.79 $(M+1)^+$.

Preparation of isopropyl (R)-4-(isobutyl(4-(4-methoxy-4-oxobutan-2-yl)-2-((3-(tri fluoromethyl)-1,2,4-thiadiazol-5-yl)amino)phenyl)amino)piperidine-1-carboxylate

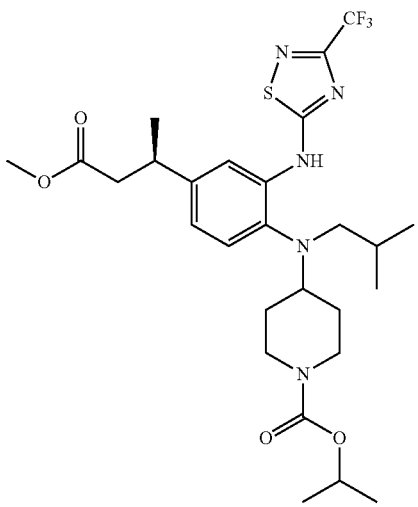 [SMILES: COC(=O)C[C@@H](C)c1ccc(N(CC(C)C)C2CCN(C(=O)OC(C)C)CC2)c(Nc2nc(C(F)(F)F)ns2)c1]

A mixture of isopropyl (R)-4-((2-amino-4-(4-methoxy-4-oxobutan-2-yl)phenyl) (isobutyl) amino)piperidine-1-carboxylate (100 mg, 0.231 mmol) and 5-chloro-3-(trifluoro methyl)-1,2,4-thiadiazole (87 mg, 0.462 mmol) in MeCN (4 mL) was stirred at 90° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (81 mg, 59% yield). LCMS (ESI) m/z calcd for $C_{27}H_{38}F_3N_5O_4S$: 585.26. Found: 586.62 $(M+1)^+$.

Preparation of (R)-3-(4-(isobutyl(1-(isopropoxycarboxyl)piperidin-4-yl)amino)-3-((3-(trifluoromethyl)-1,2,4-thiadiazol-5-yl)amino)phenyl)butanoic Acid

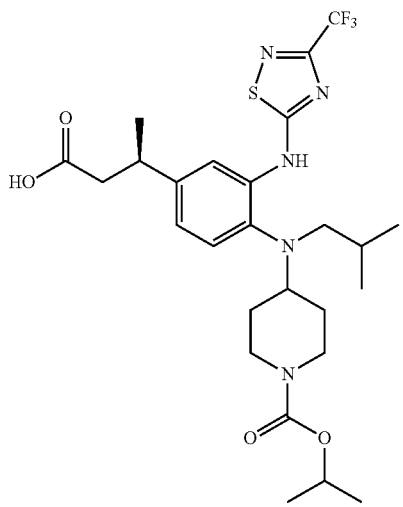 [SMILES: CC(C)CN(c1ccc([C@H](C)CC(=O)O)cc1Nc1nc(C(F)(F)F)ns1)C1CCN(C(=O)OC(C)C)CC1]

To a solution of isopropyl (R)-4-(isobutyl(4-(4-methoxy-4-oxobutan-2-yl)-2-((3-(tri fluoromethyl)-1,2,4-thiadiazol-5-yl)amino)phenyl)amino)piperidine-1-carboxylate (81 mg, 0.138 mmol) in MeOH (4 mL) was added 4N NaOH aq. (1.5 mL). After stirred at r.t. for 5 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (45 mg, 57% yield) as a white powder. $^1H$ NMR (400 MHz, CDCl$_3$) δ 9.40 (s, 1H), 7.30 (d, J=1.7 Hz, 1H), 7.20 (d, J=8.2 Hz, 1H), 7.00 (dd, J=8.2, 1.9 Hz, 1H), 4.90-4.83 (m, 1H), 4.23-4.11 (m, 2H), 3.37-3.30 (m, 1H), 2.83-2.57 (m, 7H), 1.84-1.80 (m, 2H), 1.46-1.37 (m, 6H), 1.21 (d, J=6.2 Hz, 6H), 0.84 (d, J=6.6 Hz, 6H). LCMS (ESI) m/z calcd for $C_{26}H_{36}F_3N_5O_4S$: 571.24. Found: 572.71 $(M+1)^+$.

Example 66

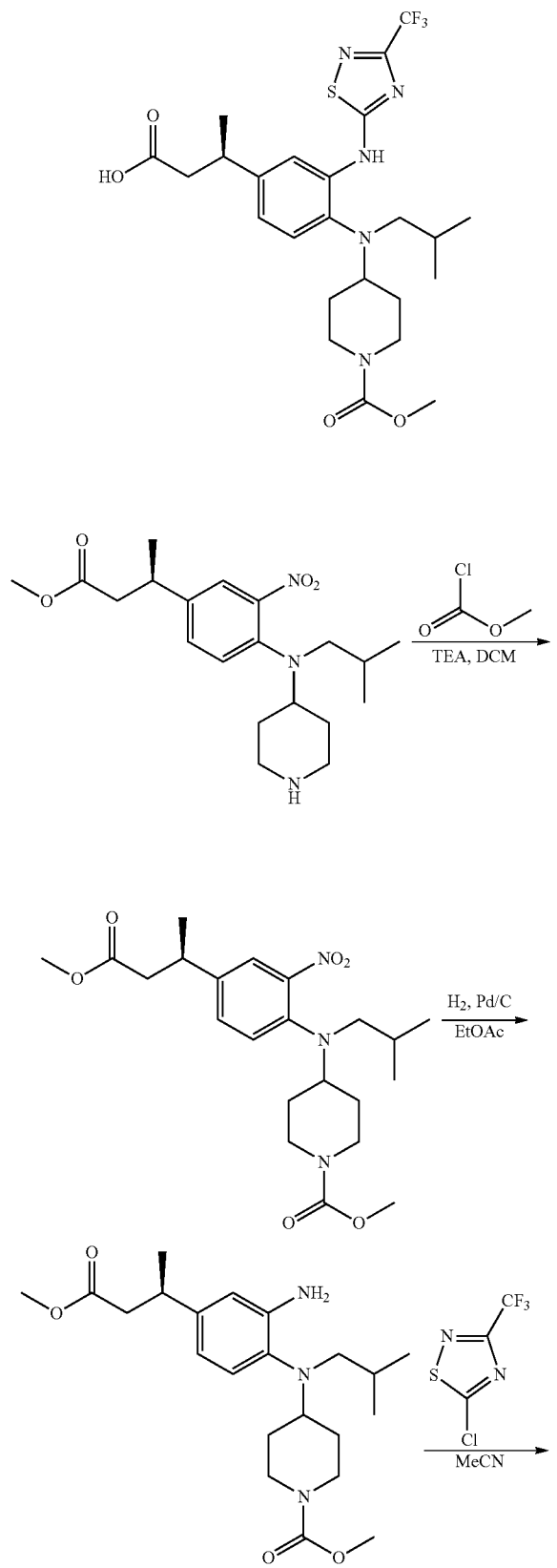

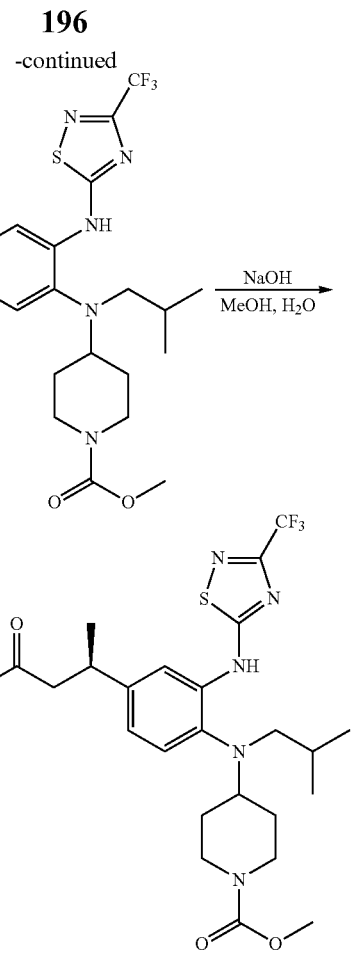

Preparation of methyl (R)-4-(isobutyl(4-(4-methoxy-4-oxobutan-2-yl)-2-nitro phenyl)amino) piperidine-1-carboxylate To a solution of methyl (R)-3-(4-(isobutyl(piperidin-4-yl)amino)-3-nitrophenyl)buta noate (200 mg, 0.53 mmol) in DCM (2 mL) was added TEA (0.22 mL, 1.59 mmol) and methyl chloroformate (0.093 mL, 1.06 mmol). After stirred at r.t. for 6 hr, the resulting mixture was partitioned between DCM and H₂O. The organic layer was washed with brine, dried over Na₂SO₄, filtered and concentrated to give the crude product which was purified by flash chromatography (silica gel, 0-30% EtOAc in PE) to afford the title compound (150 mg, 69% yield). LCMS (ESI) m/z calcd for $C_{22}H_{33}N_3O_6$: 435.24. Found: 436.54 (M+1)$^+$.

Preparation of methyl (R)-4-((2-amino-4-(4-methoxy-4-oxobutan-2-yl)phenyl) (isobutyl)amino)piperidine-1-carboxylate

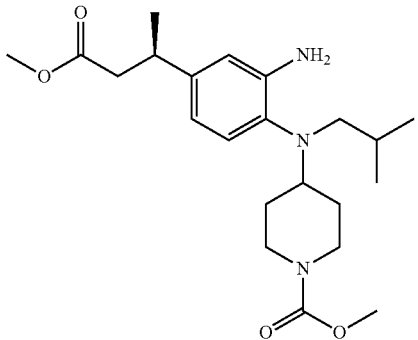 [SMILES: COC(=O)C[C@@H](C)c1ccc(N(CC(C)C)C2CCN(C(=O)OC)CC2)c(N)c1]

A mixture of methyl (R)-4-(isobutyl(4-(4-methoxy-4-oxobutan-2-yl)-2-nitrophenyl) amino)piperidine-1-carboxylate (160 mg, 0.37 mmol) and 10% Pd/C (50 mg) in EtOAc (5 mL) was stirred at r.t. under H$_2$ atmosphere for 6 hr. The resulting mixture was filtered through a pad of Celite and the filtrate was concentrated under reduced pressure to give the crude product which was purified by flash chromatography (silica gel, 0-30% EtOAc in PE) to afford the title compound (100 mg, 67% yield). LCMS (ESI) m/z calcd for $C_{22}H_{35}N_3O_4$: 405.26. Found: 406.53 (M+1)$^+$.

Preparation of methyl (R)-4-(isobutyl(4-(4-methoxy-4-oxobutan-2-yl)-2-((3-(tri fluoromethyl)-1,2,4-thiadiazol-5-yl)amino)phenyl)amino)piperidine-1-carboxylate

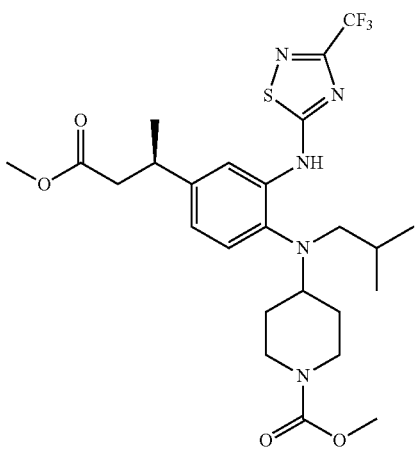 [SMILES: COC(=O)C[C@@H](C)c1ccc(N(CC(C)C)C2CCN(C(=O)OC)CC2)c(Nc2nc(C(F)(F)F)ns2)c1]

A mixture of methyl (R)-4-((2-amino-4-(4-methoxy-4-oxobutan-2-yl)phenyl) (isobutyl) amino)piperidine-1-carboxylate (100 mg, 0.247 mmol) and 5-chloro-3-(trifluoromethyl)-1,2,4-thiadiazole (70 mg, 0.37 mmol) in MeCN (2 mL) was stirred at 100° C. under N$_2$ atmosphere overnight. The resulting mixture was partitioned between EtOAc and H$_2$O.

The organic layer was washed with brine, dried over Na$_2$SO$_4$, filtered and concentrated to give the crude product which was purified by flash chromatography (silica gel, 0-30% EtOAc in PE) to afford the title compound (59 mg, 43% yield). LCMS (ESI) m/z calcd for $C_{25}H_{34}F_3N_5O_4S$: 557.23. Found: 558.51 (M+1)$^+$.

Preparation of (R)-3-(4-(isobutyl(1-(methoxycarbonyl)piperidin-4-yl)amino)-3-((3-(trifluoromethyl)-1,2,4-thiadiazol-5-yDamino)phenyl)butanoic Acid

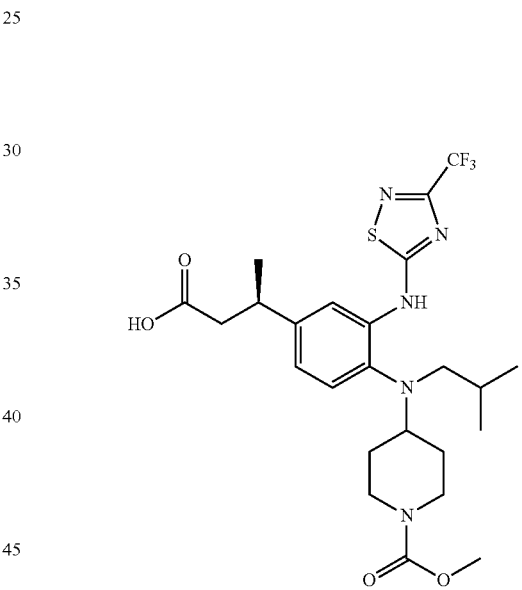

To a solution of methyl (R)-4-(isobutyl(4-(4-methoxy-4-oxobutan-2-yl)-2-((3-(tri fluoromethyl)-1,2,4-thiadiazol-5-yl)amino)phenyl)amino)piperidine-1-carboxylate (59 mg, 0.106 mmol) in MeOH (3 mL) was added 4N NaOH aq. (0.5 mL). After stirred at r.t. for 6 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (34 mg, 61% yield) as a white powder. $^1$H NMR (400 MHz, CDCl$_3$) δ 9.38 (s, 1H), 7.29 (d, J=1.7 Hz, 1H), 7.20 (d, J=8.2 Hz, 1H), 7.00 (dd, J=8.2, 1.8 Hz, 1H), 4.31-4.04 (m, 2H), 3.65 (s, 3H), 3.39-3.29 (m, 1H), 2.86-2.58 (m, 7H), 1.89-1.78 (m, 2H), 1.45-1.30 (m, 6H), 0.84 (d, J=6.6 Hz, 6H). LCMS (ESI) m/z calcd for $C_{24}H_{32}F_3N_5O_4S$: 543.21. Found: 544.36 (M+1)$^+$.

Example 67

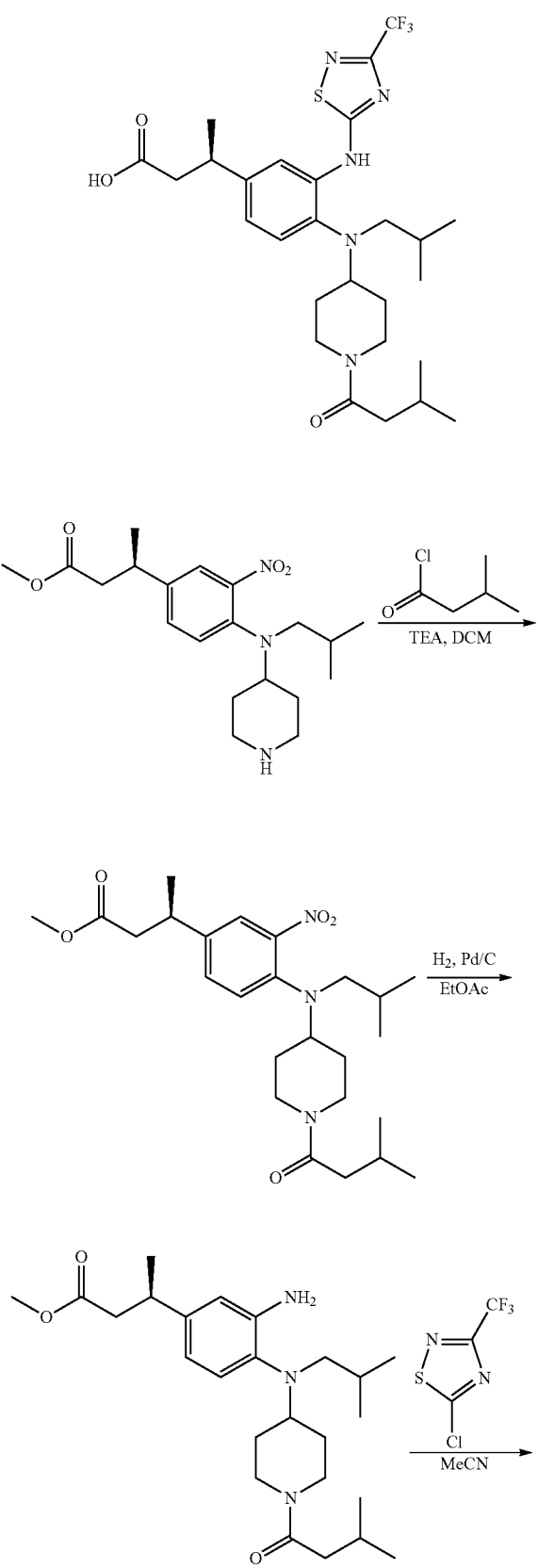

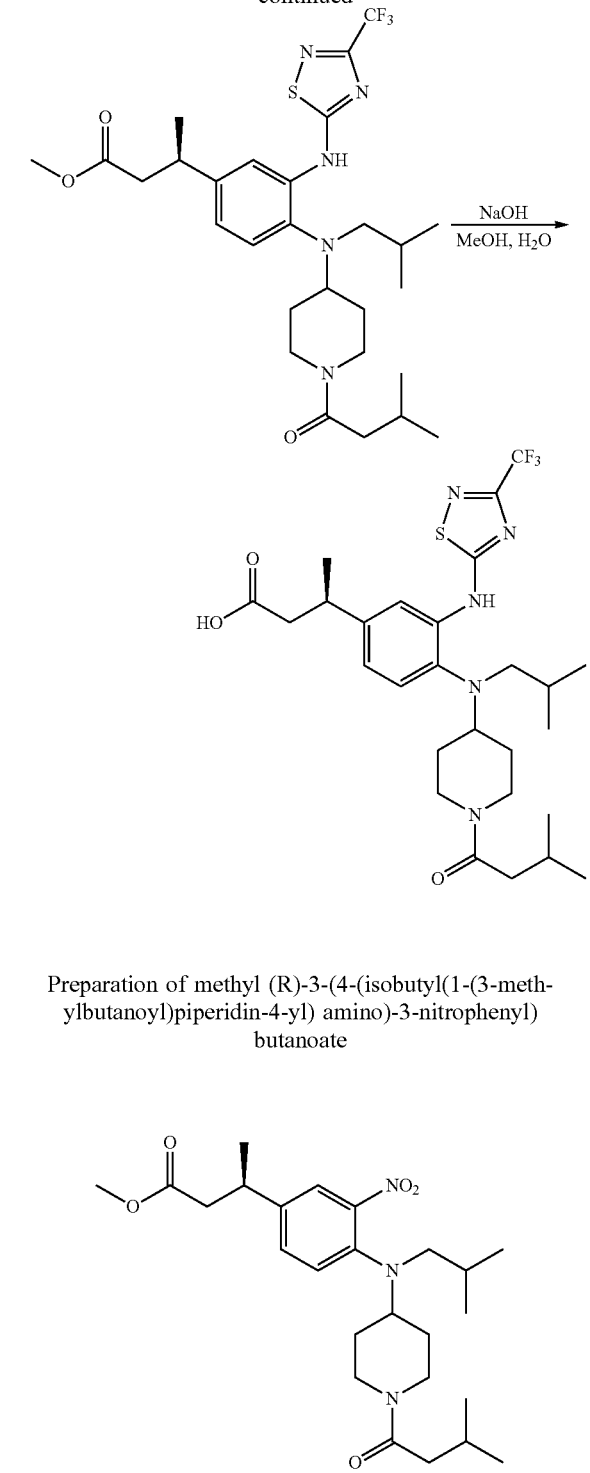

Preparation of methyl (R)-3-(4-(isobutyl(1-(3-methylbutanoyl)piperidin-4-yl) amino)-3-nitrophenyl) butanoate To a solution of methyl (R)-3-(4-(isobutyl(piperidin-4-yl) amino)-3-nitrophenyl)buta noate (377 mg, 1.0 mmol) in DCM (5 mL) was added TEA (303 mg, 3.0 mmol) and 3-methylbutanoyl chloride (241 mg, 2.0 mmol). After stirred at Et. overnight, the resulting mixture was partitioned between DCM and $H_2O$. The organic layer was washed with brine, dried over $Na_2SO_4$, filtered and concentrated to give the crude product which was purified by flash chromatography (silica gel, 0-30% EtOAc in PE) to afford the title compound (220 mg, 47% yield). LCMS (ESI) m/z calcd for $C_{25}H_{39}N_3O_5$: 461.29. Found: 462.41 (M+1)$^+$.

Preparation of methyl (R)-3-(3-amino-4-(isobutyl(1-(3-methylbutanoyl)piperidin-4-yl)amino)phenyl)butanoate

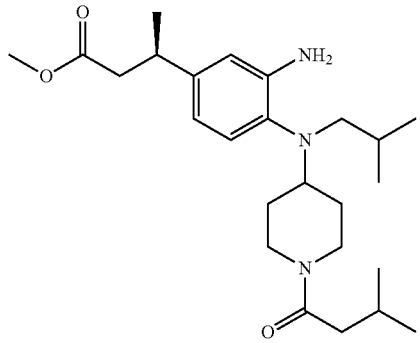 [SMILES: COC(=O)C[C@@H](C)c1ccc(N(CC(C)C)C2CCN(C(=O)CC(C)C)CC2)c(N)c1]

A mixture of methyl (R)-3-(4-(isobutyl(1-(3-methylbutanoyl)piperidin-4-yl)amino)-3-nitrophenyl)butanoate (220 mg, 0.48 mmol) and 10% Pd/C (66 mg) in EtOAc (10 mL) was stirred at r.t. under $H_2$ atmosphere for 4 hr. The resulting mixture was filtered through a pad of Celite and the filtrate was concentrated under reduced pressure to give the crude product which was purified by flash chromatography (silica gel, 0-30% EtOAc in PE) to afford the title compound (194 mg, 94% yield) as a yellow oil. LCMS (ESI) m/z calcd for $C_{25}H_{41}N_3O_3$: 431.31. Found: 432.76 (M+1)$^+$.

Preparation of methyl (R)-3-(4-(isobutyl(1-(3-methylbutanoyl)piperidin-4-yl) amino)-3-((3-(trifluoromethyl)-1,2,4-thiadiazol-5-yl)amino)phenyl)butanoate

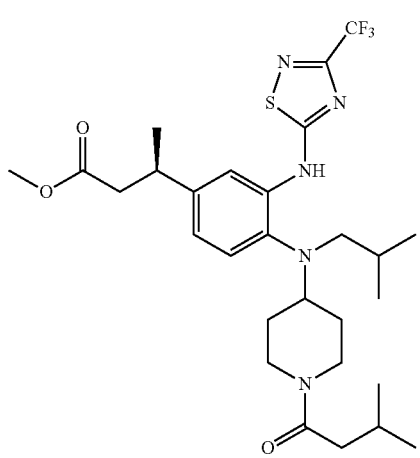 [SMILES: COC(=O)C[C@@H](C)c1ccc(N(CC(C)C)C2CCN(C(=O)CC(C)C)CC2)c(Nc2nc(C(F)(F)F)ns2)c1]

A mixture of methyl (R)-3-(3-amino-4-(isobutyl(1-(3-methylbutanoyl)piperidin-4-yl) amino)phenyl)butanoate (100 mg, 0.232 mmol) and 5-chloro-3-(trifluoromethyl)-1,2,4-thiadiazole (65 mg, 0.348 mmol) in MeCN (3 mL) was stirred at 95° C. under $N_2$ atmosphere overnight. The resulting mixture was partitioned between EtOAc and $H_2O$.

The organic layer was washed with brine, dried over $Na_2SO_4$, filtered and concentrated to give the crude product which was purified by flash chromatography (silica gel, 0-30% EtOAc in PE) to afford the title compound (60 mg, 44% yield). LCMS (ESI) m/z calcd for $C_{28}H_{40}F_3N_5O_3S$: 583.28. Found: 584.42 (M+1)$^+$.

Preparation of (R)-3-(4-(isobutyl(1-(3-methylbutanoyl)piperidin-4-yl)amino)-3-((3-(trifluoromethyl)-1,2,4-thiadiazol-5-yl)amino)phenyl)butanoic Acid

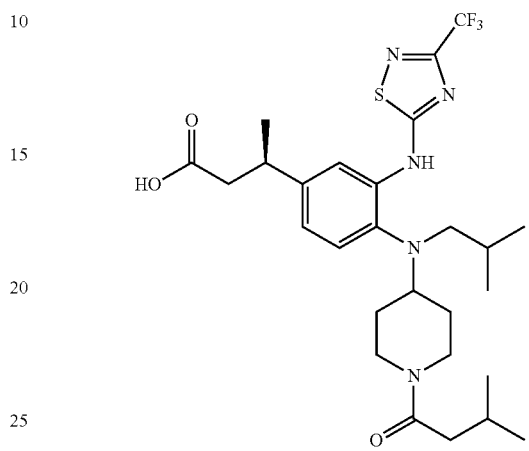

To a solution of methyl (R)-3-(4-(isobutyl(1-(3-methylbutanoyl)piperidin-4-yl) amino)-3-((3-(trifluoromethyl)-1,2,4-thiadiazol-5-yl)amino)phenyl)butanoate (60 mg, 0.10 mmol) in MeOH (3 mL) was added 4N NaOH aq. (0.5 mL). After stirred at r.t. overnight, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (32 mg, 55% yield) as a white powder. $^1$H NMR (400 MHz, CDCl$_3$) δ 9.38 (s, 1H), 7.28 (d, J=1.6 Hz, 1H), 7.20 (d, J=8.2 Hz, 1H), 7.00 (dd, J=8.2, 1.9 Hz, 1H), 4.68 (d, J=13.0 Hz, 1H), 3.88 (d, J=13.7 Hz, 1H), 3.37-3.28 (m, 1H), 2.92-2.64 (m, 6H), 2.43-2.36 (m, 1H), 2.18-1.87 (m, 5H), 1.45-1.33 (m, 6H), 0.92 (d, J=6.5 Hz, 6H), 0.84 (d, J=6.6 Hz, 6H). LCMS (ESI) m/z calcd for $C_{27}H_{38}F_3N_5O_3S$: 569.26. Found: 570.31 (M+1)$^+$.

Example 68

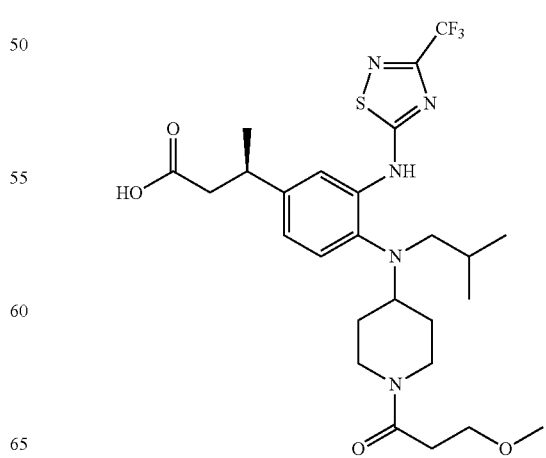

Scheme 48

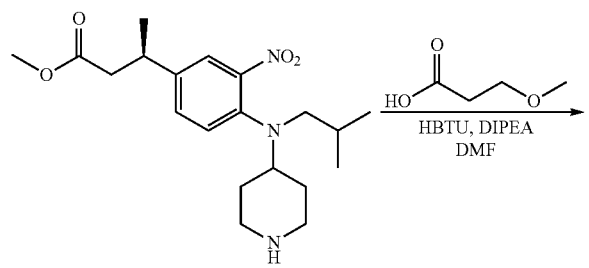

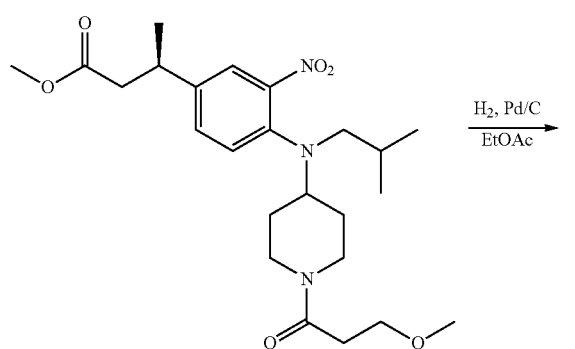

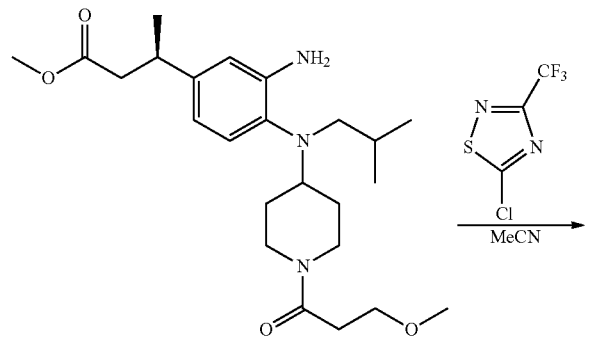

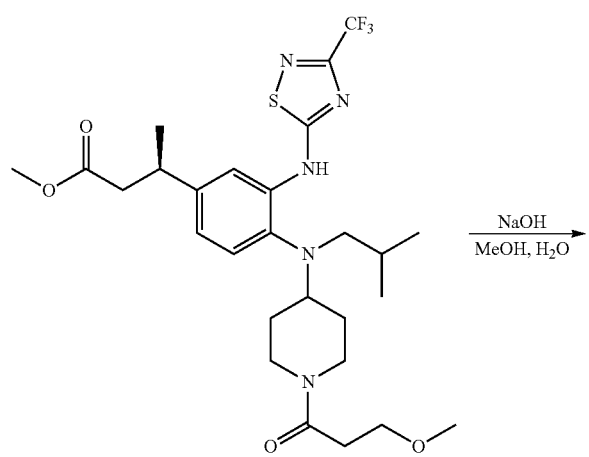

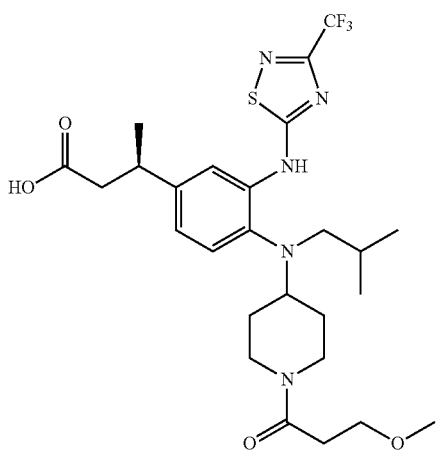 [SMILES: COCCC(=O)N1CCC(N(CC(C)C)c2ccc([C@H](C)CC(=O)O)cc2Nc2nc(C(F)(F)F)ns2)CC1]

Preparation of methyl (R)-3-(4-(isobutyl(1-(3-methoxypropanoyl)piperidin-4-yl) amino)-3-nitrophenyl)butanoate A mixture of methyl (R)-3-(4-(isobutyl(piperidin-4-yl) amino)-3-nitrophenyl)butanoate (230 mg, 0.61 mmol), 3-methoxypropanoic acid (126 mg, 1.22 mmol), HBTU (694 mg, 1.83 mmol) and DIPEA (0.3 mL, 1.83 mmol) in DMF (8 mL) was stirred at r.t. for 3 hr. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (255 mg, 90% yield). LCMS (ESI) m/z calcd for C$_{24}$H$_{37}$N$_3$O$_6$: 463.27. Found: 464.51 (M+1)$^+$.

Preparation of methyl (R)-3-(3-amino-4-(isobutyl(1-(3-methoxypropanoyl)piperidin-4-yl)amino)phenyl)butanoate

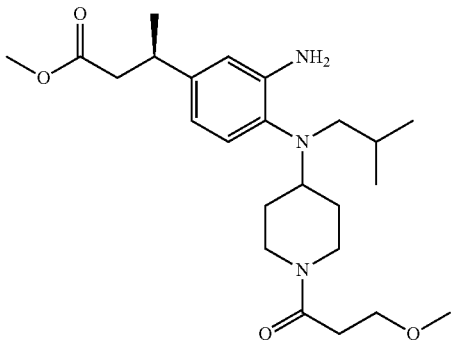

A mixture of methyl (R)-3-(4-(isobutyl(1-(3-methoxypropanoyl)piperidin-4-yl)amino)-3-nitrophenyl)butanoate (255 mg, 0.55 mmol) and 10% Pd/C (120 mg) in EtOAc (15 mL) was stirred at 50° C. under H$_2$ atmosphere for 3 hr. The resulting mixture was filtered through a pad of Celite and the filtrate was concentrated under reduced pressure to give the crude product which was purified by flash chromatography (silica gel, 0-30% EtOAc in PE) to afford the title compound (140 mg, 58% yield). LCMS (ESI) m/z calcd for C$_{24}$H$_{39}$N$_3$O$_4$: 433.29. Found: 434.71 (M+1)$^+$.

Preparation of methyl (R)-3-(4-(isobutyl(1-(3-methoxypropanoyl)piperidin-4-yl) amino)-3-((3-(trifluoromethyl)-1,2,4-thiadiazol-5-yl)amino)phenyl)butanoate

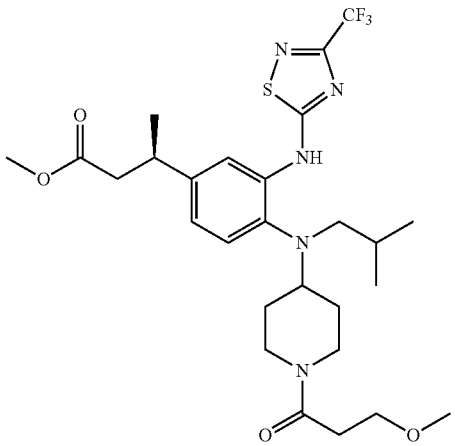

A mixture of methyl (R)-3-(3-amino-4-(isobutyl(1-(3-methoxypropanoyl)piperidin-4-yl) amino)phenyl)butanoate (140 mg, 0.323 mmol) and 5-chloro-3-(trifluoromethyl)-1,2,4-thiadiazole (121 mg, 0.646 mmol) in MeCN (5 mL) was stirred at 90° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (82 mg, 43% yield). LCMS (ESI) m/z calcd for C$_{27}$H$_{38}$F$_3$N$_5$O$_4$S: 585.26. Found: 586.80 (M+1)$^+$.

Preparation of (R)-3-(4-(isobutyl(1-(3-methoxypropanoyl)piperidin-4-yl)amino)-3-((3-(trifluoromethyl)-1,2,4-thiadiazol-5-yl)amino)phenyl)butanoic Acid

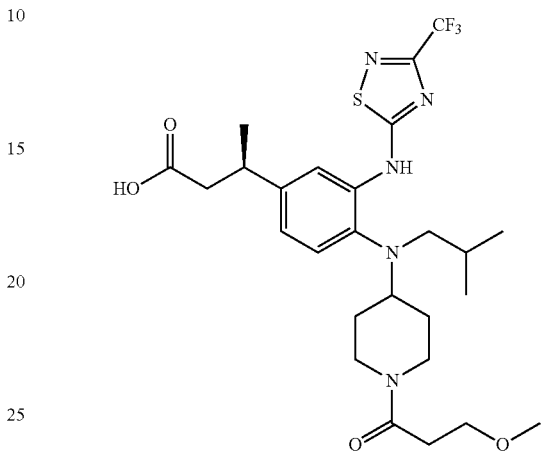

To a solution of methyl (R)-3-(4-(isobutyl(1-(3-methoxypropanoyl)piperidin-4-yl) amino)-3-((3-(trifluoromethyl)-1,2,4-thiadiazol-5-yl)amino)phenyl)butanoate (82 mg, 0.14 mmol) in MeOH (4 mL) was added 4N NaOH aq. (2 mL). After stirred at r.t. for 6 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (51 mg, 64% yield) as a white powder. $^1$H NMR (400 MHz, CDCl$_3$) δ 9.40 (s, 1H), 7.29 (d, J=1.5 Hz, 1H), 7.20 (d, J=8.2 Hz, 1H), 7.02-6.97 (m, 1H), 4.68 (d, J=13.1 Hz, 1H), 3.89 (d, J=13.8 Hz, 1H), 3.71-3.61 (m, 2H), 3.39-3.27 (m, 4H), 2.96-2.77 (m, 4H), 2.70-2.48 (m, 4H), 2.44-2.36 (m, 1H), 1.94-1.84 (m, 2H), 1.48-1.30 (m, 6H), 0.85 (d, J=6.5 Hz, 6H). LCMS (ESI) m/z calcd for C$_{26}$H$_{36}$F$_3$N$_5$O$_4$S: 571.24. Found: 572.65 (M+1)$^+$.

Example 69

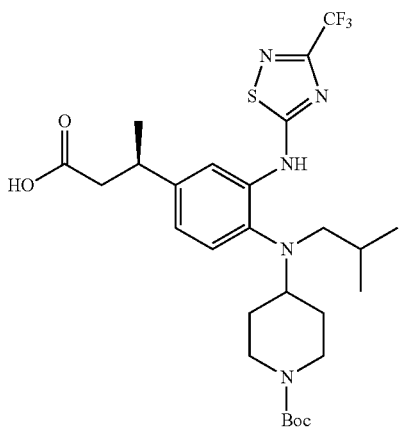

-continued

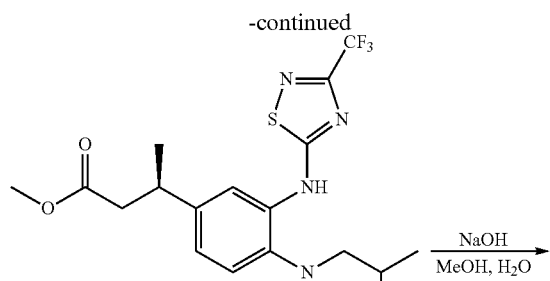

Preparation of (R)-3-(4-((1-(tert-butoxycarbonyl) piperidin-4-yl) (isobutyl)amino)-3-((3-(trifluoromethyl)-1,2,4-thiadiazol-5-yl)amino)phenyl)butanoic Acid

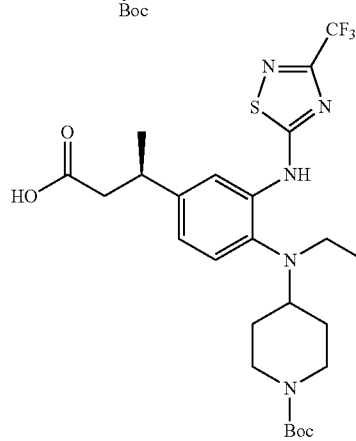

To a solution of tert-butyl (R)-4-(isobutyl(4-(4-methoxy-4-oxobutan-2-yl)-2-((3-(trifluoro methyl)-1,2,4-thiadiazol-5-yl)amino)phenyl)amino)piperidine-1-carboxylate (80 mg, 0.133 mmol) in MeOH (3 mL) was added 1N NaOH aq. (1 mL). After stirred at rt overnight, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (31 mg, 40% yield) as a white powder. $^1$H NMR (400 MHz, $CDCl_3$) δ 9.41 (s, 1H), 7.30 (d, J=1.7 Hz, 1H), 7.20 (d, J=8.2 Hz, 1H), 7.00 (dd, J=8.2, 1.9 Hz, 1H), 4.23-4.01 (m, 2H), 3.40-3.31 (m, 1H), 2.87-2.53 (m, 7H), 1.85-1.75 (m, 2H), 1.46-1.34 (m, 15H), 0.84 (d, J=6.6 Hz, 6H). LCMS (ESI) m/z calcd for $C_{27}H_{38}F_3N_5O_4S$: 585.26. Found: 586.37 (M+1)$^+$.

Example 70

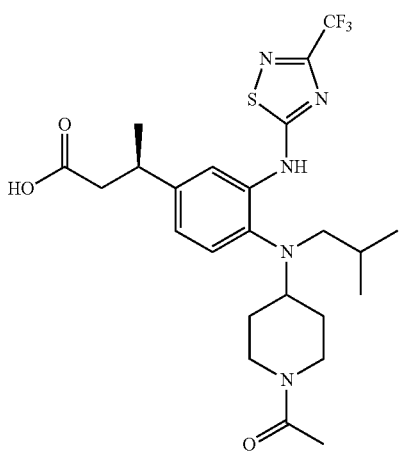

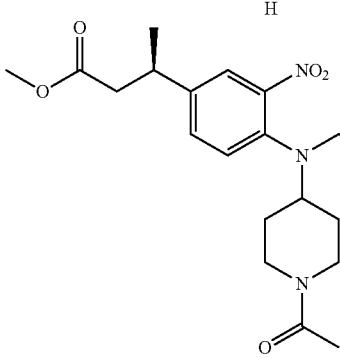

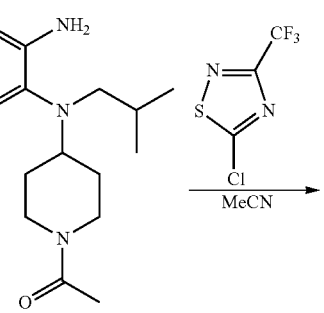

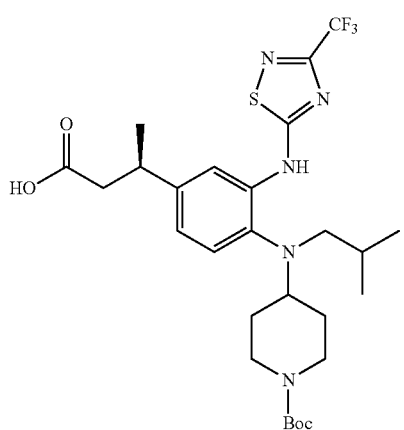 [SMILES: CC(C)CN(c1ccc([C@H](C)CC(=O)O)cc1Nc1nc(C(F)(F)F)ns1)C1CCN(C(=O)OC(C)(C)C)CC1]

209

-continued

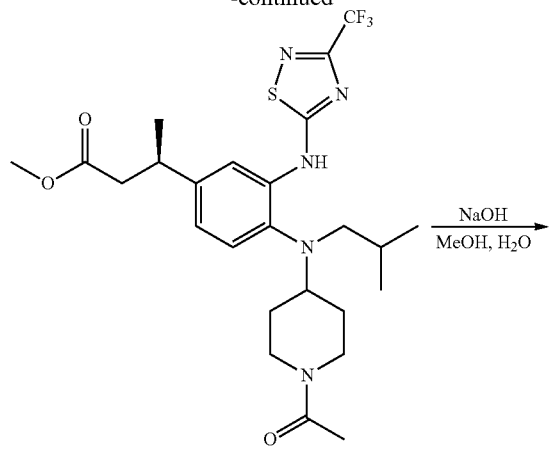

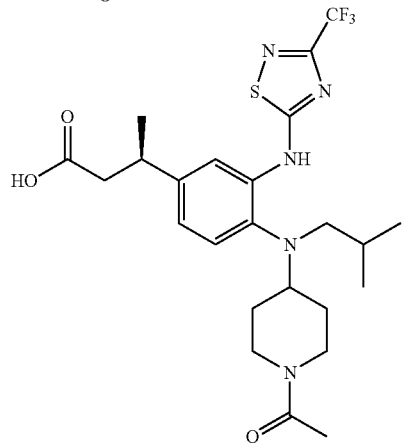

Preparation of methyl (R)-3-(4-((1-acetylpiperidin-4-yl) (isobutyl)amino)-3-nitro phenyl)butanoate

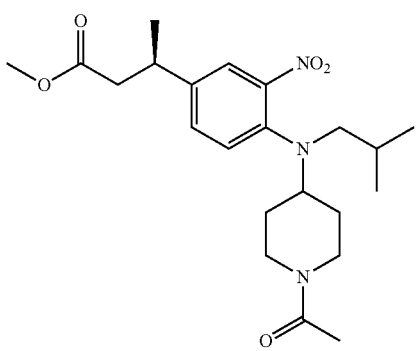 [SMILES: COC(=O)C[C@@H](C)c1ccc(N(CC(C)C)C2CCN(C(C)=O)CC2)c([N+](=O)[O-])c1]

To a solution of methyl (R)-3-(4-(isobutyl(piperidin-4-yl)amino)-3-nitrophenyl)buta noate (200 mg, 0.53 mmol) in DCM (2 mL) was added TEA (0.22 mg, 1.59 mmol) and acetyl chloride (0.075 mL, 1.06 mmol). After stirred at r.t. for 6 hr, the resulting mixture was partitioned between DCM and H₂O. The organic layer was washed with brine, dried over Na₂SO₄, filtered and concentrated to give the crude product which was purified by flash chromatography (silica gel, 0-30% EtOAc in PE) to afford the title compound (160 mg, 67% yield). LCMS (ESI) m/z calcd for C₂₂H₃₃N₃O₅: 419.24. Found: 420.21 (M+1)⁺.

210

Preparation of methyl (R)-3-(4-((1-acetylpiperidin-4-yl) (isobutyl)amino)-3-amino phenyl)butanoate

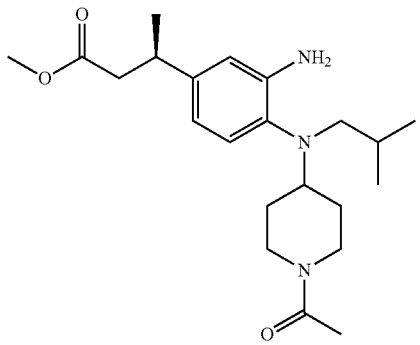 [SMILES: COC(=O)C[C@@H](C)c1ccc(N(CC(C)C)C2CCN(C(C)=O)CC2)c(N)c1]

A mixture of methyl (R)-3-(4-((1-acetylpiperidin-4-yl) (isobutyl)amino)-3-nitrophenyl) butanoate (150 mg, 0.36 mmol) and 10% Pd/C (50 mg) in EtOAc (10 mL) was stirred at r.t. under H₂ atmosphere for 6 hr. The resulting mixture was filtered through a pad of Celite and the filtrate was concentrated under reduced pressure to give the crude product which was purified by flash chromatography (silica gel, 0-30% EtOAc in PE) to afford the title compound (130 mg, 93% yield) as a yellow oil. LCMS (ESI) m/z calcd for C₂₂H₃₅N₃O₃: 389.27. Found: 390.66 (M+1)⁺.

Preparation of methyl (R)-3-(4-((1-acetylpiperidin-4-yl) (isobutyl)amino)-3-((3-(tri fluoromethyl)-1,2,4-thiadiazol-5-yl)amino)phenyl)butanoate

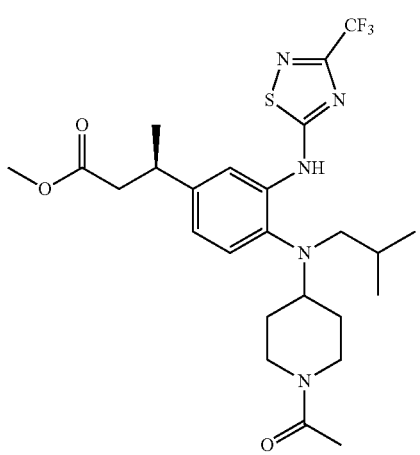 [SMILES: COC(=O)C[C@@H](C)c1ccc(N(CC(C)C)C2CCN(C(C)=O)CC2)c(Nc2nc(C(F)(F)F)ns2)c1]

A mixture of methyl (R)-3-(4-((1-acetylpiperidin-4-yl) (isobutyl)amino)-3-aminophenyl) butanoate (130 mg, 0.334 mmol) and 5-chloro-3-(trifluoromethyl)-1,2,4-thiadiazole (93 mg, 0.495 mmol) in MeCN (2 mL) was stirred at 100° C. under N₂ atmosphere overnight. The resulting mixture was partitioned between EtOAc and H₂O. The organic layer was washed with brine, dried over Na₂SO₄, filtered and concentrated to give the crude product which was purified by flash chromatography (silica gel, 0-30% EtOAc in PE) to afford the title compound (90 mg, 50% yield). LCMS (ESI) m/z calcd for C₂₅H₃₄F₃N₅O₃S: 541.23. Found: 542.51 (M+1)⁺.

211

Preparation of (R)-3-(4-((1-acetylpiperidin-4-yl)(isobutyl)amino)-3-((3-(trifluoro methyl)-1,2,4-thiadiazol-5-yl)amino)phenyl)butanoic Acid

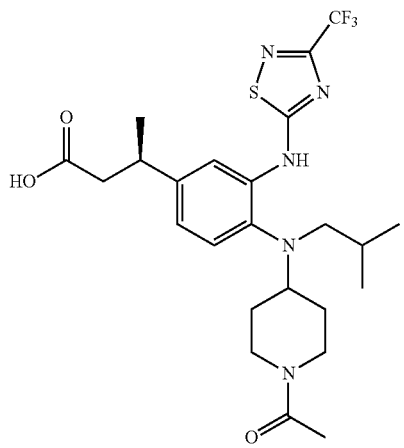 [SMILES: CC(=O)N1CCC(N(CC(C)C)c2ccc([C@H](C)CC(=O)O)cc2Nc2nc(C(F)(F)F)ns2)CC1]

To a solution of methyl (R)-3-(4-((1-acetylpiperidin-4-yl)(isobutyl)amino)-3-((3-(tri fluoromethyl)-1,2,4-thiadiazol-5-yl)amino)phenyl)butanoate (70 mg, 0.13 mmol) in MeOH (3 mL) was added 4N NaOH aq. (0.5 mL). After stirred at r.t. for 6 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (37 mg, 55% yield) as a white powder. $^1$H NMR (400 MHz, CDCl$_3$) δ 9.38 (s, 1H), 7.28 (d, J=1.7 Hz, 1H), 7.19 (d, J=8.2 Hz, 1H), 7.00 (dd, J=8.2, 1.8 Hz, 1H), 4.65 (d, J=13.6 Hz, 1H), 3.81 (d, J=14.0 Hz, 1H), 3.40-3.29 (m, 1H), 2.94-2.63 (m, 6H), 2.45-2.35 (m, 1H), 2.05 (s, 3H), 1.94-1.83 (m, 2H), 1.46-1.35 (m, 6H), 0.85 (d, J=6.6 Hz, 6H). LCMS (ESI) m/z calcd for C$_{24}$H$_{32}$F$_3$N$_5$O$_3$S: 527.22. Found: 528.35 (M+1)$^+$.

Example 71

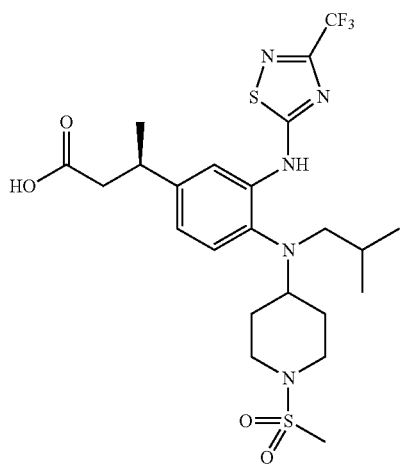

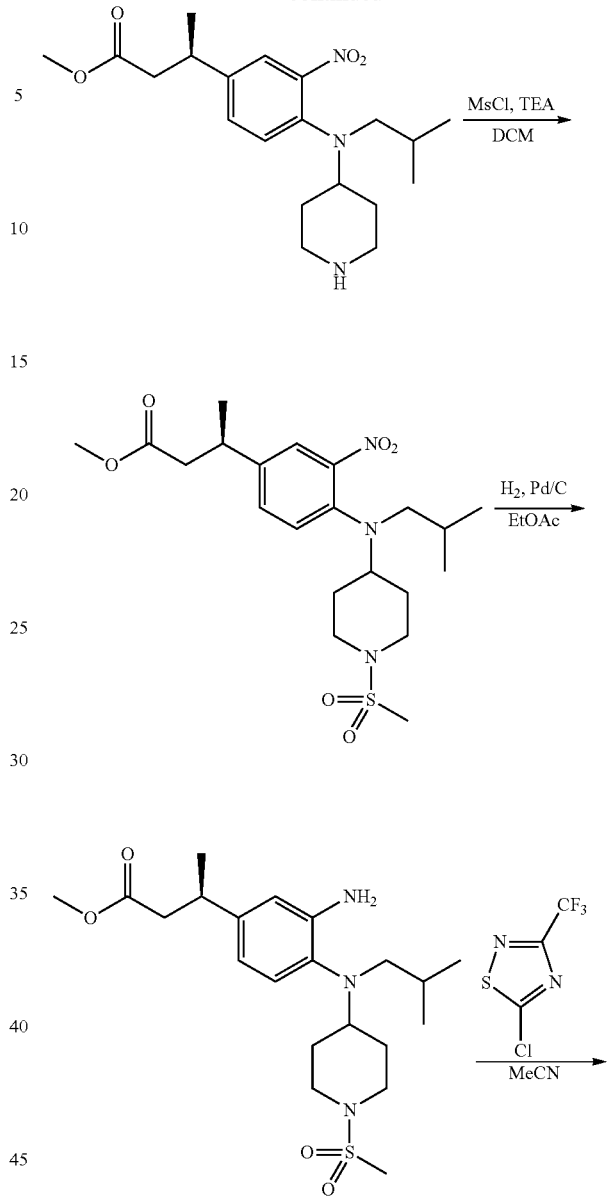

213
-continued

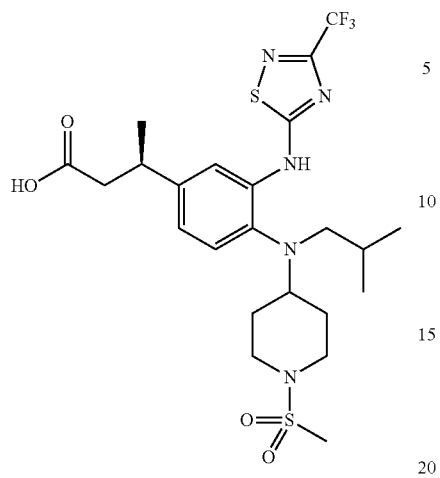

Preparation of methyl (R)-3-(4-(isobutyl(1-(methyl-sulfonyl)piperidin-4-yl)amino)-3-nitrophenyl)butanoate

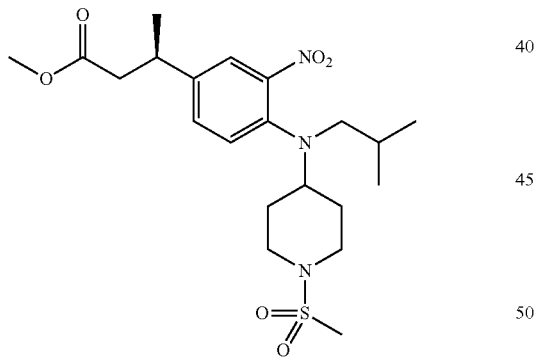

At 0° C., to a solution of methyl (R)-3-(4-(isobutyl (piperidin-4-yl)amino)-3-nitrophenyl) butanoate (300 mg, 0.8 mmol) in DCM (10 mL) was added TEA (0.33 mL, 2.4 mmol) and MsCl (0.06 mL, 0.96 mmol). After stirred at r.t. for 3 hr, the resulting mixture was partitioned between DCM and H$_2$O. The organic layer was washed with brine, dried over Na$_2$SO$_4$, filtered and concentrated to give the crude product which was purified by flash chromatography (silica gel, 0-30% EtOAc in PE) to afford the title compound (300 mg, 83% yield). LCMS (ESI) m/z calcd for C$_{21}$H$_{33}$N$_3$O$_6$S: 455.21. Found: 456.55 (M+1)$^+$.

214
Preparation of methyl (R)-3-(3-amino-4-(isobutyl(1-(methylsulfonyl)piperidin-4-yl)amino)phenyl)butanoate

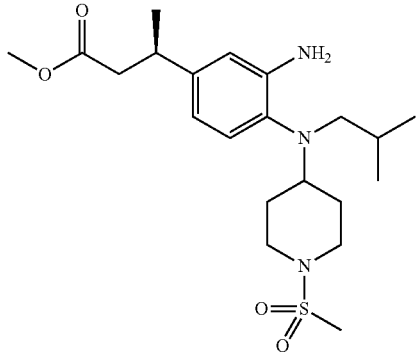 [SMILES: COC(=O)C[C@@H](C)c1ccc(N(CC(C)C)C2CCN(S(C)(=O)=O)CC2)c(N)c1]

A mixture of methyl (R)-3-(4-(isobutyl(1-(methylsulfonyl)piperidin-4-yl)amino)-3-nitro phenyl)butanoate (300 mg, 0.66 mmol) and 10% Pd/C (150 mg) in EtOAc (10 mL) was stirred at 50° C. under H$_2$ atmosphere for 2 hr. The resulting mixture was filtered through a pad of Celite and the filtrate was concentrated under reduced pressure to give the crude product which was purified by flash chromatography (silica gel, 0-30% EtOAc in PE) to afford the title compound (230 mg, 82% yield). LCMS (ESI) m/z calcd for C$_{21}$H$_{35}$N$_3$O$_4$S: 425.23. Found: 426.60 (M+1)$^+$.

Preparation of methyl (R)-3-(4-(isobutyl(1-(methylsulfonyl)piperidin-4-yl)amino)-3-((3-(trifluoromethyl)-1,2,4-thiadiazol-5-yl)amino)phenyl)butanoate

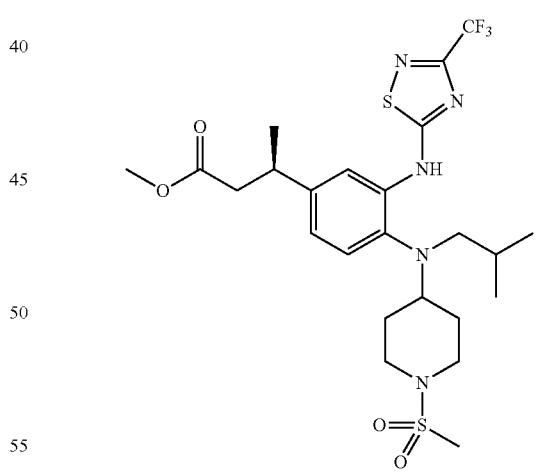

A mixture of methyl (R)-3-(3-amino-4-(isobutyl(1-(methylsulfonyl)piperidin-4-yl)amino) phenyl)butanoate (120 mg, 0.282 mmol) and 5-chloro-3-(trifluoromethyl)-1,2,4-thiadiazole (106 mg, 0.56 mmol) in MeCN (5 mL) was stirred at 90° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (100 mg, 61%

Preparation of (R)-3-(4-(isobutyl(1-(methyl-sulfonyhpiperidin-4-yl)amino)-3-((3-(trifluoromethyl)-1,2,4-thiadiazol-5-yl)amino)phenyl)butanoic Acid

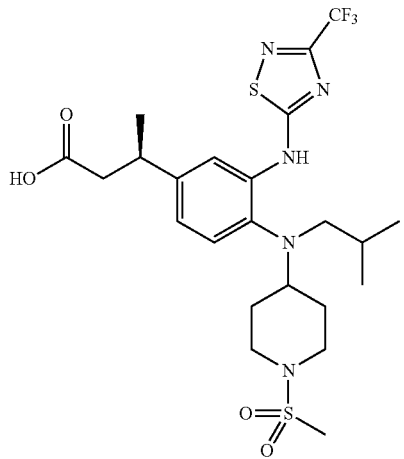 [SMILES: CC(C)CN(c1ccc([C@H](C)CC(=O)O)cc1Nc1nc(C(F)(F)F)ns1)C1CCN(S(C)(=O)=O)CC1]

To a solution of methyl (R)-3-(4-(isobutyl(1-(methyl-sulfonyl)piperidin-4-yl)amino) (trifluoromethyl)-1,2,4-thiadiazol-5-yl)amino)phenyl)butanoate (100 mg, 0.173 mmol) in MeOH (4 mL) was added 4N NaOH aq. (2 mL). After stirred at r.t. for 5 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (71 mg, 72% yield) as a white powder. $^1$H NMR (400 MHz, CDCl$_3$) δ 9.30 (s, 1H), 7.29 (d, J=1.6 Hz, 1H), 7.21 (d, J=8.2 Hz, 1H), 7.01 (dd, J=8.2, 1.8 Hz, 1H), 3.85-3.78 (m, 2H), 3.39-3.31 (m, 1H), 2.90-2.78 (m, 2H), 2.75-2.54 (m, 8H), 1.97-1.91 (m, 2H), 1.70-1.65 (m, 2H), 1.42-1.36 (m, 4H), 0.85 (d, J=6.6 Hz, 6H). LCMS (ESI) m/z calcd for C$_{23}$H$_{32}$F$_3$N$_5$O$_4$S$_2$: 563.18. Found: 564.59 (M+1)$^+$.

Example 72

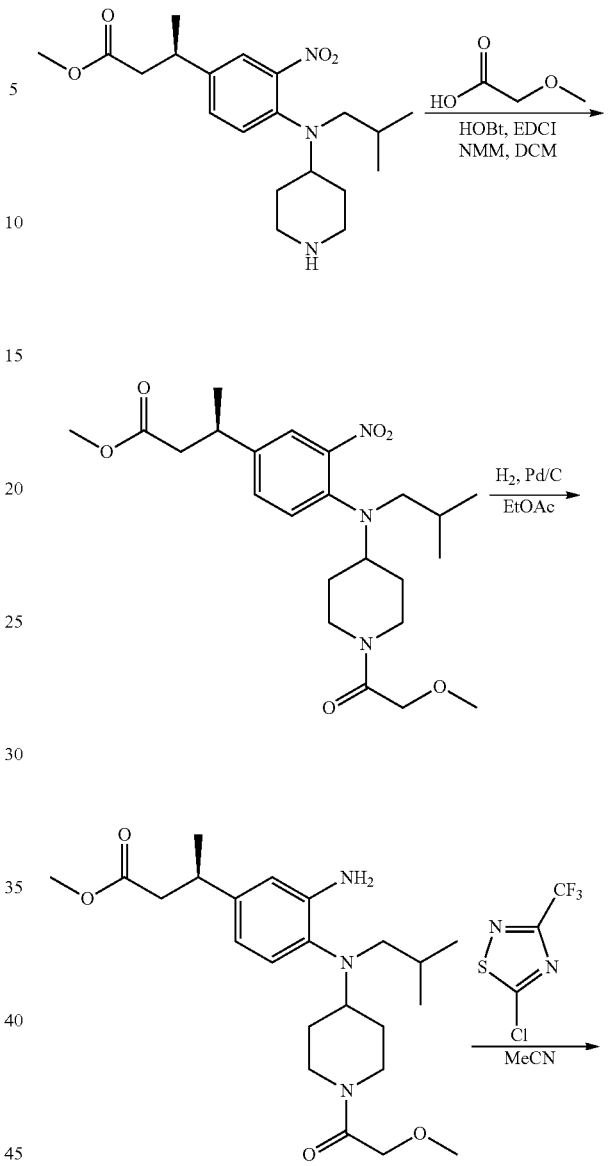

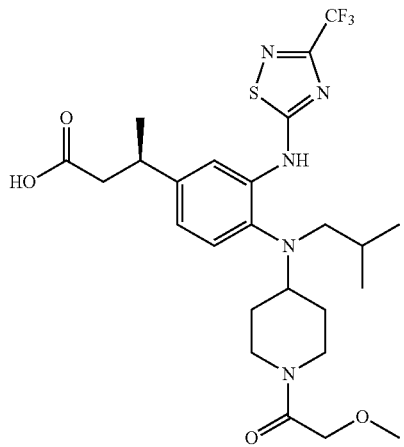

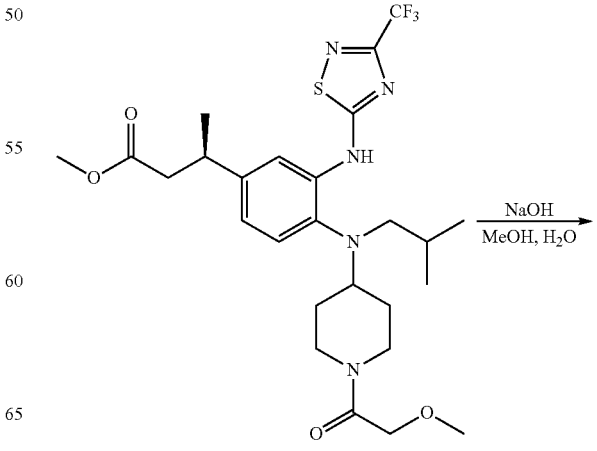

217

-continued

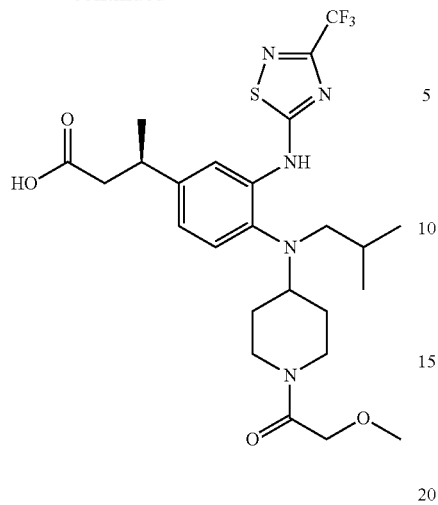

Preparation of methyl (R)-3-(4-(isobutyl(1-(2-methoxyacetyl)piperidin-4-yl) amino)-3-nitrophenyl)butanoate

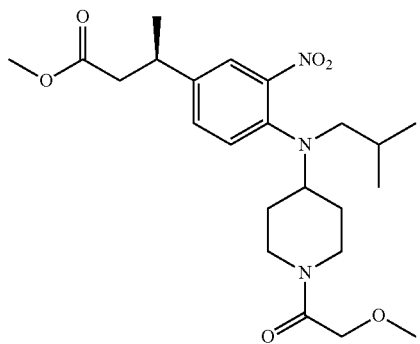

A mixture of methyl (R)-3-(4-(isobutyl(piperidin-4-yl) amino)-3-nitrophenyl)butanoate (500 mg, 1.33 mmol), 2-methoxyacetic acid (179 mg, 1.99 mmol), HOBt (197 mg, 1.46 mmol), EDCI (342 mg, 1.99 mmol) and NMM (699 mL, 6.63 mmol) in DCM (10 mL) was stirred at r.t. overnight. The resulting mixture was partitioned between DCM and H$_2$O. The organic layer was washed with brine, dried over Na$_2$SO$_4$, filtered and concentrated to give the crude product which was purified by flash chromatography (silica gel, 0-30% EtOAc in PE) to afford the title compound (450 mg, 75% yield). LCMS (ESI) m/z calcd for C$_{23}$H$_{35}$N$_3$O$_6$: 449.25. Found: 450.56 (M+1)$^+$.

218

Preparation of methyl (R)-3-(3-amino-4-(isobutyl(1-(2-methoxyacetyl)piperidin-4-yl)amino)phenyl)butanoate

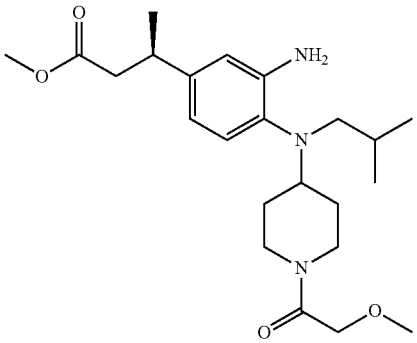

A mixture of methyl (R)-3-(4-(isobutyl(1-(2-methoxyacetyl)piperidin-4-yl)amino)-3-nitrophenyl)butanoate (450 mg, 1.0 mmol) and 10% Pd/C (220 mg) in EtOAc (20 mL) was stirred at 50° C. under H$_2$ atmosphere for 4 hr. The resulting mixture was filtered through a pad of Celite and the filtrate was concentrated under reduced pressure to give the crude product which was purified by flash chromatography (silica gel, 0-30% EtOAc in PE) to afford the title compound (330 mg, 78% yield) as a yellow oil. LCMS (ESI) m/z calcd for C$_{23}$H$_{37}$N$_3$O$_4$: 419.28. Found: 420.81 (M+1)$^+$.

Preparation of methyl (R)-3-(4-(isobutyl(1-(2-methoxyacetyl)piperidin-4-yl) amino)-3-((3-(trifluoromethyl)-1,2,4-thiadiazol-5-yl)amino)phenyl)butanoate

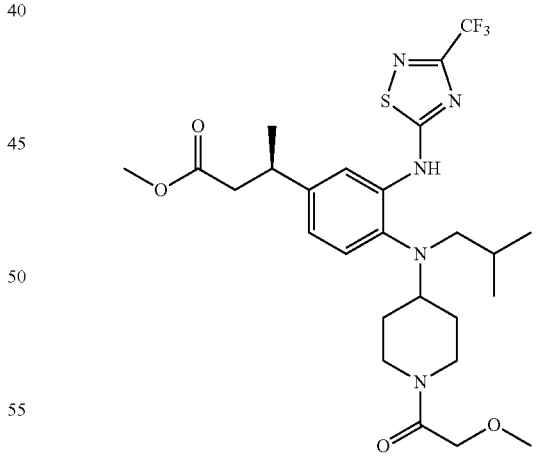

A mixture of methyl (R)-3-(3-amino-4-(isobutyl(1-(2-methoxyacetyl)piperidin-4-yl) amino)phenyl)butanoate (330 mg, 0.785 mmol) and 5-chloro-3-(trifluoromethyl)-1,2,4-thiadiazole (295 mg, 1.57 mmol) in MeCN (6 mL) was stirred at 90° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30%

EtOAc in PE) to afford the title compound (180 mg, 40% yield). LCMS (ESI) m/z calcd for $C_{26}H_{36}F_3N_5O_4S$: 571.24. Found: 572.66 (M+1)+.

Preparation of (R)-3-(4-(isobutyl(1-(2-methoxy-acetyl)piperidin-4-yl)amino)-3-((3-(trifluoromethyl)-1,2,4-thiadiazol-5-yl)amino)phenyl)butanoic Acid

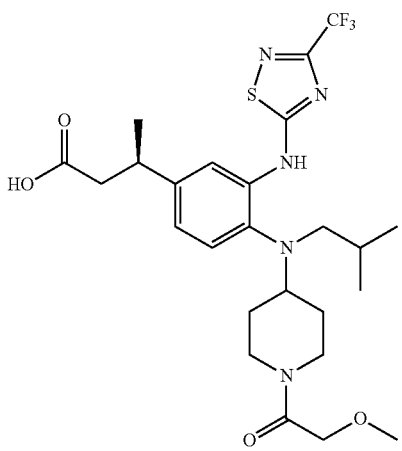

To a solution of methyl (R)-3-(4-(isobutyl(1-(2-methoxy-acetyl)piperidin-4-yl)amino)-3-((3-(trifluoromethyl)-1,2,4-thiadiazol-5-yl)amino)phenyl)butanoate (180 mg, 0.315 mmol) in MeOH (4 mL) was added 1N NaOH aq. (4 mL). After stirred at rt for 8 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (111 mg, 63% yield) as a white powder. $^1$H NMR (400 MHz, DMSO) δ 12.02 (s, 1H), 10.32 (s, 1H), 8.01 (s, 1H), 7.23 (d, J=8.2 Hz, 1H), 7.06 (d, J=8.2 Hz, 1H), 4.36 (d, J=11.4 Hz, 1H), 4.10-3.92 (m, 2H), 3.74 (d, J=12.3 Hz, 1H), 3.23 (s, 3H), 3.18-3.10 (m, 1H), 2.97-2.86 (m, 1H), 2.85-2.68 (m, 3H), 2.49-2.32 (m, 3H), 1.92-1.69 (m, 2H), 1.49-1.11 (m, 6H), 0.77 (d, J=6.5 Hz, 6H) LCMS (ESI) m/z calcd for $C_{25}H_{34}F_3N_5O_4S$: 557.23. Found: 558.60 (M+1)+.

Example 73

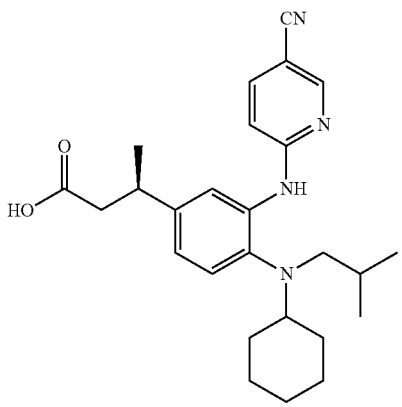

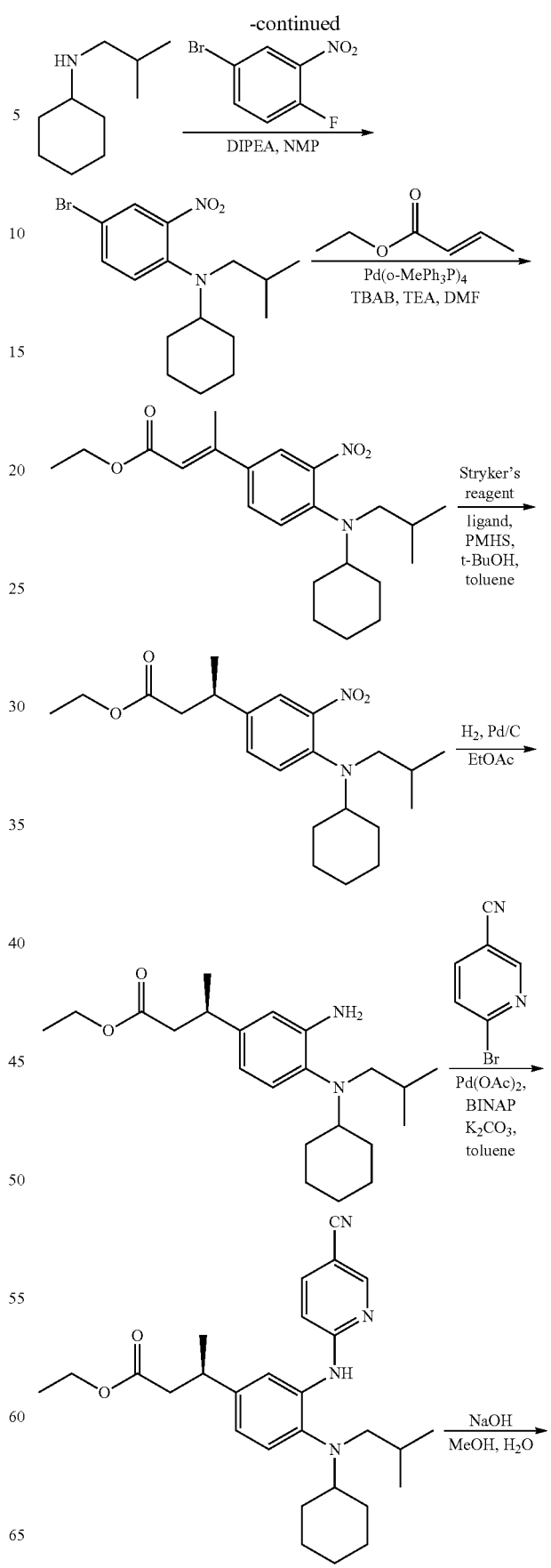

-continued

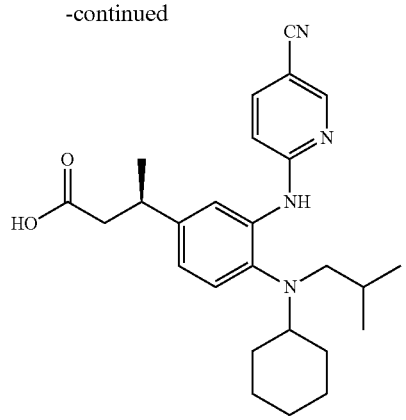

Preparation of
4-bromo-N-cyclohexyl-N-isobutyl-2-nitroaniline

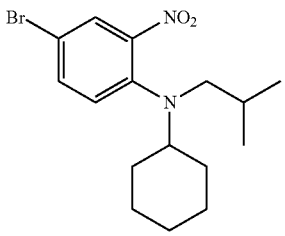 [SMILES: CC(C)CN(c1ccc(Br)cc1[N+](=O)[O-])C1CCCCC1]

A mixture of 4-bromo-1-fluoro-2-nitrobenzene (600 g, 2.72 mol), N-isobutylcyclo hexanamine (635 g, 4.09 mol) and DIPEA (855 mL, 4.91 mmol) in NMP (3.0 L) was stirred at 140° C. for 9 hr. The resulting mixture was partitioned between EtOAc and H$_2$O. The layers were separated and the organic layer was washed with brine, dried over Na$_2$SO$_4$, filtered and concentrated to give the crude product which was triturated with PE to afford the title compound (1466 g, 76% yield). LCMS (ESI) m/z calcd for C$_{16}$H$_{23}$BrN$_2$O$_2$: 354.09. Found: 355.93/357.89 (M/M+2)$^+$.

Preparation of ethyl (E)-3-(4-(cyclohexyl(isobutyl) amino)-3-n itrophenyl)but-2-enoate

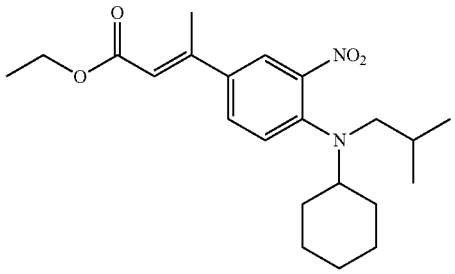 [SMILES: CCOC(=O)/C=C(\C)c1ccc(N(CC(C)C)C2CCCCC2)c([N+](=O)[O-])c1]

A mixture of 4-bromo-N-cyclohexyl-N-isobutyl-2-nitroaniline (32 g, 90.1 mmol), ethyl (E)-but-2-enoate (30.8 g, 270 mmol), TBAB (5.8 g, 18.0 mmol), Pd(o-MePh$_3$P)$_4$ (3.5 g, 4.5 mmol) and TEA (18.3 g, 181 mmol) in DMF (350 mL) was stirred at 110° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-5% EtOAc in PE) to afford the title compound (28.5 g, 81% yield) as a red oil. LCMS (ESI) m/z calcd for C$_{22}$H$_{32}$N$_2$O$_4$: 388.24. Found: 389.05 (M+1)$^+$.

Preparation of ethyl (R)-3-(4-(cyclohexyl(isobutyl)amino)-3-nitrophenyl)but anoate

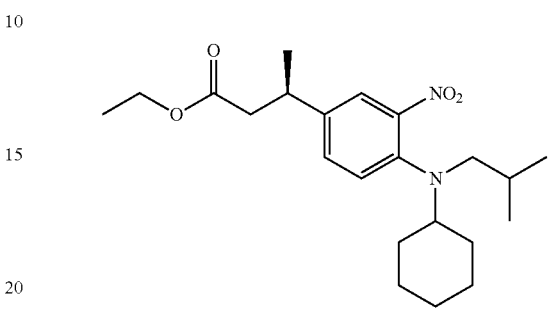

At 0° C., to a mixture of (CuHPh$_3$P)$_6$ (380 mg, 0.19 mmol) and (R,S)-PPF-P(tBu)$_2$ (30 mg, 0.055 mmol) in toluene (30 mL) was added PMHS (1.0 mL) and t-BuOH (0.81 mL) before the introduction of ethyl (E)-3-(4-(cyclohexyl(isobutyl)amino)-3-nitrophenyl) but-2-enoate (3.0 g, 7.72 mmol). After stirred at 0° C. for 4 hr, the resulting mixture was quenched with sat. NaHCO$_3$ aq. solution and extracted with EtOAc. The organic layer was washed with brine, dried over Na$_2$SO$_4$, filtered and concentrated to give the crude product which was purified by flash chromatography (silica gel, 0-5% EtOAc in PE) to afford the title compound (1.35 g, 45% yield) as a yellow oil. LCMS (ESI) m/z calcd for C$_{22}$H$_{34}$N$_2$O$_4$: 390.25. Found: 391.74 (M+1)$^+$.

Preparation of ethyl (R)-3-(3-amino-4-(cyclohexyl (isobutyl)amino)phenyl) butanoate

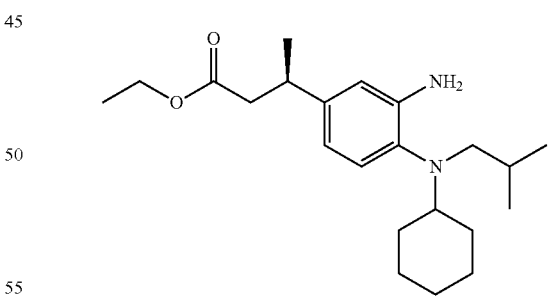

A mixture of ethyl (R)-3-(4-(cyclohexyl(isobutyl)amino)-3-nitrophenyl)butanoate (2.25 g, 5.76 mmol) and 10% Pd/C (1.0 g) in EtOAc (50 mL) was stirred at r.t. under H$_2$ atmosphere for 3 hr. The resulting mixture was filtered through a pad of Celite and the filtrate was concentrated under reduced pressure to give the crude product which was purified by flash chromatography (silica gel, 0-20% EtOAc in PE) to afford the title compound (1.8 g, 87% yield). LCMS (ESI) m/z calcd for C$_{22}$H$_{36}$N$_2$O$_2$: 360.28. Found: 361.09 (M+1)$^+$.

223

Preparation of ethyl (R)-3-(3-((5-cyanopyridin-2-yl)amino)-4-(cyclohexyl(iso butyl)amino)phenyl)butanoate

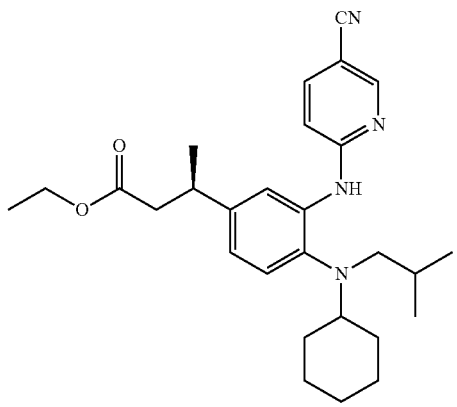

A mixture of ethyl (R)-3-(3-amino-4-(cyclohexyl(isobutyl)amino)phenyl)butanoate (150 mg, 0.42 mmol), 6-bromonicotinonitrile (152 mg, 0.83 mmol), Pd(OAc)$_2$ (4 mg, 0.0067 mmol), BINAP (5 mg, 0.0075 mmol) and K$_2$CO$_3$ (172 mg, 1.25 mmol) in toluene (10 mL) was stirred at 130° C. under N$_2$ atmosphere for 1.5 hr in macrowave apparatus. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (180 mg, 66% yield). LCMS (ESI) m/z calcd for C$_{28}$H$_{38}$N$_4$O$_2$: 462.30. Found: 463.27 (M+1)$^+$.

Preparation of (R)-3-(3-((5-cyanopyridin-2-yl)amino)-4-(cyclohexyl(isobutyl) amino)phenyl)butanoic Acid

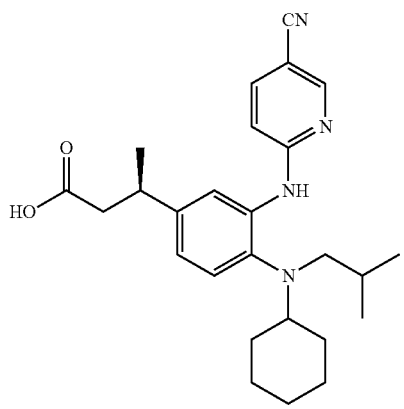 [SMILES: CC(C)CN(c1ccc([C@H](C)CC(=O)O)cc1Nc1ccc(C#N)cn1)C1CCCCC1]

224

To a solution of ethyl (R)-3-(3-((5-cyanopyridin-2-yl)amino)-4-(cyclohexyl(isobutyl) amino)phenyl)butanoate (180 mg, 0.389 mmol) in MeOH (3 mL) was added 1N NaOH aq. (0.5 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (35 mg, 21% yield) as a white powder. $^1$H NMR (400 MHz, CDCl$_3$) δ 8.54 (d, J=2.0 Hz, 1H), 8.44 (s, 1H), 8.14 (d, J=1.9 Hz, 1H), 7.65 (dd, J=8.8, 2.3 Hz, 1H), 7.12 (d, J=8.2 Hz, 1H), 6.87 (dd, J=8.2, 2.1 Hz, 1H), 6.73 (d, J=8.6 Hz, 1H), 3.34-3.25 (m, 1H), 2.80 (d, J=6.9 Hz, 2H), 2.73-2.51 (m, 3H), 1.86-1.80 (m, 2H), 1.76-1.68 (m, 3H), 1.47-1.31 (m, 6H), 1.15-1.00 (m, 3H), 0.85 (d, J=6.6 Hz, 6H). LCMS (ESI) m/z calcd for C$_{26}$H$_{34}$N$_4$O$_2$: 434.27. Found: 433.13 (M−1)$^-$.

Example 74

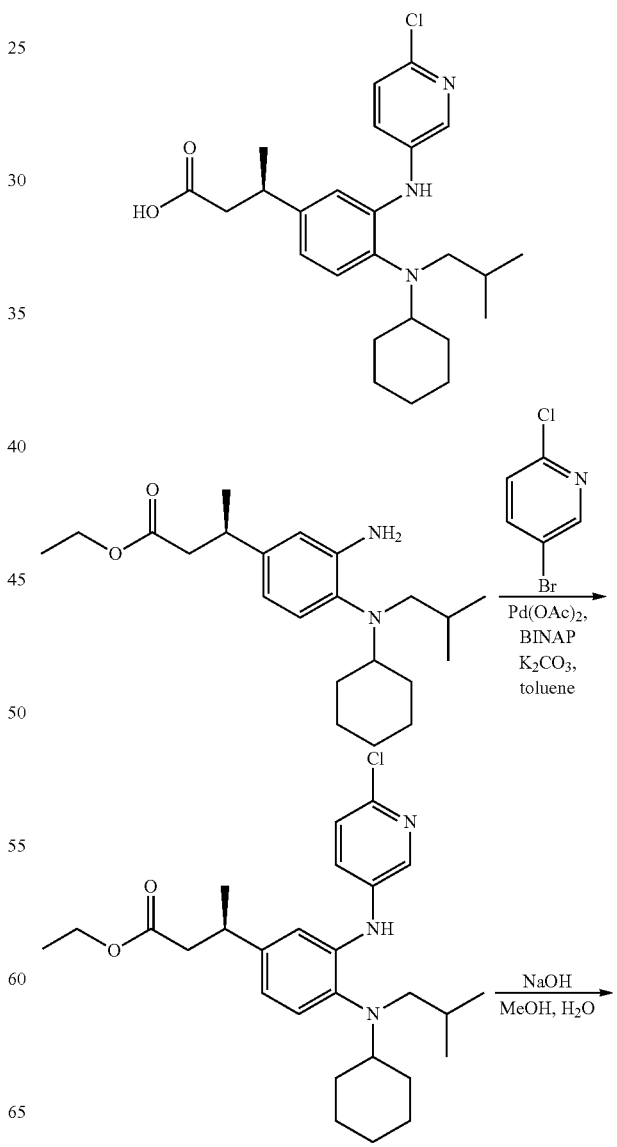

225

-continued

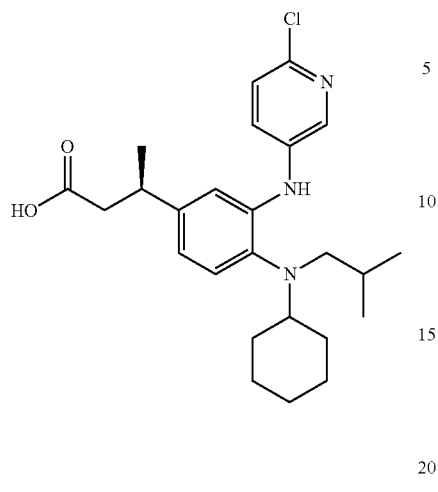

Preparation of ethyl (R)-3-(3-((6-chloropyridin-3-yl)amino)-4-(cyclohexyl(iso butyl)amino)phenyl)butanoate

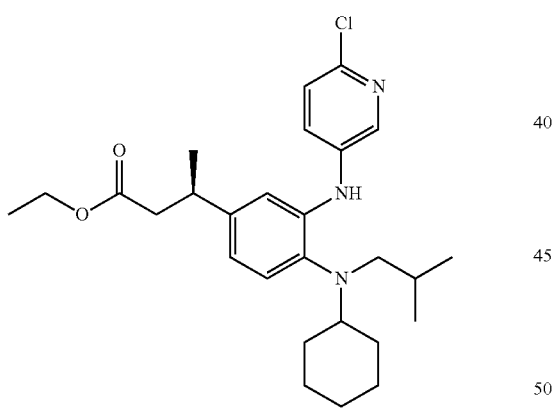

A mixture of ethyl (R)-3-(3-amino-4-(cyclohexyl(isobutyl)amino)phenyl)butanoate (150 mg, 0.42 mmol), 5-bromo-2-chloropyridine (160 mg, 0.83 mmol), Pd(OAc)$_2$ (4 mg, 0.0067 mmol), BINAP (5 mg, 0.0075 mmol) and K$_2$CO$_3$ (172 mg, 1.25 mmol) in toluene (10 mL) was stirred at 130° C. under N$_2$ atmosphere for 1.5 hr in macrowave apparatus. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (160 mg, 82% yield). LCMS (ESI) m/z calcd for C$_{27}$H$_{38}$ClN$_3$O$_2$: 471.27. Found: 472.51/474.46 (M/M+2)$^+$.

226

Preparation of (R)-3-(3-((6-chloropyridin-3-yl)amino)-4-(cyclohexyl(isobutyl) amino)phenyl)butanoic Acid

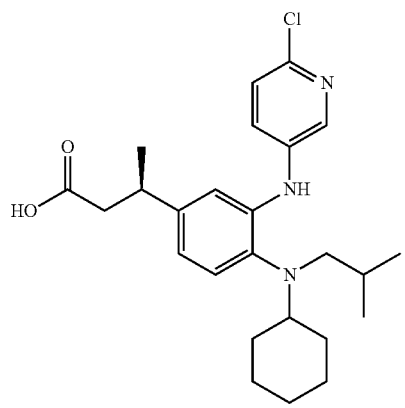 [SMILES: CC(C)CN(c1ccc([C@H](C)CC(=O)O)cc1Nc1ccc(Cl)nc1)C1CCCCC1]

To a solution of ethyl (R)-3-(3-((6-chloropyridin-3-yl)amino)-4-(cyclohexyl(isobutyl) amino)phenyl)butanoate (160 mg, 0.339 mmol) in MeOH (3 mL) was added 1N NaOH aq. (0.5 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (70 mg, 47% yield) as a white powder. $^1$H NMR (400 MHz, CDCl$_3$) δ 8.24 (d, J=2.9 Hz, 1H), 7.40 (dd, J=8.6, 3.0 Hz, 1H), 7.21 (d, J=8.6 Hz, 1H), 7.09 (dd, J=5.0, 3.0 Hz, 2H), 7.04 (s, 1H), 6.75 (dd, J=8.2, 1.9 Hz, 1H), 3.26-3.19 (m, 1H), 2.85-2.70 (m, 2H), 2.66-2.47 (m, 3H), 1.85-1.67 (m, 4H), 1.58-1.52 (m, 1H), 1.47-1.40 (m, 1H), 1.35-1.24 (m, 5H), 1.15-0.97 (m, 3H), 0.83 (d, J=6.5 Hz, 6H). LCMS (ESI) m/z calcd for C$_{25}$H$_{34}$ClN$_3$O$_2$: 443.23. Found: 444.43/446.51 (M/M+2)$^+$.

Example 75

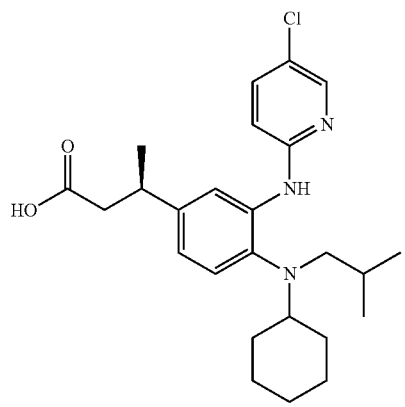

227

-continued

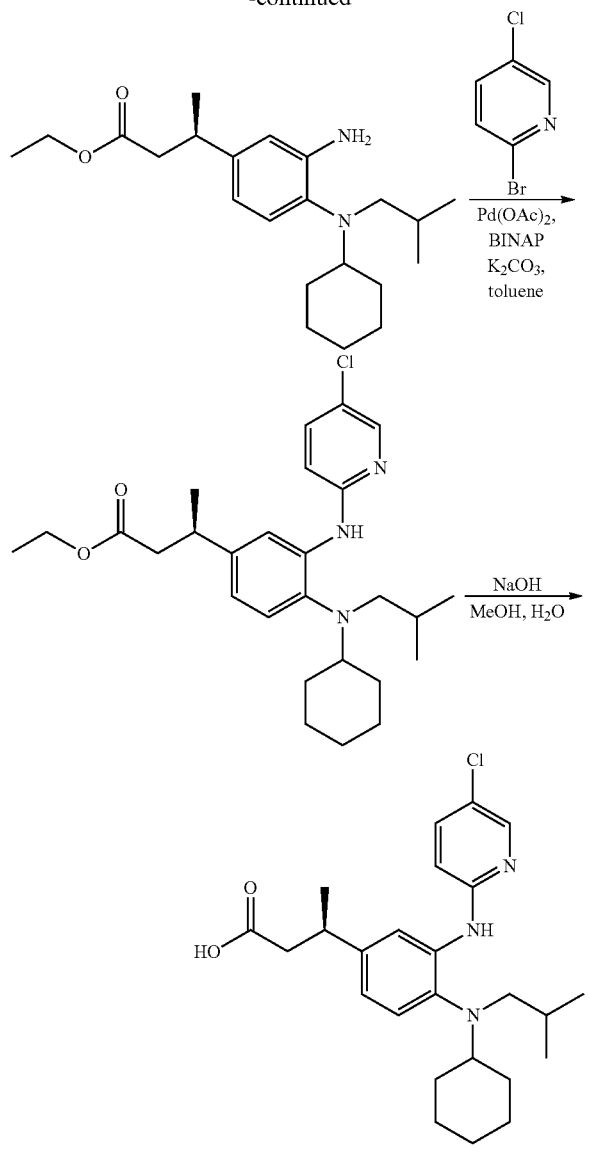

Preparation of ethyl (R)-3-(3-((5-chloropyridin-2-yl) amino)-4-(cyclohexyl(iso butyl)amino)phenyl)butanoate

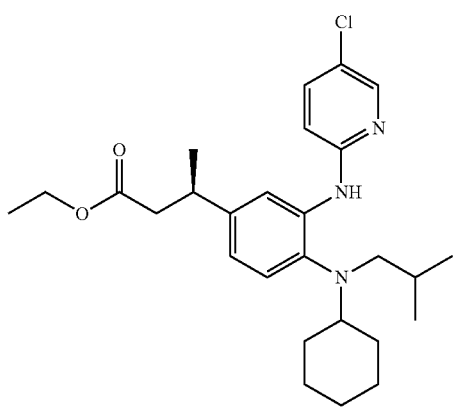 [SMILES: CCOC(=O)C[C@@H](C)c1ccc(N(CC(C)C)C2CCCCC2)c(Nc2ccc(Cl)cn2)c1]

228

A mixture of ethyl (R)-3-(3-amino-4-(cyclohexyl (isobutyl)amino)phenyl)butanoate (150 mg, 0.42 mmol), 2-bromo-5-chloropyridine (160 mg, 0.83 mmol), Pd(OAc)$_2$ (4 mg, 0.0067 mmol), BINAP (5 mg, 0.0075 mmol) and K$_2$CO$_3$ (172 mg, 1.25 mmol) in toluene (10 mL) was stirred at 130° C. under N$_2$ atmosphere for 1.5 hr in macrowave apparatus. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (10 mg, 5% yield). LCMS (ESI) m/z calcd for C$_{27}$H$_{38}$ClN$_3$O$_2$: 471.27. Found: 472.63/474.37 (M/M+2)$^+$.

Preparation of (R)-3-(3-((5-chloropyridin-2-yl) amino)-4-(cyclohexyl(isobutyl) amino)phenyl)butanoic Acid

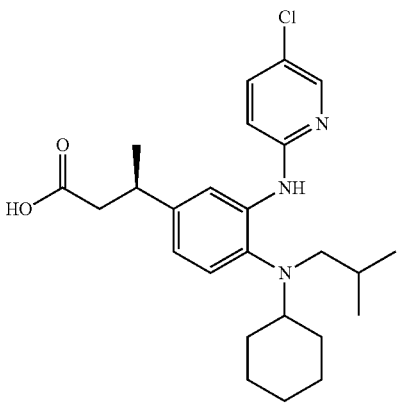 [SMILES: CC(C)CN(c1ccc([C@H](C)CC(=O)O)cc1Nc1ccc(Cl)cn1)C1CCCCC1]

To a solution of ethyl (R)-3-(3-((5-chloropyridin-2-yl) amino)-4-(cyclohexyl(isobutyl) amino)phenyl)butanoate (20 mg, 0.042 mmol) in MeOH (3 mL) was added 1N NaOH aq. (0.5 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (5 mg, 26% yield) as a white powder. $^1$H NMR (400 MHz, CDCl$_3$) δ 8.19 (s, 1H), 8.14-7.97 (m, 2H), 7.45 (dd, J=8.8, 2.5 Hz, 1H), 7.08 (d, J=8.2 Hz, 1H), 6.85-6.68 (m, 2H), 3.32-3.24 (m, 1H), 2.91-2.77 (m, 2H), 2.75-2.57 (m, 3H), 1.90-1.72 (m, 4H), 1.57-1.47 (m, 2H), 1.37-1.29 (m, 5H), 1.16-1.02 (m, 3H), 0.85 (d, J=6.6 Hz, 6H). LCMS (ESI) m/z calcd for C$_{25}$H$_{34}$ClN$_3$O$_2$: 443.23. Found: 444.35/446.24 (M/M+2)$^+$.

Example 76

Preparation of ethyl (R)-3-(4-(cyclohexyl(isobutyl) amino)-3-((5-(trifluoromethyl) pyridin-2-yl)amino) phenyl)butanoate

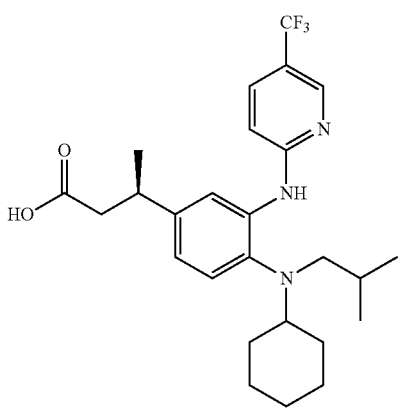

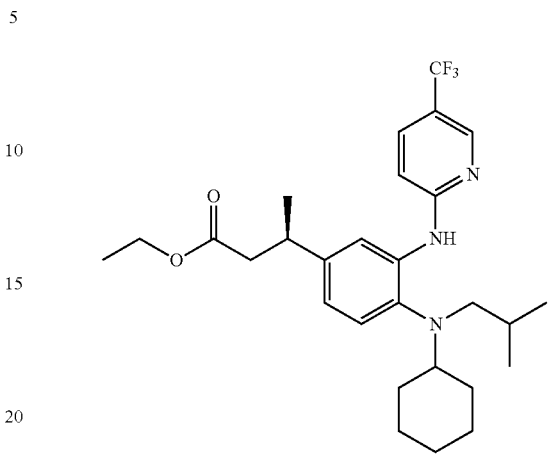

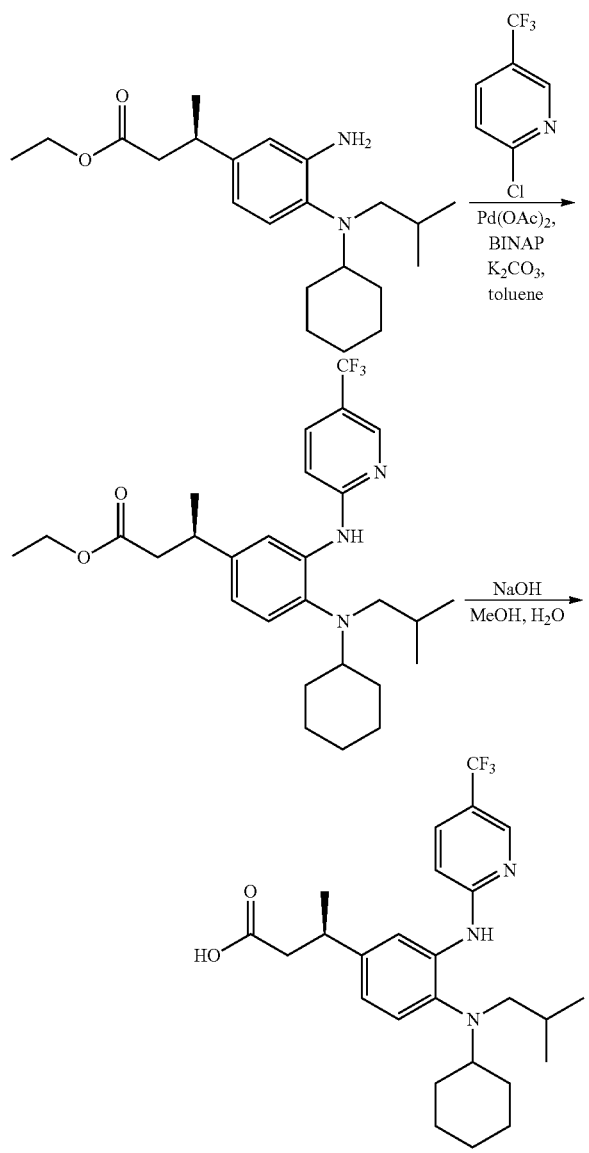

A mixture of ethyl (R)-3-(3-amino-4-(cyclohexyl (isobutyl)amino)phenyl)butanoate (150 mg, 0.42 mmol), 2-chloro-5-(trifluoromethyl)pyridine (151 mg, 0.83 mmol), Pd(OAc)$_2$ (4 mg, 0.0067 mmol), BINAP (5 mg, 0.0075 mmol) and K$_2$CO$_3$ (172 mg, 1.25 mmol) in toluene (10 mL) was stirred at 130° C. under N$_2$ atmosphere for 1 hr in macrowave apparatus. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (110 mg, 52% yield). LCMS (ESI) m/z calcd for C$_{28}$H$_{38}$F$_3$N$_3$O$_2$: 505.29. Found: 506.56 (M+1)$^+$.

Preparation of (R)-3-(4-(cyclohexyl(isobutyl) amino)-3-((5-(trifluoromethyl) pyridin-2-yl)amino) phenyl)butanoic Acid

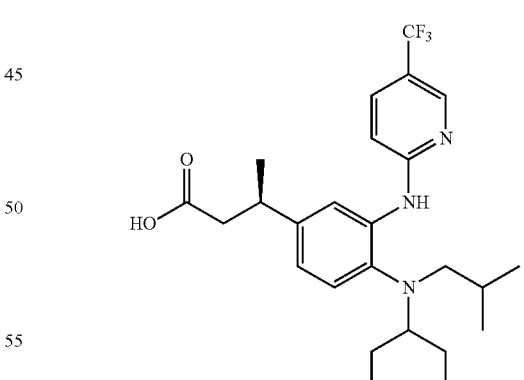

To a solution of ethyl (R)-3-(4-(cyclohexyl(isobutyl) amino)-3-((5-(trifluoromethyl) pyridin-2-yl)amino)phenyl) butanoate (110 mg, 0.218 mmol) in MeOH (3 mL) was added 1N NaOH aq. (0.5 mL). After stirred at rt overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H₂O with 0.1% formic acid) to afford the title compound (59 mg, 57% yield) as a white powder. $^1$H NMR (400 MHz, CDCl₃) δ 8.51 (s, 1H), 8.35 (s, 1H), 8.16 (d, J=1.9 Hz, 1H), 7.66 (dd, J=8.8, 2.3 Hz, 1H), 7.11 (d, J=8.2 Hz, 1H), 6.84 (dd, J=8.1, 2.0 Hz, 1H), 6.77 (d, J=8.8 Hz, 1H), 3.33-3.25 (m, 1H), 2.81 (d, J=6.7 Hz, 2H), 2.74-2.53 (m, 3H), 1.89-1.80 (m, 2H), 1.75-1.66 (m, 2H), 1.58-1.43 (m, 2H), 1.39-1.26 (m, 5H), 1.15-0.97 (m, 3H), 0.85 (d, J=6.6 Hz, 6H). LCMS (ESI) m/z calcd for $C_{26}H_{34}F_3N_3O_2$: 477.26. Found: 476.22 (M−1)⁻.

Example 77

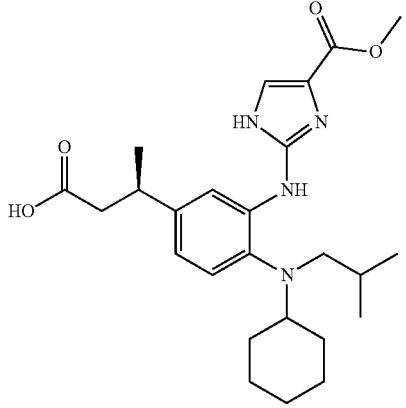 [SMILES: COC(=O)c1c[nH]c(Nc2cc([C@H](C)CC(=O)O)ccc2N(CC(C)C)C2CCCCC2)n1]

Step A (R)-ethyl 3-(4-(cyclohexyl(isobutyl)amino)-3-((4-(trifluoromethyl)-1-((2-(trimethylsilyl)ethoxy)methyl)-1H-imidazol-2-yl)amino)phenyl)butanoate

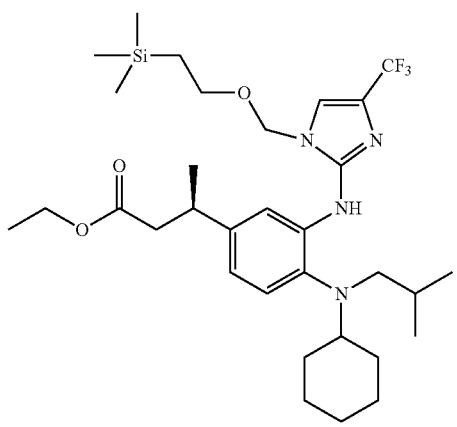 [SMILES: CCOC(=O)C[C@@H](C)c1ccc(N(CC(C)C)C2CCCCC2)c(Nc2nc(C(F)(F)F)cn2COCC[Si](C)(C)C)c1]

A mixture of (R)-ethyl 3-(3-amino-4-(cyclohexyl(isobutyl)amino)phenyl)butanoate (0.079 g, 0.219 mmol), 2-bromo-4-(trifluoromethyl)-1-((2-(trimethylsilyl)ethoxy)methyl)-1H-imidazole (0.0757 g, 0.219 mmol), Pd₂dba₃ (0.040 g, 0.044 mmol), cesium carbonate (0.357 g, 1.096 mmol), and Xantphos (0.051 g, 0.088 mmol) was flushed with nitrogen and then stirred in toluene (3.13 ml) and heated at 100° C. for 5 h, then filtered through celite, evaporated, and purified by silica gel chromatography (0-30% EtOAc/hexanes) to afford (R)-ethyl 3-(4-(cyclohexyl(isobutyl)amino)-3-((4-(trifluoromethyl)-1-((2-(trimethylsilyl)ethoxy)methyl)-1H-imidazol-2-yl)amino)phenyl)butanoate (73.5 mg, 54%). LCMS (M+H)⁺: m/z=625.5.

Step B (R)-3-(4-(cyclohexyl(isobutyl)amino)-3-((4-(methoxycarbonyl)-1H-imidazol-2-yl)amino)phenyl)butanoic Acid

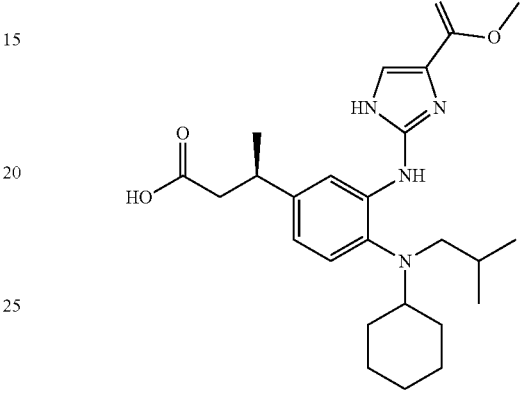

(R)-ethyl 3-(4-(cyclohexyl(isobutyl)amino)-3-((4-(trifluoromethyl)-1-((2-(trimethylsilyl)ethoxy)methyl)-1H-imidazol-2-yl)amino)phenyl)butanoate (73.5 mg, 0.118 mmol) was treated with TFA and then subjected to base hydrolysis in MeOH as previously described and purified by reverse phase chromatography (10-100% CH₃CN/H₂O (0.1% formic acid)) to afford the title compound (0.0346 g, 64%) as a white solid. LCMS (M+H)⁺: m/z=457.3.

$^1$H NMR (400 MHz, CD₃OD) δ ppm 7.77 (d, J=2.0 Hz, 1H), 7.45 (s, 1H), 7.11 (d, J=8.2 Hz, 1H), 6.80 (dd, J=8.2, 1.8 Hz, 1H), 3.81 (s, 3H), 3.13-3.25 (m, 1H), 2.82 (br. s., 2H), 2.45-2.67 (m, 3H), 1.89 (d, J=10.9 Hz, 2H), 1.72 (d, J=12.5 Hz, 2H), 1.55 (d, J=10.7 Hz, 1H), 1.22-1.47 (m, 6H), 0.99-1.22 (m, 3H), 0.82 (d, J=6.6 Hz, 6H).

Example 78

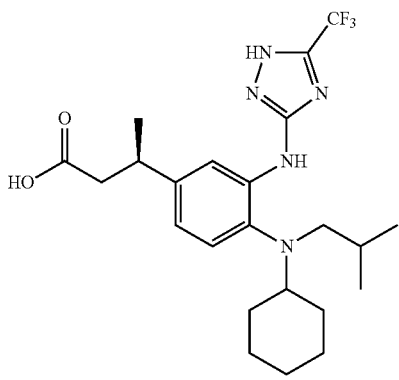

Step A

(R)-ethyl 3-(4-(cyclohexyl(isobutyl)amino)-3-((5-(trifluoromethyl)-1-((2-(trimethylsilyl)ethoxy)methyl)-1H-1,2,4-triazol-3-yl)amino)phenyl)butanoate

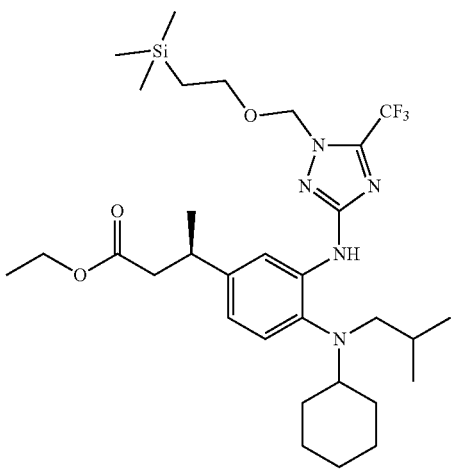 [SMILES: CCOC(=O)C[C@@H](C)c1ccc(N(CC(C)C)C2CCCCC2)c(Nc2nc(C(F)(F)F)n(COCC[Si](C)(C)C)n2)c1]

A mixture of (R)-ethyl 3-(3-amino-4-(cyclohexyl(isobutyl)amino)phenyl)butanoate (0.088 g, 0.244 mmol), 3-bromo-5-(trifluoromethyl)-1-((2-(trimethylsilyl)ethoxy)methyl)-1H-1,2,4-triazole (0.0845 g, 0.244 mmol), Pd$_2$dba$_3$ (0.045 g, 0.049 mmol), cesium carbonate (0.398 g, 1.220 mmol), and Xantphos (0.056 g, 0.098 mmol) was flushed with nitrogen and then stirred in toluene (3.5 mL) and heated at 100° C. for 3 h. The reaction mixture was filtered through celite, evaporated, and purified by silica gel chromatography (0-30% EtOAc/hexanes) to afford (R)-ethyl 3-(4-(cyclohexyl(isobutyl)amino)-3-((5-(trifluoromethyl)-1-((2-(trimethylsilyl)ethoxy)methyl)-1H-1,2,4-triazol-3-yl)amino)phenyl)butanoate (110.8 mg, 73%). $^1$H NMR (400 MHz, CDCl$_3$) δ ppm 8.66 (s, 1H), 8.22 (s, 1H), 7.12 (d, J=8.2 Hz, 1H), 6.83 (d, J=8.1 Hz, 1H), 5.44 (s, 2H), 4.11 (q, J=7.1 Hz, 2H), 3.62 (t, J=8.5 Hz, 2H), 3.30 (m, J=7.1 Hz, 1H), 2.90-3.03 (m, 1H), 2.48-2.70 (m, 4H), 1.93 (d, J=11.4 Hz, 2H), 1.74 (d, J=9.3 Hz, 2H), 1.60 (s, 1H), 0.74-1.48 (m, 20H), 0.02 (s, 9H).

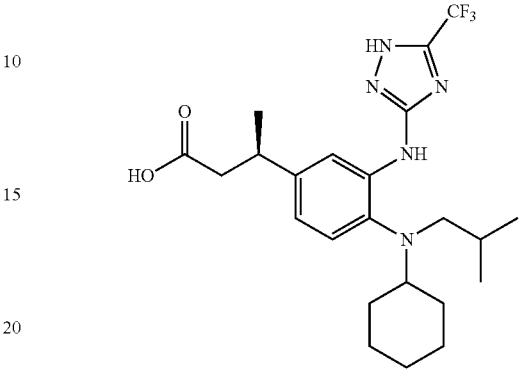

Step B

(R)-3-(4-(cyclohexyl(isobutyl)amino)-3-((5-(trifluoromethyl)-1H-1,2,4-triazol-3-yl)amino)phenyl)butanoic Acid (R)-ethyl 3-(4-(cyclohexyl(isobutyl)amino)-3-((5-(trifluoromethyl)-1-((2-(trimethylsilyl)ethoxy)methyl)-1H-1,2,4-triazol-3-yl)amino)phenyl)butanoate (110.8 mg, 0.177 mmol) was treated with TFA and then subjected to base hydrolysis as previously described and purified by reverse phase chromatography (10-100% CH$_3$CN/H$_2$O (0.1% formic acid)) to afford the title compound (0.0474 g, 57%) as a white solid. LCMS (M+H)$^+$: m/z=468.3.

$^1$H NMR (400 MHz, CD$_3$OD) δ ppm 7.96 (s, 1H), 7.20 (d, J=8.1 Hz, 1H), 6.91 (d, J=8.1 Hz, 1H), 3.18-3.29 (m, 1H), 2.86 (d, J=6.6 Hz, 2H), 2.49-2.70 (m, 3H), 1.93 (d, J=11.5 Hz, 2H), 1.76 (d, J=12.1 Hz, 2H), 1.59 (d, J=11.7 Hz, 1H), 1.02-1.47 (m, 9H), 0.86 (d, J=6.4 Hz, 6H).

Example 79

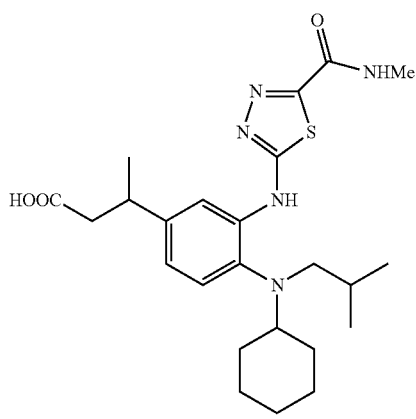

235

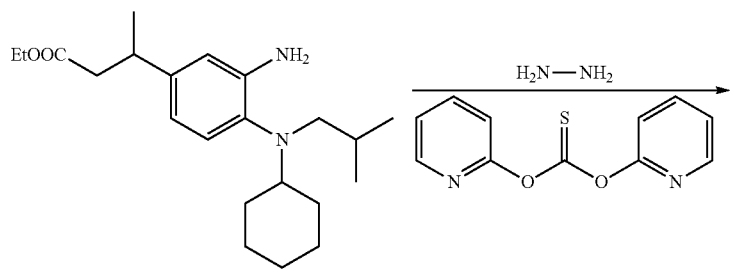

236

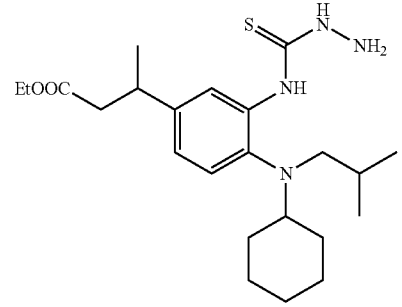 [SMILES: CCOC(=O)CC(C)c1ccc(N(CC(C)C)C2CCCCC2)c(NC(=S)NN)c1]

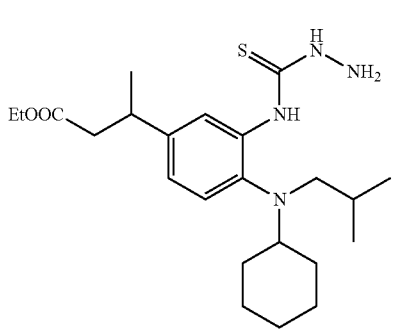

Preparation of ethyl 3-(4-(cyclohexyl(isobutyl)amino)-3-(hydrazinecarbothioamido)phenyl)butanoate

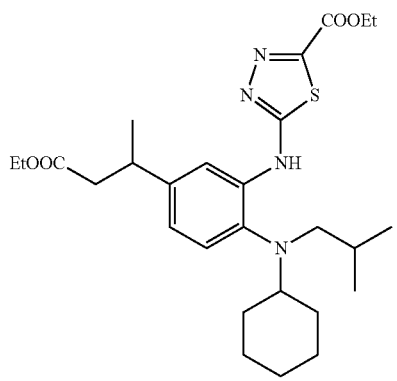 [SMILES: CCOC(=O)CC(C)c1ccc(N(CC(C)C)C2CCCCC2)c(Nc2nnc(C(=O)OCC)s2)c1]

Preparation of ethyl 5-((2-(cyclohexyl(isobutyhamino)-5-(4-ethoxy-4-oxobutan-2-yl)phenyl)amino)-1,3,4-thiadiazole-2-carboxylate To a solution of ethyl 3-(3-amino-4-(cyclohexyl(isobutyl)amino)phenyl)butanoate (705 mg, 1.95 mmol) in $CH_2Cl_2$ (10 mL) was added O,O-di(pyridin-2-yl) carbonothioate (477 mg, 2.05 mmol) and the mixture was stirred at ambient temperature for 1 h. The mixture was concentrated and dried in vacuo to provide a tan solid. To this solid was added a solution of hydrazine (0.113 mL, 2.34 mmol) in iPrOH (7 mL) and the mixture was stirred at ambient temperature for 1 h. The mixture was concentrated and purified on silica gel (EtOAc/hexanes 0-30%) to provide the title compound (366 mg, 0.81 mmol, 41.4% yield). LCMS (ESI) m/z calcd for $C_{23}H_{38}N_4O_2S$: 434.27. Found: 435.4 (M+1).

To a solution of ethyl 3-(4-(cyclohexyl(isobutyl)amino)-3-(hydrazinecarbothioamido)phenyl)butanoate (366 mg, 0.84 mmol) in $CH_2Cl_2$ (10 mL) at 0° C. was added dropwise a solution of ethyl 2-chloro-2-oxoacetate (0.094 mL, 0.84 mmol) in $CH_2Cl_2$ (2 mL). The mixture was concentrated and the resulting yellow foam was treated with sulfuric acid (1.0 mL, 18.76 mmol). After 20 min ice was added and a yellow solid appeared. The mixture was extracted with EtOAc and the organic phase was washed with saturated $NaHCO_3$/water, dried, concentrated and purified on silica gel (EtOAc/hexanes 0-10%) to provide the title compound (320 mg, 0.607 mmol, 72.1% yield) as a yellow oil. $^1H$ NMR (400

MHz, CDCl₃) δ 9.25 (br. s., 1H), 7.65 (s, 1H), 7.15 (d, J=8.0 Hz, 1H), 6.92 (dd, J=8.0, 1.5 Hz, 1H), 4.49 (q, J=7.0 Hz, 2H), 4.10 (q, J=7.2 Hz, 2H), 3.39-3.22 (m, 1H), 2.80 (br. s., 2H), 2.70-2.46 (m, 3H), 1.93-1.81 (m, 2H), 1.73 (d, J=12.5 Hz, 2H), 1.64-1.52 (m, 1H), 1.50-0.92 (m, 15H), 0.83 (d, J=6.6 Hz, 6H). LCMS (ESI) m/z calcd for $C_{27}H_{40}N_4O_4S$: 516.27. Found: 517.5 (M+1).

Preparation of 3-(4-(cyclohexyl(isobutyhamino)-3-((5-(methylcarbamoyl)-1,3,4-thiadiazol-2-yl)amino)phenyl)butanoic Acid

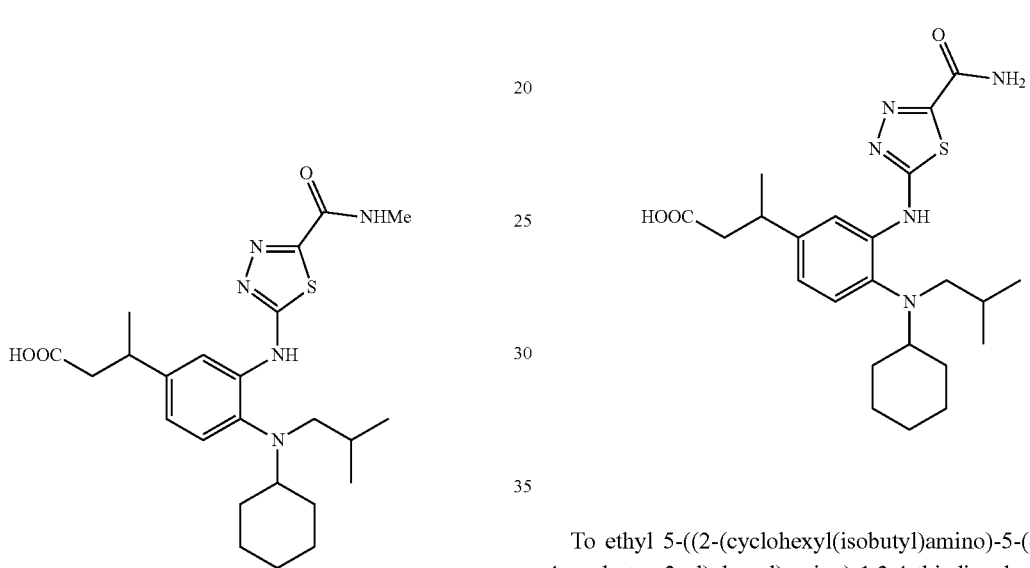

To a solution of ethyl 5-((2-(cyclohexyl(isobutyl)amino)-5-(4-ethoxy-4-oxobutan-2-yl)phenyl)amino)-1,3,4-thiadiazole-2-carboxylate (24 mg, 0.046 mmol) in THF (1 mL) was added 40% MeNH₂/water (0.2 mL) and the mixture was heated at 70° C. for 20 min. The mixture was concentrated, coevaporated with MeCN and dried in vacuo to provide ethyl 3-(4-(cyclohexyl(isobutyl)amino)-3-((5-(methylcarbamoyl)-1,3,4-thiadiazol-2-yl)amino)phenyl)butanoate (25 mg, 0.047 mmol, 102% yield) as a yellow glass. LCMS (ESI) m/z calcd for $C_{26}H_{39}N_5O_3S$: 501.3. Found: 502.4 (M+1). This residue was dissolved in THF (0.5 mL)/EtOH (0.5 mL) and lithium hydroxide (0.5 mL, 0.5 mmol) (1 M/water) was added and the mixture was stirred at ambient temperature for 1 h and then at 40° C. for 1 h. The mixture was concentrated and purified by HPLC (RP C18, MeCN/water 10-100%, 0.1% formic acid) to provide the title compound (6 mg, 0.011 mmol, 22.9% yield) as a yellow solid. ¹H NMR (400 MHz, DMSO-d₆) δ 12.5-12.3 (br. s., 1H), 9.32 (br. s., 1H), 8.88-8.80 (m, 1H), 7.79 (s, 1H), 7.16 (d, J=8.2 Hz, 1H), 6.98 (d, J=8.2 Hz, 1H), 3.18-3.05 (m, 1H), 2.80-2.75 (m, 4H), 2.70-2.30 (m, 4H), 1.85-1.75 (m, 2H), 1.65 (br. s., 2H), 1.48-1.44 (m, 1H), 1.37-1.15 (m, 6H), 1.11-0.90 (m, 3H), 0.89-0.74 (m, 6H). LCMS (ESI) m/z calcd for $C_{24}H_{35}N_5O_3S$: 473.2. Found: 474.1 (M+1).

Example 80

Preparation of 3-(3-((5-carbamoyl-1,3,4-thiadiazol-2-yl)amino)-4-(cyclohexyl(isobutyl)amino)phenyl)butanoic To ethyl 5-((2-(cyclohexyl(isobutyl)amino)-5-(4-ethoxy-4-oxobutan-2-yl)phenyl)amino)-1,3,4-thiadiazole-2-carboxylate (44 mg, 0.085 mmol) in 1,4-dioxane (0.7 mL) was added ammonium hydroxide (0.3 mL, 2.157 mmol) and the mixture was stirred at ambient temperature for 18 h. The mixture was concentrated, coevaporated with MeCN, and dried in vacuo to provide ethyl 3-(3-((5-carbamoyl-1,3,4-thiadiazol-2-yl)amino)-4-(cyclohexyl(isobutyl)amino)phenyl)butanoate (41 mg, 0.082 mmol, 96% yield) as a glass. LCMS (ESI) m/z calcd for $C_{25}H_{37}N_5O_3S$: 487.3. Found: 488.4 (M+1). To a solution of this residue in 1,4-Dioxane (1 mL)/Ethanol (0.5 mL) was added lithium hydroxide (0.420 mL, 0.841 mmol) (2 M/water) and the mixture was stirred at ambient temperature for 18 h. The mixture was partitioned between EtOAc and cold 1N HCl/water. The organic phase was dried (Na₂SO₄), concentrated and purified by HPLC (RP C18, 10-100% MeCN/water, 0.1% formic acid) to provide the title compound (6 mg, 0.012 mmol, 14.75% yield) as a yellow solid. ¹H NMR (400 MHz, DMSO-d₆) δ ppm 12.20 (br. s., 1H), 9.33 (s, 1H), 8.25 (s, 1H), 7.86-7.78 (m, 2H), 7.16 (d, J=8.2 Hz, 1H), 6.98 (d, J=8.2 Hz, 1H), 3.15-3.11 (m, 1H), 2.88-2.55 (m, 4H), 1.86-1.76 (m, 2H), 1.72-1.63 (m, 2H), 1.50 (br. s., 1H), 1.39-1.14 (m, 7H), 1.12-0.92 (m, 3H), 0.80 (d, J=6.6 Hz, 6H). LCMS (ESI) m/z calcd for $C_{23}H_{33}N_5O_3S$: 459.2. Found: 460.4 (M+1).

Example 81

Preparation of (R)-3-(3-((5-Carbamoyl-1,3,4-thiadiazol-2-yl)amino)-4-(cyclohexyl(isobutyl)amino) phenyl)butanoic

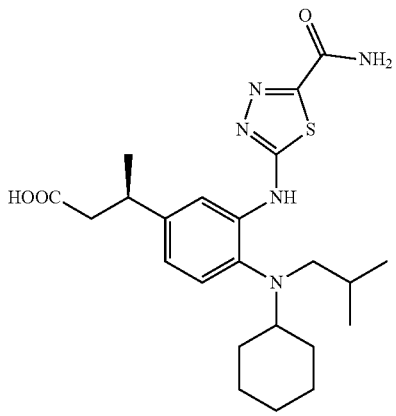 [SMILES: CC(C)CN(c1ccc([C@H](C)CC(=O)O)cc1Nc1nnc(C(N)=O)s1)C1CCCCC1]

This compound was prepared as in Example 80 from (R)-ethyl 5-((2-(cyclohexyl(isobutyl)amino)-5-(4-ethoxy-4-oxobutan-2-yl)phenyl)amino)-1,3,4-thiadiazole-2-carboxylate to provide the title compound as a yellow solid. $^1$H NMR (400 MHz, DMSO-$d_6$) δ ppm 12.20 (br. s., 1H), 9.33 (s, 1H), 8.25 (s, 1H), 7.86-7.78 (m, 2H), 7.16 (d, J=8.2 Hz, 1H), 6.98 (d, J=8.2 Hz, 1H), 3.15-3.11 (m, 1H), 2.88-2.55 (m, 4H), 1.86-1.76 (m, 2H), 1.72-1.63 (m, 2H), 1.50 (br. s., 1H), 1.39-1.14 (m, 7H), 1.12-0.92 (m, 3H), 0.80 (d, J=6.6 Hz, 6H). LCMS (ESI) m/z calcd for $C_{23}H_{33}N_5O_3S$: 459.2. Found: 460.4 (M+1).

Example 82

Step A (R)-ethyl 3-(4-(cyclohexyl(isobutyl)amino)-3-(3-(2-methoxyacetyl)thioureido)phenyl)butanoate

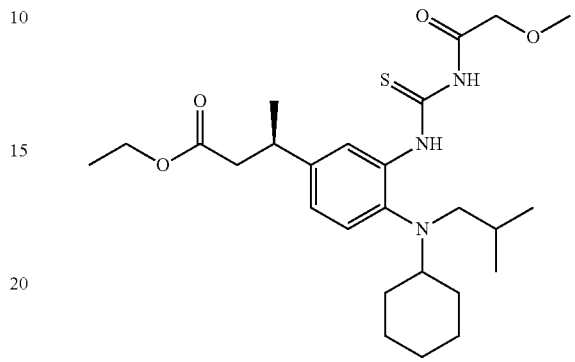

2-methoxyacetyl chloride (0.124 g, 1.139 mmol) dropwise to a solution of (R)-ethyl 3-(4-(cyclohexyl(isobutyl)amino)-3-thioureidophenyl)butanoate (0.3186 g, 0.759 mmol) and pyridine (0.123 ml, 1.519 mmol) in $CH_2Cl_2$ (7.59 ml) at 0° C. The reaction mixture was stirred at RT for 2 h, evaporated and purified by silica gel chromatography (0-40% EtOAc/hexanes) to afford (R)-ethyl 3-(4-(cyclohexyl(isobutyl)amino)-3-(3-(2-methoxyacetyl)thioureido)phenyl)butanoate (353.2 mg, 95%) as a yellow oil. LCMS (M+H)$^+$: m/z=492.4.

Step B (R)-ethyl 3-(4-(cyclohexyl(isobutyl)amino)-3-((5-(methoxymethyl)-4H-1,2,4-triazol-3-yl)amino)phenyl)butanoate

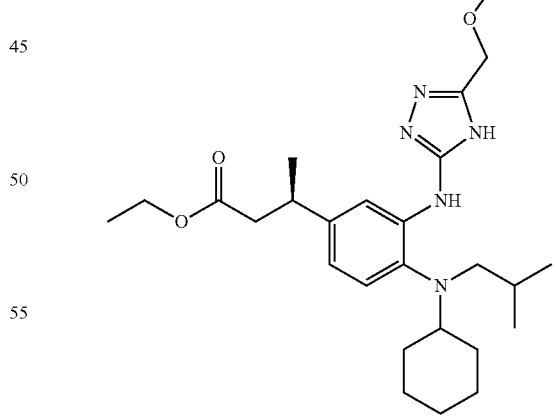

Hydrazine hydrate (0.211 ml, 4.31 mmol) was added to a solution of (R)-ethyl 3-(4-(cyclohexyl(isobutyl)amino)-3-(3-(2-methoxyacetyl)thioureido)phenyl)butanoate (0.353 g, 0.718 mmol) in chloroform (5.5 ml). The reaction mixture was heated at 80° C. for 8 h, then concentrated and purified by silica gel chromatography (0-80% EtOAc/hexanes) to afford (R)-ethyl 3-(4-(cyclohexyl(isobutyl)amino)-3-((5-

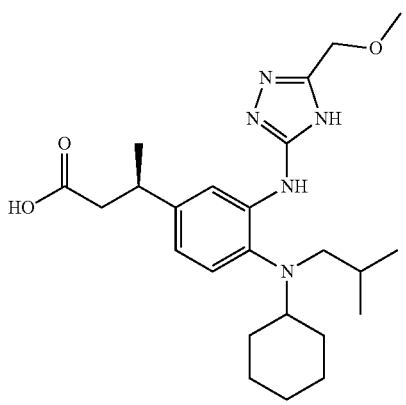 [SMILES: COCc1nnc(Nc2cc([C@H](C)CC(=O)O)ccc2N(CC(C)C)C2CCCCC2)[nH]1]

(methoxymethyl)-4H-1,2,4-triazol-3-yl)amino)phenyl)butanoate (91.3 mg, 27%) as a clear oil. LCMS (M+H)+: m/z=472.4.

Step C (R)-3-(4-(cyclohexyl(isobutyl)amino)-3-((5-(methoxymethyl)-4H-1,2,4-triazol-3-yl)amino)phenyl)butanoic Acid

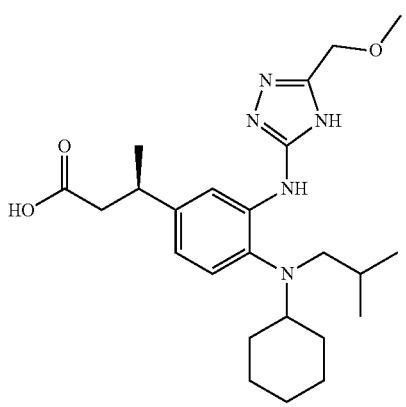

(R)-ethyl 3-(4-(cyclohexyl(isobutyl)amino)-3-((5-(methoxymethyl)-4H-1,2,4-triazol-3-yl)amino)phenyl)butanoate (91.3 mg, 0.194 mmol) was subjected to base hydrolysis as previously described and purified by reverse phase chromatography (10-100% $CH_3CN/H_2O$ (0.1% formic acid)) to afford the title compound (0.0524 g, 61%) as a white solid. LCMS (M+H)+: m/z=444.4. $^1$H NMR (400 MHz, $CD_3OD$) δ ppm 7.95 (br. s., 1H), 7.14 (d, J=8.1 Hz, 1H), 6.79 (d, J=7.9 Hz, 1H), 4.52 (s, 2H), 3.46 (s, 3H), 3.16-3.27 (m, 1H), 2.85 (br. s., 2H), 2.48-2.69 (m, 3H), 1.93 (d, J=11.4 Hz, 2H), 1.75 (d, J=12.1 Hz, 2H), 1.58 (d, J=11.4 Hz, 1H), 1.25-1.47 (m, 6H), 1.03-1.25 (m, 3H), 0.86 (d, J=6.4 Hz, 6H).

Example 83

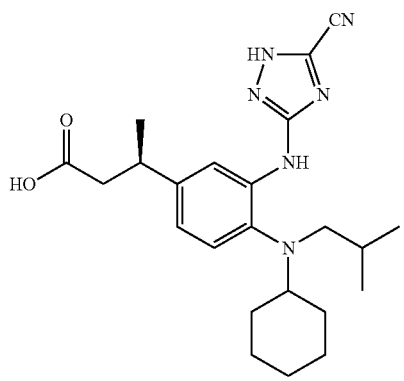

Step A 3-bromo-1-((2-(trimethylsilyl)ethoxy)methyl)-1H-1,2,4-triazole-5-carbonitrile

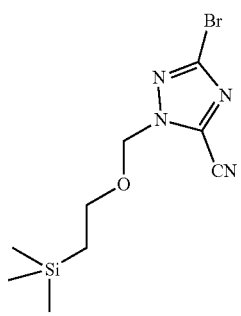 [SMILES: C[Si](C)(C)CCOCn1nc(Br)nc1C#N]

3-bromo-1H-1,2,4-triazole-5-carbonitrile (0.910 g, 5.26 mmol) was converted to 3-bromo-1-((2-(trimethylsilyl)ethoxy)methyl)-1H-1,2,4-triazole-5-carbonitrile (810.5 mg, 51%) following a previously described procedure. $^1$H NMR (400 MHz, $CDCl_3$) d ppm 5.56 (s, 2H), 3.68 (t, J=8.2 Hz, 2H), 0.95 (t, J=8.2 Hz, 2H), 0.02 (s, 9H).

Step B (R)-ethyl 3-(3-((5-cyano-1H-1,2,4-triazol-3-yl)amino)-4-(cyclohexyl(isobutyl)amino)phenyl)butanoate

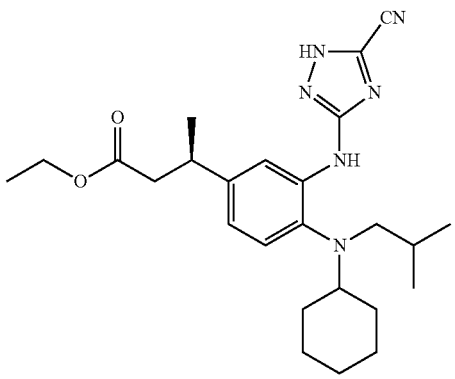 [SMILES: CCOC(=O)C[C@@H](C)c1ccc(N(CC(C)C)C2CCCCC2)c(Nc2n[nH]c(C#N)n2)c1]

A mixture of (R)-ethyl 3-(3-amino-4-(cyclohexyl(isobutyl)amino)phenyl)butanoate (0.100 g, 0.277 mmol), 3-bromo-1-((2-(trimethylsilyl)ethoxy)methyl)-1H-1,2,4-triazole-5-carbonitrile (0.101 g, 0.333 mmol), $Pd_2dba_3$ (0.051 g, 0.055 mmol), cesium carbonate (0.452 g, 1.387 mmol), and Xantphos (0.064 g, 0.111 mmol) was flushed with nitrogen and then stirred in toluene (4.0 mL) and heated at 100° C. for 2.5 h. The reaction mixture was filtered through celite, evaporated, purified by silica gel chromatography (0-30% EtOAc/hexanes) and treated with TFA as previously described to afford (R)-ethyl 3-(3-((5-cyano-1H-1,2,4-triazol-3-yl)amino)-4-(cyclohexyl(isobutyl)amino)phenyl)butanoate (67.4 mg, 54%). LCMS (M+H)+: m/z=453.4

Step C (R)-3-(3-((5-cyano-1H-1,2,4-triazol-3-yl)amino)-4-(cyclohexyl(isobutyl)amino)phenyl)butanoic Acid

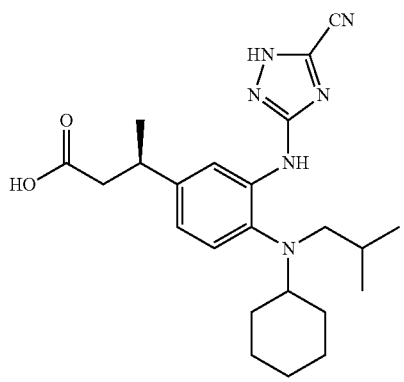 [SMILES: CC(C)CN(c1ccc([C@H](C)CC(=O)O)cc1Nc1n[nH]c(C#N)n1)C1CCCCC1]

(R)-ethyl 3-(3-((5-cyano-1H-1,2,4-triazol-3-yl)amino)-4-(cyclohexyl(isobutyl)amino)phenyl)butanoate (36.7 mg, 0.081 mmol) was subjected to base hydrolysis as previously described and purified by reverse phase chromatography (5-100% CH$_3$CN/H$_2$O (0.1% formic acid)) to afford the title compound (0.0223 g, 65%) as a white solid. LCMS (M+H)$^+$: m/z=425.3. $^1$H NMR (400 MHz, CD$_3$OD) δ ppm 7.95 (d, J=1.8 Hz, 1H), 7.17 (d, J=8.2 Hz, 1H), 6.88 (dd, J=8.2, 1.8 Hz, 1H), 3.17-3.26 (m, 1H), 2.82 (d, J=6.6 Hz, 2H), 2.48-2.66 (m, 3H), 1.89 (d, J=11.1 Hz, 2H), 1.73 (d, J=12.5 Hz, 2H), 1.56 (d, J=11.9 Hz, 1H), 1.01-1.41 (m, 9H), 0.82 (d, J=6.6 Hz, 6H).

Example 84

Step A (R)-ethyl 3-(3-((5-carbamoyl-1-((2-(trimethylsilyl)ethoxy)methyl)-1H-1,2,4-triazol-3-yl)amino)-4-(cyclohexyl(isobutyl)amino)phenyl)butanoate

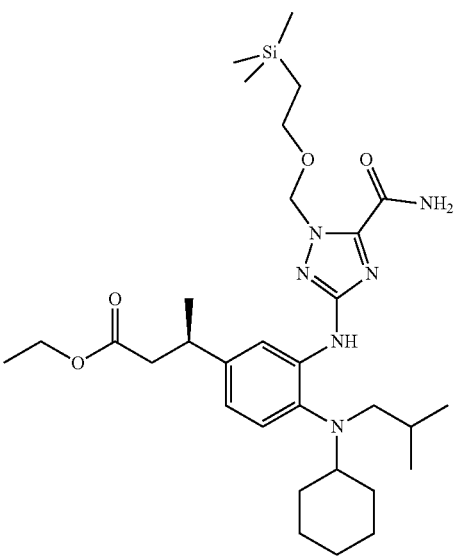 [SMILES: CCOC(=O)C[C@@H](C)c1ccc(N(CC(C)C)C2CCCCC2)c(Nc2nc(C(N)=O)n(COCC[Si](C)(C)C)n2)c1]

A solution of (R)-ethyl 3-(3-((5-cyano-1-((2-(trimethylsilyl)ethoxy)methyl)-1H-1,2,4-triazol-3-yl)amino)-4-(cyclohexyl(isobutyl)amino)phenyl)butanoate (0.194 g, 0.333 mmol), K$_2$CO$_3$ (0.046 g, 0.333 mmol), and urea hydrogen peroxide (0.376 g, 3.99 mmol) in acetone (2.77 ml) and water (1.387 ml) was stirred at RT overnight. The reaction mixture was diluted with EtOAc and the organic phase was isolated and dried (Na$_2$SO$_4$), filtered, evaporated, and purified by silica gel chromatography (0-50% EtOAc/hexanes) to afford (R)-ethyl 3-(3-((5-carbamoyl-1-((2-(trimethylsilyl)ethoxy)methyl)-1H-1,2,4-triazol-3-yl)amino)-4-(cyclohexyl(isobutyl)amino)phenyl)butanoate (177.9 mg, 89%) as a white foam. LCMS (M+H)$^+$: m/z=601.5.

Step B (R)-3-(3-((5-carbamoyl-1H-1,2,4-triazol-3-yl)amino)-4-(cyclohexyl(isobutyl)amino)phenyl)butanoic Acid

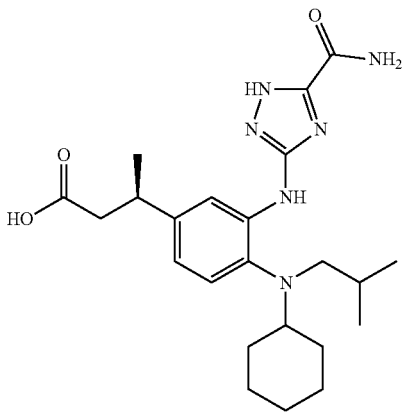 [SMILES: CC(C)CN(c1ccc([C@H](C)CC(=O)O)cc1Nc1n[nH]c(C(N)=O)n1)C1CCCCC1]

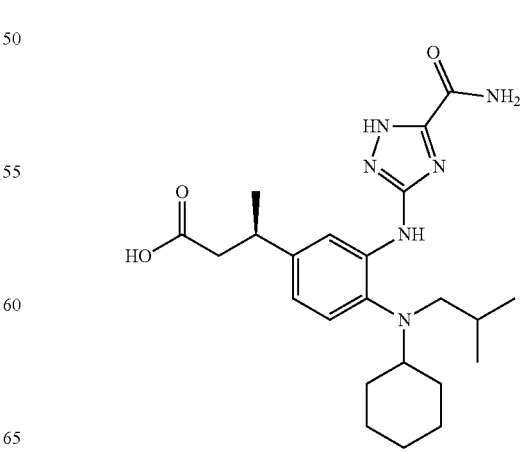

(R)-ethyl 3-(3-((5-carbamoyl-1-((2-(trimethylsilyl)ethoxy)methyl)-1H-1,2,4-triazol-3-yl)amino)-4-(cyclohexyl(isobutyl)amino)phenyl)butanoate (0.1779 g, 0.296 mmol) was treated with TFA and then subjected to base hydrolysis as previously described and purified by reverse phase chromatography (10-100% CH₃CN/H₂O (0.1% formic acid)) to afford the title compound (0.0768 g, 59%) as a white solid. LCMS (M+H)⁺: m/z=443.3. ¹H NMR (400 MHz, CD₃OD) δ ppm 8.05 (d, J=2.0 Hz, 1H), 7.13 (d, J=8.0 Hz, 1H), 6.81 (d, J=7.2 Hz, 1H), 3.17-3.27 (m, 1H), 2.82 (br. s., 2H), 2.48-2.67 (m, 3H), 1.90 (d, J=11.3 Hz, 2H), 1.72 (d, J=12.3 Hz, 2H), 1.55 (d, J=11.9 Hz, 1H), 1.23-1.42 (m, 6H), 0.99-1.22 (m, 3H), 0.82 (d, J=6.4 Hz, 6H).

Example 85

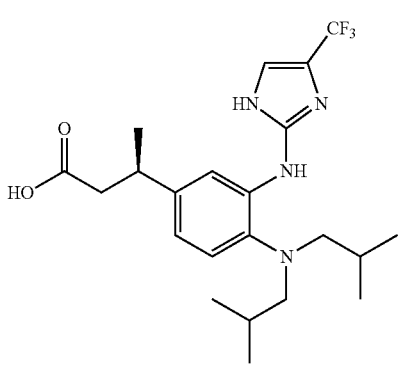 [SMILES: CC(C)CN(CC(C)C)c1ccc([C@H](C)CC(=O)O)cc1Nc1nc(C(F)(F)F)c[nH]1]

(R)-ethyl 3-(4-(diisobutylamino)-3-((4-(trifluoromethyl)-1-((2-(trimethylsilyl)ethoxy)methyl)-1H-imidazol-2-yl)amino)phenyl)butanoate

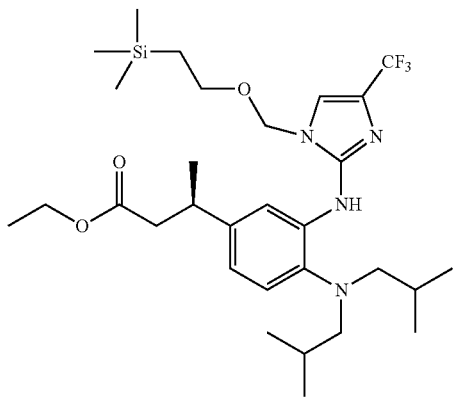 [SMILES: CCOC(=O)C[C@@H](C)c1ccc(N(CC(C)C)CC(C)C)c(Nc2nc(C(F)(F)F)cn2COCC[Si](C)(C)C)c1]

Step A
A mixture of (R)-ethyl 3-(3-amino-4-(diisobutylamino)phenyl)butanoate (0.073 g, 0.219 mmol), 2-bromo-4-(trifluoromethyl)-1-((2-(trimethylsilyl)ethoxy)methyl)-1H-imidazole (0.0757 g, 0.219 mmol), Pd₂dba₃ (0.040 g, 0.044 mmol), cesium carbonate (0.357 g, 1.096 mmol), and Xantphos (0.051 g, 0.088 mmol) was flushed with nitrogen and then stirred in toluene (3.13 ml) and heated at 100° C. for 6 h, then filtered through celite, evaporated, and purified by silica gel chromatography (0-30% EtOAc/hexanes) to afford (R)-ethyl 3-(4-(diisobutylamino)-3-((4-(trifluoromethyl)-1-((2-(trimethylsilyl)ethoxy)methyl)-1H-imidazol-2-yl)amino)phenyl)butanoate (106.2 mg, 81%). LCMS (M+H)⁺: m/z=599.6.

Step B (R)-3-(4-(diisobutylamino)-3-((4-(trifluoromethyl)-1-((2-(trimethylsilyl)ethoxy)methyl)-1H-imidazol-2-yl)amino)phenyl)butanoic acid

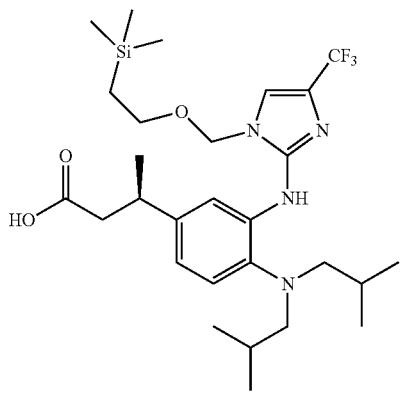 [SMILES: CC(C)CN(CC(C)C)c1ccc([C@H](C)CC(=O)O)cc1Nc1nc(C(F)(F)F)cn1COCC[Si](C)(C)C]

((R)-ethyl 3-(4-(diisobutylamino)-3-((4-(trifluoromethyl)-1-((2-(trimethylsilyl)ethoxy)methyl)-1H-imidazol-2-yl)amino)phenyl)butanoate (0.106 g, 0.177 mmol) was subjected to basic hydrolysis as previously described and purified by reverse phase chromatography (10-100% CH₃CN/H₂O (0.1% formic acid)) to afford (R)-3-(4-(diisobutylamino)-3-((4-(trifluoromethyl)-1-((2-(trimethylsilyl)ethoxy)methyl)-1H-imidazol-2-yl)amino)phenyl)butanoic acid (0.045 g, 45%). LCMS (M+H)⁺: m/z=571.1.

Step C (R)-3-(4-(diisobutylamino)-3-((4-(trifluoromethyl)-1H-imidazol-2-yl)amino)phenyl)butanoic Acid

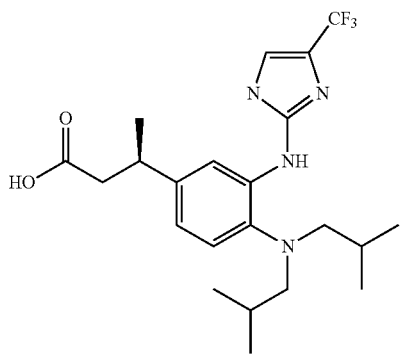 [SMILES: CC(C)CN(CC(C)C)c1ccc([C@H](C)CC(=O)O)cc1Nc1nc(C(F)(F)F)c[nH]1]

(R)-3-(4-(diisobutylamino)-3-((4-(trifluoromethyl)-1-((2-(trimethylsilyl)ethoxy)methyl)-1H-imidazol-2-yl)amino)phenyl)butanoic acid (0.025 g, 0.044 mmol) was stirred in 1 mL TFA for 2 h, evaporated to dryness, neutralized with Et₃N (1 mL), evaporated and partitioned between 1M citric acid and EtOAc. The organic phase was dried (Na₂SO₄), filtered, evaporated and purified by reverse phase chromatography (10-100% CH₃CN/H₂O (0.1% formic acid)) to afford the title compound (0.0175 g, 91%) as a white solid.

LCMS (M+H)⁺: m/z=441.1. ¹H NMR (400 MHz, CD₃OD) δ ppm 7.55 (d, J=2.0 Hz, 1H), 7.20 (d, J=1.4 Hz, 1H), 7.14 (d, J=8.2 Hz, 1H), 6.80 (dd, J=8.2, 1.8 Hz, 1H), 3.10-3.23 (m, 1H), 2.42-2.64 (m, 6H), 1.60-1.75 (m, 2H), 1.26 (d, J=7.0 Hz, 3H), 0.89 (d, J=6.6 Hz, 12H).

Example 86

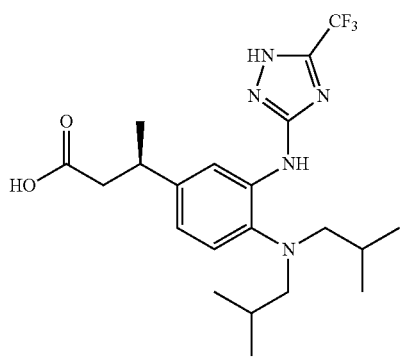 [SMILES: CC(C)CN(CC(C)C)c1ccc([C@H](C)CC(=O)O)cc1Nc1n[nH]c(C(F)(F)F)n1]

Step A (R)-ethyl 3-(4-(diisobutylamino)-3-((5-(trifluoromethyl)-1-((2-(trimethylsilyl)ethoxy)methyl)-1H-1,2,4-triazol-3-yl)amino)phenyl)butanoate

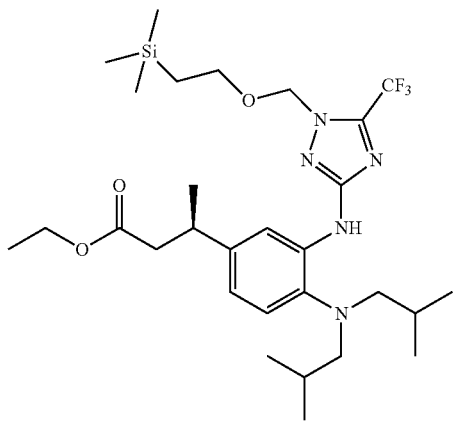 [SMILES: CCOC(=O)C[C@@H](C)c1ccc(N(CC(C)C)CC(C)C)c(Nc2nc(C(F)(F)F)n(COCC[Si](C)(C)C)n2)c1]

A mixture of (R)-ethyl 3-(3-amino-4-(diisobutylamino)phenyl)butanoate (0.082 g, 0.244 mmol), 3-bromo-5-(trifluoromethyl)-1-((2-(trimethylsilyl)ethoxy)methyl)-1H-1,2,4-triazole (0.0845 g, 0.244 mmol), Pd₂dba₃ (0.045 g, 0.049 mmol), cesium carbonate (0.398 g, 1.220 mmol), and Xantphos (0.056 g, 0.098 mmol) was flushed with nitrogen and then stirred in toluene (3.5 mL) and heated at 100° C. for 2.5 h. The reaction mixture was filtered through celite, evaporated, and purified by silica gel chromatography (0-30% EtOAc/hexanes) to afford (R)-ethyl 3-(4-(diisobutylamino)-3-((5-(trifluoromethyl)-1-((2-(trimethylsilyl)ethoxy)methyl)-1H-1,2,4-triazol-3-yl)amino)phenyl)butanoate (75 mg, 51%). LCMS (M+H)⁺: m/z=600.5.

Step B (R)-3-(4-(diisobutylamino)-3-((5-(trifluoromethyl)-1H-1,2,4-triazol-3-yl)amino)phenyl)butanoic Acid

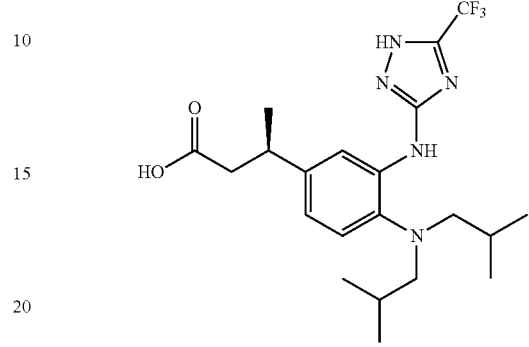

(R)-ethyl 3-(4-(diisobutylamino)-3-((5-(trifluoromethyl)-1-((2-(trimethylsilyl)ethoxy)methyl)-1H-1,2,4-triazol-3-yl)amino)phenyl)butanoate (75 mg, 0.125 mmol) was treated with TFA and then subjected to base hydrolysis as previously described and purified by reverse phase chromatography (5-100% CH₃CN/H₂O (0.1% formic acid)) to afford the title compound (0.0417 g, 76%) as a white solid. LCMS (M+H)⁺: m/z=442.3. ¹H NMR (400 MHz, CD₃OD) δ ppm 7.91 (s, 1H), 7.22 (d, J=8.2 Hz, 1H), 6.93 (d, J=8.1 Hz, 1H), 3.17-3.30 (m, 1H), 2.48-2.72 (m, 6H), 1.68 (m, 2H), 1.32 (d, J=7.0 Hz, 3H), 0.92 (d, J=6.4 Hz, 12H).

Example 87

(R)-3-(4-(diisobutylamino)-3-((5-(trifluoromethyl)-1,3,4-thiadiazol-2-yl)amino)phenyl)butanoic Acid

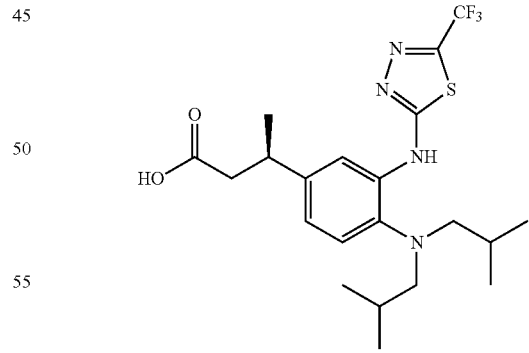

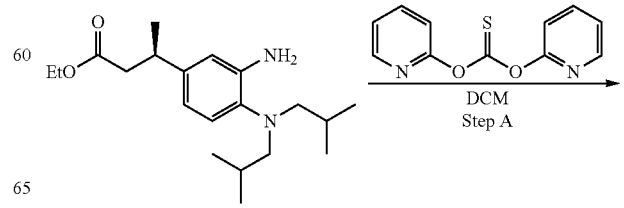

249

-continued

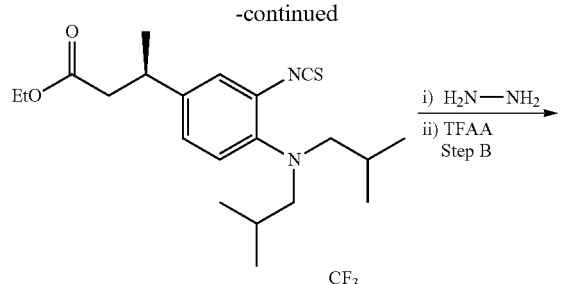

i) H₂N—NH₂
ii) TFAA
Step B

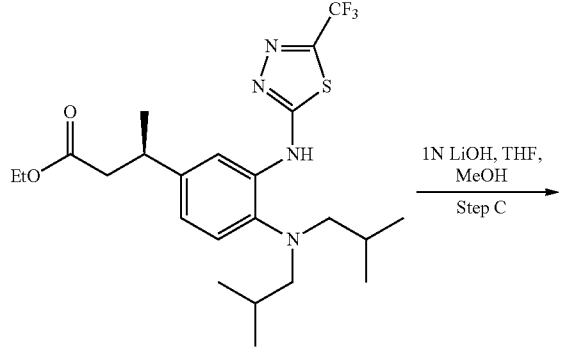

1N LiOH, THF, MeOH
Step C

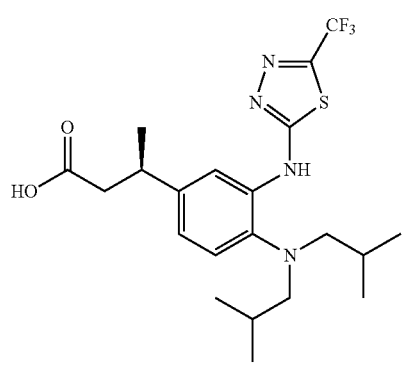

Step A (R)-ethyl 3-(4-(diisobutylamino)-3-isothiocyanatophenyl)butanoate

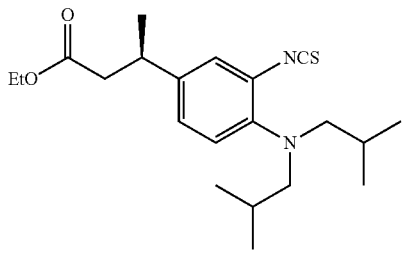

A mixture of (R)-ethyl 3-(3-amino-4-(diisobutylamino) phenyl)butanoate (210 mg, 0.628 mmol) and O,O-di(pyridin-2-yl) carbonothioate (175 mg, 0.753 mmol) in Dichloromethane (DCM) (5.000 mL) was stirred at rt for 1 h. The reaction mixture was concentrated and the crude product was used in the next step without further purification.

250

Step B (R)-ethyl 3-(4-(diisobutylamino)-3-((5-(trifluoromethyl)-1,3,4-thiadiazol-2-yl)amino)phenyl)butanoate

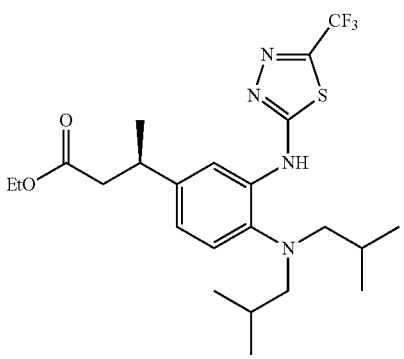 [SMILES: CC(C)CN(CC(C)C)c1ccc([C@H](C)CC(=O)O)cc1Nc1nnc(C(F)(F)F)s1]

Crude material from step A dissolved in Isopropanol (5.00 mL) was treated with hydrazine (0.024 mL, 0.753 mmol) and the mixture was stirred at r.t. for 30 min. The reaction was concentrated, redissolved in Dichloromethane (DCM) (5.000 mL) and treated with TFAA (0.177 mL, 1.256 mmol) dropwise at 0 oC and the mixture was stirred at r.t. for 16 h. The reaction was concentrated and purified by prep. TLC (DCM/MeOH 5%) to give the cyclized thiadiazole.

Step C (R)-3-(4-(diisobutylamino)-3-((5-(trifluoromethyl)-1,3,4-thiadiazol-2-yl)amino) phenyl)butanoic Acid

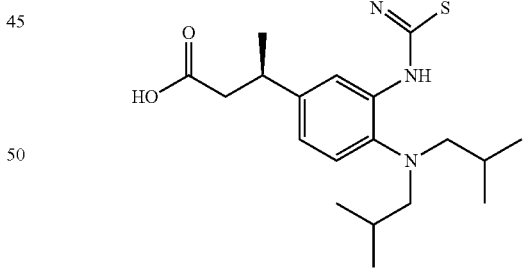

The product from step B was dissolved in THF (6 mL) and methanol (1 mL) and treated with LiOH (1N, 2 mL) and the mixture was stirred at r.t. for 4 h. The mixture was concentrated and purified by Gilson (reverse phase chromatography) to yield the carboxylic acid as a solid.

LCMS calculated for $C_{21}H_{29}F_3N_4O_2S$: 458.20, found (M+H)⁺: m/z=459.71 ¹H NMR (400 MHz, METHANOL-d₄) δ ppm 7.73 (s, 1H) 7.27 (d, J=8.1 Hz, 1H) 7.08 (d, J=8.2 Hz, 1H) 3.16-3.30 (m, 1H) 2.71 (d, J=7.0 Hz, 4H) 2.53-2.67 (m, 2H) 1.72 (dt, J=13.4, 6.7 Hz, 2H) 1.33 (d, J=6.8 Hz, 3H) 0.91 (s, 12H).

251
Example 88
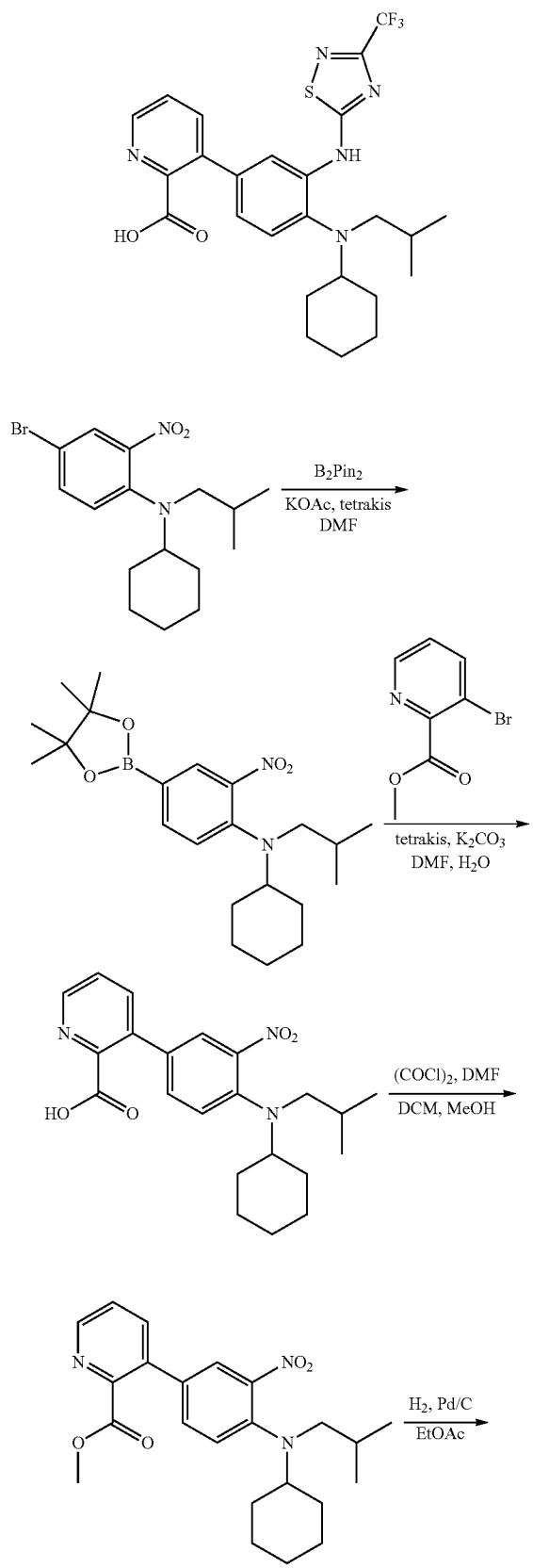
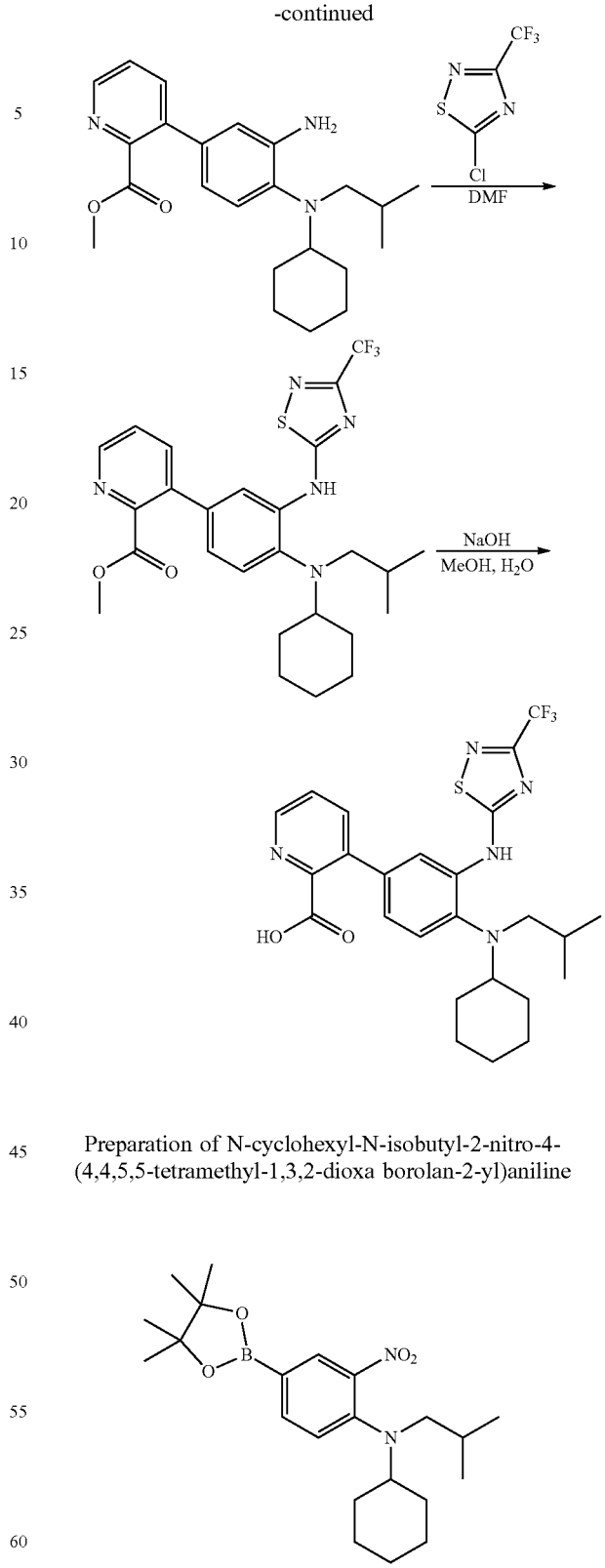
Preparation of N-cyclohexyl-N-isobutyl-2-nitro-4-(4,4,5,5-tetramethyl-1,3,2-dioxa borolan-2-yl)aniline
A mixture of 4-bromo-N-cyclohexyl-N-isobutyl-2-nitroaniline (5.0 g, 14.1 mmol), $B_2Pin_2$ (3.94 g, 15.5 mmol), tetrakis (820 mg, 0.71 mmol) and KOAc (4.15 g, 42.3 mmol) in DMF (100 mL) was stirred at 90° C. under $N_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (4.2 g, 75% yield). LCMS (ESI) m/z calcd for C$_{22}$H$_{35}$BN$_2$O$_4$: 402.27. Found: 403.46 (M+1)$^+$.

Preparation of 3-(4-(cyclohexyl(isobutyl)amino)-3-nitrophenyl)picolinic Acid

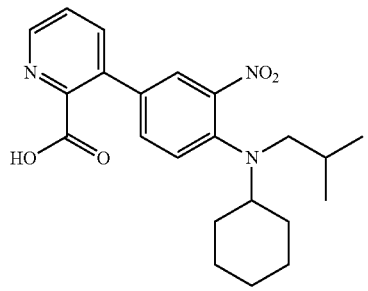 [SMILES: CC(C)CN(c1ccc(-c2cccnc2C(=O)O)cc1[N+](=O)[O-])C1CCCCC1]

A mixture of N-cyclohexyl-N-isobutyl-2-nitro-4-(4,4,5,5-tetramethyl-1,3,2-dioxaboro Ian-2-yl)aniline (1.0 g, 2.5 mmol), methyl 3-bromopicolinate (594 mg, 2.75 mmol), tetrakis (144 mg, 0.125 mmol) and K$_2$CO$_3$ (1.04 g, 7.5 mmol) in DMF (5 mL) and H$_2$O (1 mL) was stirred at 90° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-100% EtOAc in PE) to afford the title compound (900 mg, 91% yield). LCMS (ESI) m/z calcd for C$_{22}$H$_{27}$N$_3$O$_4$: 397.20. Found: 396.12 (M−1)$^-$.

Preparation of methyl 3-(4-(cyclohexyl(isobutyl) amino)-3-nitrophenyl)picolinate

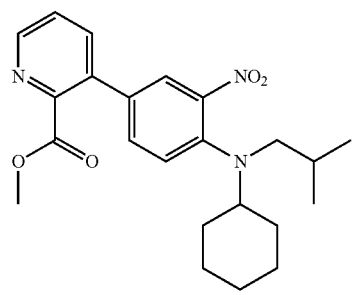 [SMILES: COC(=O)c1ncccc1-c1ccc(N(CC(C)C)C2CCCCC2)c([N+](=O)[O-])c1]

At 0° C., to a solution of 3-(4-(cyclohexyl(isobutyl) amino)-3-nitrophenyl)picolinic acid (1.1 g, 2.8 mmol) in DCM (10 mL) was added (COCl)$_2$ (0.5 mL, 5.6 mmol) and one drop of DMF. The reaction mixture was stirred at r.t. for 2 hr before the addition of MeOH (10 mL). After stirred at r.t. for 2 hr, the resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (1.0 g, 88% yield). LCMS (ESI) m/z calcd for C$_{23}$H$_{29}$N$_3$O$_4$: 411.22. Found: 412.35 (M+1)$^+$.

Preparation of methyl 3-(4-(cyclohexyl(isobutyl) amino)-3-nitrophenyl)picolinate

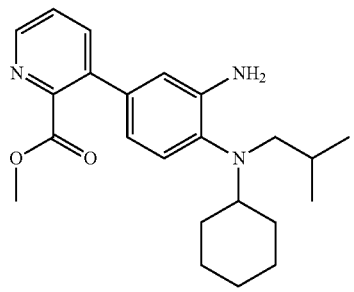

A mixture of methyl 3-(4-(cyclohexyl(isobutyl)amino)-3-nitrophenyl)picolinate (1.0 g, 2.4 mmol) and 10% Pd/C (500 mg) in EtOAc (10 mL) was stirred at 50° C. under H$_2$ atmosphere for 4 hr. The resulting mixture was filtered through a pad of Celite and the filtrate was concentrated under reduced pressure to give the crude product which was purified by flash chromatography (silica gel, 0-50% EtOAc in PE) to afford the title compound (800 mg, 87% yield). LCMS (ESI) m/z calcd for C$_{23}$H$_{31}$N$_3$O$_2$: 381.24. Found: 382.05 (M+1)$^+$.

Preparation of methyl 3-(4-(cyclohexyl(isobutyl) amino)-3-((3-(trifluoromethyl)-1,2,4-thiadiazol-5-yl) amino)phenyl)picolinate

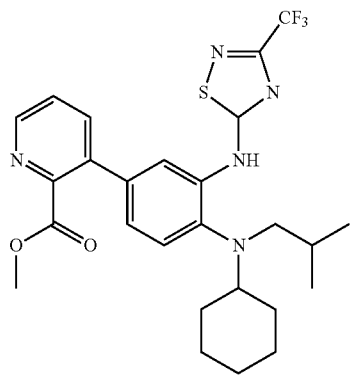 [SMILES: COC(=O)c1ncccc1-c1ccc(N(CC(C)C)C2CCCCC2)c(NC2NC(C(F)(F)F)=NS2)c1]

A mixture of methyl 3-(4-(cyclohexyl(isobutyl)amino)-3-nitrophenyl)picolinate (100 mg, 0.26 mmol) and 5-chloro-3-(trifluoromethyl)-1,2,4-thiadiazole (69 mg, 0.364 mmol) in DMF (2 mL) was stirred at 90° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (70 mg, 50% yield). LCMS (ESI) m/z calcd for C$_{26}$H$_{30}$F$_3$N$_5$O$_2$S: 533.21. Found: 534.47 (M+1)$^+$.

Preparation of 3-(4-(cyclohexyl(isobutyl)amino)-3-((3-(trifluoromethyl)-1,2,4-thiadiazol-5-yl)amino)phenyl)picolinic Acid

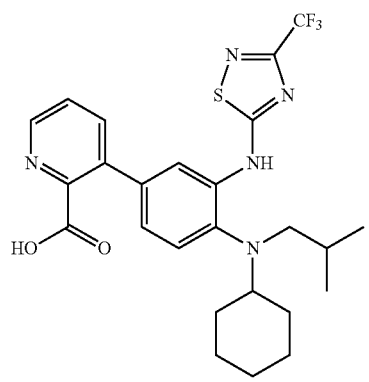 [SMILES: CC(C)CN(c1ccc(-c2cccnc2C(=O)O)cc1Nc1nc(C(F)(F)F)ns1)C1CCCCC1]

To a solution of methyl 3-(4-(cyclohexyl(isobutyl)amino)-3-((3-(trifluoromethyl)-1,2,4-thiadiazol-5-yl)amino)phenyl)picolinate (70 mg, 0.13 mmol) in MeOH (1 mL) was added 1N NaOH aq. (0.65 mL). After stirred at 60° C. for 4 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (13 mg, 19% yield) as a white powder. $^1$H NMR (400 MHz, MeOD) δ 8.59 (dd, J=4.8, 1.3 Hz, 1H), 8.01 (dd, J=7.9, 1.4 Hz, 1H), 7.86 (d, J=1.8 Hz, 1H), 7.66 (dd, J=7.9, 4.9 Hz, 1H), 7.40 (d, J=8.3 Hz, 1H), 7.25 (dd, J=8.2, 2.0 Hz, 1H), 2.93 (d, J=6.9 Hz, 2H), 2.78-2.66 (m, 1H), 1.98-1.87 (m, 2H), 1.83-1.70 (m, 2H), 1.59-1.34 (m, 5H), 1.23-1.07 (m, 3H), 0.88 (d, J=6.6 Hz, 6H). LCMS (ESI) m/z calcd for C$_{25}$H$_{28}$F$_3$N$_5$O$_2$S: 519.19. Found: 520.21 (M+1)$^+$.

Example 89

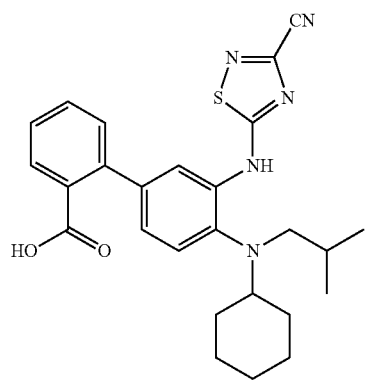

-continued

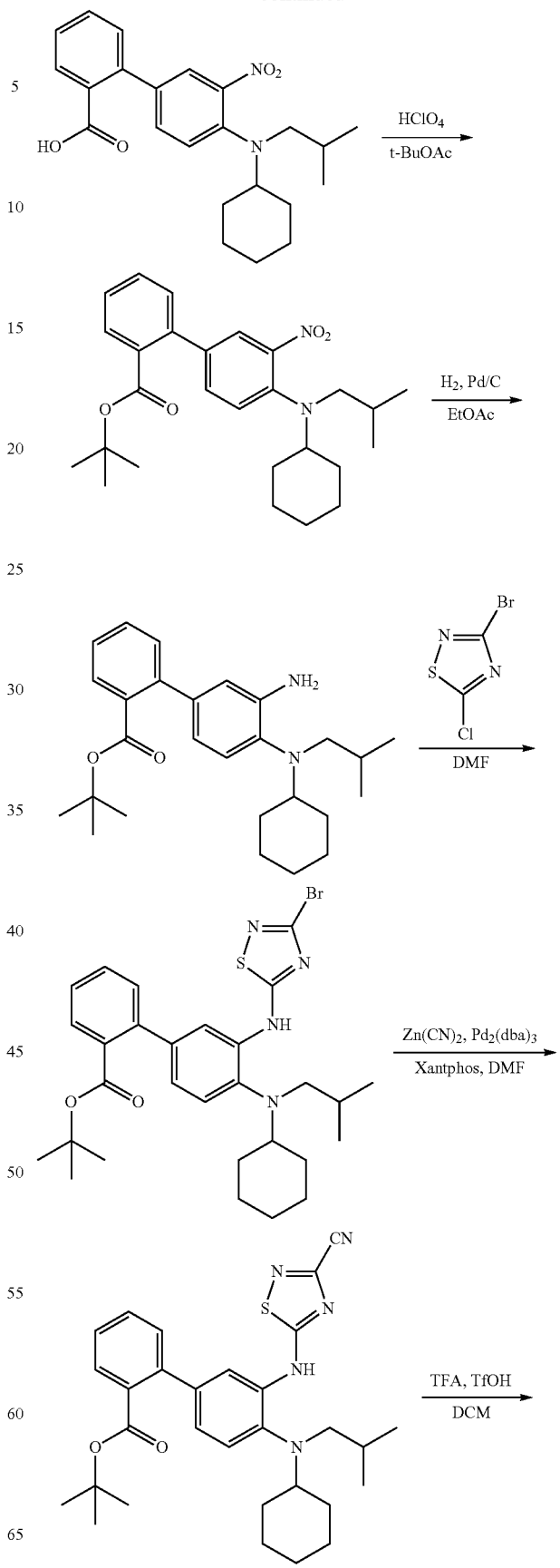

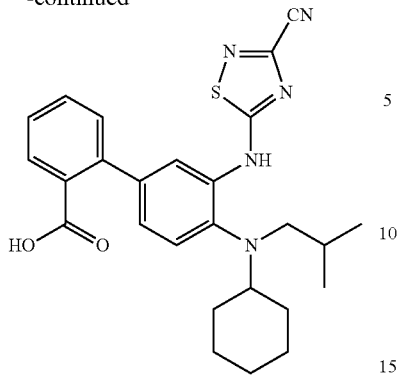

Preparation of tert-butyl 4'-(cyclohexyl(isobutyl)
amino)-3'-nitro-[1,1'-biphenyl]-2-carboxylate

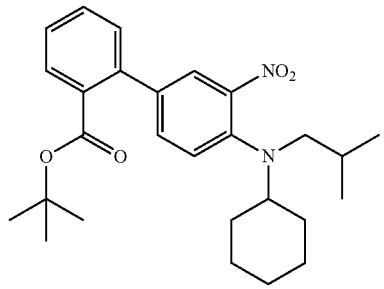 [SMILES: CC(C)CN(c1ccc(-c2ccccc2C(=O)OC(C)(C)C)cc1[N+](=O)[O-])C1CCCCC1]

To a solution of 4'-(cyclohexyl(isobutyl)amino)-3'-nitro-[1,1'-biphenyl]-2-carboxylic acid (150 mg, 0.378 mmol) in t-BuOAc (4 mL) was added HClO$_4$ (70%, 190 mg, 1.89 mmol). After stirred at r.t. for 20 min, the resulting mixture was quenched with sat. NaHCO$_3$ aq. solution and extracted with EtOAc. The organic layer was washed with brine, dried over Na$_2$SO$_4$, filtered and concentrated to give the crude product which was purified by flash chromatography (silica gel, 0-5% EtOAc in PE) to afford the title compound (128 mg, 75% yield). LCMS (ESI) m/z calcd for C$_{27}$H$_{36}$N$_2$O$_4$: 452.27. Found: 453.23 (M+1)$^+$.

Preparation of tert-butyl 3'-amino-4'-(cyclohexyl
(isobutyl)amino)-[1,1'-biphenyl]-2-carboxylate

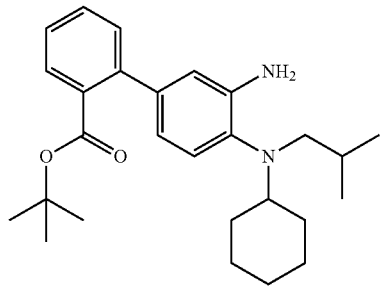 [SMILES: CC(C)CN(c1ccc(-c2ccccc2C(=O)OC(C)(C)C)cc1N)C1CCCCC1]

A mixture of tert-butyl 4'-(cyclohexyl(isobutyl)amino)-3'-nitro-[1,1'-biphenyl]-2-carboxylate (1.0 g, 2.2 mmol) and 10% Pd/C (300 mg) in EtOAc (10 mL) was stirred at 50° C. under H$_2$ atmosphere overnight. The resulting mixture was filtered through a pad of Celite and the filtrate was concentrated under reduced pressure to give the crude product which was purified by flash chromatography (silica gel, 0-30% EtOAc in PE) to afford the title compound (900 mg, 96% yield). LCMS (ESI) m/z calcd for C$_{27}$H$_{38}$N$_2$O$_2$: 422.29. Found: 423.37 (M+1)$^+$.

Preparation of tert-butyl 3'-((3-bromo-1,2,4-thiadi-
azol-5-yl)amino)-4'-(cyclohexyl (isobutyl)amino)-[1,
1'-biphenyl]-2-carboxylate

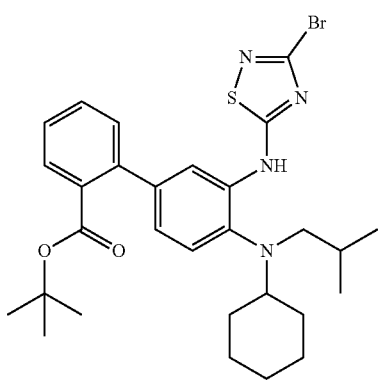 [SMILES: CC(C)CN(c1ccc(-c2ccccc2C(=O)OC(C)(C)C)cc1Nc1nc(Br)ns1)C1CCCCC1]

A mixture of tert-butyl 3'-amino-4'-(cyclohexyl(isobutyl) amino)-[1,1'-biphenyl]-2-carboxylate (500 mg, 1.18 mmol) and 3-bromo-5-chloro-1,2,4-thiadiazole (353 mg, 1.77 mmol) in DMF (10 mL) was stirred at 90° C. under N$_2$ atmosphere for 5 hr. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (370 mg, 54% yield). LCMS (ESI) m/z calcd for C$_{29}$H$_{37}$BrN$_4$O$_2$S: 584.18. Found: 585.58/587.48 (M/M+2)$^+$.

Preparation of tert-butyl 3'-((3-cyano-1,2,4-thiadi-
azol-5-yl)amino)-4'-(cyclohexyl (isobutyhamino)-[1,
1'-biphenyl]-2-carboxylate

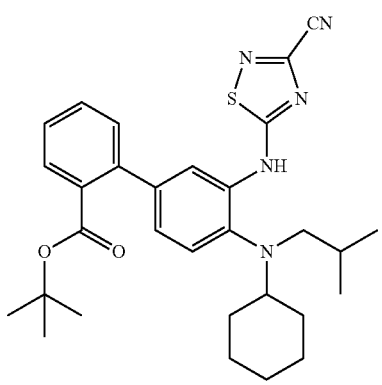 [SMILES: CC(C)CN(c1ccc(-c2ccccc2C(=O)OC(C)(C)C)cc1Nc1nc(C#N)ns1)C1CCCCC1]

A mixture of tert-butyl 3'-((3-bromo-1,2,4-thiadiazol-5-yl)amino)-4'-(cyclohexyl(isobutyl)amino)-[1,1'-biphenyl]-2-carboxylate (340 mg, 0.58 mmol), Zn(CN)$_2$ (682 mg, 5.81 mmol), Pd$_2$(dba)$_3$ (159 mg, 0.174 mmol) and Xantphos (202 mg, 0.349 mmol) in DMF (15 mL) was stirred at 80° C. under N₂ atmosphere overnight. The resulting mixture was partitioned between EtOAc and H₂O. The organic layer was washed with brine, dried over Na₂SO₄, filtered and concentrated to give the crude product which was purified by flash chromatography (silica gel, 0-10% EtOAc in PE) to afford the title compound (30 mg, 10% yield). LCMS (ESI) m/z calcd for $C_{30}H_{37}N_5O_2S$: 531.27. Found: 532.17 (M+1)⁺.

Preparation of 3'-((3-cyano-1,2,4-thiadiazol-5-yl)amino)-4'-(cyclohexyl(isobutyl) amino)-[1,1'-biphenyl]-2-carboxylic Acid

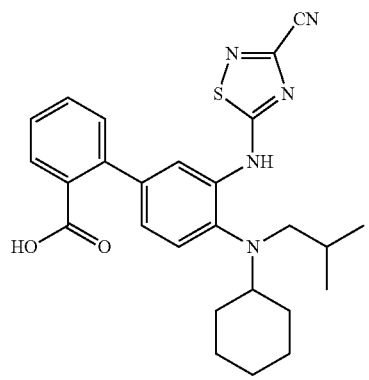 [SMILES: CC(C)CN(c1ccc(-c2ccccc2C(=O)O)cc1Nc1nc(C#N)ns1)C1CCCCC1]

To a solution of tert-butyl 3'-((3-cyano-1,2,4-thiadiazol-5-yl)amino)-4'-(cyclohexyl (isobutyhamino)-[1,1'-biphenyl]-2-carboxylate (80 mg, 0.15 mmol) in DCM (20 mL) was added TFA (2 mL) and TfOH (0.2 mL). After stirred at r.t. for 3 hr, the resulting mixture was concentrated to give the crude product which was purified by HPLC (C18, 0-100% MeCN in H₂O with 0.1% formic acid) to afford the title compound (46 mg, 63% yield) as a white powder. ¹H NMR (400 MHz, CDCl₃) δ 9.62 (br, 2H), 7.95 (dd, J=7.8, 1.0 Hz, 1H), 7.61 (td, J=7.6, 1.3 Hz, 1H), 7.50-7.41 (m, 2H), 7.36 (d, J=1.6 Hz, 1H), 7.30 (d, J=8.2 Hz, 1H), 7.10 (dd, J=8.1, 1.9 Hz, 1H), 2.87 (d, J=6.9 Hz, 2H), 2.64-2.55 (m, 1H), 1.96-1.84 (m, 2H), 1.80-1.74 (m, 2H), 1.63-1.46 (m, 2H), 1.32-1.13 (m, 5H), 0.86 (d, J=6.6 Hz, 6H) LCMS (ESI) m/z calcd for $C_{26}H_{29}N_5O_2S$: 475.20. Found: 476.31 (M+1)⁺.

Example 90

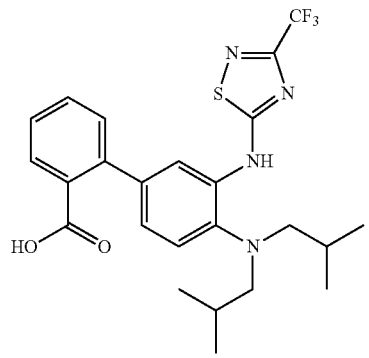

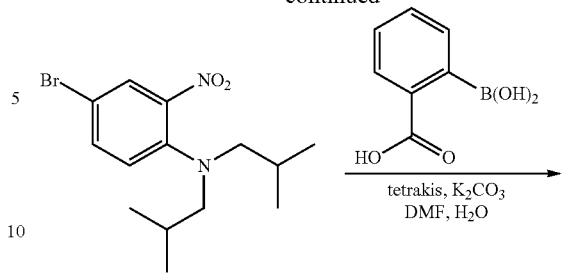

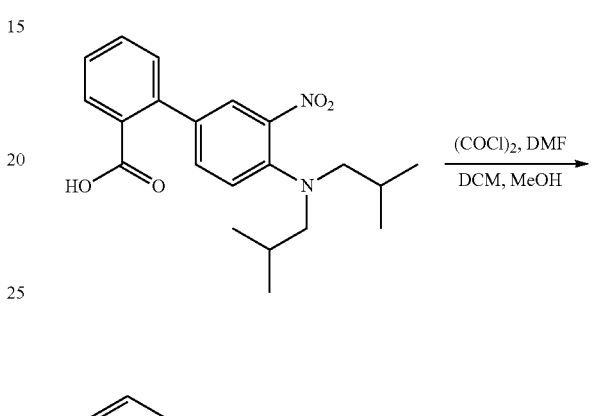

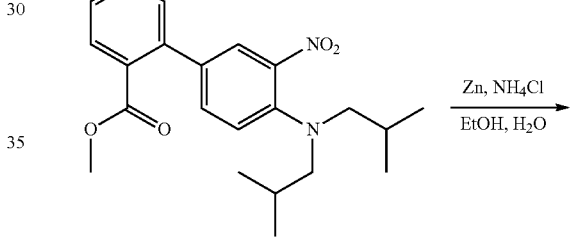

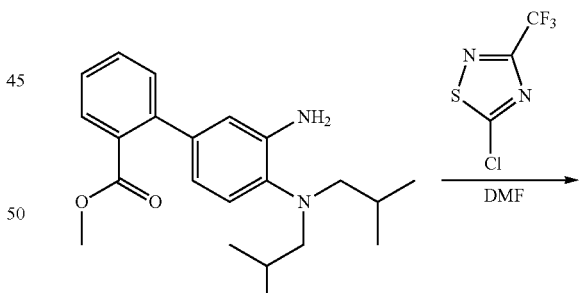

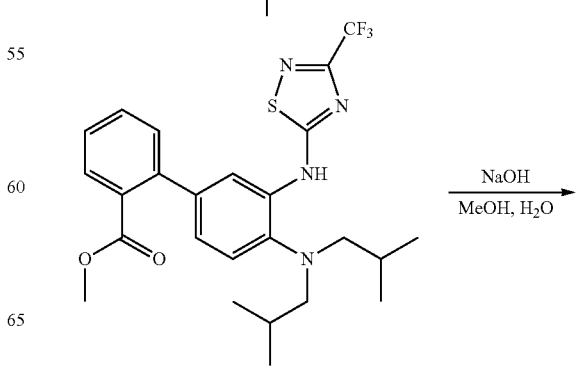

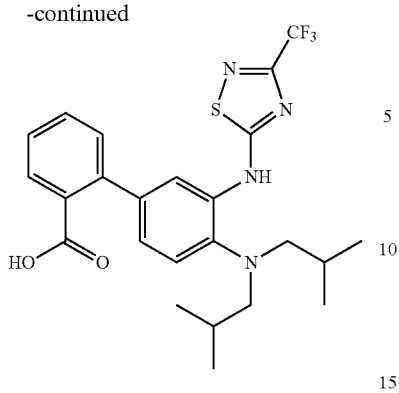

Preparation of 4'-(diisobutylamino)-3'-nitro-[1,1'-biphenyl]-2-carboxylic Acid

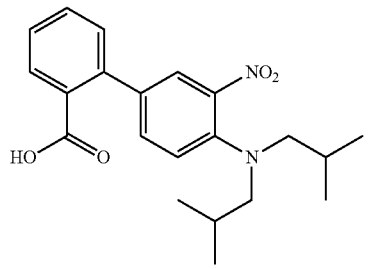 [SMILES: CC(C)CN(CC(C)C)c1ccc(-c2ccccc2C(=O)O)cc1[N+](=O)[O-]]

A mixture of 4-bromo-N,N-diisobutyl-2-nitroaniline (3.32 g, 10.0 mmol), 2-borono benzoic acid (2.0 g, 12.1 mmol), tetrakis (924 mg, 0.8 mmol) and $K_2CO_3$ (2.76 g, 20.0 mmol) in DMF (10 mL) and $H_2O$ (2 mL) was stirred at 110° C. under $N_2$ atmosphere for 3 hr. The resulting mixture was acidified with 1N HCl to pH 5-6 and partitioned between EtOAc and $H_2O$. The organic layer was washed with brine, dried over $Na_2SO_4$, filtered and concentrated to give the crude product which was purified by flash chromatography (silica gel, 0-50% EtOAc in PE) to afford the title compound (3.5 g, 94% yield). LCMS (ESI) m/z calcd for $C_{21}H_{26}N_2O_4$: 371.25. Found: 372.07 $(M+1)^+$.

Preparation of methyl 4'-(diisobutylamino)-3'-nitro-[1,1'-biphenyl]-2-carboxylate

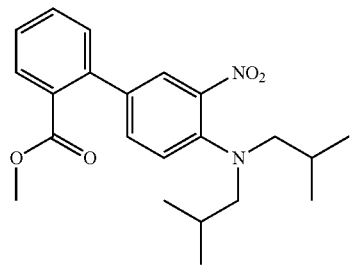 [SMILES: COC(=O)c1ccccc1-c1ccc(N(CC(C)C)CC(C)C)c([N+](=O)[O-])c1]

At 0° C., to a solution of 4'-(diisobutylamino)-3'-nitro-[1,1'-biphenyl]-2-carboxylic acid (4.0 g, 10.8 mmol) in DCM (40 mL) was added $(COCl)_2$ (3.5 g, 27.5 mmol) and one drop of DMF. The reaction mixture was stirred at r.t. for 2 hr before the addition of MeOH (10 mL). After stirred at r.t. for 2 hr, the resulting mixture was partitioned between EtOAc and $H_2O$. The organic layer was washed with brine, dried over $Na_2SO_4$, filtered and concentrated to give the crude product which was purified by flash chromatography (silica gel, 0-20% EtOAc in PE) to afford the title compound (4.0 g, 96% yield). LCMS (ESI) m/z calcd for $C_{22}H_{28}N_2O_4$: 384.20. Found: 385.80 $(M+1)^+$.

Preparation of methyl 3'-amino-4'-(diisobutylamino)-[1,1'-biphenyl]-2-carboxylate

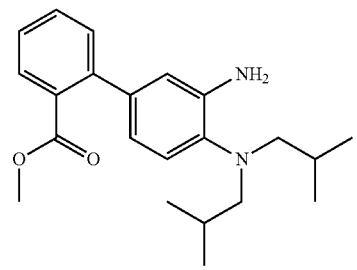 [SMILES: COC(=O)c1ccccc1-c1ccc(N(CC(C)C)CC(C)C)c(N)c1]

A mixture of methyl 4'-(diisobutylamino)-3'-nitro-[1,1'-biphenyl]-2-carboxylate (1.68 g, 4.35 mmol), Zn (2.85 g, 43.6 mmol) and $NH_4Cl$ (4.7 g, 88 mmol) in EtOH (20 mL) and $H_2O$ (5 mL) was stirred at 50° C. for 3 hr. The resulting mixture was filtered and the filrated was partitioned between EtOAc and $H_2O$. The organic layer was washed with brine, dried over $Na_2SO_4$, filtered and concentrated to give the crude product which was purified by flash chromatography (silica gel, 0-10% EtOAc in PE) to afford the title compound (750 mg, 48% yield). LCMS (ESI) m/z calcd for $C_{22}H_{30}N_2O_2$: 354.23. Found: 355.50 $(M+1)^+$.

Preparation of methyl 4'-(diisobutylamino)-3'-((3-(trifluoromethyl)-1,2,4-thiadiazol-5-yl)amino)-[1,1'-biphenyl]-2-carboxylate

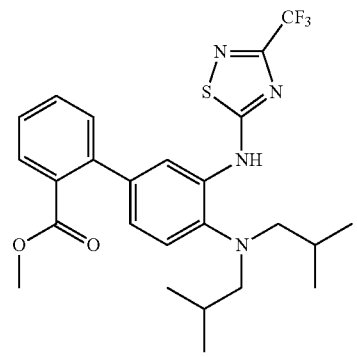 [SMILES: COC(=O)c1ccccc1-c1ccc(N(CC(C)C)CC(C)C)c(Nc2nc(C(F)(F)F)ns2)c1]

A mixture of methyl 3'-amino-4'-(diisobutylamino)-[1,1'-biphenyl]-2-carboxylate (100 mg, 0.28 mmol) and 5-chloro-3-(trifluoromethyl)-1,2,4-thiadiazole (65 mg, 0.34 mmol) in DMF (5 mL) was stirred at 90° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (60 mg, 42% yield). LCMS (ESI) m/z calcd for $C_{25}H_{29}F_3N_4O_2S$: 506.20. Found: 507.36 $(M+1)^+$.

Preparation of 4'-(diisobutylamino)-3'-((3-(trifluoromethyl)-1,2,4-thiadiazol-5-yl) amino)-[1,1'-biphenyl]-2-carboxylic Acid

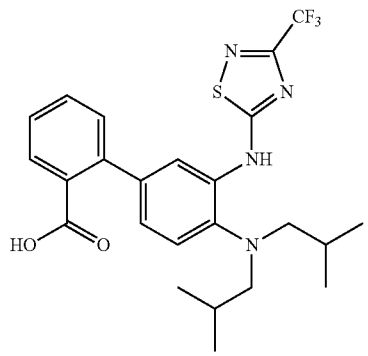 [SMILES: CC(C)CN(CC(C)C)c1ccc(-c2ccccc2C(=O)O)cc1Nc1nc(C(F)(F)F)ns1]

To a solution of methyl 4'-(diisobutylamino)-3'-((3-(trifluoromethyl)-1,2,4-thiadiazol-5-yl)amino)-[1,1'-biphenyl]-2-carboxylate (60 mg, 0.118 mmol) in MeOH (5 mL) was added 1N NaOH aq. (2 mL). After stirred at 60° C. for 5 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (19.5 mg, 34% yield) as a white powder. $^1$H NMR (400 MHz, $CDCl_3$) δ 9.54 (s, 1H), 7.95 (dd, J=7.8, 0.9 Hz, 1H), 7.60 (td, J=7.6, 1.3 Hz, 1H), 7.50-7.40 (m, 3H), 7.30 (d, J=8.2 Hz, 1H), 7.11 (dd, J=8.1, 1.9 Hz, 1H), 2.67 (d, J=7.2 Hz, 4H), 1.80-1.72 (m, 2H), 0.92 (d, J=6.6 Hz, 12H). LCMS (ESI) m/z calcd for $C_{24}H_{27}F_3N_4O_2S$: 492.18. Found: 493.13 $(M+1)^+$.

Example 91

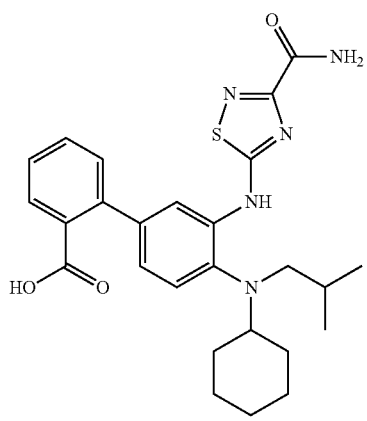

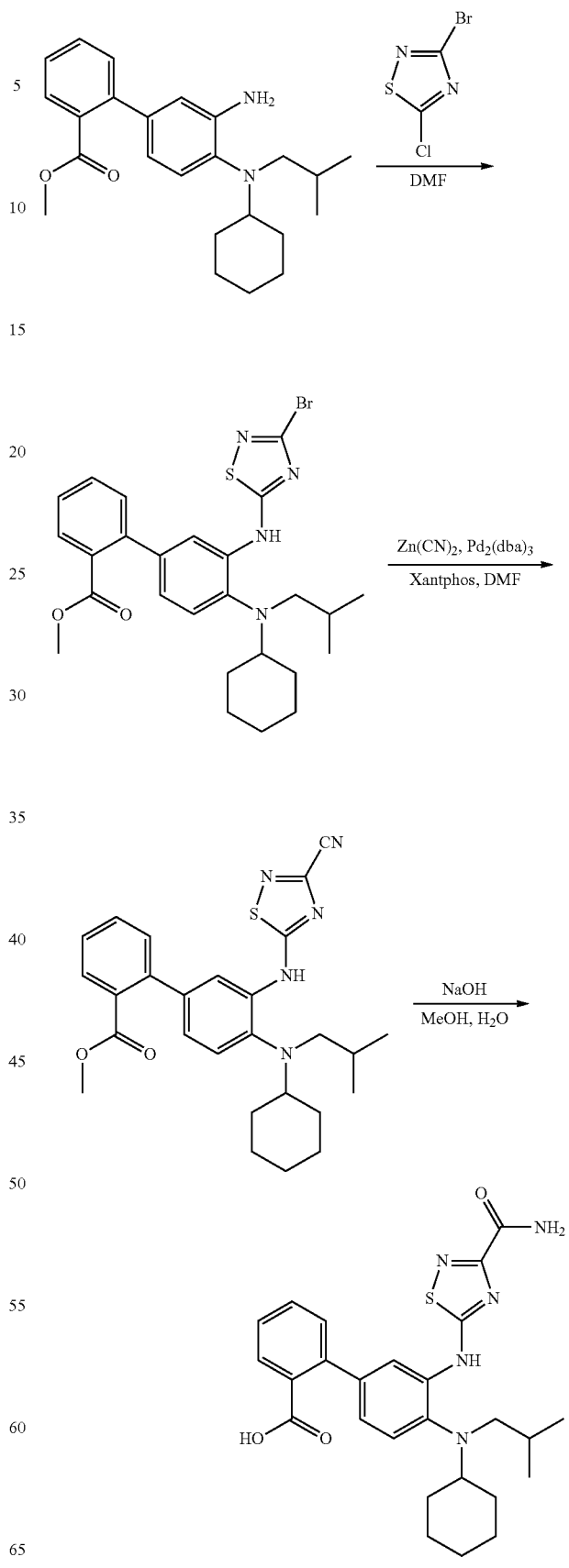

Preparation of methyl 3'-((3-bromo-1,2,4-thiadiazol-5-yl)amino)-4'-(cyclohexyl (isobutyl)amino)-[1,1'-biphenyl]-2-carboxylate

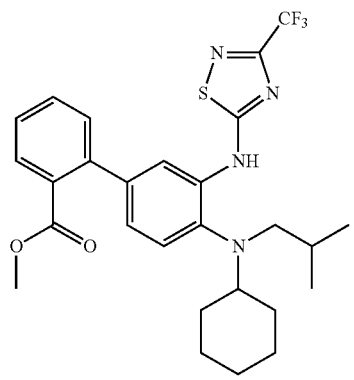 [SMILES: COC(=O)c1ccccc1-c1ccc(N(CC(C)C)C2CCCCC2)c(Nc2nc(C(F)(F)F)ns2)c1]

A mixture of methyl 3'-amino-4'-(cyclohexyl(isobutyl)amino)-[1,1'-biphenyl]-2-carboxylate (700 mg, 1.84 mmol) and 3-bromo-5-chloro-1,2,4-thiadiazole (441 mg, 2.21 mmol) in DMF (10 mL) was stirred at 90° C. under $N_2$ atmosphere for 5 hr. The resulting mixture was partitioned between EtOAc and $H_2O$. The organic layer was washed with brine, dried over $Na_2SO_4$, filtered and concentrated to give the crude product which was purified by flash chromatography (silica gel, 0-10% EtOAc in PE) to afford the title compound (550 mg, 55% yield). LCMS (ESI) m/z calcd for $C_{26}H_{31}BrN_4O_2S$: 543.52. Found: 544.67/546.19 (M/M+2)$^+$.

Preparation of methyl 3'-((3-cyano-1,2,4-thiadiazol-5-yl)amino)-4'-(cyclohexyl (isobutyhamino)-[1,1'-biphenyl]-2-carboxylate

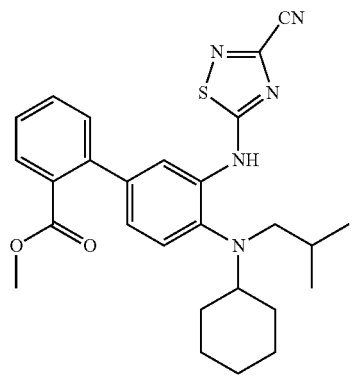 [SMILES: COC(=O)c1ccccc1-c1ccc(N(CC(C)C)C2CCCCC2)c(Nc2nc(C#N)ns2)c1]

A mixture of methyl 3'-((3-bromo-1,2,4-thiadiazol-5-yl)amino)-4'-(cyclohexyl(isobutyl) amino)-[1,1'-biphenyl]-2-carboxylate (330 mg, 0.607 mmol), $Zn(CN)_2$ (713 mg, 6.07 mmol), $Pd_2(dba)_3$ (167 mg, 0.182 mmol) and Xantphos (211 mg, 0.364 mmol) in DMF (15 mL) was stirred at 80° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-10% EtOAc in PE) to afford the title compound (80 mg, 27% yield). LCMS (ESI) m/z calcd for $C_{27}H_{31}N_5O_2S$: 489.22. Found: 490.63 (M+1)$^+$.

Preparation of 3'-((3-carbamoyl-1,2,4-thiadiazol-5-yl)amino)-4'-(cyclohexyl(iso butyl)amino)-[1,1'-biphenyl]-2-carboxylic acid

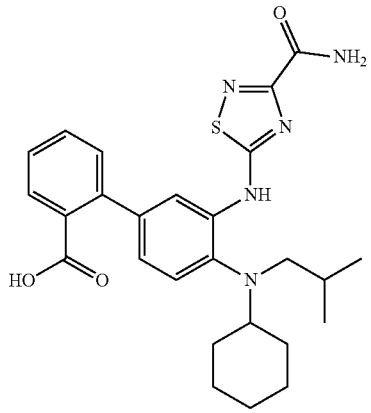 [SMILES: CC(C)CN(c1ccc(-c2ccccc2C(=O)O)cc1Nc1nc(C(N)=O)ns1)C1CCCCC1]

To a solution of methyl 3'-((3-cyano-1,2,4-thiadiazol-5-yl)amino)-4'-(cyclohexyl (isobutyhamino)-[1,1'-biphenyl]-2-carboxylate (80 mg, 0.163 mmol) in MeOH (3 mL) was added 1N NaOH aq. (0.5 mL). After stirred at 50° C. for 6 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (5 mg, 6.2% yield) as a white powder. $^1$H NMR (400 MHz, CDCl$_3$) δ 9.06 (s, 1H), 8.18 (s, 1H), 7.71 (d, J=7.4 Hz, 1H), 7.55-7.47 (m, 2H), 7.43-7.34 (m, 2H), 7.32-7.27 (m, 2H), 6.33 (s, 1H), 2.92-2.77 (m, 2H), 2.68-2.60 (m, 1H), 1.91-1.84 (m, 2H), 1.79-1.73 (m, 2H), 1.59-1.50 (m, 2H), 1.32-1.20 (m, 5H), 0.86 (d, J=6.6 Hz, 6H). LCMS (ESI) m/z calcd for $C_{26}H_{31}N_5O_3S$: 493.21. Found: 492.13 (M−1)$^-$.

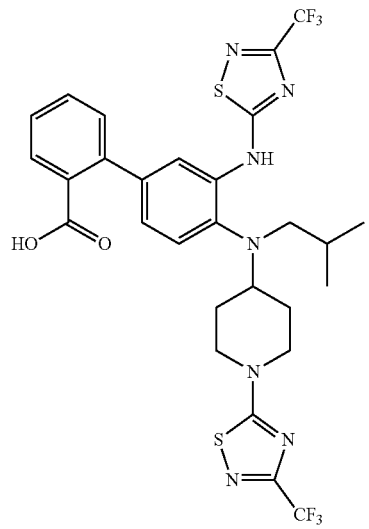

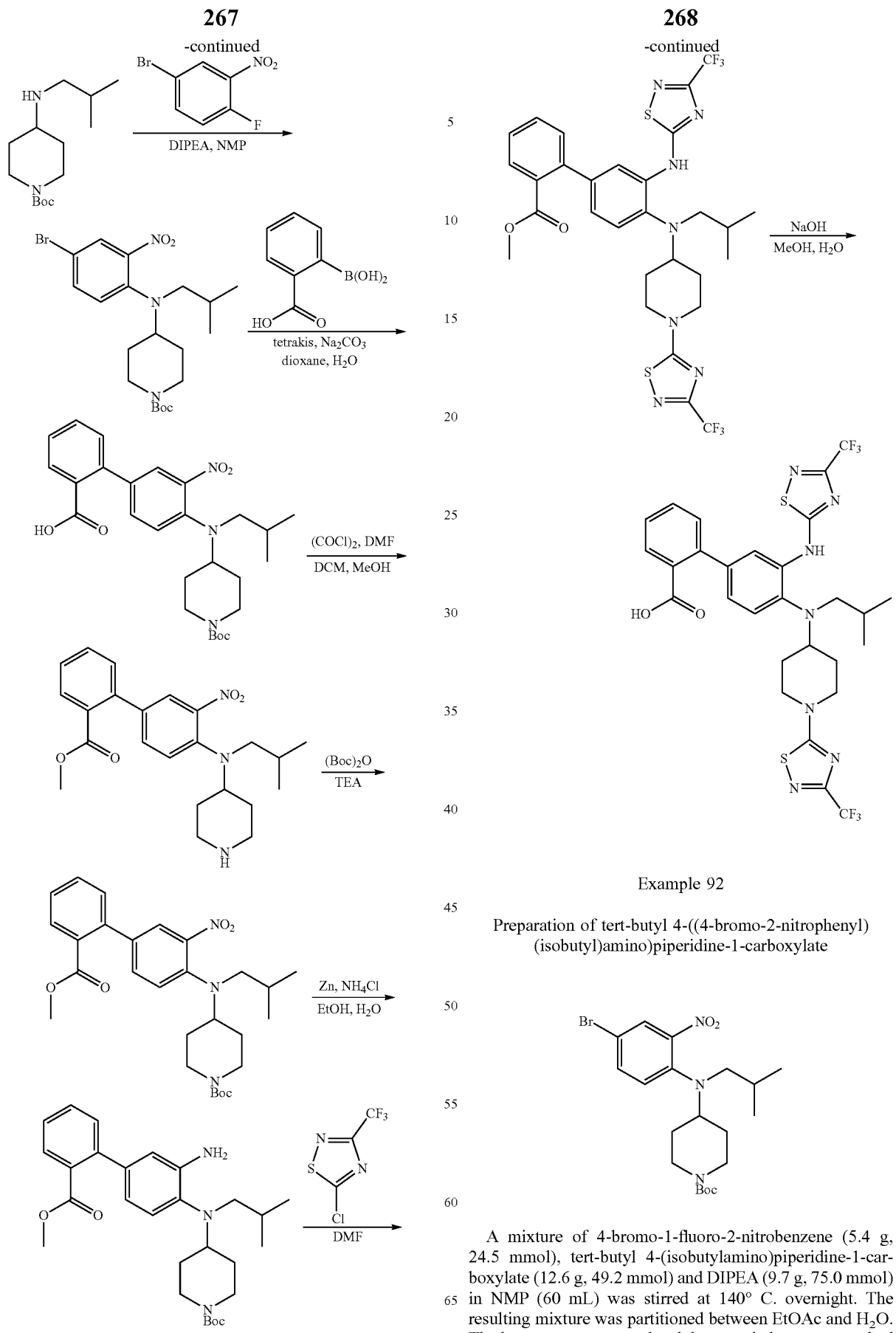

Example 92

Preparation of tert-butyl 4-((4-bromo-2-nitrophenyl)(isobutyl)amino)piperidine-1-carboxylate A mixture of 4-bromo-1-fluoro-2-nitrobenzene (5.4 g, 24.5 mmol), tert-butyl 4-(isobutylamino)piperidine-1-carboxylate (12.6 g, 49.2 mmol) and DIPEA (9.7 g, 75.0 mmol) in NMP (60 mL) was stirred at 140° C. overnight. The resulting mixture was partitioned between EtOAc and H₂O. The layers were separated and the organic layer was washed Preparation of 4'-((1-(tert-butoxycarbonyl)piperidin-4-yl) (isobutyl)amino)-3'-nitro-[1,1'-biphenyl]-2-carboxylic Acid

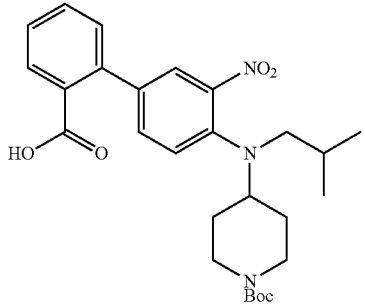 [SMILES: CC(C)CN(c1ccc(-c2ccccc2C(=O)O)cc1[N+](=O)[O-])C1CCN(C(=O)OC(C)(C)C)CC1]

A mixture of tert-butyl 4-((4-bromo-2-nitrophenyl)(isobutyl)amino)piperidine-1-carboxy late (4.2 g, 9.2 mmol), 2-borono benzoic acid (8.4 g, 50.6 mmol), tetrakis (1.06 g, 0.92 mmol) and Na$_2$CO$_3$ (5.4 g, 50.9 mmol) in dioxane (50 mL) and H$_2$O (12 mL) was stirred at 90° C. under N$_2$ atmosphere for 6 hr. The resulting mixture was acidified with 1N HCl to pH 5-6 and partitioned between EtOAc and H$_2$O. The organic layer was washed with brine, dried over Na$_2$SO$_4$, filtered and concentrated to give the crude product which was purified by flash chromatography (silica gel, 0-2% MeOH in DCM) to afford the title compound (4.2 g, 80% yield). LCMS (ESI) m/z calcd for C$_{27}$H$_{35}$N$_3$O$_6$: 497.25. Found: 498.27 (M+1)$^+$.

Preparation of methyl 4'-(isobutyl(piperidin-4-yl)amino)-3'-nitro-[1,1'-biphenyl]-2-carboxylate

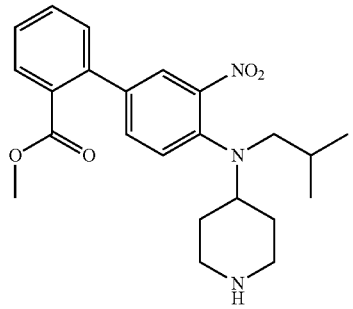 [SMILES: COC(=O)c1ccccc1-c1ccc(N(CC(C)C)C2CCNCC2)c([N+](=O)[O-])c1]

At 0° C., to a solution of 4'-((1-(tert-butoxycarbonyl)piperidin-4-yl) (isobutyl)amino)-3'-nitro-[1,1'-biphenyl]-2-carboxylic acid (4.2 g, 8.45 mmol) in DCM (40 mL) was added (COCl)$_2$ (3.2 g, 25.1 mmol) and one drop of DMF. The reaction mixture was stirred at r.t. for 2 hr before the addition of MeOH (10 mL). After stirred at r.t. for 2 hr, the resulting mixture was partitioned between EtOAc and H$_2$O. The organic layer was washed with brine, dried over Na$_2$SO$_4$, filtered and concentrated to give the crude product which was purified by flash chromatography (silica gel, 0-5% MeOH in DCM) to afford the title compound (1.2 g, 35% yield). LCMS (ESI) m/z calcd for C$_{23}$H$_{29}$N$_3$O$_4$: 411.22. Found: 412.25 (M+1)$^+$.

Preparation of tert-butyl 4-(isobutyl(2'-(methoxycarbonyl)-3-nitro-[1,1'-biphenyl]-4-yl)amino)piperidine-1-carboxylate

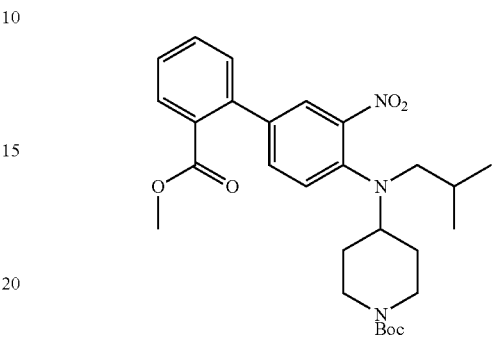

To a solution of methyl 4'-(isobutyl(piperidin-4-yl)amino)-3'-nitro-[1,1'-biphenyl]-2-car boxylate (250 mg, 0.61 mmol) and TEA (123 mg, 1.22 mmol) in DCM was added Boc$_2$O (146 mg, 0.67 mmol). After stirred at r.t. for 1 hr, the resulting mixture was partitioned between DCM and H$_2$O. The organic layer was washed with brine, dried over Na$_2$SO$_4$, filtered and concentrated to give the crude product which was purified by flash chromatography (silica gel, 0-20% EtOAc in PE) to afford the title compound (300 mg, 97% yield). LCMS (ESI) m/z calcd for C$_{28}$H$_{37}$N$_3$O$_6$: 511.27. Found: 512.65 (M+1)$^+$.

Preparation of tert-butyl 4-((3-amino-2'-(methoxycarbonyl)-[1,1'-biphenyl]-4-yl) (isobutyl)amino)piperidine-1-carboxylate

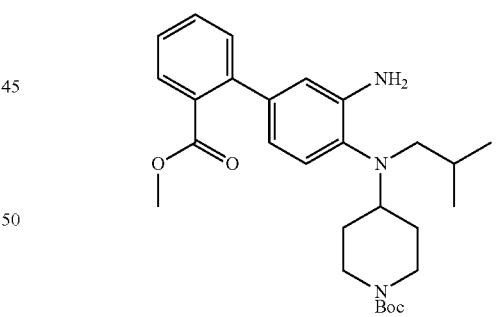

A mixture of tert-butyl 4-(isobutyl(2'-(methoxycarbonyl)-3-nitro-[1,1'-biphenyl]-4-yl) amino)piperidine-1-carboxylate (300 mg, 0.59 mmol), Zn (383 mg, 5.86 mmol) and NH$_4$Cl (631 mg, 11.8 mmol) in EtOH (10 mL) and H$_2$O (2 mL) was stirred at 50° C. for 3 hr. The resulting mixture was filtered and the filtrated was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (277 mg, 98% yield). LCMS (ESI) m/z calcd for C$_{28}$H$_{39}$N$_3$O$_4$: 481.29. Found: 482.50 (M+1)$^+$.

Preparation of methyl 4'-(isobutyl(1-(3-(trifluoromethyl)-1,2,4-thiadiazol-5-yl) piperidin-4-yl)amino)-3'-((3-(trifluoromethyl)-1,2,4-thiadiazol-5-yl)amino)-[1,1'-biphenyl]-2-carboxylate

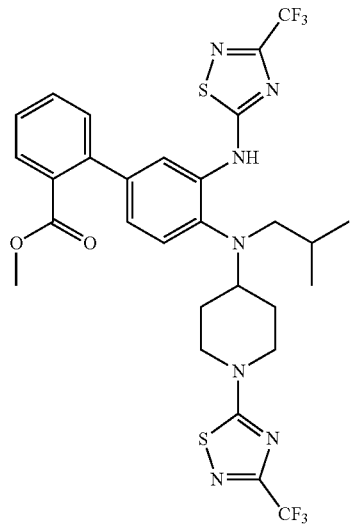 [SMILES: COC(=O)c1ccccc1-c1ccc(N(CC(C)C)C2CCN(c3nc(C(F)(F)F)ns3)CC2)c(Nc2nc(C(F)(F)F)ns2)c1]

A mixture of tert-butyl 4-((3-amino-2'-(methoxycarbonyl)-[1,1'-biphenyl]-4-yl) (isobutyl) amino)piperidine-1-carboxylate (270 mg, 0.56 mmol) and 5-chloro-3-(trifluoromethyl)-1,2,4-thiadiazole (264 mg, 1.40 mmol) in DMF (5 mL) was stirred at 90° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (80 mg, 25% yield). LCMS (ESI) m/z calcd for $C_{29}H_{29}F_6N_7O_2S_2$: 685.17. Found: 686.18 (M+1)$^+$.

Preparation of 4'-(isobutyl(1-(3-(trifluoromethyl)-1,2,4-thiadiazol-5-yl)piperidin-4-yl)amino)-3'-((3-(trifluoromethyl)-1,2,4-thiadiazol-5-yl)amino)-[1,1'-biphenyl]-2-carboxylic Acid

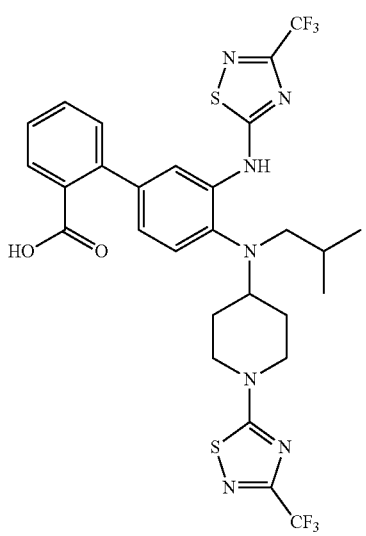 [SMILES: CC(C)CN(c1ccc(-c2ccccc2C(=O)O)cc1Nc1nc(C(F)(F)F)ns1)C1CCN(c2nc(C(F)(F)F)ns2)CC1]

To a solution of methyl 4'-(isobutyl(1-(3-(trifluoromethyl)-1,2,4-thiadiazol-5-yl) piperidin-4-yl)amino)-3'-((3-(trifluoromethyl)-1,2,4-thiadiazol-5-yl)amino)-[1,1'-biphenyl]-2-carboxylate (65 mg, 0.095 mmol) in MeOH (4 mL) was added 1N NaOH aq. (1 mL). After stirred at 50° C. for 2 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (34 mg, 53% yield) as a white powder. $^1$H NMR (400 MHz, CD$_3$OD) δ 7.95 (d, J=1.7 Hz, 1H), 7.85-7.79 (m, 1H), 7.62-7.54 (m, 1H), 7.47-7.42 (m, 3H), 7.20 (dd, J=8.2, 2.0 Hz, 1H), 4.00-3.95 (m, 2H), 3.12-2.99 (m, 3H), 2.94 (d, J=6.8 Hz, 2H), 2.16-1.92 (m, 2H), 1.92-1.65 (m, 2H), 1.57-1.44 (m, 1H), 0.88 (d, J=6.6 Hz, 6H). LCMS (ESI) m/z calcd for $C_{28}H_{27}F_6N_7O_2S_2$: 671.26. Found: 672.68 (M+1)$^+$.

Example 93

(R)-3-(4-(((cis)-4-bromocyclohexyl) (isobutyl) amino)-3-((5-(trifluoromethyl)-1H-1,2,4-triazol-3-yl)amino)phenyl)butanoic Acid

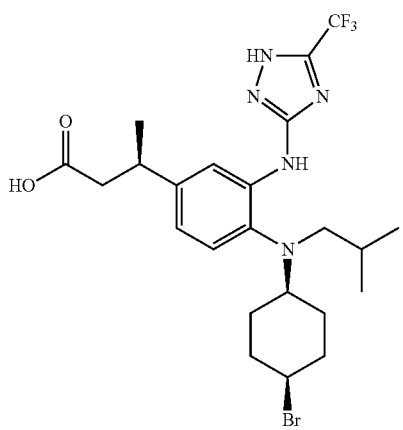 [SMILES: CC(C)CN(c1ccc([C@H](C)CC(=O)O)cc1Nc1n[nH]c(C(F)(F)F)n1)[C@H]1CC[C@@H](Br)CC1]

BBr$_3$ (1M in CH$_2$Cl$_2$) (0.83 mL, 0.834 mmol) was added dropwise to a solution of (R)-methyl 3-(4-(isobutyl((trans)-4-methoxycyclohexyl)amino)-3-((5-(trifluoromethyl)-1-((2-(trimethylsilyl)ethoxy)methyl)-1H-1,2,4-triazol-3-yl)amino)phenyl)butanoate (0.107 g, 0.167 mmol) in CH$_2$Cl$_2$ (1.67 ml) at 0° C. After 1 h, saturated aqueous NaHCO$_3$ was added and the solution was extracted with CH$_2$Cl$_2$. The organic phase was concentrated and subjected to base hydrolysis as previously described. Purification by reverse phase chromatography (10-100% CH$_3$CN/H$_2$O (0.1% formic acid)) afforded the title compound (0.0184 g, 20%) as a white solid. LCMS (M+H)$^+$: m/z=546.3, 548.3. $^1$H NMR (400 MHz, CD$_3$OD) δ ppm 7.95 (d, J=2.0 Hz, 1H), 7.21 (d, J=8.2 Hz, 1H), 6.90 (dd, J=8.2, 2.0 Hz, 1H), 4.56 (br. s., 1H), 3.17-3.25 (m, 1H), 2.88 (d, J=6.6 Hz, 2H), 2.46-2.69 (m, 3H), 1.85-2.09 (m, 4H), 1.69-1.82 (m, 4H), 1.33-1.45 (m, 1H), 1.29 (d, J=7.0 Hz, 3H), 0.85 (d, J=6.4 Hz, 6H).

Example 94

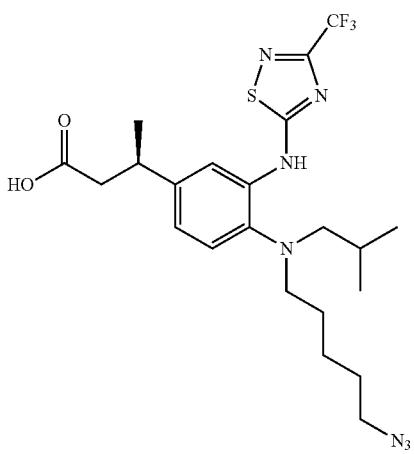 [SMILES: CC(C)CN(CCCCCN=[N+]=[N-])c1ccc([C@H](C)CC(=O)O)cc1Nc1nc(C(F)(F)F)ns1]

Preparation of 5-((4-bromo-2-nitrophenyl)
(isobutyl)amino)pentan-1-ol

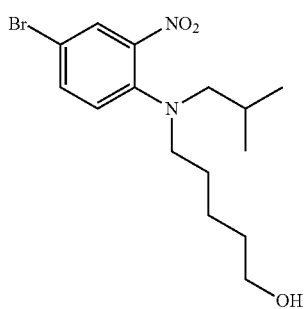 [SMILES: CC(C)CN(CCCCCO)c1ccc(Br)cc1[N+](=O)[O-]]

A mixture of 4-bromo-1-fluoro-2-nitrobenzene (7.0 g, 31.8 mmol), 5-(isobutylamino) pentan-1-ol (14 g, 88.1 mmol) and DIPEA (31 mL, 176 mmol) in NMP (100 mL) was stirred at 125° C. for 6 hr. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (10.6 g, 67% yield). LCMS (ESI) m/z calcd for C$_{15}$H$_{23}$BrN$_2$O$_3$: 358.09. Found: 359.24/361.22 (M/M+2)$^+$.

Preparation of ethyl (E)-3-(4-((5-hydroxypentyl)
(isobutyl)amino)-3-nitrophenyl) but-2-enoate

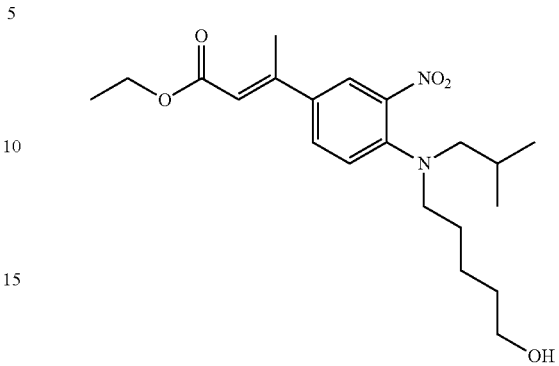

A mixture of 5-((4-bromo-2-nitrophenyl) (isobutyl) amino)pentan-1-ol (3.0 g, 8.35 mmol), methyl (E)-but-2-enoate (1.67 g, 16.7 mmol), TBAB (538 mg, 1.67 mmol), Pd(o-MePh$_3$P)$_4$ (330 mg, 0.42 mmol) and TEA (2.3 mL, 16.7 mmol) in DMF (10 mL) was stirred at 110° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-30% EtOAc in PE) to afford the title compound (1.75 g, 53% yield). LCMS (ESI) m/z calcd for C$_{21}$H$_{32}$N$_2$O$_5$: 392.23. Found: 393.57 (M+1)$^+$.

Preparation of ethyl (E)-3-(4-((5-((tert-butyldimethylsilyl)oxy)pentyl) (isobutyl) amino)-3-nitrophenyl) but-2-enoate

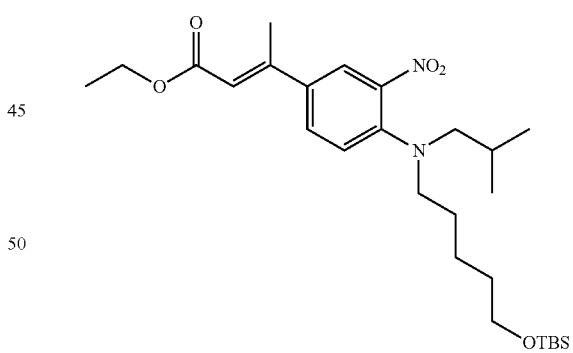

To a solution of ethyl (E)-3-(4-((5-hydroxpentyl) (isobutyl)amino)-3-nitrophenyl)but-2-enoate (2.17 g, 5.54 mmol) and 2,6-lutidine (1.48 g, 13.84 mmol) in DCM (25 mL) was added TBSOTf (2.19 g, 8.31 mmol). After stirred at r.t. for 5 hr, the resulting mixture was partitioned between DCM and H$_2$O. The organic layer was washed with brine, dried over Na$_2$SO$_4$, filtered and concentrated to give the crude product which was purified by flash chromatography (silica gel, 0-10% EtOAc in PE) to afford the title compound (1.8 g, 64% yield). LCMS (ESI) m/z calcd for C$_{27}$H$_{46}$N$_2$O$_5$Si: 506.32. Found: 507.75 (M+1)$^+$.

Preparation of ethyl (R)-3-(4-((5-((tert-butyldimethylsilyl)oxy)pentyl) (isobutyl) amino)-3-nitrophenyl)butanoate

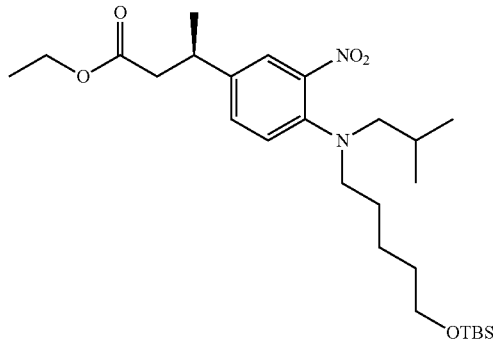 [SMILES: CCOC(=O)C[C@@H](C)c1ccc(N(CCCCCO[Si](C)(C)C(C)(C)C)CC(C)C)c([N+](=O)[O-])c1]

At −5° C., to a mixture of (CuHPh₃P)₆ (54 mg, 0.027 mmol) and (R,S)-PPF-P(tBu)₂ (54 mg, 0.099 mmol) in toluene (20 mL) was added PMHS (0.8 mL) and t-BuOH (0.4 mL) before the introduction of ethyl (E)-3-(4-((5-((tert-butyldimethylsilyl)oxy)pentyl) (iso butyl)amino)-3-nitrophenyl)but-2-enoate (1.8 g, 3.55 mmol). After stirred at −5° C. for 4 hr, the resulting mixture was quenched with sat. NaHCO₃ aq. solution and extracted with EtOAc. The organic layer was washed with brine, dried over Na₂SO₄, filtered and concentrated to give the crude product which was purified by flash chromatography (silica gel, 0-10% EtOAc in PE) to afford the title compound (1.5 g, 83% yield) as a yellow oil. LCMS (ESI) m/z calcd for $C_{27}H_{48}N_2O_5Si$: 508.33. Found: 509.29 (M+1)⁺.

Preparation of ethyl (R)-3-(3-amino-4-((5-((tert-butyldimethylsilyl)oxy)pentyl) (isobutyl)amino)phenyl)butanoate

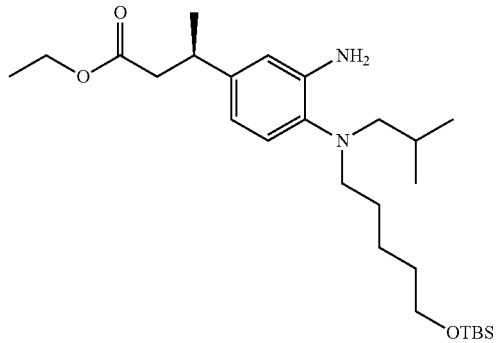

A mixture of ethyl (R)-3-(4-((5-((tert-butyldimethylsilyl)oxy)pentyl) (isobutyl) amino)-3-nitrophenyl)butanoate (1.5 g, 2.95 mmol) and 10% Pd/C (750 mg) in EtOAc (20 mL) was stirred at 50° C. under H₂ for 5 hr. The resulting mixture was filtered through a pad of Celite and the filtrate was concentrated under reduced pressure to give the crude product which was purified by flash chromatography (silica gel, 0-10% EtOAc in PE) to afford the title compound (1.22 g, 86% yield) as a yellow oil. LCMS (ESI) m/z calcd for $C_{27}H_{50}N_2O_3Si$: 478.36. Found: 479.91 (M+1)⁺.

Preparation of ethyl (R)-3-(4-((5-((tert-butyldimethylsilyl)oxy)pentyl) (isobutyl) amino)-3-((3-(trifluoromethyl)-1,2,4-thiadiazol-5-yl)amino)phenyl)butanoate

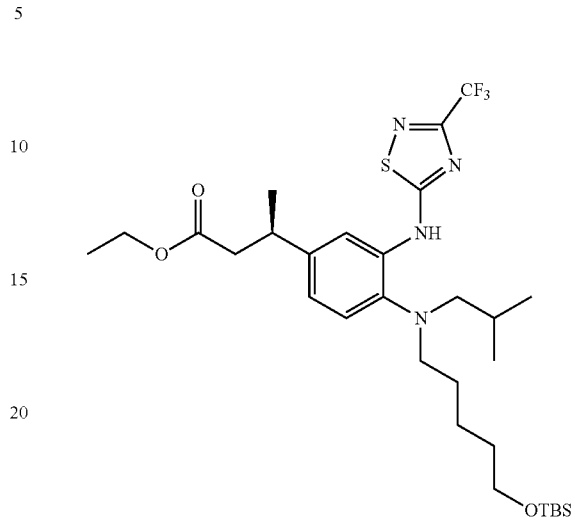

A mixture of ethyl (R)-3-(3-amino-4-((5-((tert-butyldimethylsilyl)oxy)pentyl) (isobutyl) amino)phenyl)butanoate (1.22 g, 2.55 mmol) and 5-chloro-3-(trifluoromethyl)-1,2,4-thiadiazole (720 mg, 3.83 mmol) in MeCN (10 mL) was stirred at 90° C. under N₂ atmosphere for 72 hr. The resulting mixture was partitioned between EtOAc and H₂O. The organic layer was washed with brine, dried over Na₂SO₄, filtered and concentrated to give the crude product which was purified by flash chromatography (silica gel, 0-30% EtOAc in PE) to afford the title compound (650 mg, 40% yield). LCMS (ESI) m/z calcd for $C_{30}H_{49}F_3N_4O_3SSi$: 630.32. Found: 631.66 (M+1)⁺.

Preparation of ethyl (R)-3-(4-((5-hydroxypentyl) (isobutyl)amino)-3-((3-(tri fluoromethyl)-1,2,4-thiadiazol-5-yl)amino)phenyl)butanoate

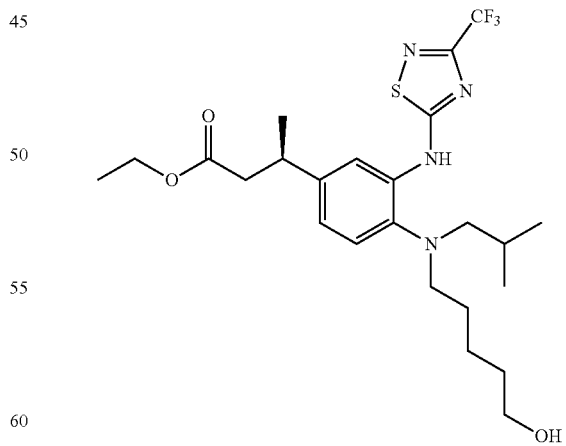

To a solution of ethyl (R)-3-(4-((5-((tert-butyldimethylsilyl)oxy)pentyl) (isobutyl) amino)-3-((3-(trifluoromethyl)-1, 2,4-thiadiazol-5-yl)amino)phenyl)butanoate (650 mg, 1.03 mmol) in THF (10 mL) was added TBAF (1N in THF, 1.55 mL). After stirred at r.t. for 48 hr, the resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (490 mg, 92% yield). LCMS (ESI) m/z calcd for C$_{24}$H$_{35}$F$_3$N$_4$O$_3$S: 516.24. Found: 517.26 (M+1)$^+$.

Preparation of ethyl (R)-3-(4-(isobutyl(5-((methylsulfonyl)oxy)pentyl)amino)-3-((3-(trifluoromethyl)-1,2,4-thiadiazol-5-yl)amino)phenyl)butanoate

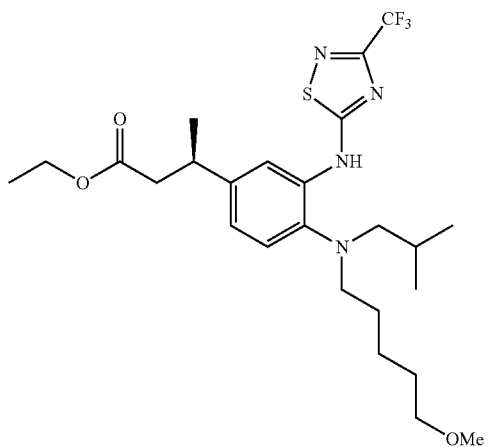 [SMILES: CCOC(=O)C[C@@H](C)c1ccc(N(CCCCCOC)CC(C)C)c(Nc2nc(C(F)(F)F)ns2)c1]

At 0° C., to a solution of ethyl (R)-3-(4-((5-hydroxypentyl) (isobutyl)amino)-3-((3-(tri fluoromethyl)-1,2,4-thiadiazol-5-yl)amino)phenyl)butanoate (810 mg, 1.57 mmol) in DCM (10 mL) was added TEA (0.26 mL, 1.88 mmol) and MsCl (216 mg, 1.88 mmol). After stirred at r.t. overnight, the resulting mixture was partitioned between DCM and H$_2$O. The organic layer was washed with brine, dried over Na$_2$SO$_4$, filtered and concentrated to give the crude product which was purified by flash chromatography (silica gel, 0-30% EtOAc in PE) to afford the title compound (780 mg, 83% yield). LCMS (ESI) m/z calcd for C$_{25}$H$_{37}$F$_3$N$_4$O$_5$S$_2$: 594.22. Found: 595.47 (M+1)$^+$.

Preparation of ethyl (R)-3-(4-((5-azidopentyl)(isobutyl)amino)-3-((3-(trifluoro methyl)-1,2,4-thiadiazol-5-yl)amino)phenyl)butanoate

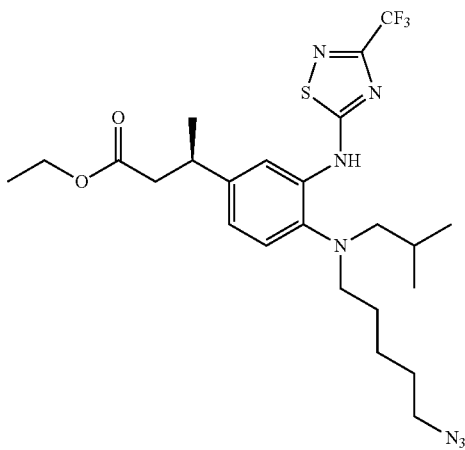 [SMILES: CCOC(=O)C[C@@H](C)c1ccc(N(CCCCCN=[N+]=[N-])CC(C)C)c(Nc2nc(C(F)(F)F)ns2)c1]

A mixture of ethyl (R)-3-(4-(isobutyl(5-((methylsulfonyl)oxy)pentyl)amino)-3-((3-(tri fluoromethyl)-1,2,4-thiadiazol-5-yl)amino)phenyl)butanoate (780 mg, 1.31 mmol) and NaN$_3$ (256 mg, 3.93 mmol) in DMF (10 mL) was stirred at 80° C. for 4 hr. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (640 mg, 90% yield). LCMS (ESI) m/z calcd for C$_{24}$H$_{34}$F$_3$N$_7$O$_2$S: 541.24. Found: 542.52 (M+1)$^+$.

Preparation of (R)-3-(4-((5-azidopentyl) (isobutyl)amino)-3-((3-(trifluoromethyl)-1,2,4-thiadiazol-5-yl)amino)phenyl)butanoic Acid

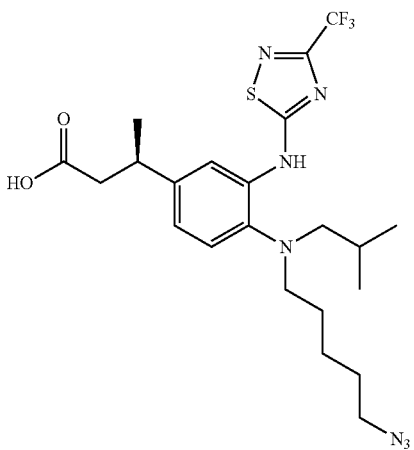 [SMILES: CC(C)CN(CCCCCN=[N+]=[N-])c1ccc([C@H](C)CC(=O)O)cc1Nc1nc(C(F)(F)F)ns1]

To a solution of ethyl (R)-3-(4-((5-azidopentyl) (isobutyl)amino)-3-((3-(trifluoro methyl)-1,2,4-thiadiazol-5-yl)amino)phenyl)butanoate (30 mg, 0.055 mmol) in MeOH (2 mL) was added 4N NaOH aq. (0.2 mL). After stirred at rt for 4 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (17.7 mg, 63% yield) as a white powder. $^1$H NMR (400 MHz, CDCl$_3$) δ 9.40 (s, 1H), 7.27 (d, J=1.4 Hz, 1H), 7.13 (d, J=8.2 Hz, 1H), 6.94 (dd, J=8.0, 1.6 Hz, 1H), 3.30-3.24 (m, 1H), 3.16-3.11 (m, 2H), 2.80-2.71 (m, 2H), 2.64-2.56 (m, 3H), 1.48-1.26 (m, 11H), 0.83 (d, J=6.6 Hz, 6H). LCMS (ESI) m/z calcd for C$_{22}$H$_{30}$F$_3$N$_7$O$_2$S: 513.21. Found: 514.49 (M+1)$^+$.

279

Example 95

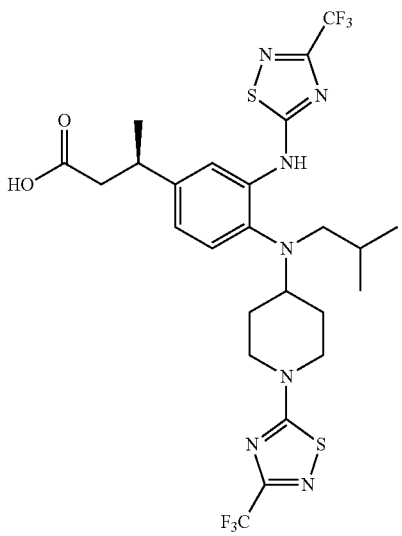 [SMILES: CC(C)CN(c1ccc([C@H](C)CC(=O)O)cc1Nc1nc(C(F)(F)F)ns1)C1CCN(c2nc(C(F)(F)F)ns2)CC1]

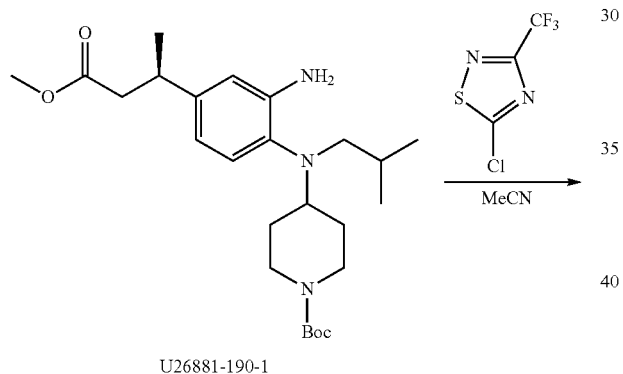

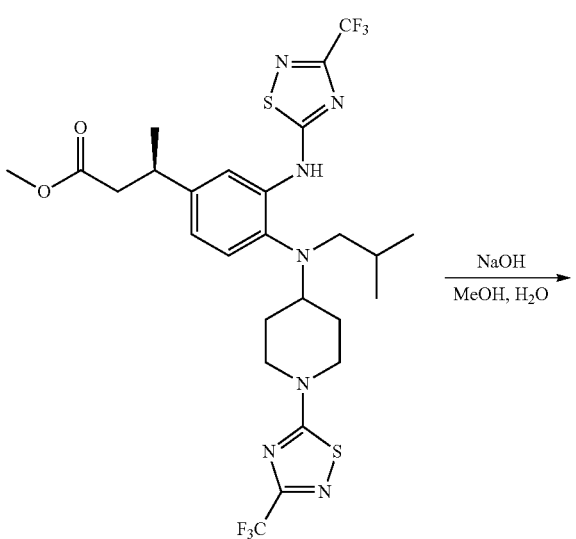

280

-continued

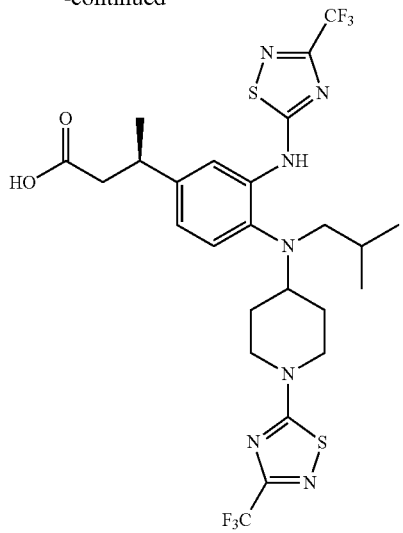

Preparation of methyl (R)-3-(4-(isobutyl(1-(3-(trifluoromethyl)-1,2,4-thiadiazol-5-yl)piperidin-4-amino)-3-((3-(trifluoromethyl)-1,2,4-thiadiazol-5-yl)amino)phenyl)butanoate

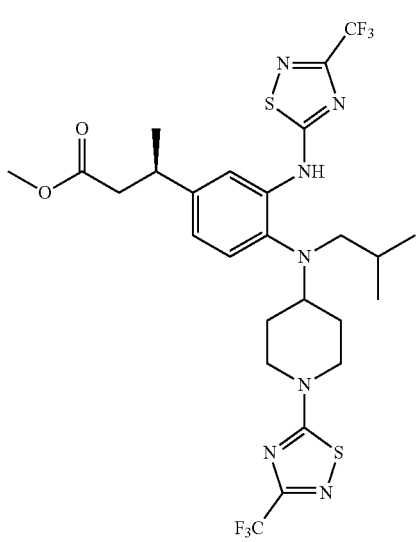 [SMILES: COC(=O)C[C@@H](C)c1ccc(N(CC(C)C)C2CCN(c3nc(C(F)(F)F)ns3)CC2)c(Nc2nc(C(F)(F)F)ns2)c1]

A mixture of tert-butyl (R)-4-((2-amino-4-(4-methoxy-4-oxobutan-2-yl)phenyl) (isobutyl) amino)piperidine-1-carboxylate (180 mg, 0.40 mmol) and 5-chloro-3-(trifluoromethyl)-1,2,4-thiadiazole (150 mg, 0.80 mmol) in MeCN (2 mL) was stirred at 90° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (70 mg, 27% yield). LCMS (ESI) m/z calcd for $C_{26}H_{31}F_6N_7O_2S_2$: 651.19. Found: 650.46 (M−1)⁻.

Preparation of (R)-3-(4-(isobutyl(1-(3-(trifluoromethyl)-1,2,4-thiadiazol-5-yl)piperidin-4-yl)amino)-3-((3-(trifluoromethyl)-1,2,4-thiadiazol-5-yl)amino)phenyl)butanoic Acid

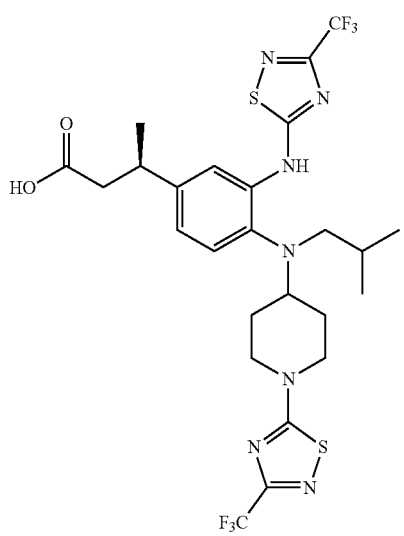 [SMILES: CC(C)CN(c1ccc([C@H](C)CC(=O)O)cc1Nc1nc(C(F)(F)F)ns1)C1CCN(c2nc(C(F)(F)F)ns2)CC1]

To a solution of methyl (R)-3-(4-(isobutyl(1-(3-(trifluoromethyl)-1,2,4-thiadiazol-5-yl)piperidin-4-yl)amino)-3-((3-(trifluoromethyl)-1,2,4-thiadiazol-5-yl)amino)phenyl)butanoate (70 mg, 0.11 mmol) in MeOH (3 mL) was added 4N NaOH aq. (0.5 mL). After stirred at rt for 6 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (51 mg, 75% yield) as a white powder. $^1$H NMR (400 MHz, $CDCl_3$) δ 9.34 (s, 1H), 7.30 (d, J=1.5 Hz, 1H), 7.22 (d, J=8.2 Hz, 1H), 7.02 (dd, J=8.2, 1.8 Hz, 1H), 4.07-3.83 (m, 2H), 3.39-3.31 (m, 1H), 3.19-3.05 (m, 2H), 2.94-2.78 (m, 3H), 2.74-2.60 (m, 2H), 2.05-1.95 (m, 2H), 1.71-1.62 (m, 2H), 1.46-1.36 (m, 4H), 0.86 (d, J=6.6 Hz, 6H). LCMS (ESI) m/z calcd for $C_{25}H_{29}F_6N_7O_2S_2$: 637.17. Found: 638.80 (M+1)$^+$.

Example 96

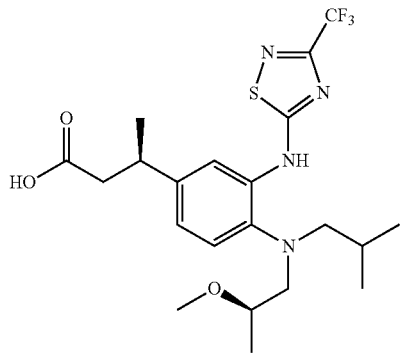

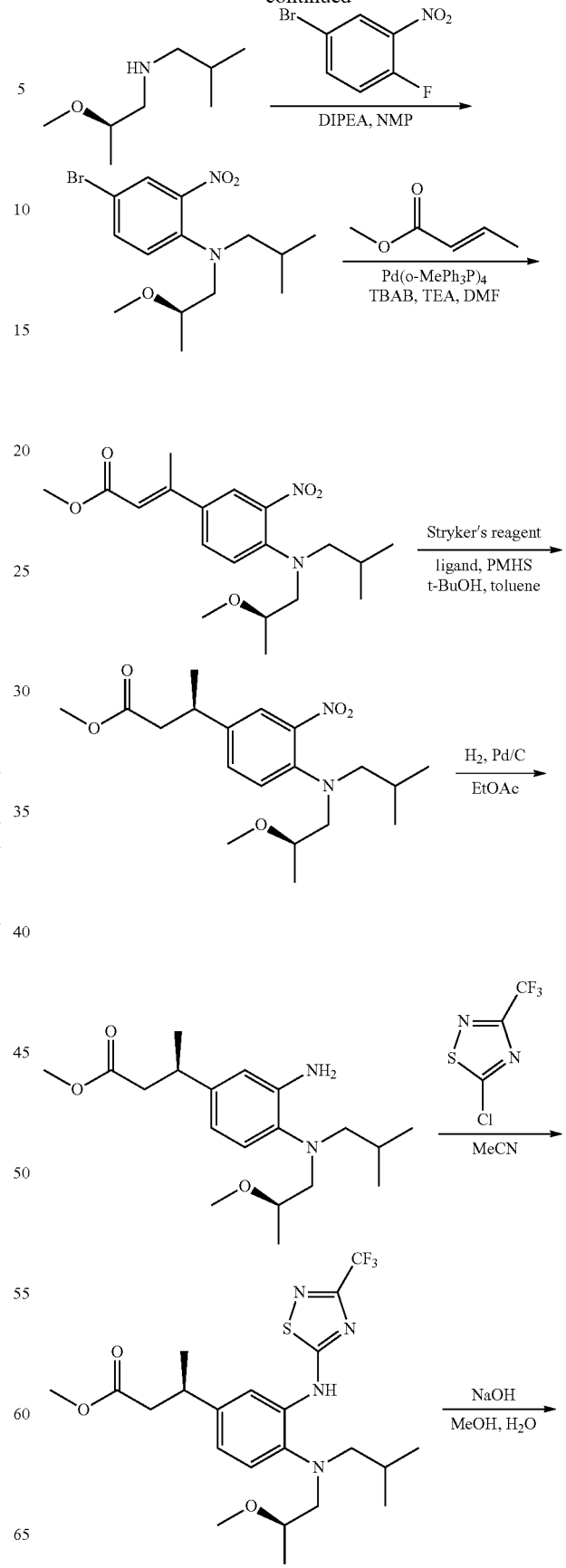

-continued

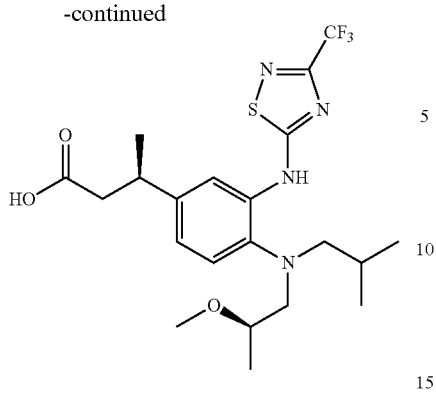

Preparation of (R)-4-bromo-N-isobutyl-N-(2-methoxypropyl)-2-nitroaniline

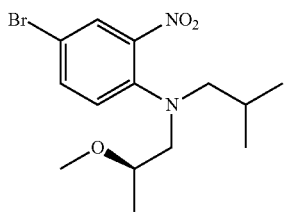 [SMILES: CO[C@H](C)CN(CC(C)C)c1ccc(Br)cc1[N+](=O)[O-]]

A mixture of 4-bromo-1-fluoro-2-nitrobenzene (1.0 g, 4.55 mmol), (R)—N-isobutyl-2-methoxypropan-1-amine (989 mg, 6.81 mmol) and DIPEA (2.4 mL, 13.6 mmol) in NMP (10 mL) was stirred at 120° C. for 6 hr. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (717 mg, 46% yield). LCMS (ESI) m/z calcd for C$_{14}$H$_{21}$BrN$_2$O$_3$: 344.07. Found: 345.27/347.33 (M/M+2)$^+$.

Preparation of methyl (R, E)-3-(4-(isobutyl(2-methoxypropyl)amino)-3-nitro phenyl)but-2-enoate

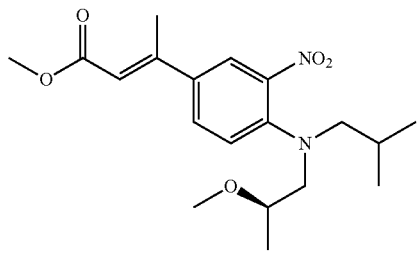 [SMILES: COC(=O)/C=C(\C)c1ccc(N(CC(C)C)C[C@@H](C)OC)c([N+](=O)[O-])c1]

A mixture of (R)-4-bromo-N-isobutyl-N-(2-methoxypropyl)-2-nitroaniline (2.15 g, 6.2 mmol), methyl (E)-but-2-enoate (1.25 g, 12.5 mmol), TBAB (400 mg, 1.24 mmol), Pd(o-MePh$_3$P)$_4$ (244 mg, 0.31 mmol) and TEA (1.7 mL, 12.5 mmol) in DMF (15 mL) was stirred at 100° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (1.15 g, 51% yield). LCMS (ESI) m/z calcd for C$_{19}$H$_{28}$N$_2$O$_5$: 364.20. Found: 365.30 (M+1)$^+$.

Preparation of methyl (R)-3-(4-(isobutyl((R)-2-methoxypropyl)amino)-3-nitro phenyl)butanoate

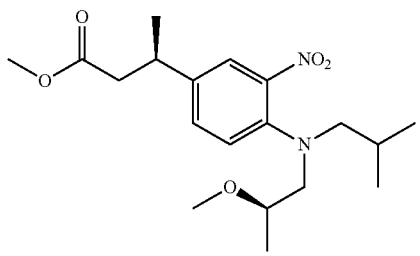 [SMILES: COC(=O)C[C@@H](C)c1ccc(N(CC(C)C)C[C@@H](C)OC)c([N+](=O)[O-])c1]

At −5° C., to a mixture of (CuHPh$_3$P)$_6$ (186 mg, 0.1 mmol) and (R,S)-PPF-P(tBu)$_2$ (21 mg, 0.038 mmol) in toluene (10 mL) was added PMHS (164 mg) and t-BuOH (112 mg) before the introduction of methyl (R,E)-3-(4-(isobutyl(2-methoxypropyl)amino)-3-nitro phenyl)but-2-enoate (500 mg, 1.37 mmol). After stirred at −5° C. for 24 hr, the resulting mixture was quenched with sat. NaHCO$_3$ aq. solution and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (460 mg, 92% yield). LCMS (ESI) m/z calcd for C$_{19}$H$_{30}$N$_2$O$_5$: 366.22. Found: 367.53 (M+1)$^+$.

Preparation of methyl (R)-3-(3-amino-4-(isobutyl((R)-2-methoxypropyl)amino) phenyl)butanoate

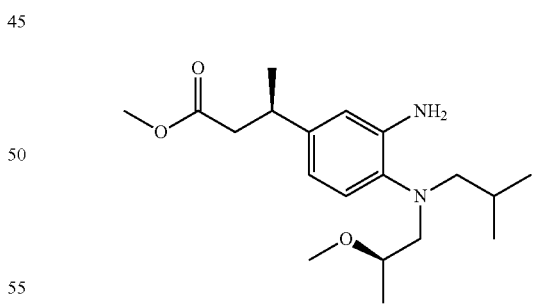

A mixture of methyl (R)-3-(4-(isobutyl((R)-2-methoxypropyl)amino)-3-nitrophenyl) butanoate (460 mg, 1.25 mmol) and 10% Pd/C (200 mg) in EtOAc (30 mL) was stirred at r.t. under H$_2$ for 2 hr. The resulting mixture was filtered through a pad of Celite and the filtrate was concentrated under reduced pressure to give the crude product which was purified by flash chromatography (silica gel, 0-30% EtOAc in PE) to afford the title compound (320 mg, 76% yield). LCMS (ESI) m/z calcd for C$_{19}$H$_{32}$N$_2$O$_3$: 336.24. Found: 337.50 (M+1)$^+$.

285

Preparation of methyl (R)-3-(4-(isobutyl((R)-2-methoxypropyl)amino)-3-((3-(tri fluoromethyl)-1,2,4-thiadiazol-5-yl)amino)phenyl)butanoate

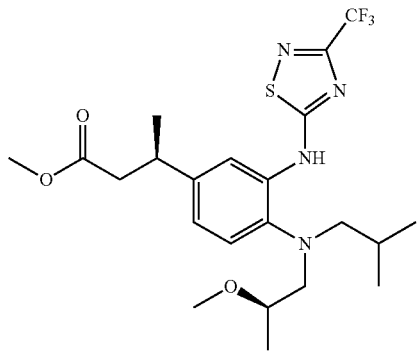 [SMILES: COC(=O)C[C@@H](C)c1ccc(N(CC(C)C)C[C@@H](C)OC)c(Nc2nc(C(F)(F)F)ns2)c1]

A mixture of methyl (R)-3-(3-amino-4-(isobutyl((R)-2-methoxypropyl)amino)phenyl) butanoate (100 mg, 0.30 mmol) and 5-chloro-3-(trifluoromethyl)-1,2,4-thiadiazole (113 mg, 0.60 mmol) in MeCN (3 mL) was stirred at 90° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (80 mg, 55% yield). LCMS (ESI) m/z calcd for $C_{22}H_{31}F_3N_4O_3S$: 488.21. Found: 489.55 (M+1)$^+$.

Preparation of (R)-3-(4-(isobutyl((R)-2-methoxypropyl)amino)-3-((3-(trifluoro methyl)-1,2,4-thiadiazol-5-yl)amino)phenyl)butanoic Acid

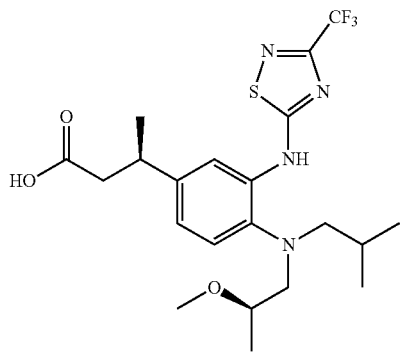 [SMILES: CO[C@H](C)CN(CC(C)C)c1ccc([C@H](C)CC(=O)O)cc1Nc1nc(C(F)(F)F)ns1]

To a solution of methyl (R)-3-(4-(isobutyl((R)-2-methoxypropyl)amino)-3-((3-(tri fluoromethyl)-1,2,4-thiadiazol-5-yl)amino)phenyl)butanoate (80 mg, 0.16 mmol) in MeOH (5 mL) was added 1N NaOH aq. (1 mL). After stirred at r.t. for overnight, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (48 mg, 62% yield) as a white powder. $^1$H NMR (400 MHz, CDCl$_3$) δ 10.71 (s, 1H), 9.36 (br, 1H), 7.82 (s, 1H), 7.14 (d, J=8.2 Hz, 1H), 6.92 (dd, J=8.2, 1.9 Hz, 1H), 3.66-3.50 (m, 4H), 3.31 (dd, J=14.6, 7.2 Hz, 1H), 3.16 (dd, J=12.6, 4.3 Hz, 1H), 2.77-2.50 (m, 5H), 1.59-1.52 (m, 1H), 1.36 (d, J=7.0 Hz, 3H), 1.08 (d, J=6.2 Hz, 3H), 0.85 (dd, J=6.6, 1.7 Hz, 6H) LCMS (ESI) m/z calcd for $C_{21}H_{29}F_3N_4O_3S$: 474.19. Found: 475.51 (M+1)$^+$.

Example 97

4'-((2-(tert-butoxycarbonyl)-2-azaspiro[3.3]heptan-6-yl) (isobutyl)amino)-3'-((3-(trifluoromethyl)-1,2,4-thiadiazol-5-yl)amino)-[1,1'-biphenyl]-2-carboxylic Acid

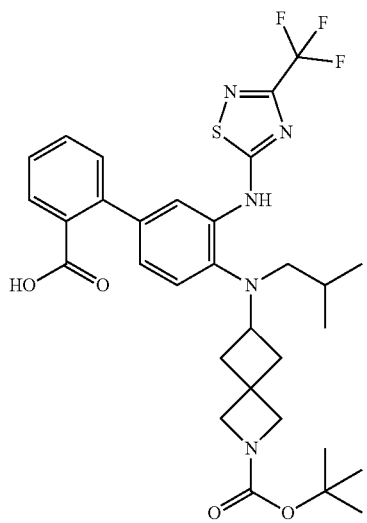 [SMILES: CC(C)CN(c1ccc(-c2ccccc2C(=O)O)cc1Nc1nc(C(F)(F)F)ns1)C1CC2(C1)CN(C(=O)OC(C)(C)C)C2]

Step A tert-butyl 6-(isobutylamino)-2-azaspiro[3.3]heptane-2-carboxylate

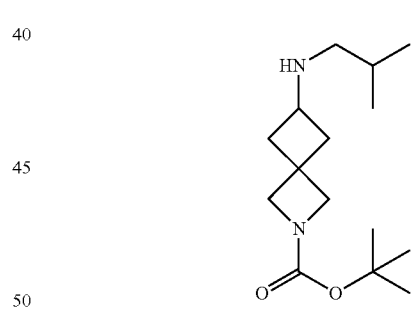

tert-Butyl 6-amino-2-azaspiro[3.3]heptane-2-carboxylate (200 mg, 0.942 mmol) and isobutyraldehyde (0.086 mL, 0.942 mmol) in ethanol (5 mL) were stirred at room temperature for 1 hour. The vessel as filled with nitrogen before 10% palladium on carbon (20 mg, 0.019 mmol) was added. The vessel was evacuated and filled with hydrogen. The mixture was hydrogenated at 60 psi overnight. The mixture was quenched with a stream of nitrogen for 5 minutes and then filtered over celite. The filtrate was concentrated to give tert-butyl 6-(isobutylamino)-2-azaspiro[3.3]heptane-2-carboxylate (257 mg, 0.938 mmol, 100% yield) as an oil. LCMS (ESI) m/z calculated for $C_{15}H_{28}N_2O_2$: $^1$H NMR (400 MHz, CHLOROFORM-d) δ ppm 3.91 (s, 2H), 3.82 (s, 2H), 3.04-3.19 (m, 1H), 2.37-2.53 (m, 2H), 2.30 (d, J=6.6 Hz, 2H), 1.79-1.89 (m, 2H), 1.61-1.73 (m, 1H), 1.43 (s, 9H), 0.89 (d, J=6.6 Hz, 6H).

Step B tert-butyl 6-((4-bromo-2-nitrophenyl) (isobutyl)amino)-2-azaspiro[3.3]heptane-2-carboxylate

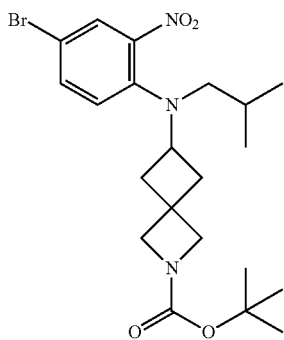 [SMILES: CC(C)CN(c1ccc(Br)cc1[N+](=O)[O-])C1CC2(C1)CN(C(=O)OC(C)(C)C)C2]

A mixture of 4-bromo-1-fluoro-2-nitrobenzene (0.118 mL, 0.958 mmol), potassium carbonate (529 mg, 3.83 mmol), and tert-butyl 6-(isobutylamino)-2-azaspiro[3.3]heptane-2-carboxylate (257 mg, 0.958 mmol) in dimethyl sulfoxide (DMSO) (2 mL) was heated at 100° C. for 6 hours. The mixture was cooled to room temperature, quenched with water, and extracted 3 times with ethyl acetate. The combined organic layers were washed with brine, dried over sodium sulfate, and concentrated. The residue was purified by reverse phase medium pressure chromatography (10% to 100% acetonitrile/water/0.1% formic acid). Fractions were concentrated to give tert-butyl 6-((4-bromo-2-nitrophenyl) (isobutyl)amino)-2-azaspiro[3.3]heptane-2-carboxylate (161 mg, 0.344 mmol, 35.9% yield, 68% purity) as an orange liquid. LCMS (ESI) m/z calculated for $C_{21}H_{30}BrN_3O_4$: 467.1, 469.1. Found: 468.4, 470.3 (M+H)$^+$.

Step C tert-butyl 6-((2'-(ethoxycarbonyl)-3-nitro-[1,1'-biphenyl]-4-yl) (isobutyl)amino)-2-azaspiro[3.3]heptane-2-carboxylate

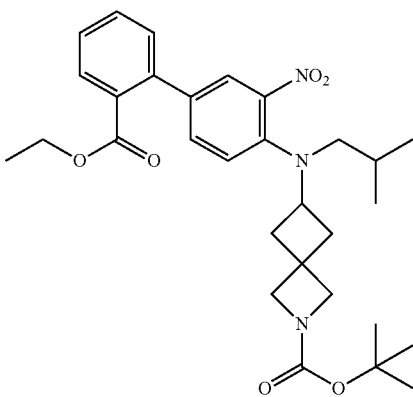 [SMILES: CCOC(=O)c1ccccc1-c1ccc(N(CC(C)C)C2CC3(C2)CN(C(=O)OC(C)(C)C)C3)c([N+](=O)[O-])c1]

A solution of potassium carbonate (191 mg, 1.38 mmol) in water (0.75 mL) was added to a solution of tert-butyl 6-((4-bromo-2-nitrophenyl) (isobutyl)amino)-2-azaspiro[3.3]heptane-2-carboxylate (162 mg, 0.346 mmol) and (2-(ethoxycarbonyl)phenyl)boronic acid (114 mg, 0.588 mmol) in N,N-dimethylformamide (DMF) (3 mL). The mixture was subject to a stream of nitrogen for 5 minutes before tetrakis (40.0 mg, 0.035 mmol) was added. The reaction vessel was immediately placed into a pre-heated 110° C. heating block. The mixture was heated for 2 hours, cooled to room temperature, and solids filtered off. The filtrate was diluted with brine and extracted 2 times with ethyl acetate. The combined organic layers were dried over sodium sulfate and concentrated. The residue was purified by silica chromatography eluting with a gradient of 0% to 30% ethyl acetate in hexanes. Fractions were concentrated to give tert-butyl 6-((2'-(ethoxycarbonyl)-3-nitro-[1,1'-biphenyl]-4-yl) (isobutyl)amino)-2-azaspiro[3.3]heptane-2-carboxylate (120 mg, 0.223 mmol, 64.5% yield) as an orange oil. LCMS (ESI) m/z calculated for $C_{30}H_{39}N_3O_6$: 537.3 Found: 538.5 (M+H)$^+$.

Step D tert-butyl 6-((3-amino-2'-(ethoxycarbonyl)-[1,1'-biphenyl]-4-yl) (isobutyl)amino)-2-azaspiro[3.3] heptane-2-carboxylate

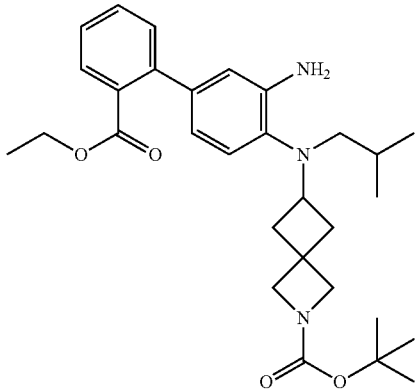

A mixture of tert-butyl 6-((2'-(ethoxycarbonyl)-3-nitro-[1,1'-biphenyl]-4-yl) (isobutyl)amino)-2-azaspiro[3.3]heptane-2-carboxylate (120 mg, 0.223 mmol) and ammonium chloride (239 mg, 4.46 mmol) in ethanol (3 mL) and water (1 mL) was cooled to 0° C. before zinc (146 mg, 2.23 mmol) was added in 1 portion. The mixture was stirred at 0° C. for 5 minutes and then allowed to warm to room temperature and stirred for 3 hours. The mixture was diluted with water and ethyl acetate and the excess zinc filtered off over cotton. The filtrate was extracted 3 times with ethyl acetate, washed with brine, dried over sodium sulfate, and concentrated. The product was purified by reverse phase medium pressure chromatography (10% to 100% acetonitrile/water/0.1% formic acid). Fractions were concentrated to give tert-butyl 6-((3-amino-2'-(ethoxycarbonyl)-[1,1'-biphenyl]-4-yl) (isobutyl)amino)-2-azaspiro[3.3]heptane-2-carboxylate (84 mg, 0.165 mmol, 74 yield). LCMS (ESI) m/z calculated for $C_{30}H_{41}N_3O_4$: 507.3. Found: 508.5 (M+H)$^+$.

Step E tert-butyl 6-((2'-(ethoxycarbonyl)-3-((3-(trifluoromethyl)-1,2,4-thiadiazol-5-yl)amino)-[1,1'-biphenyl]-4-yl)(isobutyl)amino)-2-azaspiro[3.3]heptane-2-carboxylate

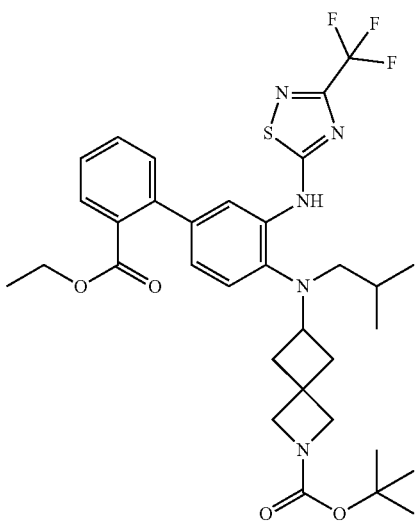 [SMILES: CCOC(=O)c1ccccc1-c1ccc(N(CC(C)C)C2CC3(C2)CN(C(=O)OC(C)(C)C)C3)c(Nc2nc(C(F)(F)F)ns2)c1]

tert-Butyl 6-((3-amino-2'-(ethoxycarbonyl)-[1,1'-biphenyl]-4-yl)(isobutyl)amino)-2-azaspiro[3.3]heptane-2-carboxylate (42 mg, 0.083 mmol) and 3-chloro-5-(trifluoromethyl)-1,2,4-thiadiazole (23 mg, 0.122 mmol) in N,N-dimethylformamide (DMF) (0.5 mL) were heated at 90° C. for 3 hours. The mixture was allowed to cool to room temperature, quenched with brine, and extracted 3 times with ethyl acetate. The combined organic layers were washed with brine, dried over sodium sulfate, and concentrated. The residue was purified by silica chromatography eluting with a gradient of 0% to 50% ethyl acetate in dichloromethane. Fractions were concentrated to give tert-butyl 6-((2'-(ethoxycarbonyl)-3-((5-(trifluoromethyl)-1,2,4-thiadiazol-3-yl)amino)-[1,1'-biphenyl]-4-yl)(isobutyl)amino)-2-azaspiro[3.3]heptane-2-carboxylate (12 mg, 0.015 mmol, 18.25% yield, 83% purity). LCMS (ESI) m/z calculated for $C_{33}H_{40}F_3N_5O_4S$: 659.3. Found: 660.4 (M+H)+.

Step F

4'-((2-(tert-butoxycarbonyl)-2-azaspiro[3.3]heptan-6-yl)(isobutyl)amino)-3'-((3-(trifluoromethyl)-1,2,4-thiadiazol-5-yl)amino)-[1,1'-biphenyl]-2-carboxylic Acid

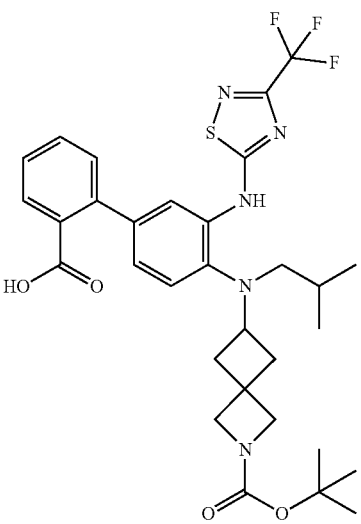 [SMILES: CC(C)CN(c1ccc(-c2ccccc2C(=O)O)cc1Nc1nc(C(F)(F)F)ns1)C1CC2(C1)CN(C(=O)OC(C)(C)C)C2]

tert-Butyl 6-((2'-(ethoxycarbonyl)-3-((5-(trifluoromethyl)-1,2,4-thiadiazol-3-yl)amino)-[1,1'-biphenyl]-4-yl)(isobutyl)amino)-2-azaspiro[3.3]heptane-2-carboxylate (12 mg, 0.018 mmol) was dissolved in methanol (0.16 mL) and tetrahydrofuran (THF) (0.16 mL) before 1M lithium hydroxide (0.364 mL, 0.364 mmol) was added. The mixture was heated at 60° C. for 3 hours. LC-MS showed no reaction. The solvents were removed and the residue slurried in 1,4-dioxane (0.400 mL). Additional 1M lithium hydroxide (0.364 mL, 0.364 mmol) was added and the mixture heated at 80° C. overnight. The mixture was quenched with 1M citric acid and extracted 3 times with ethyl acetate. The combined organic layers were washed with brine and concentrated. The residue was purified by reverse phase medium pressure chromatography (10% to 100% acetonitrile/water/0.1% formic acid).

Fractions were concentrated and the residue dried to give 4'-((2-(tert-butoxycarbonyl)-2-azaspiro[3.3]heptan-6-yl)(isobutyl)amino)-3'-((5-(trifluoromethyl)-1,2,4-thiadiazol-3-yl)amino)-[1,1'-biphenyl]-2-carboxylic acid (3.5 mg, 5.32 μmol, 29.2% yield, 96% purity). LCMS (ESI) m/z calculated for $C_{31}H_{36}F_3N_5O_4S$: 631.2. Found: 632.4 (M+H)+. $^1$H NMR (400 MHz, METHANOL-$d_4$) δ ppm 8.00 (s, 1H), 7.77 (d, J=7.4 Hz, 1H), 7.51-7.57 (m, 1H), 7.38-7.46 (m, 2H), 7.27 (d, J=8.2 Hz, 1H), 7.10-7.16 (m, 1H), 3.89 (br. s, 2H), 3.72 (br. s, 2H), 3.57-3.66 (m, 1H), 2.71 (d, J=7.0 Hz, 2H), 2.21-2.32 (m, 2H), 1.95-2.09 (m, 2H), 1.45-1.58 (m, 1H), 1.38 (s, 9H), 0.82 (d, J=6.4 Hz, 6H).

Example 98

(R)-3-(3-((3-chloro-1,2,4-thiadiazol-5-yl)amino)-4-(isobutyl(spiro[3.3]heptan-2-yl)amino)phenyl)butanoic Acid

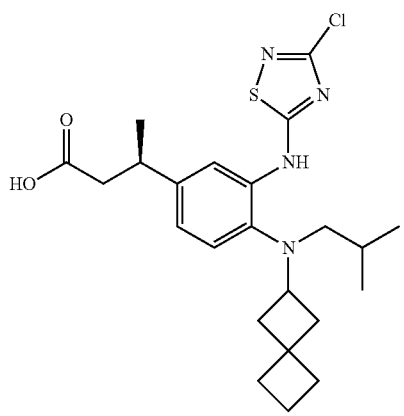 [SMILES: CC(C)CN(c1ccc([C@H](C)CC(=O)O)cc1Nc1nc(Cl)ns1)C1CC2(CCC2)C1]

Step A

N-(spiro[3.3]heptan-2-yl)isobutyramide

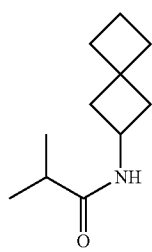

A solution of spiro[3.3]heptan-2-amine hydrochloride (0.760 g, 5.15 mmol) in DCM (25.7 ml) was cooled to 0° C. and treated by the addition of TEA (1.794 ml, 12.87 mmol), followed by the dropwise addition of isobutyryl chloride (0.593 ml, 5.66 mmol). The reaction was stirred at 0° C. for 1 hour, then for 1 hour at room temperature. The reaction was diluted with saturated NaHCO$_3$ and DCM. The combined organics were washed with 1N HCl, brine, dried over Na$_2$SO$_4$, filtered, and concentrated to give N-(spiro[3.3]heptan-2-yl)isobutyramide (0.922 g, 5.09 mmol, 99% yield) as a white solid. $^1$H NMR (400 MHz, CHLOROFORM-d) δ ppm 5.53 (br. s., 1H) 4.11-4.32 (m, 1H) 2.43 (t, J=8.33 Hz, 2H) 2.21-2.33 (m, 1H) 2.03 (t, J=6.41 Hz, 2H) 1.69-1.96 (m, 6H) 1.07-1.19 (m, 6H).

Step B

N-isobutylspiro[3.3]heptan-2-amine

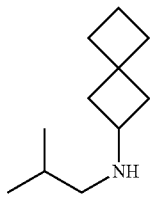

A solution of N-(spiro[3.3]heptan-2-yl)isobutyramide (0.922 g, 5.09 mmol) in THF (21.19 ml) was treated by the dropwise addition of LAH (10.17 ml, 10.17 mmol). The mixture was heated at 70° C. for 5 hours. The reaction was cooled to room temperature, then in an ice bath. The reaction was treated by the addition of 0.386 mL water, 0.386 mL of 15% NaOH, and 1.158 mL water. The reaction was stirred at room temperature for 15 minutes, and then treated with MgSO$_4$, stirred for an additional 15 minutes and filtered, rinsing with Et$_2$O. The filtrate was concentrated to give N-isobutylspiro[3.3]heptan-2-amine (0.719 g, 4.30 mmol, 85% yield) as yellow oil. $^1$H NMR (400 MHz, CHLOROFORM-d) δ ppm 3.11-3.04 (m, 1H) 2.25-2.35 (m, 3H) 1.76-2.04 (m, 7H) 1.56-1.74 (m, 4H) 0.86-0.96 (m, 6H).

Step C

N-(4-bromo-2-nitrophenyl)-N-isobutylspiro[3.3]heptan-2-amine

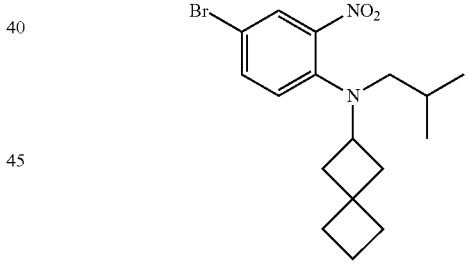

A solution of 4-bromo-1-fluoro-2-nitrobenzene (0.645 ml, 3.45 mmol), N-isobutylspiro[3.3]heptan-2-amine (0.549 g, 3.28 mmol), K$_2$CO$_3$ (0.955 g, 6.91 mmol) in DMSO (17.27 ml) was heated at 80° C. overnight. The reaction was cooled to room temperature and diluted with EtOAc and water. The combined extracts were washed with brine, dried over Na$_2$SO$_4$, filtered, and concentrated. The residue was purified by silica gel chromatography (0-7% EtOAc/hexanes) to give a residue. The residue was purified by reverse phase chromatography (0-100% ACN/H$_2$O+formic acid) to give N-(4-bromo-2-nitrophenyl)-N-isobutylspiro[3.3]heptan-2-amine (0.551 g, 43.4% yield) as an orange oil. $^1$H NMR (400 MHz, CHLOROFORM-d) δ ppm 7.90-8.01 (m, 1H) 7.39-7.49 (m, 1H) 6.89 (d, J=8.97 Hz, 1H) 3.68-3.84 (m, 1H) 2.90 (d, J=7.23 Hz, 2H) 2.14-2.29 (m, 2H) 1.96-2.06 (m, 2H) 1.69-1.92 (m, 7H) 0.80 (d, J=6.64 Hz, 6H).

Step D (E)-ethyl 3-(4-(isobutyl(spiro[3.3]heptan-2-yl)amino)-3-nitrophenyl)but-2-enoate

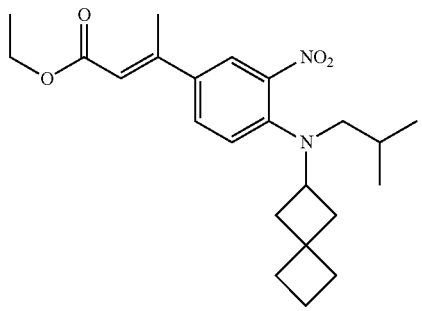 [SMILES: CCOC(=O)/C=C(\C)c1ccc(N(CC(C)C)C2CC3(CCC3)C2)c([N+](=O)[O-])c1]

A solution of N-(4-bromo-2-nitrophenyl)-N-isobutylspiro[3.3]heptan-2-amine (0.405 g, 1.103 mmol), (E)-ethyl but-2-enoate (0.274 ml, 2.205 mmol), PdCl$_2$(dppf)-CH$_2$Cl$_2$ adduct (0.018 g, 0.022 mmol), and K$_2$CO$_3$ (0.457 g, 3.31 mmol) in DMF (3.68 ml) was purged with nitrogen and heated at 110° C. for 4 hours. The reaction was cooled to room temperature and diluted with EtOAc and water. The layers were separated and the aqueous was extracted with EtOAc. The combined organics were washed with 5% LiCl (3×), brine, dried over Na$_2$SO$_4$, filtered, and concentrated onto silica gel. The residue was purified by silica gel chromatography (0-10% EtOAc/hexanes) to give a residue. The residue was taken up in EtOAc and washed with brine, dried Na$_2$SO$_4$, filtered, and concentrated onto silica gel. The residue was purified with (0-10% EtOAc/hexanes) to give (E)-ethyl 3-(4-(isobutyl(spiro[3.3]heptan-2-yl)amino)-3-nitrophenyl)but-2-enoate (0.424 g, 96% yield) as a reddish/yellow oil. $^1$H NMR (400 MHz, CHLOROFORM-d) δ ppm 8.00 (s, 1H) 7.53 (d, J=8.79 Hz, 1H) 6.92-7.04 (m, 1H) 6.15 (s, 1H) 4.14-4.32 (m, 2H) 3.85 (quin, J=7.74 Hz, 1H) 2.92-3.04 (m, 2H) 2.56 (s, 2H) 2.21-2.31 (m, 2H) 1.98-2.09 (m, 2H) 1.75-1.93 (m, 7H) 1.55-1.65 (m, 1H) 1.32 (t, J=7.05 Hz, 3H) 0.76-0.89 (m, 6H). LCMS m/z calcd for C$_{23}$H$_{32}$N$_2$O$_4$: 400.24. Found: 401.0 (M+H)$^+$.

Step E (R)-ethyl 3-(4-(isobutyl(spiro[3.3]heptan-2-yl)amino)-3-nitrophenyl)butanoate

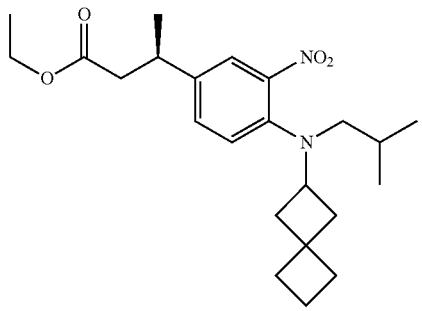 [SMILES: CCOC(=O)C[C@@H](C)c1ccc(N(CC(C)C)C2CC3(CCC3)C2)c([N+](=O)[O-])c1]

A solution of Stryker's reagent [(PPh$_3$)CuH]$_6$ (0.046 g, 0.023 mmol) and (R, S)—PPF—P(tBu)$_2$ (4.59 mg, 8.47 μmol) was purged with nitrogen. Then toluene (0.945 ml) was added. The mixture was stirred at 0° C. The mixture was then treated with poly(methylhydrosiloxane) (0.074 ml) and tBuOH (0.061 ml, 0.640 mmol). The mixture was then treated with the dropwise addition of (E)-ethyl 3-(4-(isobutyl(spiro[3.3]heptan-2-yl)amino)-3-nitrophenyl)but-2-enoate (0.212 g, 0.529 mmol) in toluene (0.945 ml). The resulting mixture was stirred at 0° C. for 4 h, then allowed to stir overnight at room temperature. The reaction was quenched by the addition of saturated NaHCO$_3$ and stirred at room temperature for 1 hour. The mixture was extracted with EtOAc and the combined organics were washed with brine, dried Na$_2$SO$_4$, filtered, and concentrated. The residue was resubmitted to the reaction conditions above. The reaction was loaded onto silica gel and purified by reverse phase chromatography (10-95% ACN/H$_2$O+formic acid) to give (R)-ethyl 3-(4-(isobutyl(spiro[3.3]heptan-2-yl)amino)-3-nitrophenyl)butanoate (0.140 g, 0.348 mmol, 65.7% yield). LCMS m/z calcd for C$_{23}$H$_{34}$N$_2$O$_4$: 402.25. Found: 403.4 (M+H)$^+$. $^1$H NMR (400 MHz, CHLOROFORM-d) δ ppm 7.61 (s, 1H) 7.21-7.32 (m, 1H) 6.96 (d, J=8.61 Hz, 1H) 4.09 (q, J=7.14 Hz, 2H) 3.74 (quin, J=7.83 Hz, 1H) 3.19-3.29 (m, 1H) 2.86 (d, J=7.14 Hz, 2H) 2.48-2.65 (m, 2H) 2.16-2.28 (m, 2H) 2.00 (t, J=6.68 Hz, 2H) 1.71-1.92 (m, 7H) 1.12-1.37 (m, 6H) 0.73-0.86 (m, 6H).

Step F (R)-ethyl 3-(3-amino-4-(isobutyl(spiro[3.3]heptan-2-yl)amino)phenyl)butanoate

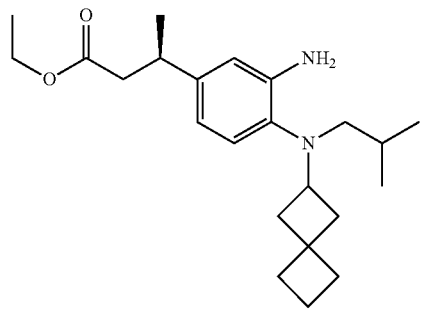 [SMILES: CCOC(=O)C[C@@H](C)c1ccc(N(CC(C)C)C2CC3(CCC3)C2)c(N)c1]

A solution of (R)-ethyl 3-(4-(isobutyl(spiro[3.3]heptan-2-yl)amino)-3-nitrophenyl)butanoate (0.100 g, 0.248 mmol) in EtOAc (1.242 ml) was purged with nitrogen. The reaction was then treated with Pd—C (10% Degussa) (0.026 g, 0.025 mmol) and placed under a hydrogen atmosphere (30 psi) for 5 hours. The reaction was filtered, and concentrated to give (R)-ethyl 3-(3-amino-4-(isobutyl(spiro[3.3]heptan-2-yl)amino)phenyl)butanoate (0.099 g, 0.266 mmol, 107% yield). LCMS m/z calcd for C$_{23}$H$_{36}$N$_2$O$_2$: 372.28. Found: 373.2 (M+H)$^+$.

Step G (R)-ethyl 3-(3-((3-chloro-1,2,4-thiadiazol-5-yl)amino)-4-(isobutyl(spiro[3.3]heptan-2-yl)amino)phenyl)butanoate

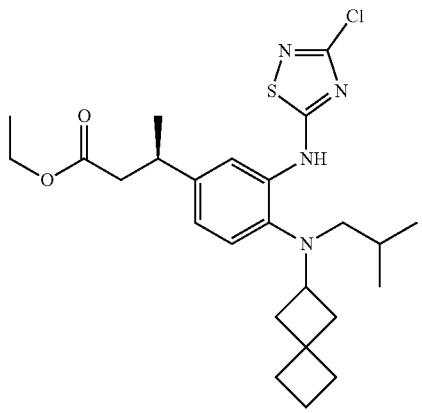 [SMILES: CCOC(=O)C[C@@H](C)c1ccc(N(CC(C)C)C2CC3(CCC3)C2)c(Nc2nc(Cl)ns2)c1]

A solution of (R)-ethyl 3-(3-amino-4-(isobutyl(spiro[3.3]heptan-2-yl)amino)phenyl)butanoate (0.049 g, 0.132 mmol) in DMF (0.658 ml) was treated with 3,5-dichloro-1,2,4-thiadiazole (0.015 ml, 0.158 mmol) and heated to 90° C. for 2 hours. The reaction was treated by additional 3,5-dichloro-1,2,4-thiadiazole (0.015 ml, 0.158 mmol) and heated an additional 2 hours. The reaction was cooled to room temperature and diluted with water and EtOAc. The combined extracts were washed with 5% LiCl (3×), brine, dried Na2SO4, filtered, and concentrated to give (R)-ethyl 3-(3-((3-chloro-1,2,4-thiadiazol-5-yl)amino)-4-(isobutyl(spiro[3.3]heptan-2-yl)amino)phenyl)butanoate (0.047 g, 72.8% yield, 30% purity). The crude residue was carried forward without purification. LCMS m/z calcd for $C_{26}H_{36}ClN_4O_2S$: 490.22. Found: 491.4 (M+H)+.

Step H (R)-3-(3-((3-chloro-1,2,4-thiadiazol-5-yl)amino)-4-(isobutyl(spiro[3.3]heptan-2-yl)amino)phenyl)butanoic Acid

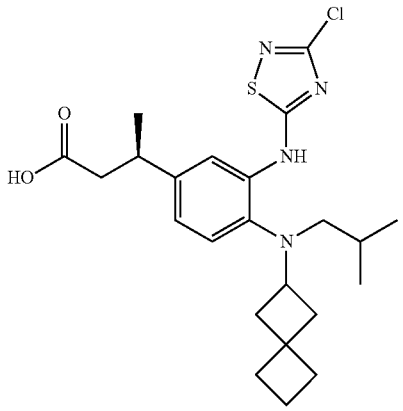 [SMILES: CC(C)CN(c1ccc([C@H](C)CC(=O)O)cc1Nc1nc(Cl)ns1)C1CC2(CCC2)C1]

A solution of (R)-ethyl 3-(3-((3-chloro-1,2,4-thiadiazol-5-yl)amino)-4-(isobutyl(spiro[3.3]heptan-2-yl)amino)phenyl)butanoate (0.047 g, 0.096 mmol) in MeOH (1.0 ml) was treated with LiOH—H2O (1M) (1.0 ml, 1.000 mmol) and the reaction was stirred at 55° C. for 2 hours. The reaction was treated with 1N HCl and concentrated. The aqueous residue was extracted with EtOAc. The combined extracts were washed with brine, dried over Na2SO4, filtered, and concentrated. The residue was purified by reverse phase chromatography (10-90% ACN/H2O+formic acid) to give (R)-3-(3-((3-chloro-1,2,4-thiadiazol-5-yl)amino)-4-(isobutyl(spiro[3.3]heptan-2-yl)amino)phenyl)butanoic acid (0.011 g, 0.024 mmol, 24.82% yield) as a white solid. LCMS m/z calcd for $C_{23}H_3ClN_4O_2S$: 462.19. Found: 463.4 (M+H)+. 1H NMR (400 MHz, DMSO-$d_6$) δ ppm 7.86-7.97 (m, 1H) 6.92-7.15 (m, 2H) 3.06-3.17 (m, 2H) 2.61 (br. s., 2H) 2.08 (br. s., 6H) 1.95 (br. s., 2H) 1.77 (br. s., 5H) 1.36-1.42 (m, 1H) 1.23 (br. s., 3H) 0.75 (br. s., 6H).

Example 99

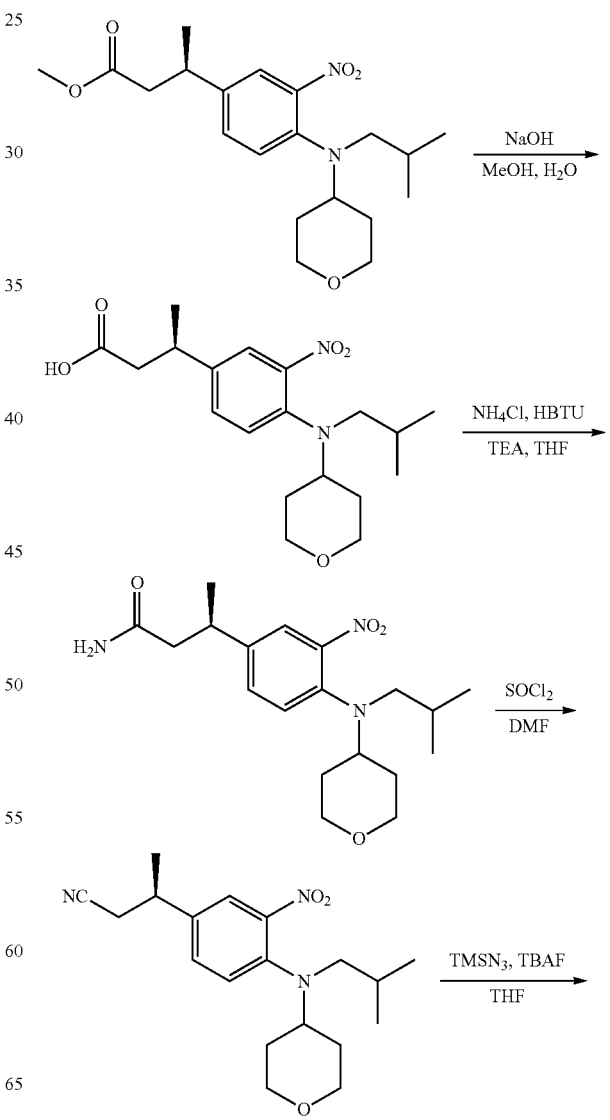

-continued

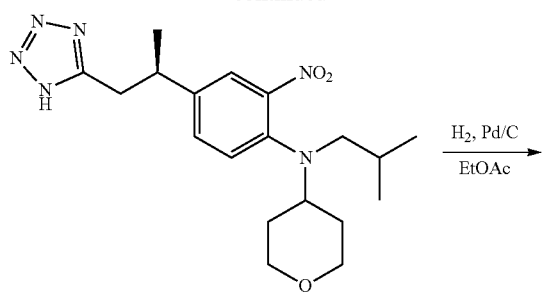

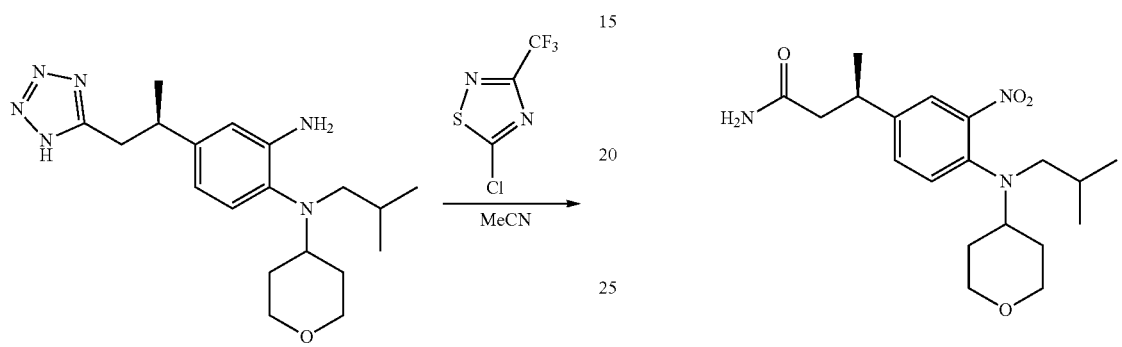

Preparation of (R)-3-(4-(isobutyl(tetrahydro-2H-pyran-4-yl)amino)-3-nitrophenyl) butanoic Acid

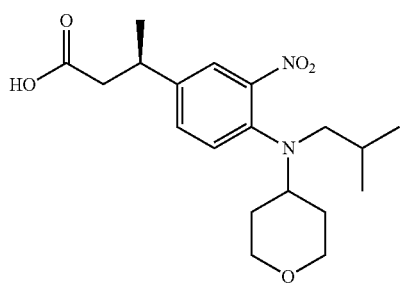 [SMILES: CC(C)CN(c1ccc([C@H](C)CC(=O)O)cc1[N+](=O)[O-])C1CCOCC1]

To a solution of methyl (R)-3-(4-(isobutyl(tetrahydro-2H-pyran-4-yl)amino)-3-nitro phenyl)butanoate (1.5 g, 3.83 mmol) in MeOH (20 mL) was added 4N NaOH aq. solution (5 mL). After stirred ar r.t. for 3 hr, the resulting mixture was neutralized with 1N HCl and extracted with EtOAc. The organic layer was washed with brine, dried over $Na_2SO_4$, filtered and concentrated to give the title compound (1.3 g, 93% yield). LCMS (ESI) m/z calcd for $C_{19}H_{28}N_2O_5$: 364.20. Found: 365.56 $(M+1)^+$.

Preparation of (R)-3-(4-(isobutyl(tetrahydro-2H-pyran-4-yl)amino)-3-nitrophenyl) butanamide

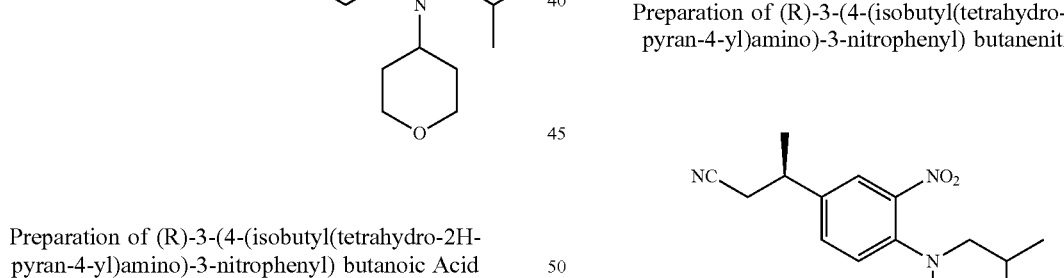

A mixture of (R)-3-(4-(isobutyl(tetrahydro-2H-pyran-4-yl)amino)-3-n itrophenyl)butan oic acid (1.3 g, 3.56 mmol), $NH_4C_1$ (381 mg, 7.12 mmol), HBTU (2.7 g, 7.11 mmol) and TEA (1 mL, 7.18 mol) in THF (13 mL) was stirred at r.t. overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-10% MeOH in DCM) to afford the title compound (1.15 g, 89% yield). LCMS (ESI) m/z calcd for $C_{19}H_{29}N_3O_4$: 363.22. Found: 364.40 $(M+1)^+$.

Preparation of (R)-3-(4-(isobutyl(tetrahydro-2H-pyran-4-yl)amino)-3-nitrophenyl) butanenitrile At 0° C., to a solution of (R)-3-(4-(isobutyl(tetrahydro-2H-pyran-4-yl)amino)-3-nitro phenyl) butanamide (1.15 g, 3.17 mmol) in DMF (20 mL) was added $SOCl_2$ (0.5 mL). After stirred at 0° C. for 5 min, the resulting mixture was quenched with sat. $NaHCO_3$ aq. solution and extracted with EtOAc. The organic layer was washed with brine, dried over $Na_2SO_4$, filtered and concentrated to give the crude product which was purified by flash chromatography (silica gel, 0-30% EtOAc in PE) to afford the title compound (1.05 g, 96% yield). LCMS (ESI) m/z calcd for $C_{19}H_{27}N_3O_3$: 345.21. Found: 346.41 $(M+1)^+$.

Preparation of (R)—N-(4-(1-(1H-tetrazol-5-yl)propan-2-yl)-2-nitrophenyl)-N-iso butyltetrahydro-2H-pyran-4-amine

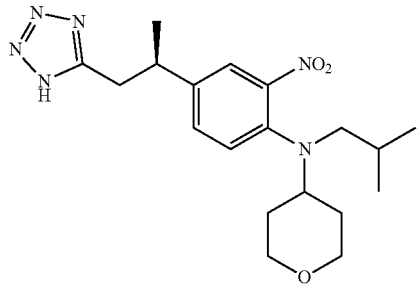 [SMILES: CC(C)CN(c1ccc([C@H](C)Cc2nnn[nH]2)cc1[N+](=O)[O-])C1CCOCC1]

A mixture of (R)-3-(4-(isobutyl(tetrahydro-2H-pyran-4-yl)amino)-3-nitrophenyl) butane nitrile (500 mg, 1.45 mmol), TABF (1N, 0.72 mL, 0.72 mmol) and TMSN$_3$ (500 mg, 4.34 mmol) in DMF was stirred 110° C. for 24 hr. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% MeOH in DCM) to afford the title compound (400 mg, 71% yield). LCMS (ESI) m/z calcd for C$_{19}$H$_{28}$N$_6$O$_3$: 388.22. Found: 389.50 (M+1)$^+$.

Preparation of (R)-4-(1-(1H-tetrazol-5-yl)propan-2-yl)-N$^1$-isobutyl-N$^1$-(tetrahydro-2H-pyran-4-yl)benzene-1,2-diamine

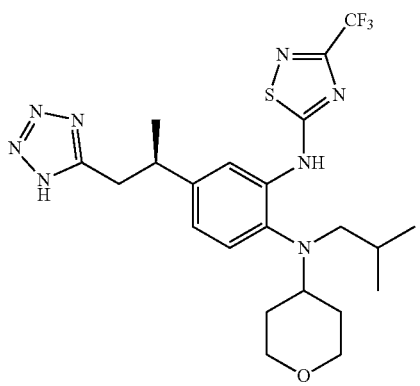 [SMILES: CC(C)CN(c1ccc([C@H](C)Cc2nnn[nH]2)cc1Nc1nc(C(F)(F)F)ns1)C1CCOCC1]

A mixture of (R)—N-(4-(1-(1H-tetrazol-5-yl)propan-2-yl)-2-nitrophenyl)-N-isobutyltetra hydro-2H-pyran-4-amine (400 mg, 1.03 mmol) and 10% Pd/C (200 mg) in EtOAc (5 mL) was stirred at 50° C. under H$_2$ atmosphere for 6 hr. The resulting mixture was filtered through a pad of Celite and the filtrate was concentrated under reduced pressure to afford the title compound (340 mg, 92% yield). LCMS (ESI) m/z calcd for C$_{19}$H$_{30}$N$_6$O: 358.25. Found: 359.71 (M+1)$^+$.

Preparation of (R)-4-(1-(1H-tetrazol-5-yl)propan-2-yl)-N$^1$-isobutyl-N$^1$-(tetrahydro-2H-pyran-4-yl)-N$^2$-(3-(trifluoromethyl)-1,2,4-thiadiazol-5-yl)benzene-1,2-diamine A mixture of (R)-4-(1-(1H-tetrazol-5-yl)propan-2-yl)-N$_1$-isobutyl-N$^1$-(tetrahydro-2H-pyran-4-yl)benzene-1,2-diamine (140 mg, 0.39 mmol) and 5-chloro-3-(trifluoro methyl)-1,2,4-thiadiazole (147 mg, 0.78 mmol) in MeCN (2 mL) was stirred at 90° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (52 mg, 26% yield) as a white powder. $^1$H NMR (400 MHz, DMSO) δ 15.91 (s, 1H), 10.36 (s, 1H), 8.03 (s, 1H), 7.22 (d, J=8.2 Hz, 1H), 7.01 (dd, J=8.2, 1.8 Hz, 1H), 3.86-3.76 (m, 2H), 3.29-3.09 (m, 5H), 2.92-2.84 (m, 1H), 2.77 (d, J=6.7 Hz, 2H), 1.73-1.60 (m, 2H), 1.57-1.43 (m, 2H), 1.35-1.19 (m, 4H), 0.77 (d, J=6.5 Hz, 6H) LCMS (ESI) m/z calcd for C$_{22}$H$_{29}$F$_3$N$_8$OS: 510.21. Found: 511.98 (M+1)$^+$.

Example 100

Preparation of (R)-4-(1-(1H-tetrazol-5-yl)propan-2-yl)-N$^2$-(3-chloro-1,2,4-thiadiazol-5-yl)-N$^1$-isobutyl-N$^1$-(tetrahydro-2H-pyran-4-yl)benzene-1,2-diamine

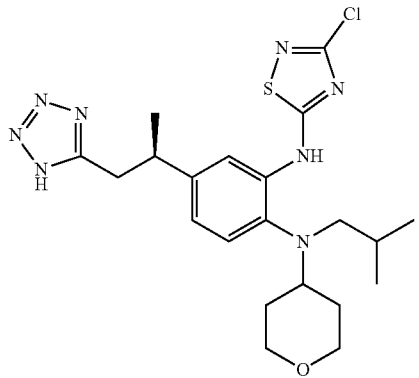

301

-continued

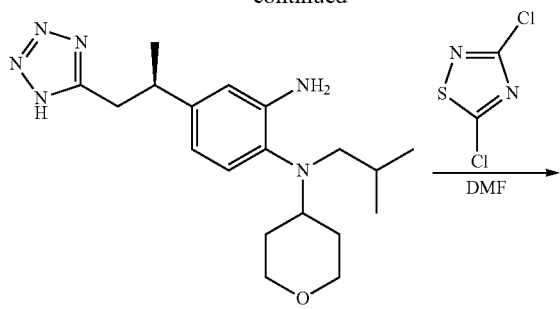

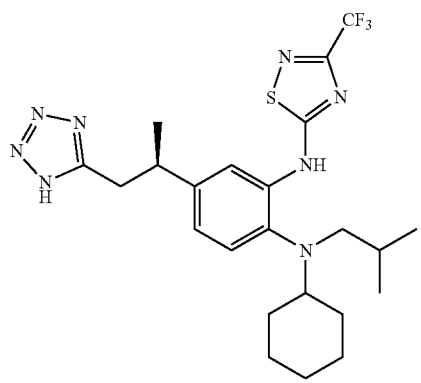

A mixture of (R)-4-(1-(1H-tetrazol-5-yl)propan-2-yl)-N¹-isobutyl-N¹-(tetrahydro-2H-pyran-4-yl)benzene-1,2-diamine (140 mg, 0.391 mmol) and 3,5-dichloro-1,2,4-thiadiazole (121 mg, 0.781 mmol) in DMF (2 mL) was stirred at 90° C. under $N_2$ atmosphere for 5 hr. The resulting mixture was partitioned between EtOAc and $H_2O$. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (51 mg, 27% yield) as a white powder. $^1$H NMR (400 MHz, DMSO) δ 15.92 (s, 1H), 10.19 (s, 1H), 7.90 (d, J=1.7 Hz, 1H), 7.22 (d, J=8.3 Hz, 1H), 7.02 (dd, J=8.2, 1.9 Hz, 1H), 3.82 (dd, J=11.1, 3.5 Hz, 2H), 3.27-3.07 (m, 5H), 2.91-2.84 (m, 1H), 2.76 (d, J=6.7 Hz, 2H), 1.68-1.59 (m, 2H), 1.55-1.40 (m, 2H), 1.36-1.18 (m, 4H), 0.77 (d, J=6.5 Hz, 6H). LCMS (ESI) m/z calcd for $C_{21}H_{29}ClN_8OS$: 476.19. Found: 477.69/479.64 (M/M+2)⁺.

Example 101

302

-continued

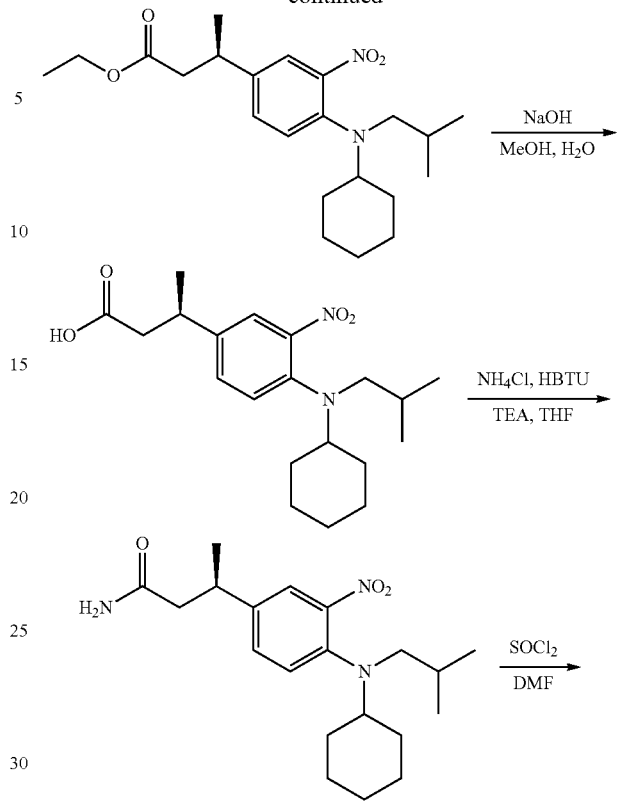

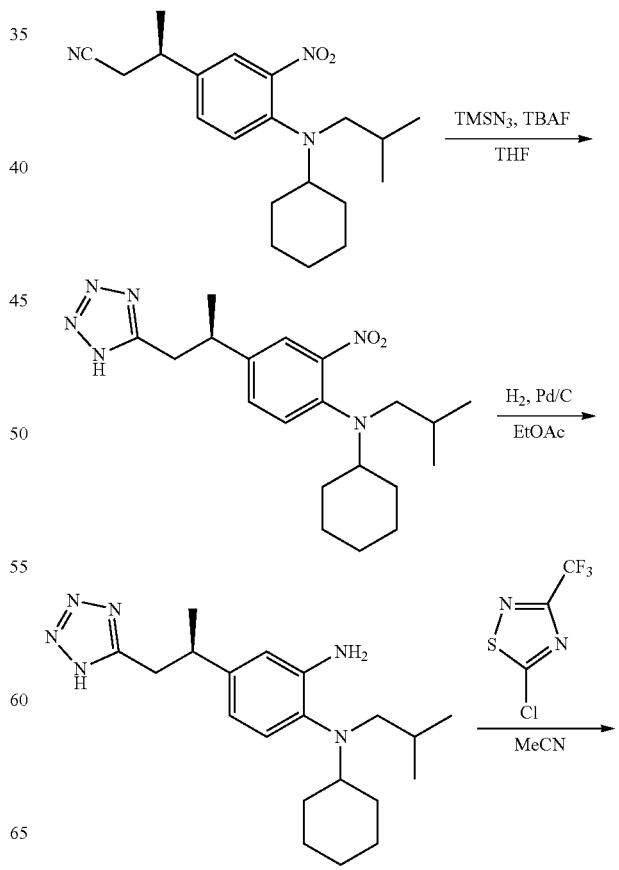

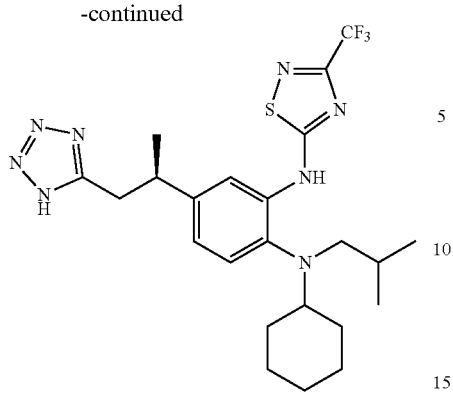

Preparation of (R)-3-(4-(cyclohexyl(isobutyl) amino)-3-nitrophenyl)butanoic Acid

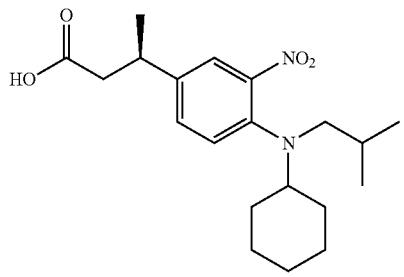 [SMILES: CC(C)CN(c1ccc([C@H](C)CC(=O)O)cc1[N+](=O)[O-])C1CCCCC1]

To a solution of ethyl (R)-3-(4-(cyclohexyl(isobutyl) amino)-3-nitrophenyl)butanoate (3.3 g, 8.35 mmol) in MeOH (20 mL) was added 1N NaOH aq. solution (10 mL). After stirred ar r.t. overnight, the resulting mixture was neutralized with 1N HCl and extracted with EtOAc. The organic layer was washed with brine, dried over $Na_2SO_4$, filtered and concentrated to give the title compound (2.6 g, 84% yield). LCMS (ESI) m/z calcd for $C_{20}H_{30}N_2O_4$: 362.22. Found: 361.24 (M−1)⁻.

Preparation of (R)-3-(4-(cyclohexyl(isobutyl) amino)-3-nitrophenyl)butanamide

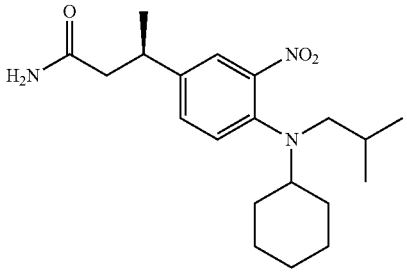 [SMILES: CC(C)CN(c1ccc([C@H](C)CC(N)=O)cc1[N+](=O)[O-])C1CCCCC1]

A mixture of (R)-3-(4-(cyclohexyl(isobutyl)amino)-3-nitrophenyl)butanoic acid (2.6 g, 7.17 mmol), $NH_4Cl$ (765 mg, 14.3 mmol), HBTU (2.72 g, 7.17 mmol) and TEA (2.0 mL, 14.3 mol) in THF (20 mL) was stirred at r.t. 1 hr. The resulting mixture was partitioned between EtOAc and $H_2O$. The organic layer was washed with brine, dried over $Na_2SO_4$, filtered and concentrated to give the crude product which was purified by flash chromatography (silica gel, 0-50% EtOAc in PE) to afford the title compound (2.5 g, 97% yield). LCMS (ESI) m/z calcd for $C_{20}H_{31}N_3O_3$: 361.24. Found: 362.10 (M+1)⁺.

Preparation of (R)-3-(4-(cyclohexyl(isobutyl) amino)-3-nitrophenyl)butanenitrile

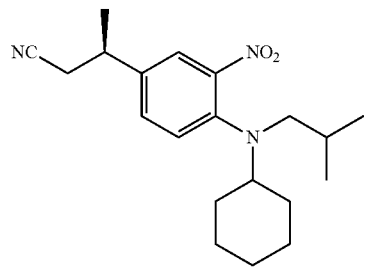 [SMILES: CC(C)CN(c1ccc([C@H](C)CC#N)cc1[N+](=O)[O-])C1CCCCC1]

At 0° C., to a solution of (R)-3-(4-(cyclohexyl(isobutyl) amino)-3-nitrophenyl)butanamide (500 mg, 1.38 mmol) in DMF (10 mL) was added $SOCl_2$ (0.5 mL). After stirred at 120° C. overnight, the resulting mixture was quenched with sat. $NaHCO_3$ aq. solution and extracted with EtOAc. The organic layer was washed with brine, dried over $Na_2SO_4$, filtered and concentrated to give the crude product which was purified by flash chromatography (silica gel, 0-20% EtOAc in PE) to afford the title compound (330 mg, 70% yield). LCMS (ESI) m/z calcd for $C_{20}H_{29}N_3O_2$: 343.23. Found: 344.47 (M+1)⁺.

Preparation of (R)-4-(1-(1H-tetrazol-5-yl)propan-2-yl)-N-cyclohexyl-N-isobutyl-2-nitroaniline

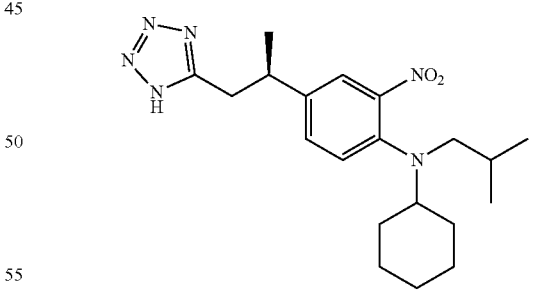

A mixture of (R)-3-(4-(cyclohexyl(isobutyl)amino)-3-nitrophenyl)butanenitrile (50 mg, 0.146 mmol), TABF (1N, 0.7 mL, 0.7 mmol) and $TMSN_3$ (252 mg, 2.19 mmol) was stirred 90° C. overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-10% MeOH in DCM) to afford the title compound (50 mg, 89% yield). LCMS (ESI) m/z calcd for $C_{20}H_{30}N_6O_2$: 386.24. Found: 385.38 (M−1)⁻.

Preparation of (R)-4-(1-(1H-tetrazol-5-yl)propan-2-yl)-N¹-cyclohexyl-N¹-isobutyl benzene-1,2-diamine

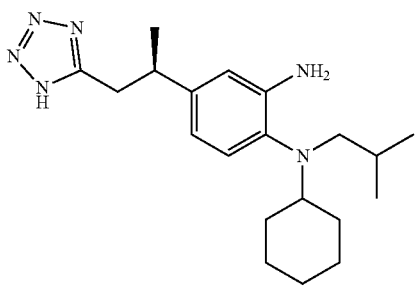 [SMILES: CC(C)CN(c1ccc([C@H](C)Cc2nnn[nH]2)cc1N)C1CCCCC1]

A mixture of (R)-4-(1-(1H-tetrazol-5-yl)propan-2-yl)-N-cyclohexyl-N-isobutyl-2-nitro aniline (308 mg, 0.797 mmol) and 10% Pd/C (150 mg) in EtOAc (20 mL) was stirred at r.t. under H₂ atmosphere overnight. The resulting mixture was filtered through a pad of Celite and the filtrate was concentrated under reduced pressure to afford the title compound (140 mg, 50% yield). LCMS (ESI) m/z calcd for $C_{20}H_{32}N_6$: 356.27. Found: 357.52 (M+1)⁺.

Preparation of (R)-4-(1-(1H-tetrazol-5-yl)propan-2-yl)-N¹-cyclohexyl-N¹-isobutyl-N²-(3-(trifluoromethyl)-1,2,4-thiadiazol-5-yl)benzene-1,2-diamine

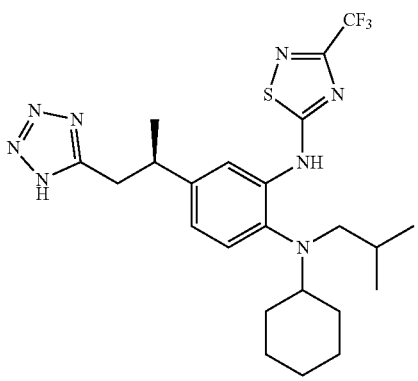 [SMILES: CC(C)CN(c1ccc([C@H](C)Cc2nnn[nH]2)cc1Nc1nc(C(F)(F)F)ns1)C1CCCCC1]

A mixture of (R)-4-(1-(1H-tetrazol-5-yl)propan-2-yl)-N¹-cyclohexyl-N¹-isobutylbenzene-1,2-diamine (70 mg, 0.196 mmol) and 5-chloro-3-(trifluoromethyl)-1,2,4-thiadiazole (74 mg, 0.392 mmol) in MeCN (3 mL) was stirred at 90° C. under N₂ atmosphere for 16 hr. The resulting mixture was partitioned between EtOAc and H₂O. The organic layer was washed with brine, dried over Na₂SO₄, filtered and concentrated to give the crude product which was purified by HPLC (C18, 0-100% MeCN in H₂O with 0.1% formic acid) to afford the title compound (27 mg, 27% yield) as a white powder. ¹H NMR (400 MHz, CDCl₃) δ 16.11 (s, 1H), 9.33 (br, 1H), 7.57 (s, 1H), 7.16 (d, J=8.2 Hz, 1H), 6.89 (dd, J=8.1, 1.8 Hz, 1H), 3.42-3.27 (m, 3H), 2.83-2.74 (m, 2H), 2.56-2.48 (m, 1H), 1.88-1.71 (m, 4H), 1.62-1.55 (m, 1H), 1.41-1.17 (m, 9H), 0.82 (d, J=6.6 Hz, 6H). LCMS (ESI) m/z calcd for $C_{23}H_{31}F_3N_8S$: 508.23. Found: 507.28 (M−1)⁻.

Example 102

Preparation of (R)-4-(1-(1H-tetrazol-5-yl)propan-2-yl)-N²-(3-chloro-1,2,4-thiadiazol-5-yl)-N¹-cyclohexyl-N¹-isobutylbenzene-1,2-diamine

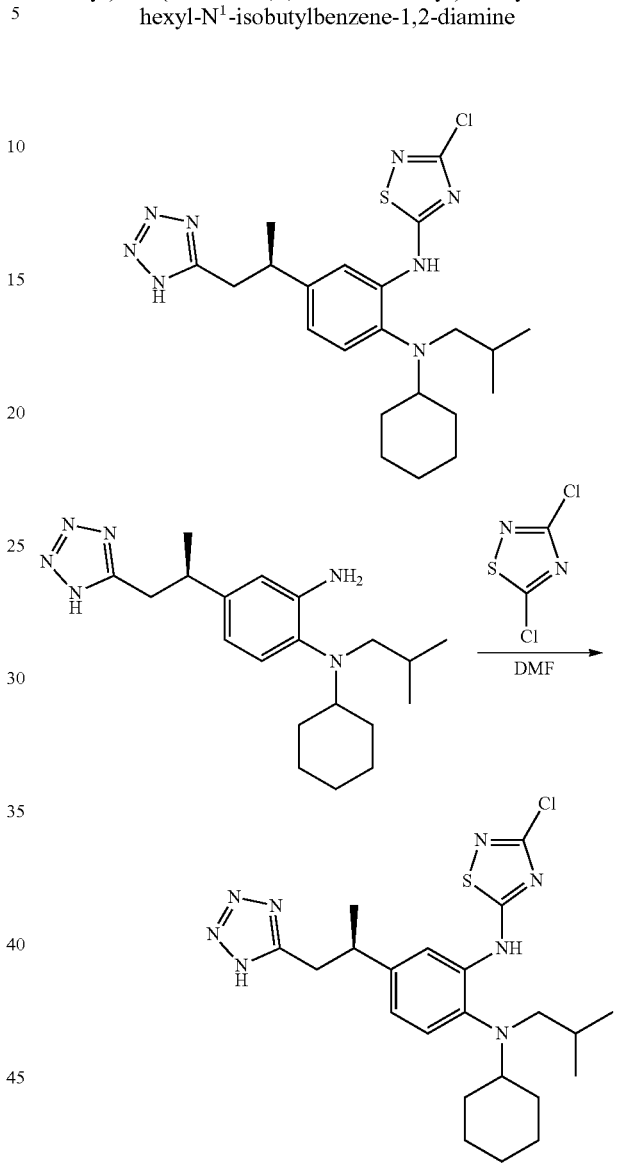

A mixture of (R)-4-(1-(1H-tetrazol-5-yl)propan-2-yl)-N¹-isobutyl-N¹-(tetrahydro-2H-pyran-4-yl)benzene-1,2-diamine (60 mg, 0.168 mmol) and 3,5-dichloro-1,2,4-thiadiazole (52 mg, 0.336 mmol) in DMF (3 mL) was stirred at 90° C. under N₂ atmosphere for 16 hr. The resulting mixture was partitioned between EtOAc and H₂O. The organic layer was washed with brine, dried over Na₂SO₄, filtered and concentrated to give the crude product which was purified by HPLC (C18, 0-100% MeCN in H₂O with 0.1% formic acid) to afford the title compound (21 mg, 26% yield) as a white powder. ¹H NMR (400 MHz, CD₃OD) δ 7.49 (d, J=1.8 Hz, 1H), 7.22 (d, J=8.2 Hz, 1H), 6.99 (dd, J=8.2, 2.0 Hz, 1H), 3.24-3.19 (m, 2H), 2.83 (d, J=6.9 Hz, 2H), 2.63-2.56 (m, 1H), 1.88-1.80 (m, 2H), 1.77-1.71 (m, 2H), 1.62-1.55 (m, 1H), 1.39-1.10 (m, 10H), 0.82 (dd, J=6.6, 1.0 Hz, 6H) LCMS (ESI) m/z calcd for $C_{22}H_{31}ClN_8S$: 474.21. Found: 475.44/477.25 (M/M+2)⁺.

Example 103

Preparation of methyl 4'-(isobutyl(tetrahydro-2H-pyran-4-yl)amino)-3'-((3-(trifluoromethyl)-1,2,4-thiadiazol-5-yl)amino)-[1,1'-biphenyl]-2-carboxylate

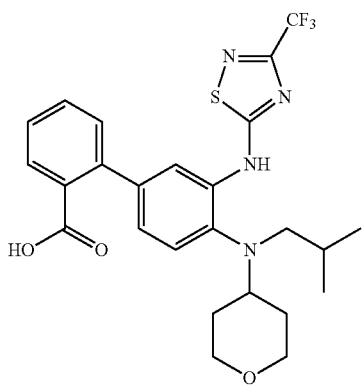

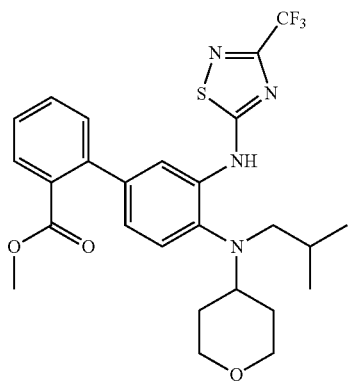 [SMILES: COC(=O)c1ccccc1-c1ccc(N(CC(C)C)C2CCOCC2)c(Nc2nc(C(F)(F)F)ns2)c1]

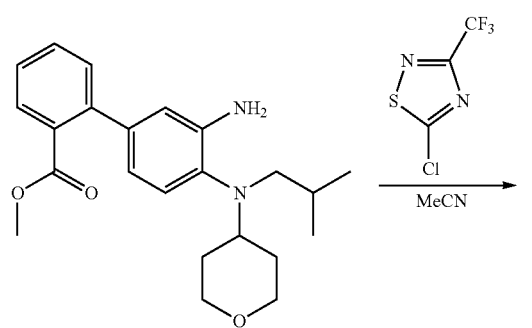

A mixture of methyl 3'-amino-4'-(isobutyl(tetrahydro-2H-pyran-4-yl)amino)-[1,1'-bi phenyl]-2-carboxylate (100 mg, 0.26 mmol) and 5-chloro-3-(trifluoromethyl)-1,2,4-thiadiazole (148 mg, 0.78 mmol) in MeCN (2 mL) was stirred at 90° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-30% EtOAc in PE) to afford the title compound (121 mg, 87% yield). LCMS (ESI) m/z calcd for $C_{26}H_{29}F_3N_4O_3S$: 534.19. Found: 535.20 (M+1)$^+$.

Preparation of 4'-(isobutyl(tetrahydro-2H-pyran-4-yl)amino)-3'-((3-(trifluoromethyl)-1,2,4-thiadiazol-5-yl)amino)-[1,1'-biphenyl]-2-carboxylic Acid

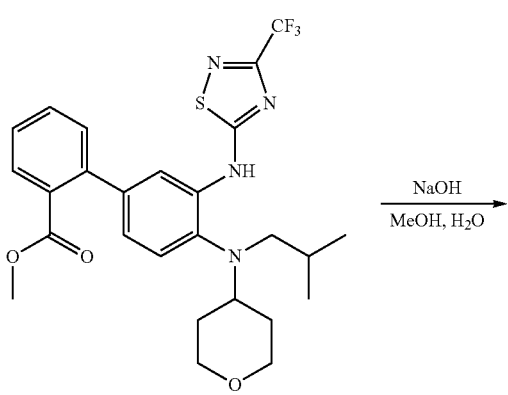

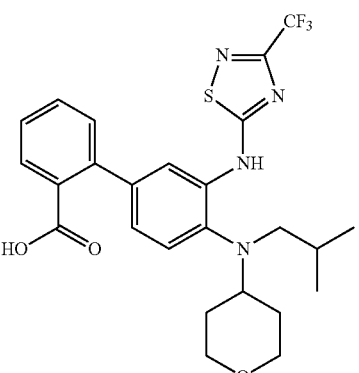

To a solution of methyl 4'-(isobutyl(tetrahydro-2H-pyran-4-yl)amino)-3'-((3-(trifluoro methyl)-1,2,4-thiadiazol-5-yl)amino)-[1,1'-biphenyl]-2-carboxylate (120 mg, 0.23 mmol) in MeOH (2.5 mL) was added 4N NaOH aq. (0.5 mL). After stirred at 50° C. for 1.5 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (42 mg, 35% yield) as a white powder. $^1$H NMR (400 MHz, CDCl$_3$) δ

9.52 (s, 1H), 7.96 (d, J=7.8 Hz, 1H), 7.61 (t, J=7.5 Hz, 1H), 7.50-7.41 (m, 2H), 7.35 (s, 1H), 7.31 (d, J=8.1 Hz, 1H), 7.13 (dd, J=8.1, 1.9 Hz, 1H), 4.00-3.91 (m, 2H), 3.33-3.20 (m, 2H), 2.92-2.80 (m, 3H), 1.79-1.74 (m, 2H), 1.68-1.60 (m, 2H), 1.50-1.29 (m, 1H), 0.87 (d, J=6.6 Hz, 6H). LCMS (ESI) m/z calcd for $C_{25}H_{27}F_3N_4O_3S$: 520.18. Found: 519.10 $(M-1)^-$.

Example 104

Isomer 2

2-(4-(cyclohexyl(isobutyl)amino)-3-((3-(trifluoromethyl)-1,2,4-thiadiazol-5-yl)amino)phenyl)cyclopropanecarboxylic Acid

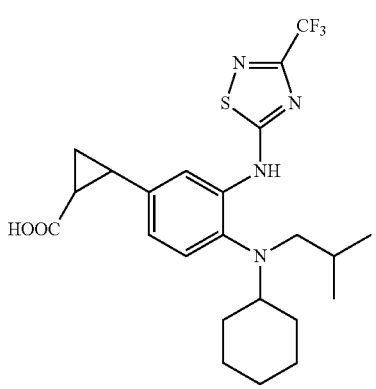

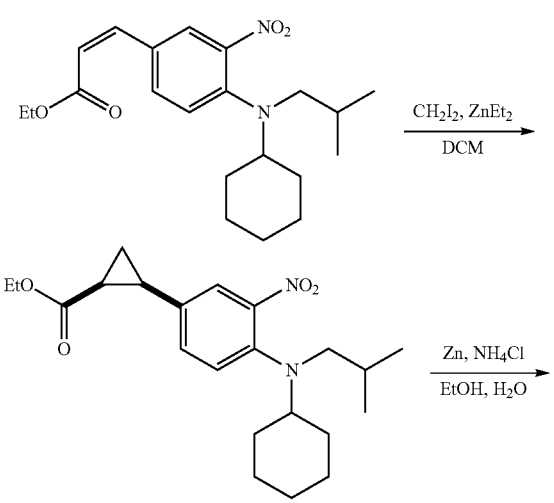

Preparation of ethyl (Z)-3-(4-(cyclohexyl(isobutyl)amino)-3-nitrophenyl)acrylate

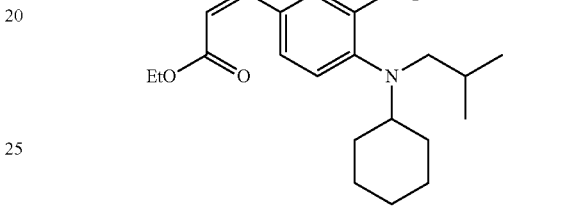

At −78° C., to a solution of ethyl 2-(bis(2,2,2-trifluoroethoxy)phosphoryl)acetate (5 g, 15.05 mmol) and 18-Crown-6 (18 g, 68.45 mmol) in THF (50 mL) was added K-HMDS (1N, 14 mL, 14 mmol) under $N_2$ atmosphere. The resulting mixture was stirred at −78° C. for 30 min before the addition of 4-(cyclohexyl(isobutyl)amino)-3-nitrobenzaldehyde (4.2 g, 13.69 mmol) in THF (10 mL). After stirred at −78° C. for 1 hr, the reaction mixture was quenched with sat. $NH_4Cl$ aq. solution and extracted with EtOAc. The organic layer was washed with brine, dried over $Na_2SO_4$, filtered and concentrated to give the crude product which was purified by flash chromatography (silica gel, 0-5% EtOAc in PE) to afford the title compound (5.0 g, 97% yield). LCMS (ESI) m/z calcd for $C_{21}H_{30}N_2O_4$: 374.22. Found: 375.42 $(M+1)^+$.

Preparation of ethyl (1S,2R)-2-(3-amino-4-(cyclohexyl(isobutyl)amino)phenyl) cyclopropane-1-carboxylate

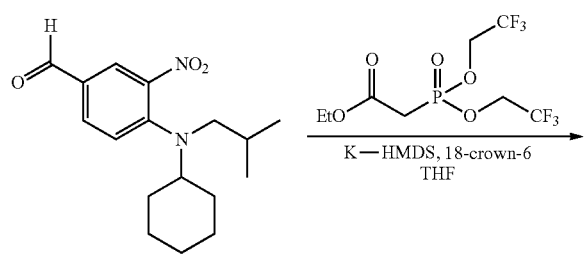

At 0° C., to a solution of ethyl (Z)-3-(4-(cyclohexyl(isobutyl)amino)-3-nitrophenyl) acrylate (100 mg, 0.267 mmol) in DCM (8 mL) was added $Zn(Et)_2$ (1N, 4 mL, 4.0 mmol) and $CH_2I_2$ (2.1 g, 8.0 mmol). After stirred at 0° C. overnight, the resulting mixture was quenched with sat.

$NH_4Cl$ aq. solution and extracted with DCM. The organic layer was washed with brine, dried over $Na_2SO_4$, filtered and concentrated to give the crude product which was purified by flash chromatography (silica gel, 0-10% EtOAc in PE) to afford the title compound (19 mg, 18% yield). LCMS (ESI) m/z calcd for $C_{22}H_{32}N_2O_4$: 388.24. Found: 389.53 (M+1)$^+$.

Preparation of ethyl (1S,2R)-2-(4-(cyclohexyl (isobutyl)amino)-3-nitrophenyl) cyclopropane-1-carboxylate

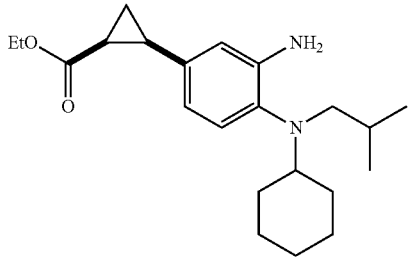

A mixture of ethyl (1S,2R)-2-(3-amino-4-(cyclohexyl(isobutyl)amino)phenyl) cyclopropane-1-carboxylate (754 mg, 1.94 mmol), zinc powder (1.27 g, 19.4 mmol) and $NH_4Cl$ (2.08 g, 38.8 mmol) in EtOH (30 mL) and $H_2O$ (10 mL) was stirred at r.t. for 2 hr. The resulting mixture was filtered and the filtrate was concentrated under reduced pressure to give the title compound (377 mg, 54% yield). LCMS (ESI) m/z calcd for $C_{22}H_{34}N_2O_2$: 358.26. Found: 359.82 (M+1)$^+$. 2-(4-(cyclohexyl(isobutyl)amino)-3-((3-(trifluoromethyl)-1,2,4-thiadiazol-5-yl)amino)phenyl)cyclopropanecarboxylic Acid

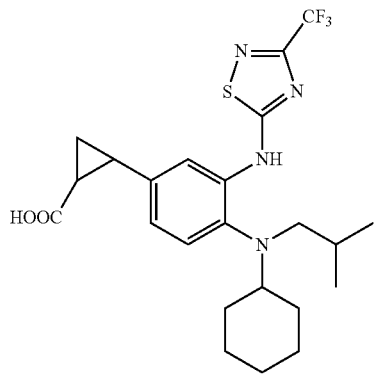 [SMILES: CC(C)CN(c1ccc(C2CC2C(=O)O)cc1Nc1nc(C(F)(F)F)ns1)C1CCCCC1]

Synthesis from intermediate ethyl (1S,2R)-2-(4-(cyclohexyl(isobutyl)amino)-3-nitrophenyl) cyclopropane-1-carboxylate and hydrolized to acid. Enantiomers separated by chiral chromatography Isomer 2

LCMS calculated for $C_{23}H_{29}F_3N_4O_2S$: 482.20, found (M+H)$^+$: m/z=483.66 $^1$H NMR (400 MHz, METHANOL-$d_4$) δ ppm 7.45 (s, 1H) 7.14-7.22 (m, 1H) 7.07-7.14 (m, 1H) 2.81 (d, J=6.6 Hz, 2H) 2.50-2.64 (m, 2H) 2.41 (q, J=8.4 Hz, 1H) 2.02 (q, J=7.6 Hz, 1H) 1.84 (d, J=11.9 Hz, 2H) 1.70 (d, J=11.9 Hz, 2H) 1.47-1.58 (m, 2H) 1.30-1.43 (m, 1H) 1.26 (m, 3H) 0.97-1.17 (m, 3H) 0.81 (d, J=6.6 Hz, 6H).

Example 105

(isomer 1)

2-(4-(cyclohexyl(isobutyl)amino)-3-((3-(trifluoromethyl)-1,2,4-thiadiazol-5-yl)amino)phenyl)cyclopropanecarboxylic Acid

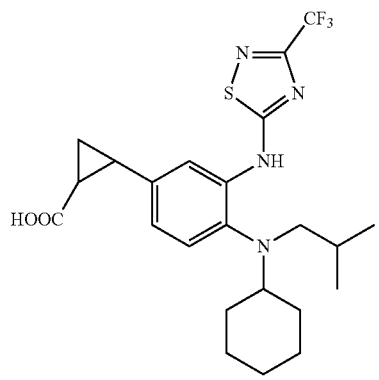 [SMILES: CC(C)CN(c1ccc(C2CC2C(=O)O)cc1Nc1nc(C(F)(F)F)ns1)C1CCCCC1]

LCMS calculated for $C_{23}H_{29}F_3N_4O_2S$: 482.20, found (M+H)$^+$: m/z=483.66 $^1$H NMR (400 MHz, METHANOL-$d_4$) δ ppm 7.54 (s, 1H) 7.20 (d, J=8.2 Hz, 1H) 7.08 (d, J=7.8 Hz, 1H) 2.83 (d, J=6.8 Hz, 2H) 2.47-2.70 (m, 2H) 2.01-2.17 (m, 1H) 1.84 (d, J=11.7 Hz, 2H) 1.70 (d, J=11.9 Hz, 2H) 1.47-1.64 (m, 2H) 1.31-1.44 (m, 2H) 1.18-1.31 (m, 2H) 0.97-1.18 (m, 3H) 0.81 (d, J=6.6 Hz, 6H).

Example 106

(R)-3-(4-(Isobutyl(tetrahydro-2H-pyran-4-yl)amino)-3-((3-(trifluoromethyl)-1,2,4-thiadiazol-5-yl)amino)phenyl)-N-methoxybutanamide

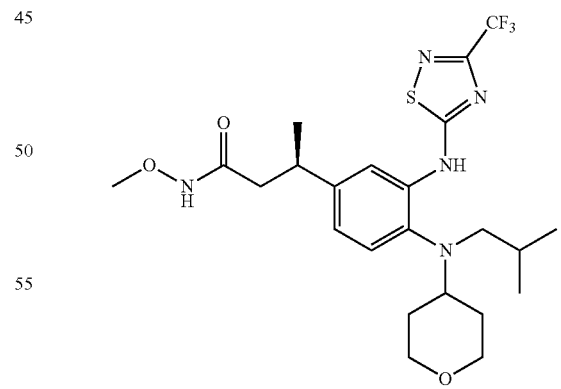

To a stirred solution of (R)-3-(4-(isobutyl(tetrahydro-2H-pyran-4-yl)amino)-3-((3-(trifluoromethyl)-1,2,4-thiadiazol-5-yl)amino)phenyl)butanoic acid (95 mg, 0.20 mmol) and DIPEA (0.102 mL, 0.586 mmol) in DMF (6 mL) was added HATU (0.111 g, 0.293 mmol). After 15 minutes the solution was treated with methoxylamine hydrochloride (33 mg, 0.39 mmol). After an additional 1 hour the solution was partitioned between EtOAc and aqueous NH₄Cl, and the phases separated. The aqueous phase was extracted with EtOAc (1×). The combined EtOAc solutions were washed with half saturated brine (1×), saturated brine (1×), dried over Na₂SO₄, and concentrated to dryness at reduced pressure. The residue was subjected to reverse phase HPLC to afford (R)-3-(4-(isobutyl(tetrahydro-2H-pyran-4-yl)amino)-3-((3-(trifluoromethyl)-1,2,4-thiadiazol-5-yl)amino)phenyl)-N-methoxybutanamide (28 mg, 28% yield). ¹H NMR (400 MHz, CDCl₃) δ 9.46 (br s, 1H), 8.20 (br s, 1H), 7.40 (br s, 1H), 7.22 (d, J=8.2 Hz, 1H), 6.97-7.05 (m, 1H), 3.90-4.00 (m, 2H), 3.64 (s, 3H), 3.37-3.50 (m, 1H), 3.23-3.33 (m, 2H), 2.75-2.90 (m, 3H), 2.30-2.41 (m, 1H), 1.50-1.81 (m, 4H), 1.17-1.45 (m, 5H), 0.85 (d, J=6.4 Hz, 6H). LCMS (ESI) m/z calcd for C₂₃H₃₂F₃N₅O₃S: 515.2. Found: 516.4 (M+H)⁺.

Example 107

(R)-3-(4-(Isobutyl(tetrahydro-2H-pyran-4-yl)amino)-3-((3-(trifluoromethyl)-1,2,4-thiadiazol-5-yl)amino)phenyl)-N-(methylsulfonyl)butanamide

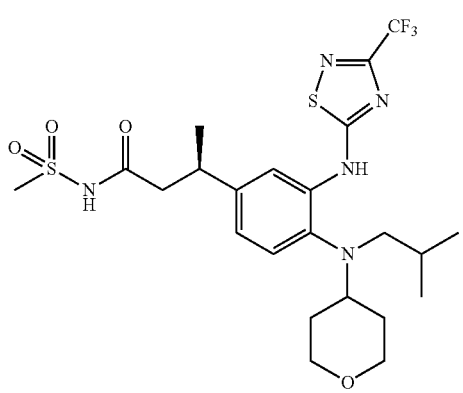 [SMILES: CC(C)CN(c1ccc([C@H](C)CC(=O)NS(C)(=O)=O)cc1Nc1nc(C(F)(F)F)ns1)C1CCOCC1]

To a stirred solution of (R)-3-(4-(isobutyl(tetrahydro-2H-pyran-4-yl)amino)-3-((3-(trifluoromethyl)-1,2,4-thiadiazol-5-yl)amino)phenyl)butanoic acid (0.125 g, 0.257 mmol) and DIPEA (0.135 mL, 0.771 mmol) in DMF (3 mL) was added HATU (0.147 g, 0.385 mmol). After 20 minutes the solution was treated with methanesulfonamide (0.122 g, 1.29 mmol). After 18 hours the cloudy solution was treated with glacial AcOH (1 mL), partitioned between EtOAc and half saturated brine, and the phases separated. The aqueous phase was extracted with EtOAc (1×). The combined EtOAc solutions were washed with water (2×), dried over Na₂SO₄, and concentrated to dryness at reduced pressure. The residue was subjected to reverse phase HPLC to afford (R)-3-(4-(isobutyl(tetrahydro-2H-pyran-4-yl)amino)-3-((3-(trifluoromethyl)-1,2,4-thiadiazol-5-yl)amino)phenyl)-N-(methylsulfonyl)butanamide (18 mg, 12% yield). ¹H NMR (400 MHz, CDCl₃) δ 9.44 (br s, 1H), 8.12 (br s, 1H), 7.48 (br s, 1H), 7.25 (d, J=8.0 Hz, 1H), 7.00 (d, J=7.9 Hz, 1H), 3.92-4.00 (m, 2H), 3.22-3.43 (m, 3H), 3.19 (s, 3H), 2.79-2.90 (m, 3H), 2.57-2.65 (m, 1H), 0.71-1.79 (m, 15H). LCMS (ESI) m/z calcd for C₂₃H₃₂F₃N₅O₄S₂: 563.2. Found: 564.4 (M+H)⁺.

Example 108

(R)—N—(N,N-Dimethylsulfamoyl)-3-(4-(isobutyl(tetrahydro-2H-pyran-4-yl)amino)-3-((3-(trifluoromethyl)-1,2,4-thiadiazol-5-yl)amino)phenyl)butanamide

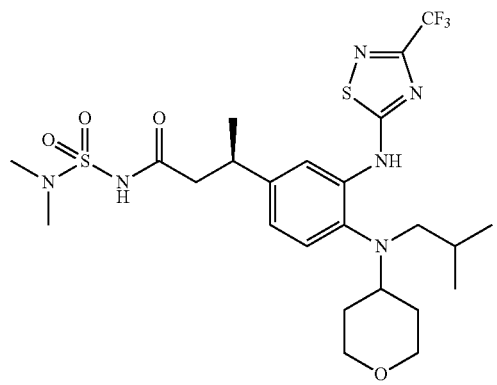 [SMILES: CC(C)CN(c1ccc([C@H](C)CC(=O)NS(=O)(=O)N(C)C)cc1Nc1nc(C(F)(F)F)ns1)C1CCOCC1]

To a stirred solution of (R)-3-(4-(isobutyl(tetrahydro-2H-pyran-4-yl)amino)-3-((3-(trifluoromethyl)-1,2,4-thiadiazol-5-yl)amino)phenyl)butanoic acid (0.117 g, 0.240 mmol) and DIPEA (0.210 mL, 1.20 mmol) in CH₂Cl₂ (4 mL) was added TBTU (93 mg, 0.29 mmol). After 25 minutes the solution was treated with N,N-dimethylsulfamide (45 mg, 0.361 mmol). After 2 hours the solution was treated with an additional portion of N,N-dimethylsulfamide (0.150 g, 1.21 mmol). After 18 hours the solution was partitioned between CH₂Cl₂ and aqueous NH₄Cl, and the phases separated. The aqueous phase was extracted with CH₂Cl₂ (1×). The combined CH₂Cl₂ solutions were washed with aqueous brine (1×), dried over Na₂SO₄, and concentrated to dryness at reduced pressure. The residue was subjected to flash chromatography on silica gel (0-100% ethyl acetate/hexanes) to give (R)—N—(N,N-dimethylsulfamoyl)-3-(4-(isobutyl(tetrahydro-2H-pyran-4-yl)amino)-3-((3-(trifluoromethyl)-1,2,4-thiadiazol-5-yl)amino)phenyl)butanamide (0.106 g, 74% yield). ¹H NMR (400 MHz, CDCl₃) δ 9.45 (br s, 1H), 7.84 (br s, 1H), 7.45 (br s, 1H), 7.25 (d, J=8.0 Hz, 1H), 7.00 (d, J=7.9 Hz, 1H), 3.91-4.01 (m, 2H), 3.22-3.42 (m, 3H), 2.78-2.90 (m, 8H), 2.55-2.62 (m, 2H), 1.52-1.80 (m, 5H), 1.36-1.46 (m, 4H), 0.86 (d, J=6.2 Hz, 6H). LCMS (ESI) m/z calcd for C₂₄H₃₅F₃N₆O₄S₂: 592.2. Found: 593.5 (M+H)⁺.

Example 109

Preparation of (R)-3-(4-(diisobutylamino)-3-((3-(trifluoromethyl)-1,2,4-thiadiazol-5-yl)amino)phenyl)-N-(methylsulfonyl)butanamide

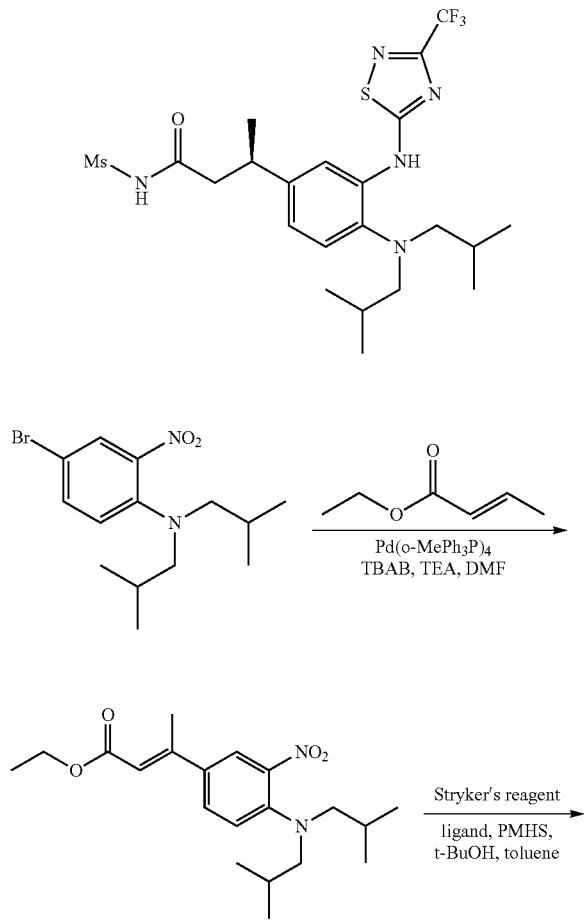

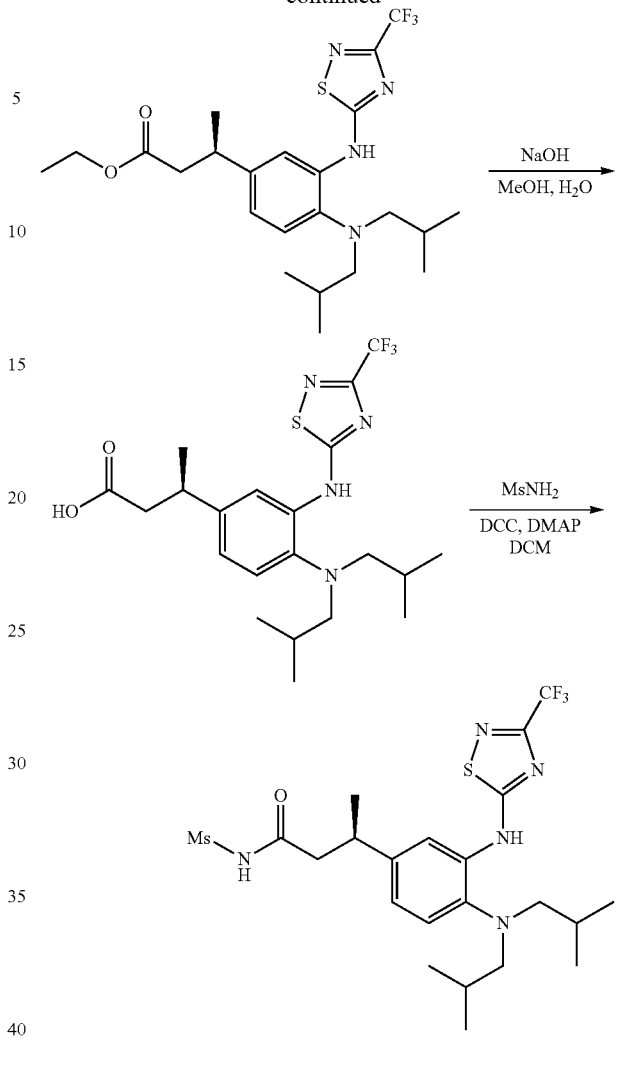

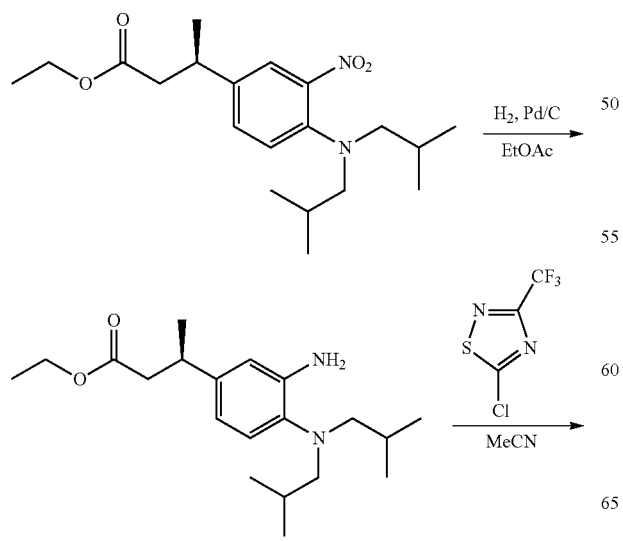

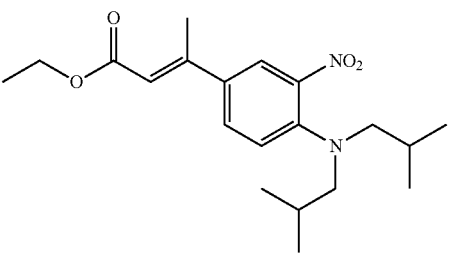 [SMILES: CCOC(=O)/C=C(\C)c1ccc(N(CC(C)C)CC(C)C)c([N+](=O)[O-])c1]

Preparation of ethyl (E)-3-(4-(diisobutylamino)-3-nitrophenyl)but-2-enoate

A mixture of 4-bromo-N,N-diisobutyl-2-nitroaniline (37 g, 112.4 mmol), ethyl (E)-pent-2-enoate (38.5 g, 337.2 mmol), TBAB (7.2 g, 22.5 mmol), Pd(o-MePh$_3$P)$_4$ (4.4 g, 5.6 mmol) and TEA (31 mL, 224.8 mmol) in DMF (185 mL) was stirred at 110° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-10% EtOAc in PE) to afford the title compound (27 g, 70% yield). LCMS (ESI) m/z calcd for $C_{20}H_{30}N_2O_4$: 362.22. Found: 363.56 (M+1)$^+$.

Preparation of ethyl (R)-3-(4-(diisobutylamino)-3-nitrophenyl)butanoate

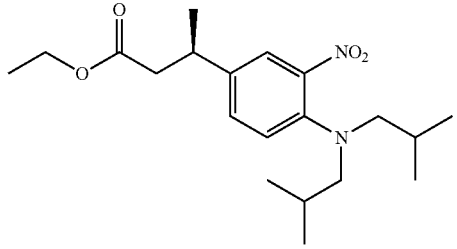 [SMILES: CCOC(=O)C[C@@H](C)c1ccc(N(CC(C)C)CC(C)C)c([N+](=O)[O-])c1]

At −5° C., to a mixture of (CuHPh$_3$P)$_6$ (2.23 g, 1.14 mmol) and (R,S)—PPF—P(tBu)$_2$ (2.24 g, 4.13 mmol) in toluene (550 mL) was added PMHS (20.7 mL) and t-BuOH (17 mL) before the introduction of ethyl (E)-3-(4-(diisobutylamino)-3-nitrophenyl)but-2-enoate (53.5 g, 147.6 mmol). After stirred at r.t. for overnight, the resulting mixture was quenched with sat. NaHCO$_3$ aq. solution and extracted with EtOAc. The organic layer was washed with brine, dried over Na$_2$SO$_4$, filtered and concentrated to give the crude product which was purified by flash chromatography (silica gel, 0-10% EtOAc in PE) to afford the title compound (51 g, 95% yield) as a yellow oil. LCMS (ESI) m/z calcd for $C_{20}H_{32}N_2O_4$: 364.24. Found: 365.58 (M+1)$^+$.

Preparation of ethyl (R)-3-(3-amino-4-(diisobutylamino)phenyl)butanoate

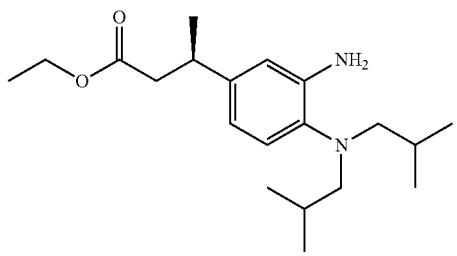

A mixture of ethyl (R)-3-(4-(diisobutylamino)-3-nitrophenyl)butanoate (65 g, 178.3 mmol) and 10% Pd/C (20 g) in EtOAc (650 mL) was stirred at 50° C. under H$_2$ atmosphere overnight. The resulting mixture was filtered through a pad of Celite and the filtrate was concentrated under reduced pressure to afford the title compound (60 g, 99% yield). LCMS (ESI) m/z calcd for $C_{20}H_{34}N_2O_2$: 334.26. Found: 335.74 (M+1)$^+$.

Preparation of ethyl (R)-3-(4-(diisobutylamino)-3-((3-(trifluoromethyl)-1,2,4-thiadiazol-5-yl)amino)phenyl)butanoate

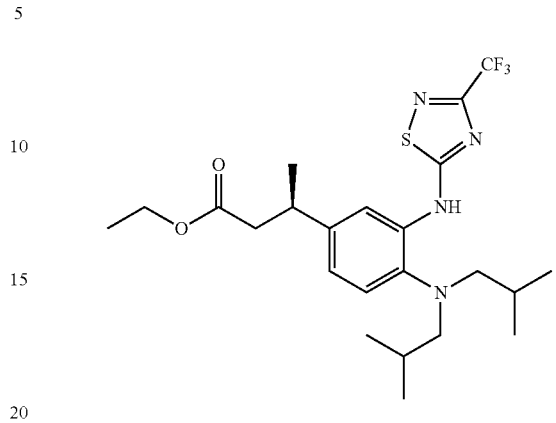

A mixture of ethyl (R)-3-(3-amino-4-(diisobutylamino)phenyl)butanoate (60 g, 179 mmol) and 5-chloro-3-(trifluoromethyl)-1,2,4-thiadiazole (41 g, 215 mmol) in MeCN (100 mL) was stirred at 90° C. under N$_2$ atmosphere for 24 hr. The resulting mixture was partitioned between EtOAc and H$_2$O. The organic layer was washed with brine, dried over Na$_2$SO$_4$, filtered and concentrated to give the crude product which was purified by flash chromatography (silica gel, 0-10% EtOAc in PE) to afford the title compound (38.5 g, 44% yield). LCMS (ESI) m/z calcd for $C_{23}H_{33}F_3N_4O_2S$: 486.23. Found: 487.71 (M+1)$^+$.

Preparation of (R)-3-(4-(diisobutylamino)-3-((3-(trifluoromethyl)-1,2,4-thiadiazol-5-yl)amino)phenyl)butanoic Acid

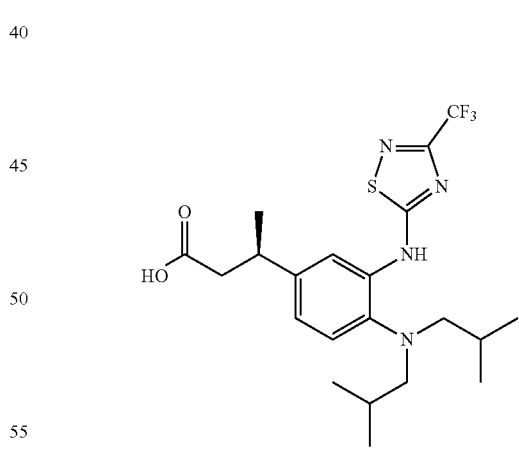

To a solution of ethyl (R)-3-(4-(diisobutylamino)-3-((3-(trifluoromethyl)-1,2,4-thiadiazol-5-yl)amino)phenyl)butanoate (38.5 g, 79.1 mmol) in MeOH (200 mL) and THF (200 mL) was added 1N LiOH aq. (316 mL). After stirred at r.t. overnight, the resulting mixture was neutralized with 1N HCl and extracted with EtOAc. The organic layer was washed with brine, dried over Na$_2$SO$_4$, filtered and concentrated to afford the title compound (27.8 g, 77% yield) as a white solid. LCMS (ESI) m/z calcd for $C_{21}H_{29}F_3N_4O_2S$: 458.20. Found: 457.19 (M−1)$^-$.

Preparation of (R)-3-(4-(diisobutylamino)-3-((3-(trifluoromethyl)-1,2,4-thiadiazol-5-yl)amino)phenyl)-N-(methylsulfonyl)butanamide

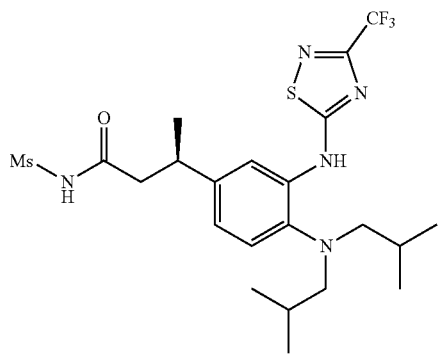 [SMILES: CC(C)CN(CC(C)C)c1ccc([C@H](C)CC(=O)NS(C)(=O)=O)cc1Nc1nc(C(F)(F)F)ns1]

At 0° C., to a suspension of (R)-3-(4-(diisobutylamino)-3-((3-(trifluoromethyl)-1,2,4-thiadiazol-5-yl)amino)phenyl) butanoic acid (150 mg, 0.327 mmol), DCC (81 mg, 0.392 mmol) and DMAP (8 mg, 0.065 mmol) in DCM (3 mL) was added MsNH$_2$ (35 mg, 0.368 mmol). After stirred at 0° C. for 3 hr, the resulting mixture was filtered and the filtrate was concentrated to give the crude product which was purified by HPLC (C18, 0-100% MeCN in H$_2$O with 0.1% formic acid) to afford the title compound (25 mg, 14% yield) as a white powder. $^1$H NMR (400 MHz, DMSO) δ 11.67 (s, 1H), 10.24 (s, 1H), 7.58 (s, 1H), 7.19 (d, J=8.3 Hz, 1H), 7.07 (dd, J=8.3, 1.9 Hz, 1H), 3.20-3.09 (m, 4H), 2.74 (d, J=7.0 Hz, 4H), 2.57-2.51 (m, 2H), 1.74-1.62 (m, 2H), 1.21 (d, J=6.9 Hz, 3H), 0.78 (dd, J=6.6, 1.9 Hz, 12H). LCMS (ESI) m/z calcd for C$_{22}$H$_{32}$F$_3$N$_5$O$_3$S$_2$: 535.19. Found: 536.42 (M+1)$^+$.

Example 110

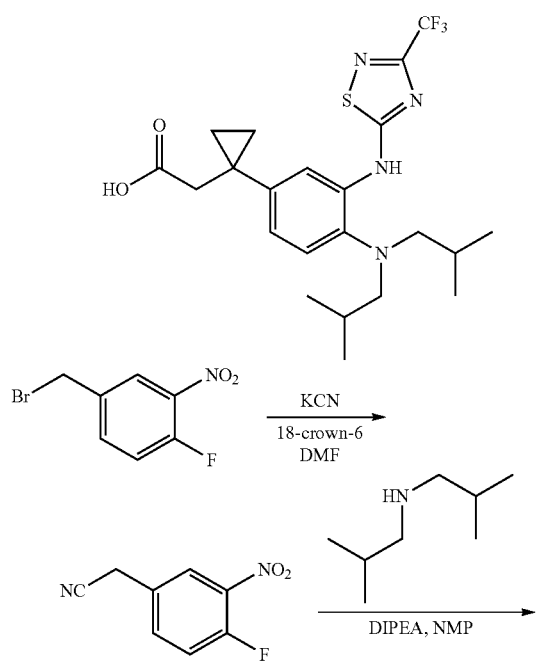

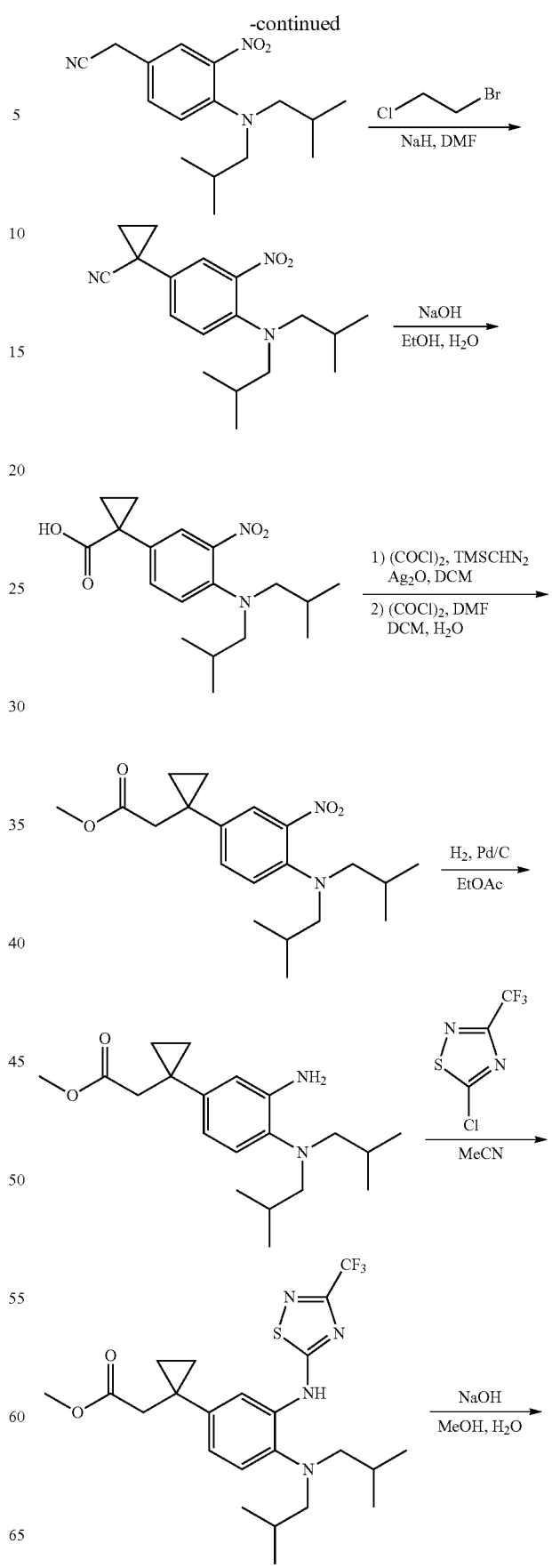

321

-continued

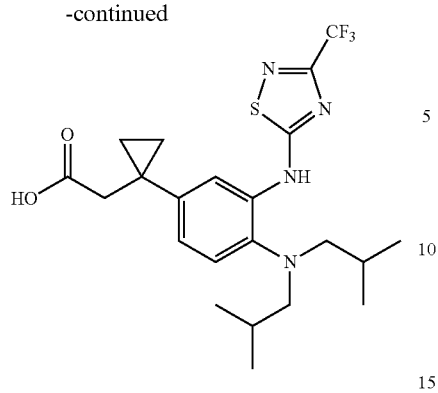

Preparation of 2-(4-fluoro-3-nitrophenyl)acetonitrile

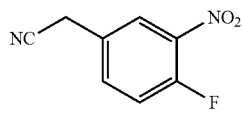 [SMILES: N#CCc1ccc(F)c([N+](=O)[O-])c1]

A mixture of 4-(bromomethyl)-1-fluoro-2-nitrobenzene (18 g, 76.9 mmol), KCN (10 g, 153.8 mmol), KI (1.3 g, 7.69 mmol) and 18-Crown-6 (10 g, 38.5 mmol) in DMF (100 mL) was stirred at r.t. overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (6.6 g, 47% yield). LCMS (ESI) m/z calcd for C$_8$H$_5$FN$_2$O$_2$: 180.03. Found: 181.37 (M+1)$^+$.

Preparation of 2-(4-(diisobutylamino)-3-nitrophenyl)acetonitrile

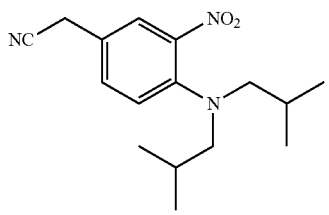 [SMILES: CC(C)CN(CC(C)C)c1ccc(CC#N)cc1[N+](=O)[O-]]

A mixture of 2-(4-fluoro-3-nitrophenyl)acetonitrile (5.8 g, 32.2 mmol) and diisobutyl amine (20.8 g, 161 mmol) was stirred at 130° C. under N$_2$ atmosphere for 2 hr. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (8.0 g, 86% yield). LCMS (ESI) m/z calcd for C$_{16}$H$_{23}$N$_3$O$_2$: 289.18. Found: 290.76 (M+1)$^+$.

322

Preparation of 1-(4-(diisobutylamino)-3-nitrophenyl)cyclopropane-1-carbonitrile

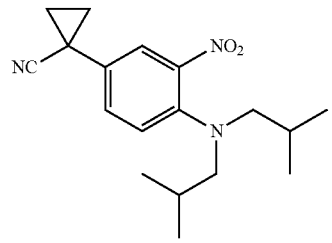 [SMILES: CC(C)CN(CC(C)C)c1ccc(C2(C#N)CC2)cc1[N+](=O)[O-]]

At 0° C., to a solution of 2-(4-(diisobutylamino)-3-nitrophenyl)acetonitrile (9 g, 31.1 mmol) and 1-bromo-2-chloroethane (6.68 g, 46.7 mmol) in DMF (100 mL) was added NaH (60%, 3.1 g, 77.7 mmol). After stirred at r.t. for 30 min, the resulting mixture was quenched with sat. NH$_4$Cl aq. solution and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (8.8 g, 94% yield). LCMS (ESI) m/z calcd for C$_{18}$H$_{25}$N$_3$O$_2$: 315.19. Found: 316.31 (M+1)$^+$.

Preparation of 1-(4-(diisobutylamino)-3-nitrophenyl)cyclopropane-1-carboxylic Acid

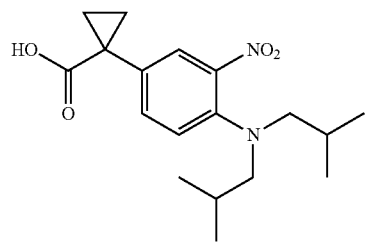 [SMILES: CC(C)CN(CC(C)C)c1ccc(C2(C(=O)O)CC2)cc1[N+](=O)[O-]]

A mixture of 1-(4-(diisobutylamino)-3-nitrophenyl)cyclopropane-1-carbonitrile (8.8 g, 27.9 mmol) and NaOH (16.8 g, 419 mmol) in EtOH (100 mL) and H$_2$O (100 mL) was stirred at 100° C. overnight. The resulting mixture was acidified with conc. HCl to pH 3-4 and extracted with EtOAc. The organic layer was washed with brine, dried over Na$_2$SO$_4$, filtered and concentrated to give the crude product which was purified by flash chromatography (silica gel, 0-100% EtOAc in PE) to afford the title compound (8.7 g, 93% yield). LCMS (ESI) m/z calcd for C$_{18}$H$_{26}$N$_2$O$_4$: 334.19. Found: 335.39 (M+1)$^+$.

323

Preparation of methyl 2-(1-(4-(diisobutylamino)-3-nitrophenyl)cyclopropyl) acetate

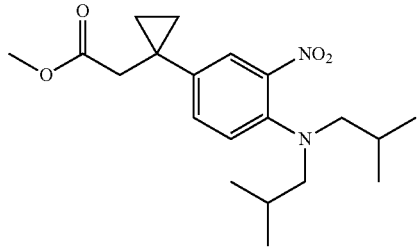 [SMILES: COC(=O)CC1(c2ccc(N(CC(C)C)CC(C)C)c([N+](=O)[O-])c2)CC1]

At 0° C., to a solution of 1-(4-(diisobutylamino)-3-nitrophenyl)cyclopropane-1-carboxylic acid (8.7 g, 26.0 mmol) in DCM (100 mL) was added (COCl)$_2$ (6.9 mL, 52.0 mmol) and 5 drops of DMF as catalyst. After stirred at 0° C. for 30 min, the resulting mixture was concentrated and the residue was dissolved in THF (50 mL) and MeCN (50 mL) and the reaction mixture was cooled to 0° C. before the addition of TMS diazomethane (2N, 130 mL, 260 mmol). After stirred at r.t. for 4.5 hr, the mixture was diluted with EtOAc and washed with H$_2$O and brine. The organic layer was concentrated and the residue was dissolved in DMF (40 mL) and H$_2$O (20 mL) before the addition of Ag$_2$O (550 mg, 2.38 mmol). The reaction mixture was stirred at 120° C. for 15 min and concentrated. The residue was diluted in DCM and treated with (COCl)$_2$ and MeOH to give the crude product which was purified by flash chromatography (silica gel, 0-20% EtOAc in PE) to afford the title compound (400 mg, 4.2% yield). LCMS (ESI) m/z calcd for C$_{20}$H$_{30}$N$_2$O$_4$: 362.22. Found: 363.45 (M+1)$^+$.

Preparation of methyl 2-(1-(3-amino-4-(diisobutylamino)phenyl)cyclopropyl) acetate

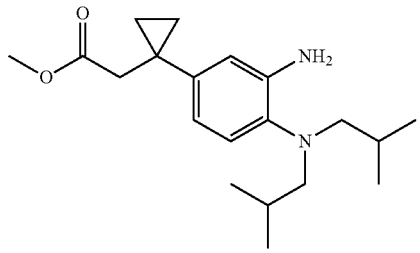 [SMILES: COC(=O)CC1(c2ccc(N(CC(C)C)CC(C)C)c(N)c2)CC1]

A mixture of methyl 2-(1-(4-(diisobutylamino)-3-nitrophenyl)cyclopropyl) acetate (360 mg, 0.99 mmol) and 10% Pd/C (100 mg) in MeOH (10 mL) was stirred at r.t. under H$_2$ atmosphere for 2 hr. The resulting mixture was filtered through a pad of Celite and the filtrate was concentrated under reduced pressure to give the crude product which was purified by flash chromatography (silica gel, 0-30% EtOAc in PE) to afford the title compound (90 mg, 25% yield). LCMS (ESI) m/z calcd for C$_{20}$H$_{32}$N$_2$O$_2$: 332.25. Found: 333.39 (M+1)$^+$.

324

Preparation of methyl 2-(1-(4-(diisobutylamino)-3-((3-(trifluoromethyl)-1,2,4-thiadiazol-5-yl)amino)phenyl)cyclopropyl)acetate

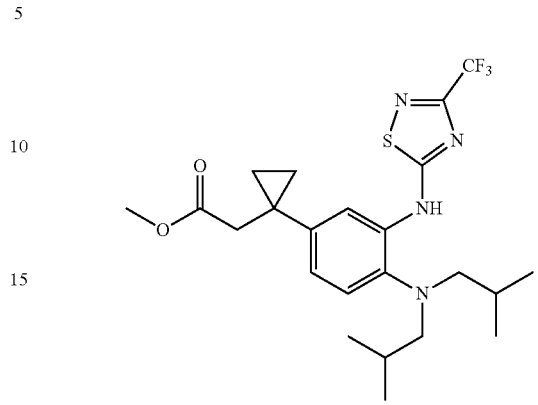

A mixture of methyl 2-(1-(3-amino-4-(diisobutylamino)phenyl)cyclopropyl)acetate (90 mg, 0.27 mmol) and 5-chloro-3-(trifluoromethyl)-1,2,4-thiadiazole (51 mg, 0.54 mmol) in MeCN (2 mL) was stirred at 90° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-20% EtOAc in PE) to afford the title compound (100 mg, 76% yield). LCMS (ESI) m/z calcd for C$_{23}$H$_{31}$F$_3$N$_4$O$_2$S: 484.21. Found: 485.29 (M+1)$^+$.

Preparation of 2-(1-(4-(diisobutylamino)-3-((3-(trifluoromethyl)-1,2,4-thiadiazol-5-yl)amino)phenyl)cyclopropyl)acetic Acid

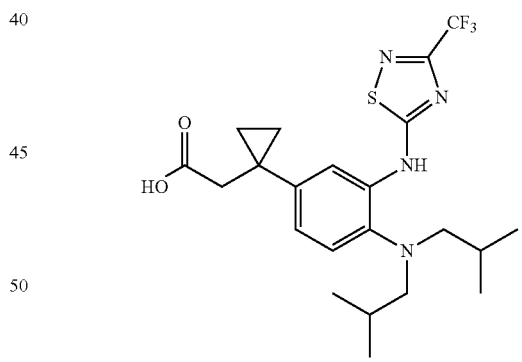

To a solution of methyl 2-(1-(4-(diisobutylamino)-3-((3-(trifluoromethyl)-1,2,4-thiadiazol-5-yl)amino)phenyl)cyclopropyl)acetate (100 mg, 0.21 mmol) in MeOH (5 mL) was added 1N NaOH aq. (1 mL). After stirred at r.t. overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (53 mg, 54% yield) as a white powder. $^1$H NMR (400 MHz, CDCl$_3$) δ 9.46 (s, 1H), 7.50 (d, J=1.7 Hz, 1H), 7.17 (d, J=8.2 Hz, 1H), 7.07 (dd, J=8.2, 2.0 Hz, 1H), 2.69 (s, 2H), 2.59 (d, J=7.2 Hz, 4H), 1.72-1.64 (m, 2H), 1.05-0.95 (m, 4H), 0.90 (d, J=6.6 Hz, 12H). LCMS (ESI) m/z calcd for $C_{22}H_{29}F_3N_4O_2S$: 470.20. Found: 471.48 $(M+1)^+$.

Example 111

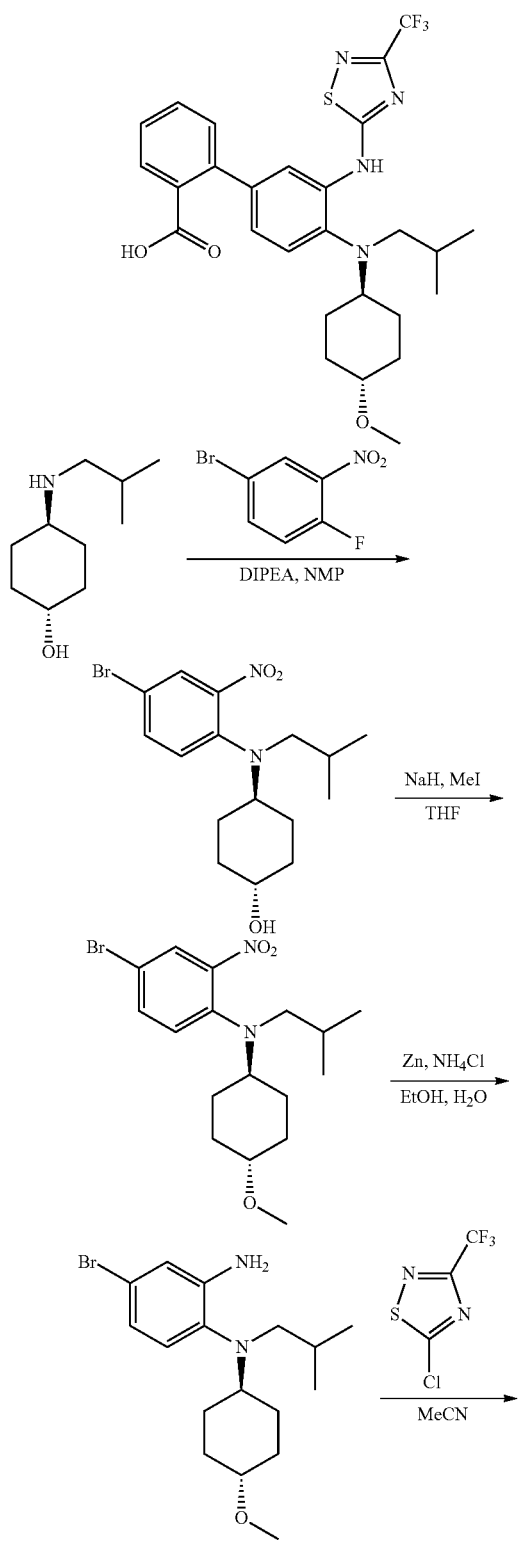

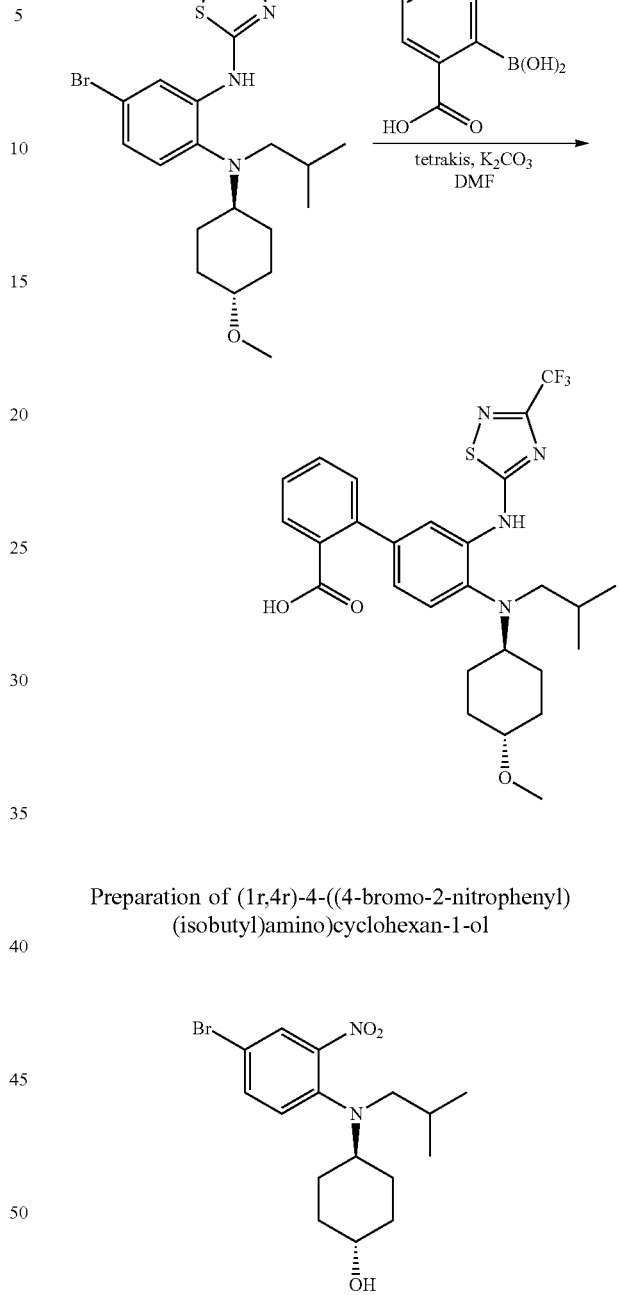

Preparation of (1r,4r)-4-((4-bromo-2-nitrophenyl)(isobutyl)amino)cyclohexan-1-ol A mixture of 4-bromo-1-fluoro-2-nitrobenzene (3.3 g, 15.0 mmol), (1r,4r)-4-(isobutyl amino)cyclohexan-1-ol (3.0 g, 17.9 mmol) and DIPEA (5.3 mL, 30.4 mmol) in NMP (50 mL) was stirred at 130° C. under $N_2$ atmosphere for 4 hr. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (3.4 g, 61% yield). LCMS (ESI) m/z calcd for chemical Formula $C_{16}H_{23}BrN_2O_3$: 370.09. Found: 371.24/373.27 $(M/M+2)^+$.

327

Preparation of 4-bromo-N-isobutyl-N-((1r,4r)-4-methoxycyclohexyl)-2-nitro aniline

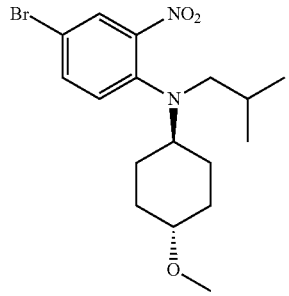 [SMILES: CO[C@H]1CC[C@H](N(CC(C)C)c2ccc(Br)cc2[N+](=O)[O-])CC1]

At 0° C., to a solution of (1r,4r)-4-((4-bromo-2-nitrophenyl)(isobutyl)amino)cyclo hexan-1-ol (1.7 g, 4.6 mmol) in THF (20 mL) was added NaH (60%, 1.1 g, 27.5 mmol). The reaction mixture was stirred at 0° C. for 2 hr before the addition of MeI (6.5 g, 45.8 mmol). After stirred at r.t. overnight, the resulting mixture was quenched with sat. NH$_4$Cl aq. solution and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (1.6 g, 91% yield). LCMS (ESI) m/z calcd for $C_{17}H_{25}BrN_2O_3$: 384.10. Found: 385.41/387.40 (M/M+2)$^+$.

Preparation of 4-bromo-N$^1$-isobutyl-N$^1$-((1r,4r)-4-methoxycyclohexyl)benzene-1,2-diamine

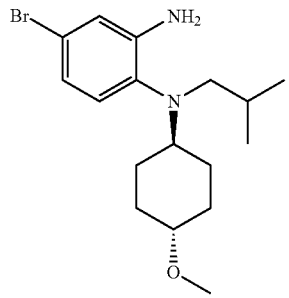 [SMILES: CO[C@H]1CC[C@H](N(CC(C)C)c2ccc(Br)cc2N)CC1]

A mixture of 4-bromo-N-isobutyl-N-((1r,4r)-4-methoxycyclohexyl)-2-nitro aniline (2.0 g, 5.2 mmol), zinc powder (3.4 g, 52 mmol) and NH$_4$C$_1$ (5.5 g, 104 mmol) in EtOH (30 mL) and H$_2$O (15 mL) was stirred at r.t. overnight. The resulting mixture was filtered and the filtrate was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (1.1 g, 60% yield). LCMS (ESI) m/z calcd for $C_{17}H_{27}BrN_2O$: 354.13. Found: 355.53/357.56 (M/M+2)$^+$.

328

Preparation of 4-bromo-N$^1$-isobutyl-N$^1$-((1r,4r)-4-methoxycyclohexyl)-N$^2$-(3-(tri fluoromethyl)-1,2,4-thiadiazol-5-yl)benzene-1,2-diamine

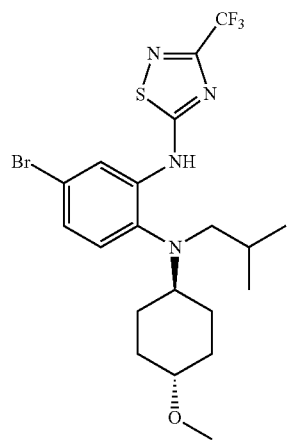 [SMILES: CO[C@H]1CC[C@H](N(CC(C)C)c2ccc(Br)cc2Nc2nc(C(F)(F)F)ns2)CC1]

A mixture of 4-bromo-N$^1$-isobutyl-N$^1$-((1r,4r)-4-methoxycyclohexyl)benzene-1,2-diamine (1.0 g, 2.8 mmol) and 5-chloro-3-(trifluoromethyl)-1,2,4-thiadiazole (1.0 g, 5.3 mmol) in MeCN (10 mL) was stirred at 90° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-30% EtOAc in PE) to afford the title compound (400 mg, 28% yield). LCMS (ESI) m/z calcd for $C_{20}H_{26}BrF_3N_4OS$: 506.10. Found: 507.24/509.48 (M/M+2)$^+$.

Preparation of 4'-(isobutyl((1r,4r)-4-methoxycyclohexyl)amino)-3'-((3-(trifluoro methyl)-1,2,4-thiadiazol-5-yl)amino)-[1,1'-biphenyl]-2-carboxylic Acid

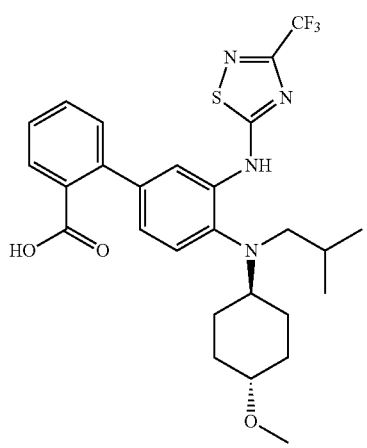 [SMILES: CO[C@H]1CC[C@H](N(CC(C)C)c2ccc(-c3ccccc3C(=O)O)cc2Nc2nc(C(F)(F)F)ns2)CC1]

A mixture of 4-bromo-N$^1$-isobutyl-N$^1$-((1 r,4r)-4-methoxycyclohexyl)-N$^2$-(3-(trifluoro methyl)-1,2,4-thiadiazol-5-yl)benzene-1,2-diamine (100 mg, 0.20 mmol), 2-boronoben zoic acid (133 mg, 0.80 mmol), tetrakis (23.2 mg, 0.02 mmol) and K$_2$CO$_3$ (55 mg, 0.40 mmol) in DMF (4 mL) and H$_2$O (1 mL) was stirred at 110° C. under N$_2$ atmosphere for 3 hr. The resulting mixture was partitioned between EtOAc and H₂O. The organic layer was washed with brine, dried over Na₂SO₄, filtered and concentrated to give the crude product which was purified by HPLC (C18, 0-100% MeCN in H₂O with 0.1% formic acid) to afford the title compound (41 mg, 38% yield) as a white powder. $^1$H NMR (400 MHz, CDCl₃) δ 9.49 (s, 1H), 7.95 (dd, J=7.7, 1.0 Hz, 1H), 7.60 (td, J=7.6, 1.3 Hz, 1H), 7.50-7.40 (m, 2H), 7.35 (d, J=1.8 Hz, 1H), 7.30 (d, J=8.2 Hz, 1H), 7.12 (dd, J=8.1, 1.9 Hz, 1H), 3.29 (s, 3H), 3.07-3.01 (m, 1H), 2.85 (d, J=6.7 Hz, 2H), 2.72-2.64 (m, 1H), 2.08-1.95 (m, 4H), 1.48-1.33 (m, 3H), 1.19-1.09 (m, 2H), 0.85 (d, J=6.6 Hz, 6H). LCMS (ESI) m/z calcd for C₂₇H₃₁F₃N₄O₃S: 548.21. Found: 549.14 (M+1)⁺.

Example 112

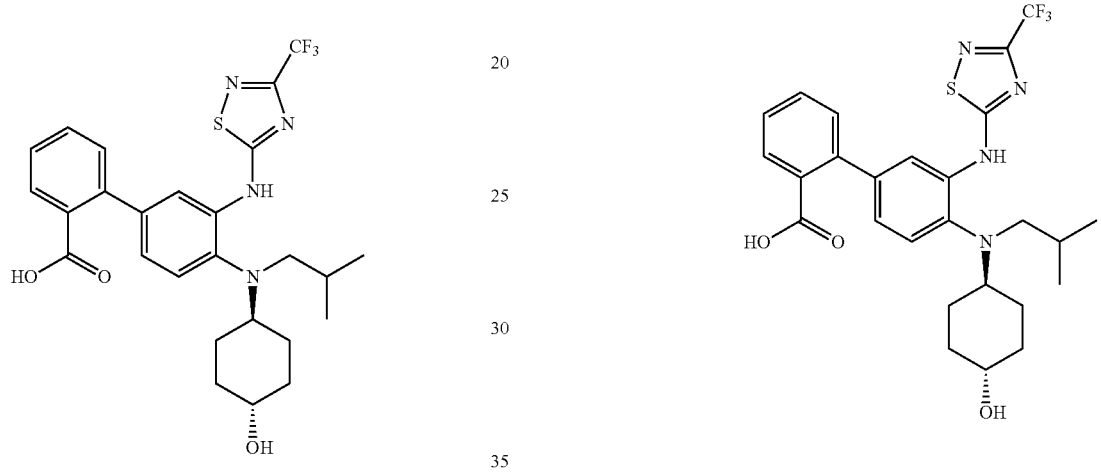

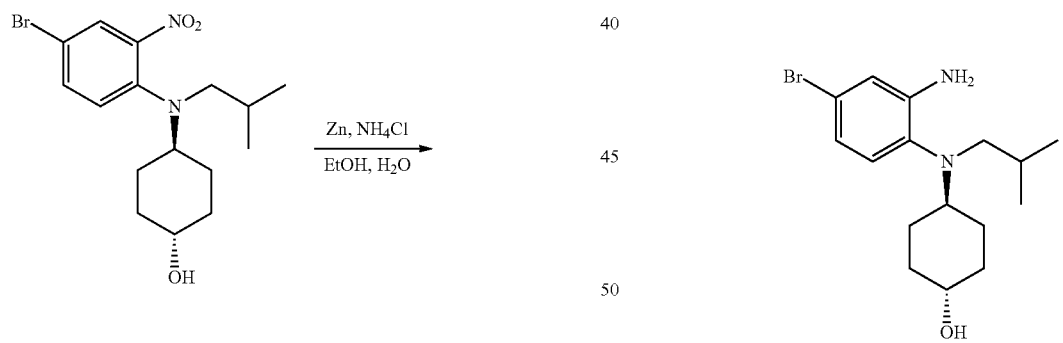

Preparation of (1r,4r)-4-((2-amino-4-bromophenyl)(isobutyl)amino)cyclohexan-1-ol A mixture of (1r,4r)-4-((4-bromo-2-nitrophenyl)(isobutyl)amino)cyclohexan-1-ol (1.7 g, 4.6 mmol), zinc powder (3.1 g, 47 mmol) and NH₄C₁ (4.9 g, 92 mmol) in EtOH (20 mL) and H₂O (10 mL) was stirred at r.t. for 6 hr. The resulting mixture was filtered and the filtrate was partitioned between EtOAc and H₂O. The organic layer was washed with brine, dried over Na₂SO₄, filtered and concentrated to give the crude product which was purified by flash chromatography (silica gel, 0-30% EtOAc in PE) to afford the title compound (1.0 g, 65% yield). LCMS (ESI) m/z calcd for C₁₆H₂₅BrN₂O: 340.12. Found: 341.42/343.40 (M/M+2)⁺.

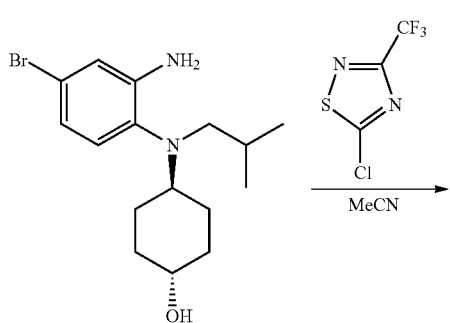

Preparation of (1r,4r)-4-((4-bromo-2-((3-(trifluoromethyl)-1,2,4-thiadiazol-5-yl)amino)phenyl)(isobutyl)amino)cyclohexan-1-ol

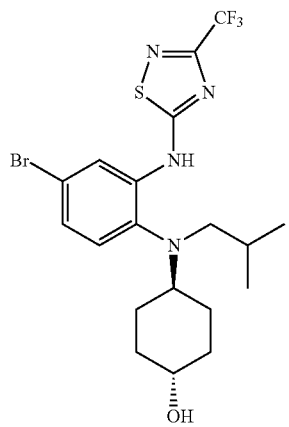 [SMILES: CC(C)CN(c1ccc(Br)cc1Nc1nc(C(F)(F)F)ns1)[C@H]1CC[C@H](O)CC1]

A mixture of (1r,4r)-4-((2-amino-4-bromophenyl)(isobutyl)amino)cyclohexan-1-ol (1.0 g, 2.9 mmol) and 5-chloro-3-(trifluoromethyl)-1,2,4-thiadiazole (830 mg, 4.4 mmol) in MeCN (10 mL) was stirred at 90° C. under N₂ atmosphere overnight. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-30% EtOAc in PE) to afford the title compound (480 mg, 33% yield). LCMS (ESI) m/z calcd for $C_{19}H_{24}BrF_3N_4OS$: 492.08. Found: 493.27/495.32 (M/M+2)⁺.

Preparation of 4'-(((1r,4r)-4-hydroxycyclohexyl)(isobutyl)amino)-3'-((3-(trifluoro methyl)-1,2,4-thiadiazol-5-yl)amino)-[1,1'-biphenyl]-2-carboxylic Acid

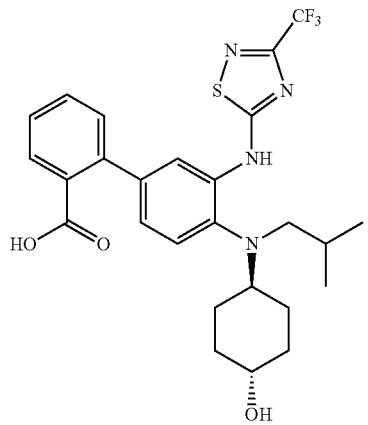 [SMILES: CC(C)CN(c1ccc(-c2ccccc2C(=O)O)cc1Nc1nc(C(F)(F)F)ns1)[C@H]1CC[C@H](O)CC1]

A mixture of (1r,4r)-4-((4-bromo-2-((3-(trifluoromethyl)-1,2,4-thiadiazol-5-yl)amino) phenyl) (isobutyl)amino)cyclohexan-1-ol (100 mg, 0.20 mmol), 2-boronobenzoic acid (133 mg, 0.80 mmol), tetrakis (23.2 mg, 0.02 mmol) and K₂CO₃ (55 mg, 0.40 mmol) in DMF (4 mL) and H₂O (1 mL) was stirred at 110° C. under N₂ atmosphere for 3 hr. The resulting mixture was partitioned between EtOAc and H₂O. The organic layer was washed with brine, dried over Na₂SO₄, filtered and concentrated to give the crude product which was purified by HPLC (C18, 0-100% MeCN in H₂O with 0.1% formic acid) to afford the title compound (41 mg, 39% yield) as a white powder. ¹H NMR (400 MHz, CDCl₃) δ 9.46 (s, 1H), 7.96 (dd, J=7.8, 1.1 Hz, 1H), 7.60 (td, J=7.6, 1.3 Hz, 1H), 7.50-7.39 (m, 2H), 7.34 (d, J=1.8 Hz, 1H), 7.29 (d, J=8.2 Hz, 1H), 7.12 (dd, J=8.1, 1.9 Hz, 1H), 3.54-3.46 (m, 1H), 2.83 (d, J=6.7 Hz, 2H), 2.68-2.62 (m, 1H), 1.99-1.87 (m, 4H), 1.46-1.18 (m, 6H), 0.84 (d, J=6.6 Hz, 6H). LCMS (ESI) m/z calcd for $C_{26}H_{29}F_3N_4O_3S$: 534.19. Found: 535.04 (M+1)⁺.

Example 113

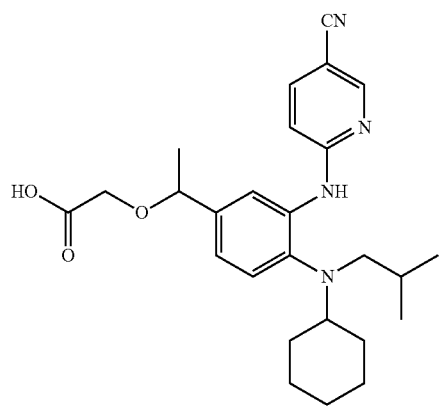

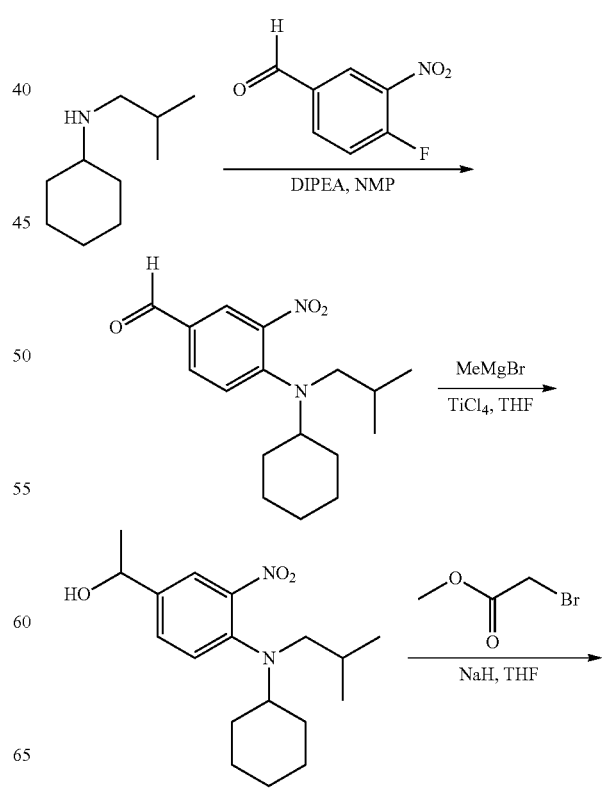

333
-continued

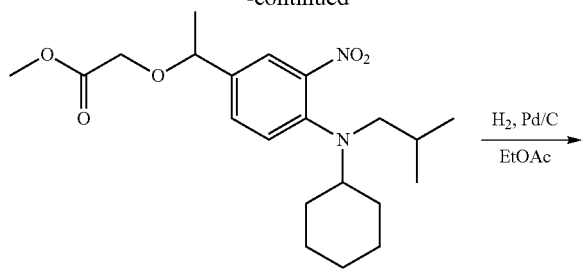

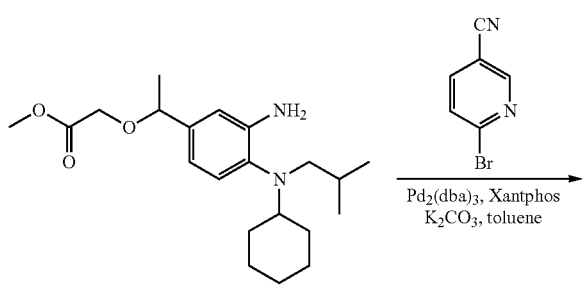 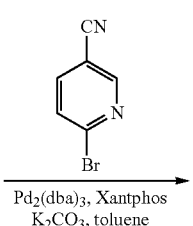

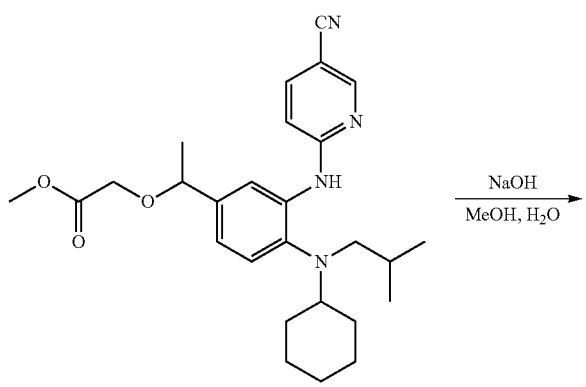

334
Preparation of 4-(cyclohexyl(isobutyl)amino)-3-nitrobenzaldehyde

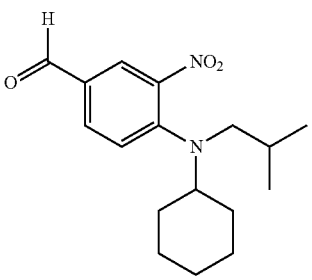 [SMILES: CC(C)CN(c1ccc(C=O)cc1[N+](=O)[O-])C1CCCCC1]

A mixture of 4-fluoro-3-nitrobenzaldehyde (13 g, 77.4 mmol), N-isobutylcyclohexan amine (24 g, 154.8 mmol) and DIPEA (30 mL, 172.6 mmol) in NMP (26 mL) was stirred at 120° C. under $N_2$ atmosphere for 3 hr. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (7.24 g, 37% yield) as a yellow oil. LCMS (ESI) m/z calcd for $C_{17}H_{24}N_2O_3$: 304.18. Found: 305.30 $(M+1)^+$.

Preparation of 1-(4-(cyclohexyl(isobutyl)amino)-3-nitrophenyl)ethan-1-ol

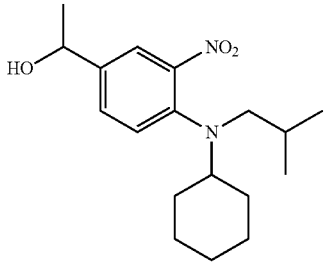 [SMILES: CC(C)CN(c1ccc(C(C)O)cc1[N+](=O)[O-])C1CCCCC1]

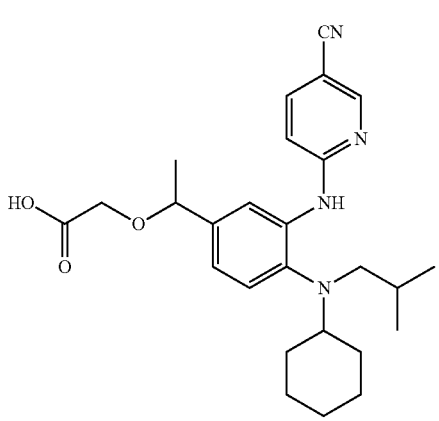

At −78° C., to a mixture of $TiCl_4$ (1.36 mL, 12.48 mmol) and MeMgBr (1N, 13.2 mL, 13.2 mmol) in THF (40 mL) was added 4-(cyclohexyl(isobutyl)amino)-3-nitrobenzaldehyde (2.0 g, 65.6 mmol). After stirred at −78° C. for 30 min, the resulting mixture was quenched with sat. $NH_4Cl$ aq. solution and extracted with EtOAc. The organic layer was washed with brine, dried over $Na_2SO_4$, filtered and concentrated to give the crude product which was purified by flash chromatography (silica gel, 0-10% EtOAc in PE) to afford the title compound (700 mg, 33% yield) as a yellow oil. LCMS (ESI) m/z calcd for $C_{18}H_{28}N_2O_3$: 320.21. Found: 321.47 $(M+1)^+$.

Preparation of methyl 2-(1-(4-(cyclohexyl(isobutyl) amino)-3-nitrophenyl)ethoxy) acetate

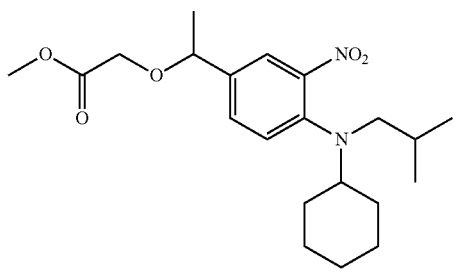 [SMILES: COC(=O)COC(C)c1ccc(N(CC(C)C)C2CCCCC2)c([N+](=O)[O-])c1]

A mixture of 1-(4-(cyclohexyl(isobutyl)amino)-3-nitrophenyl)ethan-1-ol (700 mg, 2.18 mmol), NaH (60%, 174 mg, 4.36 mmol) and methyl 2-bromoacetate (500 mg, 3.27 mmol) in THF (10 mL) was stirred at 70° C. for 48 hr. The resulting mixture was partitioned between EtOAc and $H_2O$. The organic layer was washed with brine, dried over $Na_2SO_4$, filtered and concentrated to give the crude product which was purified by flash chromatography (silica gel, 0-10% EtOAc in PE) to afford the title compound (300 mg, 35% yield) as a yellow oil. LCMS (ESI) m/z calcd for $C_{21}H_{32}N_2O_5$: 392.23. Found: 393.50 $(M+1)^+$.

Preparation of methyl 2-(1-(3-amino-4-(cyclohexyl (isobutyl)amino)phenyl) ethoxy)acetate

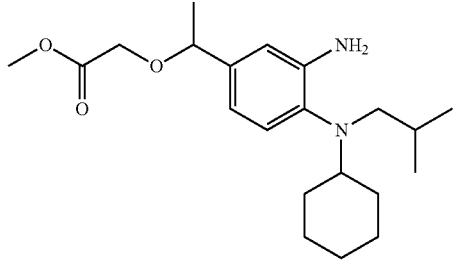

A mixture of methyl 2-(1-(4-(cyclohexyl(isobutyl) amino)-3-nitrophenyl)ethoxy) acetate (300 mg, 0.764 mmol) and 10% Pd/C (60 mg) in EtOAc (20 mL) was purged with $H_2$ and stirred at 50° C. for 4 hr. The resulting mixture was filtered through a pad of Celite and the filtrate was concentrated under reduced pressure to give the crude product which was purified by flash chromatography (silica gel, 0-30% EtOAc in PE) to afford the title compound (200 mg, 72% yield) as a yellow oil. LCMS (ESI) m/z calcd for $C_{21}H_{34}N_2O_3$: 362.26. Found: 363.53 $(M+1)^+$.

Preparation of methyl 2-(1-(3-((5-cyanopyridin-2-yl)amino)-4-(cyclohexyl(iso butyl)amino)phenyl) ethoxy)acetate

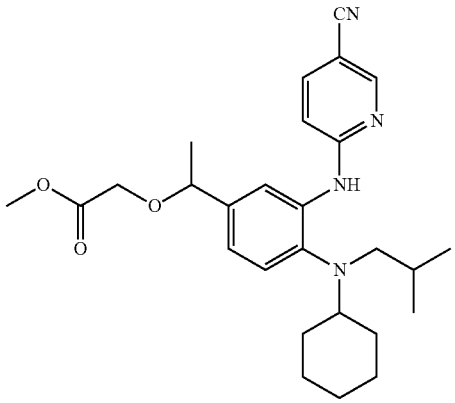 [SMILES: COC(=O)COC(C)c1ccc(N(CC(C)C)C2CCCCC2)c(Nc2ccc(C#N)cn2)c1]

A mixture of methyl 2-(1-(3-amino-4-(cyclohexyl (isobutyl)amino)phenyl)ethoxy) acetate (100 mg, 0.276 mmol), 6-bromonicotinonitrile (101 mg, 0.552 mmol), $Pd(OAc)_2$ (2.6 mg, 0.0044 mmol), BINAP (3.1 mg, 0.005 mmol) and $K_2CO_3$ (114 mg, 0.83 mmol) in toluene (5 mL) was stirred at 100° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-20% EtOAc in PE) to afford the title compound (90 mg, 70% yield). LCMS (ESI) m/z calcd for $C_{27}H_{36}N_4O_3$: 464.28. Found: 465.58 $(M+1)^+$.

Preparation of 2-(1-(3-((5-cyanopyridin-2-yl) amino)-4-(cyclohexyl(isobutyl) amino)phenyl) ethoxy)acetic Acid

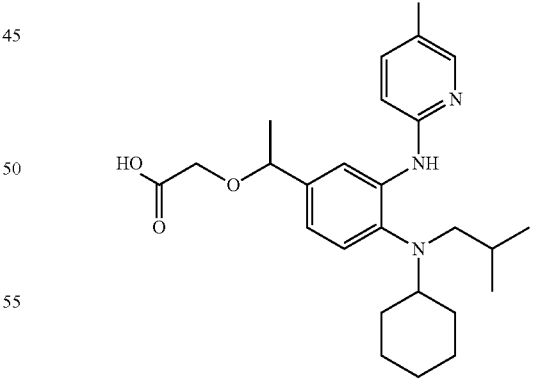

To a solution of methyl 2-(1-(3-((5-cyanopyridin-2-yl) amino)-4-(cyclohexyl(isobutyl) amino)phenyl)ethoxy)acetate (90 mg, 0.194 mmol) in MeOH (3 mL) was added 1N NaOH aq. (1 mL). After stirred at rt for 2 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (20 mg, 23% yield) as a white powder. $^1$H NMR (400 MHz, CDCl$_3$) δ 8.62-8.46 (m, 2H), 8.31 (s, 1H), 7.66 (dd, J=8.7, 2.3 Hz, 1H), 7.18 (d, J=8.1 Hz, 1H), 6.94 (dd, J=8.1, 1.8 Hz, 1H), 6.70 (d, J=8.7 Hz, 1H), 4.64-4.55 (m, 1H), 4.06-3.94 (m, 2H), 2.83 (d, J=6.9 Hz, 2H), 2.60-2.48 (m, 1H), 1.89-1.81 (m, 2H), 1.79-1.72 (m, 2H), 1.57 (d, J=6.4 Hz, 3H), 1.44-1.09 (m, 7H), 0.86 (d, J=6.6 Hz, 6H). LCMS (ESI) m/z calcd for C$_{26}$H$_{34}$N$_4$O$_3$: 450.26. Found: 451.41 (M+1)$^+$.

Example 114

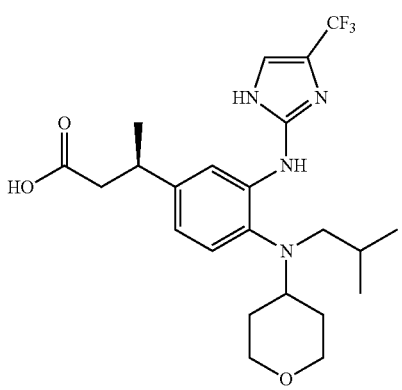

Step A 4-(trifluoromethyl)-1-((2-(trimethylsilyl)ethoxy)methyl)-1H-imidazole

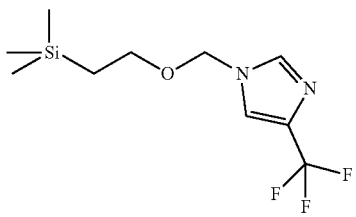 [SMILES: C[Si](C)(C)CCOCn1cnc(C(F)(F)F)c1]

A suspension of sodium hydride (60% disp in mineral oil) (0.323 g, 8.08 mmol) in 20 mL THF was stirred at 0° C. A solution of 4-(trifluoromethyl)-1H-imidazole (1.00 g, 7.35 mmol) in THF (4.5 mL) was added dropwise. The solution was stirred at RT for 1.5 h and SEM-Cl (1.694 ml, 9.55 mmol) was added. After stirring at RT overnight, saturated aqueous NaHCO$_3$ solution and EtOAc were added. The organic layer was dried (Na$_2$SO$_4$), filtered, evaporated and purified by silica gel chromatography (0-40% EtOAc/hexanes) to afford 4-(trifluoromethyl)-1-((2-(trimethylsilyl)ethoxy)methyl)-1H-imidazole (1.3426 g, 5.04 mmol, 68.6% yield). $^1$H NMR (400 MHz, CDCl$_3$) δ ppm 7.65 (s, 1H), 7.39 (s, 1H), 5.31 (s, 2H), 3.52 (t, J=8.2 Hz, 2H), 0.93 (t, J=8.2 Hz, 2H),-0.02-0.05 (m, 9H).

Step B 2-bromo-4-(trifluoromethyl)-1-((2-(trimethylsilyl)ethoxy)methyl)-1H-imidazole

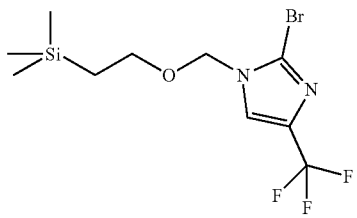 [SMILES: C[Si](C)(C)CCOCn1cc(C(F)(F)F)nc1Br]

A solution of 4-(trifluoromethyl)-1-((2-(trimethylsilyl)ethoxy)methyl)-1H-imidazole (1.14 g, 4.28 mmol), AIBN (0.141 g, 0.856 mmol) and NBS (0.990 g, 5.56 mmol) in CCl$_4$ (21.40 ml) was stirred at 60° C. for 4 h. Aqueous sodium bicarbonate solution was added and the reaction mixture was extracted with CH$_2$Cl$_2$. The organic layer was dried (Na$_2$SO$_4$), filtered, evaporated and purified by silica gel chromatography (0-30% EtOAc/hexanes) to obtain 2-bromo-4-(trifluoromethyl)-1-((2-(trimethylsilyl)ethoxy)methyl)-1H-imidazole (978.7 mg, 66% yield). $^1$H NMR (400 MHz, CDCl$_3$) □ ppm 7.45 (d, J=1.0 Hz, 1H), 5.31 (s, 2H), 3.53-3.63 (m, 2H), 0.87-1.02 (m, 2H), 0.01 (s, 9H).

Step C (R)-methyl 3-(4-(isobutyl(tetrahydro-2H-pyran-4-yl)amino)-3-((4-(trifluoromethyl)-1-((2-(trimethylsilyl)ethoxy)methyl)-1H-imidazol-2-yl)amino)phenyl)butanoate

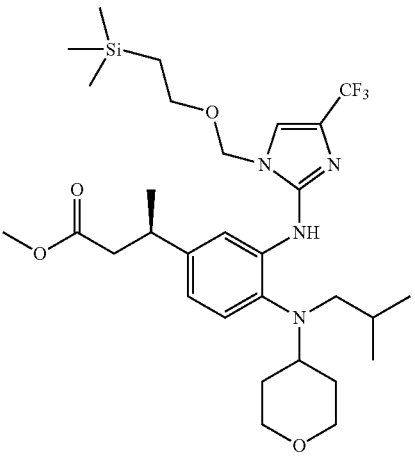 [SMILES: COC(=O)C[C@@H](C)c1ccc(N(CC(C)C)C2CCOCC2)c(Nc2nc(C(F)(F)F)cn2COCC[Si](C)(C)C)c1]

A mixture of (R)-methyl 3-(3-amino-4-(isobutyl(tetrahydro-2H-pyran-4-yl)amino)phenyl)butanoate (0.105 g, 0.301 mmol), 2-bromo-4-(trifluoromethyl)-1-((2-(trimethylsilyl)ethoxy)methyl)-1H-imidazole (0.125 g, 0.362 mmol), Pd$_2$dba$_3$ (0.055 g, 0.060 mmol), Xantphos (0.070 g, 0.121 mmol), and cesium carbonate (0.491 g, 1.507 mmol) was flushed with nitrogen and then stirred in toluene (4.3 mL). The reaction mixture was heated at 100° C. for 8 h, then filtered through celite, evaporated, and purified by silica gel chromatography (0-40% EtOAc/hexanes) to afford (R)-methyl 3-(4-(isobutyl(tetrahydro-2H-pyran-4-yl)amino)-3-((4-(trifluoromethyl)-1-((2-(trimethylsilyl)ethoxy)methyl)-

1H-imidazol-2-yl)amino)phenyl)butanoate (139.2 mg, 75 yield) as a yellow oil. LCMS (M+H)+: m/z=613.4.

Step D (R)-3-(4-(isobutyl(tetrahydro-2H-pyran-4-yl)amino)-3-((4-(trifluoromethyl)-1H-imidazol-2-yl)amino)phenyl)butanoic Acid

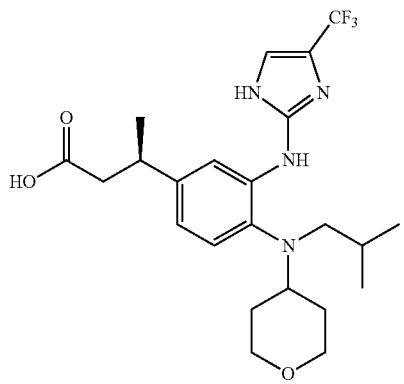

A solution of (R)-methyl 3-(4-(isobutyl(tetrahydro-2H-pyran-4-yl)amino)-3-((4-(trifluoromethyl)-1-((2-(trimethylsilyl)ethoxy)methyl)-1H-imidazol-2-yl)amino)phenyl)butanoate (139.2 mg, 0.227 mmol) in methanol (1.7 mL), tetrahydrofuran (1.7 mL), and 1M lithium hydroxide (2.3 mL, 2.272 mmol) was stirred at RT overnight. The reaction mixture was acidified with 1M citric acid and extracted with EtOAc. The organic phase was washed with brine, dried (Na₂SO₄), filtered, and evaporated. The residue was taken up in TFA (1.5 mL) and stirred at RT for 2 h and then evaporated. Residual acid was neutralized with DIEA. The residue was taken up in EtOAc and 1M citric acid and the organic phase was separated, dried and purified by reverse phase chrom. 10-100% CH3CN/H2O (0.1% FA) to afford the title compound (66.8 mg, 63%) as a white solid. LCMS (M+H)+: m/z=469.4. ¹H NMR (400 MHz, CD₃OD) δ ppm 7.71 (d, J=2.0 Hz, 1H), 7.20 (d, J=1.2 Hz, 1H), 7.15 (d, J=8.2 Hz, 1H), 6.80 (dd, J=8.0, 1.8 Hz, 1H), 3.89 (dd, J=11.3, 3.3 Hz, 2H), 3.12-3.34 (m, 3H), 2.74-2.94 (m, 3H), 2.44-2.68 (m, 2H), 1.75 (m, 2H), 1.59 (qd, J=12.0, 4.2 Hz, 2H), 1.40 (m, 1H), 1.28 (d, J=6.8 Hz, 3H), 0.84 (d, J=6.6 Hz, 6H).

Examples 115-300 were synthesized similarly to examples 1-114. Experimental data for examples 115-300

| | | | IPQA T$_{elute}$ [min] | M + 1 | M − 1 |
|---|---|---|---|---|---|
| example 115 | 3-{4-[bis(2-methylpropyl)amino]-3-[(3-phenyl-1,2,4-thiadiazol-5-yl)amino]phenyl}butanoic acid | 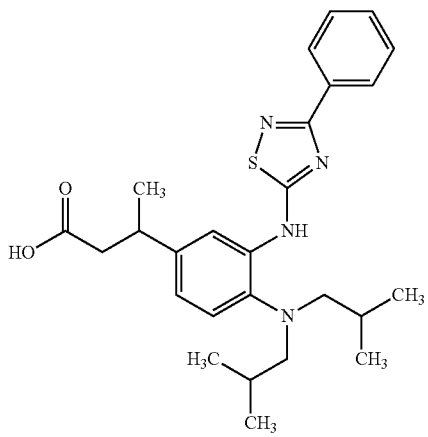 | 1.66 | 467.4 | |
| example 116 | 3-{4-[bis(2-methylpropyl)amino]-3-{[3-(4-methylpiperazin-1-yl)-1,2,4-thiadiazol-5-yl]amino}phenyl}butanoic acid | 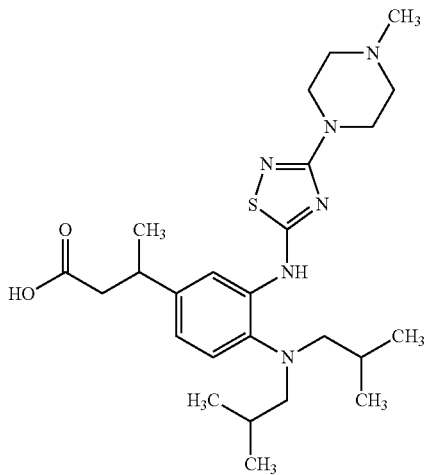 [SMILES: CC(C)CN(CC(C)C)c1ccc(C(C)CC(=O)O)cc1Nc1nc(N2CCN(C)CC2)ns1] | 1.01 | 489.5 | |

| | | IPQA $T_{elute}$ [min] | M + 1 | M − 1 |
|---|---|---|---|---|
| example 117 | 3-{4-[bis(2-methylpropyl)amino]-3-{[3-(morpholin-4-yl)-1,2,4-thiadiazol-5-yl]amino}phenyl}butanoic acid | 1.49 | 476.4 | |
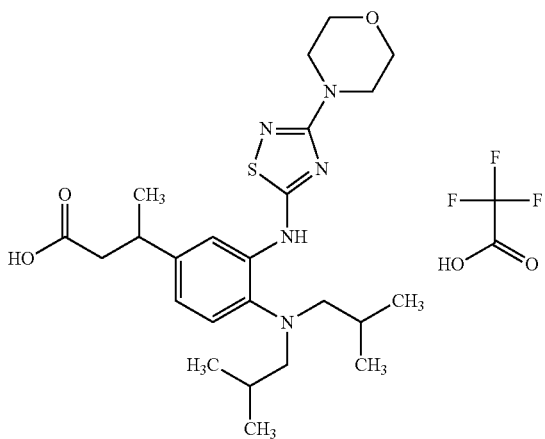 [SMILES: CC(C)CN(CC(C)C)c1ccc(C(C)CC(=O)O)cc1Nc1nc(N2CCOCC2)ns1 ; O=C(O)C(F)(F)F]
| example 118 | 3-{4-[bis(2-methylpropyl)amino]-3-{[3-(pyrrolidin-1-yl)-1,2,4-thiadiazol-5-yl]amino}phenyl}butanoic acid | 1.55 | 460.5 | |
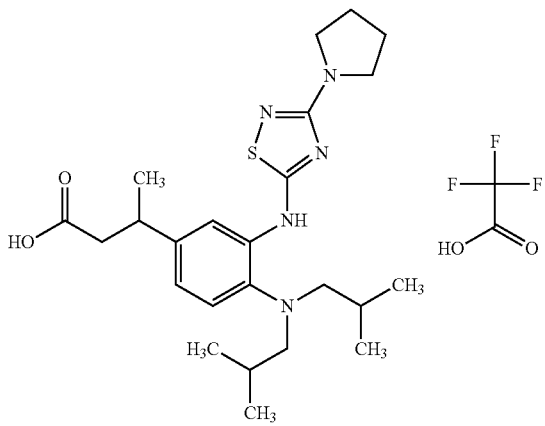 [SMILES: CC(C)CN(CC(C)C)c1ccc(C(C)CC(=O)O)cc1Nc1nc(N2CCCC2)ns1 ; O=C(O)C(F)(F)F]
example 119  3-{4-[bis(2-methylpropyl)amino]-3-[(1-methyl-1H-1,3-benzodiazol-2-yl)amino]phenyl}butanoic acid
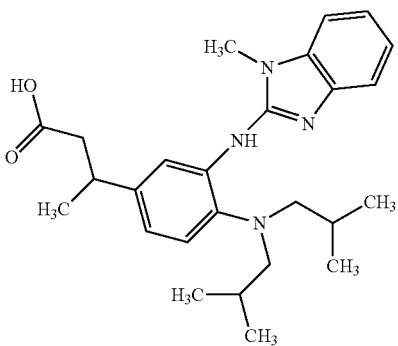 [SMILES: CC(C)CN(CC(C)C)c1ccc(C(C)CC(=O)O)cc1Nc1nc2ccccc2n1C]

-continued
| | | | IPQA $T_{elute}$ [min] | M + 1 | M − 1 |
|---|---|---|---|---|---|
| example 120 | 3-(3-{[3-(azetidin-1-yl) 1,2,4-thiadiazol-5-yl]amino}-4-[bis(2-methylpropyl)amino] phenyl)butanoic acid | 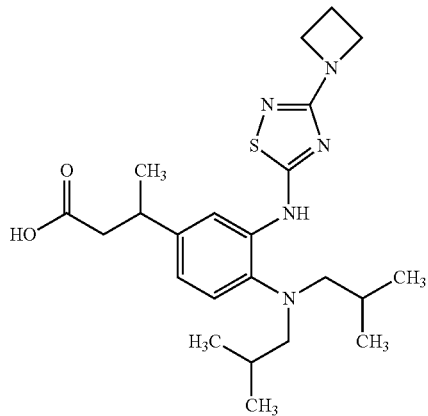 [SMILES: CC(C)CN(CC(C)C)c1ccc(C(C)CC(=O)O)cc1Nc1nc(N2CCC2)ns1] | 1.47 | 446.4 | |
| example 121 | 3-{4-[bis(2-methylpropyl)amino]-3-[(5-phenyl-1,3-oxazol-2-yl)amino]phenyl}butanoic acid | 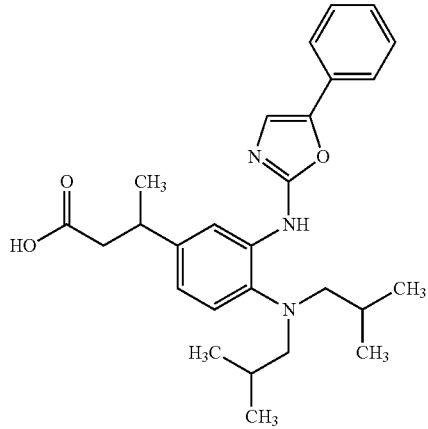 [SMILES: CC(C)CN(CC(C)C)c1ccc(C(C)CC(=O)O)cc1Nc1ncc(-c2ccccc2)o1] | 1.61 | 450.4 | |
| example 122 | 3-{4-[bis(2-methylpropyl)amino]-3-[(5-phenyl-1,2,4-oxadiazol-3-yl)amino]phenyl}butanoic acid | 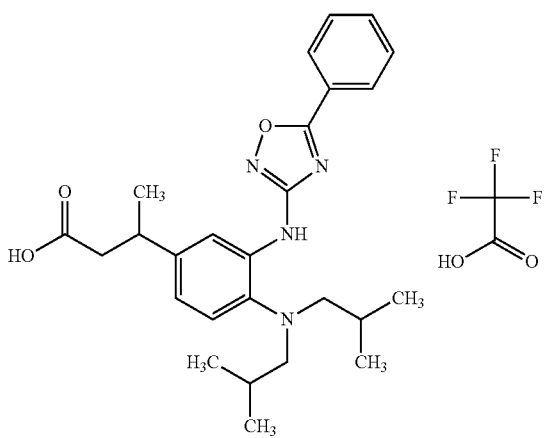 [SMILES: CC(C)CN(CC(C)C)c1ccc(C(C)CC(=O)O)cc1Nc1noc(-c2ccccc2)n1 ; O=C(O)C(F)(F)F] | 1.66 | 451.5 | |

|   | IPQA $T_{elute}$ [min] | M + 1 | M − 1 |
|---|---|---|---|
| example 123  3-{4-[bis(2-methylpropyl)amino]-3-[(5-phenyl-1,3,4-oxadiazol-2-yl)amino]phenyl}butanoic acid | 1.53 | 451.4 | |
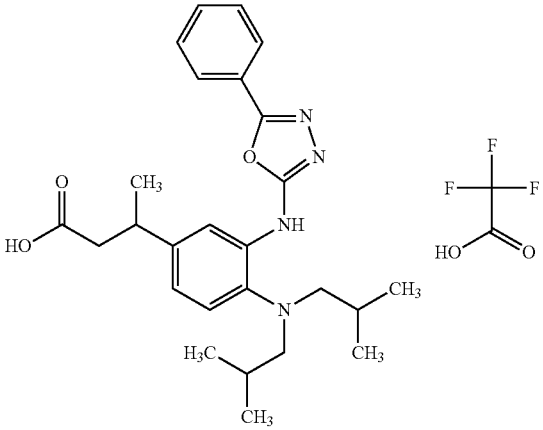 [SMILES: CC(C)CN(CC(C)C)c1ccc(C(C)CC(=O)O)cc1Nc1nnc(-c2ccccc2)o1 ; O=C(O)C(F)(F)F]
| example 124  3-{4-[bis(2-methylpropyl)amino]-3-{(3,4-dioxo-2-(phenylamino)cyclobut-1-en-1-yl]amino}phenyl}butanoic acid | 1.29 | 478.6 | 476.4 |
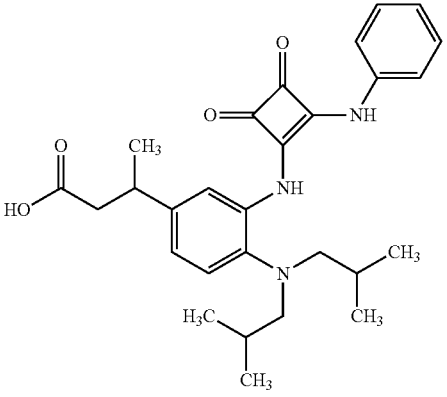 [SMILES: CC(C)CN(CC(C)C)c1ccc(C(C)CC(=O)O)cc1Nc1c(Nc2ccccc2)c(=O)c1=O]
| example 125  3-{4-[bis(2-methylpropyl)amino]-3-[(5-methyl-1,3,4-oxadiazol-2-yl)amino]phenyl}butanoic acid | 1.32 | 389.4 | |
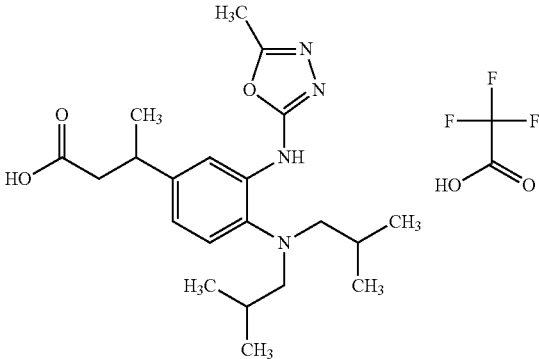 [SMILES: Cc1nnc(Nc2cc(C(C)CC(=O)O)ccc2N(CC(C)C)CC(C)C)o1 ; O=C(O)C(F)(F)F]

| | | | IPQA T_elute [min] | M + 1 | M − 1 |
|---|---|---|---|---|---|
| example 126 | 3-{4-[bis(2-methylpropyl)amino]-3-[(5-cyclopropyl-1,3,4-oxadiazol-2-yl)amino]phenyl}butanoic acid | 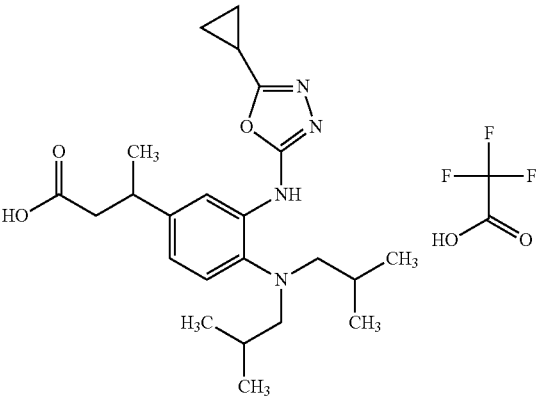 [SMILES: CC(C)CN(CC(C)C)c1ccc(C(C)CC(=O)O)cc1Nc1nnc(C2CC2)o1 ; O=C(O)C(F)(F)F] | 1.40 | 415.3 | |
| example 127 | 3-{4-[bis(2-methylpropyl)amino]-3-[(4-methoxypyrimidin-2-yl)amino]phenyl}butanoic acid | 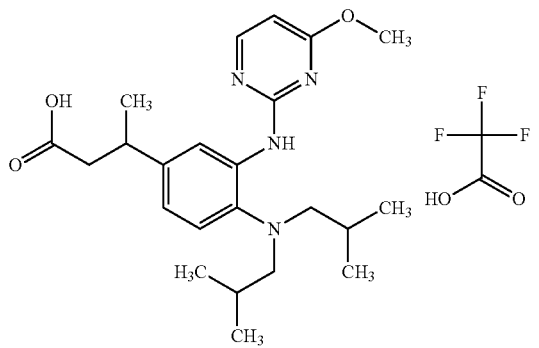 [SMILES: COc1ccnc(Nc2cc(C(C)CC(=O)O)ccc2N(CC(C)C)CC(C)C)n1 ; O=C(O)C(F)(F)F] | 1.50 | 415.3 | |
| example 128 | 3-{4-[bis(2-methylpropyl)amino]-3-[(4-phenyl-1,3-thiazol-2-yl)amino]phenyl}butanoic acid | 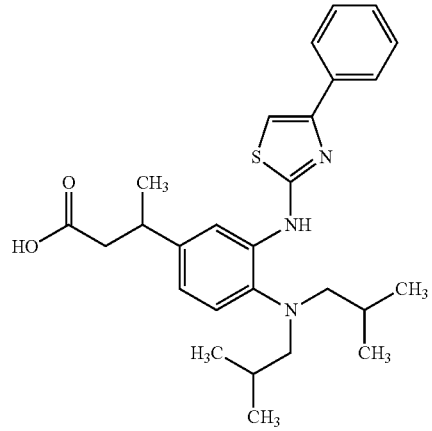 [SMILES: CC(C)CN(CC(C)C)c1ccc(C(C)CC(=O)O)cc1Nc1nc(-c2ccccc2)cs1] | 1.66 | 466.4 | |
| example 129 | 3-{4-[cyclohexyl(2-methylpropyl)amino]-3-[(oxetan-3-yl)amino]phenyl}butanoic acid | 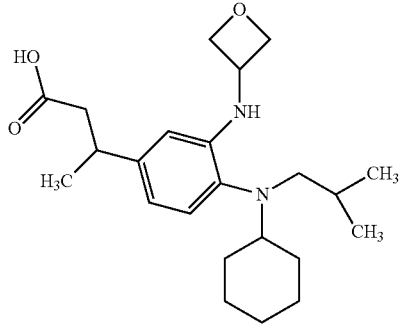 [SMILES: CC(C)CN(c1ccc(C(C)CC(=O)O)cc1NC1COC1)C1CCCCC1] | 1.27 | 387.4 | |

|  |  | IPQA $T_{elute}$ [min] | M + 1 | M − 1 |
|---|---|---|---|---|
| example 130 | 3-{4-[bis(2-methylpropyl)amino]-3-{[4-(pyridin-4-yl)-1,3-thiazol-2-yl]amino]phenyl}butanoic acid | 1.15 | 467.5 | |
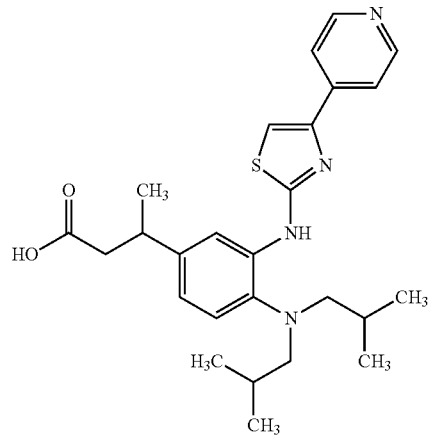 [SMILES: CC(C)CN(CC(C)C)c1ccc(C(C)CC(=O)O)cc1Nc1nc(-c2ccncc2)cs1]
| example 131 | 3-{4-[bis(2-methylpropyl)amino]-3-[(4,5,6,7-tetrahydro-1,3-benzothiazol-2-yl)amino]phenyl}butanoic acid | 1.45 | 444.4 | |
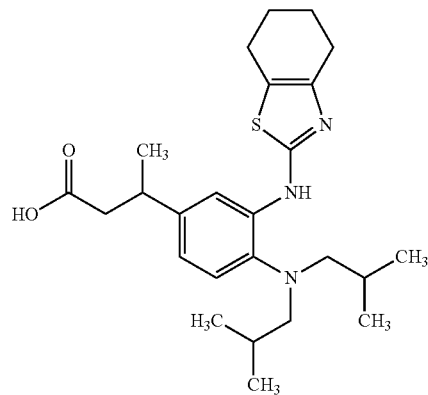 [SMILES: CC(C)CN(CC(C)C)c1ccc(C(C)CC(=O)O)cc1Nc1nc2c(s1)CCCC2]
| example 132 | 3-{4-[bis(2-methylpropyl)amino]-3-[(3-methoxy-1,2,4-thiadiazol-5-yl)amino]phenyl}butanoic acid | | | |
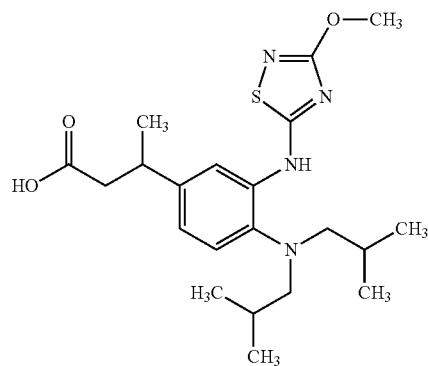 [SMILES: COc1nsc(Nc2cc(C(C)CC(=O)O)ccc2N(CC(C)C)CC(C)C)n1]

-continued

| | | IPQA T_elute [min] | M + 1 | M − 1 |
|---|---|---|---|---|
| example 133 | 3-{4-[bis(2-methylpropyl)amino]-3-[(4-tert-butyl-1,3-thiazol-2-yl)amino]phenyl}butanoic acid | 1.69 | 446.5 | |
| example 134 | 3-{4-[cyclohexyl(2-methylpropyl)amino]-3-[(1,1-dioxo-1λ⁶-thian-4-yl)amino]phenyl}butanoic acid | 1.35 | | 463.3 |
| example 135 | 3-{3-[(1-acetylpyrrolidin-3-yl)amino]-4-[cyclohexyl(2-methylpropyl)amino]phenyl}butanoic acid | 1.15 | 444.5 | |
| example 136 | 3-{4-[cyclohexyl(2-methylpropyl)amino]-3-[(pyrrolidin-3-yl)amino]phenyl}butanoic acid | 0.88 | 402.5 | |

| | | IPQA T_{elute} [min] | M + 1 | M − 1 |
|---|---|---|---|---|
| example 137 | (2E)-3-{3-[(1,3-benzoxazol-2-yl)amino]-4-[cyclohexyl(2-methylpropyl)amino]phenyl}prop-2-enoic acid 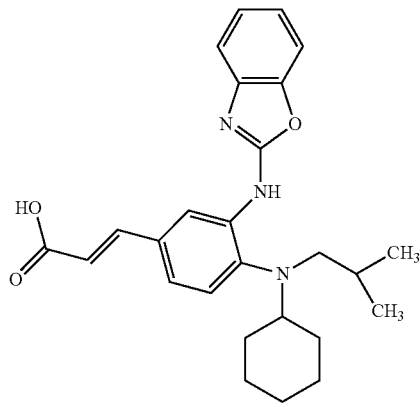 [SMILES: CC(C)CN(c1ccc(/C=C/C(=O)O)cc1Nc1nc2ccccc2o1)C1CCCCC1] | 1.59 | 432.3 | |
| example 138 | 3-{4-[bis(2-methylpropyl)amino]-3-{[4-(oxan-4-yl)-1,3-thiazol-2-yl]amino}phenyl}butanoic acid 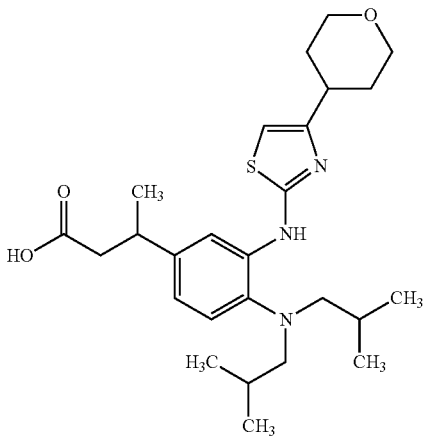 [SMILES: CC(C)CN(CC(C)C)c1ccc(C(C)CC(=O)O)cc1Nc1nc(C2CCOCC2)cs1] | 1.49 | 474.4 | |
| example 139 | 3-{4-[bis(2-methylpropyl)amino]-3-[(2,4-dimethyl-1,3-thiazol-5-yl)amino]phenyl}butanoic acid 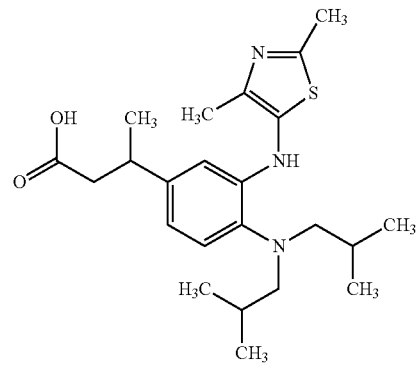 [SMILES: Cc1nc(C)c(Nc2cc(C(C)CC(=O)O)ccc2N(CC(C)C)CC(C)C)s1] | 1.40 | 418.3 | |

| | | IPQA $T_{elute}$ [min] | M + 1 | M − 1 |
|---|---|---|---|---|
| example 140 | 3-{4-[cyclohexyl(2-methylpropyl)amino]-3-[(1-methylpiperidin-4-yl)amino]phenyl}butanoic acid 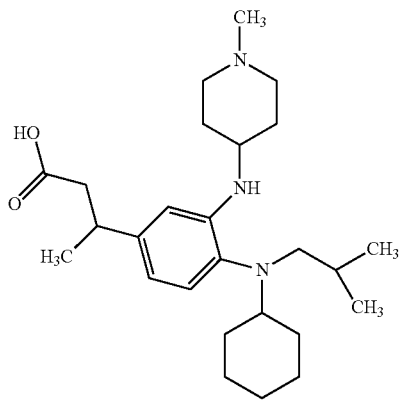 [SMILES: CC(C)CN(c1ccc(C(C)CC(=O)O)cc1NC1CCN(C)CC1)C1CCCCC1] | 0.92 | 430.5 | |
| example 141 | 3-{4-[bis(2-methylpropyl)amino]-3-[(4-cyclopropyl-1,3-thiazol-2-yl)amino]phenyl}butanoic acid 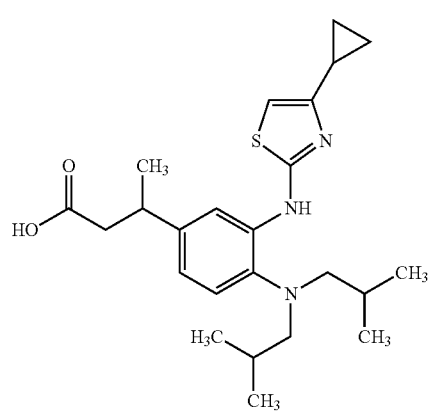 [SMILES: CC(C)CN(CC(C)C)c1ccc(C(C)CC(=O)O)cc1Nc1nc(C2CC2)cs1] | 1.57 | 430.4 | |
| example 142 | 3-{4-[bis(2-methylpropyl)amino]-3-(phenylamino)phenyl}butanoic acid 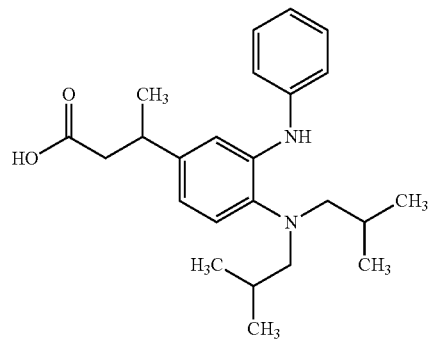 [SMILES: CC(C)CN(CC(C)C)c1ccc(C(C)CC(=O)O)cc1Nc1ccccc1] | 1.56 | 381.3 | |
| example 143 | 3-{4-[bis(2-methylpropyl)amino]-3-[(thiophen-3-yl)amino]phenyl}butanoic acid 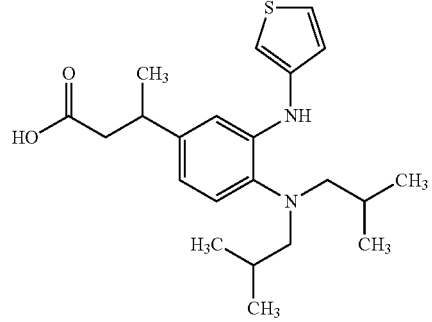 [SMILES: CC(C)CN(CC(C)C)c1ccc(C(C)CC(=O)O)cc1Nc1ccsc1] | 1.18 | 387.3 | |

-continued

| | | | IPQA T$_{elute}$ [min] | M + 1 | M − 1 |
|---|---|---|---|---|---|
| example 144 | 3-{4-[cyclohexyl(2-methylpropyl)amino]-3-[(1-methylpyrrolidin-3-yl)amino]phenyl}butanoic acid | | 0.93 | 416.5 | |
| example 145 | 3-{4-[cyclohexyl(2-methylpropyl)amino]-3-({[1,2,4]triazolo[1,5-a]pyridin-2-yl}amino)phenyl}butanoic acid | | 1.40 | 450.4 | |
| example 146 | 3-{3-[(4-benzyl-2-methyl-1,3-thiazol-5-yl)amino]-4-[bis(2-methylpropyl)amino]phenyl}butanoic acid | | 1.60 | 494.5 | |
| example 147 | 3-{4-[bis(2-methylpropyl)amino]-3-{[(5-cyclopropyl-1,2,4-oxadiazol-3-yl)methyl]amino}phenyl}butanoic acid | | 1.50 | | 427.4 |

| | | | IPQA T_{elute} [min] | M + 1 | M − 1 |
|---|---|---|---|---|---|
| example 148 | 3-{4-[cyclohexyl(2-methypropyl)amino]-3-{[(4R)-4-phenyl-4,5-dihydro-1,3-thiazol-2-yl]amino}phenyl}butanoic acid | 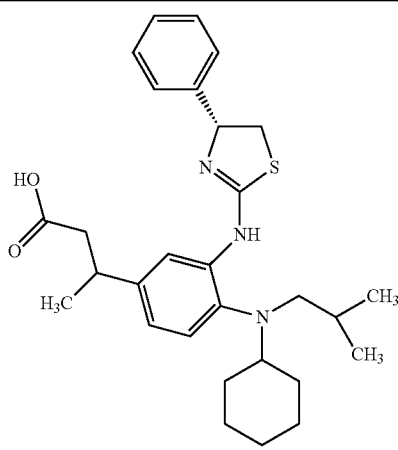 | 0.99 | 494.5 | |
| example 149 | 3-{4-[cyclohexyl(2-methylpropyl)amino]-3-{[(4S)-4-phenyl-4,5-dihydro-1,3-thiazol-2-yl]amino}phenyl}butanoic acid | 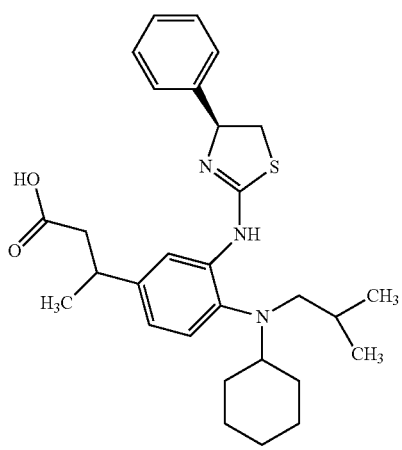 [SMILES: CC(C)CN(c1ccc(C(C)CC(=O)O)cc1NC1=N[C@@H](c2ccccc2)CS1)C1CCCCC1] | 0.90 | 494.5 | |
| example 150 | 3-{4-[cyclohexyl(2-methylpropyl)amino]-3-({5H,6H,7H,8H-[1,2,4]triazolo[1,5-a]pyridin-2-yl}amino)phenyl}butanoic acid | 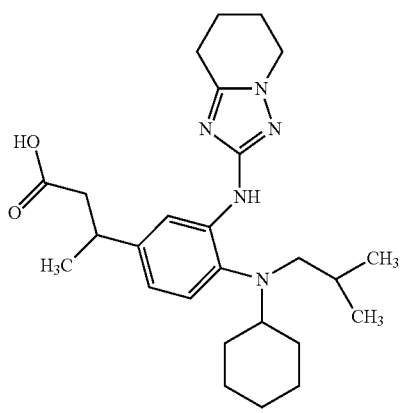 [SMILES: CC(C)CN(c1ccc(C(C)CC(=O)O)cc1Nc1nc2n(n1)CCCC2)C1CCCCC1] | 1.24 | 454.4 | |

|  |  | IPQA $T_{elute}$ [min] | M+1 | M−1 |
|---|---|---|---|---|
| example 151 | 3-{4-[cyclohexyl(2-methylpropyl)amino]-3-{[(4R)-4-methyl-4,5-dihydro-1,3-oxazol-2-yl]amino}phenyl}butanoic acid 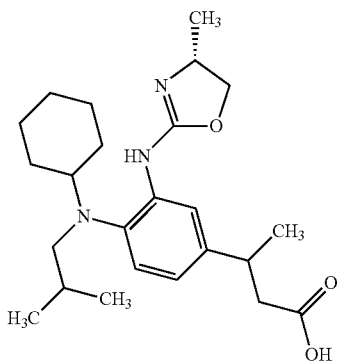 [SMILES: CC(C)CN(c1ccc(C(C)CC(=O)O)cc1NC1=N[C@H](C)CO1)C1CCCCC1] | 0.92 | 416.3 | |
| example 152 | 3-{4-[cyclohexyl(2-methylpropyl)amino]-3-{[(4S)-4-methyl-4,5-dihydro-1,3-oxazol-2-yl]amino}phenyl}butanoic acid 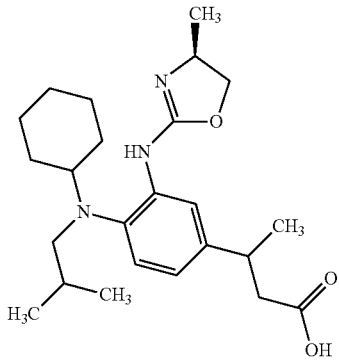 [SMILES: CC(C)CN(c1ccc(C(C)CC(=O)O)cc1NC1=N[C@@H](C)CO1)C1CCCCC1] | 0.92 | 416.3 | |
| example 153 | 3-{4-[cyclohexyl(2-methylpropyl)amino]-3-{[(4S)-4-phenyl-4,5-dihydro-1,3-oxazol-2-yl]amino}phenyl}butanoic acid 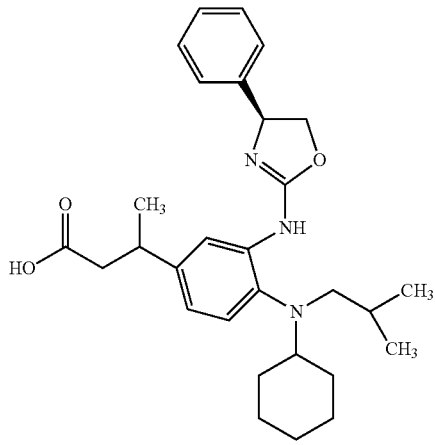 [SMILES: CC(C)CN(c1ccc(C(C)CC(=O)O)cc1NC1=N[C@@H](c2ccccc2)CO1)C1CCCCC1] | 1.01 | 478.4 | |

-continued

| | | IPQA T_elute [min] | M + 1 | M − 1 |
|---|---|---|---|---|
| example 154 | 3-{4-[cyclohexyl(2-methylpropyl)amino]-3-{[(4S)-4-(trifluoromethyl)-4,5-dihydro-1,3-thiazol-2-yl]amino}phenyl}butanoic acid | 0.98 | 486.3 | |
| example 155 | 3-{4-[cyclohexyl(2-methylpropyl)amino]-3-{[(5R)-4-oxo-5-phenyl-4,5-dihydro-1H-imidazol-2-yl]amino}phenyl}butanoic acid | | | |
| example 156 | 3-{4-[bis(2-methylpropyl)amino]-3-[(pyrimidin-2-yl)amino]phenyl}butanoic acid | 0.97 | 383.4 | |
| example 157 | 3-{4-[bis(2-methylpropyl)amino]-3-(cyclohexylamino)phenyl}butanoic acid | 1.31 | 389.5 | |

-continued

| | | | IPQA $T_{elute}$ [min] | M + 1 | M − 1 |
|---|---|---|---|---|---|
| example 158 | 3-{4-[cyclohexyl(2-methylpropyl)amino]-3-[(4-methylcyclohexyl)amino]phenyl}butanoic acid | 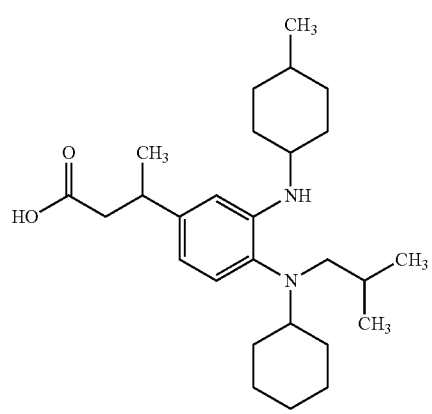 [SMILES: CC(C)CN(c1ccc(C(C)CC(=O)O)cc1NC1CCC(C)CC1)C1CCCCC1] | 1.37, 1.39 | 429.5 | |
| example 159 | 3-{4-[cyclohexyl(2-methylpropyl)amino]-3-{[(1H-imidazol-4-yl)methyl]amino}phenyl}butanoic acid | 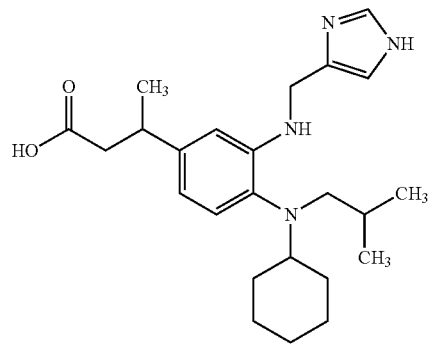 [SMILES: CC(C)CN(c1ccc(C(C)CC(=O)O)cc1NCc1c[nH]cn1)C1CCCCC1] | 0.67 | | 411.5 |
| example 160 | 3-{4-[cyclohexyl(2-methylpropyl)amino]-3-{[(pyrimidin-2-yl)methyl]amino}phenyl}butanoic acid | 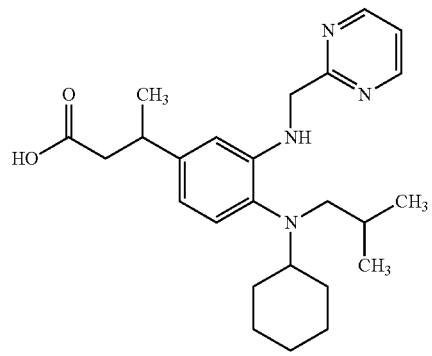 [SMILES: CC(C)CN(c1ccc(C(C)CC(=O)O)cc1NCc1ncccn1)C1CCCCC1] | 1.36 | | 423.3 |
| example 161 | 3-{4-[cyclohexyl(2-methylpropyl)amino]-3-{[(pyridin-2-yl)methyl]amino}phenyl}butanoic acid | 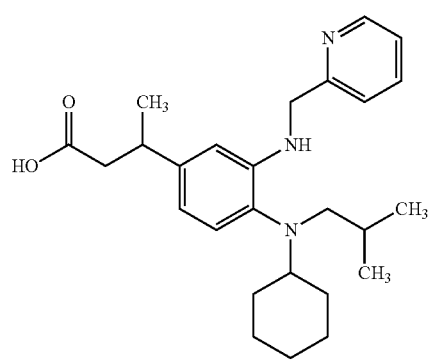 [SMILES: CC(C)CN(c1ccc(C(C)CC(=O)O)cc1NCc1ccccn1)C1CCCCC1] | 1.24 | | 422.4 |

| | | IPQA $T_{elute}$ [min] | M + 1 | M − 1 |
|---|---|---|---|---|
| example 162 | 3-{4-[cyclohexyl(2-methylpropyl)amino]-3-{[(3,4-difluorophenyl)methyl]amino}phenyl}butanoic acid | 1.24 | | 457.4 |
| example 163 | 3-{4-[cyclohexyl(2-methylpropyl)amino]-3-{[(5R)-5-methyl-4-oxo-4,5-dihydro-1H-imidazol-2-yl]amino}phenyl}butanoic acid | 1.15 | | 429.4 |
| example 164 | 3-{4-[cyclohexyl(2-methylpropyl)amino]-3-{[(5S)-5-methyl-4-oxo-4,5-dihydro-1H-imidazol-2-yl]amino}phenyl}butanoic acid | 1.15 | | 429.4 |
| example 165 | 3-{4-[cyclohexyl(2-methylpropyl)amino]-3-{[(5S)-4-oxo-5-phenyl-4,5-dihydro-1H-imidazol-2-yl]amino}phenyl}butanoic acid | 1.30 | | 491.3 |

| | | | IPQA T_elute [min] | M + 1 | M − 1 |
|---|---|---|---|---|---|
| example 166 | (3S)-3-{3-[(3-chloro-1,2,4-thiadiazol-5-yl)amino]-4-[cyclohexyl(2-methylpropyl)amino]phenyl}pentanoic acid | 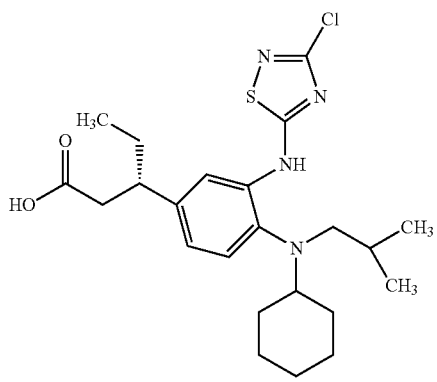 [SMILES: CC[C@@H](CC(=O)O)c1ccc(N(CC(C)C)C2CCCCC2)c(Nc2nc(Cl)ns2)c1] | 1.55 | | 463.3 |
| example 167 | 3-[3-(5-amino-1H-1,2,3,4-tetrazol-1-yl)-4-[bis(2-methylpropyl)amino]phenyl]butanoic acid | 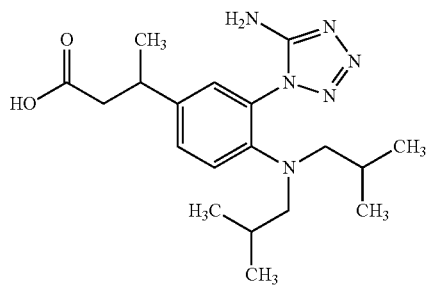 [SMILES: CC(C)CN(CC(C)C)c1ccc(C(C)CC(=O)O)cc1-n1nnnc1N] | 0.86 | | 373.2 |
| example 168 | 3-{4-[bis(2-methylpropyl)amino]-3-[(1H-1,2,3,4-tetrazol-5-yl)amino]phenyl}butanoic acid | 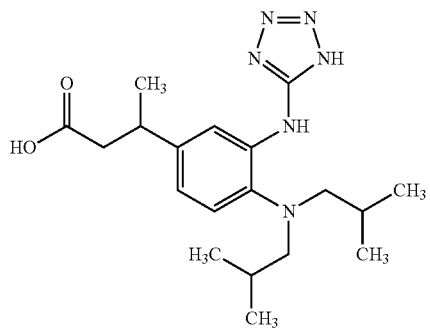 | 0.92 | | 372.9 |
| example 169 | (3R)-3-{3-[(6-chloropyridin-2-yl)amino]-4-[cyclohexyl(2-methylpropyl)amino]phenyl}butanoic acid | 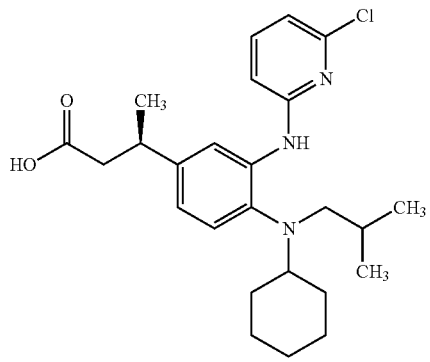 [SMILES: CC(C)CN(c1ccc([C@H](C)CC(=O)O)cc1Nc1cccc(Cl)n1)C1CCCCC1] | 1.53 | 444.2 | |

|  | IPQA $T_{elute}$ [min] | M + 1 | M − 1 |
|---|---|---|---|
| example 170 | 2-(1-{3-[(1,3-benzoxazol-2-yl)amino]-4-[cyclohexyl(2-methylpropyl)amino]phenyl}ethoxy)acetic acid | 1.54 | 466.4 |  |
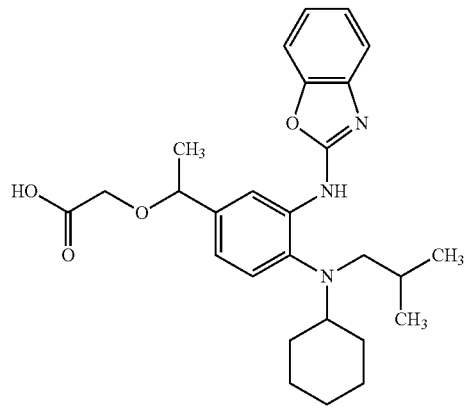 [SMILES: CC(C)CN(c1ccc(C(C)OCC(=O)O)cc1Nc1nc2ccccc2o1)C1CCCCC1]
| example 171 | 2-(1-{3-[(3-chloro-1,2,4-thiadiazol-5-yl)amino]-4-[cyclohexyl(2-methylpropyl)amino]phenyl}ethoxy)acetic acid | 1.51 |  | 465.3 |
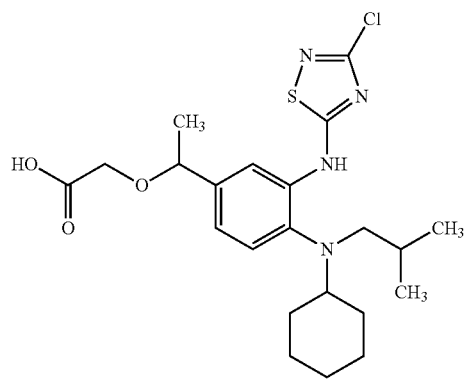 [SMILES: CC(C)CN(c1ccc(C(C)OCC(=O)O)cc1Nc1nc(Cl)ns1)C1CCCCC1]
| example 172 | (3R)-3-{4-[cyclohexyl(2-methylpropyl)amino]-3-{[6-(trifluoromethyl)pyridin-2-yl]amino}phenyl}butanoic acid | 1.61 | 478.5 |  |
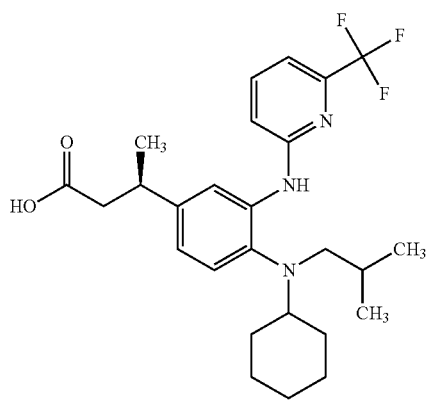 [SMILES: CC(C)CN(c1ccc([C@H](C)CC(=O)O)cc1Nc1cccc(C(F)(F)F)n1)C1CCCCC1]

-continued

| | IPQA T$_{elute}$ [min] | M + 1 | M − 1 |
|---|---|---|---|
| example 173  2-(1-{3-[(1H-1,3-benzodiazol-2-yl)amino]-4-[cyclohexyl(2-methylpropyl)amino]phenyl}ethoxy)acetic acid | 0.94 | 465.3 | |
| example 174  2-{4-[bis(2-methylpropyl)amino]-3-{[3-(trifluoromethyl)-1,2,4-thiadiazol-5-yl]amino}phenyl}cyclopropane-1-carboxylic acid | 1.55 | 457.5 | |
| example 175  4-{3-[(1,3-benzoxazol-2-yl)amino]-4-[cyclohexyl(2-methylpropyl)amino]phenyl}-1H-pyrazole-3-carboxylic acid | 1.41 | | 472.4 |

| | | | IPQA $T_{elute}$ [min] | M + 1 | M − 1 |
|---|---|---|---|---|---|
| example 176 | 4-{3-[(1,3-benzoxazol-2-yl)amino]-4-[cyclohexyl(2-methylpropyl)amino]phenyl}-1-methyl-1H-pyrazole-3-carboxylic acid | | 1.46 | 488.4 | |
| example 177 | (1R*,2R**)-2-{4-[bis(2-methylpropyl)amino]-3-[(3-chloro-1,2,4-thiadiazol-5-yl)amino]phenyl}cyclopropane-1-carboxylic acid ISOMER 1 | | 1.46 | 423.2 | |
| example 178 | 4-{3-[(1,3-benzoxazol-2-yl)amino]-4-[cyclohexyl(2-methylpropyl)amino]phenyl}-1-methyl-1H-pyrazole-5-carboxylic acid | | | | |
| example 179 | (3R)-3-{4-[cyclohexyl(2-methylpropyl)amino]-3-(cyclopentylamino)phenyl}butanoic acid | | 1.24 | 401.5 | |

-continued

| | | | IPQA $T_{elute}$ [min] | M + 1 | M − 1 |
|---|---|---|---|---|---|
| example 180 | (3R)-3-{4-[cyclohexyl(2-methylpropyl)amino]-3-[(propan-2-yl)amino]phenyl}butanoic acid | 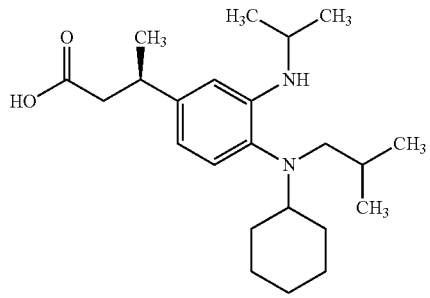 [SMILES: CC(C)CN(c1ccc([C@H](C)CC(=O)O)cc1NC(C)C)C1CCCCC1] | 1.13 | 375.5 | |
| example 181 | (3R)-3-[3-(cyclobutylamino)-4-[cyclohexyl(2-methylpropyl)amino]phenyl]butanoic acid | 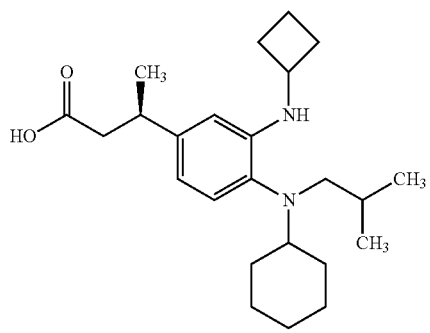 [SMILES: CC(C)CN(c1ccc([C@H](C)CC(=O)O)cc1NC1CCC1)C1CCCCC1] | 1.16 | | 385.4 |
| example 182 | (3R)-3-{4-[cyclohexyl(2-methylpropyl)amino]-3-[(4,4-dimethylcyclohexyl)amino]phenyl}butanoic acid | 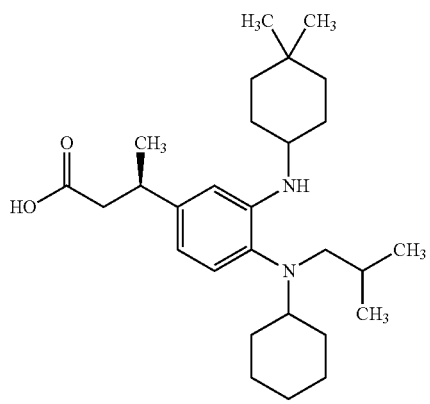 [SMILES: CC(C)CN(c1ccc([C@H](C)CC(=O)O)cc1NC1CCC(C)(C)CC1)C1CCCCC1] | 1.39 | 443.5 | |
| example 183 | (3R)-3-{4-[cyclohexyl(2-methylpropyl)amino]-3-[(3,3-dimethylcyclohexyl)amino]phenyl}butanoic acid | 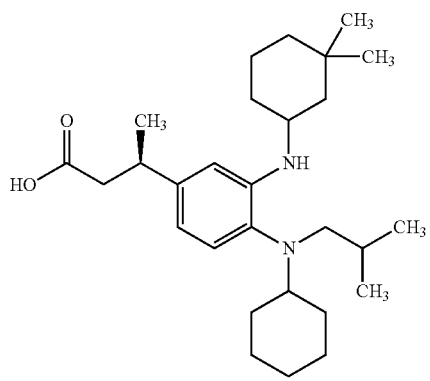 [SMILES: CC(C)CN(c1ccc([C@H](C)CC(=O)O)cc1NC1CCCC(C)(C)C1)C1CCCCC1] | 1.38 | 443.5 | |

-continued

| | | IPQA T_elute [min] | M + 1 | M − 1 |
|---|---|---|---|---|
| example 184 | (3R)-3-{4-[cyclohexyl(2-methylpropyl)amino]-3-{[(3R)-3-methylcyclohexyl]amino}phenyl}butanoic acid | 1.38 | | 429.5 |
| example 185 | (3R)-3-{4-[cyclohexyl(2-methylpropyl)amino]-3-[(4-hydroxybutan-2-yl)amino]phenyl}butanoic acid | 0.89 | | 403.5 |
| example 186 | (3R)-3-{4-[bis(2-methylpropyl)amino]-3-[(5-methyl-1,3,4-thiadiazol-2-yl)amino]phenyl}butanoic acid | 1.29 | | 403.3 |
| example 187 | 3-{4-[bis(2-methylpropyl)amino]-3-[(5-acetamido-1,3,4-thiadiazol-2-yl)amino]phenyl}butanoic acid | 1.24 | | 448.3 |

|  |  | IPQA $T_{elute}$ [min] | M + 1 | M − 1 |
|---|---|---|---|---|
| example 188 | 3-{4-[bis(2-methylpropyl)amino]-3-{[5-(methoxymethyl)-1,3,4-thiadiazol-2-yl]amino}phenyl}butanoic acid | 1.32 | | 433.3 |
| example 189 | 3-{4-[bis(2-methylpropyl)amino]-3-{[2-(methoxymethyl)-1,3-thiazol-5-yl]amino}phenyl}butanoic acid | 1.50 | | 432.3 |
| example 190 | (3R)-3-{4-[bis(2-methylpropyl)amino]-3-{[5-(methoxymethyl)-4H-1,2,4-triazol-3-yl]amino}phenyl}butanoic acid | 1.18 | 418.5 | |

-continued
| | | IPQA $T_{elute}$ [min] | M + 1 | M − 1 |
|---|---|---|---|---|
| example 191 | 3-{4-[bis(2-methylpropyl)amino]-3-{[2-(methoxymethyl)-1,3-oxazol-5-yl]amino]phenyl}butanoic acid 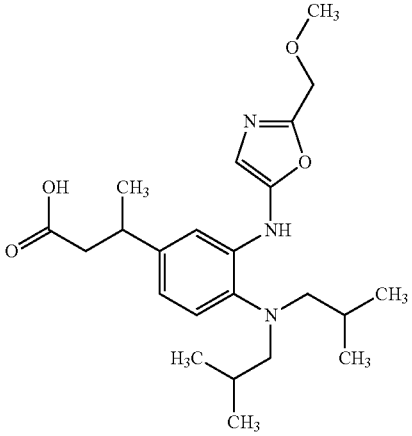 [SMILES: COCc1ncc(Nc2cc(C(C)CC(=O)O)ccc2N(CC(C)C)CC(C)C)o1] | 1.40 | | 416.3 |
| example 192 | 3-{4-[bis(2-methylpropyl)amino]-3-[(5-methanesulfonamido-1,3,4-thiadiazol-2-yl)amino]phenyl}butanoic acid 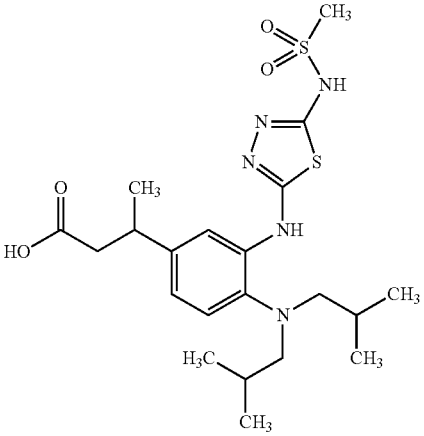 [SMILES: CC(C)CN(CC(C)C)c1ccc(C(C)CC(=O)O)cc1Nc1nnc(NS(C)(=O)=O)s1] | 1.26 | 484.2 | |
| example 193 | 3-{4-[bis(2-methylpropyl)amino]-3-{[5-(methoxymethyl)pyridin-2-yl]amino}phenyl}butanoic acid 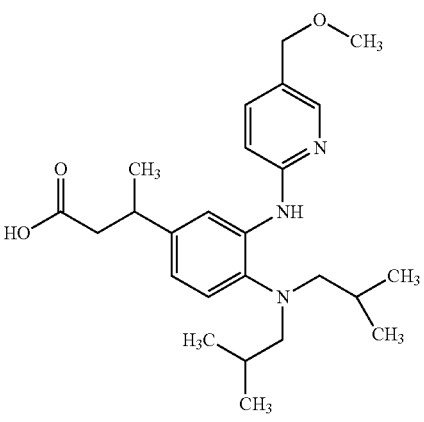 [SMILES: COCc1ccc(Nc2cc(C(C)CC(=O)O)ccc2N(CC(C)C)CC(C)C)nc1] | 1.11 | 428.6 | |

| | | IPQA T_{elute} [min] | M + 1 | M − 1 |
|---|---|---|---|---|
| example 194 | 3-{4-[bis(2-methylpropyl)amino]-3-{[5-(hydroxymethyl)pyridin-2-yl]amino}phenyl}butanoic acid | 0.93 | | 412.3 |
| example 195 | 3-{4-[bis(2-methylpropyl)amino]-3-{[5-(carbamoylmethyl)-1,3,4-thiadiazol-2-yl]amino}phenyl}butanoic acid | 1.07 | | 446.2 |
| example 196 | 3-{4-[bis(2-methylpropyl)amino]-3-[(1,3,4-thiadiazol-2-yl)amino]phenyl}butanoic acid | 1.25 | | 389.2 |
| example 197 | 3-{4-[bis(2-methylpropyl)amino]-3-[(2-oxopiperidin-4-yl)amino]phenyl}butanoic acid | 0.89 | | 400.3 |

-continued

| | | IPQA $T_{elute}$ [min] | M + 1 | M − 1 |
|---|---|---|---|---|
| example 198 | 4-({2-[bis(2-methylpropyl)amino]-5-(1-carboxypropan-2-yl)phenyl}amino)cyclohexane-1-carboxylic acid | 1.05 | | 431.4 |
| example 199 | 3-{4-[bis(2-methylpropyl)amino]-3-[(5-acetamidopyridin-2-yl)amino]phenyl}butanoic acid | 1.03 | | 439.4 |
| example 200 | 3-{4-[bis(2-methylpropyl)amino]-3-[(5-methanesulfonamido-pyridin-2-yl)amino]phenyl}butanoic acid | 1.18 | | 475.3 |

-continued

|  |  | IPQA $T_{elute}$ [min] | M + 1 | M − 1 |
|---|---|---|---|---|
| example 201 | 2-(1-{3-[(5-carbamoylpyridin-2-yl)amino]-4-[cyclohexyl(2-methylpropyl)amino]phenyl}ethoxy)acetic acid | 1.03 |  | 467.3 |
| example 202 | 3-{4-[(2-methylpropyl)(oxan-4-yl)amino]-3-{[3-(trifluoromethyl)-1,2,4-thiadiazol-5-yl]amino}phenyl}butanoic acid | 1.34 |  | 485.3 |
| example 203 | (3R)-3-{4-[bis(2-methylpropyl)amino]-3-{[5-(2-methoxyethyl)-4H-1,2,4-triazol-3-yl]amino}phenyl}butanoic acid | 1.16 | 432.4 |  |

| | | IPQA T$_{elute}$ [min] | M + 1 | M − 1 |
|---|---|---|---|---|
| example 204 | 3-{4-[bis(2-methylpropyl)amino]-3-[(5-carbamoylpyridin-2-yl)amino]phenyl}butanoic acid | 1.10 | | 425.3 |
| example 205 | 3-{3-[(3-chloro-1,2,4-thiadiazol-5-yl)amino]-4-[{2-methylpropyl)(oxetan-3-yl)amino]phenyl}butanoic acid | 1.13 | 425.1 | |
| example 206 | rel-(1R,2S)-2-{4-[bis(2-methylpropyl)amino]-3-{[3-(trifluoromethyl)-1,2,4-thiadiazol-5-yl]amino}phenyl}cyclopropane-1-carboxylic acid | 1.51 | | 455.2 |

ISOMER 1

-continued
| | IPQA $T_{elute}$ [min] | M + 1 | M − 1 |
|---|---|---|---|
| example 207 | 3-{4-[bis(2-methylpropyl)amino]-3-{[2-(hydroxymethyl)-1,3-thiazol-5-yl]amino}phenyl}butanoic acid | 1.30 | 418.3 |
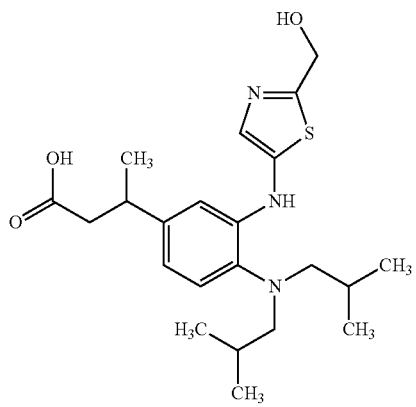 [SMILES: CC(C)CN(CC(C)C)c1ccc(C(C)CC(=O)O)cc1Nc1cnc(CO)s1]
| example 208 | 3-{3-[(5-amino-1,3,4-thiadiazol-2-yl)amino]-4-[bis(2-methylpropyl)amino]phenyl}butanoic acid | 1.09 | 406.4 |
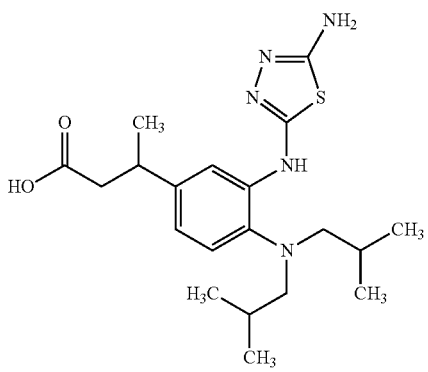 [SMILES: CC(C)CN(CC(C)C)c1ccc(C(C)CC(=O)O)cc1Nc1nnc(N)s1]
| example 209 | rel-(1R,2S)-2-{4-[bis(2-methylpropyl)amino]-3-{[3-(trifluoromethyl)-1,2,4-thiadiazol-5-yl]amino}phenyl}cyclopropane-1-carboxylic acid | 1.49 | 455.3 |
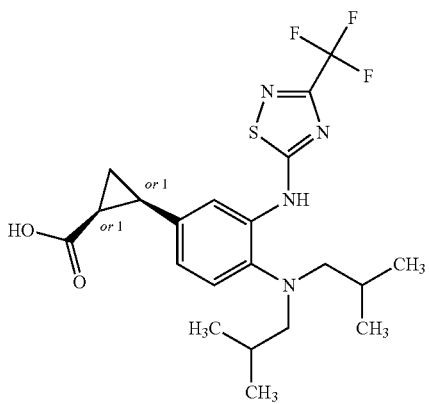
ISOMER 2

-continued
| | | IPQA $T_{elute}$ [min] | M + 1 | M − 1 |
|---|---|---|---|---|
| example 210 | (3R)-3-{3-[(5-cyclopropyl-4H-1,2,4-triazol-3-yl)amino]-4-[(2-methylpropyl)(oxan-4-yl)amino]phenyl}butanoic acid 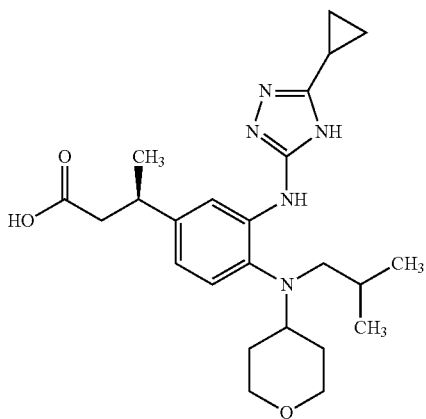 [SMILES: CC(C)CN(c1ccc([C@H](C)CC(=O)O)cc1Nc1nnc(C2CC2)[nH]1)C1CCOCC1] | 1.00 | 442.4 | |
| example 211 | (3R)-3-{3-[(4-cyclopropyl-1,3-thiazol-2-yl)amino]-4-[(2-methylpropyl)(oxan-4-yl)amino]phenyl}butanoic acid 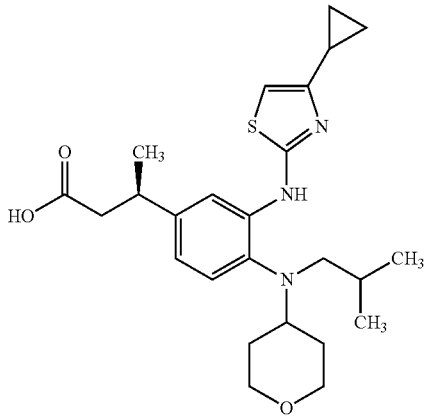 [SMILES: CC(C)CN(c1ccc([C@H](C)CC(=O)O)cc1Nc1nc(C2CC2)cs1)C1CCOCC1] | 1.28 | 458.2 | |
| example 212 | (3R)-3-{4-[(2-methylpropyl)(oxan-4-yl)amino]-3-{[5-(propan-2-yl)-4H-1,2,4-triazol-3-yl]amino}phenyl}butanoic acid 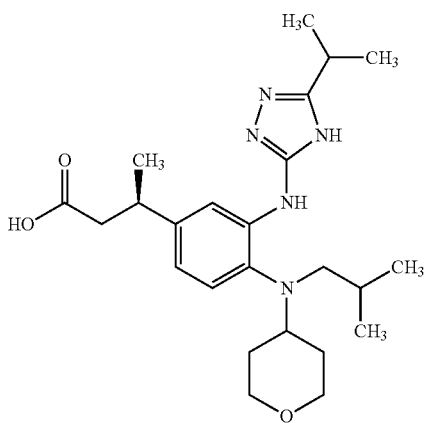 [SMILES: CC(C)CN(c1ccc([C@H](C)CC(=O)O)cc1Nc1nnc(C(C)C)[nH]1)C1CCOCC1] | 1.01 | 442.3 | |

-continued

| | | IPQA T$_{elute}$ [min] | M + 1 | M − 1 |
|---|---|---|---|---|
| example 213 | (3R)-3-(3-{[5-(methoxymethyl)-4H-1,2,4-triazol-3-yl]amino}-4-[(2-methylpropyl)(oxan-4-yl)amino]phenyl)butanoic acid | 0.94 | | 444.3 |
| example 214 | (3R)-3-{4-[cyclohexyl(2-methylpropyl)amino]-3-{[5-(2-methoxyethyl)-4H-1,2,4-triazol-3-yl]amino}phenyl}butanoic acid | 1.13 | 459.0 | 456.4 |
| example 215 | (3R)-3-{3-[(5-methyl-1,3,4-thiadiazol-2-yl)amino]-4-[(2-methylpropyl)(oxan-4-yl)amino]phenyl}butanoic acid | 1.02 | | 431.3 |

-continued
| | | | IPQA $T_{elute}$ [min] | M + 1 | M − 1 |
|---|---|---|---|---|---|
| example 216 | (3R)-3-(3-{[5-(methoxymethyl)-1,3,4-thiadiazol-2-yl]amino}-4-[(2-methylpropyl)(oxan-4-yl)amino]phenyl)butanoic acid | 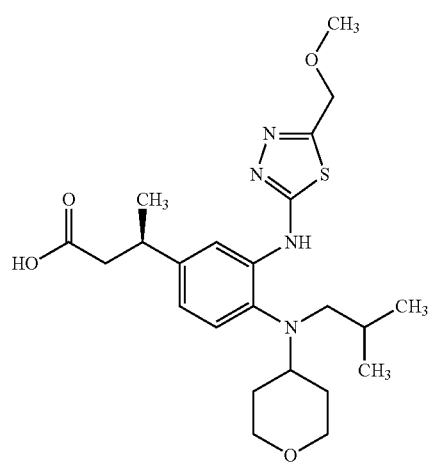 [SMILES: COCc1nnc(Nc2cc([C@H](C)CC(=O)O)ccc2N(CC(C)C)C2CCOCC2)s1] | 1.06 | 463.5 | |
| example 217 | (3R)-3-{4-[bis(2-methylpropyl)amino]-3-[(6-oxo-1,6-dihydropyridin-3-yl)amino]phenyl}butanoic acid | 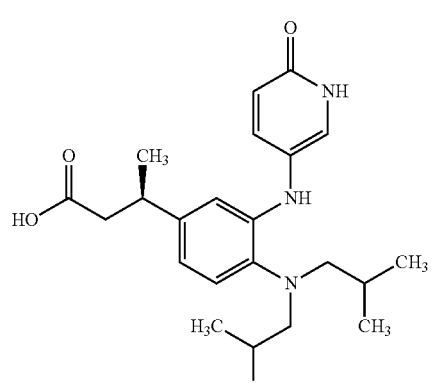 | 1.14 | 398.3 | |
| example 218 | (3R)-3-{4-[bis(2-methylpropyl)amino]-3-[(1-methyl-6-oxo-1,6-dihydropyridin-3-yl)amino]phenyl}butanoic acid | 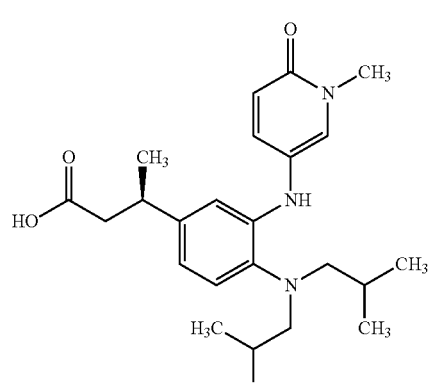 | 1.21 | 414.4 | |

| | | IPQA $T_{elute}$ [min] | M + 1 | M − 1 |
|---|---|---|---|---|
| example 219 | (3RS)-3-{4-[(2-methylpropyl)[(1rs&,4rs&)-4-hydroxycyclohexyl]amino]-3-{[5-(trifluoromethyl)-1H-1,2,4-triazol-3-yl]amino}phenyl}butanoic acid 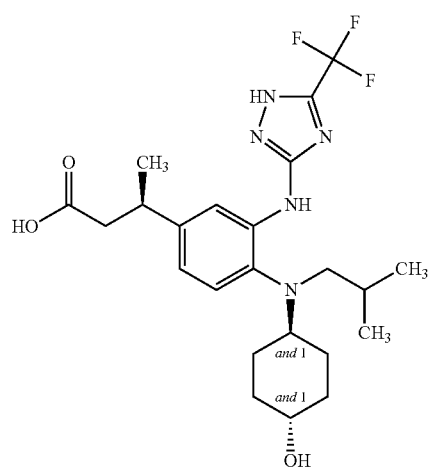 [SMILES: CC(C)CN(c1ccc([C@H](C)CC(=O)O)cc1Nc1n[nH]c(C(F)(F)F)n1)[C@H]1CC[C@H](O)CC1] | 1.04 | | 482.3 |
| example 220 | (3R)-3-{4-[bis(2-methylpropyl)amino]-3-{[4-(trifluoromethyl)-1-{[2-(trimethylsilyl)ethoxy]methyl}-1H-imidazol-2-yl]amino}phenyl}butanoic acid 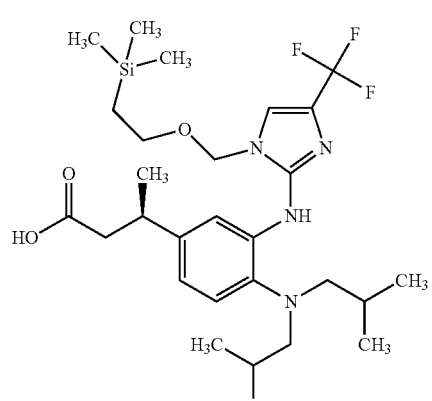 | 1.66 | | 569.4 |
| example 221 | (3RS)-3-{3-[(5-cyclopropyl-1H-1,2,4-triazol-3-yl)amino]-4-[(2-methylpropyl)[(1rs&,4rs&)-4-methoxycyclohexyl]amino]phenyl}butanoic acid 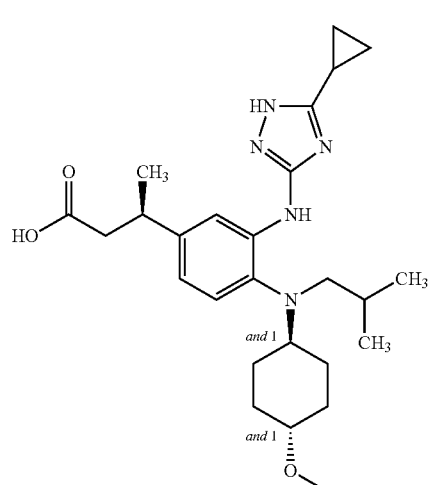 | 1.09 | | 468.4 |

| | | IPQA $T_{elute}$ [min] | M + 1 | M − 1 |
|---|---|---|---|---|
| example 222 | (3RS)-3-{3-[(5-cyano-1H-1,2,4-triazol-3-yl)amino]-4-[(2-methylpropyl)[(1rs&,4rs&)-4-methoxycyclohexyl]amino]phenyl}butanoic acid | 1.15 | | 453.3 |
| | 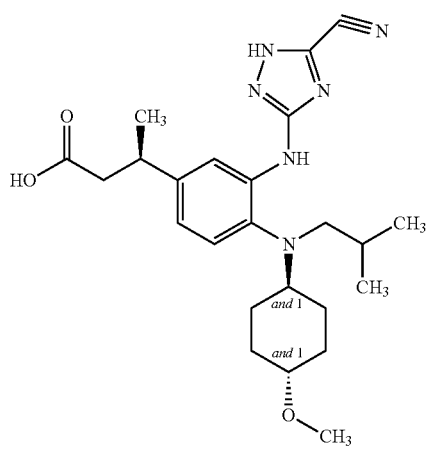 [SMILES: CO[C@H]1CC[C@H](N(CC(C)C)c2ccc([C@H](C)CC(=O)O)cc2Nc2n[nH]c(C#N)n2)CC1] | | | |
| example 223 | (3RS)-3-{3-[(5-carbamoyl-1H-1,2,4-triazol-3-yl)amino]-4-[(2-methylpropyl)[(1rs&,4rs&)-4-methoxycyclohexyl]amino]phenyl}butanoic acid | 0.99 | 473.1 | |
| | 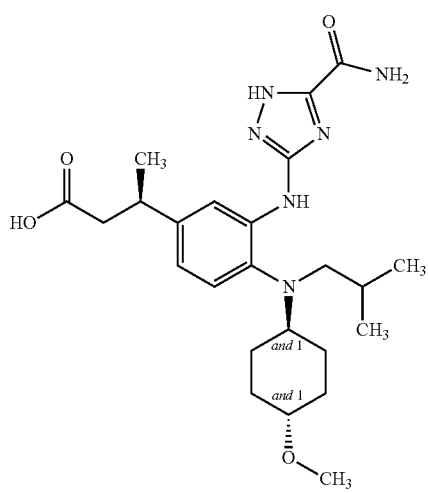 [SMILES: CO[C@H]1CC[C@H](N(CC(C)C)c2ccc([C@H](C)CC(=O)O)cc2Nc2n[nH]c(C(N)=O)n2)CC1] | | | |
| example 224 | (3RS)-3-{3-[(5-cyano-1H-1,2,4-triazol-3-yl)amino]-4-[(2-methylpropyl)[(1rs&,4rs&)-4-hydroxycyclohexyl]amino]phenyl}butanoic acid | 0.99 | | 439.3 |
| | 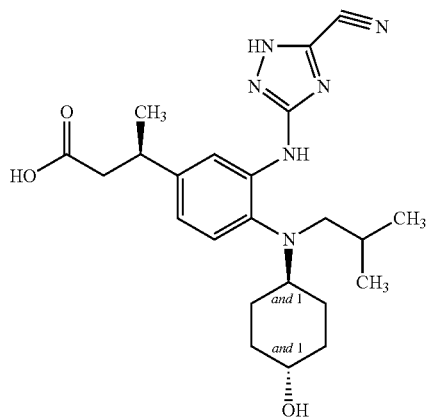 [SMILES: CC(C)CN(c1ccc([C@H](C)CC(=O)O)cc1Nc1n[nH]c(C#N)n1)[C@H]1CC[C@H](O)CC1] | | | |

|   |   | IPQA $T_{elute}$ [min] | M + 1 | M − 1 |
|---|---|---|---|---|
| example 225 | (3RS)-3-{3-[(5-carbamoyl-1H-1,2,4-triazol-3-yl)amino]-4-[(2-methylpropyl)[(1rs&,4rs&)-4-hydroxycyclohexyl]amino]phenyl}butanoic acid 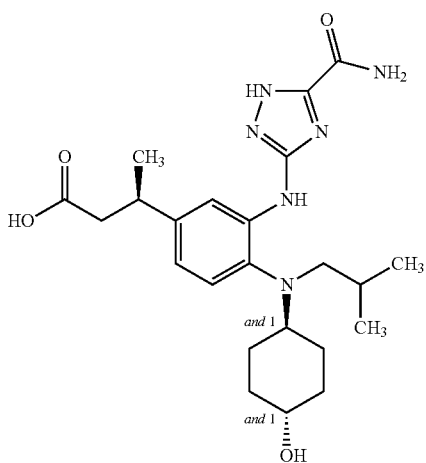 [SMILES: CC(C)CN(c1ccc([C@H](C)CC(=O)O)cc1Nc1n[nH]c(C(N)=O)n1)[C@H]1CC[C@H](O)CC1] | 0.81 | 459.1 | |
| example 226 | (3R)-3-{3-[(5-cyano-1H-1,2,4-triazol-3-yl)amino]-4-[(2-methylpropyl)(oxan-4-yl)amino]phenyl}butanoic acid 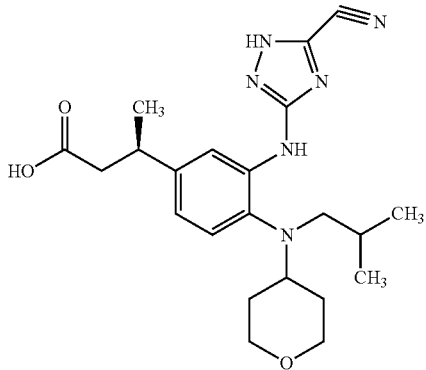 [SMILES: CC(C)CN(c1ccc([C@H](C)CC(=O)O)cc1Nc1n[nH]c(C#N)n1)C1CCOCC1] | 1.08 | 425.3 | |
| example 227 | (3R)-3-{3-[(5-carbamoyl-1H-1,2,4-triazol-3-yl)amino]-4-[(2-methylpropyl)(oxan-4-yl)amino]phenyl}butanoic acid 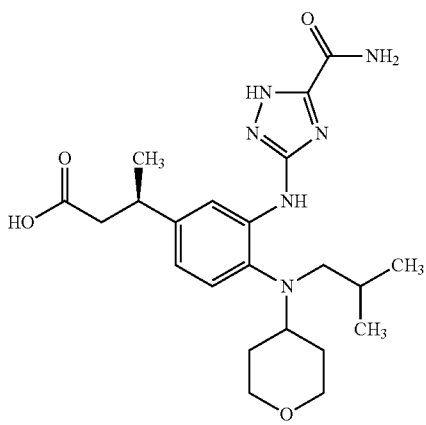 [SMILES: CC(C)CN(c1ccc([C@H](C)CC(=O)O)cc1Nc1n[nH]c(C(N)=O)n1)C1CCOCC1] | 0.91 | 445.2 | |

|  |  | IPQA $T_{elute}$ [min] | M + 1 | M − 1 |
|---|---|---|---|---|
| example 228 | (3R)-3-{3-[(4 cyano-1H-imidazol-2-yl)amino]-4-[(2-methylpropyl)(oxan-4-yl)amino]phenyl}butanoic acid 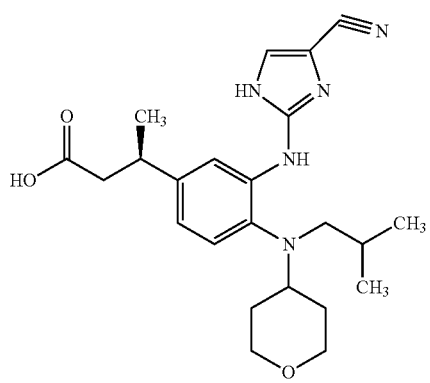 [SMILES: CC(C)CN(c1ccc([C@H](C)CC(=O)O)cc1Nc1nc(C#N)c[nH]1)C1CCOCC1] | 1.00 | 426.1 |  |
| example 229 | (3R)-3-{4-[(5-aminopentyl)(2-methylpropyl)amino]-3-{[3-(trifluoromethyl)-1,2,4-thiadiazol-5-yl]amino}phenyl}butanoic acid 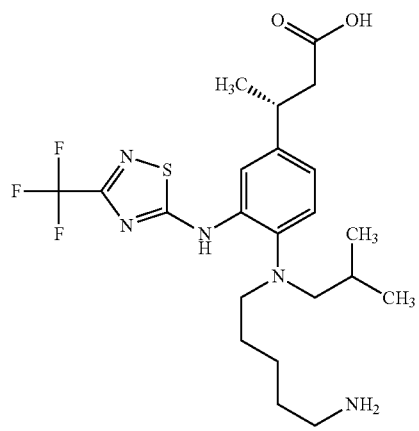 [SMILES: CC(C)CN(CCCCCN)c1ccc([C@H](C)CC(=O)O)cc1Nc1nc(C(F)(F)F)ns1] |  |  |  |
| example 230 | (3R)-3-{3-[(4-carbamoyl-1H-imidazol-2-yl)amino]-4-[(2-methylpropyl)(oxan-4-yl)amino]phenyl}butanoic acid 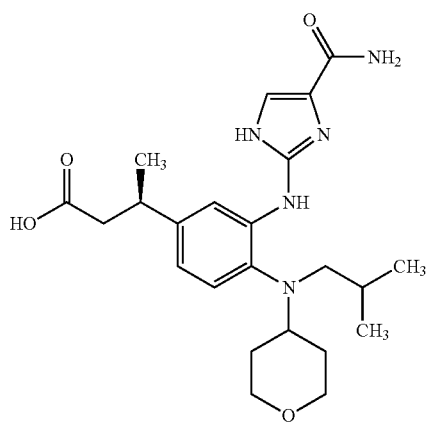 [SMILES: CC(C)CN(c1ccc([C@H](C)CC(=O)O)cc1Nc1nc(C(N)=O)c[nH]1)C1CCOCC1] | 0.79 | 444.2 |  |

| | | | IPQA | | |
|---|---|---|---|---|---|
| | | | $T_{elute}$ [min] | M + 1 | M − 1 |
| example 231 | (3R)-3-{3-[(5-chloropyrimidin-2-yl)amino]-4-[(2-methylpropyl)(oxan-4-yl)amino]phenyl}butanoic acid | | 1.34 | 445.4 | |
| example 232 | (3R)-3-(3-{[4-(methylcarbamoyl)-1H-imidazol-2-yl]amino}-4-[(2-methylpropyl)(oxan-4-yl)amino]phenyl)butanoic acid | | 0.82 | 458.3 | |
| example 233 | (3R)-N-hydroxy-3-{4-[(2-methylpropyl)(oxan-4-yl)amino]-3-{[3-(trifluoromethyl)-1,2,4-thiadiazol-5-yl]amino}phenyl}butanoic amide | | 1.16 | 502.3 | 500.3 |

|   |   | IPQA $T_{elute}$ [min] | M + 1 | M − 1 |
|---|---|---|---|---|
| example 234 | 4-(1-aminoethyl)-N1-(2-methylpropyl)-N1-(oxan-4-yl)-N2-[3-(trifluoromethyl)-1,2,4-thiadiazol-5-yl]benzene-1,2-diamine 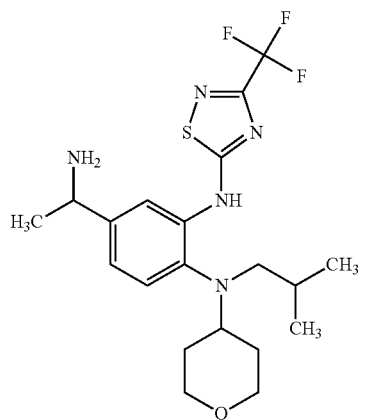 [SMILES: CC(C)CN(c1ccc(C(C)N)cc1Nc1nc(C(F)(F)F)ns1)C1CCOCC1] | 0.89 | 444.2 | 442.3 |
| example 235 | 3-{4-[cyclohexyl(2-methylpropyl)amino]-3-[(1,3,4-thiadiazol-2-yl)amino]phenyl}butanoic acid 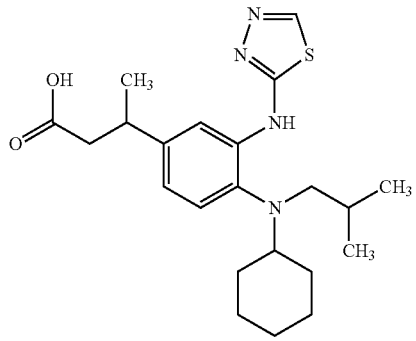 [SMILES: CC(C)CN(c1ccc(C(C)CC(=O)O)cc1Nc1nncs1)C1CCCCC1] | 1.20 |  | 415.3 |
| example 236 | (3R)-3-(3-{[4-(cyclopropylcarbamoyl)-1H-imidazol-2-yl]amino}-4-[(2-methylpropyl)(oxan-4-yl)amino]phenyl)butanoic acid 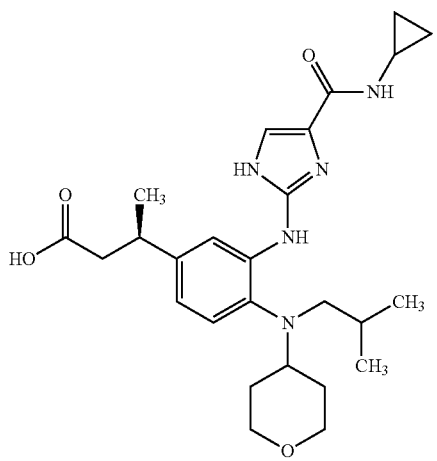 [SMILES: CC(C)CN(c1ccc([C@H](C)CC(=O)O)cc1Nc1nc(C(=O)NC2CC2)c[nH]1)C1CCOCC1] | 0.88 | 484.3 |  |

-continued
| | | IPQA $T_{elute}$ [min] | M + 1 | M − 1 |
|---|---|---|---|---|
| example 237 | (3R)-3-(3-{[3-(methylcarbamoyl)-1H-1,2,4-triazol-5-yl]amino}-4-[(2-methylpropyl)(oxan-4-yl)amino]phenyl)butanoic acid 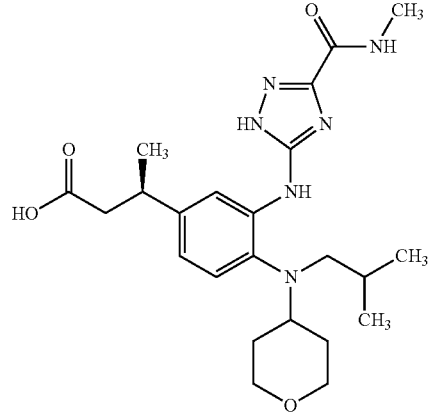 [SMILES: CNC(=O)c1n[nH]c(Nc2cc([C@H](C)CC(=O)O)ccc2N(CC(C)C)C2CCOCC2)n1] | 0.95 | 459.4 | |
| example 238 | 3-{4-[cyclohexyl(2-methylpropyl)amino]-3-{[5-(cyclopropylcarbamoyl)-1,3,4-thiadiazol-2-yl]amino}phenyl}butanoic acid 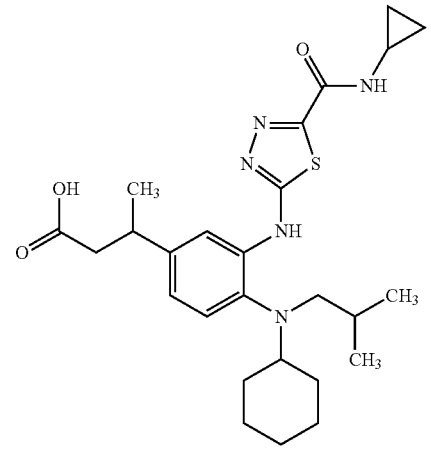 [SMILES: CC(C)CN(c1ccc(C(C)CC(=O)O)cc1Nc1nnc(C(=O)NC2CC2)s1)C1CCCCC1] | 1.30 | 500.4 | |
| example 239 | (3R)-3-{3-[(6-carbamoylpyridin-3-yl)amino]-4-[(2-methylpropyl)(oxan-4-yl)amino]phenyl}butanoic acid 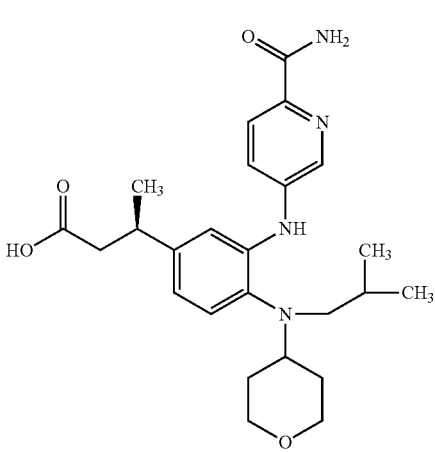 [SMILES: CC(C)CN(c1ccc([C@H](C)CC(=O)O)cc1Nc1ccc(C(N)=O)nc1)C1CCOCC1] | 0.99 | 455.3 | |

| | | IPQA $T_{elute}$ [min] | M + 1 | M − 1 |
|---|---|---|---|---|
| example 240 | (3R)-3-{3-[(5-carbamoylpyridin-2-yl)amino]-4-[(2-methylpropyl)(oxan-4-yl)amino]phenyl}butanoic acid | 0.85 | | 453.3 |
| example 241 | (3R)-3-{4-[(2-methylpropyl)(oxan-4-yl)amino]-3-{[5-(trifluoromethyl)pyrimidin-2-yl]amino}phenyl}butanoic acid | 1.37 | | 481.3 |
| example 242 | (3R)-3-{4-[(2-methylpropyl)(oxan-4-yl)amino]-3-[(1H-1,2,4-triazol-5-yl)amino]phenyl}butanoic acid | 0.91 | | 402.4 |

-continued

| | | IPQA $T_{elute}$ [min] | M + 1 | M − 1 |
|---|---|---|---|---|
| example 243 | (3RS)-3-(3-{[5-(methoxymethyl)-1H-1,2,4-triazol-3-yl]amino}-4-[(2-methylpropyl)[(1rs&,4rs&)-4-methoxycyclohexyl]amino]phenyl)butanoic acid | 1.01 | 474.4 | |
| example 244 | 3-{4-[cyclohexyl(2-methylpropyl)amino]-3-{[5-(dimethylcarbamoyl)-1,3,4-thiadiazol-2-yl]amino}phenyl}butanoic acid | 1.30 | 486.4 | |
| example 245 | 3-{4-[cyclohexyl(2-methylpropyl)amino]-3-({5-[(propan-2-yl)carbamoyl]-1,3,4-thiadiazol-2-yl}amino)phenyl}butanoic acid | 1.40 | 502.1 | |

| | | | IPQA $T_{elute}$ [min] | M + 1 | M - 1 |
|---|---|---|---|---|---|
| example 246 | (3RS)-3-(3-{[5-(methylcarbamoyl)-1H-1,2,4-triazol-3-yl]amino}-4-[(2-methylpropyl)[(1rs&,4rs&)-4-methoxycyclohexyl]amino]phenyl)butanoic acid | | 1.05 | | 487.4 |
| example 247 | (3RS)-3-(3-{[5-(methoxymethyl)pyridin-2-yl]amino}-4-[(2-methylpropyl)[(1rs&,4rs&)-4-methoxycyclohexyl]amino]phenyl)butanoic acid | | 0.94 | | 482.4 |
| example 248 | (3R)-3-{3-[(5-carbamoylpyrimidin-2-yl)amino]-4-[(2-methylpropyl)(oxan-4-yl)amino]phenyl}butanoic acid | | 0.97 | | 454.3 |

-continued

| | | IPQA T_elute [min] | M + 1 | M − 1 |
|---|---|---|---|---|
| example 249 | (1-{4-[(2-methylpropyl)(oxan-4-yl)amino]-3-{[3-(trifluoromethyl)-1,2,4-thiadiazol-5-yl]amino}phenyl}ethyl)urea | 1.15 | 487.3 | 485.3 |
| example 250 | 3-{4-[bis(2-methylpropyl)amino]-3-{[2-(propan-2-yl)-2H-1,2,3,4-tetrazol-5-yl]amino}phenyl}butanoic acid | 1.50 | | 415.3 |
| example 251 | 3-{4-[bis(2-methylpropyl)amino]-3-[(2-methyl-2H-1,2,3,4-tetrazol-5-yl)amino]phenyl}butanoic acid | 1.40 | | 387.3 |
| example 252 | 3-{4-[bis(2-methylpropyl)amino]-3-[(1-methyl-1H-1,2,3,4-tetrazol-5-yl)amino]phenyl}butanoic acid | 1.30 | | 387.3 |

-continued

| | | | IPQA $T_{elute}$ [min] | M + 1 | M − 1 |
|---|---|---|---|---|---|
| example 253 | (3R)-3-{3-[(6-carbamoylpyridazin-3-yl)amino]-4-[(2-methylpropyl)(oxan-4-yl)amino]phenyl}butanoic acid | | 0.93 | 454.3 | |
| example 254 | (3R)-3-{3-[(5-cyanopyrimidin-2-yl)amino]-4-[(2-methylpropyl)(oxan-4-yl)amino]phenyl}butanoic acid | | 1.21 | 436.3 | |
| example 255 | (3R)-3-{4-[(2-methylpropyl)[5-({4-[3-(trifluoromethyl)-3H-diazirin-3-yl]phenyl}formamido)pentyl]amino]-3-{[3-(trifluoromethyl)-1,2,4-thiadiazol-5-yl]amino}phenyl}butanoic acid | | | | |

|  |  |  | IPQA $T_{elute}$ [min] | M + 1 | M − 1 |
|---|---|---|---|---|---|
| example 256 | 3-hydroxy-4-[(1-{4-[(2-methylpropyl)(oxan-4-yl)amino]-3-{[3-(trifluoromethyl)-1,2,4-thiadiazol-5-yl]amino}phenyl}ethyl)amino]cyclobut-3-ene-1,2-dione | | 1.12 | 540.3 | 538.4 |
| example 257 | (3R)-3-(3-{[5-(methylcarbamoyl)-1,3,4-thiadiazol-2-yl]amino}-4-[(2-methylpropyl)(oxan-4-yl)amino]phenyl)butanoic acid | | 1.00 | | 474.3 |
| example 258 | (3R)-3-(4-{bis[(2R)-2-methoxypropyl]amino}-3-{[3-(trifluoromethyl)-1,2,4-thiadiazol-5-yl]amino}phenyl)butanoic acid | | 1.32 | 491.5 | |

| | | IPQA $T_{elute}$ [min] | M + 1 | M − 1 |
|---|---|---|---|---|
| example 259 | 3-(4-{[5-({[(4E)-cyclooct-4-en-1-yloxy]carbonyl}amino)pentyl](2-methylpropyl)amino}-3-{[3-(trifluoromethyl)-1,2,4-thiadiazol-5-yl]amino}phenyl)butanoic acid | 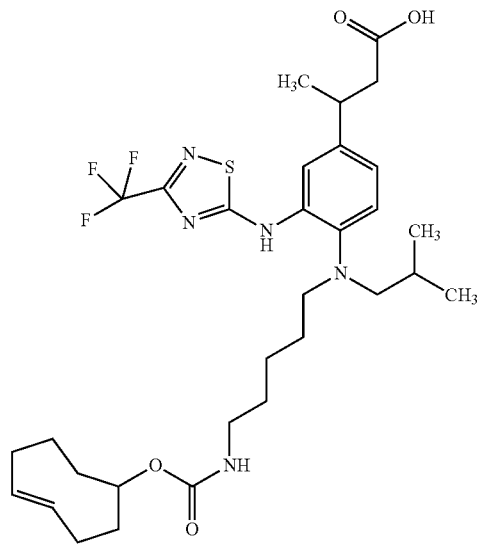 [SMILES: CC(C)CN(CCCCCNC(=O)OC1CC/C=C/CCC1)c1ccc(C(C)CC(=O)O)cc1Nc1nc(C(F)(F)F)ns1] | | |
| example 260 | (3R)-3-{3-[(5-chloro-6-methylpyridin-2-yl)amino]-4-[(2-methylpropyl)(oxan-4-yl)amino]phenyl}butanoic acid | 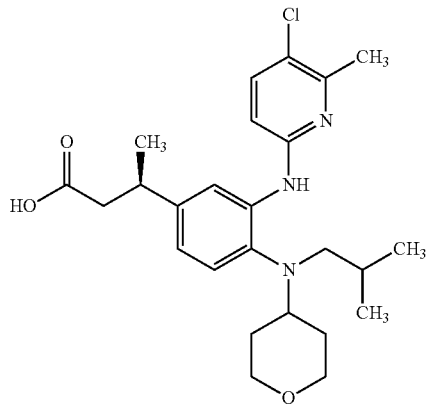 [SMILES: Cc1nc(Nc2cc([C@H](C)CC(=O)O)ccc2N(CC(C)C)C2CCOCC2)ccc1Cl] | 1.39 | 458.4 |
| example 261 | (3R)-3-{3-[(5-carbamoyl-1,3,4-thiadiazol-2-yl)amino]-4-[(2-methylpropyl)(oxan-4-yl)amino]phenyl}butanoic acid | 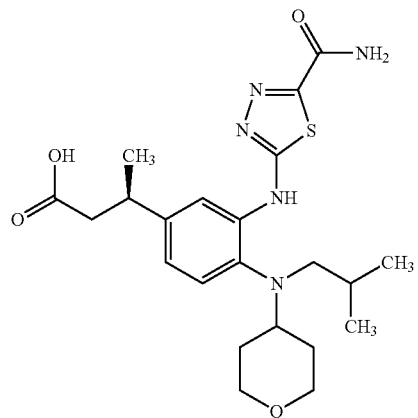 [SMILES: CC(C)CN(c1ccc([C@H](C)CC(=O)O)cc1Nc1nnc(C(N)=O)s1)C1CCOCC1] | 1.00 | 460.2 |

-continued
| | | IPQA T_{elute} [min] | M + 1 | M − 1 |
|---|---|---|---|---|
| example 262 | (3R)-3-(4-{[1-(methylcarbamoyl)piperidin-4-yl](2-methylpropyl)amino}-3-{[3-(trifluoromethyl)-1,2,4-thiadiazol-5-yl]amino}phenyl)butanoic acid 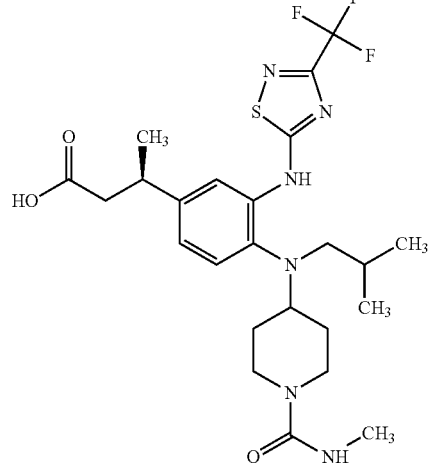 | 1.17 | | 541.5 |
| example 263 | (3R)-3-{3-[(2-carbamoylpyrimidin-5-yl)amino]-4-[(2-methylpropyl)(oxan-4-yl)amino]phenyl}butanoic acid 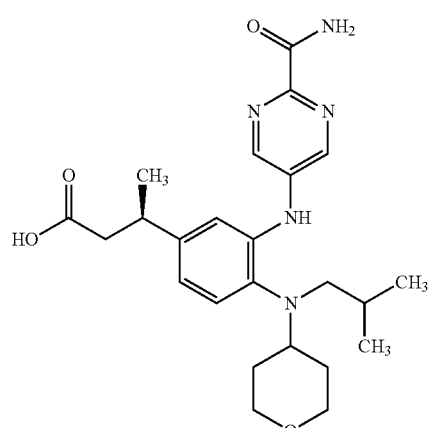 | 0.91 | | 454.4 |
| example 264 | (3R)-3-{3-[(5-carbamoylpyrazin-2-yl)amino]-4-[(2-methylpropyl)(oxan-4-yl)amino]phenyl}butanoic acid 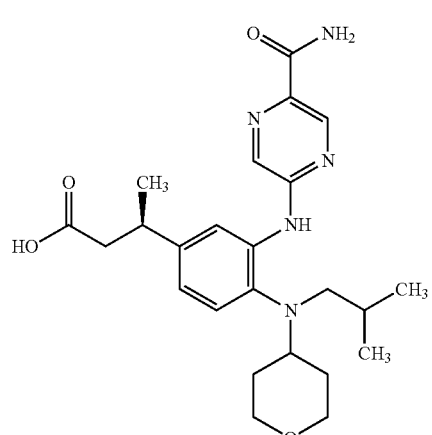 | 0.97 | | 454.4 |

-continued

| | | IPQA T_elute [min] | M + 1 | M − 1 |
|---|---|---|---|---|
| example 265 | 5-({5-[(2R)-1-carboxypropan-2-yl]-2-[(2-methylpropyl)(oxan-4-yl)amino]phenyl}(2-carboxypyrimidin-5-yl)amino)pyrimidine-2-carboxylic acid | 0.79 | 579.3 | |
| example 266 | 3'-[(6-chloropyridin-2-yl)amino]-4'-[cyclohexyl(2-methylpropyl)amino]-[1,1'-biphenyl]-2-carboxylic acid | 1.56 | 478.2 | |
| example 267 | 4-{4-[(2-methylpropyl)(oxan-4-yl)amino]-3-{[3-(trifluoromethyl)-1,2,4-thiadiazol-5-yl]amino}phenyl}pyridine-3-carboxylic acid | 1.12 | 522.3 | |
| example 268 | 4'-({bicyclo[1.1.1]pentan-1-yl}(2-methylpropyl)amino)-3'-[2-(4-methylphenyl)acetamido]-[1,1'-biphenyl]-2-carboxylic acid | 1.49 | 483.3 | |

| | | | IPQA T_elute [min] | M + 1 | M − 1 |
|---|---|---|---|---|---|
| example 269 | 3-{4-[(2-methylpropyl)(oxan-4-yl)amino]-3-{[3-(trifluoromethyl)-1,2,4-thiadiazol-5-yl]amino}phenyl}pyridine-2-carboxylic acid | 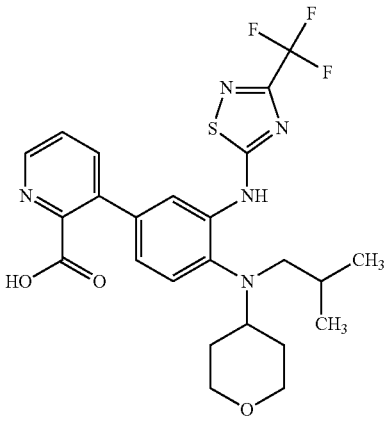 [SMILES: CC(C)CN(c1ccc(-c2cccnc2C(=O)O)cc1Nc1nc(C(F)(F)F)ns1)C1CCOCC1] | 1.15 | | 522.3 |
| example 270 | 3-{3-[(3-chloro-1,2,4-thiadiazol-5-yl)amino]-4-[(2-methylpropyl)(oxan-4-yl)amino]phenyl}pyridine-2-carboxylic acid | 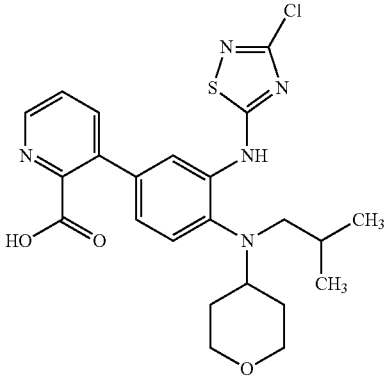 [SMILES: CC(C)CN(c1ccc(-c2cccnc2C(=O)O)cc1Nc1nc(Cl)ns1)C1CCOCC1] | 1.05 | | 486.3 |
| example 271 | 4'-{[1-(2-hydroxyethyl)piperidin-4-yl](2-methylpropyl)amino}-3'-{[3-(trifluoromethyl)-1,2,4-thiadiazol-5-yl]amino}-[1,1'-biphenyl]-2-carboxylic acid | 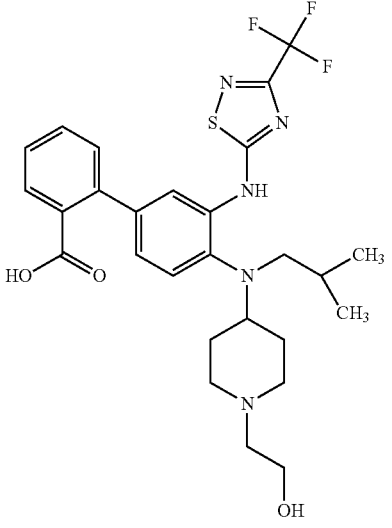 [SMILES: CC(C)CN(c1ccc(-c2ccccc2C(=O)O)cc1Nc1nc(C(F)(F)F)ns1)C1CCN(CCO)CC1] | | | |

-continued

| | | | IPQA T$_{elute}$ [min] | M + 1 | M − 1 |
|---|---|---|---|---|---|
| example 272 | 4'-[(2-methylpropyl)(piperidin-4-yl)amino]-3'-{[3-(trifluoromethyl)-1,2,4-thiadiazol-5-yl]amino}-[1,1'-biphenyl]-2-carboxylic acid | 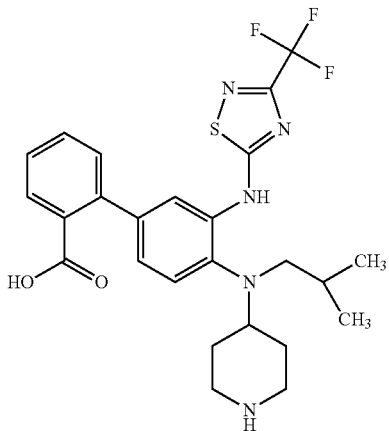 [SMILES: CC(C)CN(c1ccc(-c2ccccc2C(=O)O)cc1Nc1nc(C(F)(F)F)ns1)C1CCNCC1] | 1.00 | 520.4 | |
| example 273 | 4'-({1-[(tert-butoxy)carbonyl]piperidin-4-yl}-(2-methylpropyl)amino)-3'-{[3-(trifluoromethyl)-1,2,4-thiadiazol-5-yl]amino}-[1,1'-biphenyl]-2-carboxylic acid | 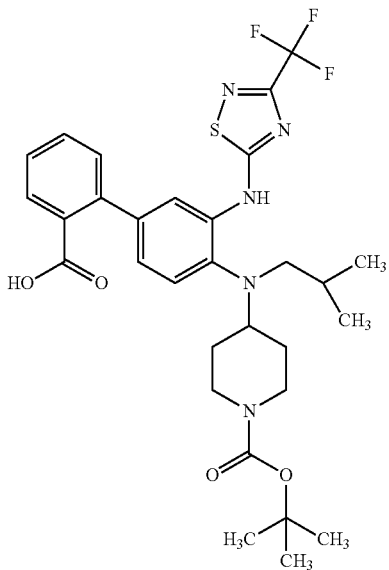 [SMILES: CC(C)CN(c1ccc(-c2ccccc2C(=O)O)cc1Nc1nc(C(F)(F)F)ns1)C1CCN(C(=O)OC(C)(C)C)CC1] | 1.52 | 618.4 | |
| example 274 | 4'-[(1-methylpiperidin-4-yl)(2-methylpropyl)amino]-3'-{[3-(trifluoromethyl)-1,2,4-thiadiazol-5-yl]amino}-[1,1'-biphenyl]-2-carboxylic acid | 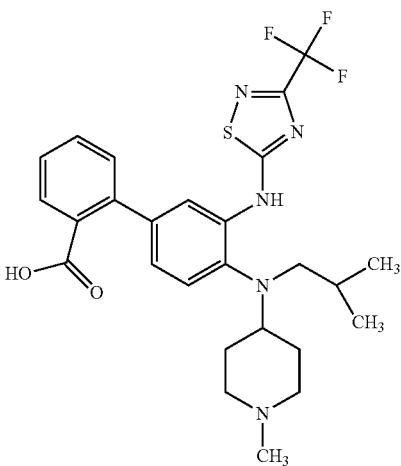 [SMILES: CC(C)CN(c1ccc(-c2ccccc2C(=O)O)cc1Nc1nc(C(F)(F)F)ns1)C1CCN(C)CC1] | 1.01 | 534.3 | |

| | | IPQA $T_{elute}$ [min] | M + 1 | M − 1 |
|---|---|---|---|---|
| example 275 | 5-({2'-carboxy-4-[cyclohexyl(2-methylpropyl)amino]-[1,1'-biphenyl]-3-yl}amino)-1,2,4-thiadiazole-3-carboxylic acid 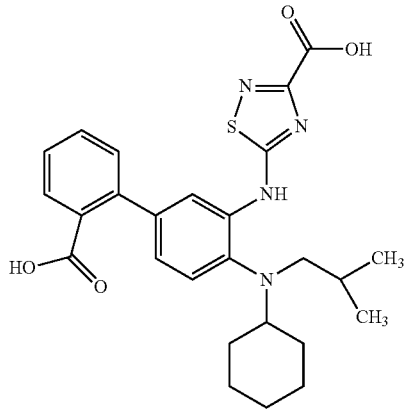 [SMILES: CC(C)CN(c1ccc(-c2ccccc2C(=O)O)cc1Nc1nc(C(=O)O)ns1)C1CCCCC1] | 1.31 | | 495.3 |
| example 276 | 4'-[(2-methylpropyl)[(1s,4s)-4-methoxycyclohexyl]amino]-3'-{[3-(trifluoromethyl)-1,2,4-thiadiazol-5-yl]amino}-[1,1'-biphenyl]-2-carboxylic acid 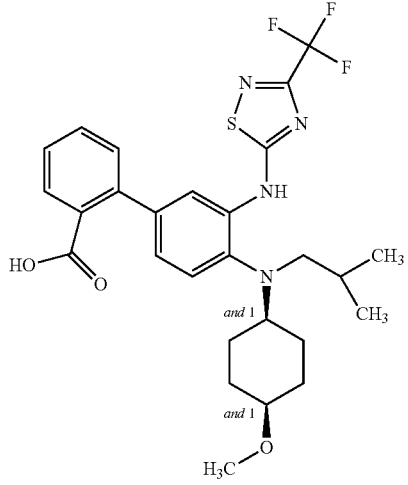 [SMILES: CO[C@H]1CC[C@@H](N(CC(C)C)c2ccc(-c3ccccc3C(=O)O)cc2Nc2nc(C(F)(F)F)ns2)CC1] | 1.51 | | 549.1 |
| example 277 | 3'-[(2-cyanoethyl)amino]-4'-[cyclohexyl(2-methylpropyl)amino]-[1,1'-biphenyl]-2-carboxylic acid 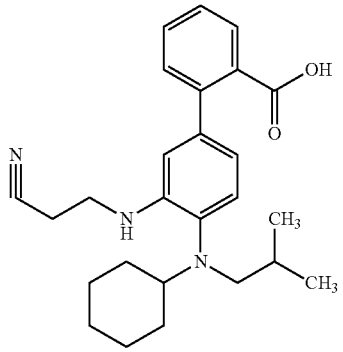 [SMILES: CC(C)CN(c1ccc(-c2ccccc2C(=O)O)cc1NCCC#N)C1CCCCC1] | 1.46 | | 418.3 |

-continued
| | | | IPQA $T_{elute}$ [min] | M + 1 | M − 1 |
|---|---|---|---|---|---|
| example 278 | 3-{3-[(1H-1,3-benzodiazol-2-yl)amino]-4-[cyclohexyl(2-methylpropyl)amino]phenyl}pyridine-2-carboxylic acid | 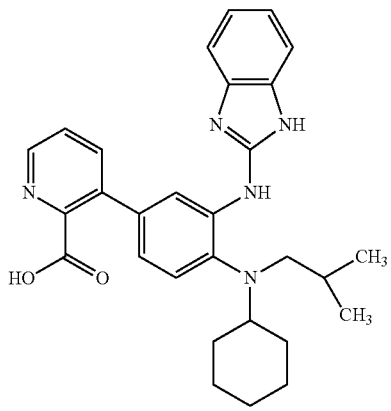 [SMILES: CC(C)CN(c1ccc(-c2cccnc2C(=O)O)cc1Nc1nc2ccccc2[nH]1)C1CCCCC1] | 0.89 | 484.4 | |
| example 279 | 4'-[(2-methylpropyl)[(1s,4s)-4-hydroxycyclohexyl]amino]-3'-{[3-(trifluoromethyl)-1,2,4-thiadiazol-5-yl]amino}-[1,1'-biphenyl]-2-carboxylic acid | 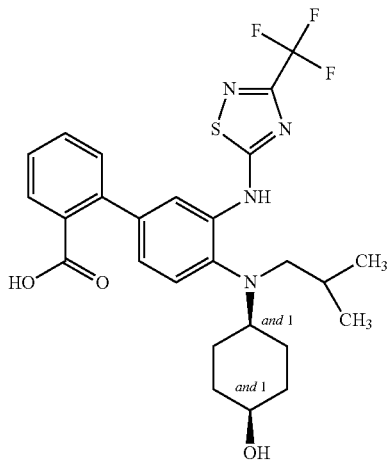 [SMILES: CC(C)CN(c1ccc(-c2ccccc2C(=O)O)cc1Nc1nc(C(F)(F)F)ns1)[C@H]1CC[C@@H](O)CC1] | 1.36 | 533.3 | |
| example 280 | 4'-[bis(2-methylpropyl)amino]-3'-[(1-methyl-1H-pyrazol-3-yl)amino]-[1,1'-biphenyl]-2-carboxylic acid | 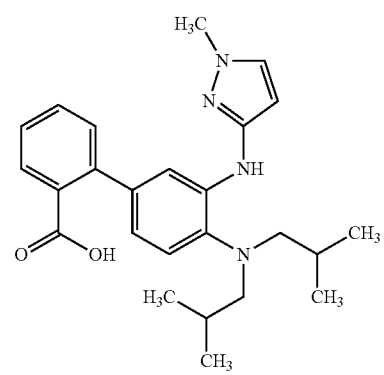 [SMILES: CC(C)CN(CC(C)C)c1ccc(-c2ccccc2C(=O)O)cc1Nc1ccn(C)n1] | 1.09 | 419.4 | |

-continued

|  |  | IPQA $T_{elute}$ [min] | M + 1 | M − 1 |
|---|---|---|---|---|
| example 281 | 4-{3-[(1,3-benzoxazol-2-yl)amino]-4-[cyclohexyl(2-methylpropyl)amino]phenyl}pyridine-3-carboxylic acid | 1.44 | 485.4 | |
| example 282 | 4'-[cyclohexyl(2-methylpropyl)amino]-N-methanesulfonyl-3-'{[3-(trifluoromethyl)-1,2,4-thiadiazol-5-yl]amino}-[1,1'-biphenyl]-2-carboxamide | 1.57 | 596.4 | |
| example 283 | N-(5-aminopentyl)-4'-[cyclohexyl(2-methylpropyl)amino]-3'-{[3-(trifluoromethyl)-1,2,4-thiadiazol-5-yl]amino}-[1,1'-biphenyl]-2-carboxamide | | | |

-continued
|  |  |  | IPQA $T_{elute}$ [min] | M + 1 | M − 1 |
|---|---|---|---|---|---|
| example 284 | 3'-[(1,3-benzoxazol-2-yl)amino]-4'-[cyclohexyl(2-methoxyethyl)amino]-[1,1'-biphenyl]-2-carboxylic acid | 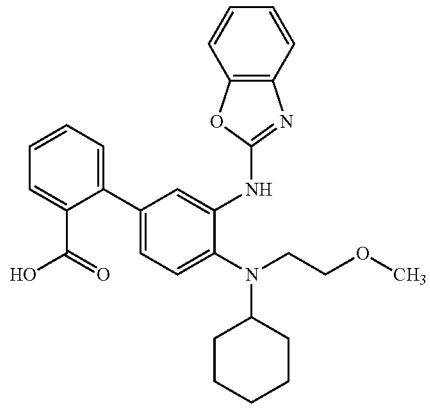 [SMILES: COCCN(c1ccc(-c2ccccc2C(=O)O)cc1Nc1nc2ccccc2o1)C1CCCCC1] | 1.41 | 486.3 |  |
| example 285 | 3'-[(1H-1,3-benzodiazol-2-yl)amino]-4'-[cyclohexyl(2-methoxyethyl)amino]-[1,1'-biphenyl]-2-carboxylic acid | 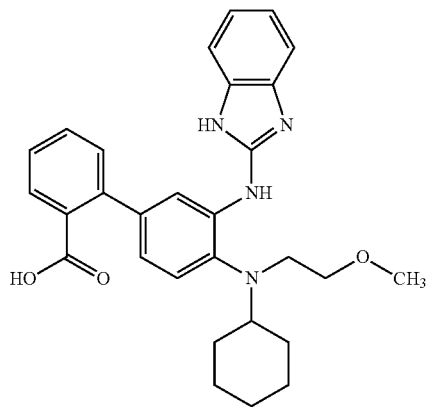 [SMILES: COCCN(c1ccc(-c2ccccc2C(=O)O)cc1Nc1nc2ccccc2[nH]1)C1CCCCC1] | 0.91 | 485.4 |  |
| example 286 | 4'-[bis(2-methylpropyl)amino]-3'-[(3-methyl-1,2,4-thiadiazol-5-yl)amino]-[1,1'-biphenyl]-2-carboxylic acid | 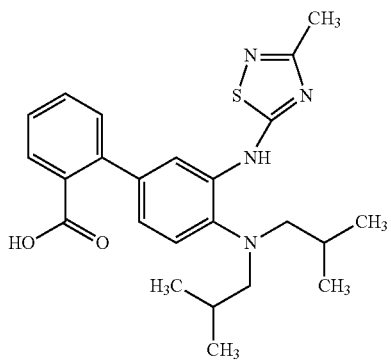 [SMILES: Cc1nsc(Nc2cc(-c3ccccc3C(=O)O)ccc2N(CC(C)C)CC(C)C)n1] | 1.42 | 439.2 |  |

| | | IPQA T_elute [min] | M + 1 | M − 1 |
|---|---|---|---|---|
| example 287 | 4'-[cyclohexyl(2-methylpropyl)amino]-3'-[(5-methoxy-1H-1,3-benzodiazol-2-yl)amino]-[1,1'-biphenyl]-2-carboxylic acid | 1.02 | 513.3 | |
| example 288 | 4'-[bis(2-methylpropyl)amino]-3'-[(3-cyclopropyl-1,2,4-thiadiazol-5-yl)amino]-[1,1'-biphenyl]-2-carboxylic acid | 1.52 | 465.3 | |
| example 289 | 3-{3-[(1,3-benzoxazol-2-yl)amino]-4-[cyclohexyl(2-methylpropyl)amino]phenyl}pyridine-4-carboxylic acid | 1.83 | 485.4 | |
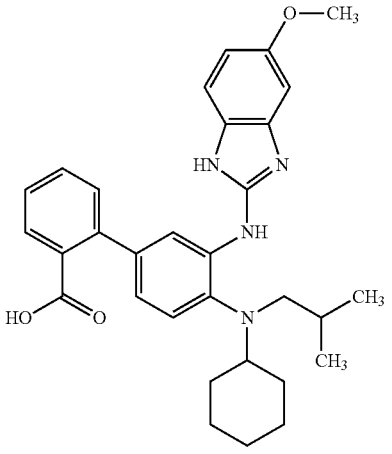 [SMILES: COc1ccc2[nH]c(Nc3cc(-c4ccccc4C(=O)O)ccc3N(CC(C)C)C3CCCCC3)nc2c1]
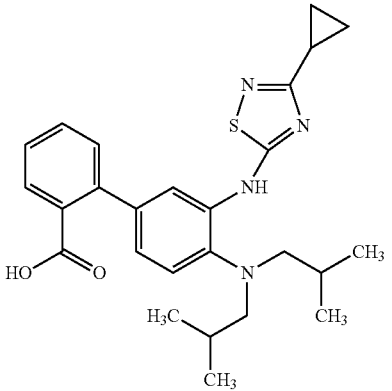 [SMILES: CC(C)CN(CC(C)C)c1ccc(-c2ccccc2C(=O)O)cc1Nc1nc(C2CC2)ns1]
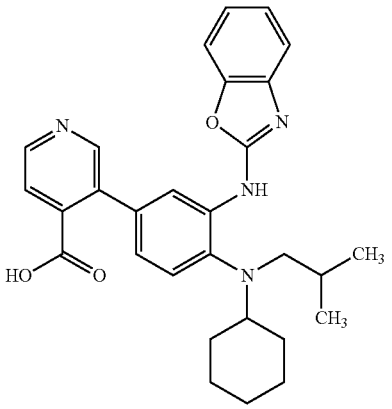 [SMILES: CC(C)CN(c1ccc(-c2cnccc2C(=O)O)cc1Nc1nc2ccccc2o1)C1CCCCC1]

-continued
| | | IPQA T$_{elute}$ [min] | M + 1 | M − 1 |
|---|---|---|---|---|
| example 290 | 3-{3-[(1,3-benzoxazol-2-yl)amino]-4-[cyclohexyl(2-methylpropyl)amino]phenyl}pyridine-2-carboxylic acid 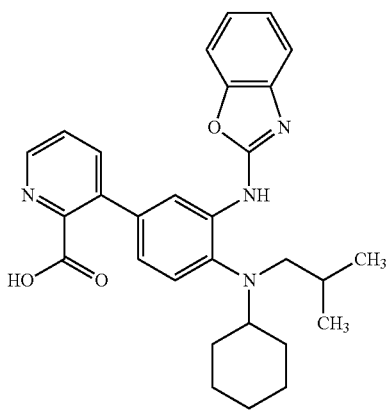 [SMILES: CC(C)CN(c1ccc(-c2cccnc2C(=O)O)cc1Nc1nc2ccccc2o1)C1CCCCC1] | 1.44 | 485.4 | |
| example 291 | 3'-[(1,3-benzoxazol-2-yl)amino]-4'-[(2-methylpropyl)(oxan-4-yl)amino]-[1,1'-biphenyl]-2-carboxylic acid 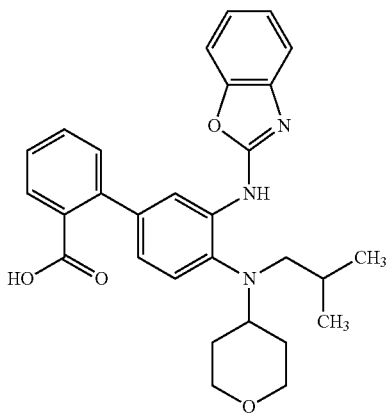 [SMILES: CC(C)CN(c1ccc(-c2ccccc2C(=O)O)cc1Nc1nc2ccccc2o1)C1CCOCC1] | 1.36 | 486.3 | |
| example 292 | 2-{3-[(1,3-benzoxazol-2-yl)amino]-4-[cyclohexyl(2-methylpropyl)amino]phenyl}pyridine-3-carboxylic acid 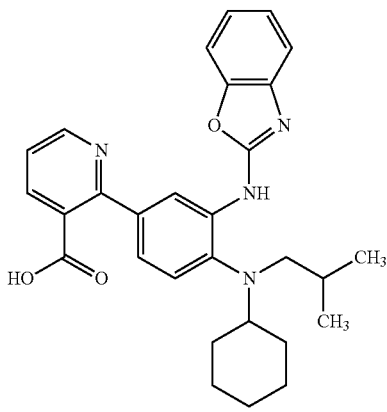 | 1.37 | 485.3 | |

|   |   | IPQA $T_{elute}$ [min] | M + 1 | M − 1 |
|---|---|---|---|---|
| example 293 | 3'-[(1,3-benzoxazol-2-yl)amino]-4'-[bis(2-methylpropyl)amino]-[1,1'-biphenyl]-2-carboxylic acid 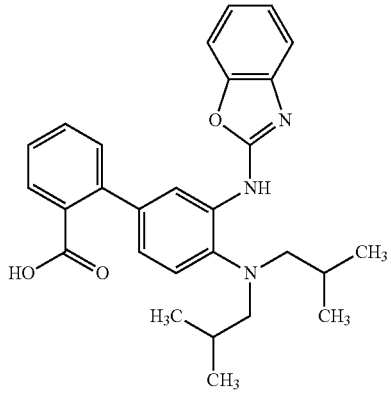 [SMILES: CC(C)CN(CC(C)C)c1ccc(-c2ccccc2C(=O)O)cc1Nc1nc2ccccc2o1] | 1.53 | 458.3 | |
| example 294 | 4'-[bis(2-methylpropyl)amino]-3'-[(3-chloro-1,2,4-thiadiazol-5-yl)amino]-[1,1'-biphenyl]-2-carboxylic acid 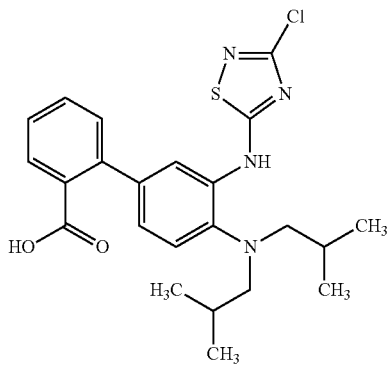 [SMILES: CC(C)CN(CC(C)C)c1ccc(-c2ccccc2C(=O)O)cc1Nc1nc(Cl)ns1] | 1.48 | 459.2 | |
| example 295 | 4'-[bis(2-methylpropyl)amino]-3'-[(5-cyclopropyl-1,3,4-thiadiazol-2-yl)amino]-[1,1'-biphenyl]-2-carboxylic acid 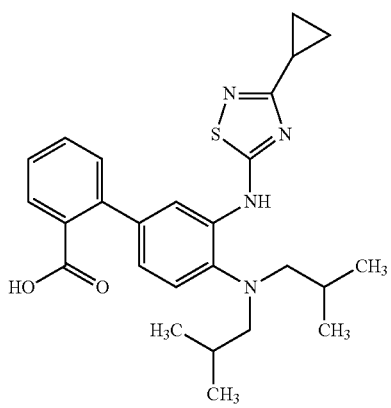 [SMILES: CC(C)CN(CC(C)C)c1ccc(-c2ccccc2C(=O)O)cc1Nc1nc(C2CC2)ns1] | 1.40 | 465.3 | |

-continued
| | | IPQA T$_{elute}$ [min] | M + 1 | M − 1 |
|---|---|---|---|---|
| example 296 | 3'-[(1H-1,3-benzodiazol-2-yl)amino]-4'-[(2-methylpropyl)(oxan-4-yl)amino]-[1,1'-biphenyl]-2-carboxylic acid 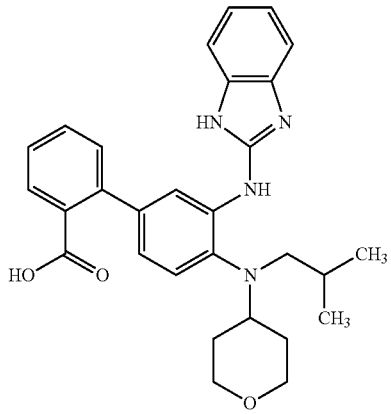 [SMILES: CC(C)CN(c1ccc(-c2ccccc2C(=O)O)cc1Nc1nc2ccccc2[nH]1)C1CCOCC1] | 0.86 | 485.3 | |
| example 297 | 3'-[(1H-1,3-benzodiazol-2-yl)amino]-4'-[bis(2-methylpropyl)amino]-[1,1'-biphenyl]-2-carboxylic acid 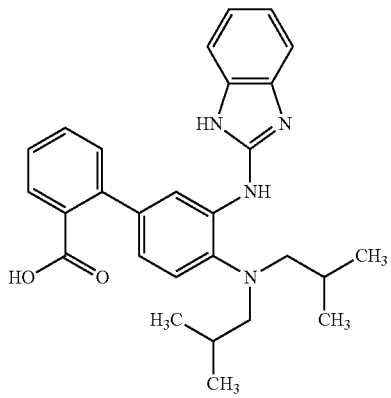 [SMILES: CC(C)CN(CC(C)C)c1ccc(-c2ccccc2C(=O)O)cc1Nc1nc2ccccc2[nH]1] | 0.96 | 457.3 | |
| example 298 | 4'-[bis(2-methylpropyl)amino]-3'-[(5-methyl-1,3,4-thiadiazol-2-yl)amino]-[1,1'-biphenyl]-2-carboxylic acid 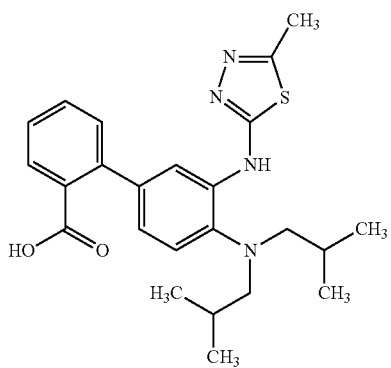 [SMILES: Cc1nnc(Nc2cc(-c3ccccc3C(=O)O)ccc2N(CC(C)C)CC(C)C)s1] | 1.32 | 439.2 | |

| | | | IPQA $T_{elute}$ [min] | M + 1 | M − 1 |
|---|---|---|---|---|---|
| example 299 | 4'-[cyclohexyl(2-methylpropyl)amino]-3'-{[4-(trifluoromethyl)-1,3-thiazol-2-yl]amino}-[1,1'-biphenyl]-2-carboxylic acid | 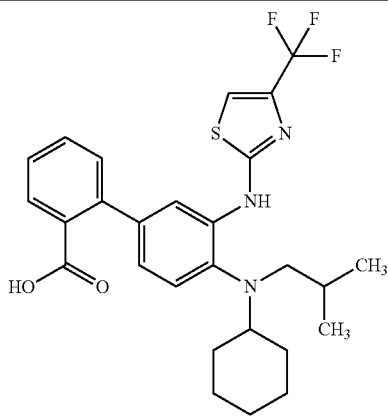 | 1.62 | 518.4 | |
| example 300 | S)-3-(3-((2-chloropyrimidin-4-yl)amino)-4-(cyclohexyl(isobutyl)amino)phenyl)butanoic acid | 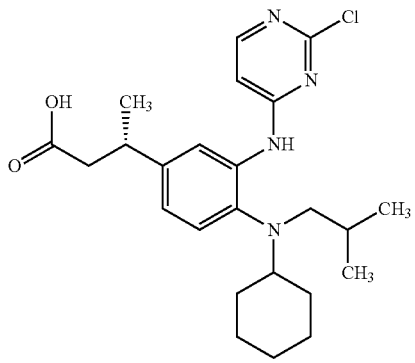 [SMILES: CC(C)CN(c1ccc([C@@H](C)CC(=O)O)cc1Nc1ccnc(Cl)n1)C1CCCCC1] | 1.12 | 445.4 | |

Study Design:

To understand its toxicokinetics and potential effect on hepatic functions, EXAMPLE 23 was orally dosed to Beagle dogs for 7 consecutive days. The detailed study design is presented as follows:

| Category | Item | Description |
|---|---|---|
| Species | Beagle Dog | non-naïve, N = 1 male and N = 1 female, fasted overnight and fed 8 hr post dosing, collecting 8 hr sample before returning food |
| Compound Formulation | EXAMPLE 23 PO | 1% methylcellulose (MC) |
| In-life | 20 mg/kg, 10 mL/kg, BID (twice a day) for 7 days | 2/timepiont Sampling plasma for TK: at predose, 0.5, 1, 2, 4, 6, 8, 12 (prior to $2^{nd}$ dosing), 24 hr on Day 1 and 7. Sampling serum for clinical chem: Day −2 and −1: at 0 hr before first meal; Day 1 and 7: at predose, 0.5, 1, 2, 4, 6, 8, 12 hr (prior to $2^{nd}$ dosing); Day 2, 3, 4, 5, 6, 8: at 0 hr prior to the $1^{st}$ dose. |

Results and Conclusions:

EXAMPLE 23 was quantifiable in plasma for up to 24 hours post the start of the oral dose on Days 1 and 7. $T_{max}$ occurred at 0.5 hours post dose on Days 1 and 7. There was ~3-fold increase in systemic exposures (i.e. $C_{max}$ and $AUC_{0-12}$ values) on Day7 in comparison to that of Day1 for both dogs. On Day 7, an average of ~66- and ~25-fold therapeutic coverage in Cmax and $AUC_{0-12}$, respectively, was achieved for the predicted human efficacious dose (see Table 1).

EXAMPLE 23 was well tolerated throughout the study and no clinical observations were made. Body weights were constant for both male and female dogs over the study as shown in FIG. 1. Hepatic functions measured by serum ALT (alanine aminotransferase), AST (aspartate aminotransferase), ALP (alkaline phosphatase) and T-Bil (total bilirubin) levels were determined to be in the normal variable ranges (see FIG. 2).

TABLE 1

Summary of EXAMPLE 23 toxicokinetics in Beagle dogs following 7 day repeat oral administration

| Period | Dose mg/kg | Sex | Subject | Tmax hr | Cmax µg/mL | AUC (0-12 hr) µg * hr/mL | Therapeutic Index Cmax | Therapeutic Index AUC (0-12 hr) |
|---|---|---|---|---|---|---|---|---|
| Day1 | 20 | Male | 1 | 0.5 | 2.4 | 5.1 | 31 | 14 |
| Day1 | 20 | Female | 1 | 0.5 | 1.0 | 1.5 | 13 | 4 |
| Day7 | 20 | Male | 1 | 0.5 | 6.3 | 14.9 | 81 | 40 |
| Day7 | 20 | Female | 1 | 0.5 | 3.9 | 3.8 | 50 | 10 |

1. Predicted human efficacious exposures: Cmax = 0.078 µg/mL; AUC (0-12 hr) = 0.376 µg * hr/mL

CETSA

Cellular Thermal Shifting assays were used to directly monitor the ligand binding to target proteins in cells. Hela cells were transduced with BacMam virus expressing ePL tagged IDO1 overnight. The cells were then plated over the compounds for 3 hours at 37° C. in cell culture medium containing 1% FBS. The plates were then sealed and heated at 53° C. for 3 min. InCell Hunter reagents were added and luminescence was read in 90 min.

References:

1. Molina, D. M., et al. Monitoring drug target engagement in cells and tissues using the cellular thermal shift assay. *Science* 2013, 341 (6141), 84-87.

2. Jafari, R., et al. The cellular thermal shift assay for evaluating drug target interactions in cells. *Nature Protocols* 2014, 9 (9), 2100-2122.

3. Jensen, A. J., et al. CETSA: A target engagement assay with potential to transform drug discovery. *Future Medicinal Chemistry* 2015, 7 (8), 975-978.

4. Martinez Molina, D.; Nordlund, P. The Cellular Thermal Shift Assay: A Novel Biophysical Assay for in Situ Drug Target Engagement and Mechanistic Biomarker Studies. In *Annual Review of Pharmacology and Toxicology*, 2016; Vol. 56, pp 141-161.

| | pXC50_1 | pXC50_2 |
|---|---|---|
| Example 6 | 7.86 | 7.68 |
| Example 11 | 6.95 | 6.72 |
| Example 16 | 6.59 | 6.5 |
| Example 20 | 8.02 | |
| Example 23 | 6.48 | 6.63 |
| Example 44 | 8.77 | |
| Example 51 | 8.77 | |
| Example 67 | 7.14 | 7.3 |
| Example 110 | 6.89 | 6.86 |
| Example 283 | <4 | |

IDO1 HeLa RapidFire MS Assay

Compounds of the present invention were tested via high-throughput cellular assays utilizing detection of kynurenine via mass spectrometry and cytotoxicity as endpoints. For the mass spectrometry and cytotoxicity assays, human epithelial HeLa cells (CCL-2; ATCC®, Manassas, Va.) were stimulated with human interferon-γ (IFN-γ) (Sigma-Aldrich Corporation, St. Louis, Mo.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 1 mM or 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ) HeLa cells for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ) HeLa cells for both the mass spectrometry and cytotoxicity assays.

Frozen stocks of HeLa cells were washed and recovered in DMEM high glucose medium with HEPES (Thermo Fisher Scientific, Inc., Waltham, Mass.) supplemented with 10% v/v certified fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 100,000 cells/mL in the supplemented DMEM medium. 50 µL of either the cell suspension, for the mass spectrometry assay, or medium alone, for the cytotoxicity assay, were added to the low control wells, on the previously prepared 384-well compound plates, resulting in 5,000 cells/well or 0 cells/well respectively. IFN-γ was added to the remaining cell suspension at a final concentration of 10 nM, and 50 µL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 10 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula $100-(100*((U-C2)/(C1-C2)))$, where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula $100-(100*((U-C2)/(C1-C2)))$, where U was the unknown value, C1 was the average of the high (0% cytotoxicity) control wells and $C_2$ was the average of the low (100% cytotoxicity) control wells.

Curve fitting was performed with the equation $y=A+((B-A)/(1+(10x/10C)D))$, where A was the minimum response, B was the maximum response, C was the log(XC50) and D was the Hill slope. The results for each test compound were recorded as pIC50 values for the mass spectrometry assay and as pCC50 values for the cytotoxicity assay (—C in the above equation).

IDO1 PBMC RapidFire MS Assay

Compounds of the present invention were tested via high-throughput cellular assays utilizing detection of kynurenine via mass spectrometry and cytotoxicity as endpoints. For the mass spectrometry and cytotoxicity assays, human peripheral blood mononuclear cells (PBMC) (PB003F; AllCells®, Alameda, Calif.) were stimulated with human interferon-γ (IFN-γ) (Sigma-Aldrich Corporation, St. Louis, Mo.) and lipopolysaccharide from Salmonella minnesota (LPS) (Invivogen, San Diego, Calif.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 1 mM or 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ/−LPS) PBMCs for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ/+LPS) PBMCs for both the mass spectrometry and cytotoxicity assays.

Frozen stocks of PBMCs were washed and recovered in RPMI 1640 medium (Thermo Fisher Scientific, Inc., Waltham, Mass.) supplemented with 10% v/v heat-inactivated fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 1,000,000 cells/mL in the supplemented RPMI 1640 medium. 50 µL of either the cell suspension, for the mass spectrometry assay, or medium alone, for the cytotoxicity assay, were added to the low control wells, on the previously prepared 384-well compound plates, resulting in 50,000 cells/well or 0 cells/well respectively. IFN-γ and LPS were added to the remaining cell suspension at final concentrations of 100 ng/ml and 50 ng/ml respectively, and 50 µL of the stimulated cells were added to all remaining wells on the 384-well compound plates. The plates, with lids, were then placed in a 37° C., 5% CO2 humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 40 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as IDO1 inhibition versus compound concentration following normalization using the formula $100-(100*((U-C2)/(C1-C2)))$, where U was the unknown value, C1 was the average of the high (100% kynurenine; 0% inhibition) control wells and $C_2$ was the average of the low (0% kynurenine; 100% inhibition) control wells. The data for dose responses in the cytotoxicity assay were plotted as % cytotoxicity versus compound concentration following normalization using the formula $100-(100*((U-C2)/(C1-C2)))$, where U was the unknown value, C1 was the average of the high (0% cytotoxicity) control wells and $C_2$ was the average of the low (100% cytotoxicity) control wells.

Curve fitting was performed with the equation $y=A+((B-A)/(1+(10x/10C)D))$, where A was the minimum response, B was the maximum response, C was the log(XC50) and D was the Hill slope. The results for each test compound were recorded as pIC50 values for the mass spectrometry assay and as pCC50 values for the cytotoxicity assay (—C in the above equation).

Table of Biological Activities of examples 1-300

| | IDO1_HELA_PXC50 | | HELA_IDO1_TOX_PXC50 | PBMC PXC50 | | PBMC TOX PXC50 |
|---|---|---|---|---|---|---|
| Example 1 | = 8.4 | < | 5 | = 9.1 | < | 5 |
| Example 2 | = 8.1 | < | 5 | = 8.8 | < | 5 |
| Example 3 | | | | = 8.8 | < | 5 |
| Example 4 | = 8.2 | < | 5 | = 8.4 | < | 5 |

Table of Biological Activities of examples 1-300

| | IDO1_HELA_PXC50 | | HELA_IDO1_TOX_PXC50 | | PBMC PXC50 | | PBMC TOX PXC50 |
|---|---|---|---|---|---|---|---|
| Example 5 | = | 7.6 | < | 5 | = | 8.3 | < | 5 |
| Example 6 | | | | | = | 9.2 | < | 5 |
| Example 7 | | | | | = | 9.2 | < | 5 |
| Example 8 | | | | | = | 9.1 | < | 5 |
| Example 9 | = | 8.6 | < | 5 | = | 9 | < | 5 |
| Example 10 | | | | | = | 9.1 | < | 5 |
| Example 11 | | | | | = | 9 | < | 5 |
| Example 12 | | | | | = | 9 | < | 5 |
| Example 13 | | | | | = | 8.9 | < | 5 |
| Example 14 | | | | | = | 8.9 | < | 5 |
| Example 15 | = | 8.1 | < | 5 | = | 8.5 | < | 5 |
| Example 16 | | | | | = | 8.8 | < | 5 |
| Example 17 | = | 8.2 | < | 5 | = | 8.7 | < | 5 |
| Example 18 | | | | | = | 8.7 | < | 5 |
| Example 19 | = | 8.3 | < | 5 | = | 8.6 | < | 5 |
| Example 20 | = | 8.6 | < | 5 | = | 8.6 | < | 5 |
| Example 21 | = | 7.5 | < | 5 | = | 8.6 | = | 5.2 |
| Example 22 | = | 8.6 | < | 5 | = | 8.6 | < | 5 |
| Example 23 | = | 8.4 | < | 5 | = | 8.5 | < | 5 |
| Example 24 | | | | | = | 8.6 | < | 5 |
| Example 25 | | | | | = | 8.5 | < | 5 |
| Example 26 | | | | | = | 8.5 | < | 5 |
| Example 27 | | | | | = | 8.4 | < | 5 |
| Example 28 | = | 8.2 | < | 5 | = | 8.3 | < | 5 |
| Example 29 | | | | | = | 8.2 | < | 5 |
| Example 30 | | | | | = | 8.1 | < | 5 |
| Example 31 | = | 7.7 | = | 5 | = | 8 | < | 5 |
| Example 32 | | | | | = | 8 | < | 5 |
| Example 33 | | | | | = | 8.2 | < | 5 |
| Example 34 | | | | | = | 8.2 | < | 5 |
| Example 35 | | | | | = | 9.3 | < | 5 |
| Example 36 | | | | | = | 9.2 | < | 5 |
| Example 37 | = | 8.3 | < | 5 | = | 8.9 | < | 5 |
| Example 38 | = | 8.7 | < | 5 | = | 9.1 | < | 5 |
| Example 39 | = | 8.6 | < | 5 | = | 9 | < | 5 |
| Example 40 | = | 7.9 | < | 5 | = | 8.6 | < | 5 |
| Example 41 | | | | | = | 8.1 | < | 5 |
| Example 42 | = | 8.3 | < | 5 | = | 9.3 | < | 5 |
| Example 43 | | | | | = | 9.2 | < | 5 |
| Example 44 | | | | | = | 9.2 | < | 5 |
| Example 45 | = | 8.4 | < | 5 | = | 8.9 | < | 5 |
| Example 46 | | | | | = | 8.8 | = | 5.2 |
| Example 47 | | | | | = | 9.1 | < | 5 |
| Example 48 | | | | | = | 9 | < | 5 |
| Example 49 | = | 8.2 | < | 5 | = | 8.7 | < | 5 |
| Example 50 | | | | | = | 8.8 | < | 5 |
| Example 51 | | | | | = | 8.8 | < | 5 |
| Example 52 | | | | | = | 8 | < | 5 |
| Example 53 | | | | | = | 8.8 | < | 5 |
| Example 54 | | | | | = | 8.7 | < | 5 |
| Example 55 | | | | | = | 8.5 | < | 5 |
| Example 56 | | | | | = | 8.4 | < | 5 |
| Example 57 | = | 8.1 | < | 5 | = | 8.3 | < | 5 |
| Example 58 | = | 8 | < | 5 | = | 8.1 | < | 5 |
| Example 59 | = | 8 | < | 5 | = | 8.2 | < | 5 |
| Example 60 | | | | | = | 8 | < | 5 |
| Example 61 | = | 8.2 | < | 5 | = | 8.7 | < | 5 |
| Example 62 | | | | | = | 8.4 | < | 5 |
| Example 63 | | | | | = | 8.2 | < | 5 |
| Example 64 | | | | | = | 9 | < | 5 |
| Example 65 | = | 8.4 | < | 5 | = | 8.9 | < | 5 |
| Example 66 | | | | | = | 8.8 | = | 5.2 |
| Example 67 | | | | | = | 8.7 | < | 5 |
| Example 68 | | | | | = | 8.7 | < | 5 |
| Example 69 | | | | | = | 8.6 | < | 5 |
| Example 70 | | | | | = | 8.5 | < | 5 |
| Example 71 | = | 7.7 | < | 5 | = | 8.3 | < | 5 |
| Example 72 | = | 7.4 | < | 5 | = | 8 | < | 5 |
| Example 73 | = | 8.4 | < | 5 | = | 9.1 | < | 5 |
| Example 74 | = | 8.4 | < | 5 | = | 9.1 | = | 6.5 |
| Example 75 | = | 8.5 | < | 5 | = | 8.8 | < | 5 |
| Example 76 | = | 8.4 | < | 5 | = | 8.6 | < | 5 |
| Example 77 | | | | | = | 8.8 | < | 5 |
| Example 78 | | | | | = | 8.5 | < | 5 |

-continued

| | Table of Biological Activities of examples 1-300 | | | | | | | |
|---|---|---|---|---|---|---|---|---|
| | IDO1_HELA_PXC50 | | | HELA_IDO1_TOX_PXC50 | | PBMC PXC50 | | PBMC TOX PXC50 |
| Example 79 | | | | | | = | 8.3 | < | 5 |
| Example 80 | | | | | | = | 8.8 | < | 5 |
| Example 81 | = | 8.1 | < | 5 | = | 8.4 | < | 5 |
| Example 82 | = | 7.8 | < | 5 | = | 8.1 | < | 5 |
| Example 83 | | | | | = | 8.1 | < | 5 |
| Example 84 | | | | | = | 8.1 | < | 5 |
| Example 85 | | | | | = | 8.6 | < | 5 |
| Example 86 | | | | | = | 8.4 | < | 5 |
| Example 87 | = | 8.1 | < | 5 | = | 8.4 | < | 5 |
| Example 88 | = | 8.3 | < | 5 | = | 8.4 | < | 5 |
| Example 89 | | | | | = | 8.4 | < | 5 |
| Example 90 | = | 7.6 | < | 5 | = | 8 | < | 5 |
| Example 91 | = | 7.7 | < | 5 | = | 8 | < | 5 |
| Example 92 | = | 8.3 | < | 5 | = | 9 | = | 6.1 |
| Example 93 | | | | | = | 8.9 | < | 5 |
| Example 94 | | | | | = | 8.9 | < | 4.3 |
| Example 95 | | | | | = | 8.8 | < | 5 |
| Example 96 | | | | | = | 8 | < | 5 |
| Example 97 | | | | | = | 8.2 | < | 5 |
| Example 98 | | | | | = | 8.1 | < | 5 |
| Example 99 | | | | | = | 8.9 | < | 5 |
| Example 100 | | | | | = | 8.7 | < | 5 |
| Example 101 | = | 8.6 | < | 5 | = | 8.8 | < | 5 |
| Example 102 | = | 8.1 | < | 5 | = | 8.3 | < | 5 |
| Example 103 | = | 8.5 | < | 5 | = | 8.8 | < | 5 |
| Example 104 | = | 8.5 | < | 5 | = | 8.6 | < | 5 |
| Example 105 | = | 8.2 | < | 5 | = | 8.5 | < | 5 |
| Example 106 | | | | | = | 8.2 | < | 5 |
| Example 107 | | | | | = | 8.2 | = | 5.3 |
| Example 108 | | | | | = | 8.6 | < | 5 |
| Example 109 | = | 7.5 | < | 5 | = | 8 | < | 5 |
| Example 110 | | | | | = | 8.5 | = | 5.2 |
| Example 111 | = | 8 | < | 5 | = | 8.4 | < | 5 |
| Example 112 | = | 7.8 | < | 5 | = | 8.1 | = | 6.1 |
| Example 113 | = | 8 | < | 5 | = | 8.3 | < | 5 |
| Example 114 | | | | | = | 7.8 | < | 5 |
| example 115 | = | 5.5 | < | 4.3 | = | 5.7 | = | 4.9 |
| example 116 | = | 4.4 | < | 4.3 | | | < | 4.3 |
| example 117 | = | 5.4 | < | 4.3 | | | < | 4.3 |
| example 118 | = | 5.3 | < | 4.3 | | | < | 4.3 |
| example 119 | = | 5.9 | < | 4.3 | | | < | 4.3 |
| example 120 | = | 5 | < | 4.3 | | | = | 4.7 |
| example 121 | = | 5.1 | = | 4.4 | | | | |
| example 122 | = | 4.6 | < | 4.3 | | | | |
| example 123 | = | 5 | < | 4.3 | | | | |
| example 124 | = | 4.9 | < | 4.3 | | | | |
| example 125 | = | 5.9 | < | 4.3 | | | | |

Table of Biological Activities of examples 1-300

| | IDO1_HELA_PXC50 | | HELA_IDO1_TOX_PXC50 | | PBMC PXC50 | | PBMC TOX PXC50 | |
|---|---|---|---|---|---|---|---|---|
| example 126 | = | 6.2 | < | 4.3 | | | | |
| example 127 | = | 5.6 | < | 4.3 | | | | |
| example 128 | = | 5.6 | = | 4.4 | | | | |
| example 129 | = | 5.8 | < | 4.3 | | | | |
| example 130 | = | 5.8 | < | 4.3 | | | | |
| example 131 | = | 6.2 | = | 4.7 | | | | |
| example 132 | = | 4.8 | < | 4.3 | | | | |
| example 133 | = | 5.4 | = | 4.5 | | | | |
| example 134 | = | 5.5 | < | 5 | | | | |
| example 135 | = | 5.4 | < | 5 | | | | |
| example 136 | = | 5.5 | = | 5.1 | | | | |
| example 137 | = | 5 | < | 5 | | | | |
| example 138 | = | 5.3 | < | 4.3 | | | | |
| example 139 | < | 5 | < | 5 | < | 5 | < | 5 |
| example 140 | = | 5.5 | < | 5 | | | | |
| example 141 | = | 6.1 | < | 5 | | | | |
| example 142 | = | 6.8 | < | 5 | | | | |
| example 143 | = | 6.5 | < | 5 | | | | |
| example 144 | = | 5.5 | < | 5 | | | | |
| example 145 | = | 6.1 | < | 5 | | | | |
| example 146 | < | 5 | < | 5 | | | | |
| example 147 | < | 5 | < | 5 | | | | |
| example 148 | = | 6.2 | < | 5 | | | | |
| example 149 | = | 6.1 | < | 5 | | | | |
| example 150 | = | 5.5 | < | 5 | | | | |
| example 151 | = | 5.7 | < | 5 | = | 5.6 | < | 5 |
| example 152 | = | 5.5 | = | 5.4 | = | 5.5 | < | 5 |
| example 153 | = | 5.4 | < | 5 | = | 5.7 | < | 5 |
| example 154 | = | 7.5 | < | 5 | = | 7.7 | < | 5 |
| example 155 | = | 6 | < | 5 | = | 5.8 | < | 5 |
| example 156 | < | 5 | < | 5 | = | 5.1 | < | 5 |
| example 157 | = | 6 | < | 5 | = | 6.1 | < | 5 |
| example 158 | = | 6 | < | 5 | = | 6.2 | < | 5 |
| example 159 | = | 5 | < | 5 | = | 5.3 | < | 5 |
| example 160 | < | 5 | < | 5 | < | 5 | < | 5 |
| example 161 | = | 5.6 | < | 5 | = | 5.7 | < | 5 |
| example 162 | = | 6 | < | 5 | = | 6.4 | < | 5 |

-continued

Table of Biological Activities of examples 1-300

| | IDO1_HELA_PXC50 | | HELA_IDO1_TOX_PXC50 | | PBMC PXC50 | | PBMC TOX PXC50 | |
|---|---|---|---|---|---|---|---|---|
| example 163 | = | 5.7 | < | 5 | = | 5.5 | < | 5 |
| example 164 | = | 6.2 | < | 5 | = | 6.5 | < | 5 |
| example 165 | = | 6.1 | < | 5 | = | 5.8 | < | 5 |
| example 166 | = | 8 | < | 5 | = | 9.5 | = | 5.1 |
| example 167 | < | 5 | < | 5 | = | 5.2 | < | 5 |
| example 168 | < | 5 | < | 5 | < | 5 | < | 5 |
| example 169 | = | 7.6 | < | 5 | = | 8.1 | < | 5 |
| example 170 | = | 6.3 | < | 5 | = | 6.5 | < | 5 |
| example 171 | = | 6.8 | < | 5 | = | 7.6 | < | 5 |
| example 172 | = | 7.1 | < | 5 | = | 7.4 | < | 5 |
| example 173 | = | 7.7 | < | 5 | = | 7.6 | < | 5 |
| example 174 | = | 7.9 | < | 5 | = | 7.9 | < | 5 |
| example 175 | = | 5.3 | < | 5 | | | | |
| example 176 | = | 5.5 | < | 5 | | | | |
| example 177 | = | 6.8 | < | 5 | = | 7.5 | < | 5 |
| example 178 | = | 5.5 | < | 5 | | | | |
| example 179 | = | 6.6 | < | 5 | = | 6.9 | | |
| example 180 | = | 5.4 | < | 5 | | | | |
| example 181 | = | 6.5 | < | 5 | = | 6.8 | < | 5 |
| example 182 | = | 5.3 | < | 5 | | | | |
| example 183 | = | 6.4 | < | 5 | = | 6.7 | < | 5 |
| example 184 | = | 6.3 | < | 5 | | | | |
| example 185 | = | 5.8 | < | 5 | | | | |
| example 186 | = | 7.1 | < | 5 | | | | |
| example 187 | < | 5 | < | 5 | | | | |
| example 188 | = | 6.9 | < | 5 | | | | |
| example 189 | = | 6.7 | < | 5 | | | | |
| example 190 | = | 7.1 | < | 5 | | | | |
| example 191 | = | 5.7 | < | 5 | | | | |
| example 192 | = | 5.3 | < | 5 | | | | |
| example 193 | = | 7 | < | 5 | | | | |
| example 194 | = | 6.7 | < | 5 | | | | |
| example 195 | = | 5.5 | < | 5 | | | | |
| example 196 | = | 6.8 | < | 5 | | | | |
| example 197 | | | | | | | | |
| example 198 | < | 5 | < | 5 | | | | |
| example 199 | = | 5.2 | < | 5 | | | | |

-continued

Table of Biological Activities of examples 1-300

| | IDO1_HELA_PXC50 | | HELA_IDO1_TOX_PXC50 | | PBMC PXC50 | | PBMC TOX PXC50 | |
|---|---|---|---|---|---|---|---|---|
| example 200 | < | 5 | < | 5 | | | | |
| example 201 | < | 5 | < | 5 | | | | |
| example 202 | = | 8.5 | < | 5 | = | 8.8 | < | 5 |
| example 203 | = | 7.2 | < | 5 | = | 7.5 | < | 5 |
| example 204 | = | 5.5 | < | 5 | | | | |
| example 205 | < | 5 | < | 5 | | | | |
| example 206 | = | 7.5 | < | 5 | | | | |
| example 207 | = | 6.2 | < | 5 | | | | |
| example 208 | = | 5.8 | < | 5 | | | | |
| example 209 | = | 7.7 | < | 5 | = | 7.3 | < | 5 |
| example 210 | = | 7.3 | < | 5 | = | 7.4 | < | 5 |
| example 211 | = | 7.6 | < | 5 | = | 7.7 | < | 5 |
| example 212 | = | 6.7 | < | 5 | = | 7.2 | < | 5 |
| example 213 | = | 6.1 | < | 5 | = | 6.7 | < | 5 |
| example 214 | = | 7.9 | < | 5 | = | 7.9 | < | 5 |
| example 215 | = | 7.7 | < | 5 | = | 7.5 | < | 5 |
| example 216 | = | 7.3 | | | = | 7.4 | < | 5 |
| example 217 | | | | | = | 5.4 | < | 5 |
| example 218 | | | | | = | 5.7 | < | 5 |
| example 219 | | | | | = | 7 | < | 5 |
| example 220 | | | | | = | 6.4 | < | 5 |
| example 221 | | | | | = | 7.4 | < | 5 |
| example 222 | | | | | = | 6.7 | < | 5 |
| example 223 | | | | | = | 6.3 | < | 5 |
| example 224 | | | | | = | 5.8 | < | 5 |
| example 225 | | | | | = | 5.1 | < | 5 |
| example 226 | | | | | = | 6.9 | < | 5 |
| example 227 | | | | | = | 6.3 | < | 5 |
| example 228 | | | | | = | 7.8 | < | 5 |
| example 229 | | | | | = | 7.3 | < | 5 |
| example 230 | | | | | = | 5.5 | < | 5 |
| example 231 | | | | | = | 7.6 | < | 5 |
| example 232 | | | | | = | 5.5 | < | 5 |
| example 233 | | | | | = | 7.7 | < | 5 |
| example 234 | | | | | = | 6.3 | < | 5 |
| example 235 | | | | | = | 7.7 | < | 5 |
| example 236 | | | | | < | 5 | < | 5 |

-continued

Table of Biological Activities of examples 1-300

| | IDO1_HELA_PXC50 | | HELA_IDO1_TOX_PXC50 | | PBMC PXC50 | | PBMC TOX PXC50 | |
|---|---|---|---|---|---|---|---|---|
| example 237 | | | | | = | 6.7 | < | 5 |
| example 238 | | | | | = | 7.7 | < | 5 |
| example 239 | | | | | = | 7.6 | < | 5 |
| example 240 | | | | | = | 5.6 | < | 5 |
| example 241 | | | | | = | 7.1 | < | 5 |
| example 242 | | | | | = | 6.4 | < | 5 |
| example 243 | | | | | = | 7.5 | < | 5 |
| example 244 | | | | | = | 7.3 | = | 5.7 |
| example 245 | | | | | = | 6.4 | < | 5 |
| example 246 | | | | | = | 7.6 | < | 5 |
| example 247 | | | | | = | 7.5 | < | 5 |
| example 248 | | | | | < | 5 | < | 5 |
| example 249 | | | | | = | 7.7 | < | 5 |
| example 250 | | | | | = | 5.9 | < | 5 |
| example 251 | | | | | = | 5.7 | < | 5 |
| example 252 | | | | | = | 5.4 | < | 5 |
| example 253 | | | | | = | 6.5 | < | 5 |
| example 254 | | | | | = | 6.9 | < | 5 |
| example 255 | | | | | = | 7.7 | < | 4.3 |
| example 256 | | | | | = | 5.6 | < | 5 |
| example 257 | | | | | = | 7.5 | < | 5 |
| example 258 | | | | | = | 7.1 | < | 5 |
| example 259 | | | | | = | 7 | < | 4.3 |
| example 260 | | | | | = | 7.4 | < | 5 |
| example 261 | | | | | = | 7.5 | < | 5 |
| example 262 | = | 7 | < | 5 | = | 7.7 | < | 5 |
| example 263 | | | | | = | 6.3 | < | 5 |
| example 264 | | | | | = | 7.1 | < | 5 |
| example 265 | | | | | < | 5 | < | 5 |
| example 266 | = | 6.7 | < | 5 | = | 7.2 | < | 5 |
| example 267 | | | | | = | 7.4 | < | 5 |
| example 268 | | | | | = | 5.7 | < | 5 |
| example 269 | = | 6.5 | < | 5 | = | 7.5 | < | 5 |
| example 270 | = | 5.8 | < | 5 | | | | |
| example 271 | = | 5.2 | < | 5 | | | | |
| example 272 | = | 5.3 | < | 5 | | | | |
| example 273 | = | 8.1 | < | 5 | | | | |

-continued

Table of Biological Activities of examples 1-300

| | IDO1_HELA_PXC50 | | HELA_IDO1_TOX_PXC50 | | PBMC PXC50 | | PBMC TOX PXC50 | |
|---|---|---|---|---|---|---|---|---|
| example 274 | = | 6 | < | 5 | | | | |
| example 275 | = | 5.2 | < | 5 | | | | |
| example 276 | = | 8.4 | < | 5 | < | 5 | < | 5 |
| example 277 | = | 6.5 | < | 5 | | | | |
| example 278 | = | 7.3 | < | 5 | | | | |
| example 279 | = | 7 | < | 5 | = | 7.7 | < | 5 |
| example 280 | = | 5.6 | < | 5 | | | | |
| example 281 | = | 7 | < | 5 | | | | |
| example 282 | = | 7.3 | < | 5 | | | | |
| example 283 | = | 5.3 | < | 5 | | | | |
| example 284 | = | 6.4 | < | 5 | = | 6.7 | < | 5 |
| example 285 | = | 6.1 | < | 5 | | | | |
| example 286 | = | 6.3 | < | 5 | = | 6.7 | < | 5 |
| example 287 | = | 8.1 | < | 5 | = | 8.1 | < | 5 |
| example 288 | = | 6.5 | < | 5 | = | 7 | < | 5 |
| example 289 | = | 5.9 | < | 5 | = | 6.3 | < | 5 |
| example 290 | = | 6.9 | < | 5 | = | 7.3 | < | 5 |
| example 291 | = | 7 | < | 5 | = | 6.9 | < | 5 |
| example 292 | = | 6.1 | < | 5 | | | | |
| example 293 | = | 6.2 | < | 5 | | | | |
| example 294 | = | 7.4 | < | 5 | = | 7.7 | < | 5 |
| example 295 | = | 7.9 | < | 5 | = | 8.6 | < | 5 |
| example 296 | = | 6.2 | < | 5 | | | | |
| example 297 | = | 7.3 | < | 5 | = | 7.7 | < | 5 |
| example 298 | = | 6.6 | < | 5 | = | 7.4 | < | 5 |
| example 299 | = | 7.8 | < | 5 | = | 8.2 | < | 5 |
| example 300 | = | 8.4 | < | 5 | = | 8.6 | < | 5 |

What is claimed is:

1. The compound

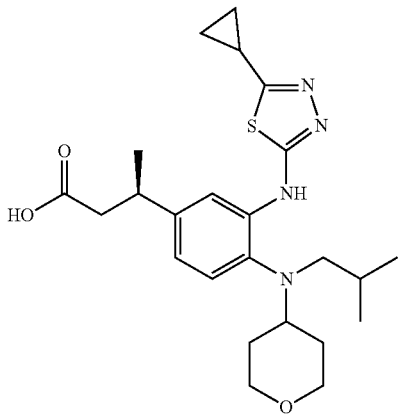 [SMILES: CC(C)CN(c1ccc([C@H](C)CC(=O)O)cc1Nc1nnc(C2CC2)s1)C1CCOCC1]

or a pharmaceutically acceptable salt thereof.

2. A pharmaceutical composition comprising a compound or salt thereof according to claim 1.

3. A method of treating a disease or condition that would benefit from inhibition of IDO1 comprising the step of administration of a composition according to claim 2 to a subject in need thereof, wherein said disease or condition is inflammation associated with HIV infection; chronic viral infections involving hepatitis B virus or hepatitis C virus; cancer; or sepsis.

4. The method of claim 3 wherein in said disease or condition, biomarkers of IDO activity are elevated.

5. The method of claim 3 wherein said biomarkers are plasma kynurenine or the plasma kynurenine/tryptophan ratio.

* * * * *